United States Patent
Calias et al.

(10) Patent No.: US 12,409,210 B2
(45) Date of Patent: *Sep. 9, 2025

(54) CNS DELIVERY OF THERAPEUTIC AGENTS

(71) Applicant: TAKEDA PHARMACEUTICAL COMPANY LIMITED, Osaka (JP)

(72) Inventors: Pericles Calias, Melrose, MA (US); Jing Pan, Boxborough, MA (US); Jan Powell, Concord, MA (US); Lawrence Charnas, Natick, MA (US); Thomas McCauley, Cambridge, MA (US); Teresa Leah Wright, Lexington, MA (US); Richard Pfeifer, North Granby, CT (US); Zahra Shahrokh, Weston, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,155

(22) Filed: Aug. 16, 2022

(65) Prior Publication Data

US 2023/0165942 A1 Jun. 1, 2023

Related U.S. Application Data

(60) Continuation of application No. 16/573,557, filed on Sep. 17, 2019, now Pat. No. 11,471,516, which is a continuation of application No. 15/016,141, filed on Feb. 4, 2016, now Pat. No. 10,456,454, which is a division of application No. 13/168,961, filed on Jun. 25, 2011, now Pat. No. 9,283,181.

(60) Provisional application No. 61/358,857, filed on Jun. 25, 2010, provisional application No. 61/360,786, filed on Jul. 1, 2010, provisional application No. 61/387,862, filed on Sep. 29, 2010, provisional application No. 61/435,710, filed on Jan. 24, 2011, provisional application No. 61/442,115, filed on Feb. 11, 2011, provisional application No. 61/476,210, filed on Apr. 15, 2011, provisional application No. 61/495,268, filed on Jun. 9, 2011.

(51) Int. Cl.
| | | |
|---|---|---|
| A61K 38/43 | (2006.01) | |
| A61K 9/00 | (2006.01) | |
| A61K 9/08 | (2006.01) | |
| A61K 9/19 | (2006.01) | |
| A61K 35/76 | (2015.01) | |
| A61K 35/761 | (2015.01) | |
| A61K 38/46 | (2006.01) | |
| A61K 38/47 | (2006.01) | |
| A61K 47/02 | (2006.01) | |
| A61K 47/26 | (2006.01) | |
| C07K 14/65 | (2006.01) | |
| C12N 9/24 | (2006.01) | |
| C12N 9/42 | (2006.01) | |

(52) U.S. Cl.
CPC ............ *A61K 38/47* (2013.01); *A61K 9/0019* (2013.01); *A61K 9/0085* (2013.01); *A61K 9/08* (2013.01); *A61K 9/19* (2013.01); *A61K 35/76* (2013.01); *A61K 35/761* (2013.01); *A61K 38/46* (2013.01); *A61K 38/465* (2013.01); *A61K 47/02* (2013.01); *A61K 47/26* (2013.01); *C07K 14/65* (2013.01); *C12N 9/2402* (2013.01); *C12N 9/2437* (2013.01); *C12Y 301/06008* (2013.01); *C12Y 301/06013* (2013.01); *C12Y 302/01045* (2013.01); *C12Y 302/01046* (2013.01); *C12Y 302/0105* (2013.01); *C12Y 310/01001* (2013.01)

(58) Field of Classification Search
None
See application file for complete search history.

(56) References Cited

U.S. PATENT DOCUMENTS

| | | |
|---|---|---|
| 4,743,265 A | 5/1988 | Whitehouse et al. |
| 5,222,982 A | 6/1993 | Ommaya |
| 5,972,333 A | 10/1999 | Hopwood et al. |
| 6,118,045 A | 9/2000 | Reuser et al. |
| 6,217,552 B1 | 4/2001 | Barbut et al. |
| 6,534,300 B1 | 3/2003 | Canfield |
| 6,537,785 B1 | 3/2003 | Canfield |
| 7,351,410 B2 | 4/2008 | van Bree et al. |
| 7,396,811 B2 | 7/2008 | LeBowitz et al. |
| 7,442,372 B2 | 10/2008 | Kakkis |

(Continued)

FOREIGN PATENT DOCUMENTS

| | | |
|---|---|---|
| CN | 1788017 A | 6/2006 |
| CN | 101410408 A | 4/2009 |

(Continued)

OTHER PUBLICATIONS

Desai et al., Microbiol. Mol. Biol. Rev. 61:47-64, 1997 (Year: 1997).*

(Continued)

*Primary Examiner* — David Steadman
(74) *Attorney, Agent, or Firm* — Proskauer Rose LLP

(57) ABSTRACT

The present invention provides an effective and less invasive approach for direct delivery of therapeutic agents to the central nervous system (CNS). In some embodiments, the present invention provides methods including a step of administering intrathecally to a subject suffering from or susceptible to a lysosomal storage disease associated with reduced level or activity of a lysosomal enzyme, a composition comprising a replacement enzyme for the lysosomal enzyme.

5 Claims, 147 Drawing Sheets

(56) References Cited

U.S. PATENT DOCUMENTS

| | | |
|---|---|---|
| 7,560,424 B2 | 7/2009 | LeBowitz et al. |
| 7,629,309 B2 | 12/2009 | LeBowitz et al. |
| 8,026,209 B2 | 9/2011 | Gaillard et al. |
| 8,333,959 B2 | 12/2012 | Kipp et al. |
| 8,545,837 B2 | 10/2013 | Zhu et al. |
| 9,220,677 B2 | 12/2015 | Zhu et al. |
| 9,283,181 B2 | 3/2016 | Calias et al. |
| 9,320,711 B2 | 4/2016 | Natoli et al. |
| 9,770,410 B2 | 9/2017 | Salamat-Miller et al. |
| 9,814,764 B2 | 11/2017 | Concino et al. |
| 10,456,454 B2 | 10/2019 | Calias et al. |
| 10,660,944 B2 * | 5/2020 | Salamat-Miller ...... A61K 38/51 |
| 11,065,308 B2 | 7/2021 | Natoli et al. |
| 11,260,112 B2 | 3/2022 | Zhu et al. |
| 2002/0052311 A1 | 5/2002 | Solomon et al. |
| 2002/0095133 A1 | 7/2002 | Gillis et al. |
| 2002/0099025 A1 | 7/2002 | Heywood |
| 2003/0040479 A1 | 2/2003 | Demopulos et al. |
| 2003/0072761 A1 | 4/2003 | LeBowitz |
| 2003/0082176 A1 | 5/2003 | LeBowitz et al. |
| 2003/0181426 A1 | 9/2003 | Eisenach |
| 2004/0005309 A1 | 1/2004 | LeBowitz et al. |
| 2004/0006008 A1 | 1/2004 | LeBowitz et al. |
| 2004/0010290 A1 | 1/2004 | Schroeppel et al. |
| 2004/0172665 A1 | 9/2004 | Reuser et al. |
| 2004/0243058 A1 | 12/2004 | Barbut et al. |
| 2004/0248262 A1 | 12/2004 | Koeberl et al. |
| 2005/0042227 A1 | 2/2005 | Zankel et al. |
| 2005/0048047 A1 | 3/2005 | Kakkis |
| 2005/0208090 A1 | 9/2005 | Keimel et al. |
| 2005/0244400 A1 | 11/2005 | LeBowitz et al. |
| 2005/0281805 A1 | 12/2005 | LeBowitz et al. |
| 2006/0029656 A1 | 2/2006 | O'Donnell et al. |
| 2006/0153829 A1 | 7/2006 | Fan |
| 2006/0177433 A1 | 8/2006 | Treco et al. |
| 2008/0003211 A1 | 1/2008 | Fogh et al. |
| 2008/0076120 A1 | 3/2008 | Donaldson et al. |
| 2008/0299640 A1 | 12/2008 | LeBowitz et al. |
| 2009/0017005 A1 | 1/2009 | Kakkis |
| 2009/0041741 A1 | 2/2009 | Sly et al. |
| 2009/0123451 A1 | 5/2009 | Dodge et al. |
| 2009/0130079 A1 | 5/2009 | Dodge et al. |
| 2009/0191178 A1 | 7/2009 | Zankel et al. |
| 2009/0246187 A1 | 10/2009 | Nilsson |
| 2009/0291062 A1 | 11/2009 | Fraunhofer et al. |
| 2009/0297592 A1 | 12/2009 | Sakuraba et al. |
| 2010/0068195 A1 | 3/2010 | Vellard et al. |
| 2010/0260706 A1 | 10/2010 | Bogin et al. |
| 2011/0105560 A1 | 5/2011 | Wustman |
| 2011/0318323 A1 | 12/2011 | Zhu et al. |
| 2011/0318324 A1 | 12/2011 | Salamat-Miller et al. |
| 2011/0318327 A1 | 12/2011 | Concino et al. |
| 2012/0003202 A1 | 1/2012 | Calias et al. |
| 2012/0009171 A1 | 1/2012 | Salamat-Miller et al. |
| 2012/0014936 A1 | 1/2012 | Natoli et al. |
| 2012/0148558 A1 | 6/2012 | Kakkis |
| 2012/0213762 A1 | 8/2012 | LeBowitz et al. |
| 2013/0168961 A1 | 7/2013 | Stahlkopf et al. |
| 2013/0295071 A1 | 11/2013 | Salamat-Miller et al. |
| 2013/0295077 A1 | 11/2013 | Concino et al. |
| 2014/0271598 A1 | 9/2014 | Zhu et al. |
| 2018/0071212 A1 | 3/2018 | Salamat-Miller et al. |
| 2018/0085438 A1 | 3/2018 | Concino et al. |
| 2019/0183984 A1 | 6/2019 | Natoli et al. |

FOREIGN PATENT DOCUMENTS

| | | | |
|---|---|---|---|
| EP | 2174661 A1 | 4/2010 | |
| EP | 3103469 A1 | 12/2016 | |
| EP | 2020438 B1 * | 4/2018 | ......... A01K 67/0275 |
| JP | 2005-506340 A | 3/2005 | |
| JP | 2007-504166 A | 3/2007 | |
| JP | 2007-519404 A | 7/2007 | |
| JP | 2009-525963 A | 7/2009 | |
| JP | 2009-532394 A | 9/2009 | |
| JP | 2011-521627 A | 7/2011 | |
| JP | 6466538 B2 | 2/2019 | |
| JP | 6522072 B2 | 5/2019 | |
| RU | 2209080 C2 | 7/2003 | |
| TW | 106108979 | 10/2018 | |
| UA | 11577 U | 1/2006 | |
| WO | WO 1994/017819 A1 | 8/1994 | |
| WO | WO 2002/087510 A2 | 11/2002 | |
| WO | WO 2003/032727 A1 | 4/2003 | |
| WO | WO 2003/032913 A2 | 4/2003 | |
| WO | WO 2003/090695 A2 | 11/2003 | |
| WO | WO 2003/102583 A1 | 12/2003 | |
| WO | WO 2004/043373 A2 | 5/2004 | |
| WO | WO 2004/050151 A1 | 6/2004 | |
| WO | WO 2005/002515 A2 | 1/2005 | |
| WO | WO 2005/021064 A2 | 3/2005 | |
| WO | WO 2005/073367 A1 | 8/2005 | |
| WO | WO 2005/078077 A2 | 8/2005 | |
| WO | WO 2005/089462 A2 | 9/2005 | |
| WO | WO 2007/084737 A2 | 7/2007 | |
| WO | WO 2007/141346 A2 | 12/2007 | |
| WO | WO 2008/070769 A1 | 6/2008 | |
| WO | WO 2009/017005 A1 | 2/2009 | |
| WO | WO 2009/073569 A2 | 6/2009 | |
| WO | WO 2009/091994 A2 | 7/2009 | |
| WO | WO 2009/131698 A2 | 10/2009 | |
| WO | WO 2009/137721 A2 | 11/2009 | |
| WO | WO 2011/163647 A2 | 12/2011 | |
| WO | WO 2011/163648 A1 | 12/2011 | |
| WO | WO 2011/163649 A2 | 12/2011 | |
| WO | WO 2011/163650 A2 | 12/2011 | |
| WO | WO 2011/163651 A2 | 12/2011 | |
| WO | WO 2011/163652 A2 | 12/2011 | |
| WO | WO 2012/023623 A2 | 2/2012 | |

OTHER PUBLICATIONS

Raibekas et al., Biochemistry 44:9871-9879, 2005 (Year: 2005).*
Murayama et al., J. Biochem. 105:323-326, 1989 (Year: 1989).*
Cook et al., "Intracerebroventricular administration of drugs," Pharmacotherapy 29:832-845, 2009 (Year: 2009).*
Alam et al., Strategy for effective brain drug delivery, European Journal of Pharmaceutical Sciences, vol. 40, 2010, pp. 385-403 (19 pages).
Altschul et al., "Basic logic alignment search tool," J. Mol. Biol., 215(3): 403-410, 1990.
Altschul et al., "Gapped BLAST and PSI-BLAST: a new generation of protein database search programs," Nucleic Acids Res. 25: 3389-3402, 1997.
Altschul et al., "Local alignment statistics," 266:460-80, Methods in Enzymology., 1996.
Ammaya et al., "Subcutaneous Reservoir and Pump for Sterile Access to Ventricular Cerebrospinal Fluid," Lancet 2(7315): 983-984, 1963.
Anonymous, TKT to Present Research on Intrathecal Delivery of I2S for Hunter Syndrome at ASHG, PRNewswire, 1 (2004).
Anonymous, TKT's Research Findings on Intrathecal Delivery of I2S Presented at ASHG, Evaluate Ltd, 1 (2004).
Auclair et al., Repeated intrathecal injections of recombinant human 4-sulphatase remove dural storage in mature mucopolysaccharidosis VI cats primed with a short-course tolerisation regime, Molecular Genetics and Metabolism, vol. 99, 2010, pp. 132-141 (10 pages).
Baskin, G. et al., "Genetic galactocerebrosidase deficiency (globoid cell leukodystrophy, Krabbe disease) in rhesus monkeys (*Macaca mulatta*)," Lab Anim. Sci., 48(5): 476-482, 1998.
Baum, H. et al., "The assay of arylsulphatases A and B in human urine," Clin Chim Acta. 4(3): 453-455, 1959.
Begley et al., "Lysosomal storage diseases and the blood-brain barrier," Curr Pharm Des 14(16): 1566-1580, 2008.
Belichenko et al., Penetration, diffusion, and uptake of recombinant human alpha-L-iduronidase after intraventricular injection into the rat brain, Mol. Genet. Metab., 86(1-2): 141-149, 2005.
Beniaminovitz et al., "Prevention of rejection in cardiac transplantation by blockage of the interleukin-2 receptor with a monoclonal antibody," N. Engl. J. Med. 342(9): 613-619, 2000.

(56) References Cited

OTHER PUBLICATIONS

Berard et al., "A review of interleukin-2 receptor antagonists in solid organ transplantation," Pharmacotherapy 19(10): 1127-1137, 1999.
Bielicki et al., "Recombinant human sulphamidase: expression, amplification, purification and characterization," Journal of Biochemistry, 329(Pt 1): 145-150, 1998.
Biswas S. et al., "Substrate reduction intervention by L-cycloserine in twitcher mice (globoid cell leukodystrophy) on a B6; CAST/Ei background," Neurosci. Lett., 347(1): 33-36, 2003.
Blasberg, R.G. et al., "Intrathecal chemotherapy: brain tissue profiles after ventriculocisternal perfusion," J Pharmacol Exp Ther. 195(1): 73-83, 1975.
Bobo et al., "Convection-enhanced delivery of macromolecules in the brain," Proc. Natl. Acad. Sci. U.S.A. 91(6), 2076-2080, 1994.
Bowman, R.H., "Inhibition of citrate metabolism by sodium fluoroacetate in the perfused rat heart and the effect on phosphofructokinase activity and glucose utilization," 93(2): 13C-15C, 1964.
Branco et al., "Selective deletion of antigen-specific, activated T cells by a humanized MAB to CD2 (MEDI-507) is mediated by NK cells," Transplantation 68(10): 1588-1596, 1999.
Burrow, T. Andrew and Leslie, Nancy D., Review of the use of idursulfase in the treatment of mucopolysaccharidosis II, Biologics: Targets and Therapy, 2(2):311-320 (2008).
Butt MT, "Morphologic changes associated with intrathecal catheters for direct delivery to the central nervous system im preclinical studies," Toxicol. Pathol., 39(1): 213-219, 2011.
Cabrera-Salazar, M.A. et al., "Intracerebroventricular delivery of glucocerebrosidase reduces substrates and increases lifespan in a mouse model of neuronopathic Gaucher disease," Exp Neurol. 225(2): 436-444, 2010.
Champion K. J. et al., Identification and characterization of a novel homozygous deletion in the x-N-acetylglucosaminidase gene in a patient with Sanfilippo type B syndrome (mucopolysaccharidosis I IIB), Molecular Genetics and Metabolism, 100: 51-56 (2010).
Chirmule et al., "Readministration of adenovirus vector in nonhuman primate lungs by blockage of CD40-CD40 ligand interactions," J. Virol. 74(7): 3345-3352, 2000.
Chiro et al., "Spinal descent of cerebrospinal fluid in man," Neurology 26(1): 1-8, 1976.
Clarke, L. A., Idursulfase for the treatment of mucopolysaccharidosis II, Expert Opin. Pharmacother., 9(2):311-317 (2008).
Colvin, "Plastic syringes challenge glass market dominance", Plastics Today, Jul. 31, 2004 (https://www.plasticstoday.com/content/plastics-syringes-challenge-glass-market-dominance/2069487054797). (5 pages).
Cressent, A. et al., Improved Behavior and Neuropathology in the Mouse Model of Sanfilippo Type IIIB Disease after Adeno-Associated Virus-Mediated Gene Transfer in the Striatum, The Journal of Neuroscience, 24(45): 10229-10239 (2004).
Daniele et al., Uptake of recombinant iduronate-2-sulfatase into neuronal and glial cells in vitro Biochimica et Biophysica Acta 1588, 2002, pp. 203-209 (7 pages).
Dekaban AS., "Changes in brain weights during the span of human life: relation of brain weights to body heights and body weights," Ann Neurol 4: 345-356, 1978.
Descartes, M. et al., Enzyme Replacement Therapy for MPS II: Developing a Pre-Medication Protocol, University of Alabama and Children's Hospital of Alambama, 1 (2007).
Desnick, R.J., "Enzyme replacement and enhancement therapies for lysosomal diseases," J. Inherit. Metab. Dis., 27(3): 385-410, 2004.
Dickson, P. et al., Intrathecal enzyme replacement therapy: Successful treatment of brain disease via the cerebrospinal fluid, Molecular Genetics & Metabolism, 91(1):61-68 (2007).
Dickson, P.I., Novel Treatments and Future Perspectives: Outcomes of Intrathecal Drug Delivery, International Journal of Clinical Pharmacology and Therapeutics, 47:1 S124-127 (2009).
Eckhoff et al., "The safety and efficacy of a two-dose daclizumab (zenapax) induction therapy in liver transplant recipients," Transplantation 69(9): 1867-1872, 2000.
Ekberg et al., "Daclizumab prevents acute rejection and improves patient survival post transplantation: 1 year pooled analysis," Transpl. Int. 13(2): 151-159, 2000.
Elaprase Idursulface, European Medicines Agency—Science, Medicines, Health, XP-002716697, pp. 1-3 (2007).
Elaprase (idursulfase), http://www.elaprase.com/pdf/Elaprase_Overview_Sheet110811.pdf, REV 5, 2011. (10 pages).
Esposito, S. et al, Heparan N-sulfatase gene: two novel mutations and transient expression of 15 defects, Biochimica et Biophysica Acta 1501, 1-11: 1 (2000).
European Patent Office, Notice of Opposition for EP Application No. 16179150.4, 21 pages, Sep. 14, 2021.
European Patent Office, Notice of Opposition for EP Application No. 19192679.9, 28 pages, May 10, 2022.
European Search Report for EP, 11799034.1, 8 pages, Mar. 12, 2014.
Extended European Search Report for EP11799035.8, 7 pages, Dec. 16, 2013.
Extended European Search Report for 11799039.0, 12 pages, Jun. 10, 2014.
Extended European Search Report for EP Patent Application No. 21188176.8, 8 pages, dated Jan. 27, 2022.
Felice, B.R. et al., Safety Evaluation of Chronic Intrathecal Administration of Idursulfase-IT in Cynomolgus Monkeys, Toxicology Pathology, 39:879-892 (2011).
Fenstermacher et al., "Drug "diffusion" within the brain," Ann NY Acad Sci 531: 29-39, 1988.
Ficko-Blean E, et al., "Structural and mechanistic insight into the basis of mucopolysaccharidosis IIIb," PNAS, 105(18): 6560-6565, 2008.
Fishwild et al., "Differential effects of administration of a human anti-CD4 monoclonal antibody, HM6G, in nonhuman primates," Clin. Immunol. 92(2): 138-152, 1999.
Fu, H. et al., Restoration of Central Nervous System a-N-Acetylglucosaminidase Activity and Therapeutic Benefits in Mucopolysaccharidosis IIIB Mice by a Single Intracisternal Recombinant Adeno-Associated Viral Type 2 Vector Delivery, The Journal of Gene Medicine, 12:624-633 (2010).
Fu, H. et al., Significantly Increased Lifespan and Improved Behavioral Performances by rAAV Gene Delivery in Adult Mucopolysaccharidosis IIIB Mice, Gene Therapy 14:1065-1077 (2007).
Garbuzova-Davis, S. et al., Transplantation of Human Umbilical Cord Blood Cells Benefits an Animal Model of Sanfilippo Syndrome Type B, Stem Cells and Development, 14:384-394 (2005).
Garcia, A.R. et al., Intrathecal Delivery of Iduronate 2-Sulfatase to the CNS of Cynomolgous Monkeys, Shire Human Genetic Therapies, 1 (2007).
Garcia, A.R. et al., Preclinical dose ranging studies for enzyme replacement therapy with idursulfase in a knock-out mouse model of MPS II, Molecular Genetics and Metabolism, 91: 183-190 (2007).
Gaziev et al., "Chronic graft-versus-host disease: is there an alternative to the conventional treatment?," Bone Marrow Transplant, 25(7): 689-696, 2000.
Genbank accession No. NM000263, *Homo sapiens* N-Acetylglucosaminidase, Alpha (NAGLU) mRNA, 1-4 (accessed May 3, 2014).
Genecards, Galactosylceramidase, http://www.genecards.org/cgi-bin/carddisp.pl?gene=GALC&search=Galactocerebrosidase, 2012.
Ghersi-Egea, J.F. et al, "Rapid distribution of intraventricularly administered sucrose into cerebrospinal fluid cisterns via subarachnoid velae in rat," Neuroscience 75(4): 1271-1288, 1996.
Graham et al., "Characteristics of a human cell line transformed by DNA from human adenovirus type 5," J. Gen Virol., 36(1): 59-74, 1977.
Greene, H.L. et al., Metachromatic leukodystrophy. Treatment with arylsulfatase-A, Arch Neural., 20: 147-153 (1969).
Grubb JH et al., "New strategies for enzyme replacement therapy for lysosomal storage diseases," Rejuvenation Research 13(2-3): 229-236, 2010.
Gummert et al., "Newer immunosuppressive drugs: a review," J. Am. Soc. Nephrol, 10(6): 1366-1380, 1999.

(56) References Cited

OTHER PUBLICATIONS

Hashimoto R, "N-terminal deletion mutants of insulin-like growth factor-II (IGF-II) show Thr7 and Leu8 important for binding to insulin and IGF-I receptors and Leu8 critical for all IGF-II functions," J Biol Chem., 270(30); 18013-18018, 1995.
Hemsley, K. M. et al., Effect of high dose, repeated intracerebrospinal fluid injection of sulphamidase on neuropathology in mucopolysaccharidosis type IIIA mice, Genes Brain Behav., 7: 740-753 (2008).
Hemsley et al. Examination of intravenous and intra-CSF protein delivery for treatment of neurological disease. European journal of Neuroscience. 2009, Mar. 6, v.29, Issue 6, pp. 1197-1214.
Hemsley, Kim M. et al., "Injection of recombinant human sulfamidase into the CSF via the cerebellomedullary cistern in MPS IIIA mice," Mol Genet Metab. 90(3): 313-328, 2007.
Henry ML, "Cyclosporine and tacrolimus (FK506): a comparison of efficacy and safety profiles," Clin. Transplant, 13(3): 209-220, 1999.
History of Changes for Study: NCT00920647 (A Safety and Dose Ranging Study of Idursulfase (Intrathecal) Administration, ClinicalTrials. gov archive, Apr. 30, 2019, 11 pages.
Hong et al., "Immunosuppressive agents in organ transplantation: past, present, and future," Semin. Nephrol. 20(2): 108-125, 2000.
Hood RD, Development and Reproductive Toxicology: A practical approach, 276, 2006.
Hoogerbrugge, P.M., et al., "Effect of bone marrow transplantation on enzyme levels and clinical course in the neurologically affected," J. Clin. Invest., 81(6): 1790-1794, 1988.
Hovland DN, et al., "Six-month continuous intraputamenal infusion toxicity study of recombinant methionyl human glial cell line-derived neurotrophic factor (r-metHuGDNF in rhesus monkeys," Toxicol. Pathol., 35(7): 1013-1029, 2007.
Ideguchi et al., "Local adenovirus-mediated CFLA40immunoglobulin expression suppresses the immune responses to adenovirus vectors in the brain," Neuroscience 95(1): 217-226, 2000.
International Preliminary Report on Patentability for PCT/US11/41928, 36 pages (Mar. 29, 2013).
International Search Report for PCT/US11/41922, mailed Feb. 14, 2012. 4 pages.
International Search Report for PCT/US11/41924, mailed Nov. 7, 2011. 4 pages.
International Search Report for PCT/US11/41925, mailed Feb. 14, 2012. 4 pages.
International Search Report for PCT/US11/41926, mailed May 13, 2013. 5 pages.
International Search Report for PCT/US11/41927, mailed Mar. 9, 2012. 4 pages.
International Search Report for PCT/US11/41928, 13 pages (Sep. 26, 2012).
Ito et al., "Induction of CTL responses by simultaneous administration of liposomal peptide vaccine with anti-CD40 and anti-CTLA-4 mAb," J. Immunol. 164(3): 1230-1235, 2000.
Japanese Pharmacopeia Saline solution "My Run" attachment, Dec. 2015 Revision, (5 pages).
Johanson CE, et al., "Multiplicity of cerebrospinal fluid functions: New challenges in health and disease," Cerebrospinal Fluid Res., 14(5): 10, 2008.
Johnson, K., "Globoid leukodystrophy in the cat," J. Am. Vet. Med. Assoc., 157(12): 2057-2064, 1970.
Joshi S. et al., "Targeting the brain: rationalizing the novel methods of drug delivery to the central nervous system," Neurocrit Care 6(3): 200-212, 2007.
Kakkis, E. et al., Intrathecal enzyme replacement therapy reduces lysosomal storage in the brain and meninges of the canine model of MPS I, Molecular Genetics and Metabolism 83:163-174 (2004).
Kang, H. et al., Significantly increased lifespan and improved behavioral performances by rAAV gene delivery in adult mucopolysaccharidosis IIIB mice, Gene Therapy, 14:1066-1077 (2007).
Kerwin, Bruce A., Polysorbates 20 and 80 Used in the Formulation of Protein Biotherapeutics: Structure and Degradation Pathways, Journal of Pharmaceutical Sciences, 97: 2924-2935 (2008).

Kobayashi T. et al., "The Twitcher mouse: an enzymatically authentic model of human globoid cell leukodystrophy (Krabbe disease)," Brain Res., 202(2): 479-483, 1980.
Kondo et al., Galactocerebrosidase-deficient oligodendrocytes maintain stable central myelin by exogenous replacement of the missing enzyme in mice, PNAS, vol. 102, No. 51, Dec. 20, 2005, pp. 18670-18675 (6 pages).
Krewson, CE et al., "Distribution of nerve growth factor following direct delivery to brain interstitium," Brain Res. 680(1-2): 196-206, 1995.
Kroin JS, "Intrathecal Drug Administration Present Use and Future Trends", Clin Pharmacokinet, 22(5):319-326 (1992). (10 pages).
Kurlberg et al., "Blockage of the B7-CD28 pathway by CTLA4-Ig counteracts rejectioand prolongs survival in a mouse model of small bowel transplantation," Scand. J. Immunol, 51(3): 224-230, 2000.
Lamsa, J.C et al., Delivery of 12S to the Canine CNS: Comparison of Intracisternal, Intralumbar and Intraventricular Dose Routes as Potential Treatents for Severe MPS II, Shire HGT, 1 (2006).
Lamsa, J.C. et al., Intrathecal Delivery of Iduronate 2-Sulfatase for MPS II to the Canine CNS, ASHG Annual Meeting, 1 (2004).
Lazorthes et al., Advances in Drug Delivery Systems and Application in Neurosurgery, 18: 143-192, 1991.
Lee, et al., "Single-dose intracerebroventricular administration of galactocerebrosidase improves survival in a mouse model of globoid cell leukodystrophy," FASEB Journal, 21(10): 2520-2527, 2007.
Levine S. et al., "L-cycloserine slows the clinical and pathological course in mice with globoid cell leukodystrophy (twitcher mice)," J. Neurosci. Res., 60(2): 231-236, 2000.
Li HH, et al., "Mouse model of Sanfilippo syndrome type B produced by targeted disruption of the gene encoding alpha-N-acetylglucosaminidase," PNAS 96(25): 14505-14510, 1999.
Li, et al., "Attenuated plasticity in neurons and astrocytes in the mouse model of Sanfilippo syndrome type B," J Neurosci Res, 69(1): 30-8, 2002.
Lin, D., et al., "Central nervous system-directed AAV2/5-mediated gene therapy synergizes with bone marrow transplantation in the murine model of globoid-cell leukodystrophy," Mol. Ther., 15(1): 44-52, 2007.
Liu et al., "Cell Biology", Human Science & Technology Publisher, pp. 124-125 (2008).
English translation of: Liu et al., "Cell Biology", Human Science & Technology Publisher, pp. 124-125 (2008).
Lu, Y. et al., Direct Brain Delivery of Iduronate 2-Sulfastase Reduces Glycosaminoglycan Accumulation and Improves Histopathology in the CNS and Peripheral Tissue of Hunter Mice, Shire HGT, 1 (2007).
Luca, Tonia, "Axons mediate the distribution of arylsulfatase A within the mouse hippocampus upon gene delivery," Mol Ther. 12(4): 669-679, 2005.
Marinova-Mutafchieva et al., "A comparative study into the mechanisms of action of anti-tumor necrosis factor alpha, anti-CD4, and combined anti-tumor necrosis factor alpha/anti-CD4 treatment in early collagen-induced arthritis," Arthritis Rheum 43: 638-644, 2000.
Mather et al., "Culture of testicular cells in hormone-supplemented serum-free medium," Ann N.Y. Acad. Sci., 383: 44-68, 1982.
Mather, "Establishment and characterization of two distinct mouse testicular epithelial cell lines," Biol. Reprod., 23: 243-251, 1980.
Matheus, MG et al., "Brain MRI findings in patients with mucopolysaccharidosis types I and Ii and mild clinical presentation," Neuroradiology 46(8): 666-672, 2004.
Matzner, U. et al., Enzyme replacement improves nervous system pathology and function in a mouse model for metachromatic leukodystrophy, Human Molecular Genetics, 14(9):1139-1152 (2005).
Meikle et al., "Diagnosis of lysosomal storage disorders: evaluation of lysosome-associated membrane protein LAMP-1 as a diagnostic marker," Clin Chem., 43(8 Pt 1): 1325-1335, 1997.
Middaugh et al., "Determination of the apparent thermodynamic activities of saturated protein solutions," J. Biol. Chem. 254(2): 367-370, 1979.

(56) References Cited

OTHER PUBLICATIONS

Muñoz-Rojas, M; V. et al. Intrathecal administration of recombinant human Nacetylgalactosamine 4-sulfatase to a MPS VI patient with pachymeningitis cervicalis. Molecular Genetics and Metabolism. vol. 99, pp. 346-350. Apr. 2010.
Moder, KG., "New medications for use in patients with rheumatoid arthritis," Ann. Allergy Asthma Immunol. 84(3): 280-284, 2000.
Nagaraja, TN et al., "In normal rat, intraventricularly administered insulin-like growth factor-1 is rapidly cleared from CSF with limited distribution into brain," Cerebrospinal Fluid Res. 2: 1-15, 2005.
Nail S.L. et al., "Fundamentals of freeze-drying, in Development and manufacture of protein pharmaceuticals," Nail S.L. editor New York: Kluwer Academic/Plenum Publishers, 281-353, 2002.
Neufeld EF, Muenzer J., "The mucopolysaccharidoses," In: Scriver CR, Beaudet AI, Sly WS, et al, eds. The Metabolic and Molecular Bases of Inherited Disease. www.ommbid.com 8th ed. New York, NY: McGraw-Hill; 2001:3421-3452.
Neufeld, E.F., Enzyme Replacement therapy. Lysosomal disorders of the Brain, ed. F.M.a.W. Platt, S.V. 2004: Oxford University Press: 327-338, 2004.
Nevins, TE., "Overview of new immunosuppressive therapies," Curr. Opin. Pediatr. 12(2): 146-150, 2000.
Nguyen et al., "Convective distribution of macromolecules in the primate brain demonstrated using computerized tomography and magnetic resonance imaging," J. Neurosurg. 98(3), 584-590, 2003.
Office Action for CL Patent Application No. 0468-2020, 16 pages, dated Jan. 18, 2022.
Ohmi, et al., "Activated microglia in cortex of mouse models of mucopolysaccharidoses I and IIIB," Proc Natl Acad Sci, 100(4): 1902-7, 2002.
Okuyama, T. et al., Japan Elaprase® Treatment (JET) study: Idursulfase enzyme replacement therapy in adult patients with attenuated Hunter syndrome (Mucopolysaccharidosis II, MPS II), Molecular Genetics and Metabolism, 99:18-25 (2010).
Ommaya et al., "Implantable devices for chronic access and drug delivery to the central nervous system," Cancer Drug Delivery, 1(2): 169-179, 1984.
Pardridge WM., "Drug transport in brain via the cerebrospinal fluid," Fluids Barriers CNS, 8(1): 7, 2011.
Passini, MA et al., "Distribution of a lysosomal enzyme in the adult brain by axonal transport and by cells of the rostral migratory stream," J Neurosci 22(15): 6437-6446, 2002.
Penn, RD et al., "Intrathecal ciliary neurotrophic factor delivery for treatment of amyotrophic lateral sclerosis (phase I trial)," Neurosurgery 40(1): 94-99, 1997.
Phosphate Buffer Calculation, http://www.egr.msu.edu/biofuelcell/tools/phosphate/phosphate. html, Dec. 31, 2000, accessed Aug. 28, 2012. (2 pages).
Ponce RP, et al., "Immunogenicity of biologically-derived therapeutics: assessment and interpretation of nonclinical safety studies," Regul. Toxicol. Pharmacol., 54(2): 164-182, 2009.
Ponticelli et al., "Promising new agents in the prevention of transplant rejection," Drugs R.D. 1(1), 55-60, 1999.
Potter et al., "Review—the use of immunosuppressive agents to prevent neutralizing antibodies against a transgene product," Ann. N.Y. Acad. Sci. 875: 159-174, 1999.
Pritchard, D. et al., "Globoid cell leucodystrophy in polled Dorset sheet," Vet. Pathol., 17(4): 399-405, 1980.
Przepiorka et al., "A phase II study of BTI-322, a monoclonal anti-CD2 antibody, for treatment of steroid-resistant acute graft-versus-host disease," Blood 92(11): 4066-4071, 1998.
Qi et al., "Effect of tacrolimus (FK506) and sirolimus (rapamycin) mono- and combination therapy in prolongation of renal allograft survival in the monkey," Transplantation 69(7), 1275-1283, 2000.
Rieselbach RE et al., "Subarachnoid distribution of drugs after lumbar injection," N Engl J Med. 267(25): 1273-1278, 1962.
Savas, et al., "Intracerebral injection of sulfamidase delays neuropathology in murine MPS-IIIa," Mol Genet Metab., 82(4): 273-285, 2004.

Schlessingerman, A., Mass of an Adult, obtained from hypertextbook.com/facts/2003/AlexSchlessingerman.shtml, 2003, 2 pages.
Scientific Discussion—Elaprase, European Medicines Agency, Science, Medicines, Health, Jan. 18, 2007 (Jan. 18, 2007), pp. 1-43.
Shahrokh et al., "Intrathecal delivery of protein therapeutics to treat genetic diseases involving the CNS, in: Injectable Drug Delivery 2010: Formulations Focus," ONdrugDelivery, pp. 16-20, 2010.
Shire Human Genetic Therapies, Intrathecal Delivery of Protein Therapeutics to Treat Genetic Diseases Involving the CNS, www.ondrugdelivery.com, pp. 16-20, (Publically available on Jun. 30, 2010).
Simard JM et al., "Brain oedema in focal ischaemia: molecular pathophysiology and theoretical implications," Lancet Neurol. 6(3): 258-268, 2007.
Sinow, C.S., Construction of an IGF-NAGLU Fusion Protein for Treatment of Sanfilippo B Syndrome, California State Science Fair, 1 (2008).
Sjoberg, M. et al., Long-term Intrathecal Morphine and Bupivacaine in Patients with Refractory Cancer Pain, Anesthesiology, 80:284-297 (1994).
Slavik et al., "CD28/CTLA-4 and CD80/CD86 families: signaling and function," Immunol Res. 19(1): 1-24, 1999.
Stamatovic SM, et al., "Brain endothelial cell-cell junctions: how to "open" the blood brain barrier," Curr. Neuropharmacol., 6(3): 179-192, 2008.
Stroobants S. et al., "Intracerebroventricular enzyme infusion corrects central nervous system pathology and dysfunction in a mouse model of metachromatic leukodystrophy," Hum Mol Genet. 20(14): 2760-2769, 2011.
Sturk, et al., "Combined Intracerebroventricular Intraperitoneal Enzyme Replacement Therapy Improves Survival and Reduces Brain Psychosine in a Mouse Model of Krabbe Disease," European Task Force on Brain and Neurogenerative Lysosomal Storage Diseases, http://www.brains4brain.eu/assets/files/abstract-francoforte-2009.pdf p. 42, 2009.
Tang, X. et al., "Design of freeze-drying processes for pharmaceuticals: Practical advice," Pharm. Res., 21(2): 191-200, 2004.
Tippin, B. et al., Insulin-like Growth Factor-2 Peptide Fusion Enables Uptake and Lysosomal Delivery of N-Acetylglucosamindidase to Mucopolysaccharidosis IIIB Fibrboblasts, MPS Scientific Program: Plenary Papers, entire document: p. 100 (Jun. 26, 2010).
Toyoshima, E. et al., "Nerve conduction studies in the Twitcher mouse (murine globoid cell leukodystrophy)," J. Neurol. Sci., 74(2-3): 307-318, 1986.
Tsai et al., "Intrathecal treatment with anti-Noga-A antibody improves functional recovery in adult rats after stroke" Exp Brain Res, Aug. 24, 2007.
Urlaub and Chasin, "Isolation of Chinese hamster cell mutants deficient in dihydrofolate reductase activity," Proc. Natl. Acad. Sci. USA, 77(7): 4216-4220, 1980.
Vedolin, L. et al., "Correlation of MR imaging and MR spectroscopy findings with cognitive impairment in mucopolysaccharidosis II," AJNR Am J Neuroradial 28(6): 1029-1033, 2007.
Vertemati, T. et al., Multidisciplinary Evaluation in 12 Mucopolysaccharidose Type II or Hunter Syndrome Patients Prior Enzyme Replacement Therapy, CREIM, UNIFESP, 1 (2007).
Vite, Charles H. et al., "Biodistribution and pharmacodynamics of recombinant human alpha-L-iduronidase (rhIDU) in mucopolysaccharidosis type I-affected cats following multiple intrathecal administrations," Mol Genet Metab 103(3): 268-274, 2011.
Vogler, C. et al., "Overcoming the blood-brain barrier with high-dose enzyme replacement therapy in murine mucopolysaccharidosis VII," Proc Natl Acad Sci USA 102(41): 14777-14782, 2005.
Waheed, A. et al., "Purification of mammalian arylsulfatase A enzymes by subunit affinity chromatography," Int J Pept Protein Res., 26(4): 362-372, 1985.
Walkley, "Cell Pathology of lysosomal storage disorders," Brain Pathol., 8, 175-93, 1998.
Wang, W. and Roberts, C., Aggregation of Therapeutic Proteins, published by John Wiley & Sons, Inc., Hoboken, New Jersey (2010).
Wang et al., "Lyophilization and development of solid protein pharmaceuticals," Int. J. Pharm., 203(1-2): 1-60, 2000.

(56) References Cited

OTHER PUBLICATIONS

Wang et al., "Treatment reduces or stabilizes brain imaging abnormalities in patients with MPS I and II," Molecular Genetics and Metabolism, 98(4): 406-11, 2009.
Watson et al., "Intrathecal administration of AAV vectors for the treatment of lysosomal storage in the brains of MPS I mice," Gene Ther., 13(11): 917-925, 2006.
Weber, B. et al., Novel Mutations in Sanfilippo A syndrome: Implications for Enzyme function, Hum. Mol. Genet., 6(9): 1573-1579 (1997).
Wenger, D.A. et al., Galactosylceramide Lipidosis: Globoid Cell Leukodystrophy (Krabbe Disease), in the Metabolic and Molecular Bases of Inherited Disease, C.R. Scriver, Beaudet, A., Sly, W.S. and Valle, D. Editor 2001 McGraw-Hill, 3669-3687, 2001.
Wenger, D.A., "Murine, canine and non-human primate models of Krabbe disease," Mol. Med. Today, 6(11): 449-451, 2000.
Williams N.A. et al., "The lyophilization of pharmaceuticals; A literature review." J. Parenter Sci. Technol., 38(2): 48-59, 1984.
Wiseman et al., "Daclizumab: a review of its use in the prevention of acute rejection in renal transplant recipients," Drugs 58(6): 1029-1042, 1999.
Won, C., Stabilizers against heat-induced aggregation of RPR 114849, an acidic fibroblast growth factor (aFGF), International Journal of Pharmaceutics, 167:25-36 (1998).
Wraith, J.E. et al., Mucopolysaccharidosis type II (Hunter syndrome): a clinical review and recommendations for treatment in the era of enzyme replacement therapy, Eur. J. Pediatr., 167: 247-277 (2008).
Written Opinion for PCT/US11/41922, mailed Feb. 14, 2012. 5 pages.
Written Opinion for PCT/US11/41924, mailed Nov. 7, 2011. 12 pages.
Written Opinion for PCT/US11/41925, mailed Feb. 14, 2012. 7 pages.
Written Opinion for PCT/US11/41926, 8 pages mailed May 13, 2013. 8 pages.
Written Opinion for PCT/US11/41927, mailed Mar. 9, 2012. 6 pages.
Written Opinion for PCT/US11/41928, 13 pages (Sep. 26, 2012).
Yan Q et al., "Distribution of intracerebral ventricularly administered neurotrophins in rat brain and its correlation with trk receptor expression," Exp Neurol. 127(1): 23-36, 1994.
Yeager A. et al., "Prolonged survival and remyelination after hematopoietic cell transplantation in the twitcher mouse," Science, 225(4666): 1052-1054, 1984.
Ideguchi, M., et al., "Local Adenovirus-mediated CTLA4-Immunoglobulin Expression Suppresses the Immune Responses to Adenovirus Vectors in the Brain", Department of Neurosurgery, Yamaguchi University School of Medicine, Neuroscience vol. 95, No. 1, 2000, pp. 217-226 (10 pages).
Enns, et al., "Central Nervous System Therapy for Lysosomal Storage Disorders", Neurosurg Focus vol. 24 (3&4): E11, Mar./Apr. 2008 (12 pages).

* cited by examiner

Vehicle
cerebral cortex 3 dose I2S
cerebral cortex 3 dose I2S
cerebellar
cortex

Port-A-Cath Low Profile Intrathecal Implantable Access System 12S positive neurons, glial cells, and meningeal cells were found within the layer I (Panel A), layer III (Panel B) and layer VI (Panel C) of the brain. This animal was in the 30 mg dose group. (40X magnification)

30 mg dose group. Original magnification = 40X.

WT Vehicle IT treated

WT= Wild type; IT treated mice received 4 weekly doses of 520 mg/kg brain weight of rhASA1 (0.21 mg), 4X magnification.

** P<0.001; * P<0.05
T-Spinal cord = total spinal cord
T-GM = total gray matter
L-GM = lumbar gray matter
C-GM = cervical gray matter
T-WM = total white matter
L-WM = lumbar white matter
C-WM = cervical white matter WT= Wild type; IT treated mice received 4 weekly doses of 520 mg/kg brain weight of rhASA1 (0.21 mg), 20X magnification.

62-133 #458

Slice 4

Anatomical label
1. Subcortical WM
2. Periventricular WM and deep white matter
3. 3.Subcortical WM 1 cm 62-133    Slice 6    #780

1 cm

Anatomical label

4. Corpus callosum and pericallosal subcortical WM
5. Internal capsule, GPi
6. Internal capsule, caudate nucleus
7. Deep white matter
8. Subcortical WM and cortex
9. putamen
10. Temporal subcortical WM and cortex 1 cm Anatomical label
11. Deep Grey matter
12. Deep grey matter
13. Deep WM, Frontal periventricular & subcortical
14. Subcortical white and cortex, superficial sagittal Anatomical label
15. Corpus callosum and pericallosal subcortical WM
16. Deep Subcortical WM
17. Deep grey
18. Deep grey
19. Periventricular WM
20. Subcortical WM
21. hippocampus Anatomical label
22. Corpus callosum
23. Deep WM 1 cm Anatomical label
24. Subcortical WM, occipital lobe
25. Cerebellar White Matte, including dentate nucleus (WM)

Comparison of non-compartmental PK parameters in the brain

| | | | IT | | IV | | Ratio |
|---|---|---|---|---|---|---|---|
| | Parameter | Unit | Mean | SD | Mean | SD | IT/IV |
| 1 mg/kg | $\lambda z$ | 1/hr | 0.016 | 0.003 | 0.011 | 0.005 | |
| | $t_{1/2}$ | hr | 45 | 7 | 71 | 23 | |
| | $C_{max}$ | ug/g | 257 | 90 | 0.1 | 0.0 | 3212 |
| | $AUC_{0-192hr}$ | hr*ug/g | 8393 | 2457 | 7 | 2 | 1136 |
| 10 mg/kg | $\lambda z$ | 1/hr | 0.014 | 0.001 | 0.102 | 0.180 | |
| | $t_{1/2}$ | hr | 49 | 4 | 60 | 53 | |
| | $C_{max}$ | ug/g | 2628 | 265 | 1.8 | 0.2 | 1501 |
| | $AUC_{0-192hr}$ | hr*ug/g | 83962 | 10083 | 86 | 66 | 978 |

CNS DELIVERY OF THERAPEUTIC AGENTS

CROSS REFERENCE TO RELATED APPLICATIONS

This application is a continuation of U.S. patent application Ser. No. 16/573,557, filed Sep. 17, 2019, which is a continuation of U.S. Pat. No. 10,456,454 (U.S. application Ser. No. 15/016,141), filed Feb. 4, 2016, which is a divisional of U.S. Pat. No. 9,283,181 (U.S. application Ser. No. 13/168,961), filed Jun. 25, 2011, which claims priority to U.S. Provisional Patent Applications 61/358,857, filed Jun. 25, 2010; 61/360,786, filed Jul. 1, 2010; 61/387,862, filed Sep. 29, 2010; 61/435,710, filed Jan. 24, 2011; 61/442,115, filed Feb. 11, 2011; 61/476,210, filed Apr. 15, 2011; and 61/495,268 filed on Jun. 9, 2011; the entirety of each of which is hereby incorporated by reference. This application relates to US applications entitled "Methods and Compositions for CNS Delivery of Heparan N-Sulfatase," filed Jun. 25, 2011 (U.S. application Ser. No. 13/168,957); "Methods and Compositions for CNS Delivery of lduronate-2-Sulfatase," filed Jun. 25, 2011 (U.S. application Ser. No. 13/168,966); "Methods and Compositions for CNS Delivery of β-Galactocerebrosidase," filed Jun. 25, 2011 (U.S. application Ser. No. 13/168,970) "Methods and Compositions for CNS Delivery of Arylsulfatase A," filed Jun. 25, 2011 (U.S. application Ser. No. 13/168,963); "Treatment of Sanfilippo Syndrome Type B," filed Jun. 25, 2011 (U.S. application Ser. No. 13/168,969); the entirety of each of which is hereby incorporated by reference.

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many have believed that the barrier to diffusion at the brain's surface, as well as the lack of effective and convenient delivery methods, were too great an obstacle to achieve adequate therapeutic effect in the brain for any disease.

Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

Thus, there remains a great need to effectively deliver therapeutic agents to the brain. More particularly, there is a great need for more effective delivery of active agents to the central nervous system for the treatment of lysosomal storage disorders.

SUMMARY

The present invention provides an effective and less invasive approach for direct delivery of therapeutic agents to the central nervous system (CNS). The present invention is, in part, based on the unexpected discovery that a replacement enzyme for a lysosomal storage disease can be directly introduced into the cerebrospinal fluid (CSF) of a subject in need of treatment at a high concentration (e.g., greater than about 3 mg/ml, 4 mg/ml, 5 mg/ml, 10 mg/ml or more) such that the enzyme effectively and extensively diffuses across various surfaces and penetrates various regions across the brain, including deep brain regions. More surprisingly, the present inventors have demonstrated that such high protein concentration delivery can be acheived using simple saline or buffer-based formulations and without inducing substantial adverse effects, such as severe immune response, in the subject. Therefore, the present invention provides a highly efficient, clinically desirable and patient-friendly approach for direct CNS delivery for the treatment of various diseases and disorders that have CNS components, in particular, lysosomal storage diseases. The present invention represents a significant advancement in the field of CNS targeting and enzyme replacement therapy.

Among other things, the present invention provides methods of intrathecal (IT) administration of a therapeutic agent (e.g., a replacement enzyme) to a subject in need of treatment. In some embodiments, a replacement enzyme can be a recombinant, gene-activated or natural enzyme. As used herein, the terms "intrathecal administration," "intrathecal injection," "intrathecal delivery," or grammatic equvilents, refer to an injection into the spinal canal (intrathecal space surrounding the spinal cord). In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine. It is contemplated that lumbar IT administration or delivery distinguishes over cisterna magna delivery (i.e., injection via the space around and below the cerebellum via the opening between the skull and the top of the spine) in that lumbar IT administration or delivery according to our invention provides better and more effective delivery to the distal spinal canal, while cisterna magna delivery, among other things, typically does not deliver well to the distal spinal canal.

In one aspect, the present invention provides methods including a step of administering intrathecally to a subject suffering from or susceptible to a lysosomal storage disease associated with reduced level or activity of a lysosomal enzyme, a composition comprising a replacement enzyme for the lysosomal enzyme at a concentration of greater than about 5 mg/ml (e.g., greater than 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 75 mg/ml, or 100 mg/ml).

In some embodiments, the composition further comprises one or more of (i) a buffering agent, (ii) a surfactant, or (iii) a tonicifier. In some embodiments, the composition has a pH of approximately 3.0-8.0 (e.g., 4.0-7.5, 5.0-7.5, 5.5-7.7, 5.5-7.0, 6.0-7.0, 6.5-7.5, 6.5-7.0, or 5.5-6.5). In some embodiments, the composition comprises a replacement enzyme in a formulation that is not synthetic CSF.

In some embodiments, the composition is administered at a single dose volume of less than about 15 mL (e.g., less than about 10 ml, 9 ml, 8 ml, 7 ml, 6 ml, 5 ml, 4 ml, 3 ml, 2 ml, 1.5 ml, 1.0 ml, or 0.5 ml).

In some embodiments, the intrathecal administration of the composition does not result in substantial adverse effect in the subject. In certain embodiments, the intrathecal administration of the composition does not result in an adaptive T-cell mediated immune response.

In yet another aspect, the present invention provides methods including a step of administering to a subject suffering from or susceptible to a lysosomal storage disease associated with reduced level or activity of a lysosomal enzyme, a composition comprising a replacement enzyme for the lysosomal enzyme, which administering involves intrathecal administration of the composition in absence of concurrent immunosuppressant therapy. In some embodiments, the method does not involve an immune tolerance induction in the subject being treated. In certain embodiments, the method does not involve a pre-treatment or preconditioning of the subject using T-cell immunosuppressive agent.

In a further aspect, the present invention provides methods including a step of administering intrathecally to a subject suffering from or susceptible to a lysosomal storage disease associated with reduced level or activity of a lysosomal enzyme, a composition comprising a replacement enzyme for the lysosomal enzyme at a therapeutically effective dose and an administration interval such that at least about 10% (e.g., at least about 15%, 20%, 25%, 30%, 35%, 40%, 45%, 50%, 55%, 60%, 65%, 70%, 75%, 80%, 85%, 90%, or 95%) of normal levels or activities of the lysosomal enzyme in one or more tissues of brain, spinal cord and peripheral organs is achieved.

In some embodiments, the one or more tissues of brain to which the enzyme is delivered comprise a meningeal tissue. In some embodiments, the meningeal tissue is selected from the group consisting of pia mater, dura mater, and arachnoid tissue.

In some embodiments, the one or more tissues of brain to which the enzyme is delivered comprise a tissue of the cerebrum. In certain embodiments, the tissue of the cerebrum is a surface or shallow tissue of the cerebrum. In certain embodiments, the surface or shallow tissue of the cerebrum is selected from the group consisting of pia mater tissues, cerebral cortical ribbon tissues, hippocampus, tissues within 4 mm from the surface of the surface of the cerebrum, Virchow Robin space, blood vessels within the VR space, the hippocampus, portions of the hypothalamus on the inferior surface of the brain, the optic nerves and tracts, the olfactory bulb and projections, and combinations thereof.

In some embodiments, the tissue of the cerebrum to which the enzyme is delivered is a deep tissue of the cerebrum. In certain embodiments, the deep tissue of the cerebrum is selected from the group consisting of tissues internal to the cerebral cortical ribbon, tissues below 4 mm from the surface of the surface of the cerebrum, tissues below 6 mm from the surface of the surface of the cerebrum, tissues below 10 mm from the surface of the surface of the cerebrum, the diencephalon, the hypothalamus, thalamus, prethalamus, and subthalamus, the metencephalon, the cerebral peduncles, the red nucleus, the cranial nerve III nucleus, deep grey matter, the lentiform nuclei, the basal ganglia, caudate, putamen, amygdala, globus pallidus, and combinations thereof.

In some embodiments, the one or more tissues of brain to which the enzyme is delivered comprise a tissue of the cerebellum. In certain embodiments, the tissue of the cerebellum is selected from the group consisting of tissues of the molecular layer, tissues of the Purkinje cell layer, tissues of the Granular cell layer, cerebellar peduncles, and combination thereof. In some embodiments, the tissue of the cerebellum is a deep tissue of the cerebellum. In certain embodiments, the deep tissue of the cerebellum is selected from the group consisting of tissues of the Purkinje cell layer, tissues of the Granular cell layer, deep cerebellar white matter tissue, and deep cerebellar nuclei tissue.

In some embodiments, the one or more tissues of brain to which the enzyme is delivered comprise a tissue of the brainstem. In certain embodiments, the tissue of the brainstem is selected from the group consisting of brain stem white matter tissue and/or brain stem nuclei tissue.

In some embodiments, the one or more tissues of the spinal cord to which the enzyme is delivered is a surface or shallow tissue of the spinal cord. In certain embodiments, the surface or shallow tissue of the spinal cord is selected from the group consisting of pia matter, the tracts of white matter, and tissue within 4 mm from the surface of the surface of the spinal cord. In some embodiments, the one or more tissues of the spinal cord is a deep tissue of the spinal cord. In certain embodiments, the deep tissue of the spinal cord is selected from the group consisting of spinal cord grey matter and ependymal cells, and tissue below 4 mm from the surface of the surface of the spinal cord.

In some embodiments, the one or more tissues of brain to which the enzyme is delivered comprise surface or shallow tissues. In certain embodiments, the surface or shallow tissues are selected from the group consisting of pia mater, dura mater, and arachnoid tissues of meningeal, pia mater tissues, cerebral cortical ribbon tissues, tissues within 4 mm from the surface of the surface of the cerebrum, and combination thereof.

In some embodiments, the tissues to which the enzyme is delivered comprise deep tissues. In certain embodiments, the deep brain tissues are selected from deep white matter, of the cerebrum, deep gray matter of the spinal cord, corpus callosum, periventricular tissue, thalamus, basal ganglia, diencephalon, fimbria, tissues below the cerebral cortical ribbon, tissues below 4 mm from the surface of the surface of the cerebrum, tissues below 6 mm from the surface of the surface of the cerebrum, tissues below 10 mm from the surface of the surface of the cerebrum, Purkinje cell layer, tissues of the Granular cell layer, deep cerebellar white matter tissue, and deep cerebellar nuclei tissue, and combination thereof.

In some embodiments, the therapeutically effective dose ranges from 0.005 mg/kg brain weight to 100 mg/kg brain weight. In certain embodiments, the therapeutically effective dose is greater than 1 mg/kg brain weight (e.g., greater than 5, 10, 15, 20, 25, 30, 35, 40, 45, or 50 mg/kg brain weight). In certain embodiments, the therapeutically effective dose is greater than 10 mg/kg brain weight. In certain embodiments, the therapeutically effective dose is greater than 30 mg/kg brain weight.

In some embodiments, the administration interval is once every two weeks. In some embodiments, the administration interval is once every month. In some embodiments, the administration interval is once every two months. In some embodiments, the administration interval is twice per month. In some embodiments, the administration interval is once every week. In some embodiments, the administration interval is twice or several times per week. In some embodiments, the administration is continuous, such as through a continuous perfusion pump.

In another aspect, the present invention provides methods including a step of administering to a subject suffering from or susceptible to a lysosomal storage disease associated with reduced level or activity of a lysosomal enzyme, a composition comprising a replacement enzyme for the lysosomal enzyme, which administering involves intrathecal administration of the composition so that the replacement enzyme is delivered to a deep brain tissue at least 5 mm below the external surface (e.g., at least 6 mm, 7 mm, 8 mm, 9 mm, 10 mm, 11 mm, 12 mm, or deeper below the external surface). In some embodiments, the replacement enzyme is delivered to a deep brain tissue at least 10 mm below the external surface. In certain embodiments, the replacement enzyme is specifically delivered to cellular lysosomes of the deep brain tissue.

In some embodiments, the deep brain tissues to which the enzyme is delivered are selected from deep white matter, of the cerebrum, deep gray matter of the spinal cord, corpus collosum, periventricular tissue, thalamus, fimbria, tissues below the cerebral cortical ribbon, tissues below 4 mm from the surface of the surface of the cerebrum, tissues below 6 mm from the surface of the surface of the cerebrum, tissues below 10 mm from the surface of the surface of the cerebrum, Purkinje cell layer, tissues of the Granular cell layer, deep cerebellar white matter tissue, and deep cerebellar nuclei tissue, and combination thereof.

In yet another aspect, the present invention provides methods including a step of administering intrathecally to a subject suffering from or susceptible to a lysosomal storage disease associated with reduced level or activity of a lysosomal enzyme, a composition comprising a replacement enzyme for the lysosomal enzyme that is produced from human cells.

In some embodiments, the lysosomal storage disease is selected from the group consisting of aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leukodystrophy, mucolipidosis type I, sialidosis types I/II, mucolipidosis types II/III, mucolipidosis type IV, I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome type A, B, or D (mucopolysaccharidosis type IIIB, mucopolysaccharidosis type IIIC, mucopolysaccharidosis type IIID), mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

In some embodiments, the lysosomal storage disease is selected from the group consisting of Hunters Syndrome, metachromatic leukodystrophy (MLD) disease, Sanfilippo syndrome type A, Sanfilippo syndrome type B, and globoid cell leukodystrophy (GLD) disease. In certain embodiments, the replacement enzyme is selected from the group consisting of recombinant iduronate-2-sulfatase (I2S), arylsulfatase A (ASA), heparan N-sulfatase (HNS), alpha-N-acetylglucosaminidase (Naglu) and β-galactosidase (GLC). In some embodiments, the replacement enzyme contains mannose-6-phosphate (M6P) residues. In some embodiments, the replacement enzyme is a fusion protein comprising a lysosomal targeting moiety.

In some embodiments, the replacement enzyme is delivered to neurons, glial cells, perivascular cells and/or meningeal cells. In certain embodiments, the replacement enzyme is further delivered to the neurons in the spinal cord.

In some embodiments, the intrathecal administration further results in systemic delivery of the replacement enzyme in peripheral target tissues. In certain embodiments, the peripheral target tissues are selected from liver, kidney, and/or heart, endothelium, bone marrow and bone marrow derived cells, spleen, lung, lymph node, bone and cartilage, ovary and testis.

In some embodiments, the intrathecal administration results in lysosomal localization of the replacement enzyme in brain target tissues, spinal cord neurons and/or peripheral target tissues. In some embodiments, the intrathecal administration results in reduction of GAG storage in the brain target tissues, spinal cord neurons and/or peripheral target tissues. In certain embodiments, the GAG storage is reduced by at least 20%, 40%, 50%, 60%, 80%, 90%, 1-fold, 1.5-fold, or 2-fold as compared to a control.

In some embodiments, the intrathecal administration results in reduced vacuolization in neurons. In some embodiments, the neurons comprise Purkinje cells.

In some embodiments, the intrathecal administration results in increased enzymatic activity of the replacement enzyme in the brain target tissues, spinal cord neurons and/or peripheral target tissues. In certain embodiments, the enzymatic activity is increased by at least 1-fold, 2-fold, 3-fold, 4-fold, 5-fold, 6-fold, 7-fold, 8-fold, 9-fold or 10-fold as compared to a control. In certain embodiments, the increased enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg.

In some embodiments, the enzymatic activity is increased in the lumbar region. In certain embodiments, the increased enzymatic activity in the lumbar region is at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In some embodiments, the lysosomal storage disease is associated with peripheral symptoms and the method further comprises administering the replacement enzyme intravenously to the subject. In certain embodiments, the intravenous administration is no more frequent than weekly administration (e.g., no more frequent than biweekly, monthly, once every two months, once every three months, once every four months, once every five months, or once very six months). In certain embodiments, the intraveneous administration is more frequent than monthly administration, such as twice weekly, weekly, every other week, or twice monthly. In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intraveneous administration. In some embodiments, an intravenous administration replaces an intrathecal administration in an administration schedule, such as in a schedule of intrathecal administration weekly, every other week, twice monthly, or monthly, every third or fourth or fifth administration in that schedule can be replaced with an intravenous administration in place of an intraveneous administration. In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, or a year or more) followed by intrathecal administations (e.g., weekly, every other week, twice monthly, or monthly dosing for more than two weeks, a month, two months, three months, four months, five months, six months, or a year or more). In some embodiments, intrathecal administrations are performed first (e.g., weekly, every other week, twice monthly, monthly, once every two months, once every three months dosing for two weeks, a month, two months, three months, four months, five months, six months, or a year or more) followed by intraveneous administations (e.g., weekly, every other week, twice monthly, or monthly dosing for more than two weeks, a month, two months, three months, four months, five months, six months, or a year or more).

In some embodiments, the lysosomal storage disease is associated with peripheral symptoms and the method includes administering the replacement enzyme intrathecally but does not involve administering the replacement enzyme intravenously to the subject. In certain embodiments, the intrathecal administration of the replacement enzymes amelioriates or reduces one or more of the peripherial symptoms of the enyme replacement deficiency of the subject.

In another aspect, the present invention provides methods of treating Hunters Syndrome including a step of administering intrathecally to a subject in need of treatment a recombinant iduronate-2-sulfatase (I2S) enzyme at a therapeutically effective dose and an administration interval such that at least one symptom or feature of the Hunters Syndrome is reduced in intensity, severity, or frequency, or has delayed onset. In some embodiments, the at least one symptom or feature of the Hunters Syndrome is cognitive impairment; white matter lesions; dilated perivascular spaces in the brain parenchyma, ganglia, corpus callosum, and/or brainstem; atrophy; and/or ventriculomegaly.

In yet another aspect, the present invention provides methods of treating metachromatic leukodystrophy (MLD) disease including a step of administering intrathecally to a subject in need of treatment a recombinant arylsulfatase A (ASA) enzyme at a therapeutically effective dose and an administration interval such that at least one symptom or feature of the MLD disease is reduced in intensity, severity, or frequency, or has delayed onset. In some embodiments, the at least one symptom or feature of the MLD disease is increased intracranial pressure, hydrocephalus ex vacuo, accumulated sulfated glycolipids in the myelin sheaths in the central and peripheral nervous system and in visceral organs, progressive demyelination, axonal loss within the CNS and PNS, and/or motor and cognitive dysfunction.

In still another aspect, the present invention provides methods of treating Sanfilippo syndrome type A (Sanfilippo A) disease including a step of administering intrathecally to a subject in need of treatment a recombinant heparan N-sulfatase (HNS) enzyme at a therapeutically effective dose and an administration interval such that at least one symptom or feature of the Sanfilippo A disease is reduced in intensity, severity, or frequency, or has delayed onset.

In another aspect, the present invention provides methods of treating Sanfilippo syndrome type B (Sanfilippo B) disease including a step of administering intrathecally to a subject in need of treatment a recombinant alpha-N-acetyl-glucosaminidase (Naglu) enzyme at a therapeutically effective dose and an administration interval such that at least one symptom or feature of the Sanfilippo B disease is reduced in intensity, severity, or frequency, or has delayed onset.

In some embodiments, the at least one symptom or feature of the Sanfilippo A or Sanfilippo B disease is hearing loss, impaired speech development, deficits in motor skills, motoric hyperactivity, progressive cognitive impairment, aggressiveness and/or sleep disturbances.

In some embodiments, the recombinant Naglu enzyme is a fusion protein comprising Naglu and a lysosomal targeting moiety. In certain embodiments, the lysosomal targeting moiety is IGF-II.

In another aspect, the present invention provides methods of treating globoid cell leukodystrophy (GLD) disease including a step of administering intrathecally to a subject in need of treatment a recombinant β-galactosidase (GLC) enzyme at a therapeutically effective dose and an administration interval such that at least one symptom or feature of the GLD disease is reduced in intensity, severity, or frequency, or has delayed onset. In some embodiments, the at least one symptom or feature of the GLD disease is irritability, convulsion, mental deterioration, deafness, blindness, myoclonic seizures, excessive muscle tone, developmental delay, regression of developmental skills, hypersensitivity, tremor, ataxia, spasticity, episodic severe vomiting, leukodystrophy, cerebral atrophy, impaired development of globoid cells and/or demyelination.

In yet another aspect, the present invention provides devices for intrathecal administration, including a fluid access port; a hollow body having a first flow orifice in fluid communication with the fluid access port and a second flow orifice configured for insertion into spinal cord; and a securing mechanism for securing the insertion of the hollow body in the spinal cord. In some embodiments, the securing mechanism comprises one or more nobs mounted on the surface of the hollow body and a sutured ring adjustable over the one or more nobs. In some embodiments, the fluid access port is comprises a reservoir. In certain embodiments, the fluid access port is implantable. In certain embodiments, the fluid access port is an injectable port. In some embodiments, the fluid access port is a mechanical pump.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 7A depicts exemplary results using 50 mM NaCl and hGalC. FIG. 7B depicts exemplary results illustrating 150 mM NaCl and hGalC. FIG. 7C depicts exemplary results illustrating 500 mM NaCl and hGalC. FIG. 7D depicts exemplary results illustrating 150 mM NaCl and mouse GalC.

FIG. 88A illustrates the cross-sectional view of brain tissue extracted from the cerebrum of the primate, while FIG. 88B illustrates that particular areas of the region corresponding to three areas of white matter tissue (designated W1, W2 and W3), the white matter near the ventricle (VW) and the surface gray matter (SG) tissues of the section identified in FIG. 88A.

FIG. 89A, FIG. 89B, FIG. 89C and FIG. 89D are illustrative of a filament staining of the cerebrum tissues of the primate intrathecally administered iduronate-2-sulfatase (I2S) and respectively correspond to the three areas of the white matter (W1, W2 and W3) and the surface gray matter (SG) regions identified in FIG. 87. FIG. 89A illustrates oligodendrocyte uptake of intrathecally-administered I2S in the white matter (W1) tissues. FIG. 89B and FIG. 89C illustrate oligodendrocyte uptake and axonal association of the intrathecally-administered I2S in the W2 and W3 white matter tissues respectively. FIG. 89D illustrates neuronal uptake of the intrathecally-administered I2 Sin the surface gray matter (SG) tissues.

FIG. 119 is an exemplary illustration showing the concentration of ASA in brain punches of juvenile Cynomolgus monkeys following EOW IT dosing of rhASA1 at 1.8 mg/dose for 6-months (main necropsy).

FIG. 120 is an exemplary illustration showing the concentration of ASA in brain punches of juvenile Cynomolgus monkeys following EOW IT dosing of rhASA1 at 6.0 mg/dose for 6-months (main necropsy).

FIG. 121 is an exemplary illustration showing the concentration of rhASA in brain punches of juvenile cynomolgus monkeys following EOW IT dosing of rhASA1 at 18.6 mg/dose for 6-months (main necropsy).

FIG. 122 is an exemplary illustration showing the concentration of rhASA in brain punches of juvenile cynomolgus monkeys following EOW IT dosing (PBS-control) for 6-months (main necropsy).

FIG. 123 is an exemplary illustration showing the concentration of rhASA in brain punches of juvenile cynomolgus monkeys following EOW IT dosing of vehicle for 6-months (main necropsy).

FIG. 124 is an exemplary illustration showing the concentration of rhASA in brain punches of juvenile cynomolgus 1 monkeys following EOW IT Dosing of rhASA1 at 1.8 mg/dose for 6-months (main necropsy).

FIG. 125 is an exemplary illustration showing the concentration of rhASA in brain punches of juvenile cynomolgus monkeys following EOW IT dosing of rhASA1 at 6.0 mg/dose for 6 months (main necropsy).

FIG. 126 is an exemplary illustration showing the concentration of rhASA in brain punches of juvenile cynomolgus following EOW IT dosing of rhASA1 at 18.6 mg/dose for 6-months (main necropsy).

FIG. 127 is an exemplary illustration showing the concentration of rhASA in selected punches from surface of brain for device control, vehicle, 1.8 mg, 6.0 mg and 18.6 mg treated animals. (male and female separate, device control data is from recovery necropsy, all other data from main necropsy)

FIG. 128 is an exemplary illustration showing the concentration of rhASA in selected punches from deep white area of brain for device control, vehicle, 1.8 mg, 6.0 mg and 18.6 mg treated animals. (male and female separate, device control data is from recovery necropsy, all other data from main necropsy)

FIG. 129 is an exemplary illustration showing the concentration of rhASA in selected punches from deep grey area of brain for device control, vehicle, 1.8 mg, 6.0 mg and 18.6 mg treated animals. (male and female separate, device control data is from recovery necropsy, all other data from main necropsy)

FIG. 130 is an exemplary illustration showing the concentration of rhASA in selected punches from various regions in device control, vehicle, 1.8. mg, 6.0 mg and 18.6 mg treated animals. (male and female combined, device control data is from recovery necropsy, all other data from main necropsy)

Figure 131:
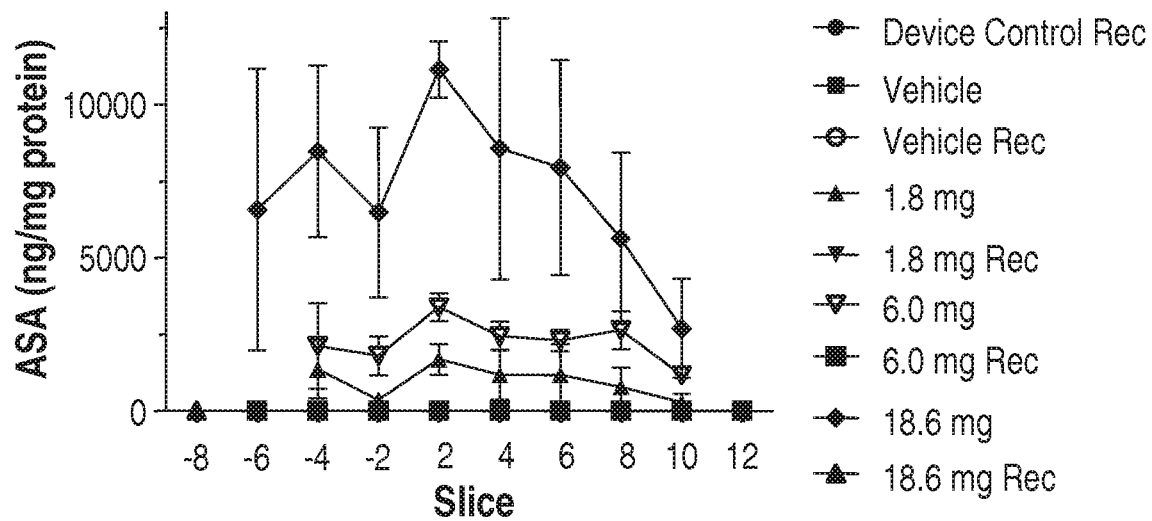
Figure 131:
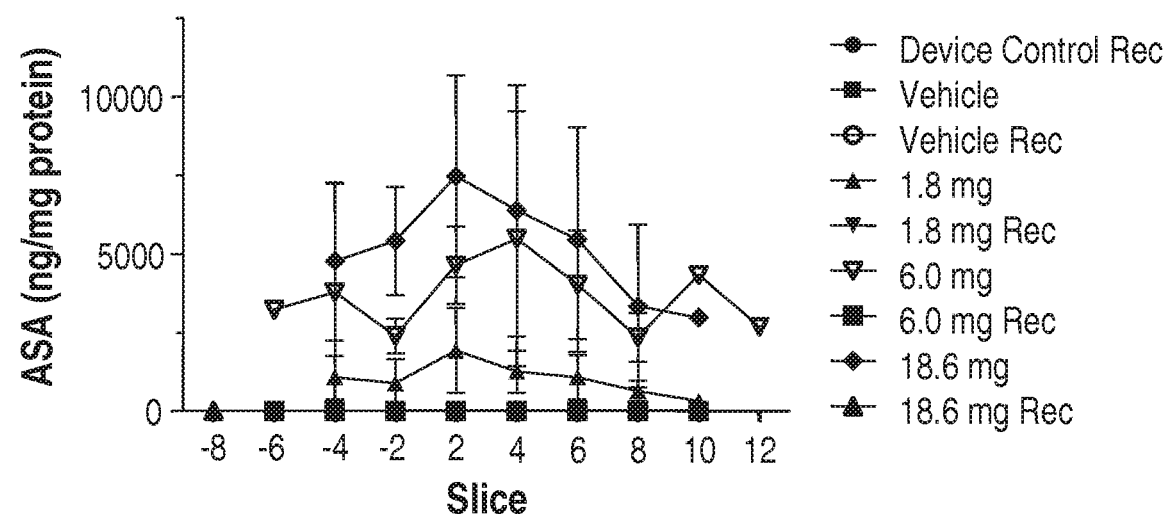

FIG. 131 is an exemplary illustration showing the concentration of rhASA in spinal cord sections of juvenile cynomolgus monkeys following EOW IT dosing for 6-months (recover necropsy).

Figure 132:
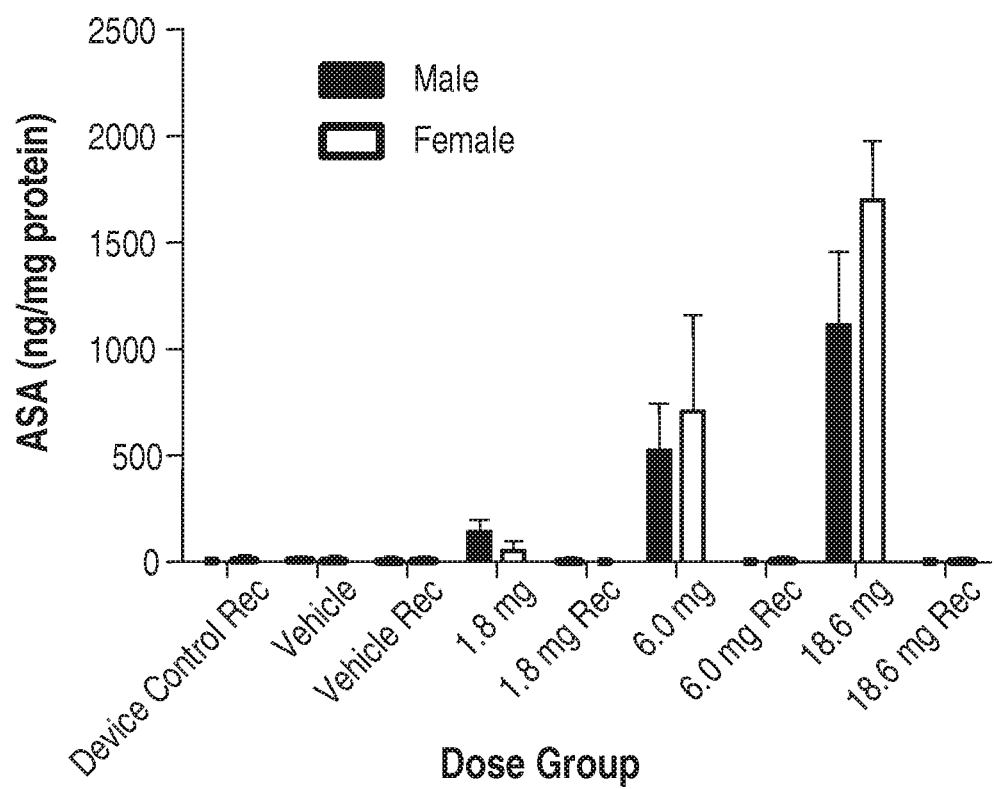

FIG. 132 is an exemplary illustration showing the concentration of rhASA in liver of juvenile cynomolgus monkeys following EOW IT dosing for 6-Months (047-021) (recover necropsy).

Figure 133:
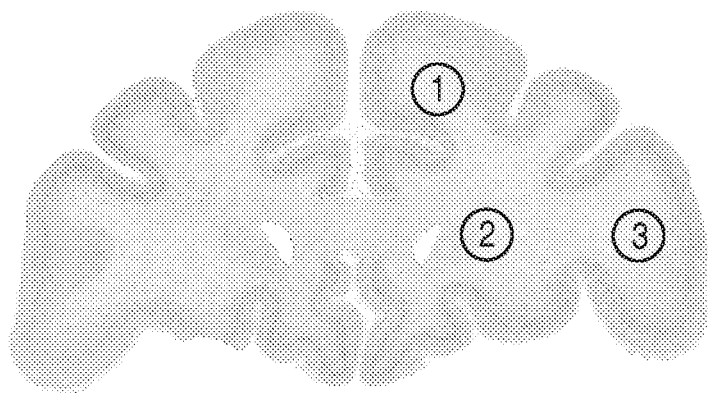

FIG. 133 is an exemplary illustration showing the anatomical locations of brain punches in the subcortical WM, periventricular WM (and deep white matter) and subcortical WM.

Figure 134:
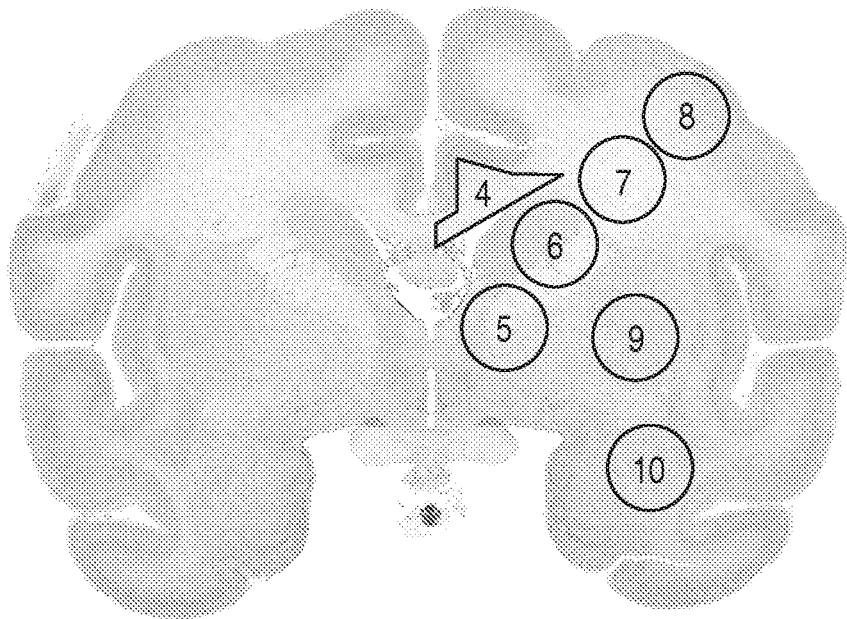

FIG. 134 is an exemplary illustration showing the anatomical locations of brain punches in the corpus callosum and pericallosal subcortical WM, internal capsule—GPi, internal capsule—caudate nucleus, deep white matter, subcortical WM and cortex, putamen, and temporal subcortical WM and cortex.

Figure 135:
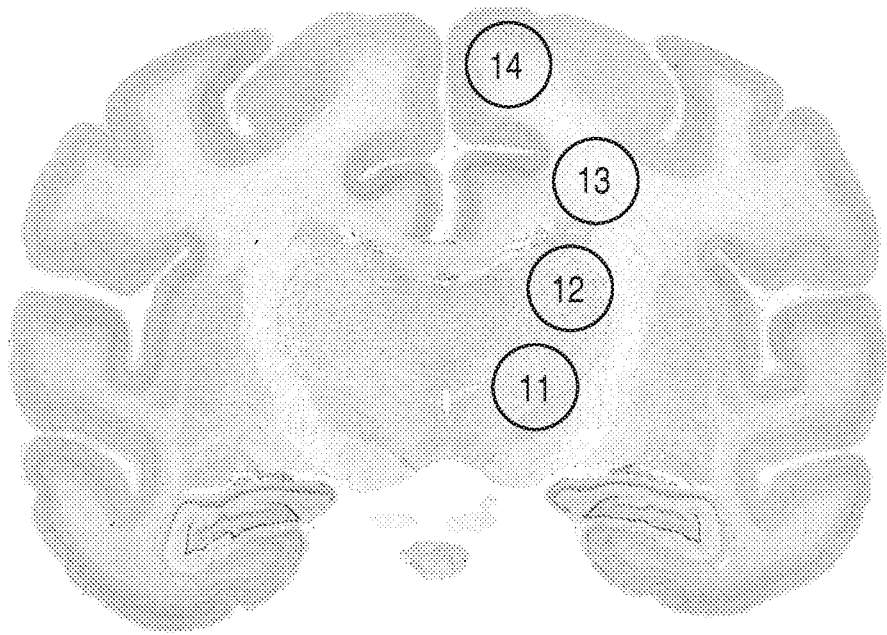

FIG. 135 is an exemplary illustration showing the anatomical locations of brain punches in the deep grey matter, deep WM (frontal periventricular and subcortical), and subcotical white and cortex—superficial sagittal.

Figure 136:
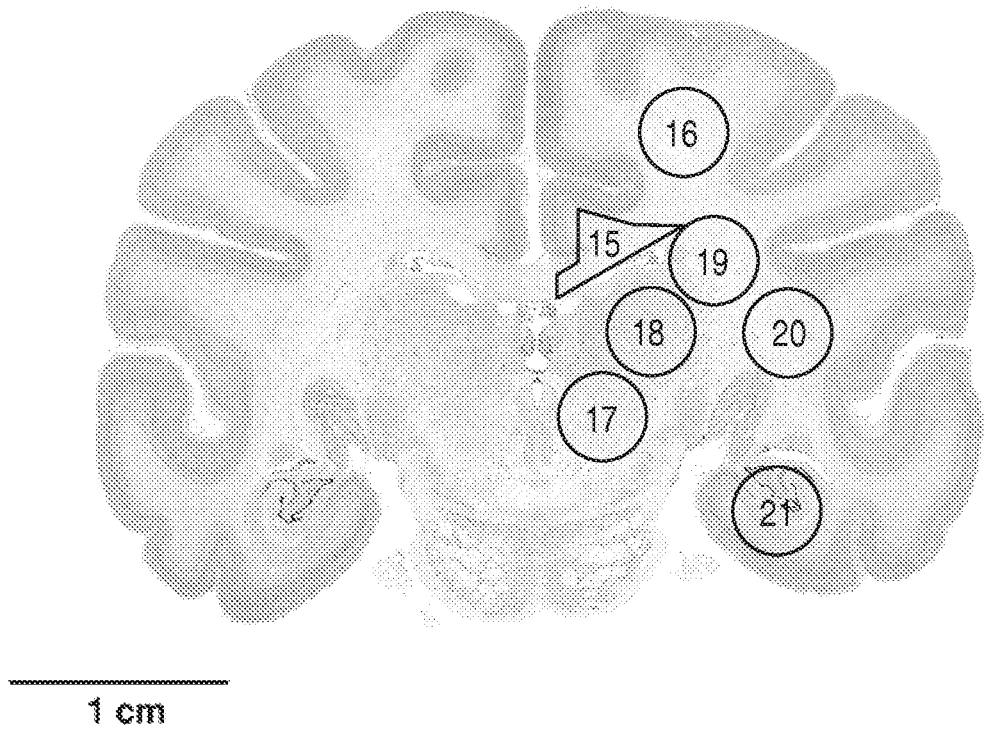

FIG. 136 is an exemplary illustration showing the anatomical locations of brain punches in the corpus callosum and pericallosal subcortical WM, deep subcortical WM, deep grey, periventricular WM, subcortical WM and hippocampus.

Figure 137:
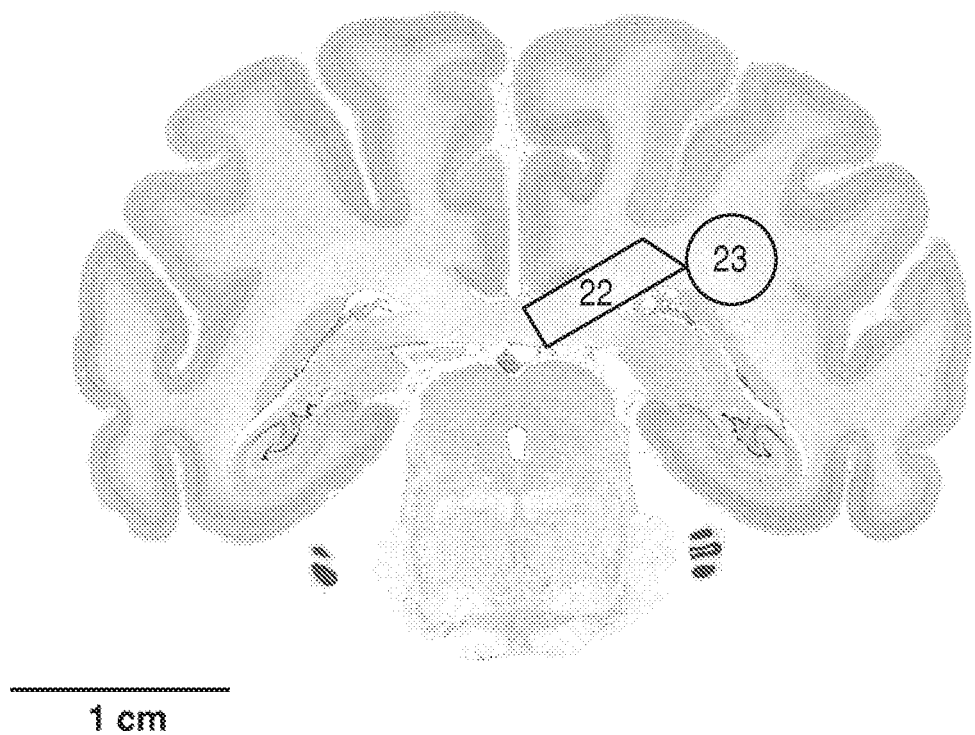

FIG. 137 is an exemplary illustration showing the anatomical locations of brain punches in the corpus callosum and deep WM.

Figure 138:
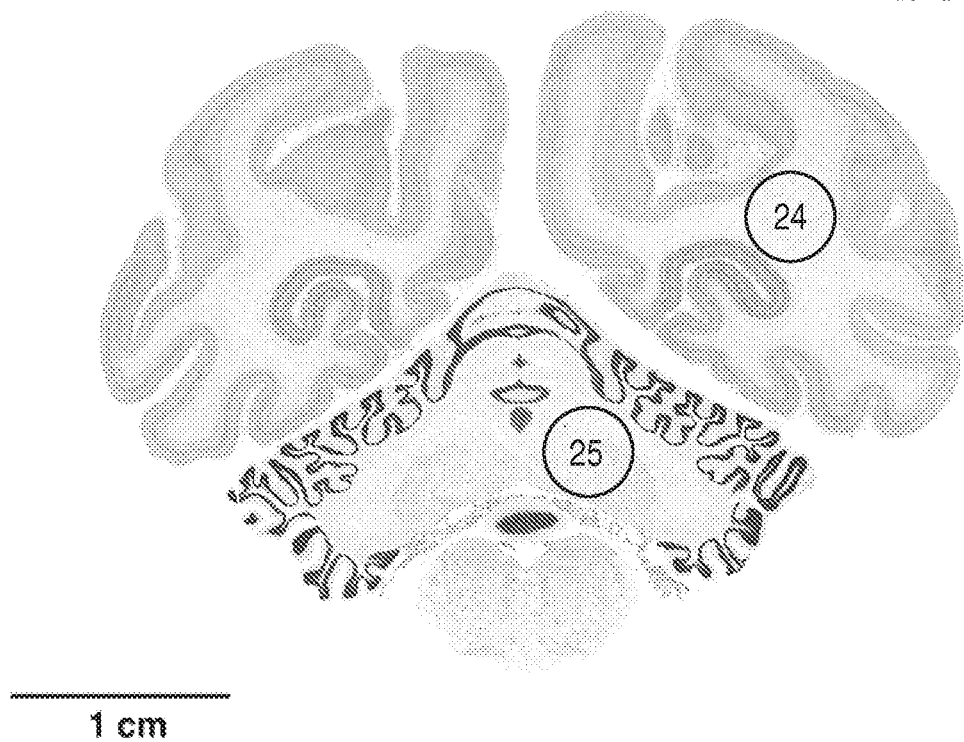
Figure 139A:
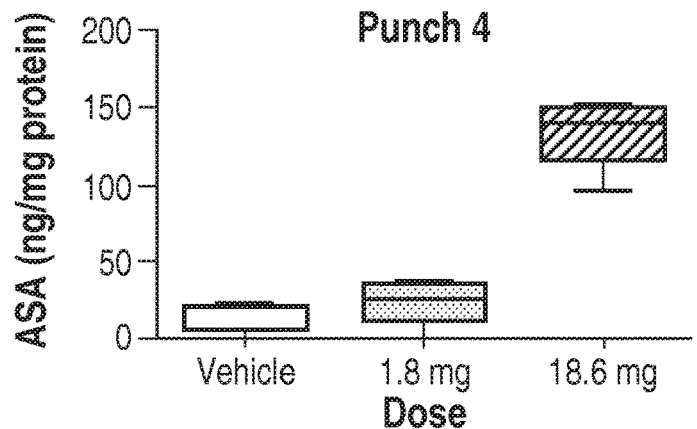
Figure 139B:
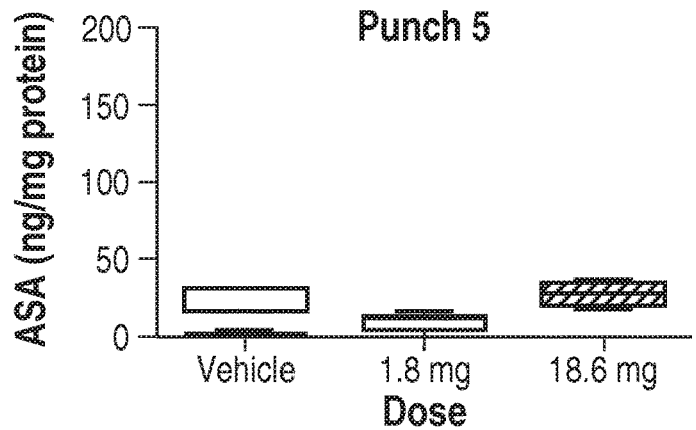
Figure 139C:
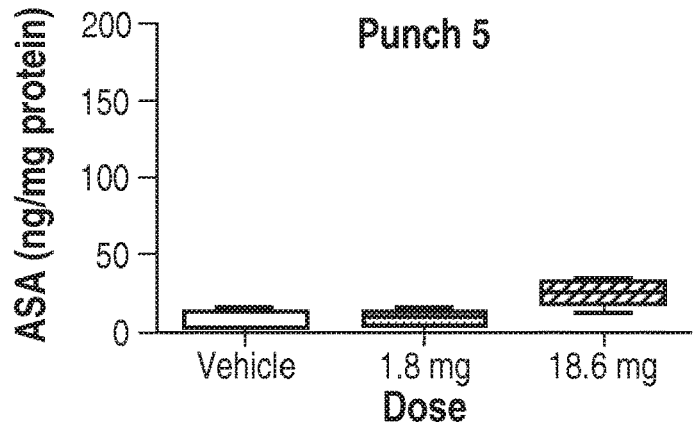
Figure 139D:
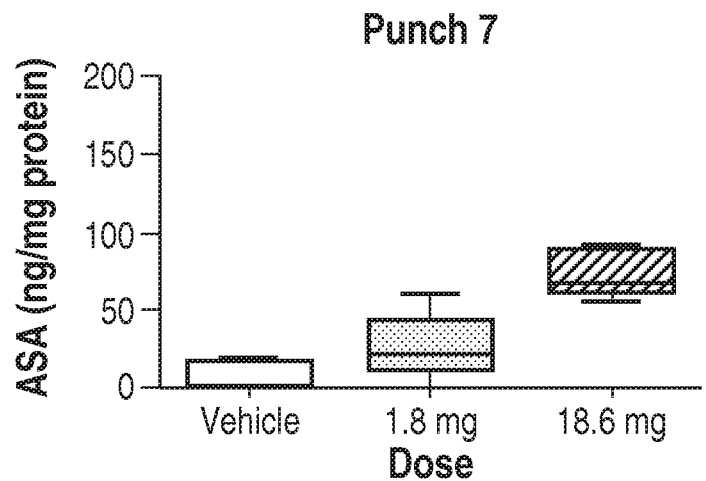
Figure 139E:
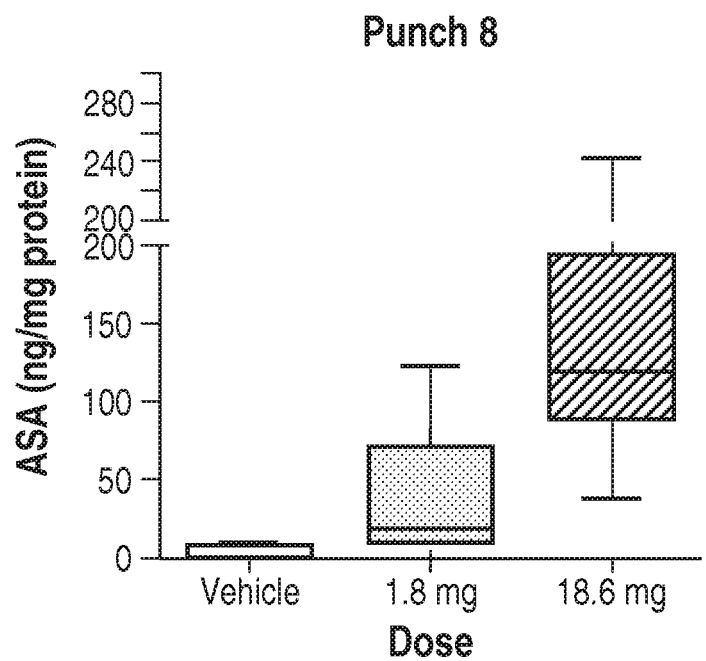
Figure 139F:
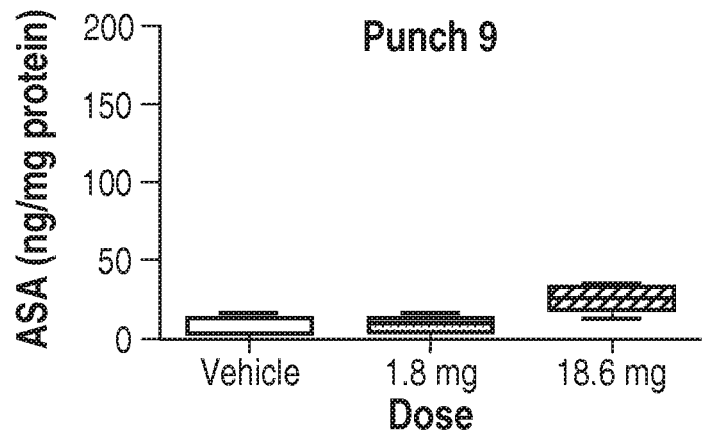
Figure 139G:
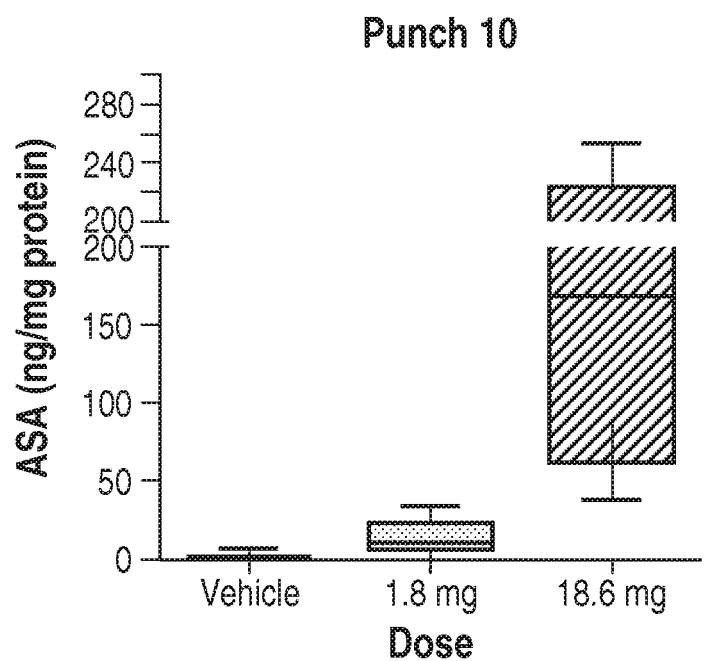

FIG. 138 is an exemplary illustration showing the anatomical locations of brain punches in the subcortical WM—occipital lobe and cerebellar white matte, including dentate nucleus (WM).

FIG. 139A-G illustrate the concentration of recombinant human arylsulfatase A (ASA) in extracted tissue punches from the brain tissues of adult and juvenile cynomolgus monkeys administered either a vehicle, 1.8 mg rhASA or 18.6 mg rhASA. Each of FIG. 139A-G corresponds to a region of the brain tissue depicted in FIG. 134.

Figure 140A:
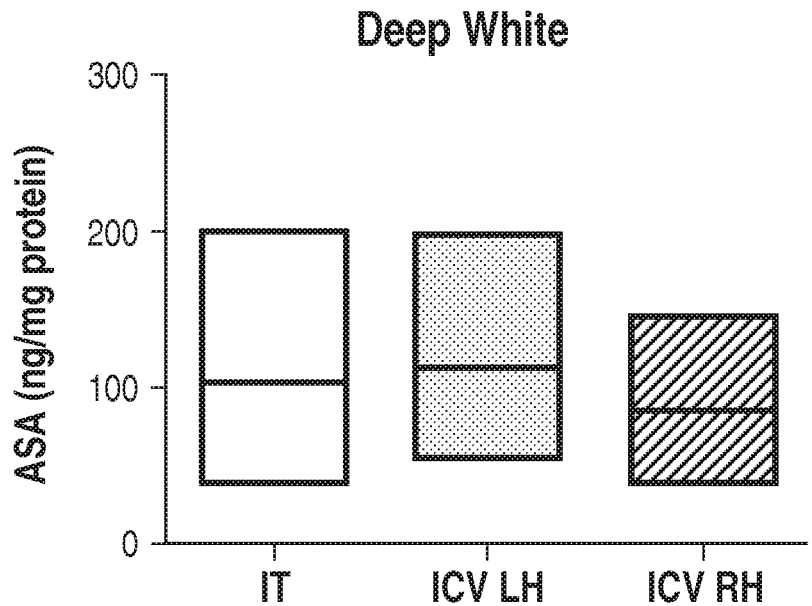
Figure 140B:
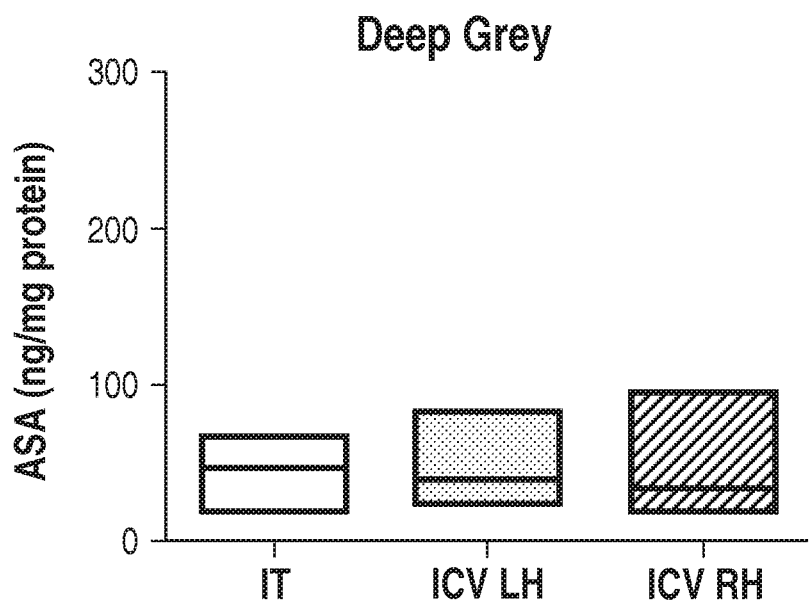

FIG. 140A and FIG. 140B is an exemplary illustration showing the comparison of the concentrations of recombinant human arylsulfatase A (ASA) detected in the deep white matter (FIG. 140A) or in the deep grey matter FIG. 140B) brain tissues of adult and juvenile cynomolgus monkeys which were intrathecally (IT) or intracerebroventricularly (ICV) administered rhASA.

Figure 141A:
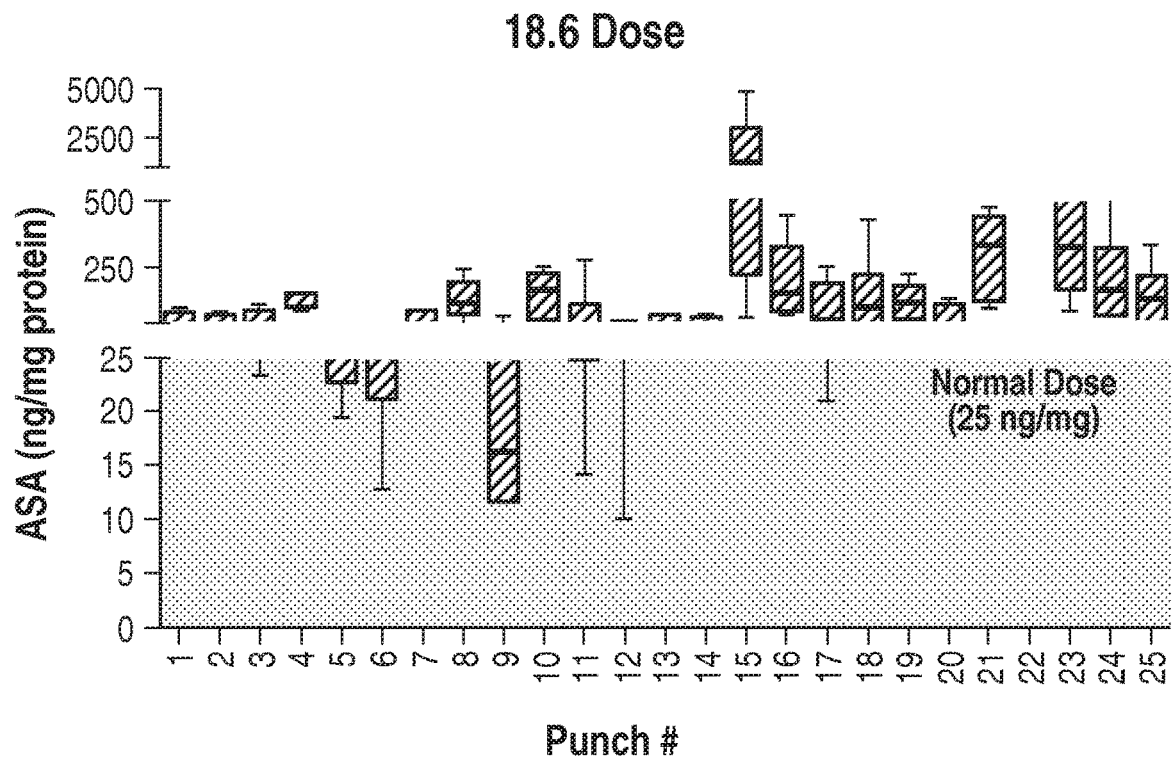
Figure 141B:
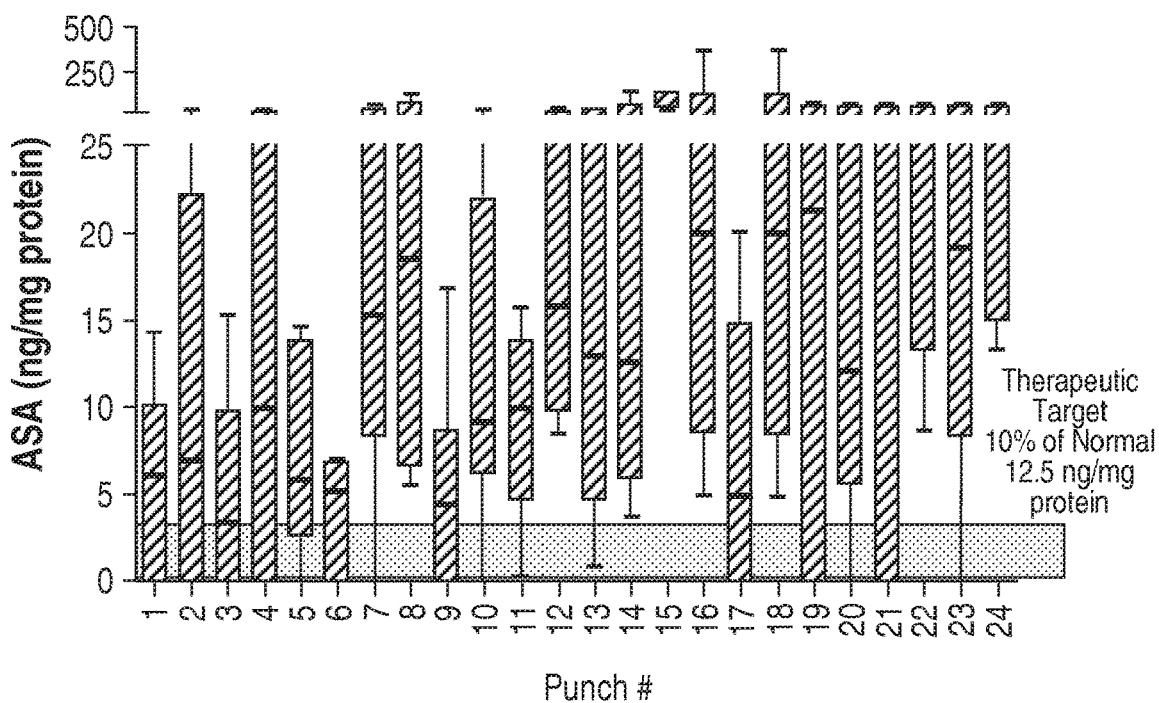

FIG. 141A is an exemplary illustration showing the concentrations of ASA detected in several tissue punches obtained from juvenile (<12 months of age) cynomolgus monkeys IT-administered an 18.6 or a 1.8 mg dose of recombinant human arylsulfatase A (rhASA). As illustrated in both FIG. 141A-B, the concentration of ASA delivered to the tissues were within, or otherwise exceeded the target therapeutic concentration of 2.5 ng/mg rhASA. The anatomical regions of brain tissue which correspond to each of the punch numbers depicted in FIG. 141A and FIG. 141B are the: subcortical white matter (1); periventricular white matter and deep white matter (2); subcortical white matter (3); subcortical white matter (4); internal capsule (5); internal capsule caudate nucleus (6); deep white matter (7); subcortical white matter and cortex (8); putamen (9); temporal subcortical white matter and cortex (10), deep grey matter (11), deep grey matter (12), frontal periventricular & subcortical (13); subcortical white matter, cortex superficial perifalxian (14); corpus callosum and pericallosal subcortical white matter (15); deep subcortical white matter (16); deep grey matter (17); deep grey matter (18); periventricular white matter (19); deep subcortical white matter (20); hippocampus (21); corpus callosum (22); deep white matter (23); subcortical white matter, occipital lobe (24); and cerebellar white matter (25).

Figure 142A:
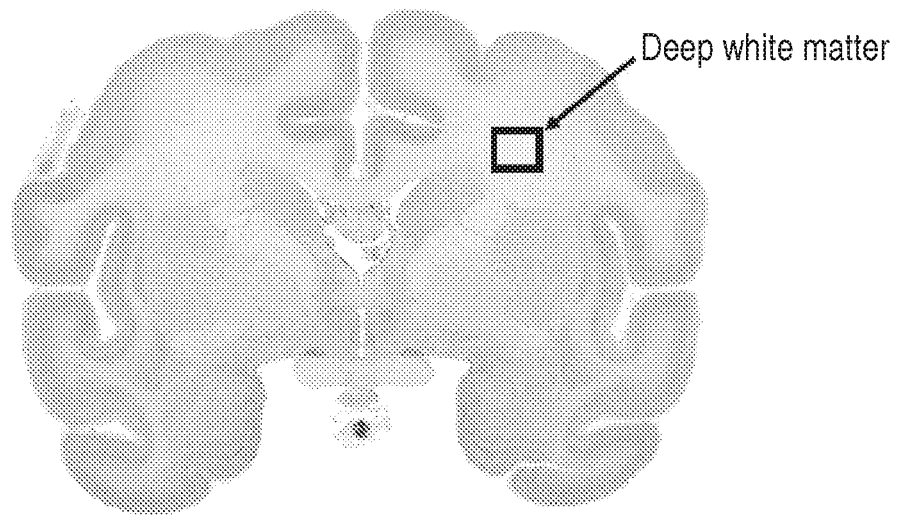
Figure 142B:
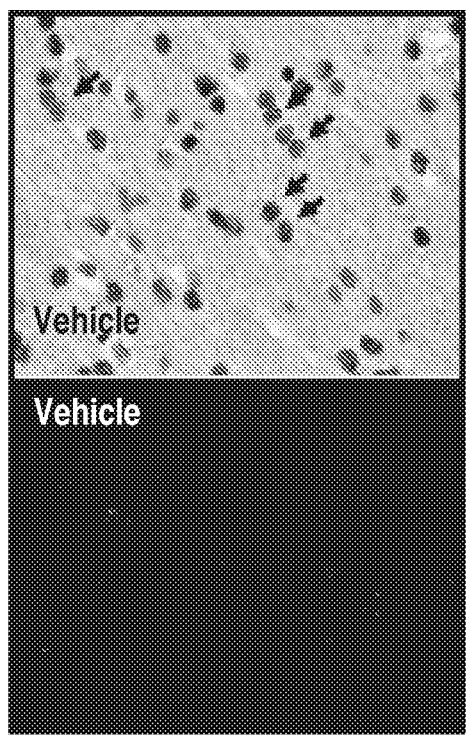
Figure 142B:
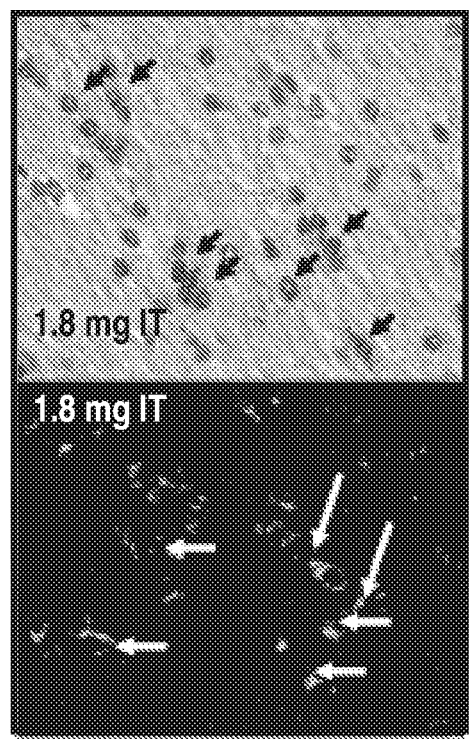
Figure 142C:
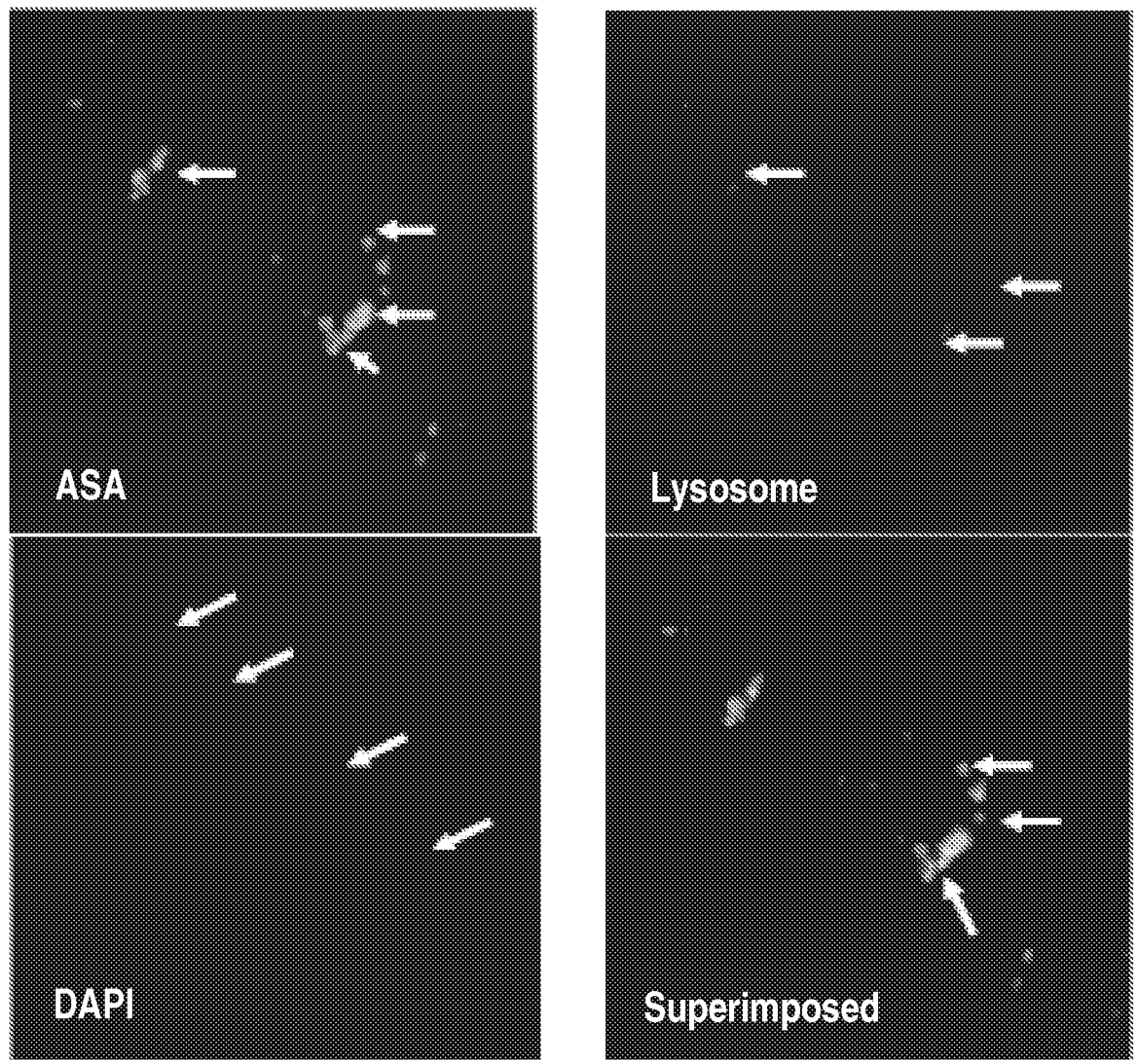

FIG. 142A illustrates the area of deep white matter tissue extracted from a cynomolgus monkey IT-administered 1.8 mg of ASA. FIG. 142B illustrates immunostaining of the deep white matter tissue and distribution of ASA in relevant cells. In FIG. 142B, the protein (ASA) is illustrated in the right bottom box. FIG. 142C illustrates that the IT-administered ASA showed organelle co-localization in the deep white matter tissues of the cynomolgus monkey and in particular in the lysosomes. In FIG. 142C, the ASA immunostaining is illustrated in the top left box.

Figure 143:
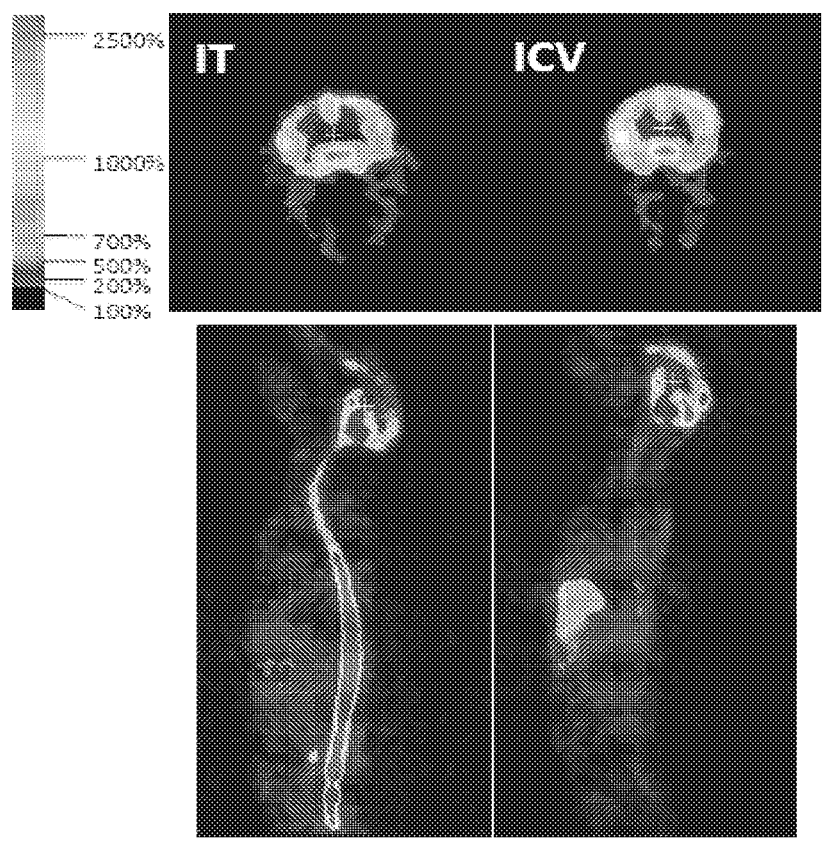

FIG. 143 compares the distribution of $^{124}$I-labeled arylsulfatase A (ASA) using PET scanning 24 hours following either IT- or ICV-administration of such labeled ASA to a cynomolgus monkey.

Figure 144:
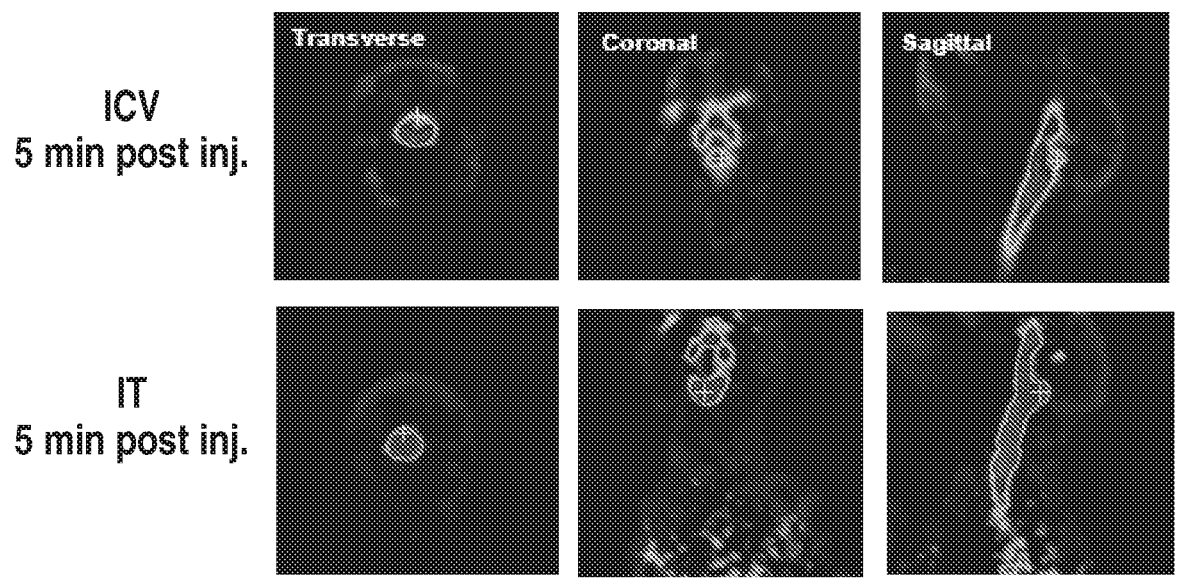

FIG. 144 illustrates the distribution of $^{124}$I-labeled ASA immediately following ICV administration to a cynomolgus monkey, and compares the distribution of IT-administered $^{124}$I-labeled ASA within 2-5 hours. As demonstrated, IT administration delivered the $^{124}$I-labeled ASA to the same initial compartments (cisternae and proximal spine) as that shown for the ICV administration.

Figure 145:
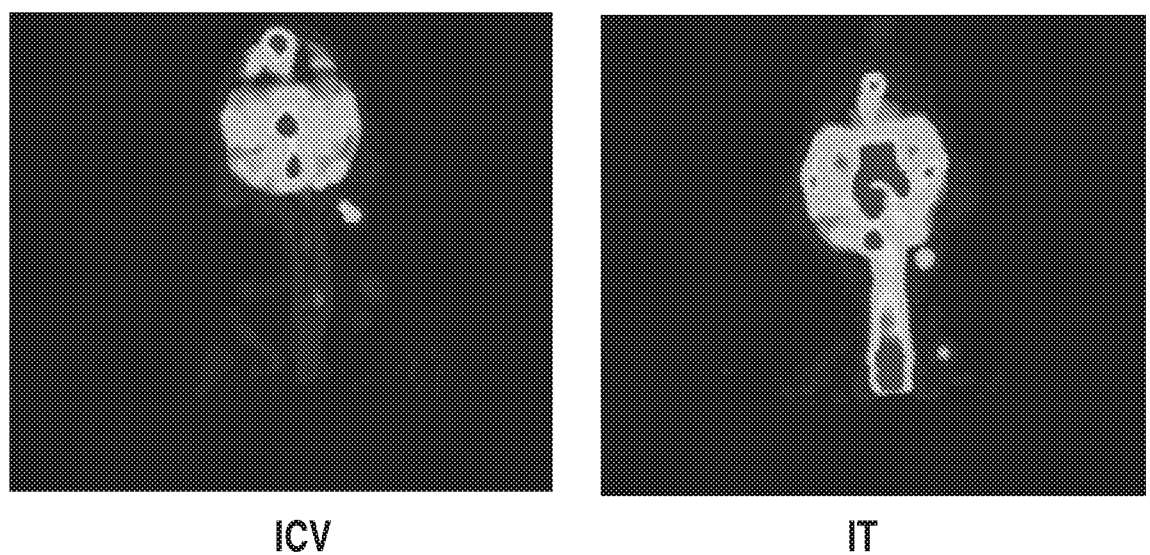

FIG. 145 depicts exemplary ICV and IT administration in a mouse model.

Figure 146A:
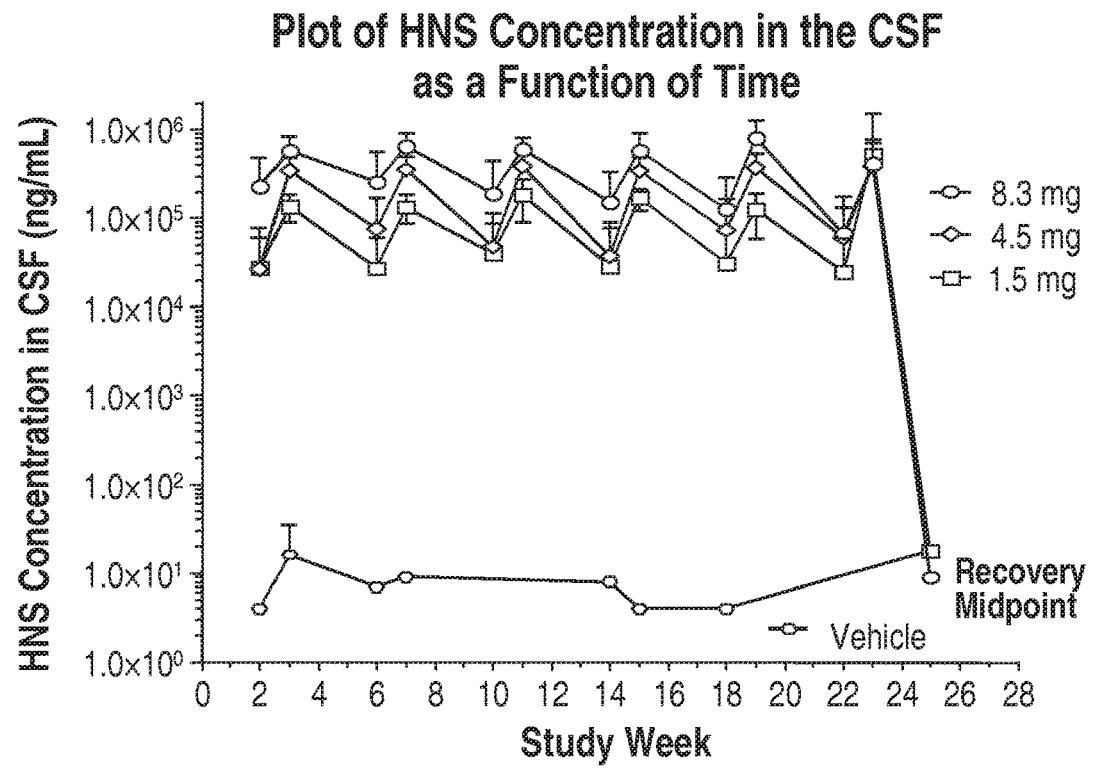
Figure 146B:
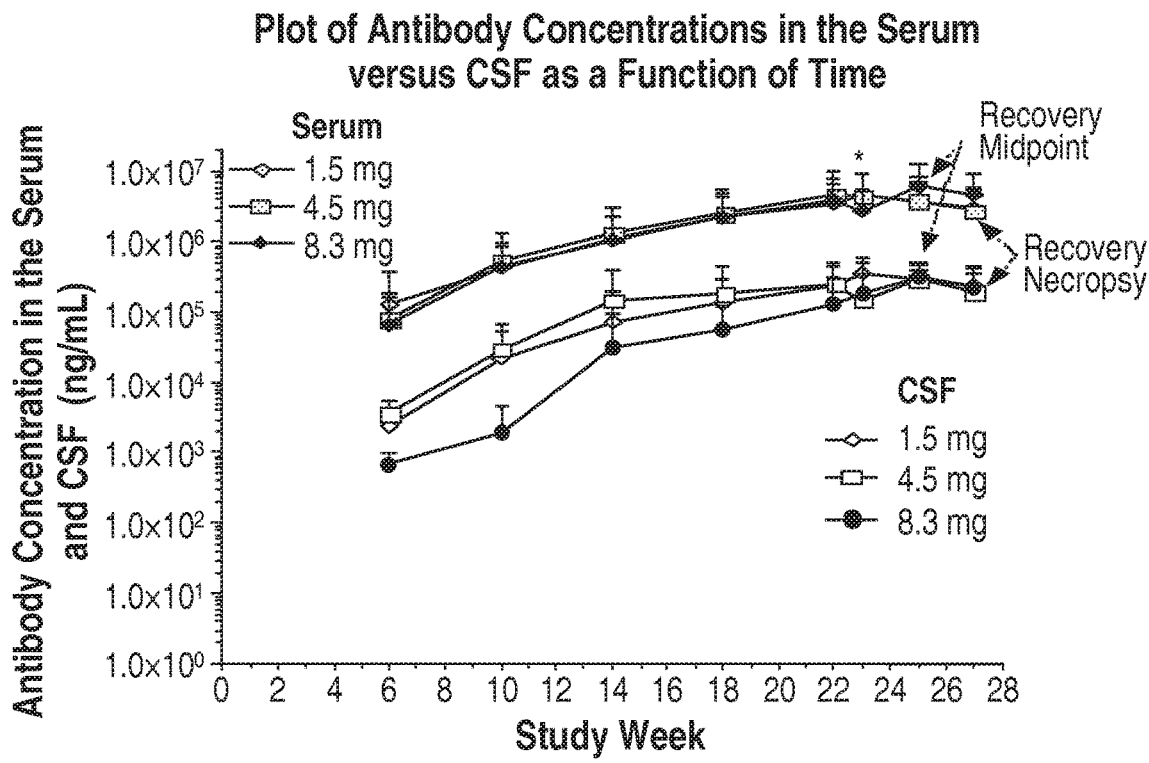
Figure 146C:
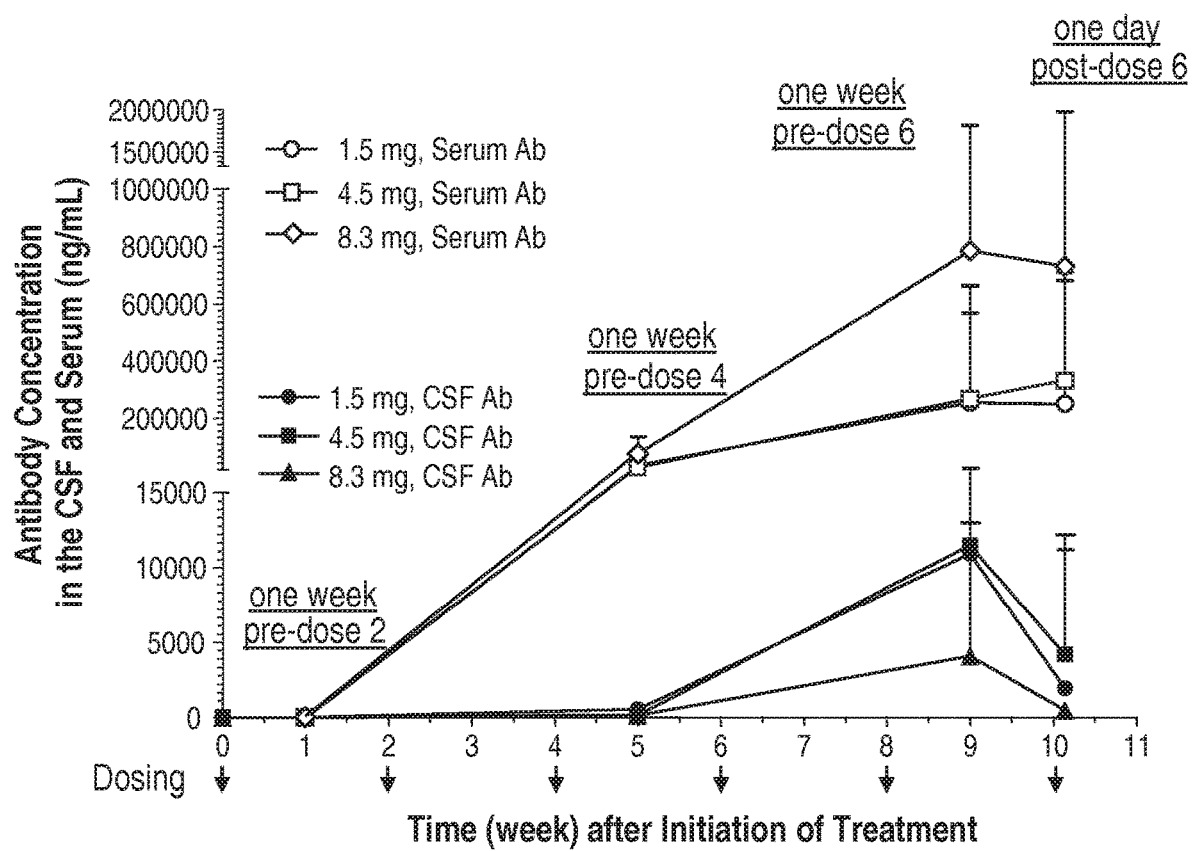

FIG. 146A depicts an exemplary result illustrating CSF concentrations of HNS as a function of time at 1.5, 4.5 and 8.3 mg doses following 6 months of dosing. FIG. 146B details an exemplary result illustrating Anti-FINS antibody concentrations in the CSF after 6 months of IT administration of 1.5, 4.5 and 8.3 mg doses in monkeys. Data are shown for male and females combined. FIG. 146C details an exemplary result illustrating Anti-HNS antibody concentrations in the CSF after 6 months of IT administration of 1.5, 4.5 and 8.3 mg doses in monkeys following 6 months of dosing. Data are shown for male and females combined. The two highest concentrations (32,205 ng/mL and 15,467 ng/mL) post IT dose 6 at 8.3 mg of HNS were excluded from the plot because no CSF samples were taken predose 6.

Figure 147A:
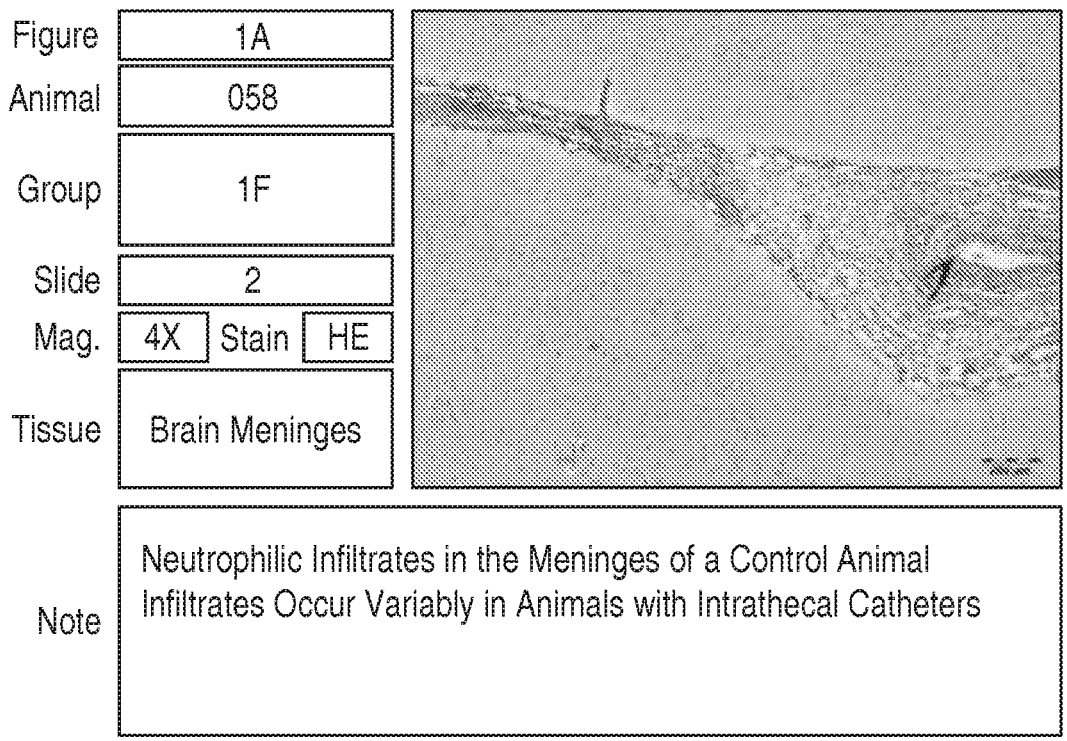
Figure 147B:
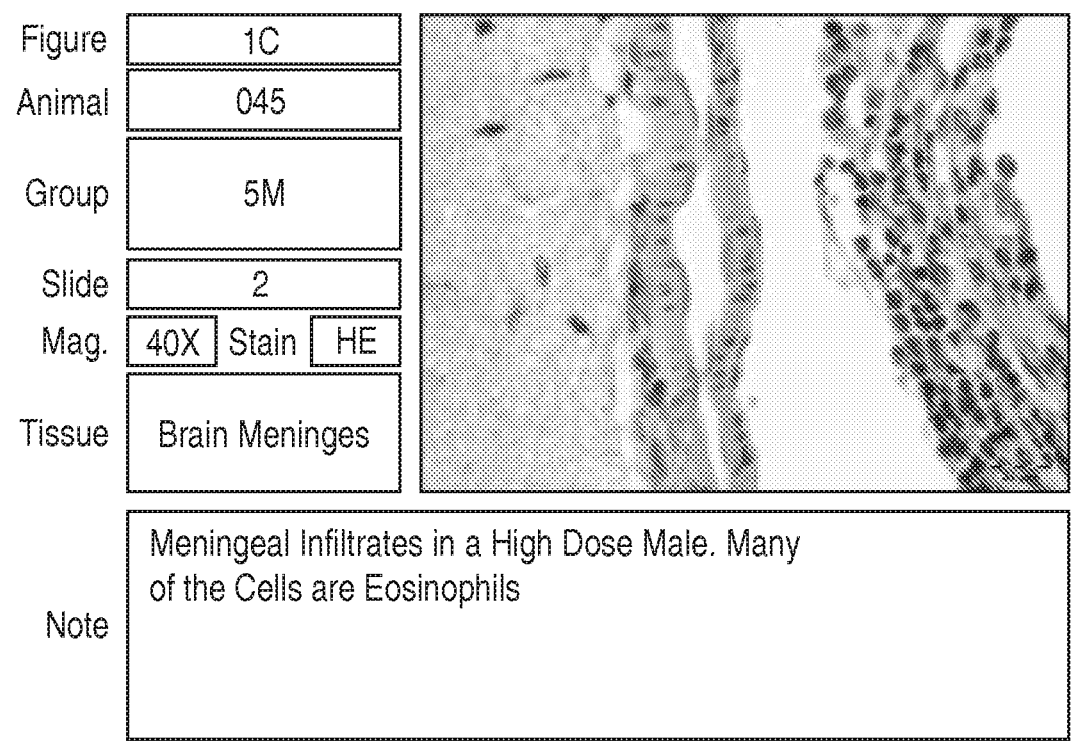
Figure 147C:
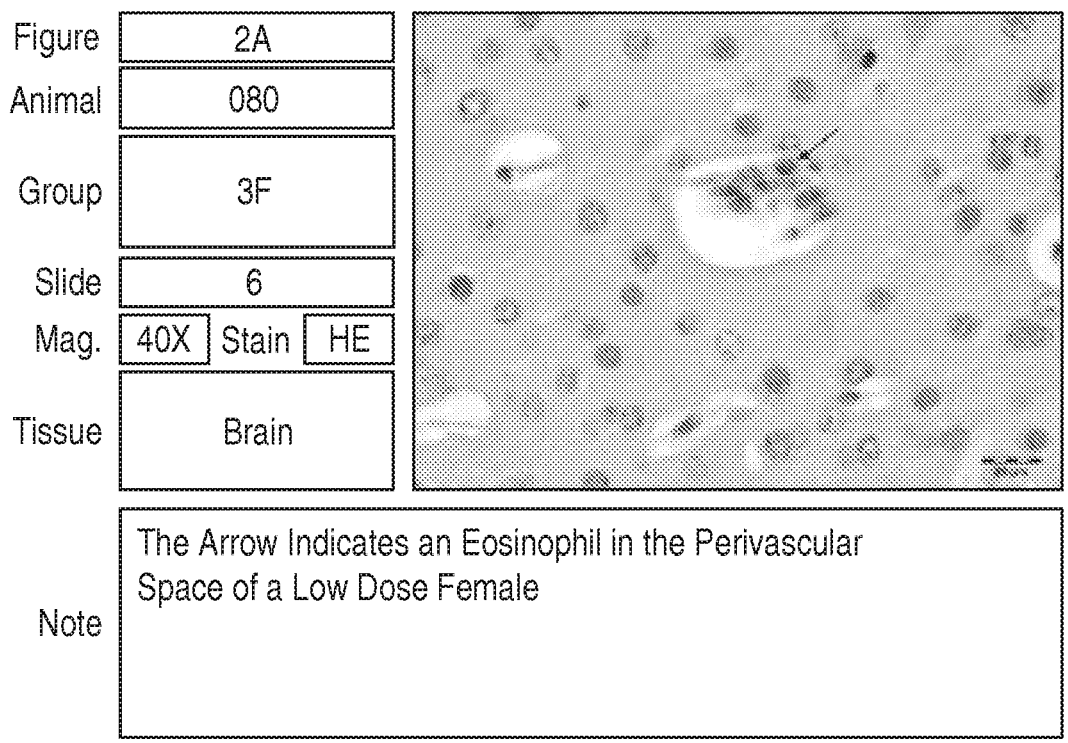
Figure 147D:
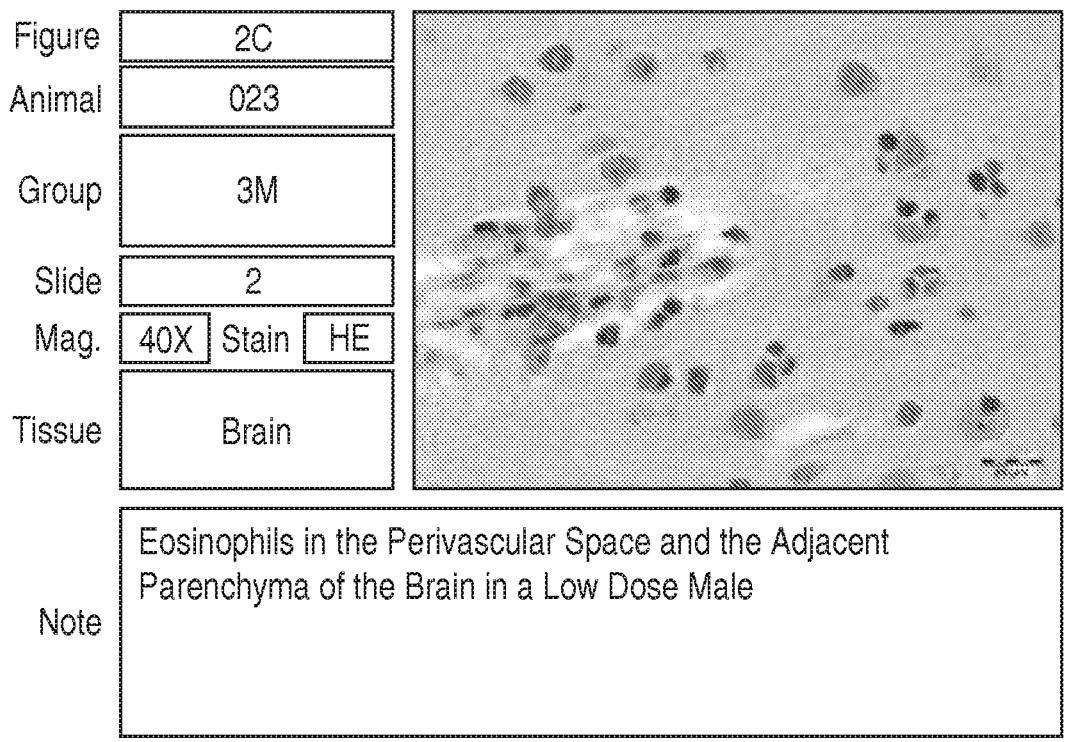
Figure 147E:
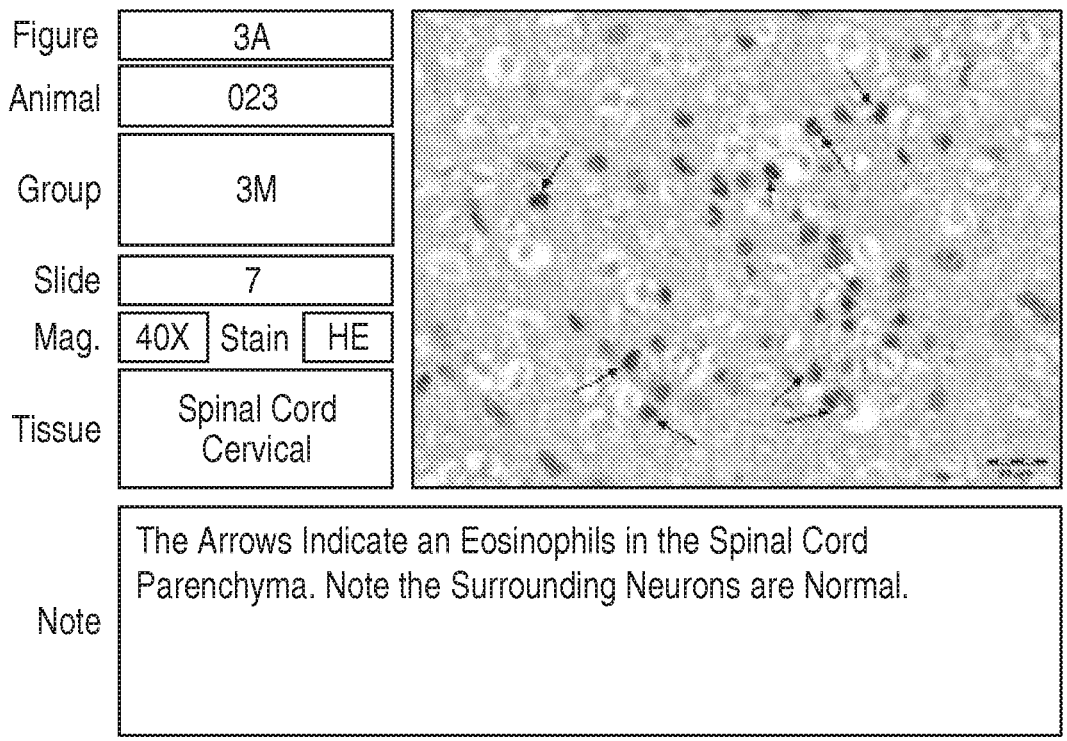
Figure 147F:
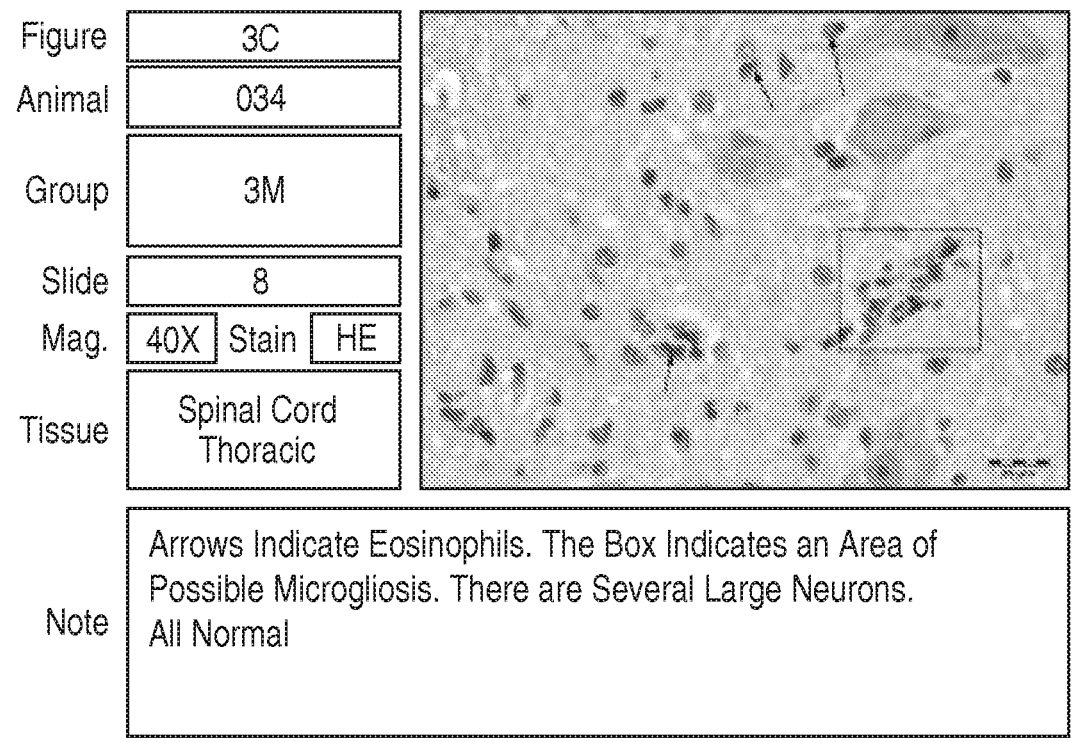

FIG. 147A-F depicts an exemplary result illustrating representative images of tissue sections from the meninges and parenchyma of the brain stained with hematoxylin and eosin. FIG. 147A depicts an exemplary result illustrating a low-power view of neutrophilic infiltrates local to the IT catheter in a DC monkey. FIG. 147B depicts an exemplary result illustrating a high-power view of eosinophilic infiltrates in the meninges of a high-dose (8.3 mg/dose) monkey; the overall severity of infiltrates was similar to the mid-dose (4.5 mg/dose) group (not shown). FIG. 147C depicts an exemplary result illustrating a high-power view of a low-dose (1.5 mg/dose) monkey showing eosinophils in the perivascular space (brain parenchyma). FIG. 147D depicts an exemplary result illustrating a low-dose monkey (1.5 mg/dose) showing eosinophils in the perivascular space and adjoining parenchyma. FIG. 147E depicts an exemplary result illustrating eosinophils in the spinal cord parenchyma (indicated by arrows) of a low-dose group animal; neurons in the area are normal. FIG. 147F depicts an exemplary result illustrating eosinophils and an area of microgliosis (arrows indicate eosinophils; the box indicates an area of microgliosis) in a low-dose (1.5 mg/dose) monkey. There are several large neurons in the area, all of which are normal. Scale bars: 200 um.

Figure 148A:
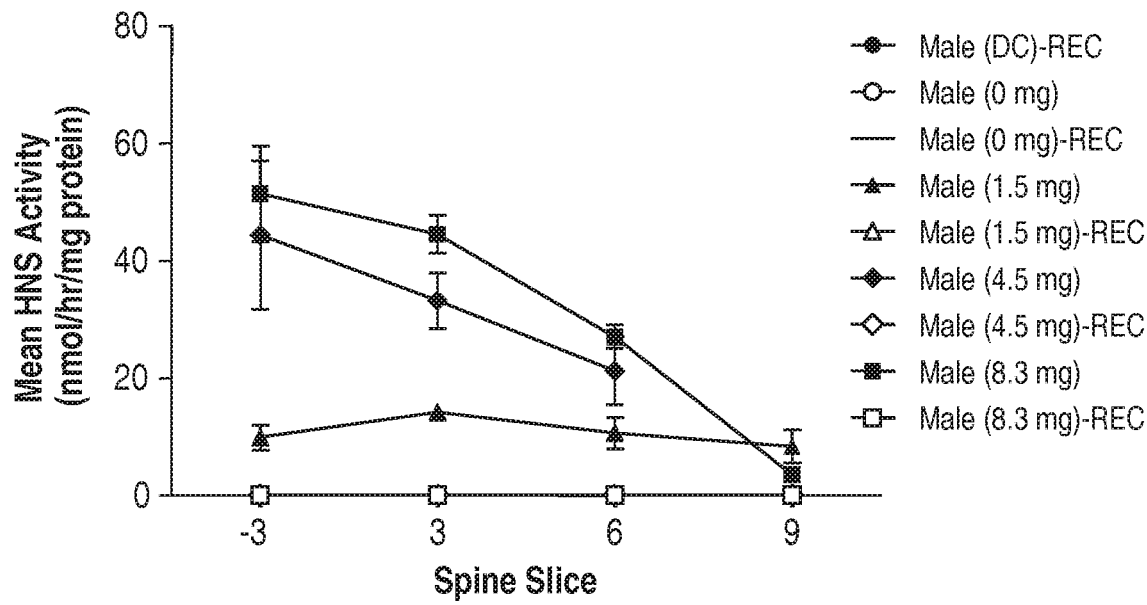
Figure 148B:
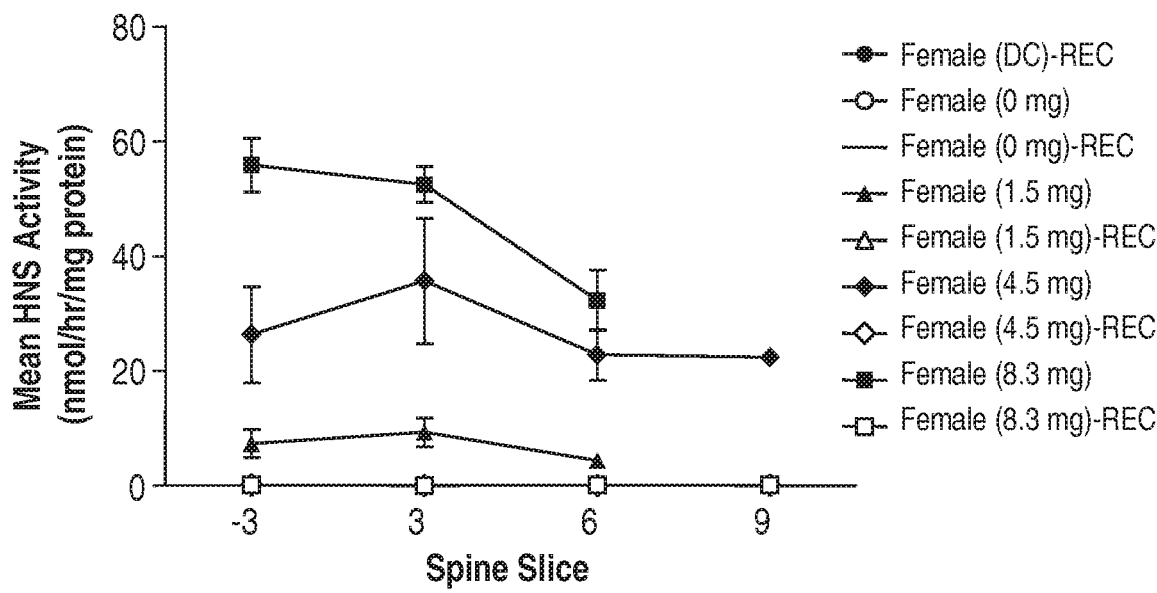
Figure 148C:
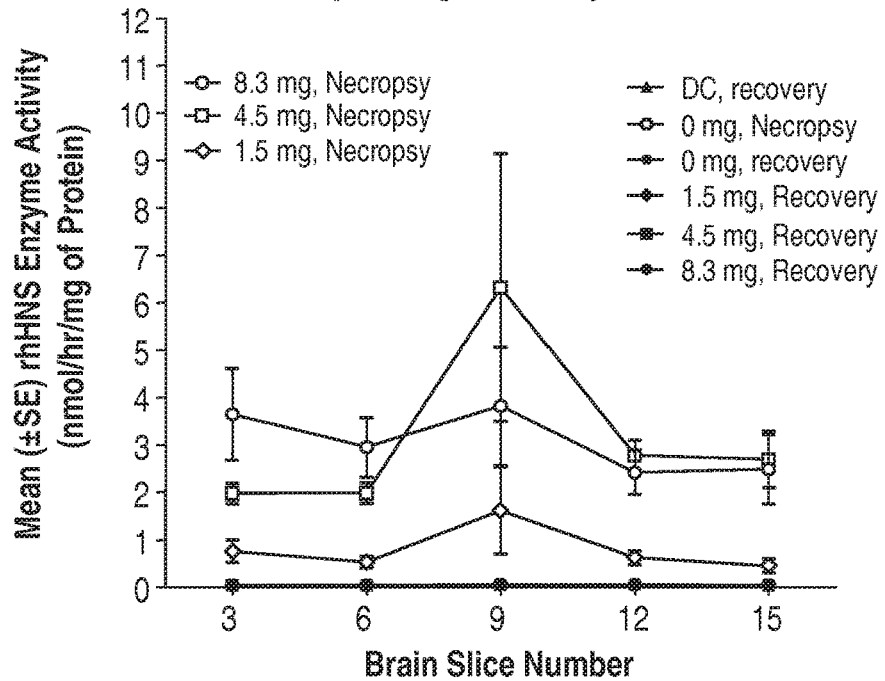
Figure 148D:
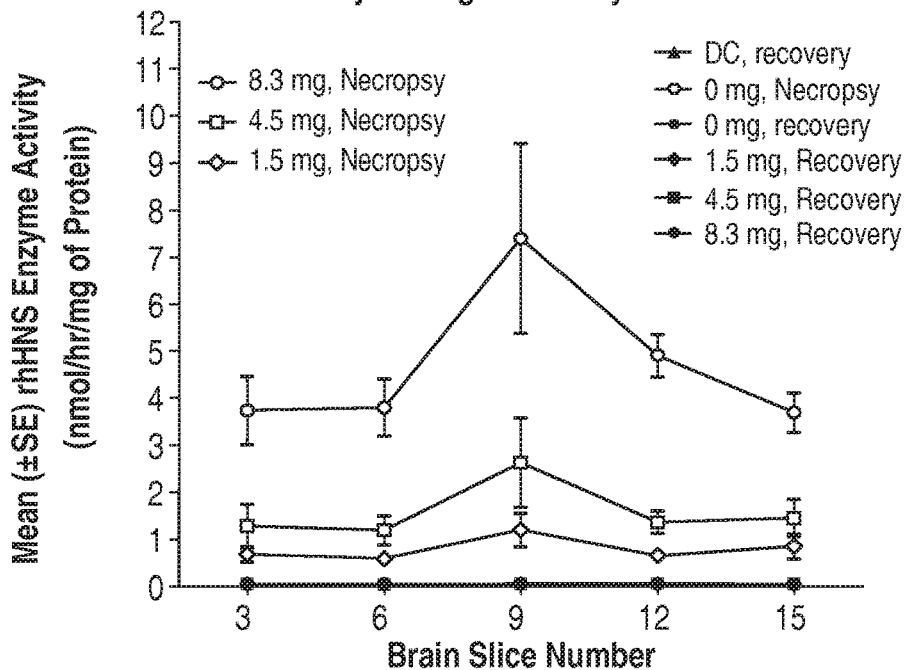

FIG. 148A-D depicts an exemplary result illustrating HNS enzyme activity in monkey spinal cords and brains. FIG. 148A/B depicts an exemplary result illustrating activity in the spinal cords of (A) male and (B) female monkeys. Slice −3=lumbar, slices 3, 6=thoracic, and slice 9=cervical; 0=catheter tip. FIG. 148C/D depicts an exemplary result illustrating FINS activity in the brains of (C) male and (D) female monkeys. Slices are numbered rostral to caudal (3 to 15). All tissue samples were collected approximately 24 hours after the last dose or 4 weeks after the last dose for the recovery animals. DC, device control. The data represent mean±SEM for n=4 monkeys per treatment group.

Figure 149A:
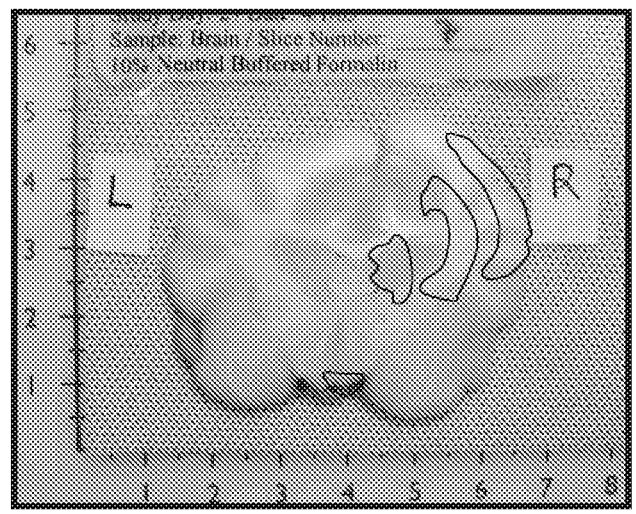
Figure 149A:
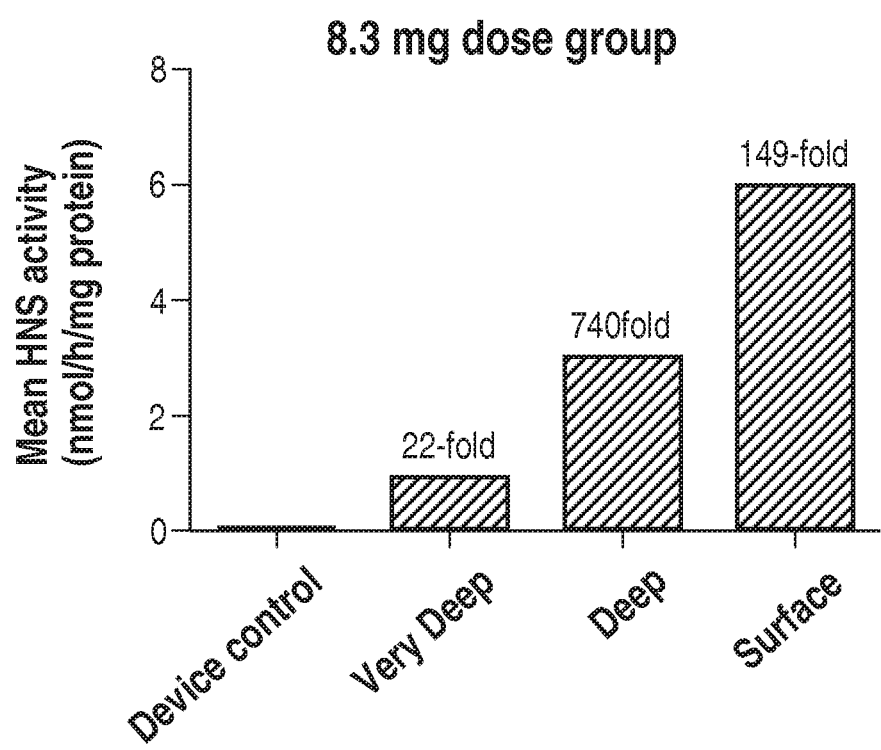
Figure 149B:
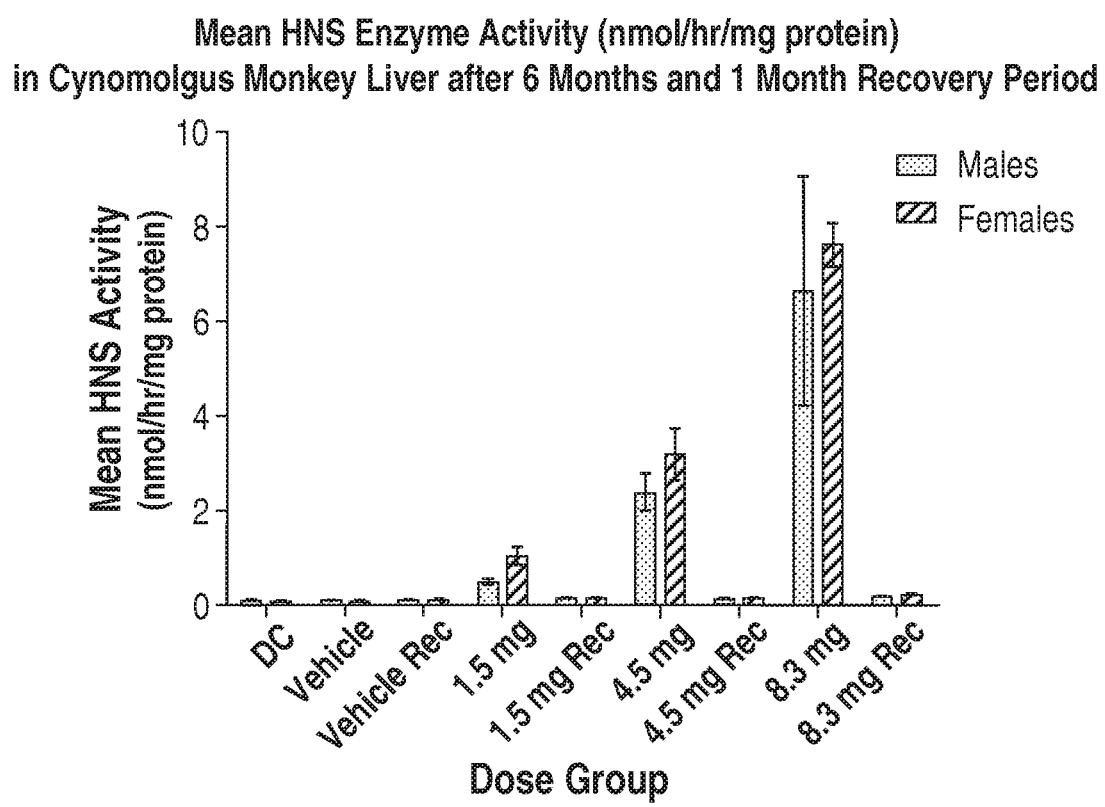

FIG. 149A and FIG. 149B depicts an exemplary result illustrating enzyme activity in monkey brain and liver. FIG. 149A depicts an exemplary result illustrating HNS activity distribution in the high-dose (8.3 mg/dose) group monkey brain. The fold-change in activity for surface, deep, and very deep (periventricular) areas of the brain compared with endogenous levels (DC group) is shown. All tissue samples were collected approximately 24 hours after the last dose or 4 weeks after the last dose for the recovery animals. The data represent mean±SEM for n=6 monkeys (both sexes), brain slices 6 and 9. Data for two monkeys were not included; at necropsy the catheters were not found to be patent. FIG. 149B shows HNS activity in monkey liver. All tissue samples were collected approximately 24 hours after the last dose or 4 weeks after the last dose for the recovery animals. DC, device control. Rec, recovery. The data represent mean±SEM for n=4 monkeys per treatment group except for the low-dose (4.5 mg/dose) female group (n=3).

Figure 150A:
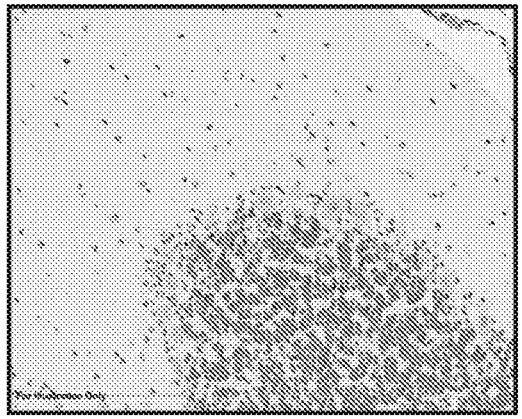
Figure 150B:
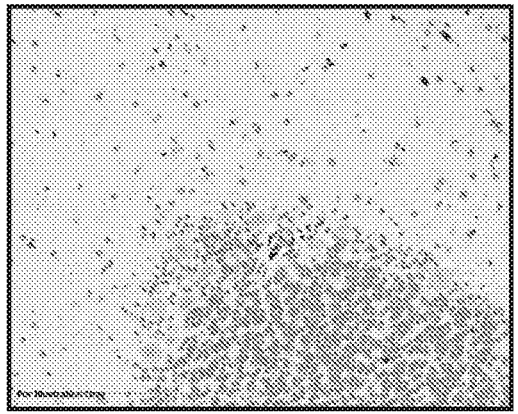
Figure 150C:
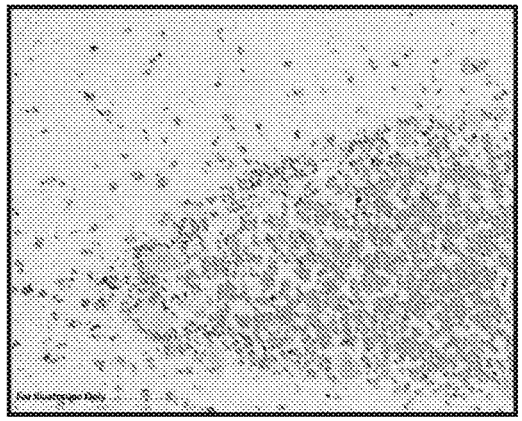
Figure 150D:
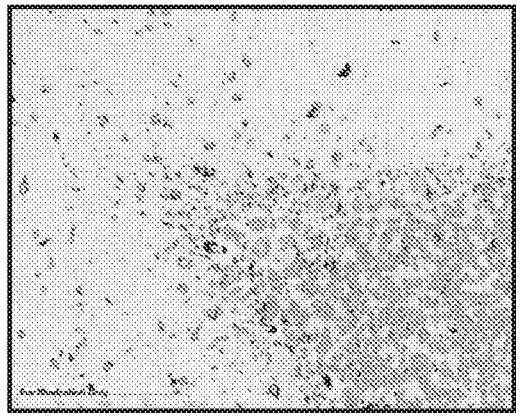

FIG. 150A-D depicts an exemplary result illustrating HNS localization in juvenile cynomolgus monkey cerebellum: 3-month interim cohort. FIG. 150A depicts an exemplary result illustrating cerebellum of a vehicle control animal (0 mg/dose) negative for HNS immunostaining; 20× magnification. FIG. 150B depicts an exemplary result illustrating cerebellum of a low-dose (1.5 mg/dose) animal showing minimal positive staining limited to the molecular layer; 20× magnification. FIG. 150C depicts an exemplary result illustrating cerebellum of a mid-dose (4.5 mg/dose) animal showing minimal staining in the outer granular layer; 20× magnification. FIG. 150D depicts an exemplary result illustrating moderate staining in the cerebellum of a high-dose (8.3 mg/dose) animal including molecular, outer granular layer, and Purkinje cells; 20× magnification.

Figure 151:
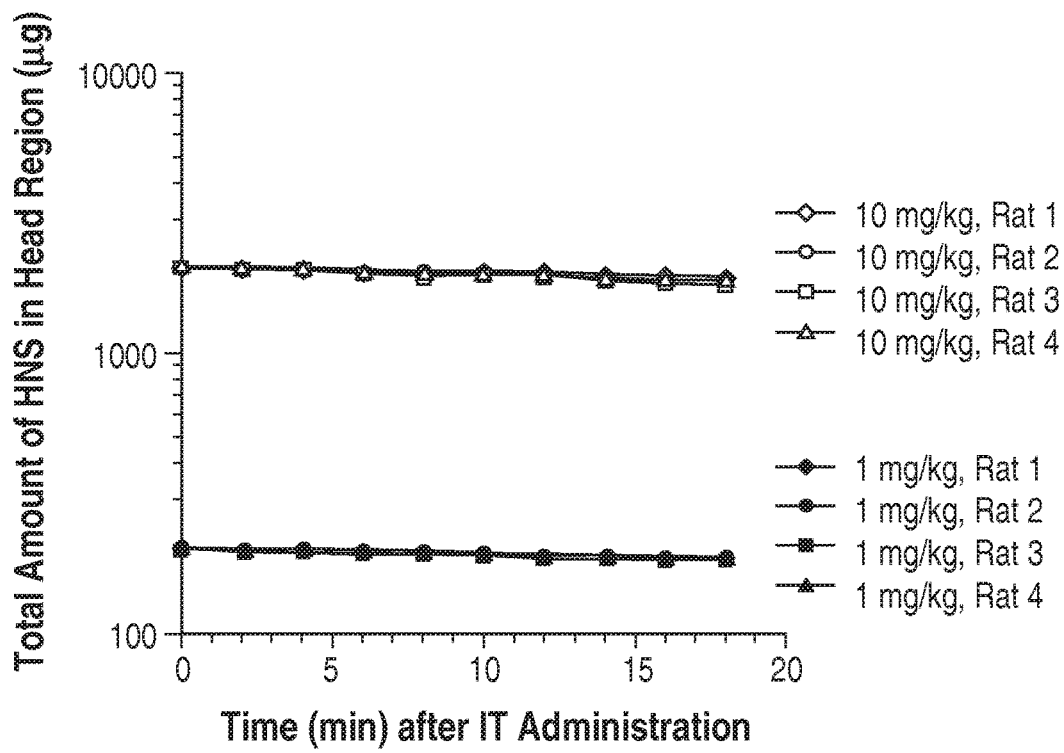

FIG. 151 depicts an exemplary study of the concentration of HNS in the head region plotted with time in the first 20 minutes after IT dosing of $^{124}$I-FINS at 1 and 10 mg/kg.

Figure 152:
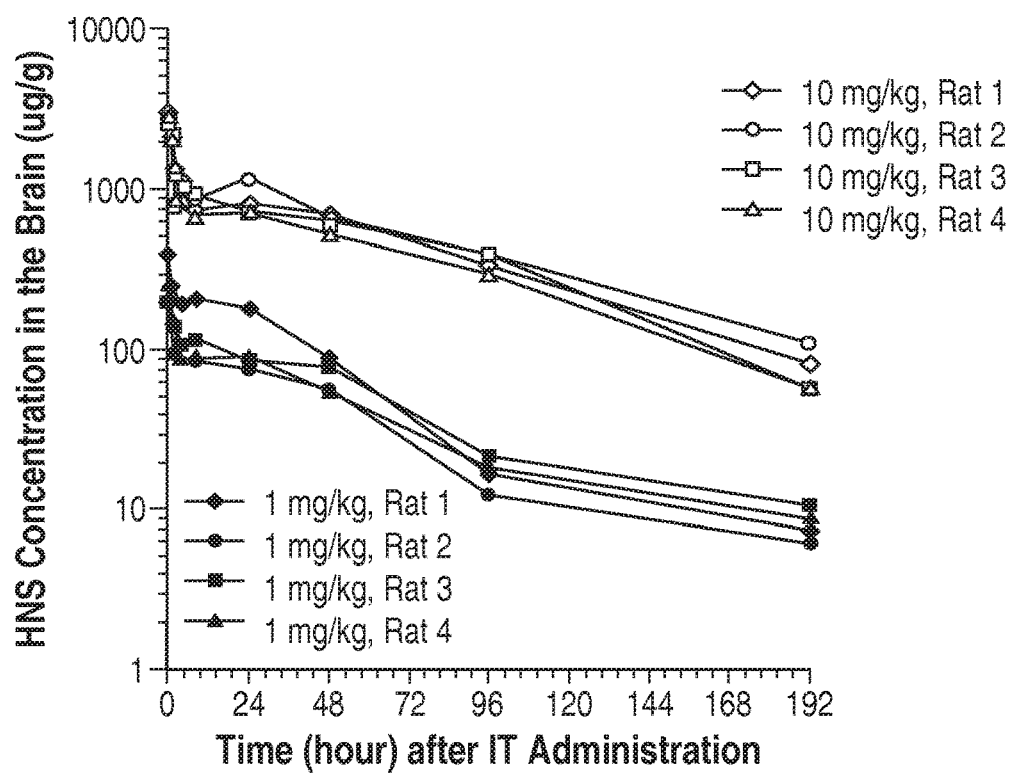

FIG. 152 depicts an exemplary study of the concentration of HNS in the brain plotted with time after IT dosing of $^{124}$I-HNS at 1 and 10 mg/kg.

Figure 153:
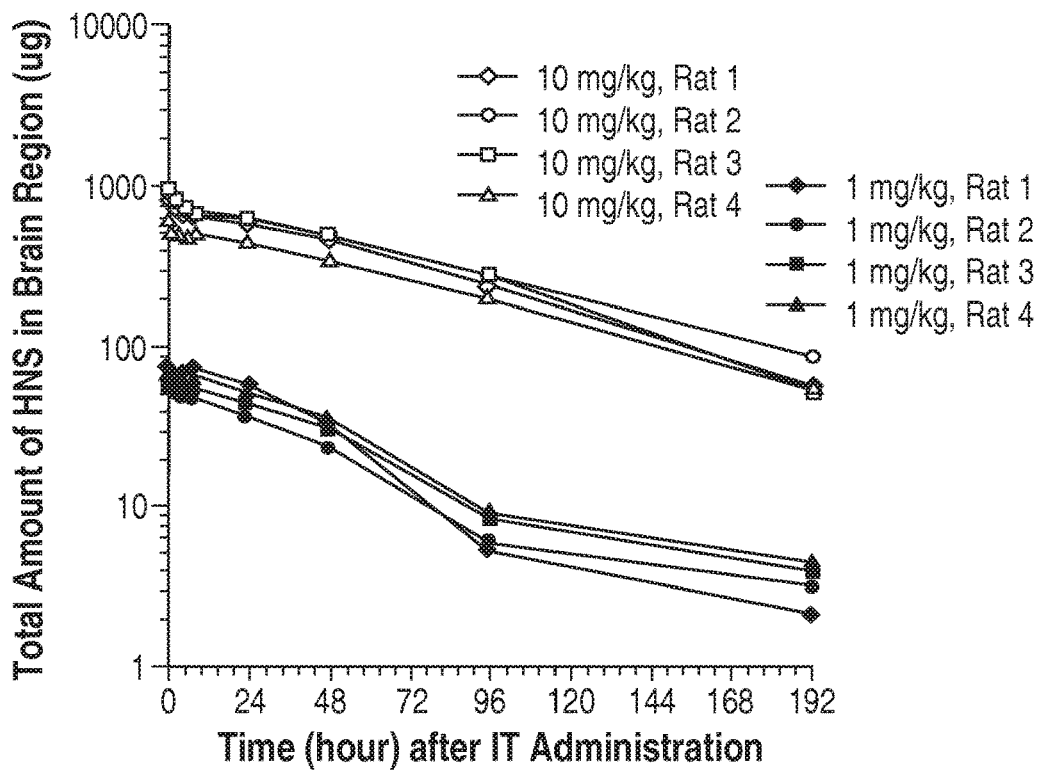

FIG. 153 depicts an exemplary study of the concentration of HNS in the brain region plotted with time after IT dosing of $^{124}$I-HNS at 1 and 10 mg/kg.

Figure 154:
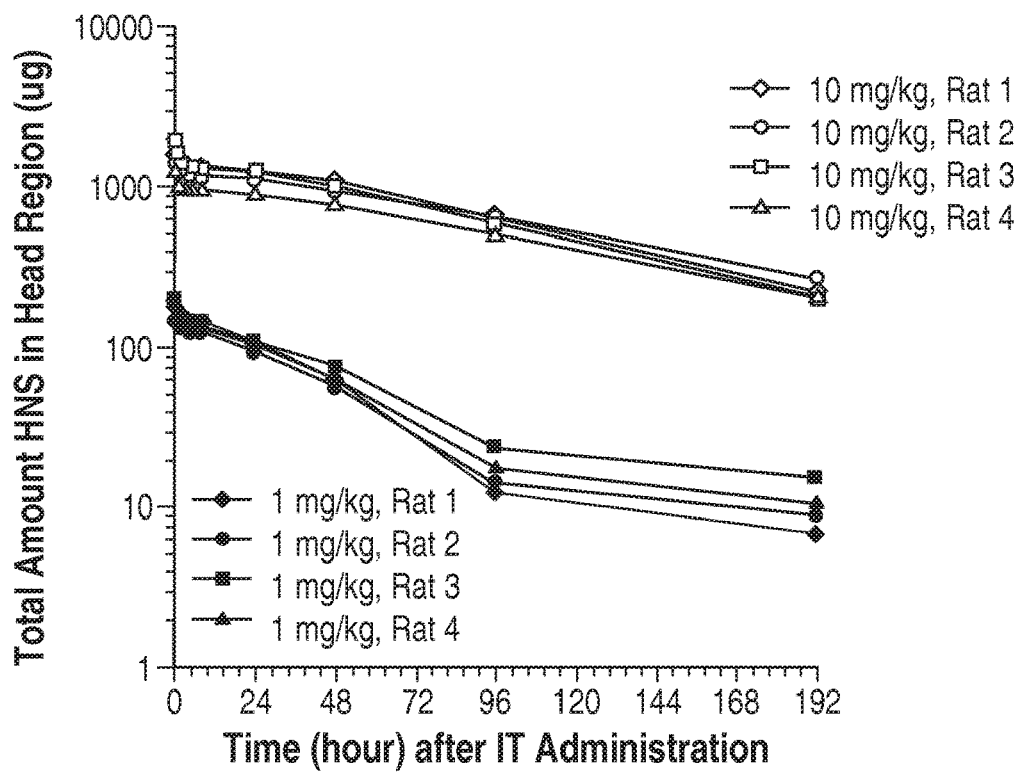

FIG. 154 depicts an exemplary study of the concentration of HNS in the head region plotted with time after IT dosing of $^{124}$I-HNS at 1 and 10 mg/kg.

Figure 155:
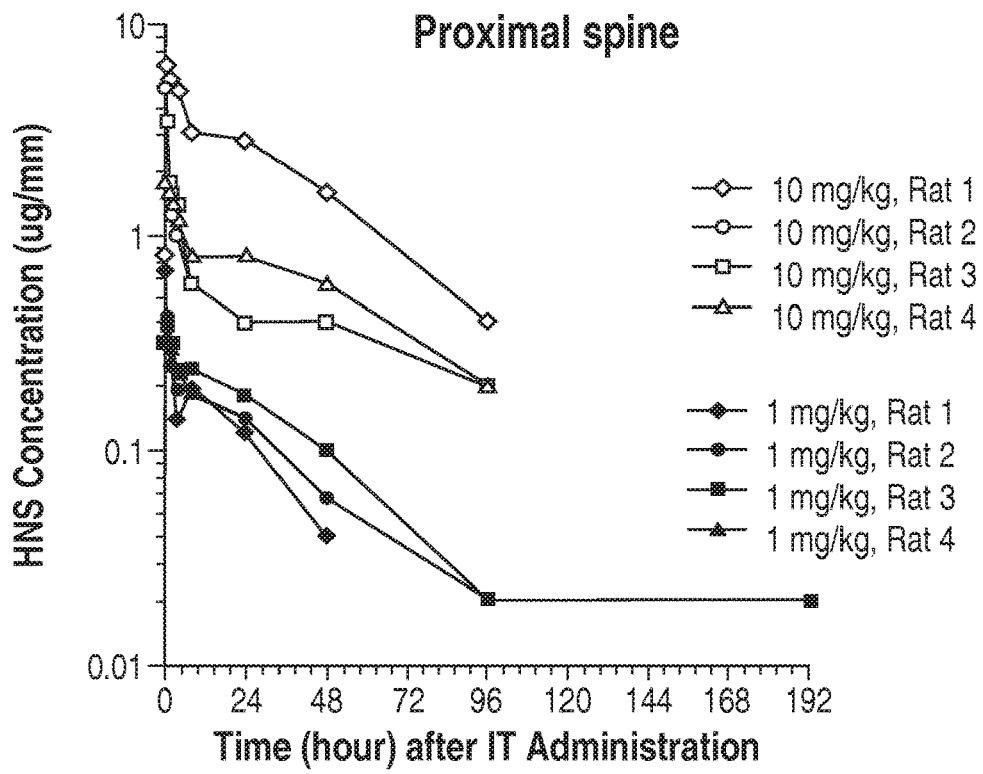

FIG. 155 depicts an exemplary study of the concentration of HNS in the proximal spine plotted with time after IT dosing of $^{124}$I-HNS at 1 and 10 mg/kg.

Figure 156:
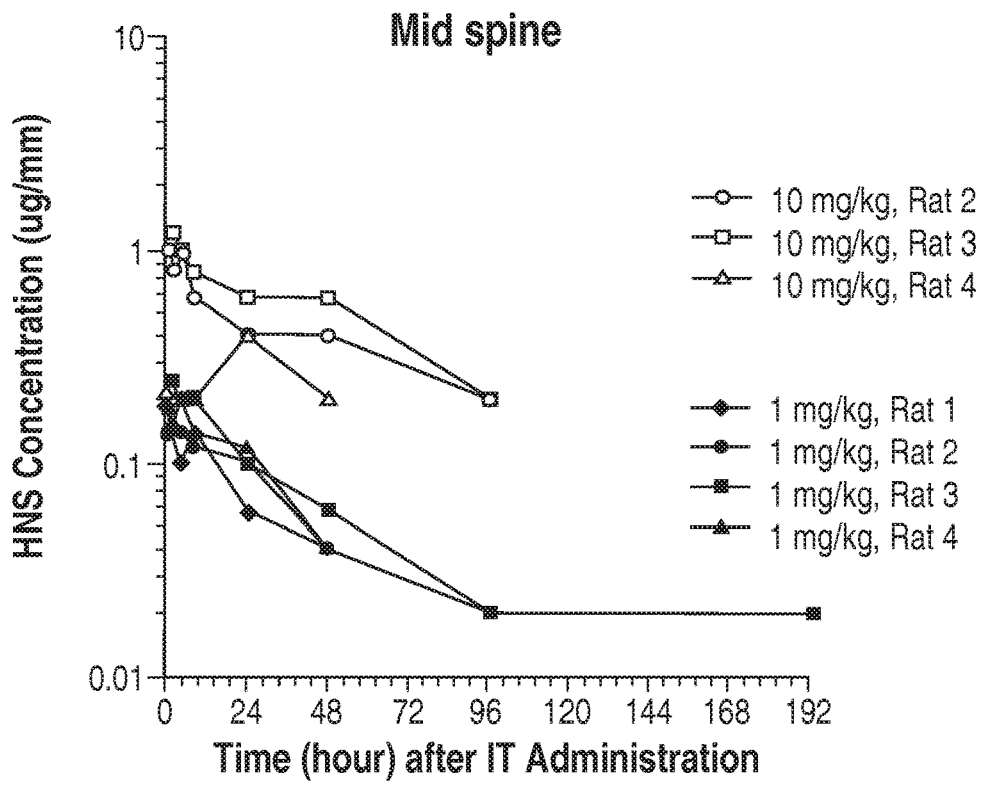

FIG. 156 depicts an exemplary study of the concentration of HNS in the mid-spine plotted with time after IT dosing of $^{124}$I-HNS at 1 and 10 mg/kg.

Figure 157:
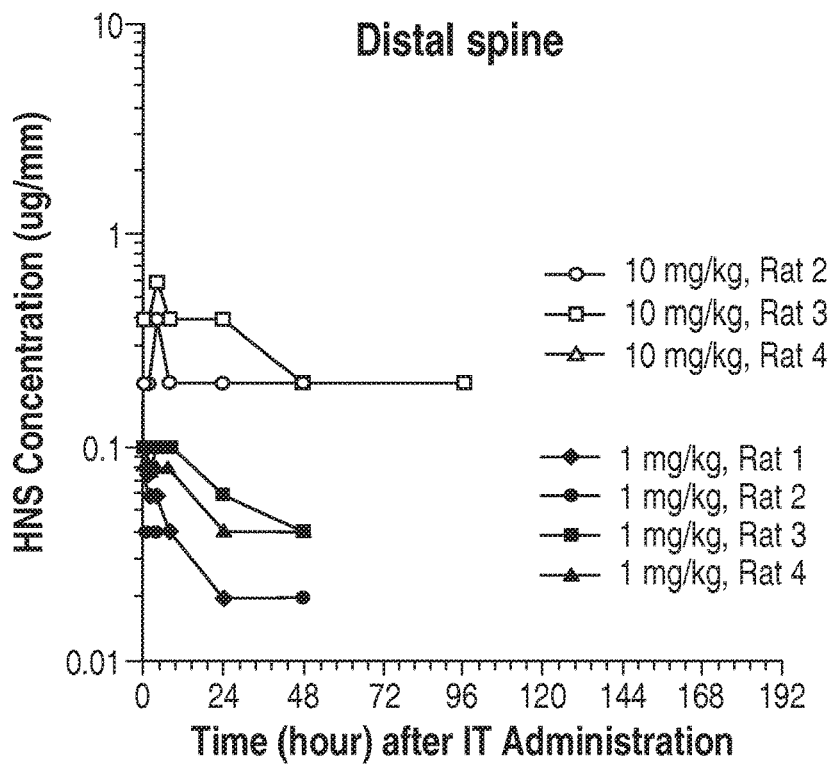

FIG. 157 depicts an exemplary study of the concentration of HNS in the distal spine plotted with time after IT dosing of $^{124}$I-HNS at 1 and 10 mg/kg.

Figure 158:
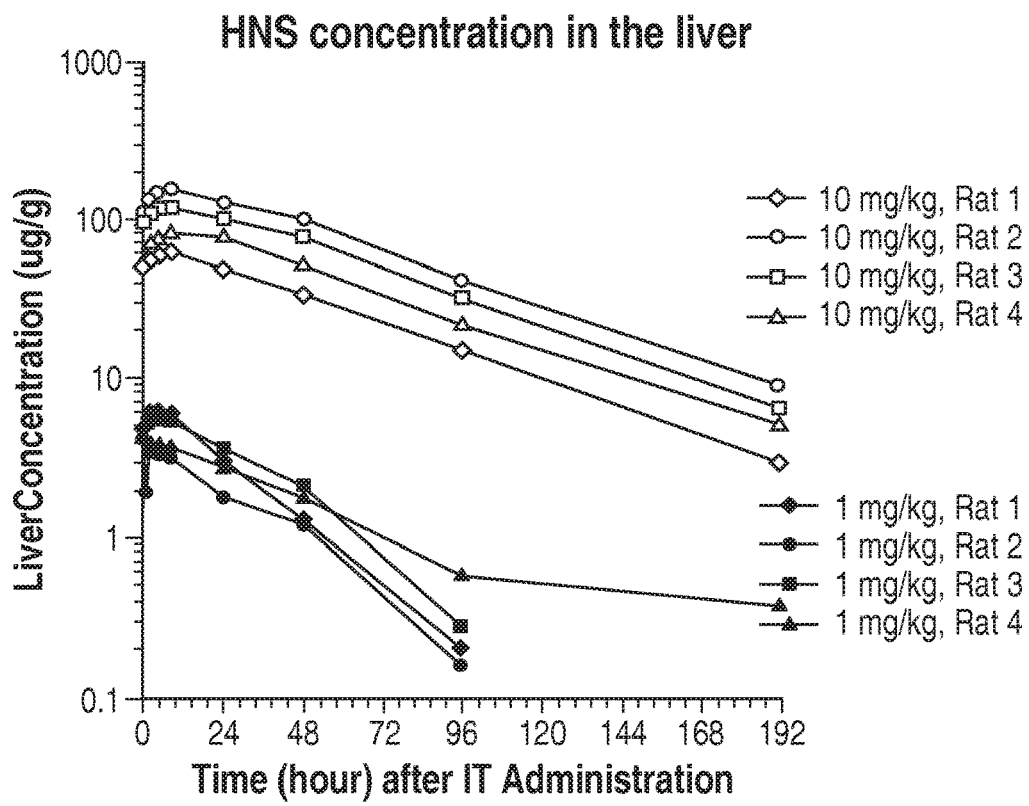

FIG. 158 depicts an exemplary study of the concentration of HNS in the liver plotted with time after IT dosing of $^{124}$I-HNS at 1 and 10 mg/kg.

Figure 159:
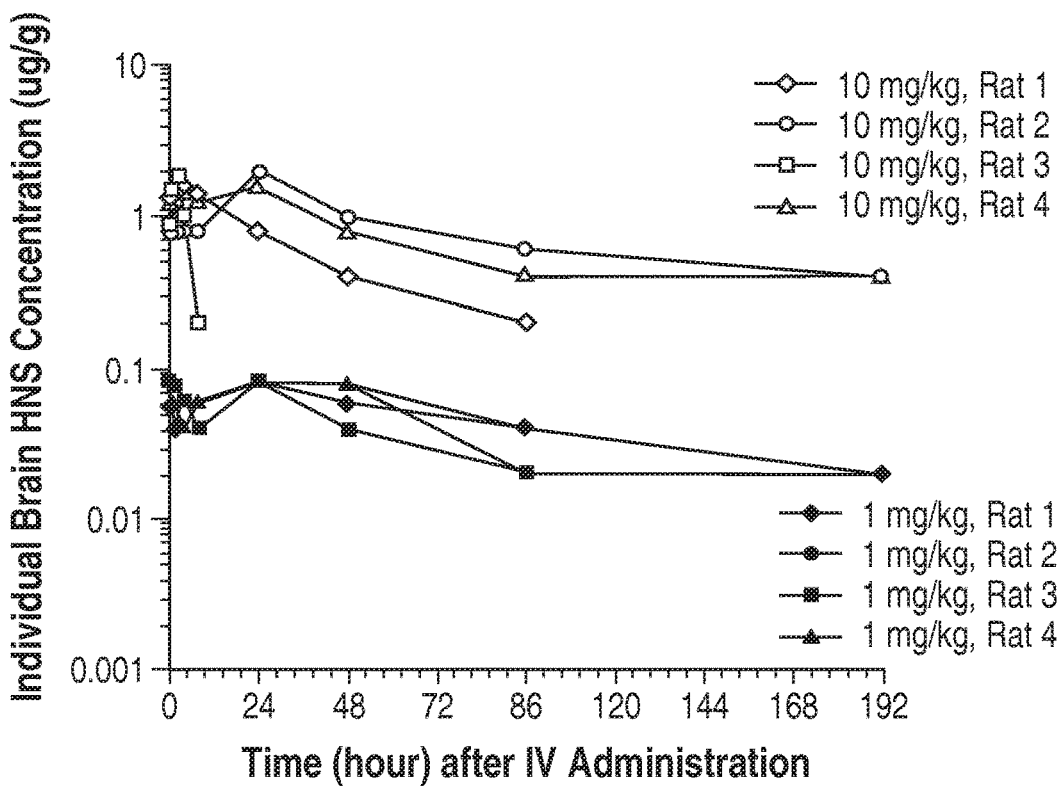
Figure 159:
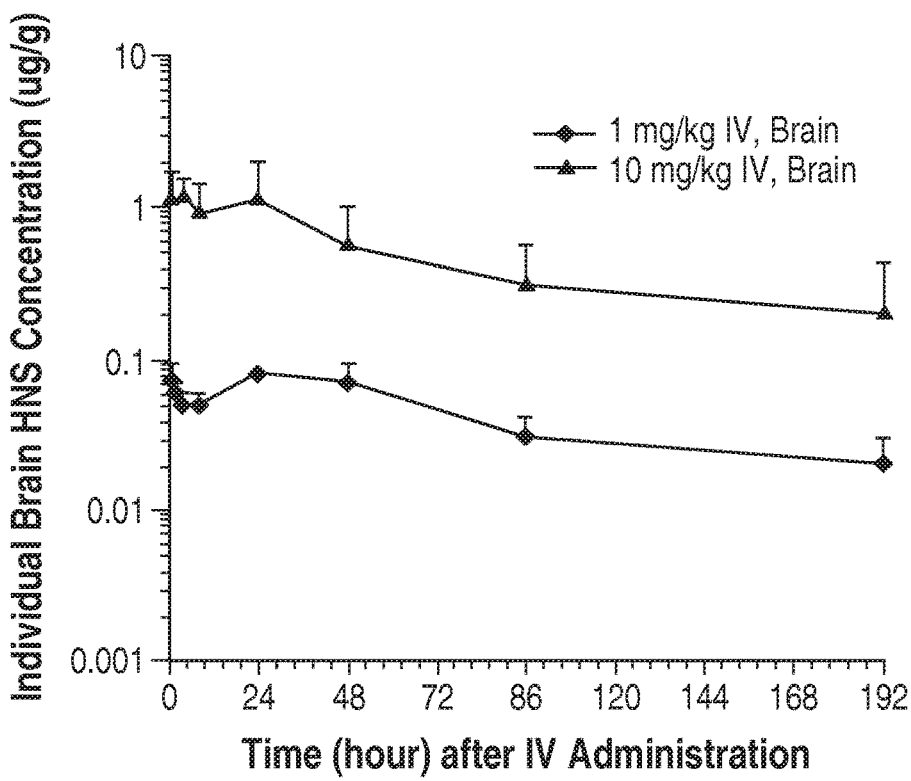

FIG. 159 depicts an exemplary study of the concentration of HNS in the brain plotted with time after IT dosing of $^{124}$I-HNS at 1 and 10 mg/kg, individual (top) and mean±SD (bottom).

Figure 160:
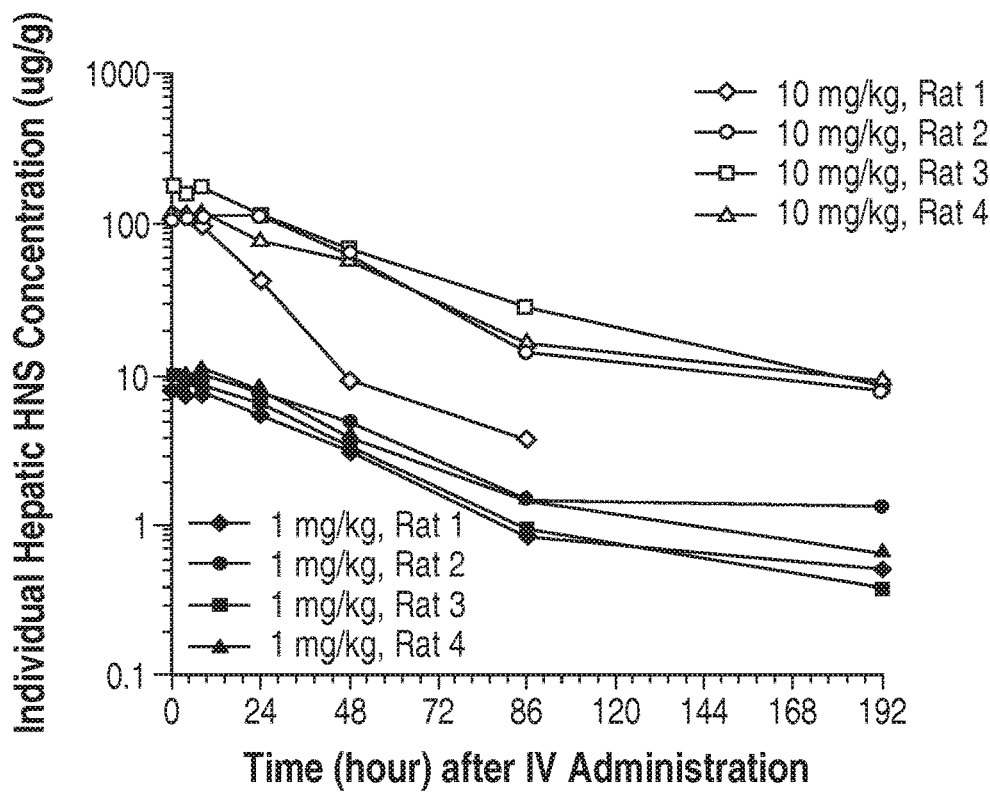
Figure 160:
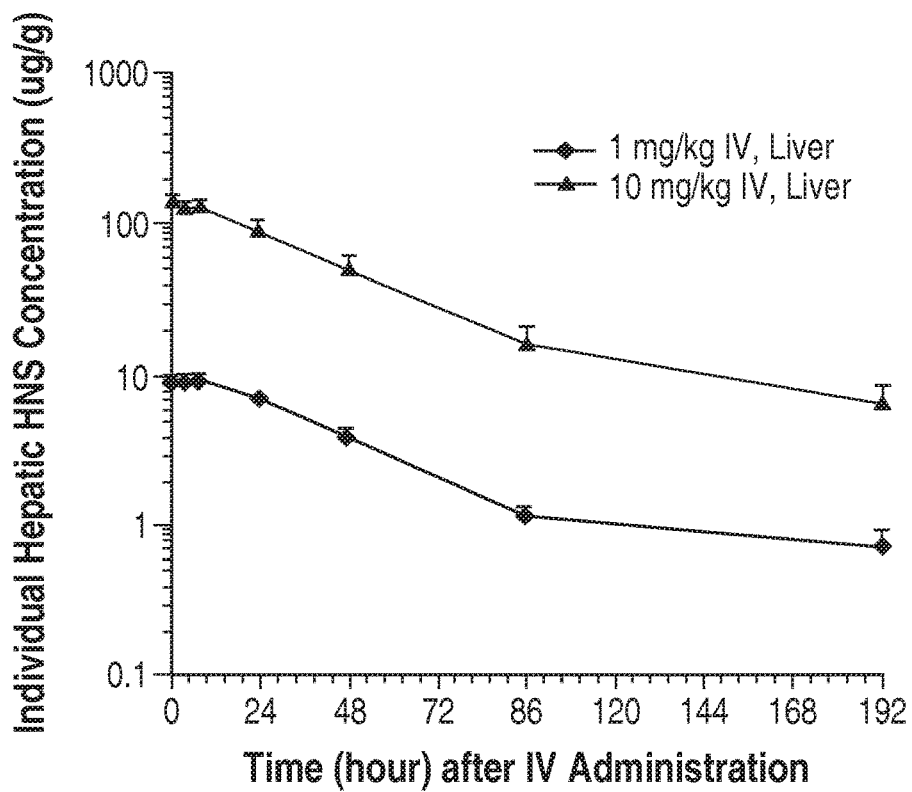

FIG. 160 depicts an exemplary study of the hepatic concentration of HNS plotted with time after IT dosing of $^{124}$I-HNS at 1 and 10 mg/kg, individual (top) and mean±SD (bottom).

Figure 161:
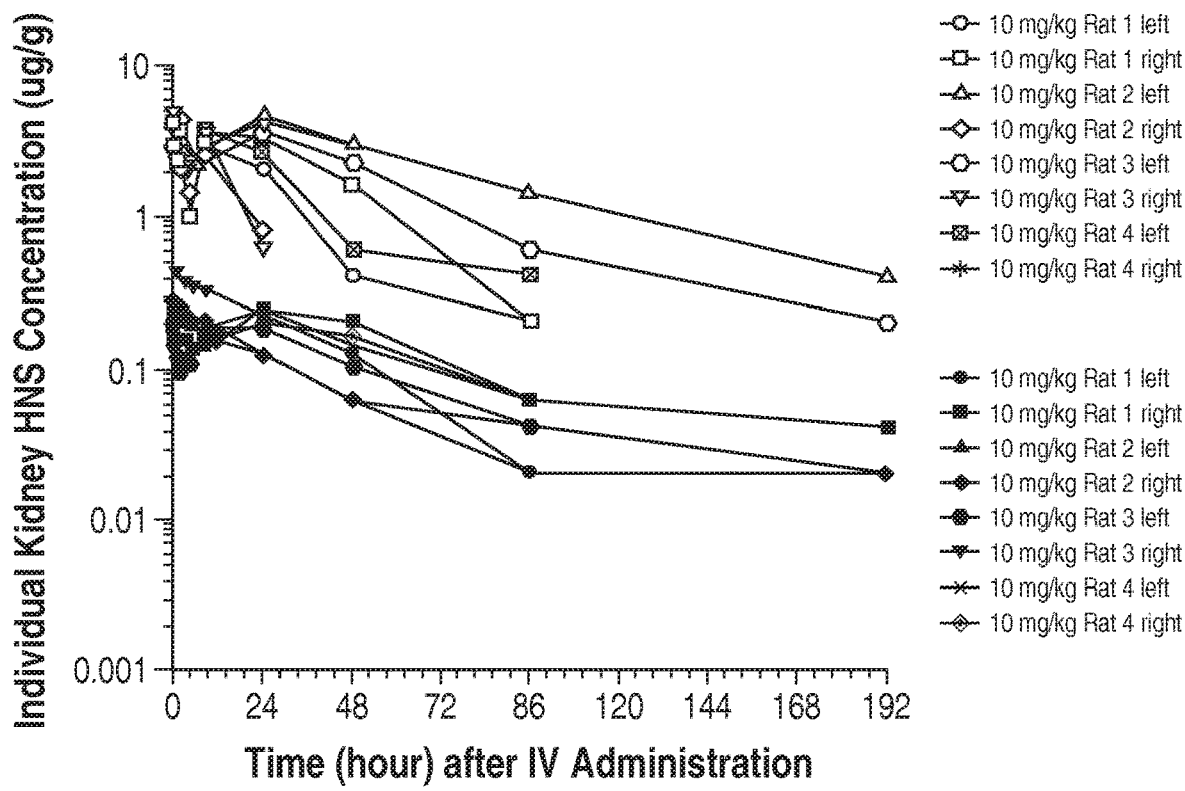
Figure 161:
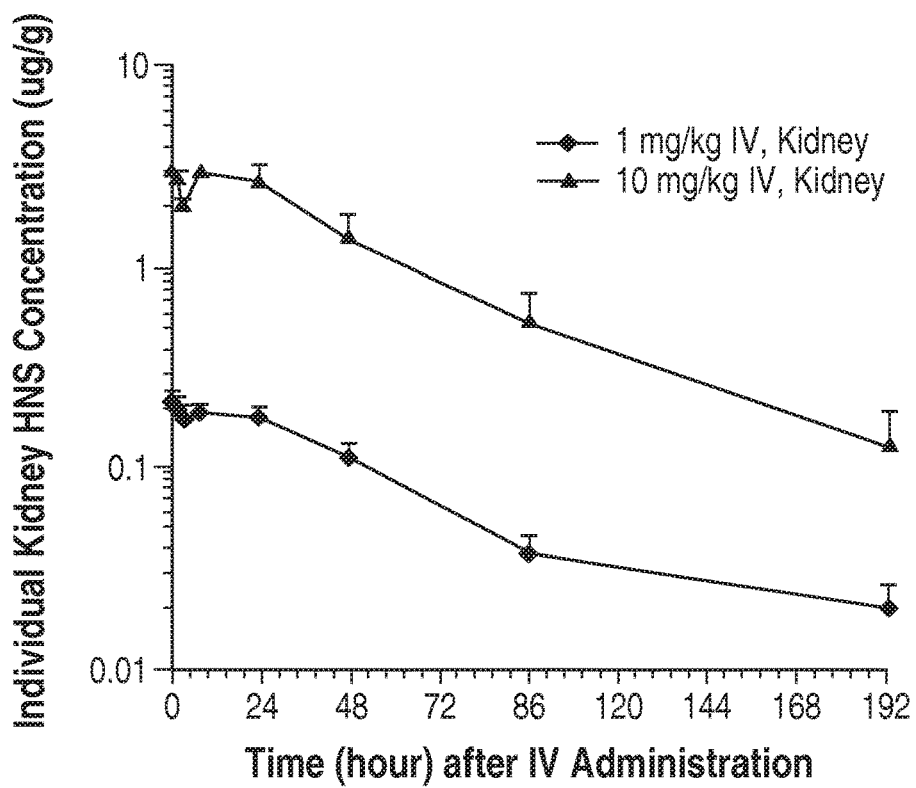

FIG. 161 depicts an exemplary study of the renal concentration of HNS plotted with time after IT dosing of $^{124}$I-HNS at 1 and 10 mg/kg, individual (top) and mean±SD (bottom).

Figure 162:
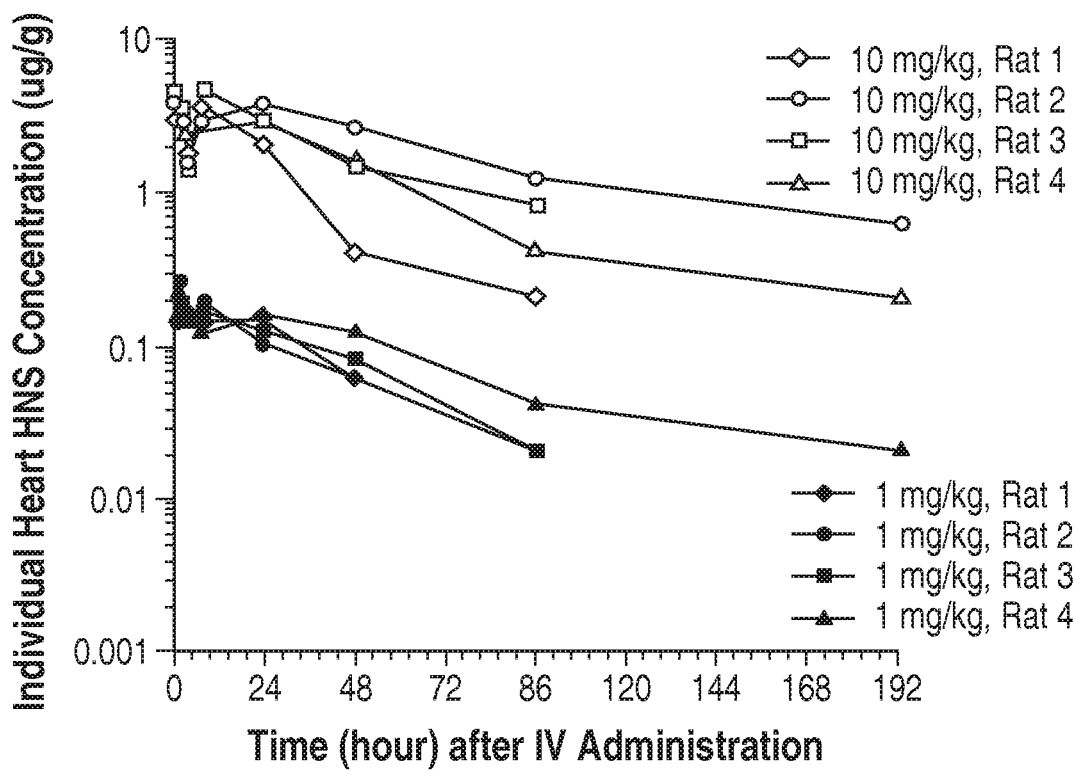
Figure 162:
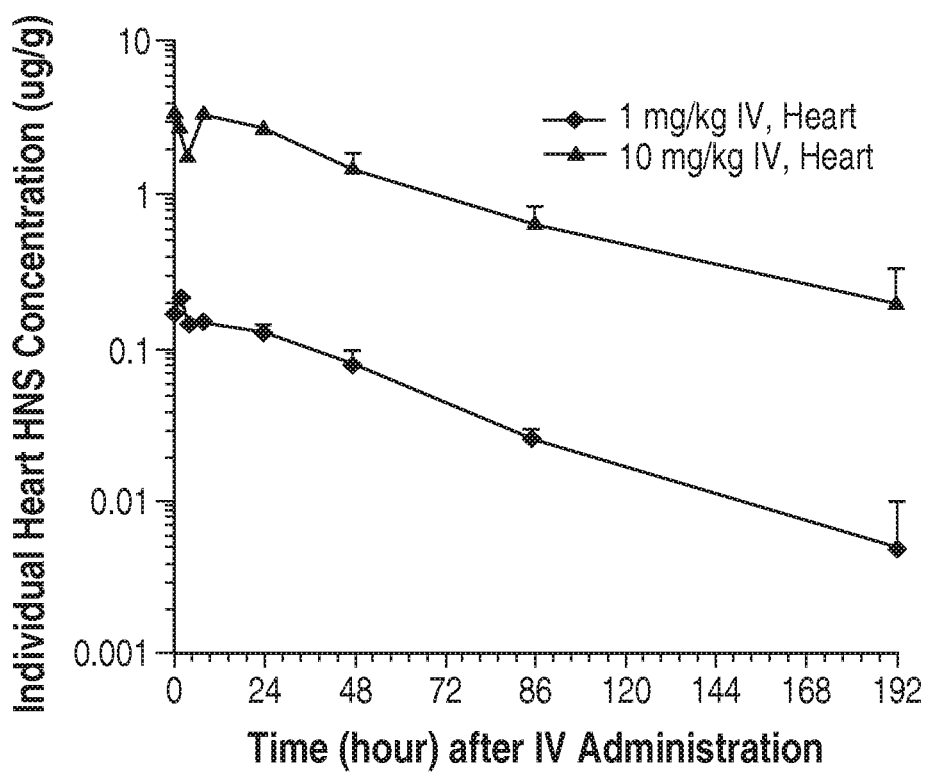

FIG. 162 depicts an exemplary study of the heart concentration of HNS plotted with time after IT dosing of $^{124}$I-HNS at 1 and 10 mg/kg, individual (top) and mean±SD (bottom).

Figure 163:
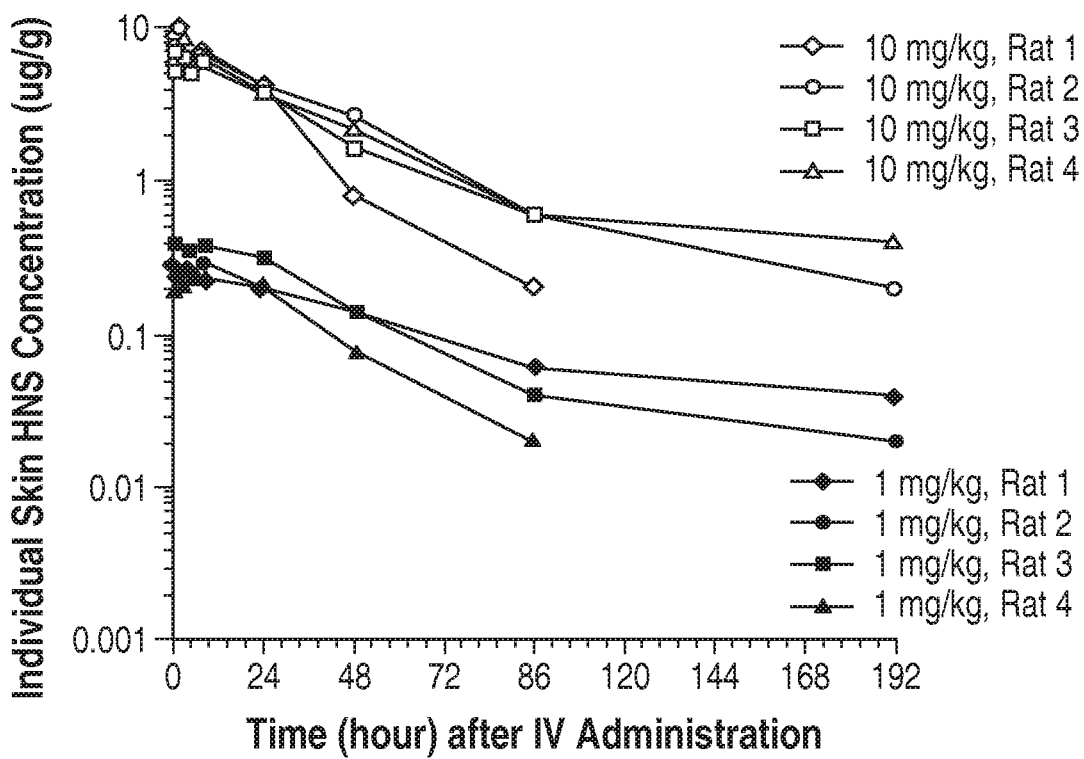
Figure 163:
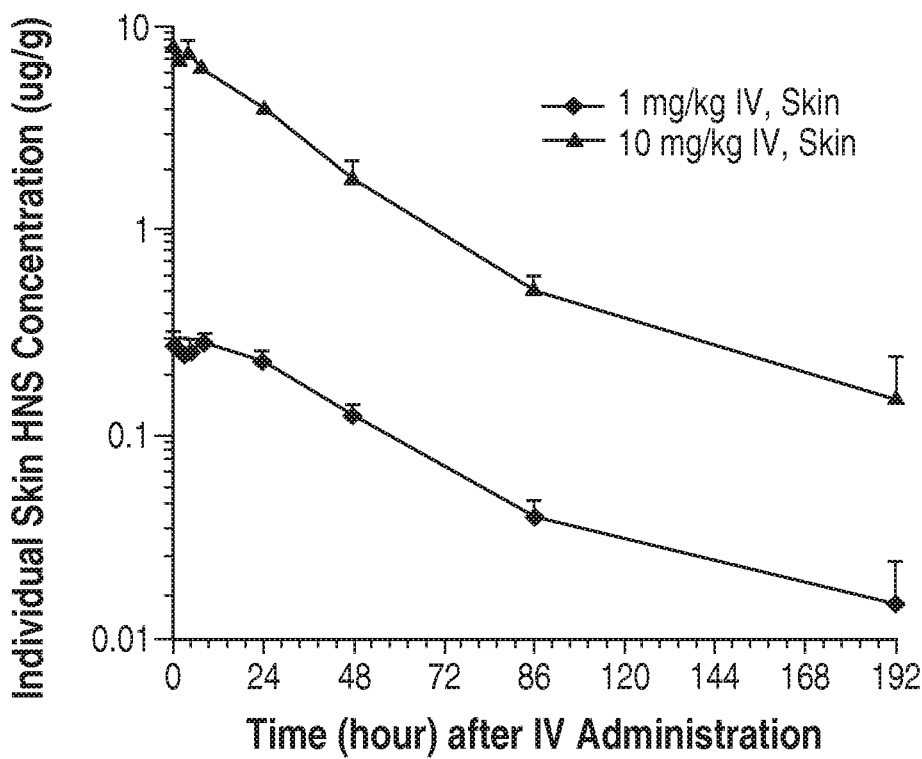

FIG. 163 depicts an exemplary study of the skin concentration of HNS plotted with time after IT dosing of $^{124}$I-HNS at 1 and 10 mg/kg, individual (top) and mean±SD (bottom).

Figure 164:
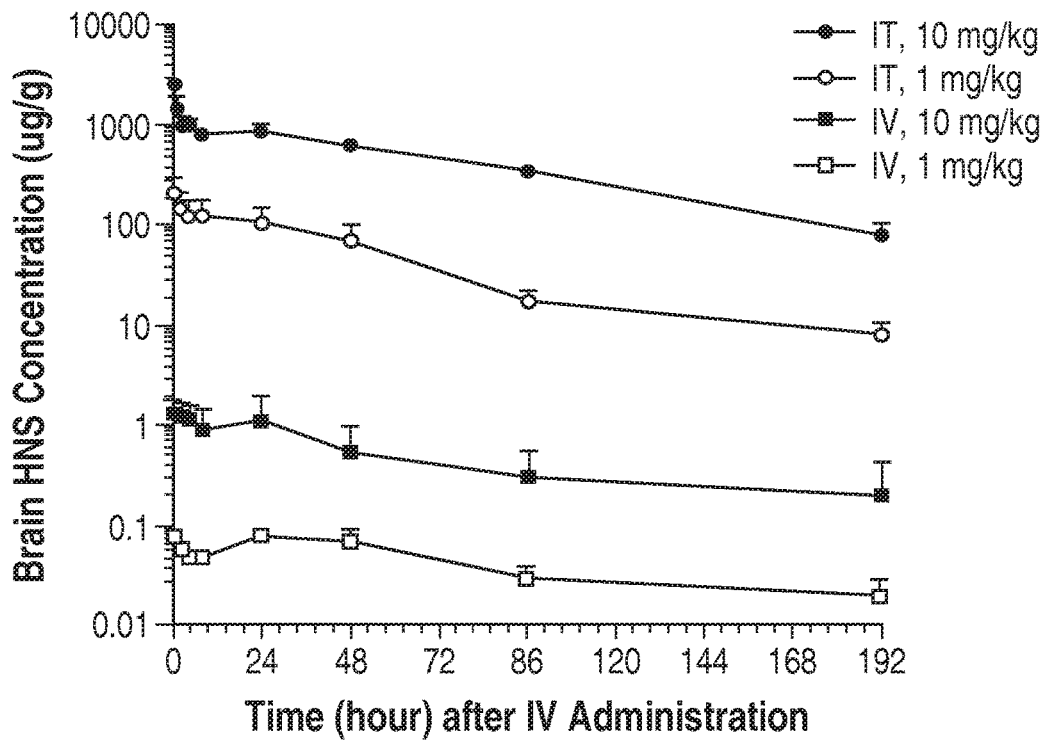

FIG. 164 depicts an exemplary study of the brain concentration of HNS plotted with time after IT dosing of $^{124}$I-HNS at 1 and 10 mg/kg (top), and a comparison of the non-compartmental PK parameters in the brain (bottom).

Figure 165:
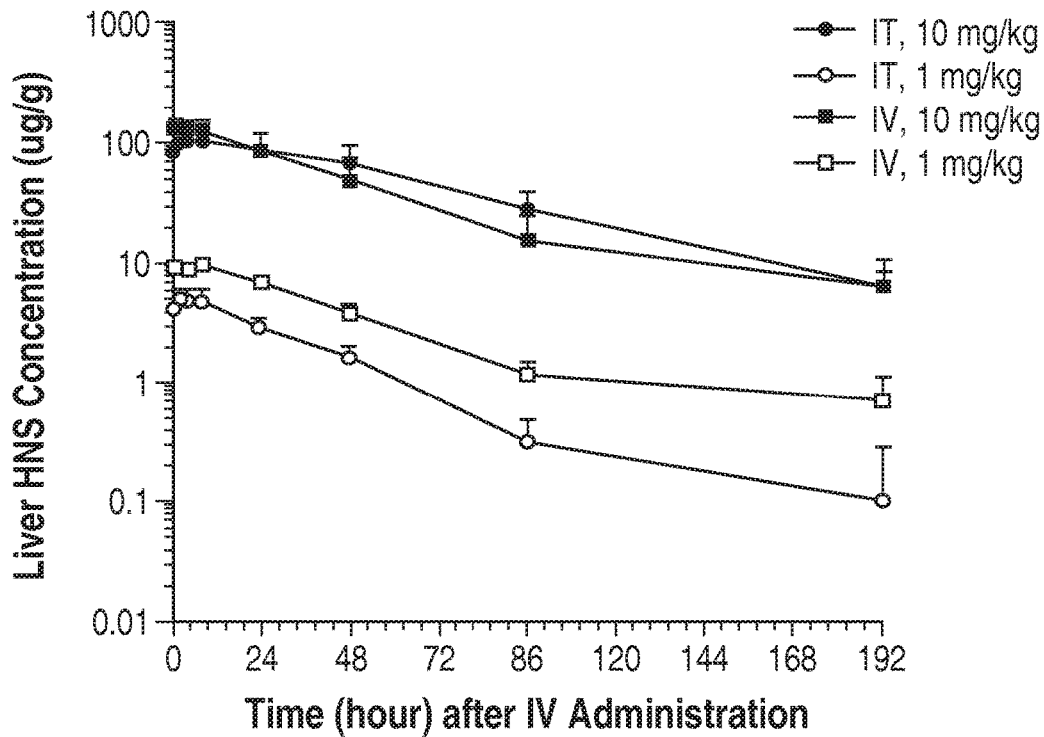

FIG. 165 depicts an exemplary study of the liver concentration of HNS plotted with time after IT dosing of 124I-HNS at 1 and 10 mg/kg (top), and a comparison of the non-compartmental PK parameters in the liver (bottom).

Figure 166:
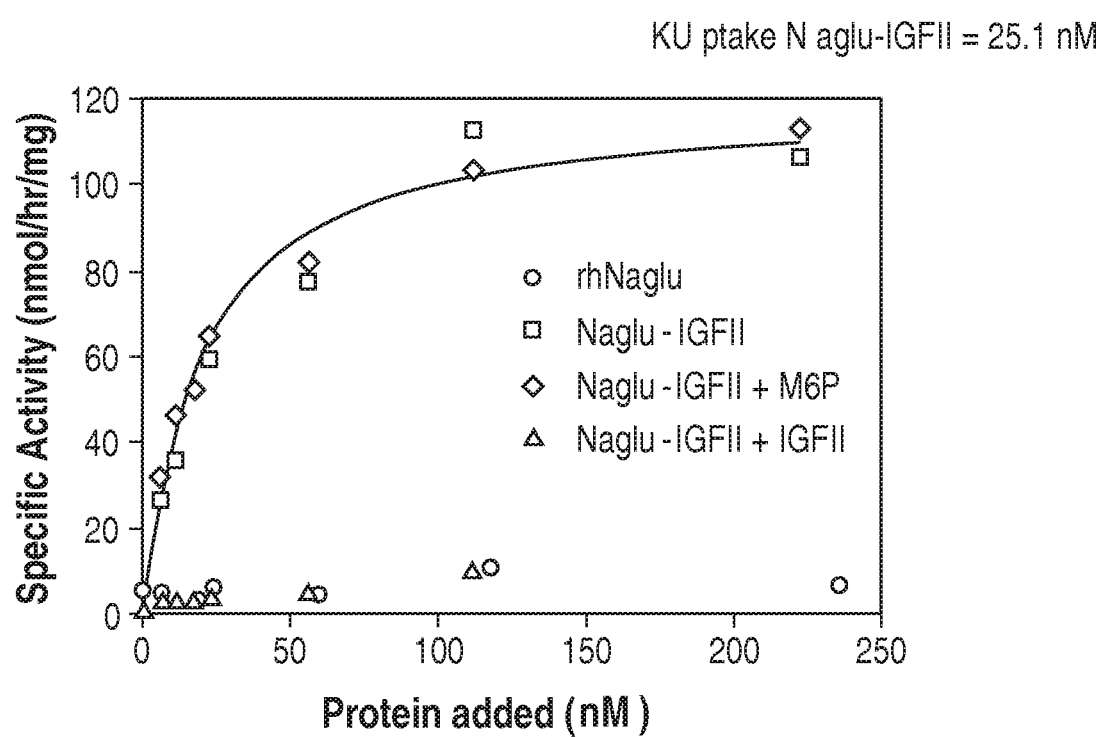

FIG. 166 illustrates exemplary primary fibroblast cells from normal human were used for cellular internalization study of rhNaglu and Naglu-IGFII. Cellular uptake of rhNaglu was minimum, while the cellular uptake of Naglu-IGFII was much pronounced. The saturating curve of Naglu-IGFII internalization indicated a receptor mediated uptake. This uptake was inhibited by IGFII, but not by mannose-6-phosphate.

Figure 167:
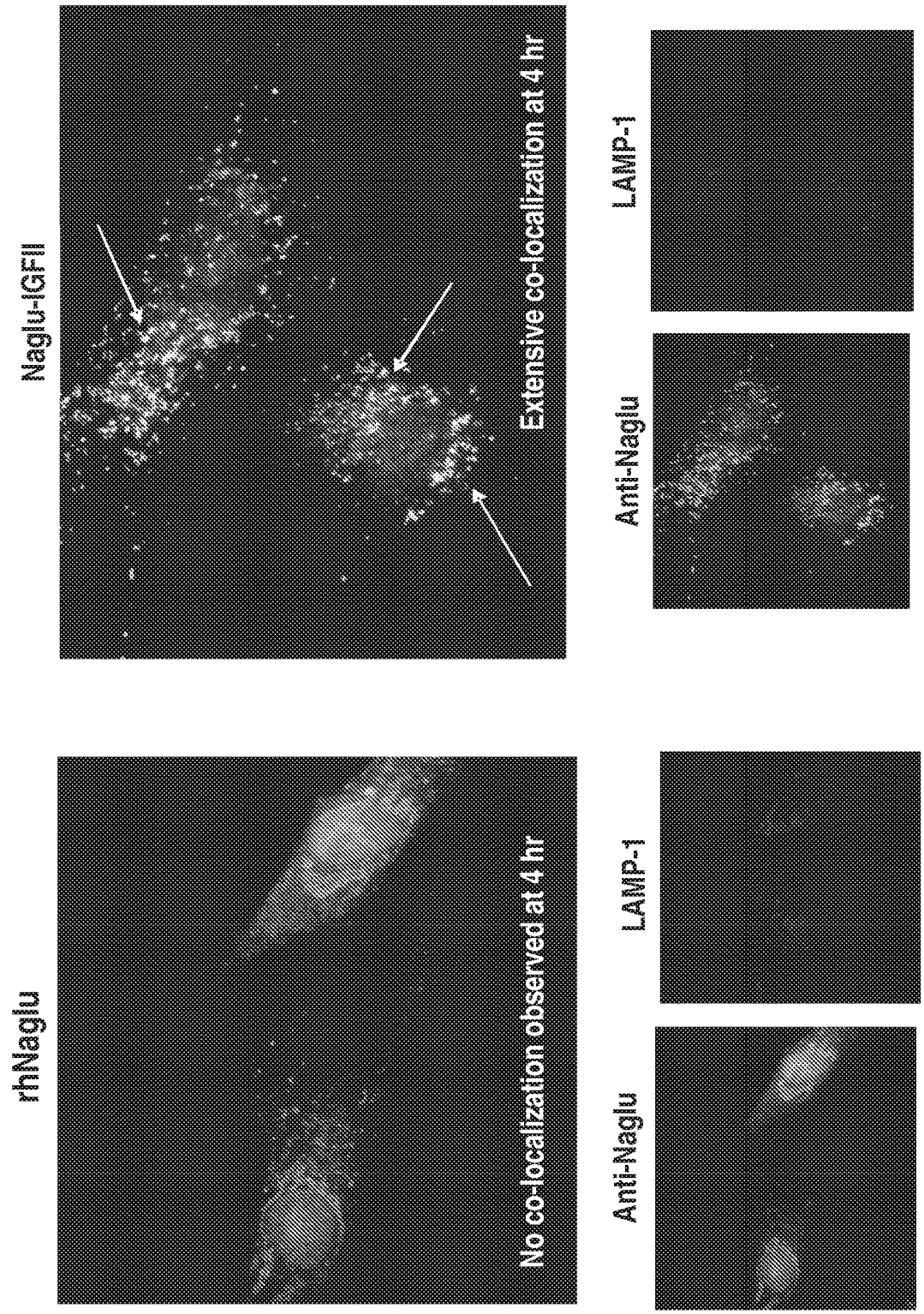

FIG. 167 depicts results of an exemplary confocal microscopy study using a Sanfilippo B subject's fibroblast cells (GM01426). Extensive internalization of Naglu-IGFII, and co-localization of Naglu-IGFII with Lamp-1 was observed.

Figure 168:
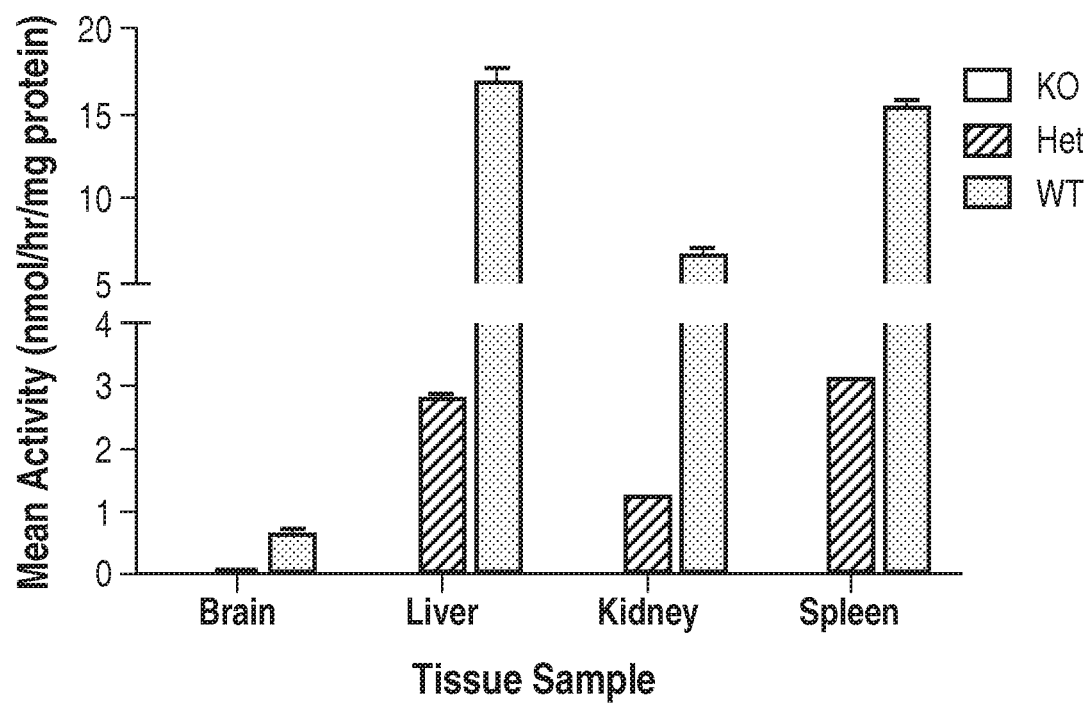

FIG. 168 is an exemplary illustration showing Naglu activity in wild type (WT), Naglu−/− (KO) and heterozygote Naglu+/− (Het) mouse. Total deficiency of Naglu in Sanfilippo B mouse was observed in brain, liver, kidney and spleen.

Figure 169:
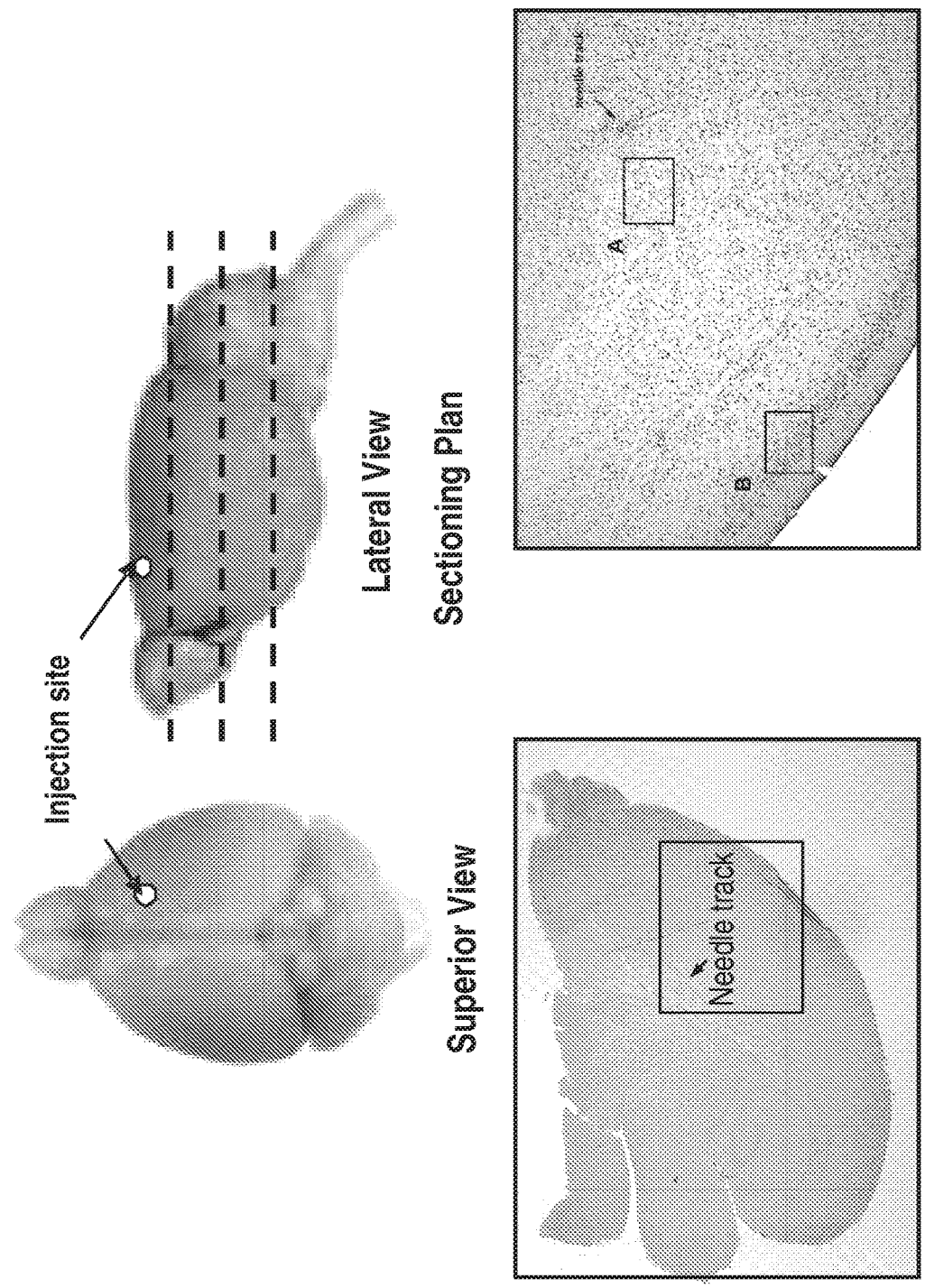

FIG. 169 depicts superior and lateral view of the mouse brain to indicate the site of intracisternal injection (IC) and the sectioning plane for histology analyses. Middle micrograph, a transversal section of mouse brain viewed at 1× magnitude. Boxed area indicates the field for 4× microscopy image in the bottom micrograph. Bottom micrograph, 4× image of histology slide. Box A and B indicates the field of 40× microscopy image in FIG. 170 and FIG. 171.

Figure 170:
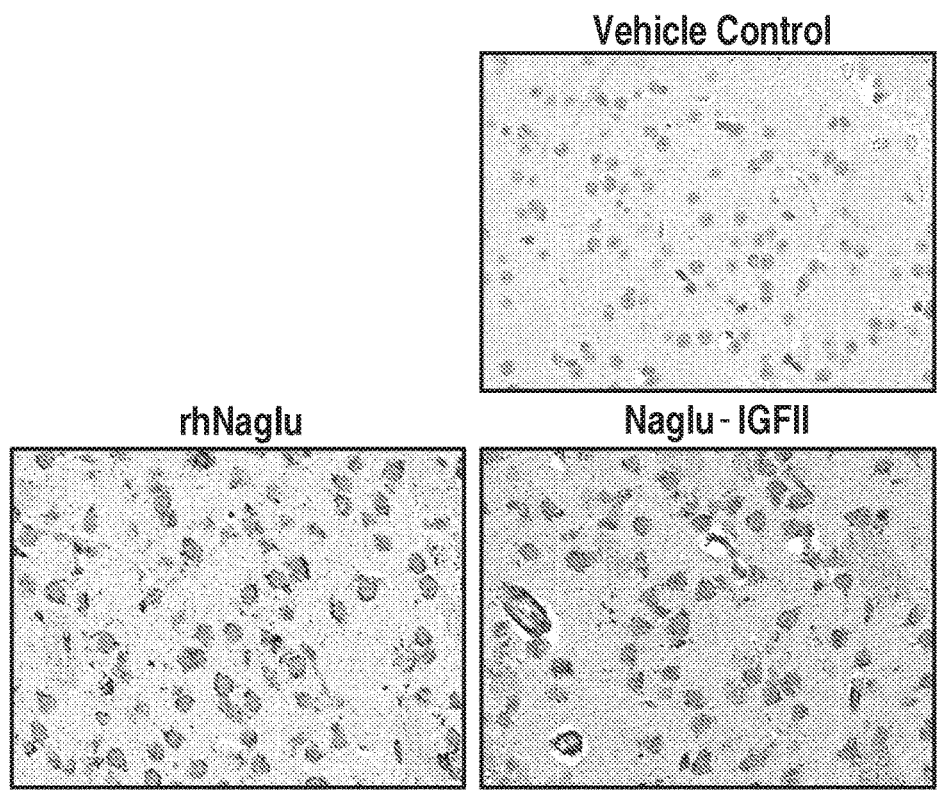

FIG. 170 depicts exemplary immunohistochemistry of the cerebral cortex in Sanfilippo B mice 7 days after intracisternal injection (IC) 40×. Both rhNaglu and Naglu-IGFII exhibited extensive cellular uptake in neurons as well as in glial cells, and the distribution and cellular uptake patterns were very similar between the two proteins. (anti-human Naglu monoclonal antibody).

Figure 171:
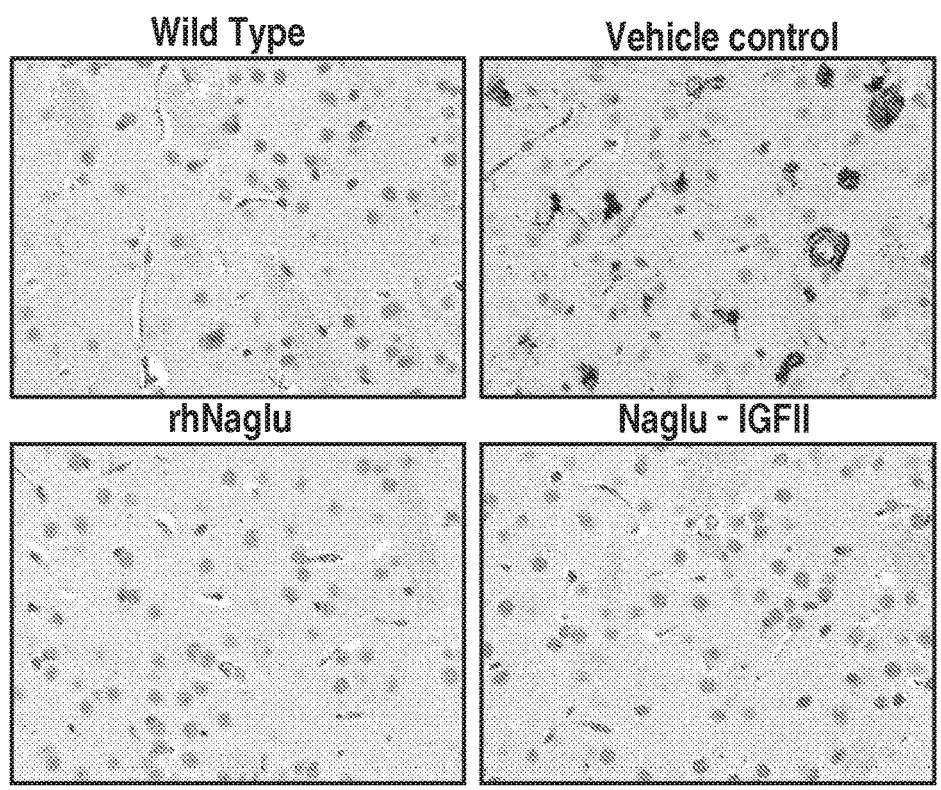

FIG. 171 depicts exemplary LAMP-1 immunostaining of the cerebral cortex at 40× magnification. Comparing to the brain of wild type mouse, increased lysosomal storage was observed in the brain of vehicle treated Sanfilippo B mouse, as demonstrated by the increased LAMP-1 immunostaining positive spots. The brain of both rhNalgu and Naglu-IGFII treated Sanfilippo B mouse exhibited reduction of lysosomal storage that was very similar to wt mouse.

Figure 172A:
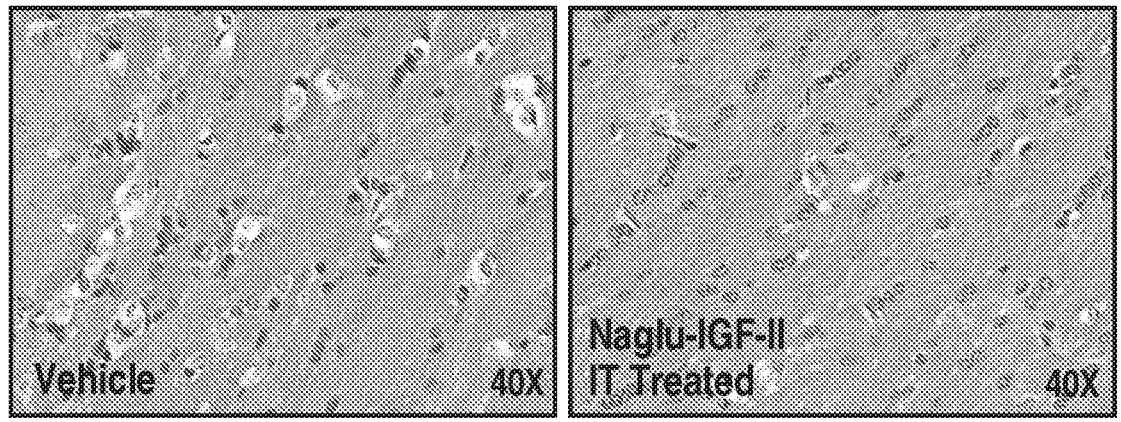
Figure 172B:
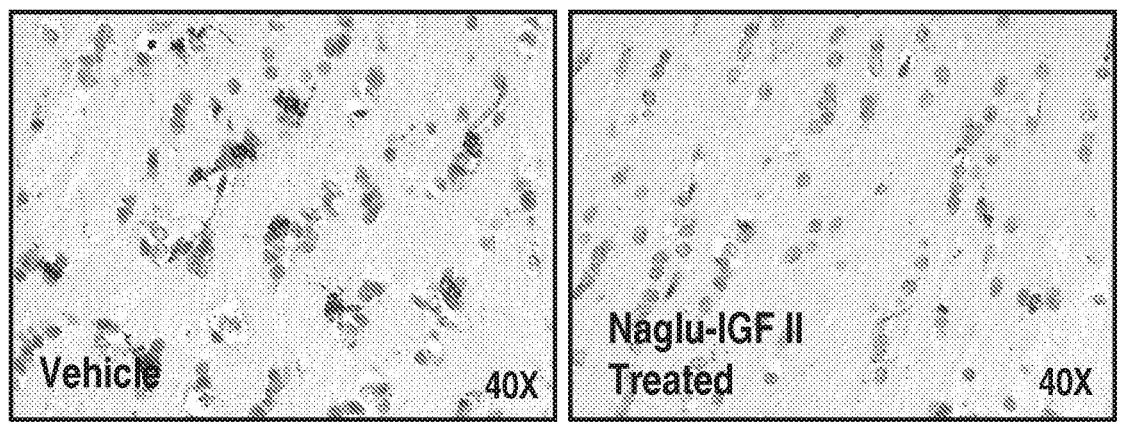

FIG. 172A illustrates widespread reduction of cellular vacuolation in the white matter tissues of Naglu-deficient mice IT-administered Naglu relative to the same Naglu-deficient mice that were administered the vehicle. FIG. 172B illustrates a marked reduction in lysosomal associated membrane protein 1 (LAMP1) immunostaining in the white matter tissues of Naglu-deficient mice intrathecally-administered Naglu relative to the same Naglu-deficient mice that were administered a vehicle.

Figure 173A:
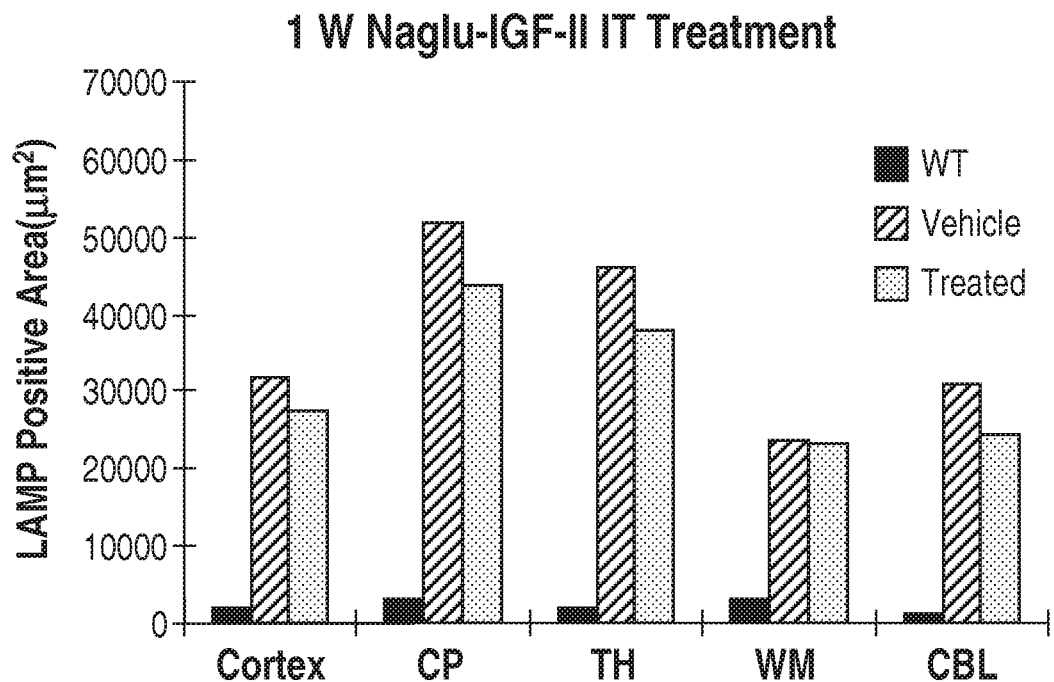
Figure 173B:
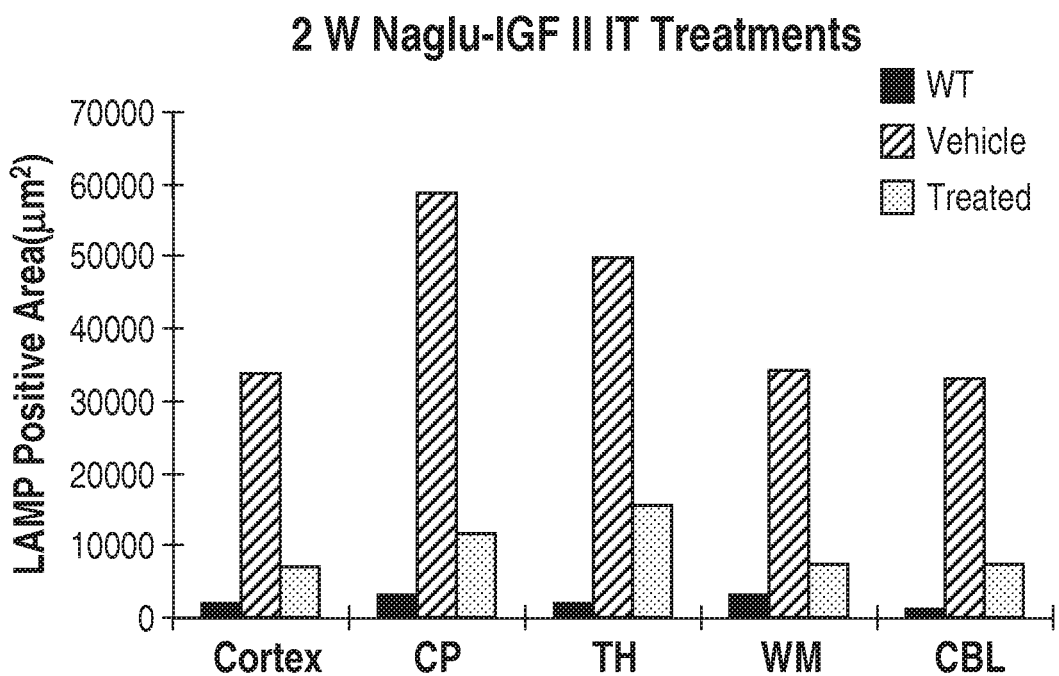

FIG. 173A and FIG. 173B quantitatively illustrates and compares the concentration of LAMP measured in the cerebral cortex, caudate nucleus and putamen (CP), thalamus (TH), cerebellum (CBL) and white matter (WM) of the Naglu-deficient mice which were administered Naglu relative to both the wild-type and Naglu-deficient mice that were administered a vehicle. The LAMP-positive areas in each area of brain tissue analyzed were further reduced following the intrathecal administration of three doses of Naglu over the course of seven days (FIG. 173A) relative to two doses of Naglu over the course of two weeks (FIG. 173B).

Figure 174:
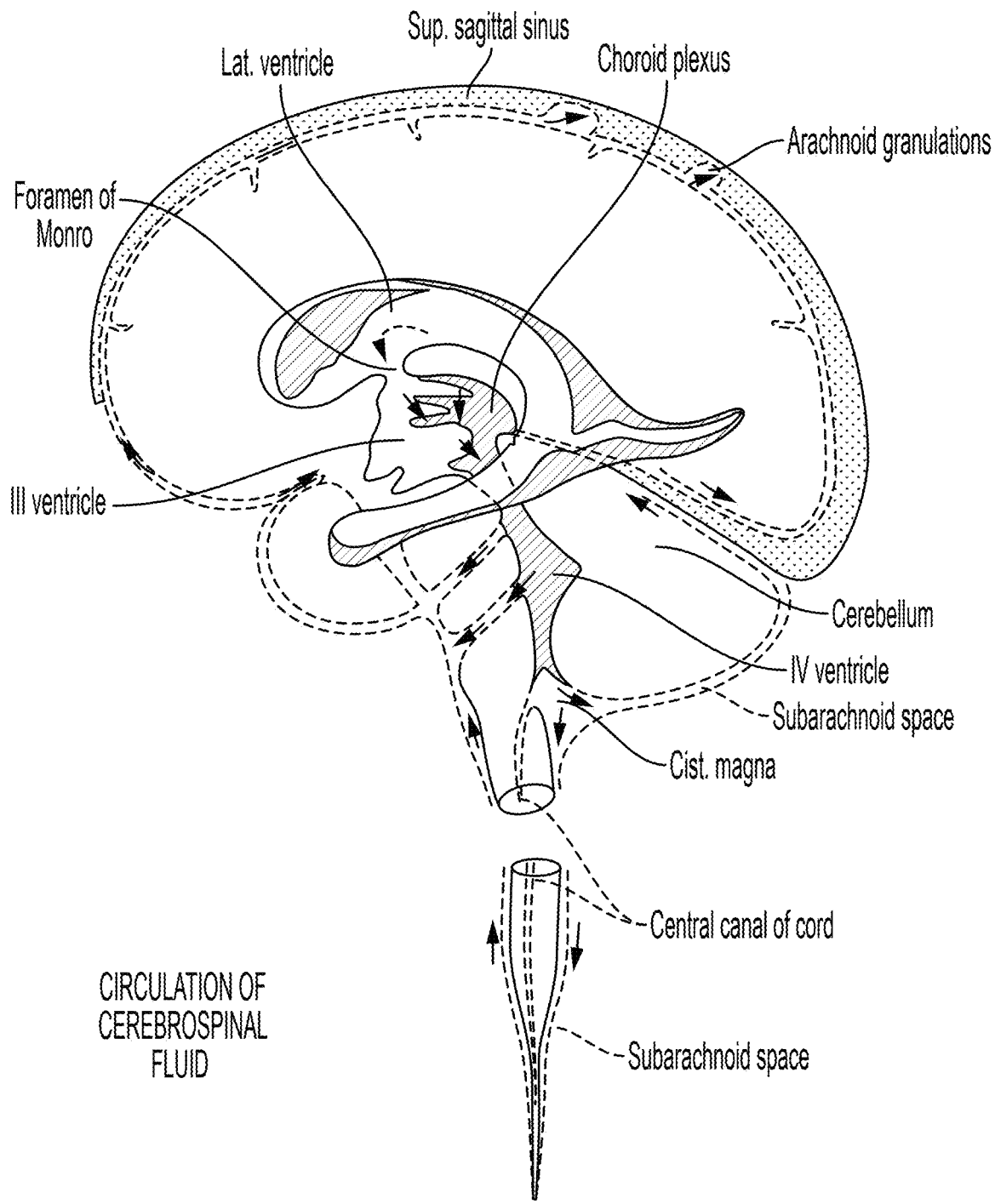

FIG. 174 illustrates an exemplary midsagittal anatomical diagram of human CNS is used as a reference in this figure, to demonstrate the site of IT injection in wt cannulated Rat. Arrows indicate the approximate anatomic location of IT injection in the spinal cord the cerebral cortex region where tissues were taken for immunohistochemistry study.

Figure 175:
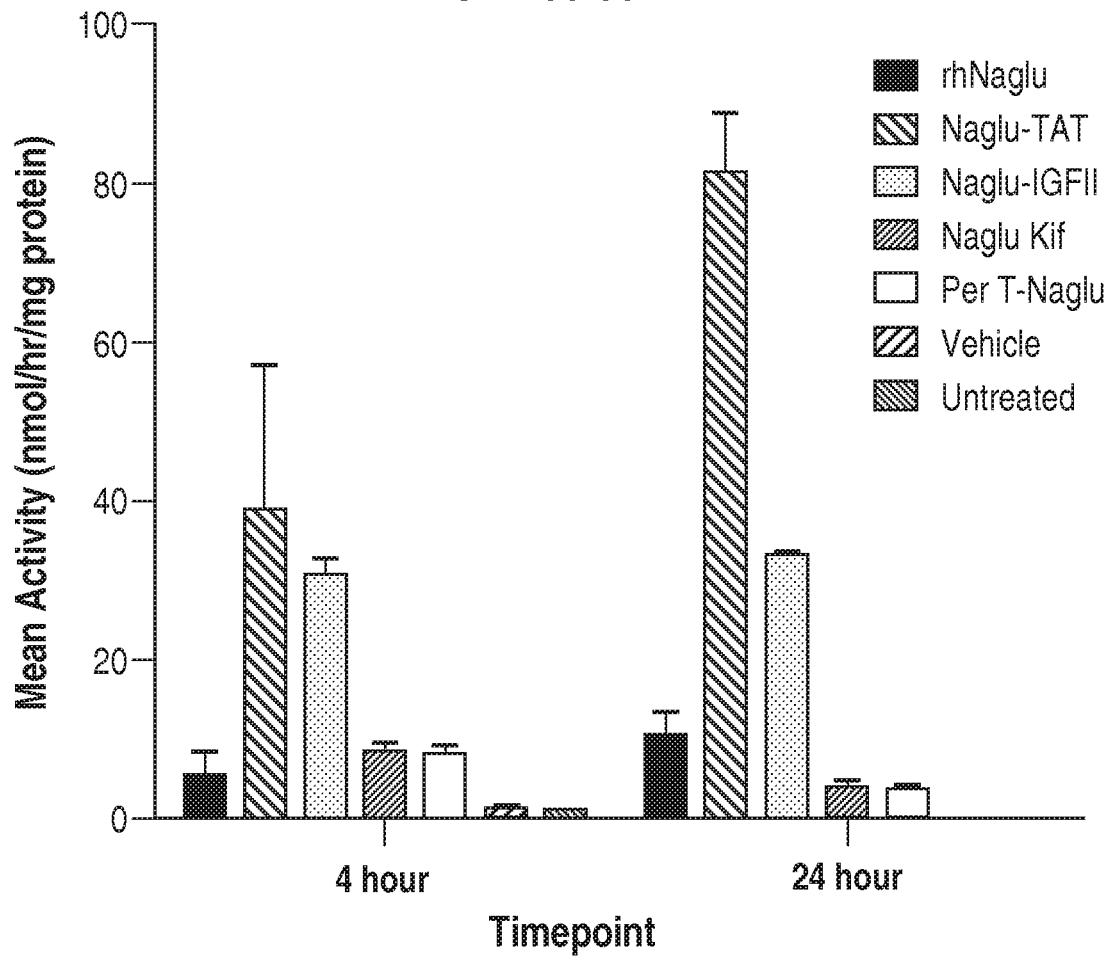

FIG. 175 illustrates exemplary Naglu activity in the brain after IT injection. Naglu activity was significantly higher in the brain of Naglu-TAT and Naglu-IGFII injected wt rat.

Figure 176:
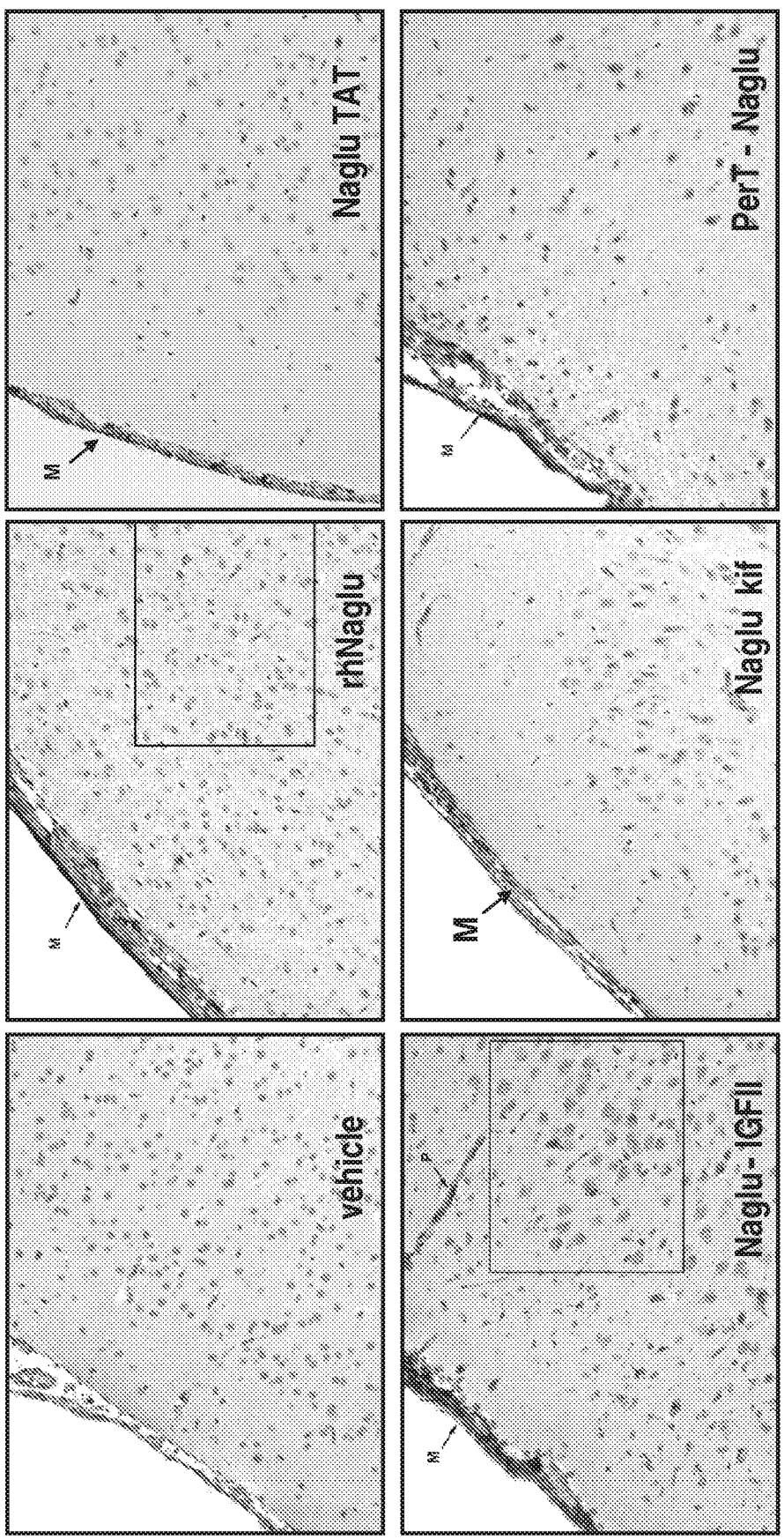

FIG. 176 depicts exemplary Naglu immunostaining of the cerebral cortex of rhNaglu, Naglu-TAT, Naglu-IGFII, Naglu-kif and PerT-Naglu treated wt cannulated rat 24 hr after IT injection 20×. Naglu-IGFII was the only protein exhibited extensive distribution well into the parenchyma of the brain. Cellular uptake into neurons and glial cells was also evident in Naglu-IGFII treated rat. On the other hand, in rhNaglu, Naglu-TAT, Naglu kif and PerT-Naglu treated groups, the protein remained in the meninges (M).

Figure 177:
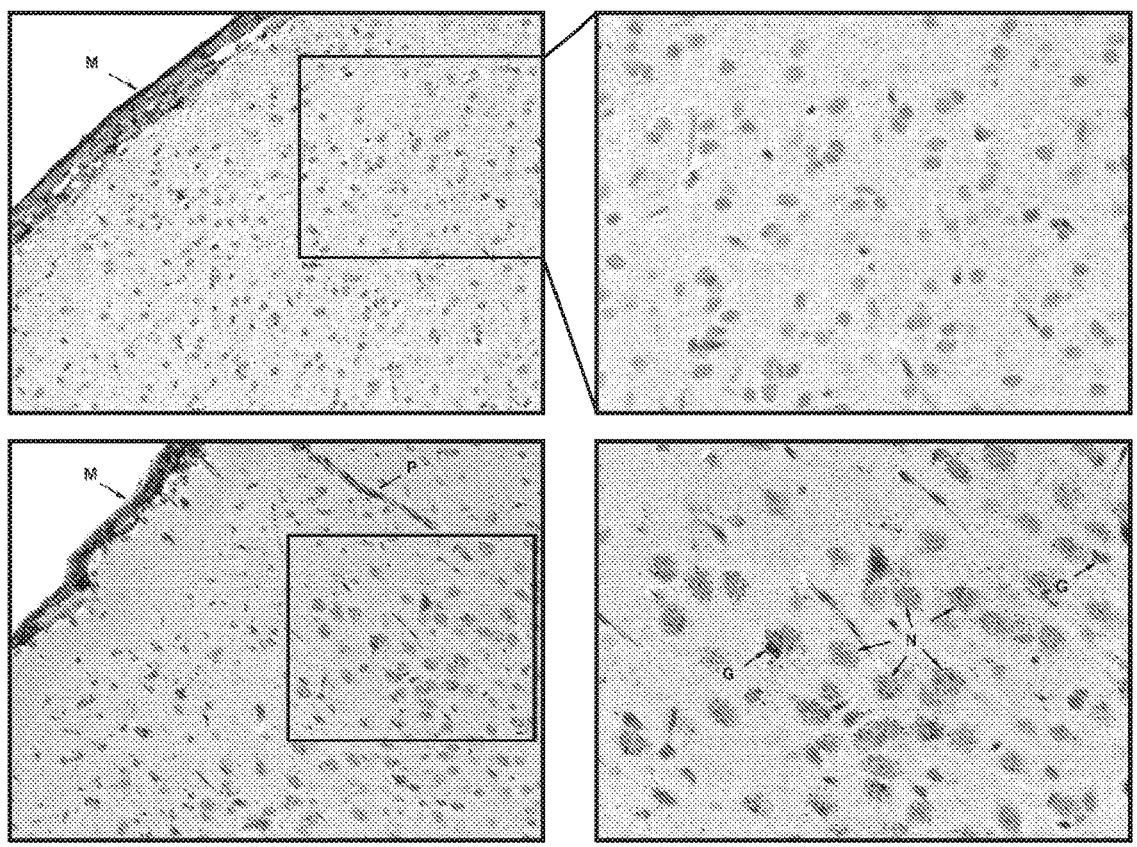

FIG. 177 depicts exemplary high power magnification of the selected slides from FIG. 176. Upper panel, in the rhNaglu treated wt cannulated rat, rhNaglu remained at the meninges (M), no positive staining found in the parenchyma of the brain. Lower panel, in Naglu-IGFII treated wt cannulated rat, extensive distribution was observed well into the parenchyma of the brain, and cellular uptake was observed in neurons and glial cells.

Figure 178:
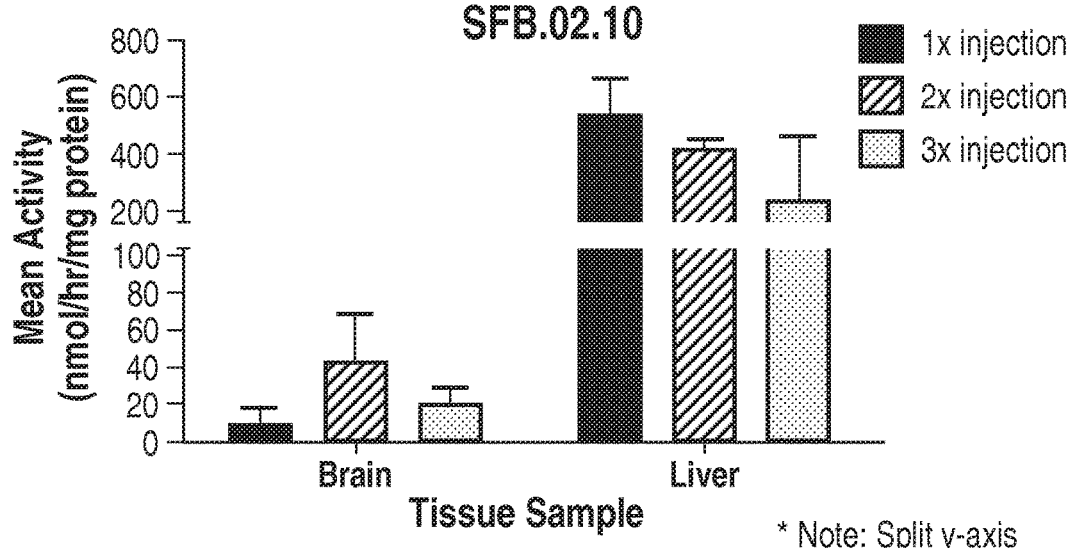

FIG. 178 illustrates exemplary Naglu activity in brain and liver 24 hr after last IT injection. Among the three treated groups, Naglu activity in the brain did not show significant differences, the same was true for the Naglu activity in the liver. This result indicated that the Naglu activity detected in the brain and liver was largely due to the last injection, which occurred 24 hr prior to sacrifice.

Figure 179:
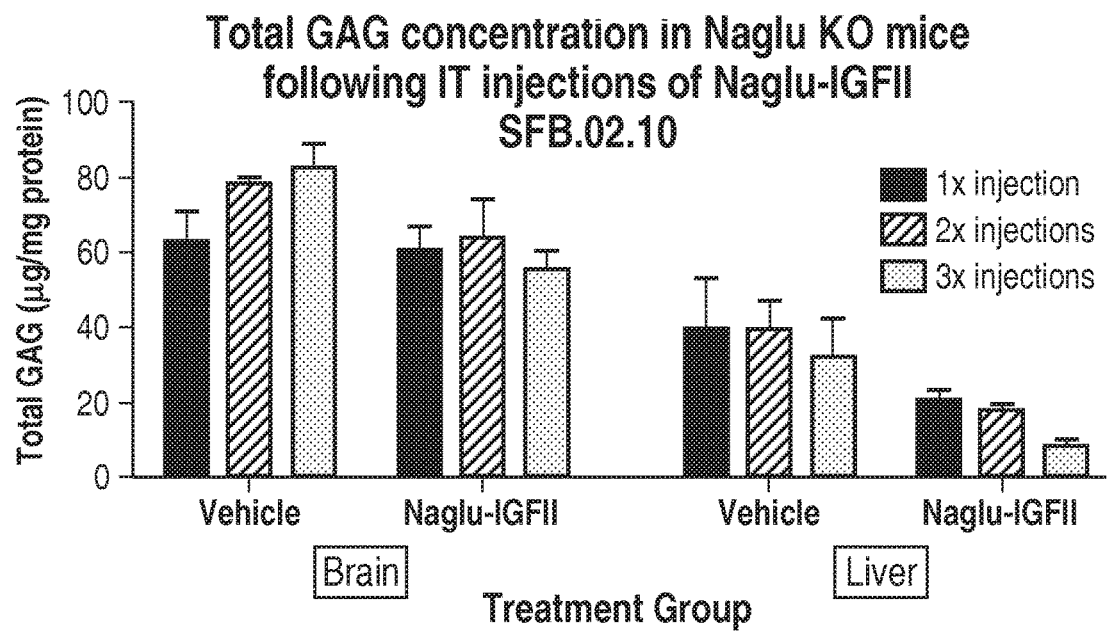

FIG. 179 illustrates exemplary total GAG level in the brain and liver after IT injection of Naglu-IGFII. Total GAG in the brain of vehicle treated Sanfilippo B mice exhibited progressive increases, a reflection of accumulative effect as the Sanfilippo B mice aging. A statistically significant reduction of GAG in the brain was observed in 3× injection group ($p<0.05$). Statistically significant reductions of GAG in liver were also observed in 2× and 3× injection groups ($p<0.05$).

The quicker and more drastic change of GAG level in liver than in the brain is a phenomenon that also has been observed in IT delivery of I2S for Hunter Syndrome.

Figure 180:
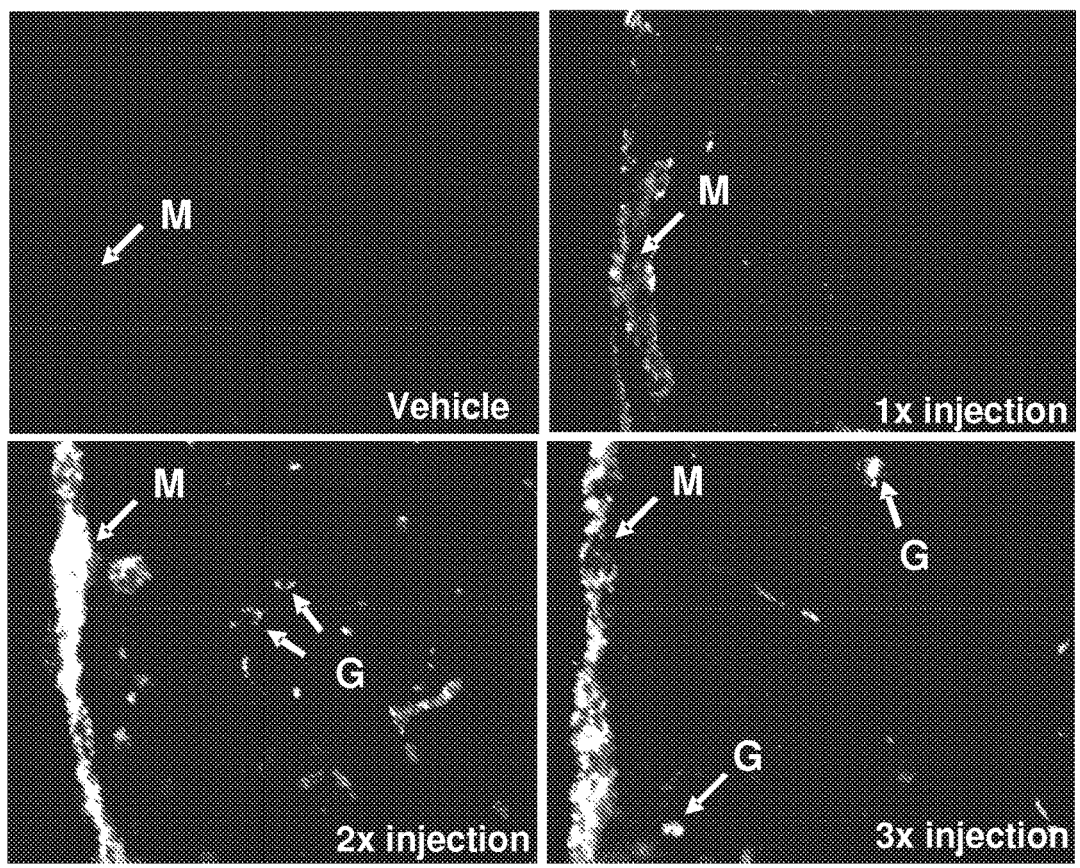

FIG. 180 depicts exemplary biodistribution of Naglu in the brain of Sanfilippo B mice after IT injection. Naglu immunofluorescent staining revealed the Naglu-IGFII protein on the meninges (M) and parenchyma of the brain. Cellular uptake was observed in the 2× and 3× injection groups. G: glial cells.

Figure 181:
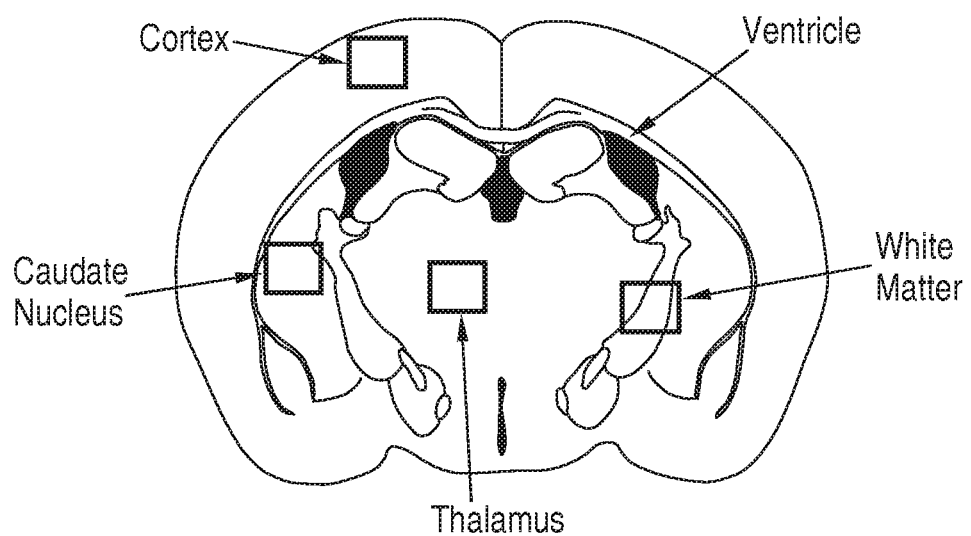

FIG. 181 is an exemplary illustration showing a coronal section of the mouse brain. Boxes indicate where the pictures for LAMP-1 immunostaining were taken. To demonstrate the extent of protein distribution and efficacy, cerebral cortex and subcortical tissues such as caudate nucleus, thalamus and white matter were selected for LAMP-1 immunostaining.

Figure 182:
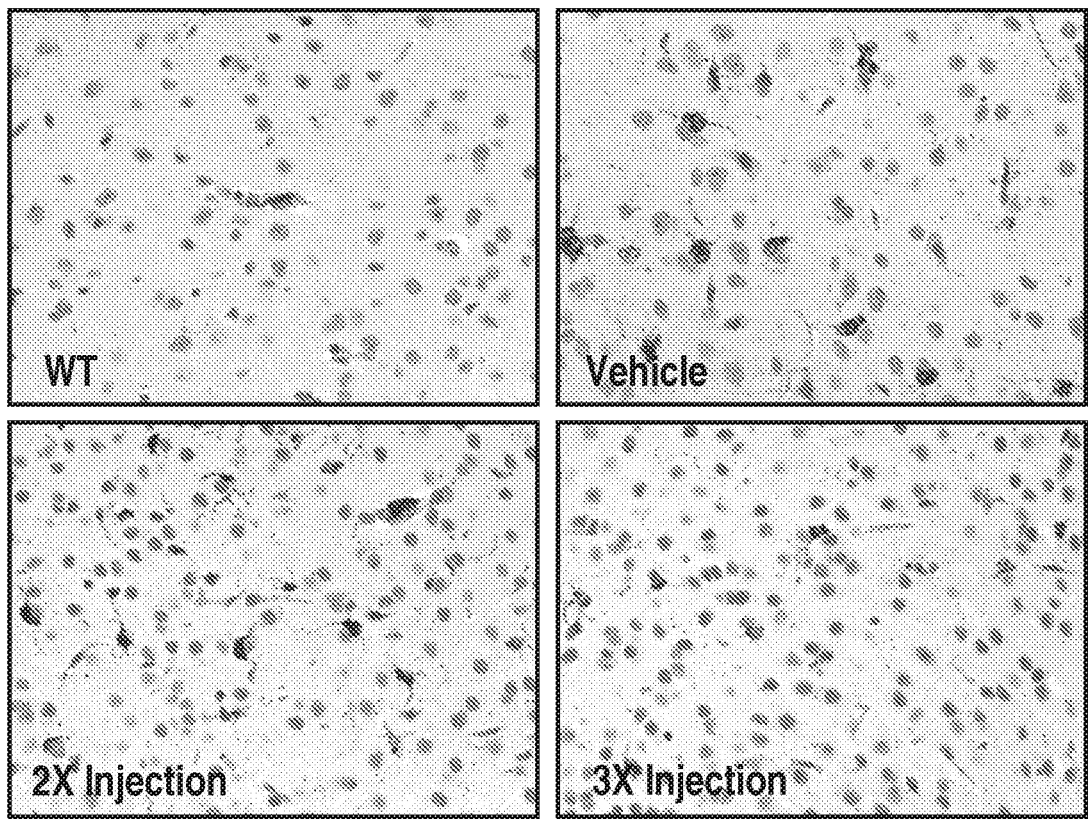

FIG. 182 is an exemplary illustration showing the LAMP-1 immunostaining of cerebral cortex at 40× magnification. Comparing to the brain of wild type mouse, increased lysosomal storage was observed in the brain of vehicle treated Sanfilippo B mouse, as seen by the increased LAMP-1 immunostaining positive spots. Reduction of lysosomal storage after Naglu-IGFII IT injection was evident by the reduced size of positive spots of 2× injection treated Sanfilippo B mouse brain, and the reduced size and number of positive spots of the 3× injection treated Sanfilippo B mouse brain.

Figure 183:
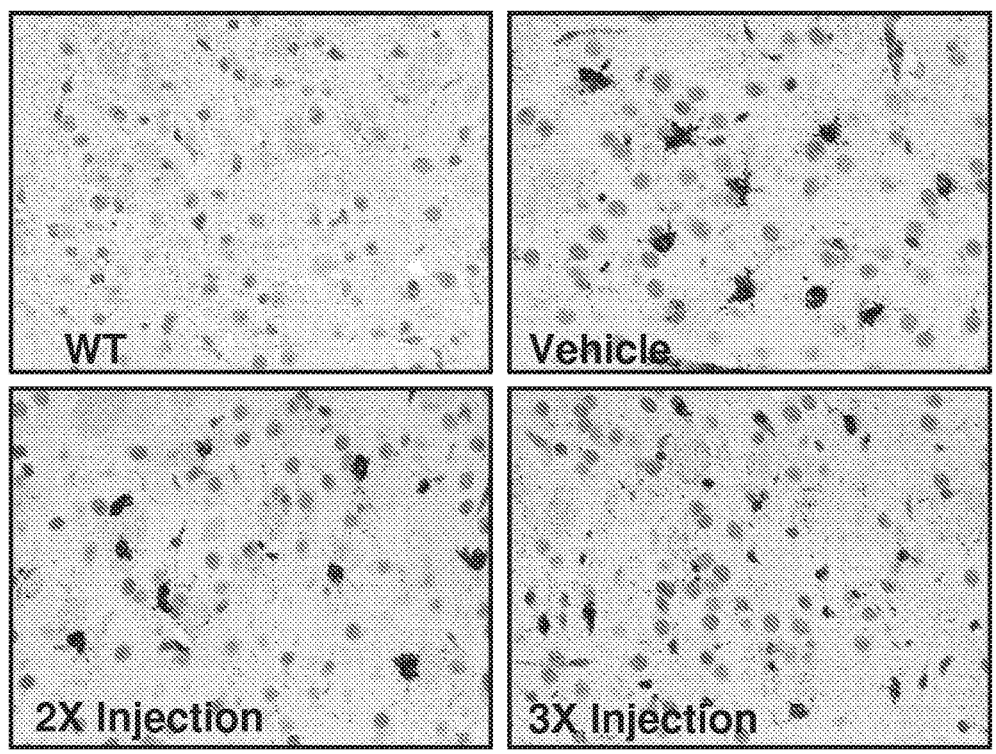

FIG. 183 is an exemplary illustration showing LAMP-1 immunostaining of the caudate nucleus, a subcortical nucleus (40×). Similar to what was seen in the cerebral cortex, increased lysosomal storage was observed in the brain of vehicle treated Sanfilippo B mouse, as seen by the increased LAMP-1 immunostaining positive spots. Reduction of lysosomal storage after Naglu-IGFII IT injection was evident by the reduced size of positive spots of 2× injection treated Sanfilippo B mouse brain and by the reduced size and number of positive spots of the 3× injection treated Sanfilippo B mouse brain.

Figure 184:
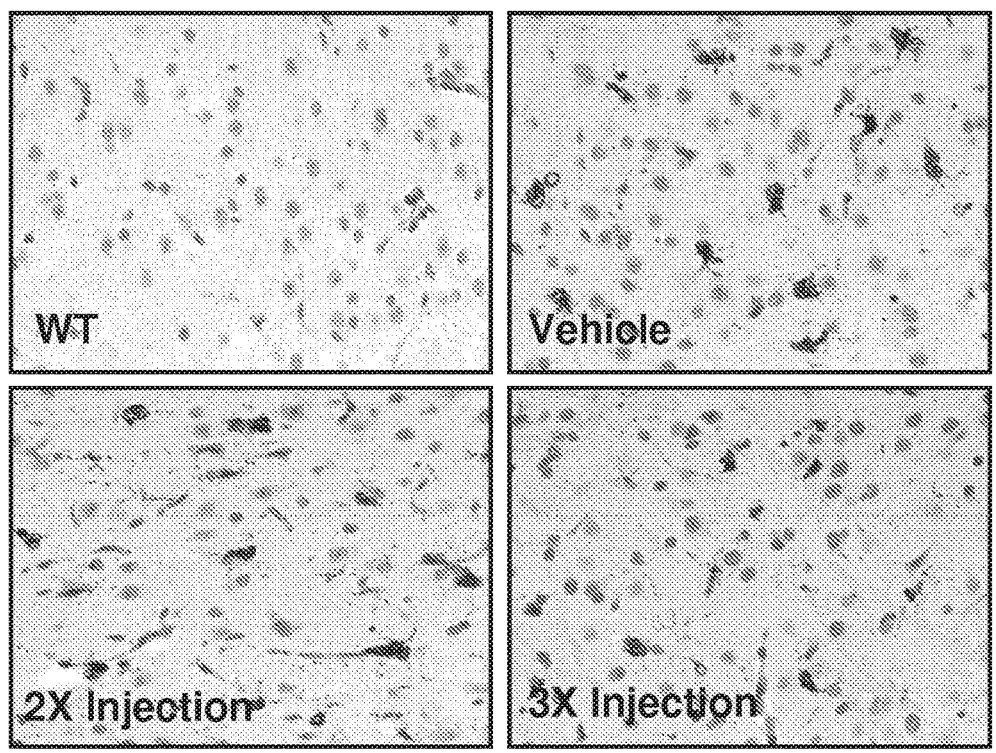

FIG. 184 is an exemplary illustration showing LAMP-1 immunostaining of the thalamus, a diencephalic nuclei (40×). Reduction of lysosomal storage after Naglu-IGFII IT injection was evident by the reduced size of positive spots of 2× injection treated Sanfilippo B mouse brain and by the reduced size and number of positive spots of the 3× injection treated Sanfilippo B mouse brain.

Figure 185:
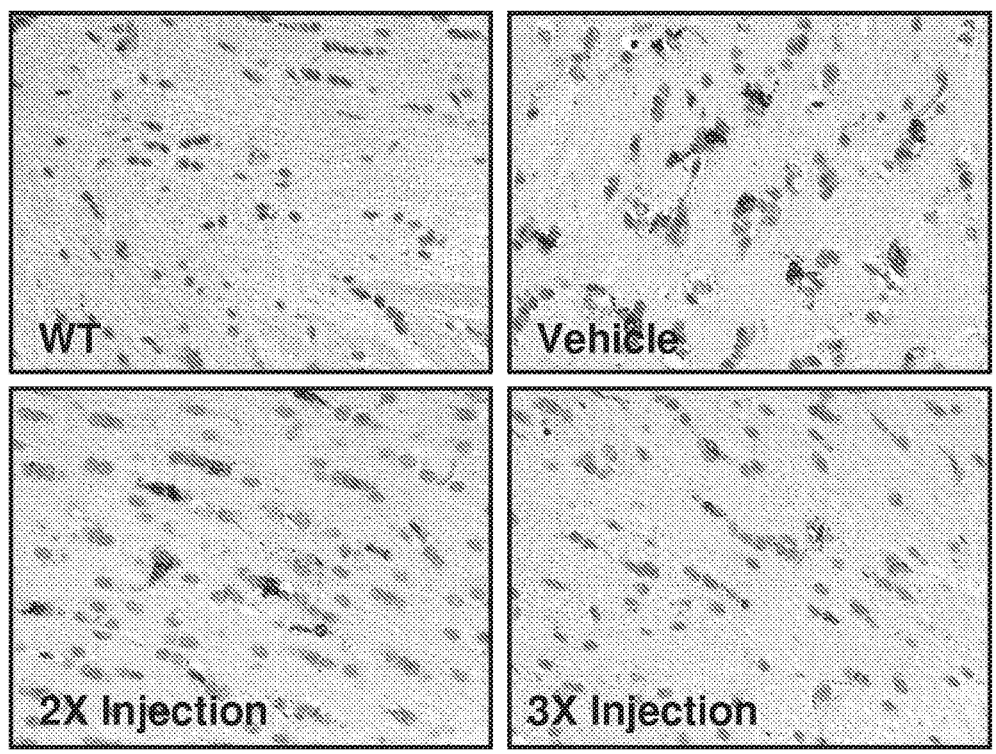

FIG. 185 is an exemplary illustration showing LAMP-1 immunostaining of white matter (40×). The longitudinal track of neuron axon fibers distinguishes the white matter from grey matters presented in FIGS. 181-184. Nonetheless, the same pattern of increases of lysosomal storage could be seen in vehicle treated Sanfilippo B mouse's brain when compared to the wild type mouse. Reduction of lysosomal storage after Naglu-IGFII IT injection was evident by the reduced size and reduced number of positive spots in the 2× and 3× injection treated Sanfilippo B mouse brain.

Figure 186:
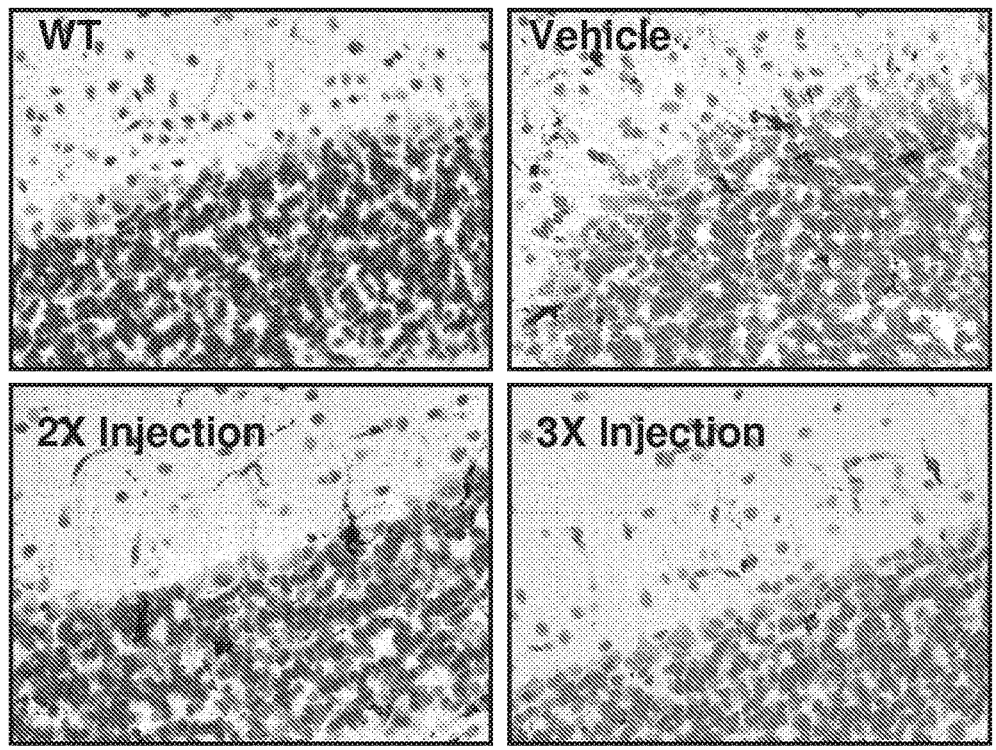

FIG. 186 is an exemplary illustration showing LAMP-1 immunostaining of the cerebellar cortex. The morphology of cerebellar cortex was evident by the densely populated granular neurons, the hypocellular Molecular layer, and the single layer of Purkinje neurons between the granular neurons and the molecular layer. Purkinje neurons were identified by the large cytoplasm and occasional dendrites protruding into the Molecular layer.

Figure 187:
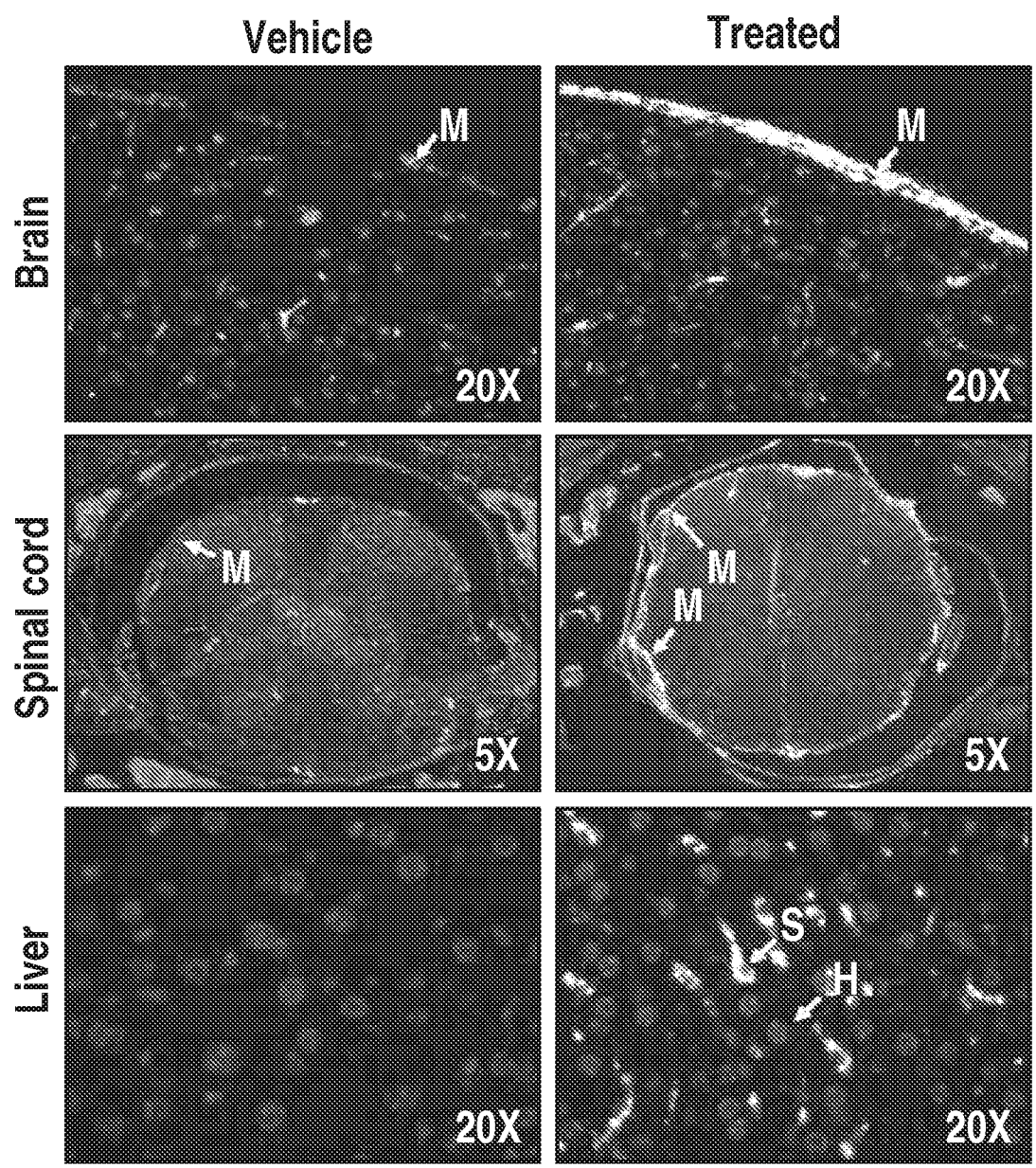

FIG. 187 is an exemplary illustration showing Naglu staining in the brain, spinal cord and liver. In the brain and spinal cord, injected Naglu was detected in meninges (M) only by IHC and no Naglu positive staining was detected in any other regions. In the liver, sinunoidal cells (S) were Naglu positive and no Naglu uptake was found in hepatocytes (H).

Figure 188:
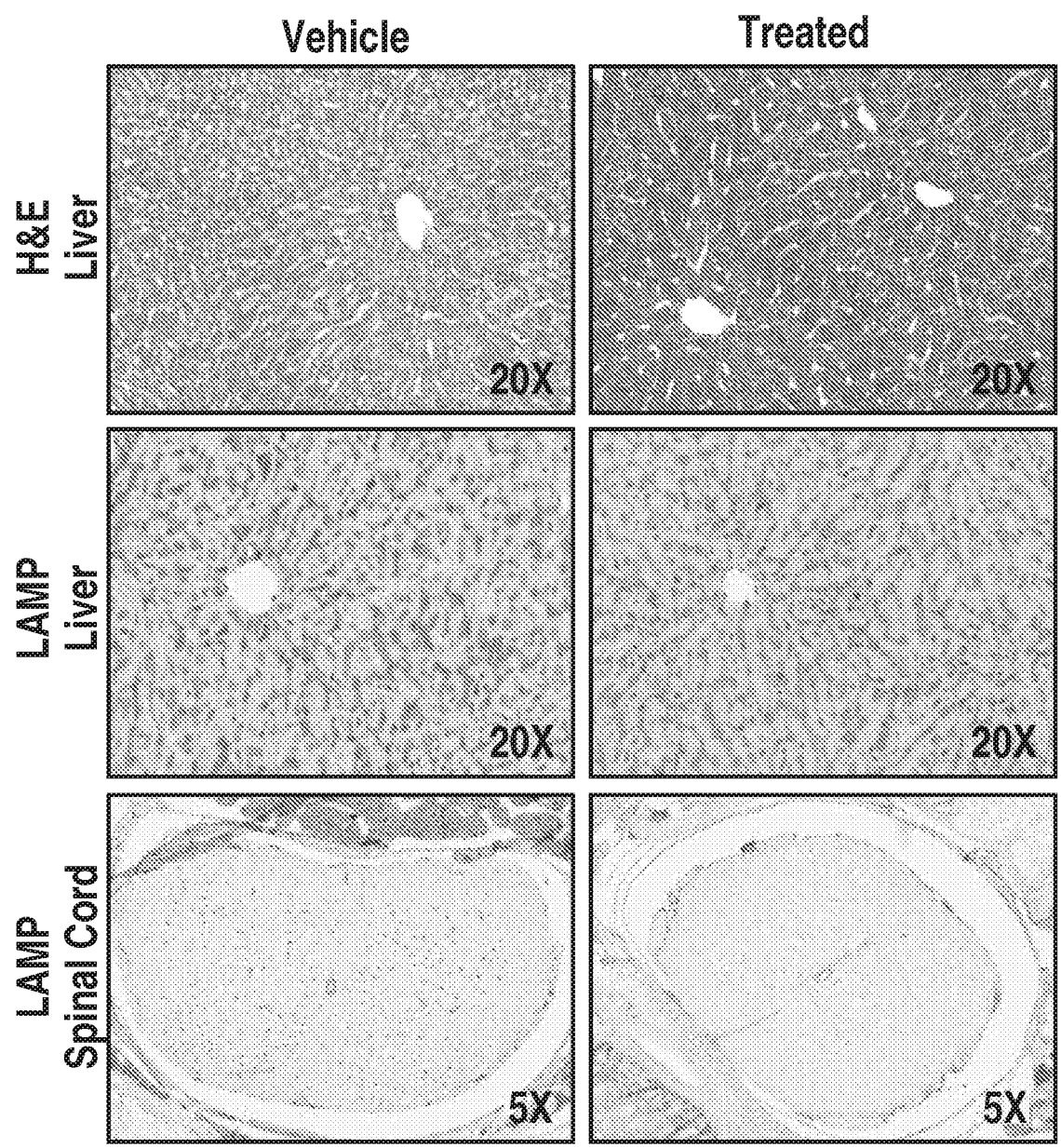

FIG. 188 is an exemplary illustration showing LAMP immunostaining and H & E staining of the liver and spinal cord. Compared with the vehicle animals, LAMP staining was decreased throughout in both livers and spinal cords treated with Naglu. H & E staining showed that cellular vacuolation in hepatocytes was reduced in the treated group compared with vehicle treated animals.

Figure 189A:
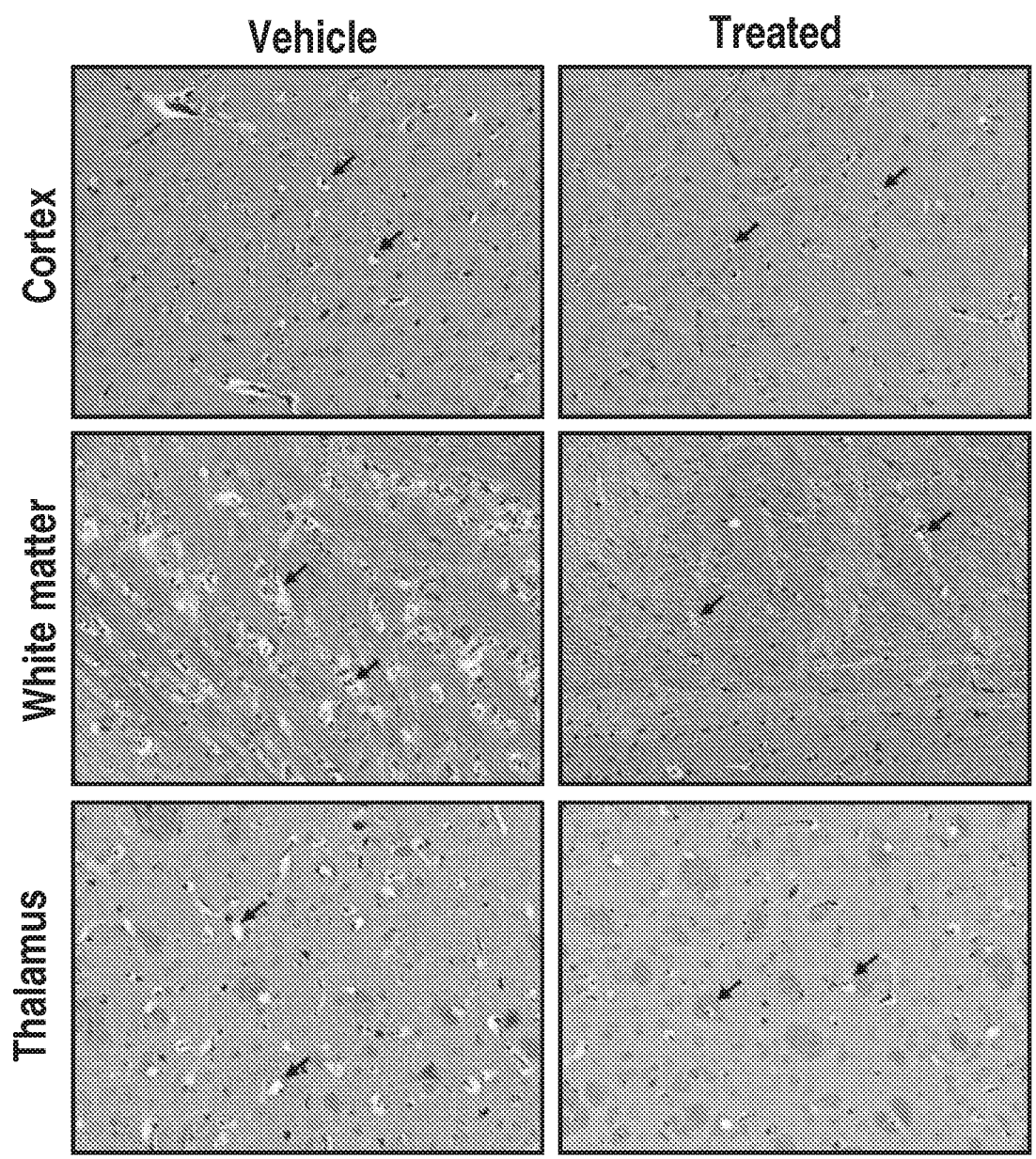
Figure 189B:
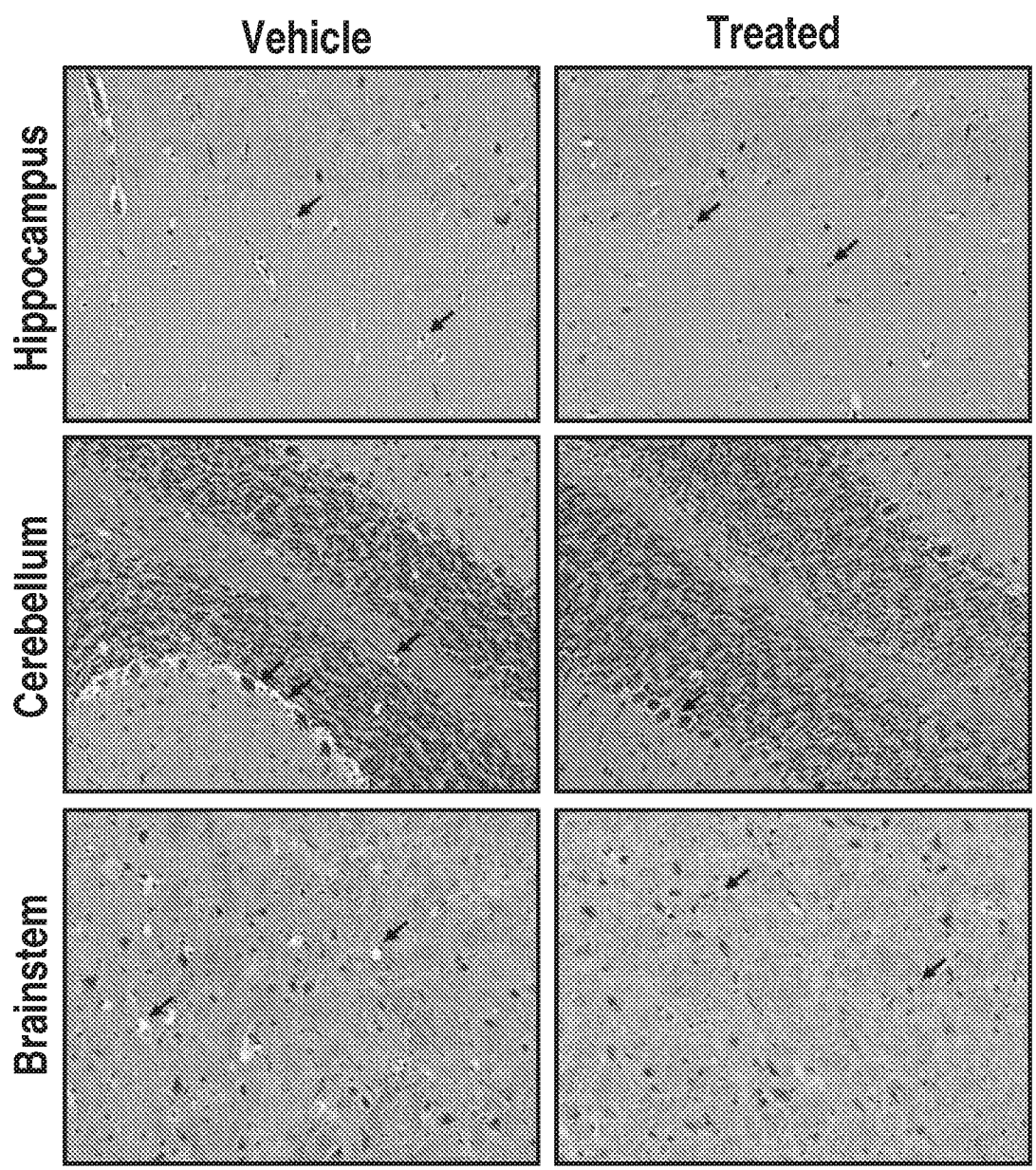

FIG. 189A and FIG. 189B is an exemplary illustration showing H & E staining of the brain and morphology improvement of the brain after 6 every other week (EOW) IT injections of Naglu for 3 months. In the treated brain, the cellular vacuolation (arrows) in all examined regions decreased compared with the vehicle group.

Figure 190A:
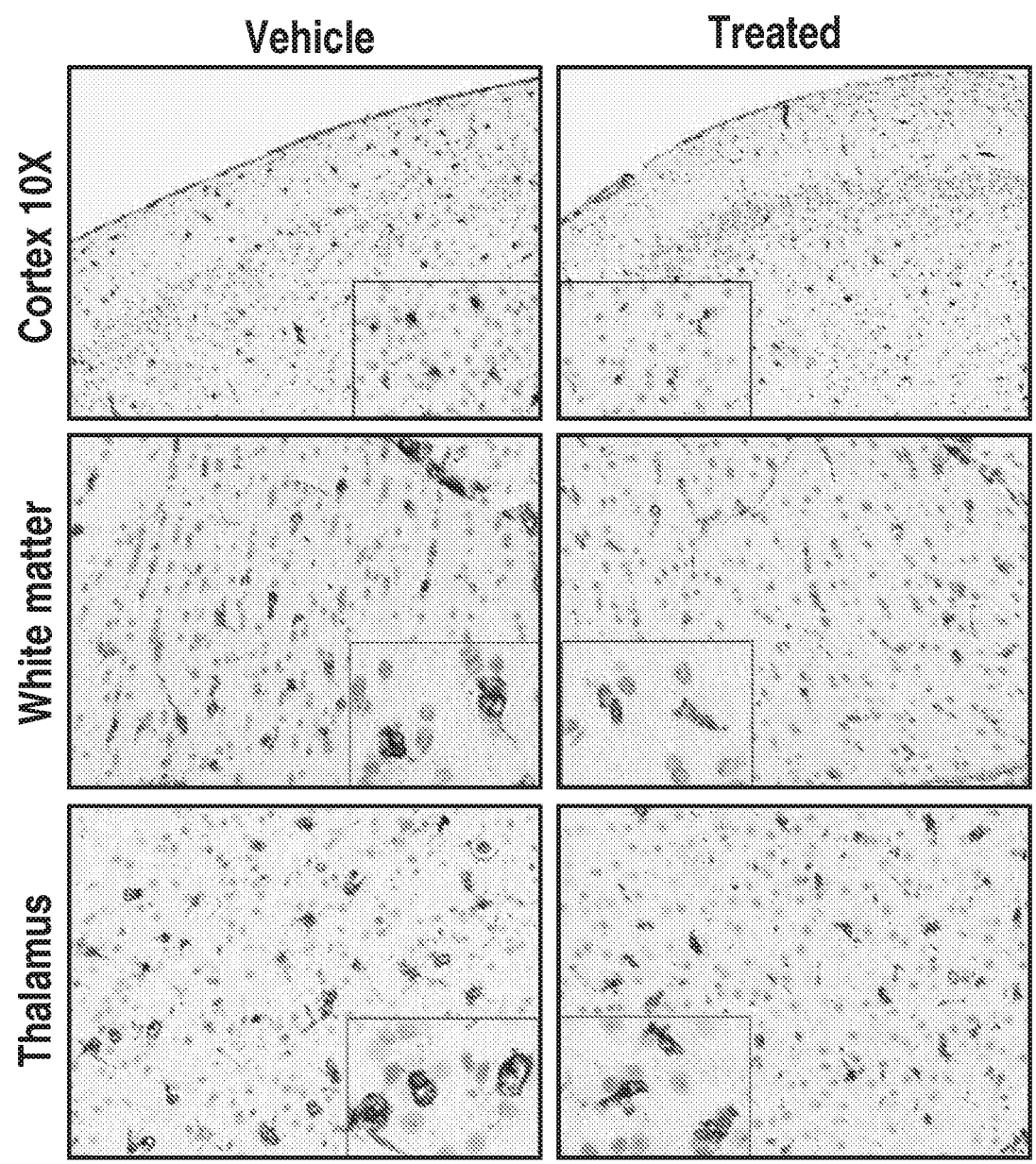
Figure 190B:
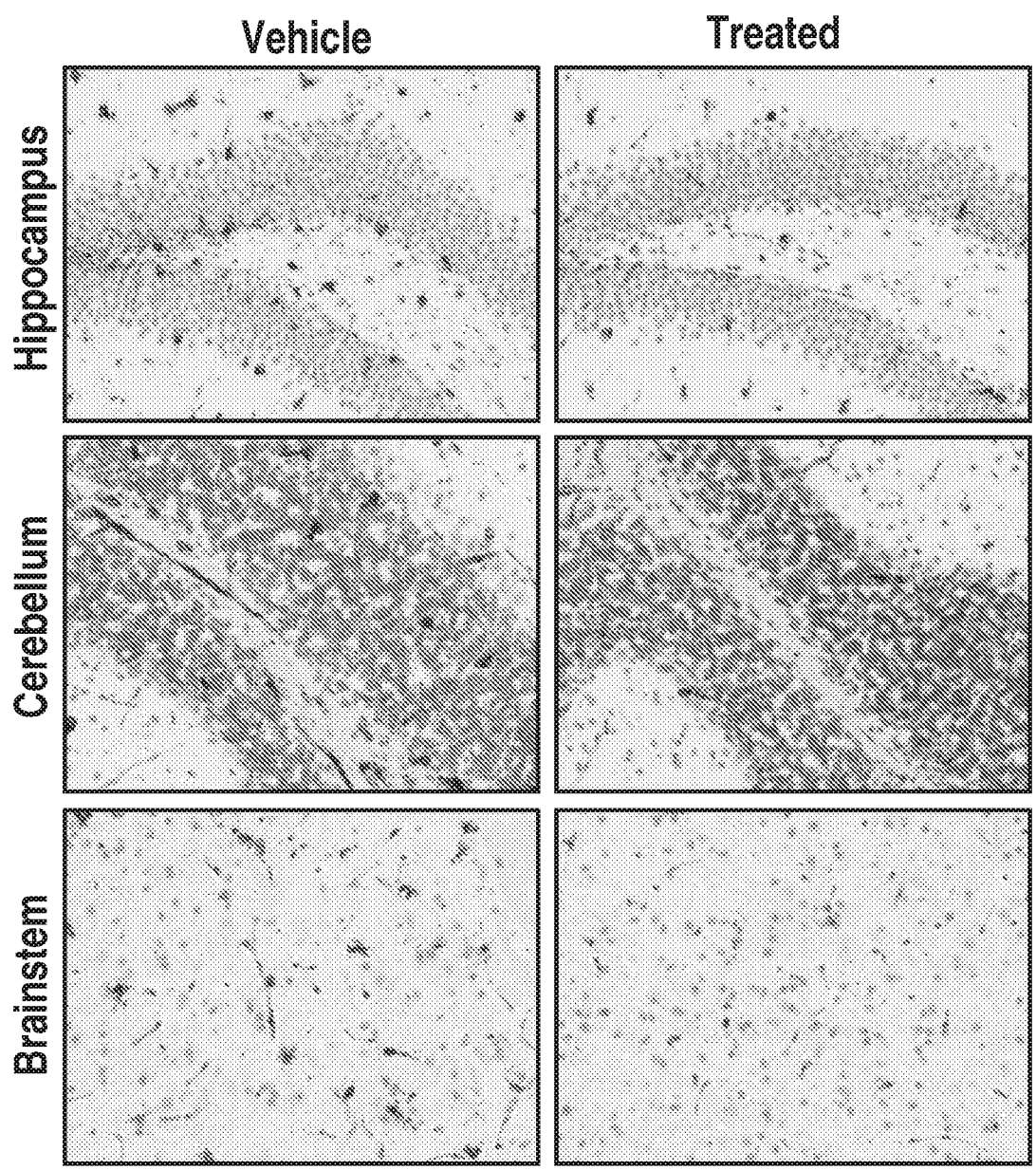

FIG. 190A and FIG. 190B are exemplary illustrations showing LAMP immunostaining in various brain regions after 6 IT Naglu injections for 3 months. Compared with the vehicle treated group, Naglu IT administration to Sanfilippo B mice resulted in a reduction of lysosomal activity in all examined regions revealed by LAMP immunostaining. This reduction was characterized by the decrease in the number of LAMP positive cells, smaller cell size and lighter staining. A marked reduction was found in the cerebellum and brainstem, which are located in the caudate part of the brain close to the spinal cord, compared with other brain regions. A clear reduction was also found in the deep brain regions, including the white matter, hippocampus, and thalamus.

Figure 191A:
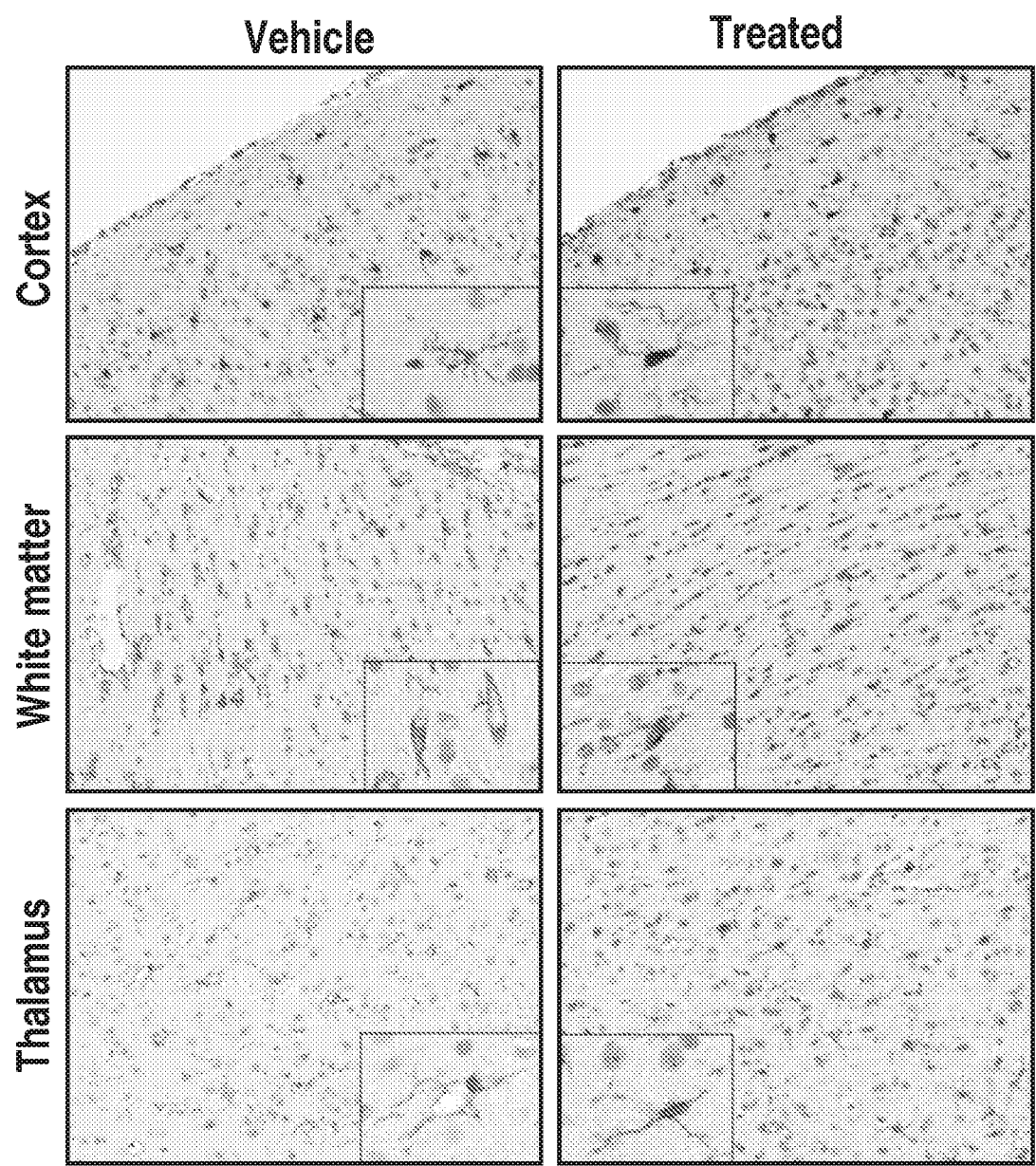
Figure 191B:
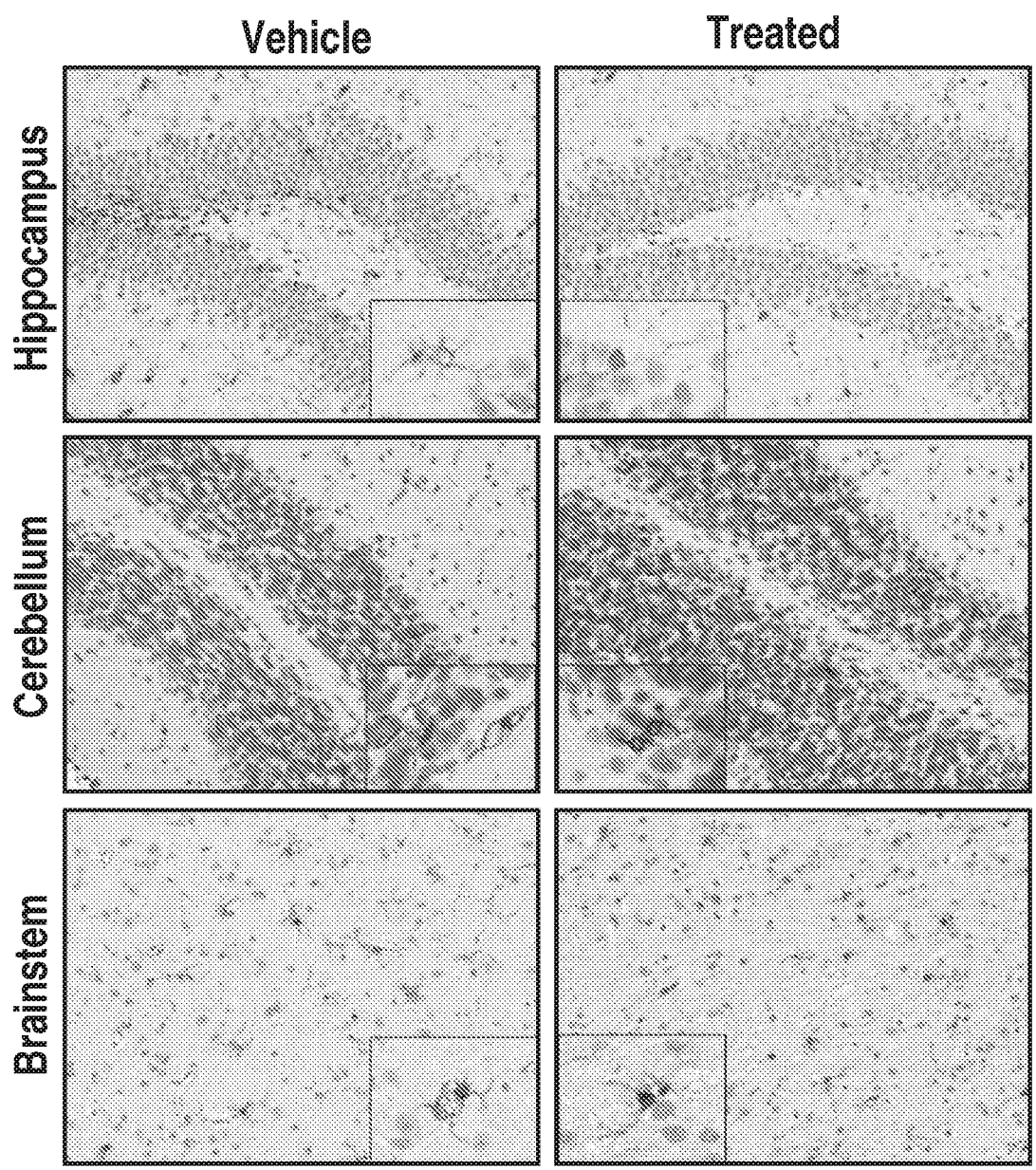

FIG. 191A and FIG. 191B are exemplary illustrations showing Iba IHC in various brain regions after 6 IT Naglu injections for 3 months, which revealed activation of microglial cells. Compared with vehicle treated group, no decrease in the number of positive cells and staining intensity was observed in the Naglu treated group. However, the cellular morphology of positive microglial cells changed with reduced cell size in all examined brain regions compared to large and vacuolated ones in the vehicle group (inserts).

Figure 192A:
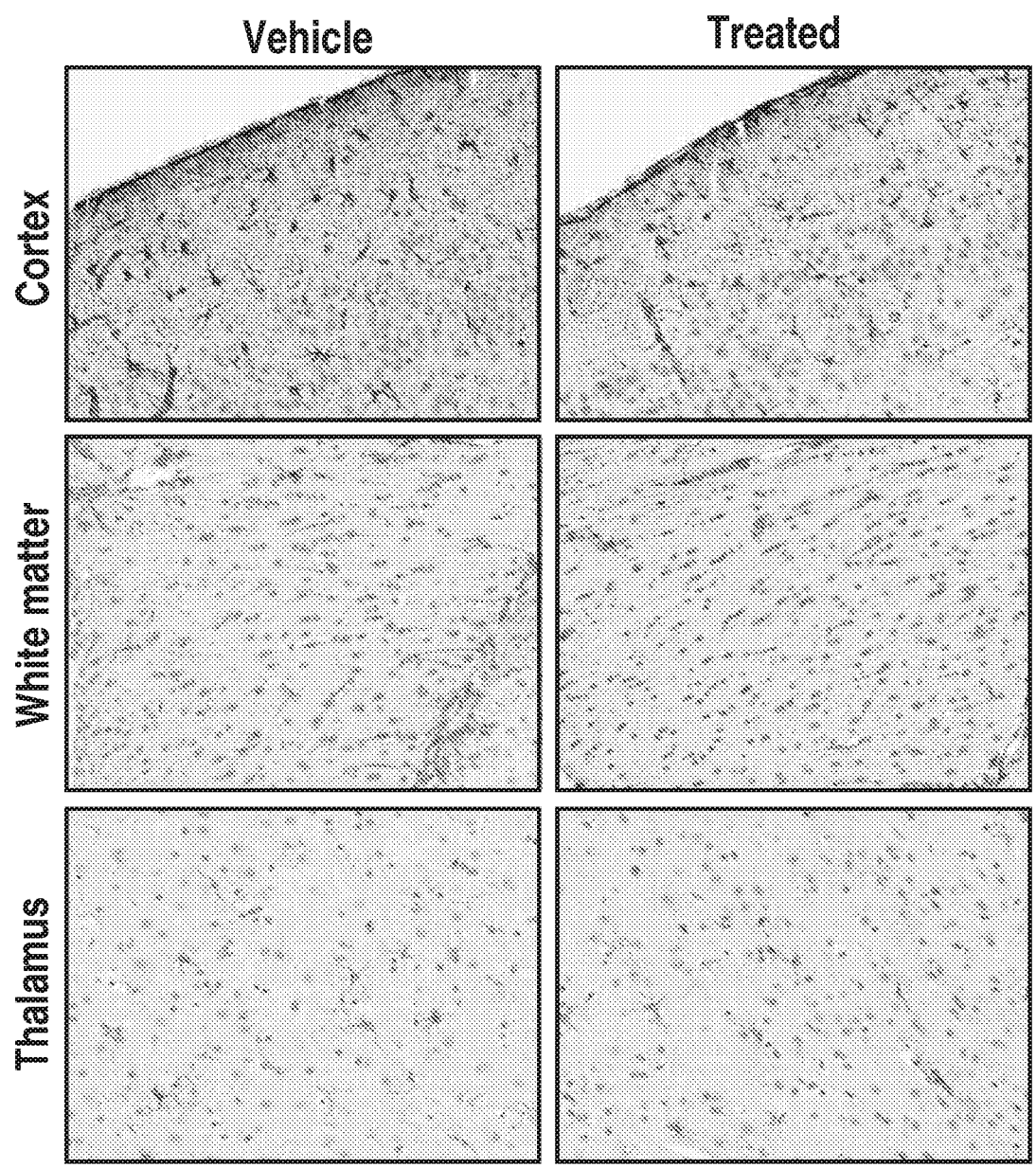
Figure 192B:
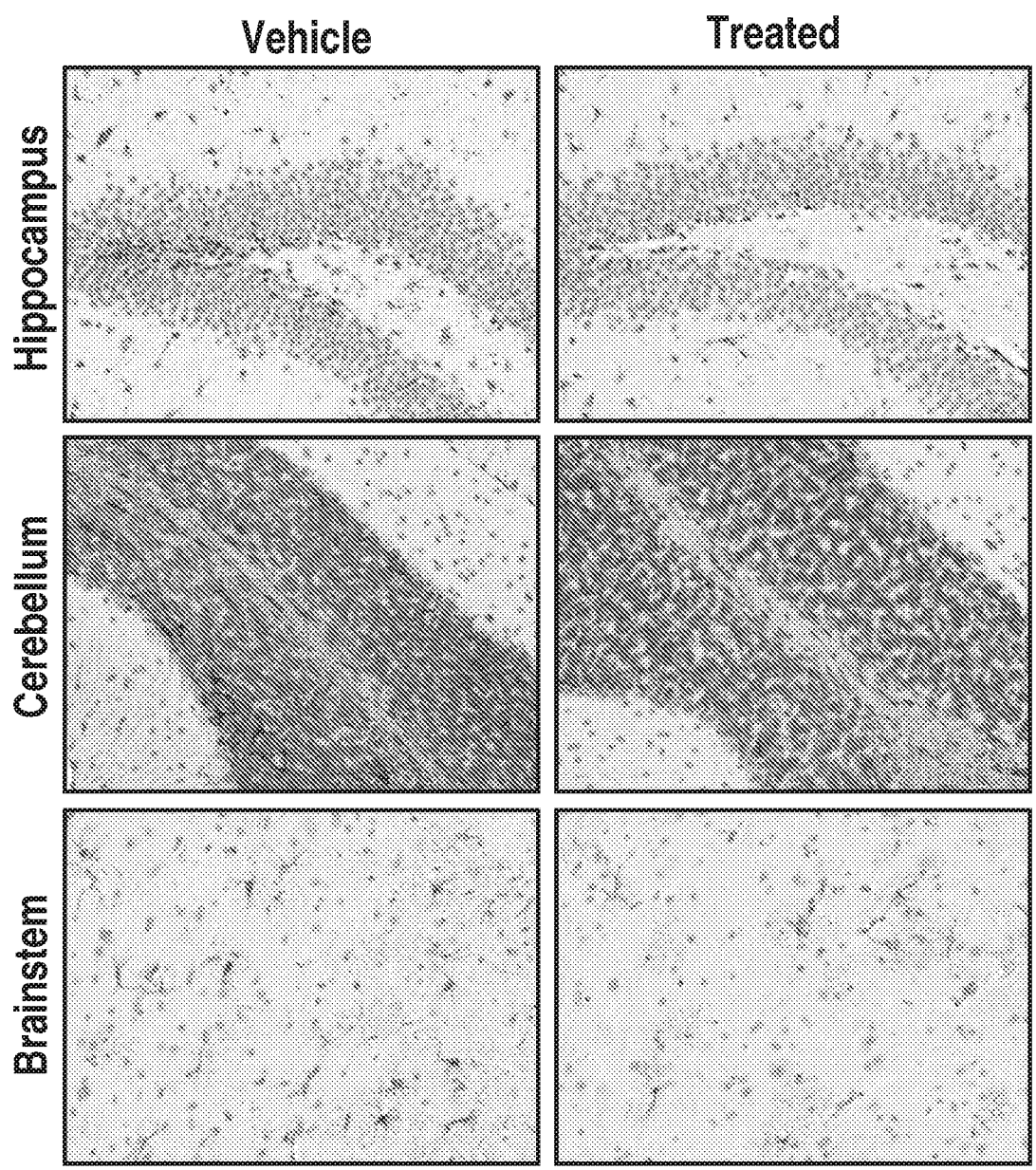

FIG. 192A and FIG. 192B are exemplary illustrations showing GFAP IHC in various brain regions after 6 IT Naglu injections for 3 months, which revealed astrocytic activation. Compared with the vehicle treated group, GFAP positive staining was decreased in the cerebellum and brainstem, and slightly decreased in other examined regions.

DEFINITIONS

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme sub startes) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmalarity consistent with the cerebrospinal fluid. Synthetic CSF is also referred to as artifical CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo syndrome type B). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides, among other things, improved methods for effective direct delivery of a therapeutic agent to the central nervous system (CNS). As discussed above, the present invention is based on unexpected discovery that a replacement enzyme for a lysososmal storage disease can be directly introduced into the cerebrospinal fluid (CSF) of a subject in need of treatment at a high concentration without inducing substantial adverse effects in the subject. More surprisingly, the present inventors found that the replacement enzyme may be delivered in a simple saline or buffer-based formulation, without using synthetic CSF. Even more unexpectedly, intrathecal delivery according to the present invention does not result in substantial adverse effects, such as severe immune response, in the subject. Therefore, in some embodiments, intrathecal delivery according to the present invention may be used in absence of concurrent immunosuppressant therapy (e.g. without induction of immune tolerance by pre-treatment or pre-conditioning).

In some embodiments, intrathecal delivery according to the present invention permits efficient diffusion across various brain tissues resulting in effective delivery of the replacement enzyme in various target brain tissues in surface, shallow and/or deep brain regions. In some embodiments, intrathecal delivery according to the present invention resulted in sufficient amount of replacement enzymes entering the peripheral circulation. As a result, in some cases, intrathecal delivery according to the present invention resulted in delivery of the replacement enzyme in peripheral tissues, such as liver, heart, and kidney. This discovery is unexpected and can be particular useful for the treatment of lysosomal storage diseases that have both CNS and peripheral components, which would typically require both regular intrathecal administration and intravenous administration. It is contemplated that intrathecal delivery according to the present invention may allow reduced dosing and/or frequency of iv injection without compromising therapeutic effects in treating peripheral symptoms.

The present invention provides various unexpected and beneficial features that allow efficient and convenient delivery of replacement enzymes to various brain target tissues, resulting in effective treatment of lysosomal storage diseases that have CNS indications.

Various aspects of the invention are described in detail in the following sections. The use of sections is not meant to limit the invention. Each section can apply to any aspect of the invention. In this application, the use of "or" means "and/or" unless stated otherwise.

Lysosomal Storage Diseases and Replacement Enzymes

Inventive methods according to the present may be used to treat any lysosomal storage diseases, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome (type A, B, C or D), mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

In some embodiments, lysosomal storage diseases to be treated using inventive methods of the present invention include Hunters Syndrome, metachromatic leukodystrophy (MLD) disease, Sanfilippo syndrome type A, Sanfilippo syndrome type B, and globoid cell leukodystrophy (GLD) disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in the Table below:

TABLE 1

| Disease Name | Enzyme Deficiency | Substance Stored |
| --- | --- | --- |
| Pompe Disease | Acid-α1, 4-Glucosidase | Glycogen α1-4 linked Oligosaccharides |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo syndrome type A (MPS IIIA) | Heparan N-Sulfatase | Heparan Sulfate |
| Sanfilippo syndrome type B (MPS IIIB) | α-N-Acetylglucosaminidase | Heparan Sulfate |
| Sanfilippo syndrome type C (MPS IIIC) | Acetyl-CoA-Glucosaminide Acetyltransferase | Heparan Sulfate |
| Sanfilippo syndrome type D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |

TABLE 1-continued

| Disease Name | Enzyme Deficiency | Substance Stored |
|---|---|---|
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

Replacement Enzymes

Inventive methods according to the present invention may be used to deliver any replacement enzymes. As used herein, replacement enzymes suitable for the present invention may include any enzyme that can act to replace at least partial activity of the deficient or missing lysosomal enzyme in a lysosomal storage disease to be treated. In some embodiments, a replacement enzyme is capable of reducing accumulated substance in lysosomes or that can rescue or ameliorate one or more lysosomal storage disease symptoms.

In some embodiments, a suitable replacement enzyme may be any lysosomal enzyme known to be associated with the lysosomal storage disease to be treated. In some embodiments, a suitable replacement enzyme is an enzyme selected from the enzyme listed in Table 1 above. In some embodiments, a replacement enzyme suitable for the present invention is iduronate-2-sulfatase (I2S), arylsulfatase A (ASA), heparan N-sulfatase (HNS), alpha-N-acetylglucosaminidase (Naglu) or β-galactosidase (GLC).

In some embodiments, a replacement enzyme suitable for the invention may have a wild-type or naturally occurring sequence. In some embodiments, a replacement enzyme suitable for the invention may have a modified sequence having substantial homology or identify to the wild-type or naturally-occurring sequence (e.g., having at least 70%, 75%, 80%, 85%, 90%, 95%, 98% sequence identity to the wild-type or naturally-occurring sequence).

A replacement enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contains a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In some embodiments, replacement enzymes for use in the present invention may be conjugated or fused to a lysosomal targeting moiety that is capable of binding to a receptor on the surface of brain cells. A suitable lysosomal targeting moiety can be IGF-I, IGF-II, RAP, p9'7, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

Intrathecal Delivery

According to the present invention, a replacement enzyme is delivered to the CNS. In some embodiments, a replacement enzyme is delivered to the CNS by administering into the cerebrospinal fluid (CSF) of a subject in need of treatment. In some embodiments, intrathecal administration is used to deliver a desired replacement enzyme into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Stable Formulations for IT Delivery

In some embodiments, desired enzymes are delivered in stable formulations for intrathecal delivery. Certain embodiments of the invention are based, at least in part, on the discovery that various formulations disclosed herein facilitate the effective delivery and distribution of one or more therapeutic agents (e.g., enzymes) to targeted tissues, cells and/or organelles of the CNS. Among other things, formulations described herein are capable of solubilizing high concentrations of therapeutic agents (e.g., proteins or enzymes) and are suitable for the delivery of such therapeutic agents to the CNS of subjects for the treatment of diseases having a CNS component and/or etiology. The compositions described herein are further characterized by improved stability and improved tolerability when administered to the CNS of a subject (e.g., intrathecally) in need thereof.

Before the present invention, traditional unbuffered isotonic saline and Elliott's B solution, which is artificial CSF, were typically used for intrathecal delivery. A comparison depicting the compositions of CSF relative to Elliott's B solution is included in Table 2 below. As shown in Table 2, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible with the formulations intended to deliver some therapeutic agents, and in particular proteins or enzymes. For example, the calcium salts present in Elliott's B Solution are capable of mediating protein precipitation and thereby reducing the stability of the formulation.

TABLE 2

| Solution | $Na^+$ mEq/L | $K^+$ mEq/L | $Ca^{++}$ mEq/L | $Mg^{++}$ mEq/L | $HCO_3^-$ mEq/L | $Cl^-$ mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

Thus, in some embodiments, formulations suitable for intrathecal delivery according to the present invention are not synthetic or artificial CSF.

In some embodiments, formulations for intrathecal delivery have been formulated such that they are capable of stabilizing, or alternatively slowing or preventing the degradation, of one or more therapeutic agents formulated therewith (e.g., recombinant proteins). As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent is of particular importance. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In some embodiments, therapeutic agents (e.g., desired enzymes) are soluble in formulations of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Thus, suitable formulations for intrathecal administration may contain a therapeutic agent (e.g., enzyme) of interest at various concentrations. In some embodiments, suitable formulations may contain a protein or enzyme of interest at a concentration up to about 300 mg/ml (e.g., up to about 250 mg/ml, up to 200 mg/ml, up to 150 mg/ml, up to 100 mg/ml, up to 90 mg/ml, up to 80 mg/ml, up to 70 mg/ml, up to 60 mg/ml, up to 50 mg/ml, up to 40 mg/ml, up to 30 mg/ml, up to 25 mg/ml, up to 20 mg/ml, up to 10 mg/ml). In some embodiments, suitable formulations may contain a protein or enzyme of interest at a concentration ranging between about 0-300 mg/ml (e.g., about 1-250 mg/ml, about 1-200 mg/ml, about 1-150 mg/ml, about 1-100 mg/ml, about 10-100 mg/ml, about 10-80 mg/ml, about 10-70 mg/ml, about 1-60 mg/ml, about 1-50 mg/ml, about 10-150 mg/ml, about 1-30 mg/ml). In some embodiments, formulations suitable for intrathecal delivery may contain a protein of interest at a concentration of approximately 1 mg/ml, 3 mg/ml, 5 mg/ml, 10 mg/ml, 15 mg/ml, 20 mg/ml, 25 mg/ml, 50 mg/ml, 75 mg/ml, 100 mg/ml, 150 mg/ml, 200 mg/ml, 250 mg/ml or 300 mg/ml.

In some embodiments, isotonic solutions are used. In some embodiments, slightly hypertonic solutions (e.g., up to 300 mM (e.g., up to 250 mM, 200 mM, 175 mM, 150 mM, 125 mM) sodium chloride in 5 mM sodium phosphate at pH 7.0) and sugar-containing solutions (e.g., up to 3% (e.g., up to 2.4%, 2.0%, 1.5%, 1.0%) sucrose in 5 mM sodium phosphate at pH 7.0) have been demonstrated to be well tolerated in monkeys. In some embodiments, a suitable CNS bolus formulation composition is saline (e.g., 150 mM NaCl in water).

Many therapeutic agents, and in particular the proteins and enzymes of the present invention, require controlled pH and specific excipients to maintain their solubility and stability in the pharmaceutical compositions of the present invention. Table 3 below identifies certain exemplary aspects of protein formulations considered to be important for maintaining the solubility and stability of the protein therapeutic agents of the present invention.

TABLE 3

| Parameter | Typical Range/Type | Rationale |
|---|---|---|
| pH | 5 to 7.5 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

The pH of the pharmaceutical composition is an additional factor which is capable of altering the solubility of a therapeutic agent (e.g., an enzyme or protein) in an aqueous pharmaceutical composition. In some embodiments, pharmaceutical compositions of the present invention contain one or more buffers. In some embodiments, compositions according to the invention contain an amount of buffer sufficient to maintain the optimal pH of said composition between about 4.0-8.0, between about 5.0-7.5, between about 5.5-7.0, between about 6.0-7.0 and between about 6.0-7.5. In other embodiments, the buffer comprises up to about 50 mM (e.g., up to about 45 mM, 40 mM, 35 mM, 30 mM, 25 mM, 20 mM, 15 mM, 10 mM, 5 mM) of sodium phosphate. Suitable buffers include, for example acetate, succinate, citrate, phosphate, other organic acids and tris (hydroxymethyl) aminomethane ("Tris"). Suitable buffer concentrations can be from about 1 mM to about 100 mM, or from about 3 mM to about 20 mM, depending, for example, on the buffer and the desired isotonicity of the formulation. In some embodiments, a suitable buffering agent is present at a concentration of approximately 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM.

In some embodiments, formulations contain an isotonicity agent to keep the formulations isotonic. As used in connection with IT delivery, by "isotonic" is meant that the formulation of interest has essentially the same osmolarity as human CSF. Isotonic formulations will generally have an osmolarity from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight.

In some embodiments, formulations may contain a stabilizing agent to protect the protein. Typically, a suitable stabilizing agent is a non-reducing sugar such as sucrose, raffinose, trehalose, or amino acids such as glycine, arginine and methionine. The amount of stabilizing agent in a formulation is generally such that the formulation will be isotonic. However, hypertonic formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectants.

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes to subjects suffering from lysosomal storage disorders.

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONA-QUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc.

In some embodiments, suitable formulations may further include one or more bulking agents, in particular, for lyophilized formylations. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Formulations in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

In some embodiments, formulations according to the present invention are in a liquid or aqueous form. In some embodiments, formulations of the present invention are lyophilized. Such lyophilized formulations may be reconstituted by adding one or more diluents thereto prior to administration to a subject. Suitable diluents include, but are not limited to, sterile water, bacteriostatic water for injection and sterile saline solution. Preferably, upon reconstitution, the therapeutic agent contained therein is stable, soluble and demonstrates tolerability upon administration to a subject The pharmaceutical compositions of the present invention are characterized by their tolerability. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Device for Intrathecal Delivery

Figure 1:
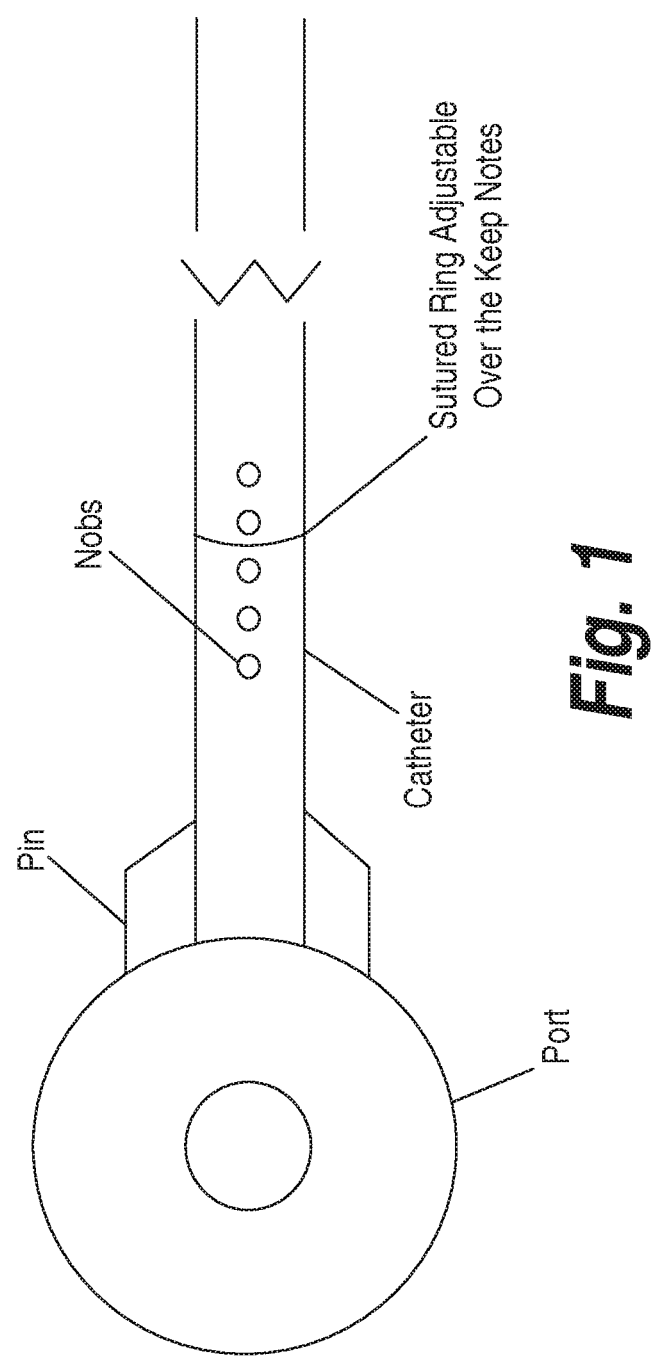
FIG. 1 illustrates an exemplary diagram of an intrathecal drug delivery device (IDDD) with a securing mechanism.

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example shown in FIG. 1, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external.

Figure 2A:
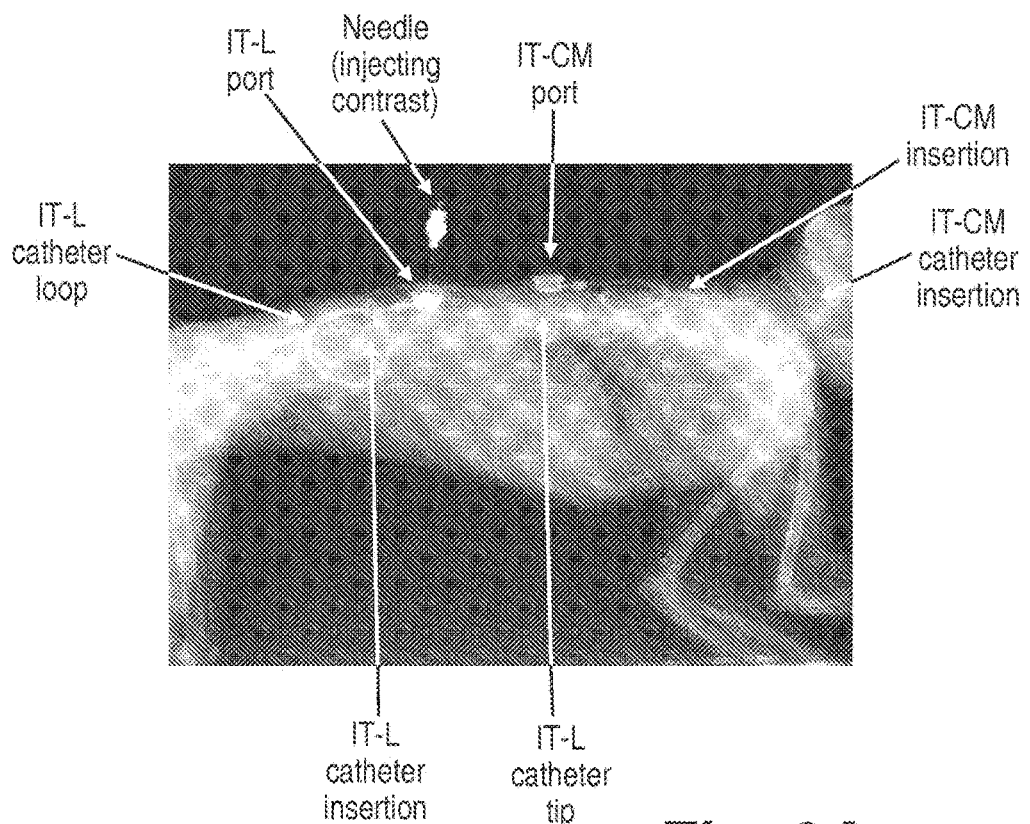
FIG. 2A depicts exemplary locations within a patient's body where an IDDD may be placed.
Figure 2B:
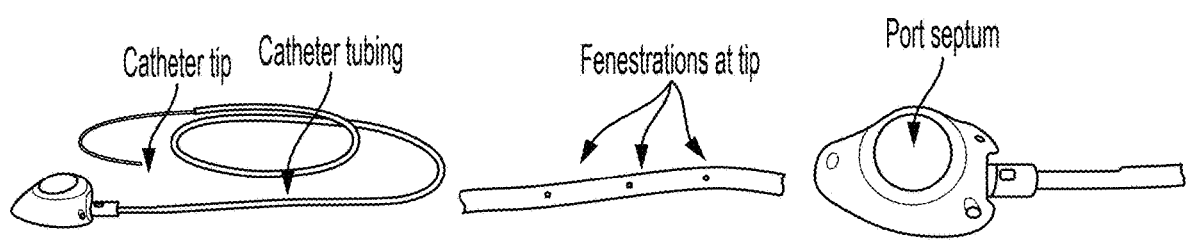
FIG. 2B depicts various components of an intrathecal drug delivery device (IDDD)
Figure 2C:
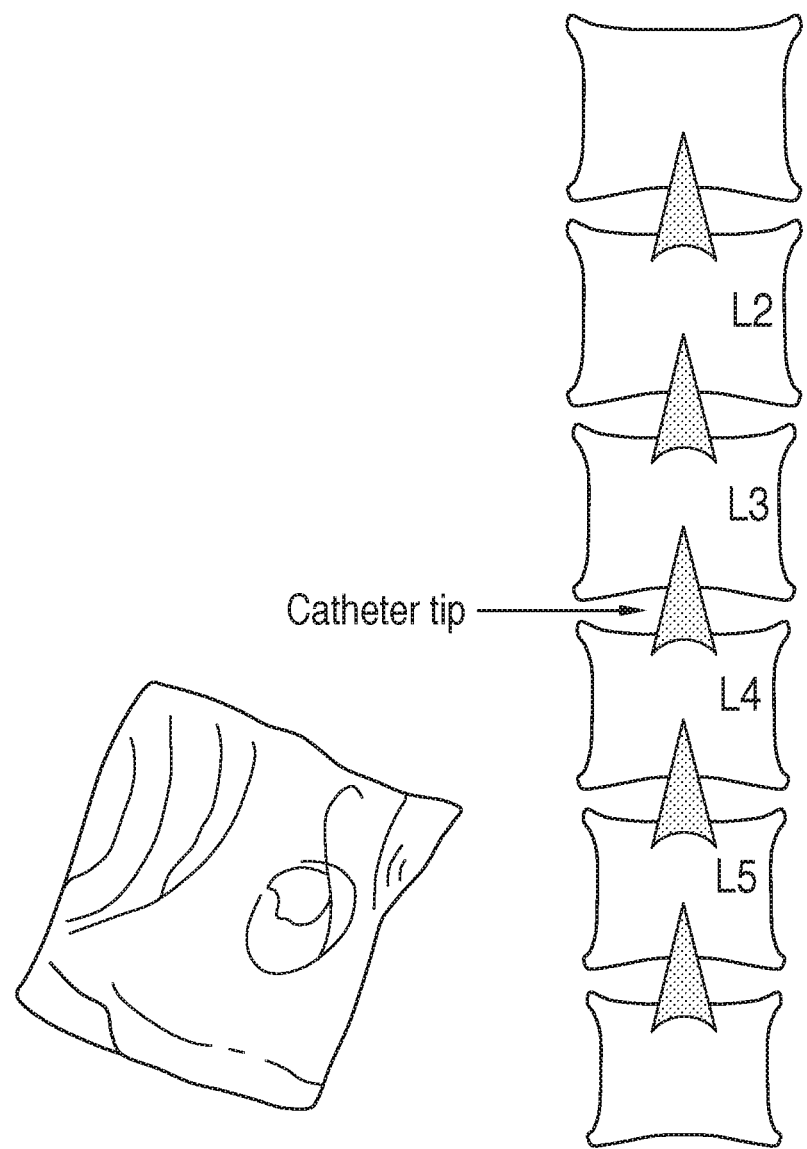
FIG. 2C depicts an exemplary insertion location within a patient's body for IT-lumbar injection.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the the cal space to the desired level (generally L3-L4) (FIG. 2).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes administered using inventive methods and compositions of the present invention are able to effectively and extensively diffuse across the brain surface and penetrate various layers or regions of the brain, including deep brain regions. In addition, inventive methods and compositions of the present invention effectively deliver therapeutic agents (e.g., replacement enzymes) to various tissues, neurons or cells of spinal cord, including the lumbar region, which is hard to target by existing CNS delivery methods such as ICV injection. Furthermore, inventive methods and compositions of the present invention deliver sufficient amount of therapeutic agents (e.g., replacement enzymes) to blood stream and various peripheral organs and tissues.

Thus, in some embodiments, a therapeutic protein (e.g., a replacement enzyme) is delivered to the central nervous system of a subject. In some embodiments, a therapeutic protein (e.g., a replacement enzyme) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system.

In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, therapeutic agents (e.g., enzymes) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, therapeutic agents (e.g., enzymes) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, therapeutic agents (e.g., enzymes) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, therapeutic agents (e.g., enzymes) are delivered to one or more tissues of the brainstem. In some embodiments, the targeted one or more tissues of the brainstem include brain stem white matter tissue and/or brain stem nuclei tissue.

In some embodiments, therapeutic agents (e.g., enzymes) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, therapeutic agents (e.g., enzymes) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, therapeutic agents (e.g., enzymes) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, therapeutic agents (e.g., enzymes) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, therapeutic agents (e.g., enzymes) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a therapeutic protein (e.g., a replacement enzyme) in accordance with the present invention is delivered to one or more of the peripheral target tissues.

Biodistribution and Bioavailability

In various embodiments, once delivered to the target tissue, a therapeutic agent (e.g., a replacement enzyme) is localized intracellularly. For example, a therapeutic agent (e.g., enzyme) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a therapeutic agent (e.g., a replacement enzyme) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a therapeutic agent (e.g., a replacement enzyme) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a therapeutic agent (e.g., a replacement enzyme) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a therapeutic agent (e.g., a replacement enzyme) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a therapeutic agent (e.g., a replacement enzyme) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a therapeutic agent (e.g., a replacement enzyme) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a therapeutic agent (e.g., a replacement enzyme) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a therapeutic agent (e.g., a replacement enzyme) delivered according to the present invention achieves a concentration of at least 30 µg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a therapeutic agent (e.g., a replacement enzyme) delivered according to the present invention achieves a concentration of at least 20 µg/ml, at least 15 µg/ml, at least 10 µg/ml, at least 7.5 µg/ml, at least 5 µg/ml, at least 2.5 µg/ml, at least 1.0 µg/ml or at least 0.5 µg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Lysosomal Storage Diseases By Intrathecal Administration

The lysosomal storage diseases represent a group of relatively rare inherited metabolic disorders that result from defects in lysosomal function. The lysosomal diseases are characterized by the accumulation of undigested macromolecules, including those enzyme substrates, within the lysosomes (see Table 1), which results in an increase in the size and number of such lysosomes and ultimately in cellular dysfunction and clinical abnormalities.

Inventive methods described herein can advantageously facilitate the delivery of one or more therapeutic agents (e.g., one or more replacement enzymes) to targeted organelles. For example, because lysosomal storage disorders such as Hunter syndrome are characterized by an accumulation of glycosaminoglycans (GAG) in the lysosomes of affected cells, the lysosomes represent a desired target organelle for the treatment of the lysosomal storage disorders.

Inventive methods and compositions of the present invention are particularly useful for treating those diseases having a CNS etiology or component. Lysosomal storage diseases having a CNS etiology or component, include for example and without limitation Sanfilippo syndrome Type A, Sanfilippo syndrome type B, Hunter syndrome, metachromatic leukodystrophy and globoid cell leukodystrophy. Prior to the present invention, traditional therapies are limited in that they are administered to subjects intravenously, and are generally only effective in treating the somatic symptoms of the underlying enzyme deficiency. The compositions and methods of the present invention may advantageously be administered directly into the CNS of a subject suffering from a disease having such a CNS etiology thereby achieving a therapeutic concentration within the affected cells and tissues of the CNS (e.g., the brain), thus overcoming the limitations associated with traditional systemic administration of such therapeutic agents.

In some embodiments, inventive methods and compositions of the invention are useful for treating both the neurologic and the somatic sequelae or symptoms of lysosomal storage disorders. For example, some embodiments of the invention relate to compositions and methods of delivering one or more therapeutic agents to the CNS of a subject (e.g., intrathecally, intraventricularly or intracisternally) for the treatment of the CNS or neurologic sequelae and manifestations of a lysosomal storage disease, while also treating the systemic or somatic manifestations of that lysosomal storage disease. For example, some compositions of the present invention may be administered to a subject intrathecally, thereby delivering one or more therapeutic agents to the CNS of the subject and treating the neurological sequelae, coupled with the intravenous administration of one or more therapeutic agents to deliver such therapeutic agents to both the cells and tissues of the systemic circulation (e.g., cells and tissues of heart, lungs, liver, kidney or lymph nodes) to thereby treat the somatic sequelae. For example, a subject having or otherwise affected by a lysosomal storage disease (e.g., Hunter syndrome) may be administered a pharmaceutical composition comprising one or more therapeutic agents (e.g., iduronate-2-sulfatase) intrathecally at least once per week, biweekly, monthly, bimonthly or more to treat the neurologic sequelae, while a different therapeutic agent is administered to the subject intravenously on a more frequent basis (e.g., once per day, every other day, three times a week or weekly) to treat the systemic or somatic manifestations of the disease.

For example, patients suffering from Hunter syndrome exhibit histological changes in the brains which may include atrophy, cortical neuronal swelling, cerebral white matter reduction, dilated perivascular spaces and Purkinje cell dendrite swelling. Magnetic resonance imagining/spectroscopy studies have shown that severe diffuse lesions involving the white matter, brain atrophy, and hydrocephalus were more common in patients with cognitive impairment compared to those without impairment. (Vedolin, L., et al., AJNR Am J Neuroradiol (2007) 28, 1029-1033). Even patients without extreme neurologic sequelae such as mental retardation or developmental delays were shown to have brain abnormalities that included atrophy, ventriculomegaly, and enlarged perivascular spaces. (Matheus, M G, et al., Neuroradiology (2004) 46, 666-672.)

As a non-limiting example, mucopolysaccharidosis type IIIA (MPS IIIA; Sanfilippo syndrome type A) is the most severe form of Sanfilippo syndrome type A and affects approximately 1 in 100,000 people worldwide. Sanfilippo syndrome type A (Sanfilippo A) is characterized by a deficiency of the enzyme heparan N-sulfatase (HNS), an exosulfatase involved in the lysosomal catabolism of glycosaminoglycan (GAG) heparan sulfate (Neufeld E F, et al. The Metabolic and Molecular Bases of Inherited Disease (2001) pp. 3421-3452). In the absence of this enzyme, GAG heparan sulfate accumulates in lysosomes of neurons and glial cells, with lesser accumulation outside the brain.

As a non-limiting example, mucopolysaccharidosis type IIIB (MPS IIIB; Sanfilippo syndrome type B disease) is an autosomal recessive disorder that is characterized by a deficiency of the enzyme alpha-N-acetyl-glucosaminidase (Naglu). In the absence of this enzyme, GAG heparan sulfate accumulates in lysosomes of neurons and glial cells, with lesser accumulation outside the brain.

As a non-limiting example, globoid cell leukodystrophy (GLD) is a rare autosomal recessive lysosomal storage disorder caused by defective function of galactocerebrosidase (GALC). GALC is a soluble lysosomal acid hydrolase enzyme which degrades galactosylceramide, a normal component of myelin, into galactose and ceramide, and psychosine (galactosylsphingosine), a toxic byproduct of galactosylceramide synthesis, into galactose and sphingosine. GALC deficiency leads to neurologic injury of the central and peripheral nervous systems (CNS and PNS respectively) in two related, but distinct pathways. The first pathway leads to excessive psychosine accumulation with resultant apoptosis of myelinating cells. In the second pathway, galactosylceramide accumulates and is phagocytosed in activated microglia, producing the characteristic globoid cell for which the disease is named. In contrast to other lysosomal storage diseases which accumulate undegraded substrate, there is generally no increase in total galactosylceramide in neural tissue.

A defining clinical feature of this disorder is central nervous system (CNS) degeneration, which results in loss of, or failure to attain, major developmental milestones. The progressive cognitive decline culminates in dementia and premature mortality. The disease can manifests itself in young children (Early-onset GLD), or in individuals of any age (Late-onset GLD). The lifespan of an individual affected with Early-onset GLD typically does not extend beyond the age of two years. Late-onset GLD can appear in individuals of any age and the progression of the disease can vary greatly.

Metachromatic Leukodystrophy Disease (MLD) is an autosomal recessive disorder resulting from a deficiency of the enzyme Arylsulfatase A (ASA). ASA, which is encoded by the ARSA gene in humans, is an enzyme that breaks down cerebroside 3-sulfate or sphingolipid 3-O-sulfogalactosylceramide (sulfatide) into cerebroside and sulfate. In the absence of the enzyme, sulfatides accumulate in the nervous system (e.g., myelin sheaths, neurons and glial cells) and to a lesser extent in visceral organs. The consequence of these molecular and cellular events is progressive demyelination and axonal loss within the CNS and PNS, which is accompanied clinically by severe motor and cognitive dysfunction.

A defining clinical feature of this disorder is central nervous system (CNS) degeneration, which results in cognitive impairment (e.g., mental retardation, nervous disorders, and blindness, among others).

As a non-limiting example, MLD can manifest itself in young children (Late-infantile form), where affected children typically begin showing symptoms just after the first year of life (e.g., at about 15-24 months), and generally do not survive past the age of 5 years. MLD can manifest itself in children (Juvenile form), where affected children typically show cognitive impairment by about the age of 3-10 years, and life-span can vary (e.g., in the range of 10-15 years after onset of symptoms). MLD can manifest itself in adults (Adult-onset form) and can appear in individuals of any age (e.g., typically at age 16 and later) and the progression of the disease can vary greatly.

Thus, in some embodiments, inventive methods and compositions deliver one or more therapeutic agents (e.g., one or more replacement enzymes) to one or more organelles (e.g., the lysosomes) of target tissues and cells of the brain, spinal cord and/or peripheral organs to effect treatment various lysosomal storage diseases. As used herein, the terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a patient suffering from or susceptible to a lysosomal disease. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to decreased lysosomal storage (e.g., macromolecules stored such as GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology).

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control.

In certain embodiments, treatment according to the present invention results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological or biological markers which are associated with the lysosomal storage diseases. Such reduction or elimination may be particularly evident in the cells and tissues of the CNS (e.g., neurons and oligodendrocytes). For example, in some embodiments, upon administration to a subject the pharmaceutical compositions of the present invention demonstrate or achieve a reduction in the accumulation of the biomarker lysosomal associated membrane protein 1 (LAMP1) in the CNS cells and tissues of the subject (e.g., in the cerebral cortex, cerebellum, caudate nucleus and putamen, white matter and/or thalamus). LAMP1 is a glycoprotein highly expressed in lysosomal membranes and its presence is elevated many patients with a lysosomal storage disorder. (Meikle, et al. Clin Chem. (1997) 43:1325-1335.) The presence or absence of LAMP1 in patients (e.g., as determined by LAMP staining) with a lysosomal storage disease therefore may provide a useful indicator of lysosomal activity and a marker for both the diagnosis and monitoring of lysosomal storage diseases.

Accordingly, some embodiments of the present invention relate to methods of reducing or otherwise eliminating the presence or accumulation of one or more pathological or biological markers associated with a disease (e.g., a lysosomal storage disease). Similarly, some embodiments of the invention relate to methods of increasing the degradation (or the rate of degradation) of one or more pathological or biological markers (e.g., LAMP1) associated with lysosomal storage diseases.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same disease, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having the disease or having the potential to develop the disease. The individual can have residual endogenous lysosomal enzyme expression and/or activity, or no measurable activity. For example, the individual having Sanfilippo syndrome type A may have HNS expression levels that are less than about 30-50%, less than about 25-30%, less than about 20-25%, less than about 15-20%, less than about 10-15%, less than about 5-10%, less than about 0.1-5% of normal HNS expression levels.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potteret al., 1999, Ann. N.Y. Acad. Sci. 875, 159-174; Slavik et al., 1999, Immunol. Res. 19, 1-24; Gaziev et al., 1999, BoneMarrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additionalimmunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every three months, bimonthly (once every two months), monthly (once every month), biweekly (once every two weeks), weekly).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined base on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban AS. "Changes in brain weights during the span of human life: relation of brain weights to body heights and body weights," Ann Neurol 1978; 4:345-56. Thus, in some embodiments, the dosages can be converted as shown in Table 4.

TABLE 4

Dosage conversion
Correlation between Brain Weights, body weights and ages of males

| Age (year) | Brain weight (kg) | Body weight (kg) |
|---|---|---|
| 3 (31-43 months) | 1.27 | 15.55 |
| 4-5 | 1.30 | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14;5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a therapeutic agent (e.g., a replacement enzyme). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Examples of IT Delivery of GalC Protein

Example 1: Physiochemical Characterization of Galc Formulation for Intrathecal Delivery The present Example describes physiochemical characterization of GalC in order to understand its behavior and stability under different solution conditions during intrathecal (IT) delivery of the protein.

Among other things, the present Example describes a GalC formulation which is important for successful IT delivery of GalC. In some embodiments, this formulation includes 5 mM Na phosphate+150 mM NaCl, pH 6.0+ 0.005% poloysorbate 20. In some embodiments, this formulation includes <5 mM, <10 mM, <15 mM and <20 mM Na phosphate. In some embodiments, this formulation includes a pH ≥5.5 and ≤pH 7.0. with 150 mM NaCl.

Figure 3:
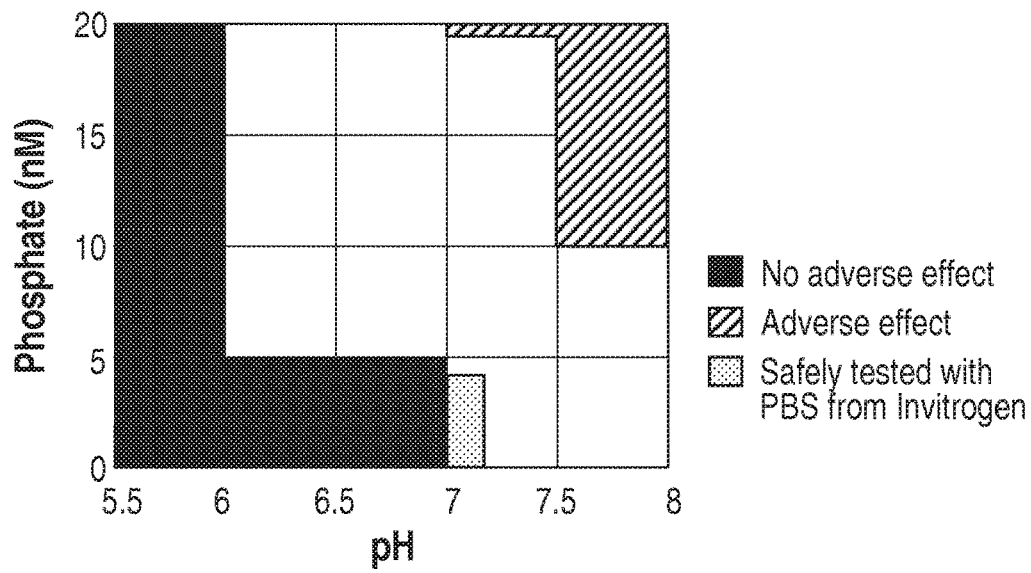
FIG. 3 depicts exemplary results summarizing vehicles tested in adult monkeys.
Figure 4:
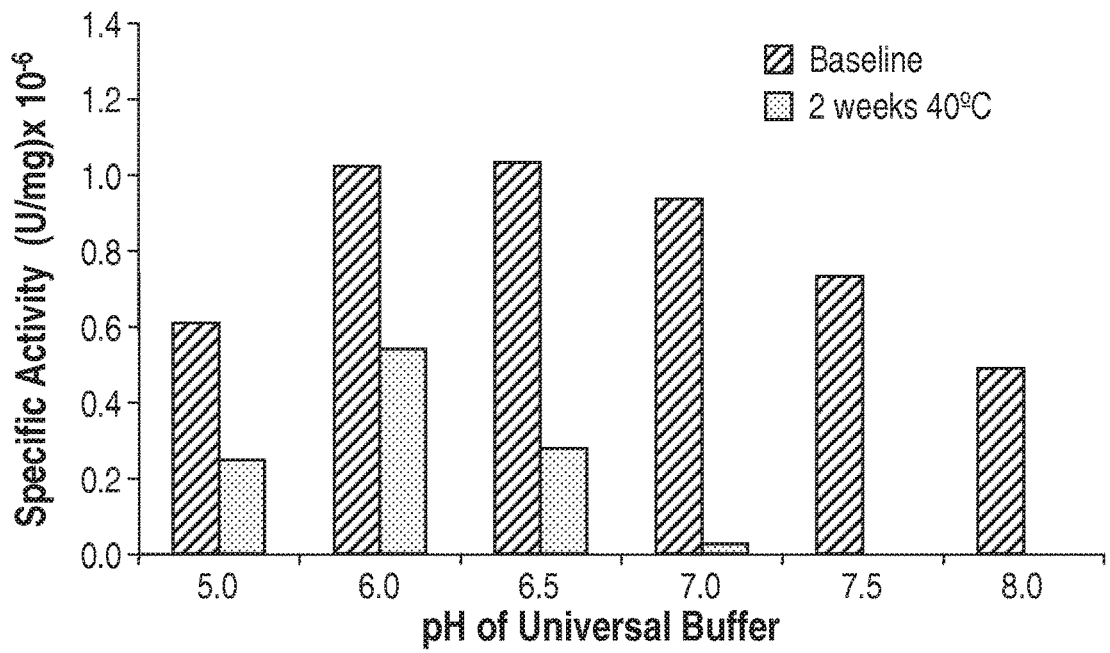
FIG. 4 depicts exemplary results illustrating the stability of hGalC in a thermal screen of hGalC as a function of pH.
Figure 5:
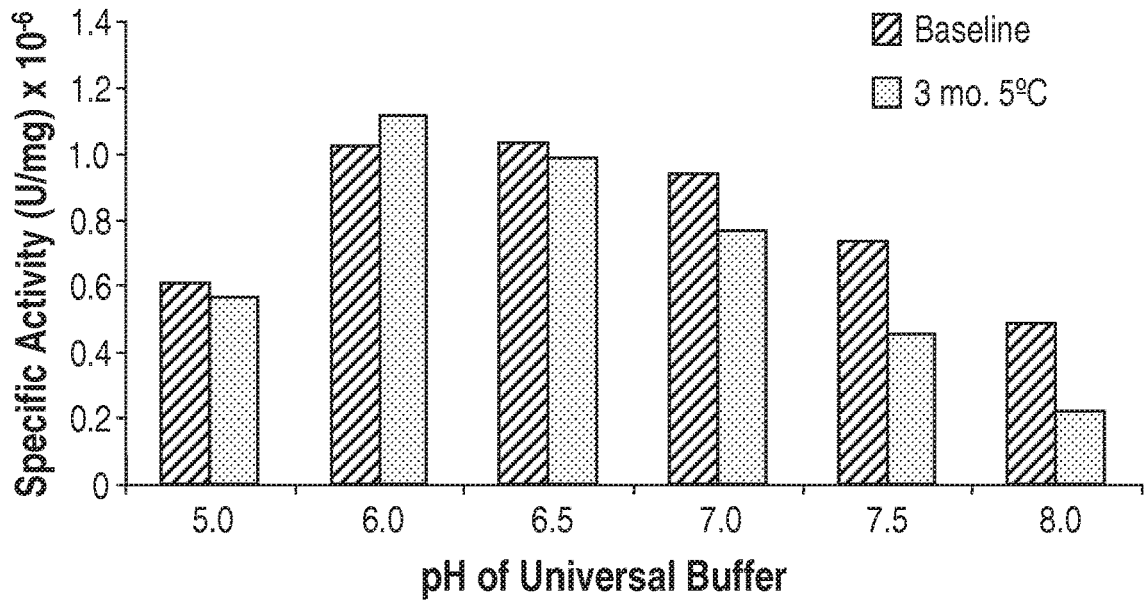
FIG. 5 depicts exemplary results illustrating the specific activity of hGalC as a function of pH.

PBS delivery vehicles of varying phosphate molarity and pH were tested in adult cynomologous monkeys (FIG. 3). 5 mM phosphate in a pH range of 5.5-7.0 showed no adverse effect whereas 20 mM phosphate between pH 7.0-7.5 and 10-20 mM phosphate between pH 7.5-8.0 showed an adverse effect in the monkeys (FIG. 3). Thermal stability of hGalC (1 mg/ml) in 3 mM citrate, phosphate and borate buffer with 50 mM NaCl, was investigated as a function of pH within the range of pH 5.0-8.0 (FIG. 4). hGalC specific activity was measured at baseline (20-25° C.) and at 2 weeks at 40° C. with the highest specific activity retained between pH 6.0-6.5 (FIG. 4). hGalC specific activity was additionally measured at 3 months at 5° C. with the highest specific activity retained between pH 6.0-6.5 (FIG. 5). The melting temperature of hGalc was measured as a function of pH (Table 5) and also measured independently in different formulations (Table 6).

TABLE 5

Melting Temperature of hGalC (1 mg/mL) as a Function of pH

| pH of Universal Buffer | Tm (° C.) |
|---|---|
| 4.5* | 61.6 |
| 5.0* | 63.0 |
| 6.0 | 60.8 |
| 6.5 | 58.9 |
| 7.0 | 57.3 |
| 7.5 | 56.5 |

*[GalC] < 1 mg/mL due to precipitation

TABLE 6

Melting Temperature of hGalC (1 mg/mL) in Different Formulations

| Formulation (pH 6.0) | Tm (° C.) |
|---|---|
| 5 mM phosphate, 50 mM NaCl | 61.6 |
| 5 mM phosphate, 150 mM NaCl | 60.2 |
| 5 mM phosphate, 500 mM NaCl | 59.5 |
| 5 mM phosphate, 5% Dextrose | 63.8 |
| 5 mM phosphate, 150 mM NaCl, 1% NaTC | 56.8 |

Figure 6:
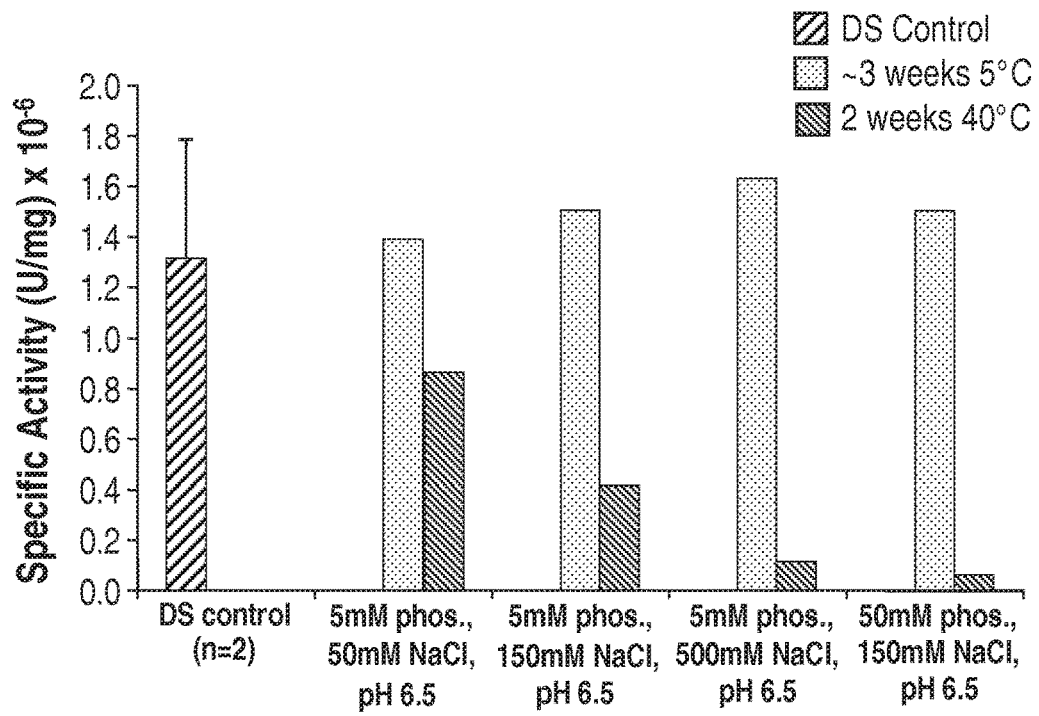
FIG. 6 depicts exemplary results illustrating a thermal screen of hGalC as a function of salt concentration.

Thermal stability of hGalC, as determined by retention of hGalC specific activity at ~3 weeks at 5° C. and 2 weeks at 40° C., was also evaluated as a function of salt concentration (FIG. 6). Results showed that hGalC retained high specific activity after 3 weeks at 5° C. in a variety of salt concentrations ranging from 5 mM phosphate+50 mM NaCl (abbreviated herein as 5+50) to 50 mM phosphate+150 mM NaCl (abbreviated herein as 50+150), at pH 6.5 (FIG. 6).

Sedimentation Analysis of hGalC

Figure 7A:
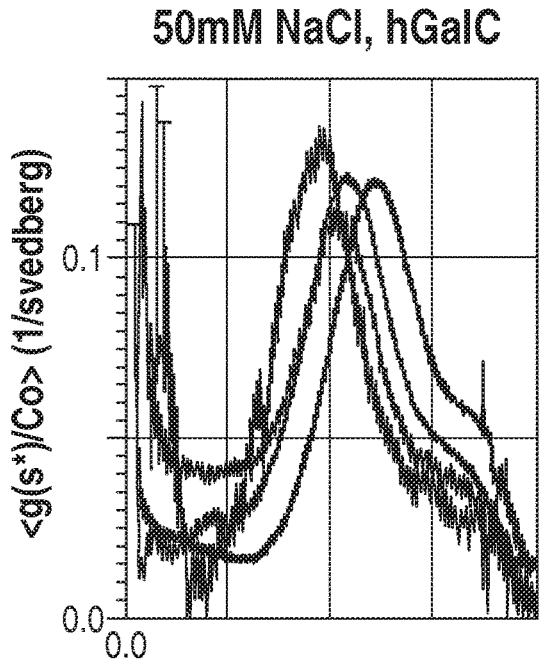
FIG. 7A-D depicts exemplary results illustrating sedimentation velocity runs of GalC comparing different ionic strengths in 5 mM Na phosphate, pH 6.0 buffer.
Figure 7B:
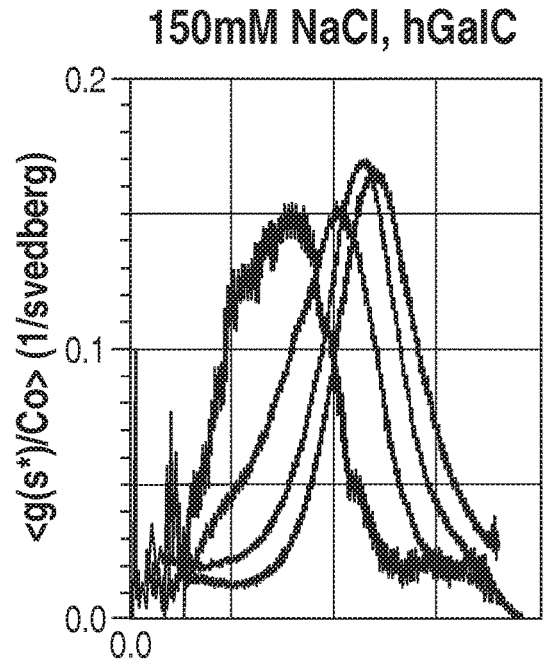
Figure 7C:
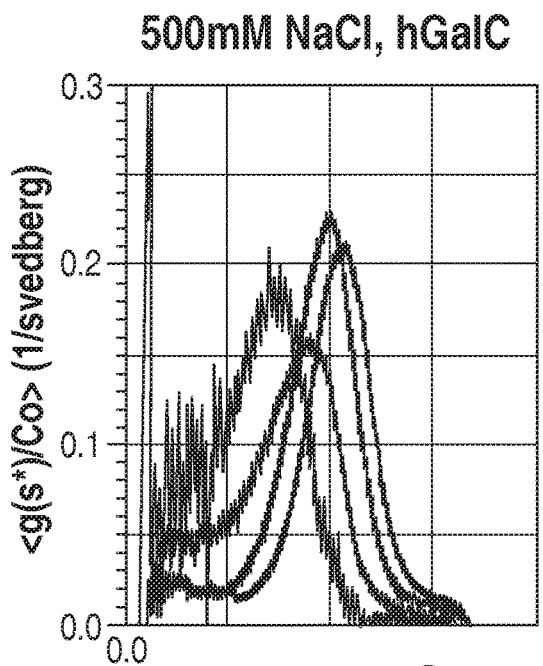
Figure 7D:
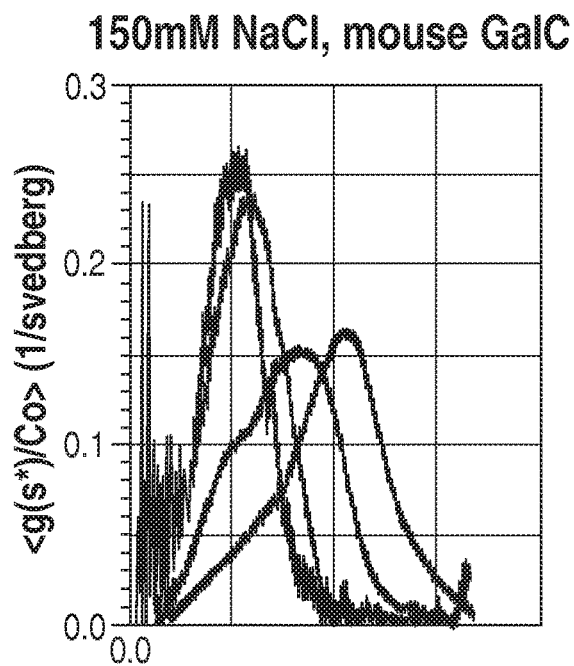

Sedimentation velocity is an analytical ultracentrifugation (AUC) method that measures the rate at which molecules move in response to centrifugal forces generated in a centrifuge and is a useful technique for determine protein association state in solution. The first sedimentation velocity run was a dilution series of human GalC in 5 mM Na phosphate, pH 6.0 with 150 mM NaCl (FIG. 7B) to assess the sample for self-association and/or nonideality. The dilution series was plotted as normalized g(s*) curves (g(s*)) vs s*) at each concentration. The general shift in the curves to lower s values upon dilution indicates dissociation, and this is a rapidly reversible self-associating system. Comparing different ionic strengths (FIGS. 7A, B & C), it is apparent that the sets of curves shift to lower s values upon raising the ionic strength indicating that ionic interactions are also involved in the association process and that the self association is decreased at higher salt concentrations.

Figure 8:
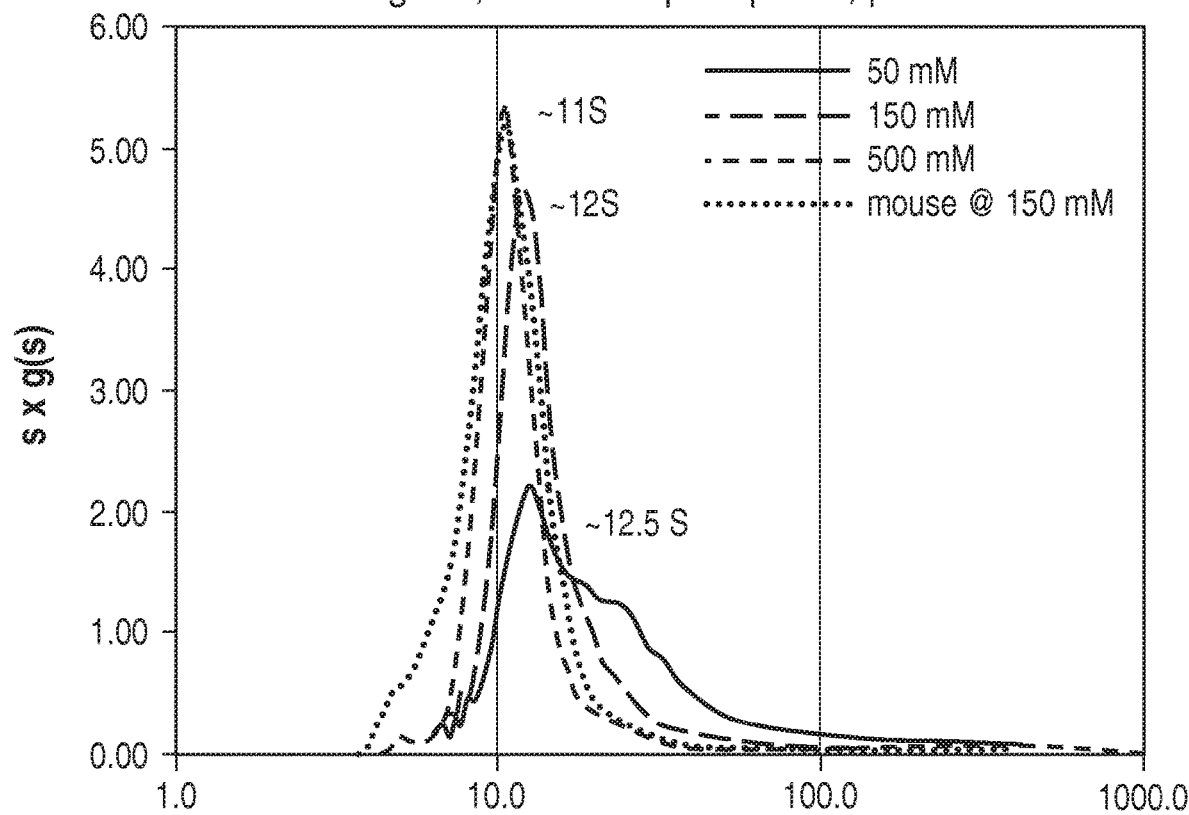
FIG. 8 depicts exemplary results illustrating GalC AUC profile as a function of salt concentration (1 mg/mL GalC, 5 mM Na phosphate, pH 6.0) (Y axis=s*g(s*); X axis=s*).

The mouse GalC was also run at the same time at 150 mM NaCl to compare with hGalC. Comparing corresponding ionic strengths (150 mM NaCl), it is apparent that the free energy of self-association of mGalC is less than that of hGalC. The curves in FIG. 7A-D were cut off at about 20S to show the dissociation more clearly; however, when these runs are analyzed using the wide distribution analysis (WDA) and the results are plotted on a log scale, higher aggregates (s*>20S) can clearly be seen. The aggregation to high oligomers (FIG. 8) is especially visible at 50 mM NaCl, somewhat decreased in 10 mM NaCl and significantly reduced, but present, in 500 mM NaCl at pH 6.0. The WDA curve from the highest concentration from each of the ionic strengths is plotted in FIG. 8.

Self-Association in Universal Buffer at pH 6.0

Figure 9:
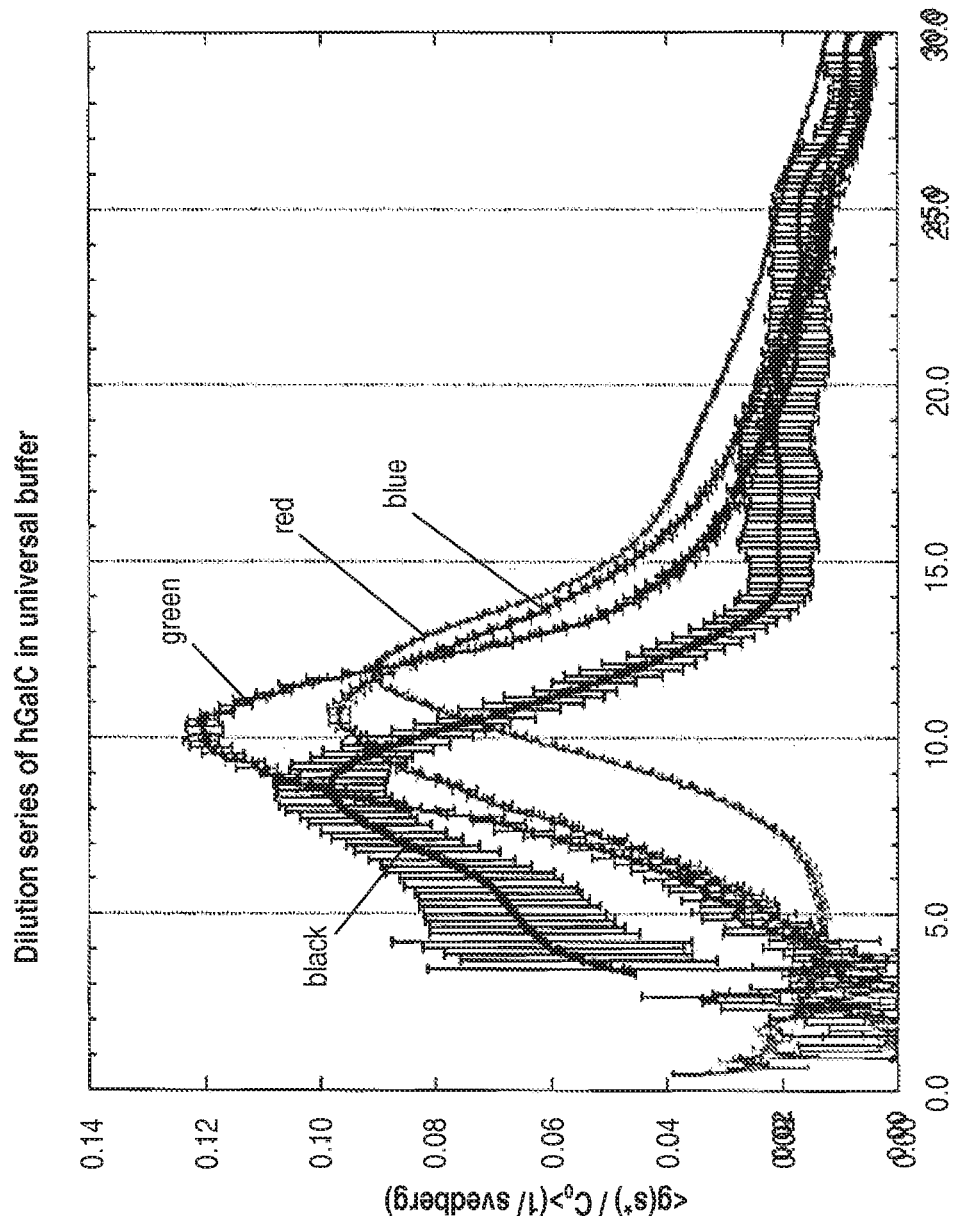
FIG. 9 depicts exemplary results illustrating a dilution series of hGalC in universal buffer, pH 6.0 (Y-axis=<g(s*)/$C\theta_0$>(1/svedberg); X-axis=s*(svedbergs)).

Under these conditions in the universal buffer, the self association appears to be of about the same magnitude as in the phosphate buffer, pH 6.0, as seen in FIG. 9. The effect of pH on the energetics of hGalC self-association in universal buffer was also investigated.

Dilution series were performed at pH 4.5, 5.0, 6.0, 6.5, 7.0 and 7.5. The samples at pH 4.5 and 5.0 were insoluble with essentially 100% of the hGalC having precipitated leaving nothing to measure in the supernatant.

Figure 10:
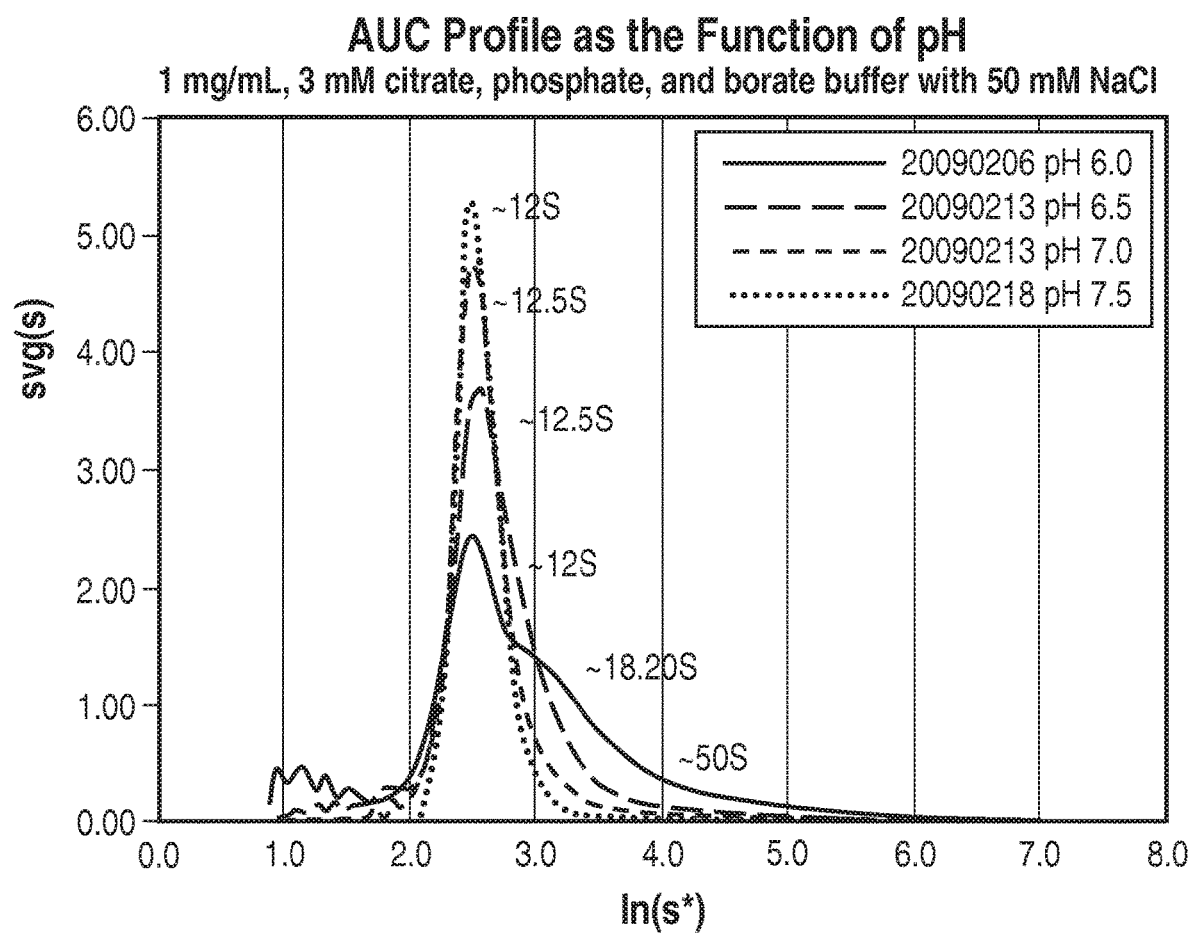
FIG. 10 depicts exemplary results illustrating a GalC AUC profile as a function of pH (1 mg/mL, 3 mM citrate, phosphate and borate buffer with 50 mM NaCl).

The effect of pH is clearly shown in FIG. 10 where the least amount of self-association is observed at pH 7.5 and considerable self-association is observed at pH 6.0. The trend is similar to that seen with variations in ionic strength with higher pH. Increasing both ionic strength and pH shifts the equilibrium to favor the smaller oligomers at the highest concentration (all about 1.0 mg/mL). Decrease in concentration by ⅓ serial dilutions (see FIG. 7A-D) shifts the equilibrium toward the smallest species which appears to have a sedimentation coefficient of about 5.2S. The peak that occurs at about 10-13S likely represents a tetramer of the 5S species. Efforts to fit these data to a self-association model have so far been unsuccessful and is likely due to the inherent micro-heterogeneity arising from variable degrees of glycosylation.

Self-Association in Universal Buffer at pH 6.0

Figure 11:
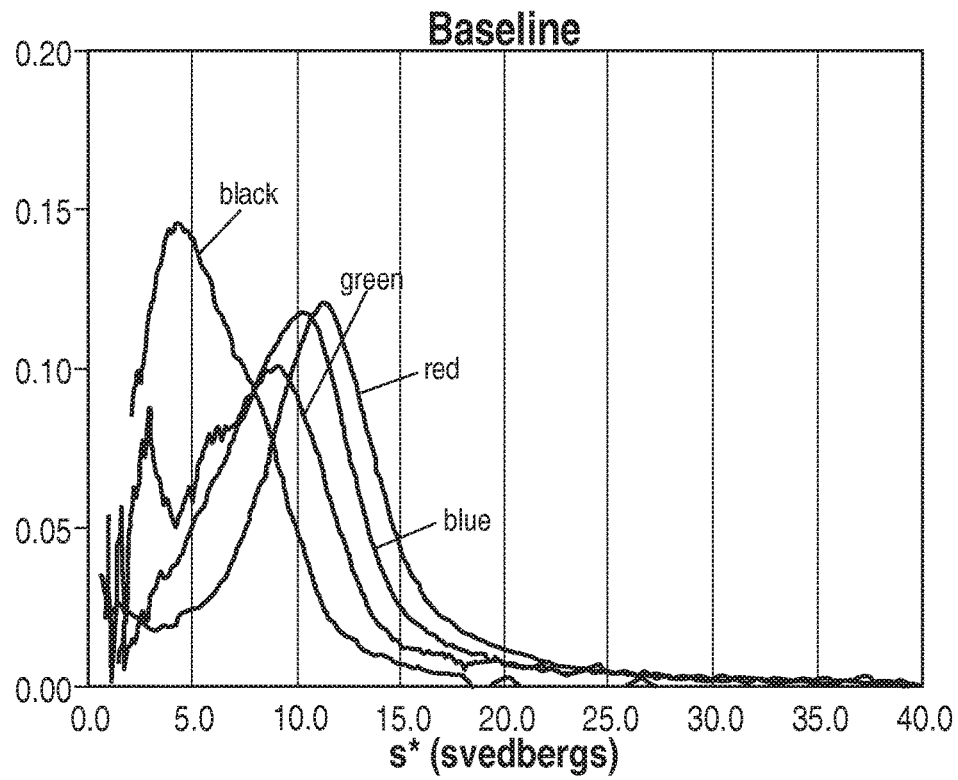
FIG. 11 depicts exemplary results illustrating the baseline reading from a WDA analysis at the highest concentration at pH 6.0, in 5 mM Na phosphate and 150 mM NaCl.
Figure 12:
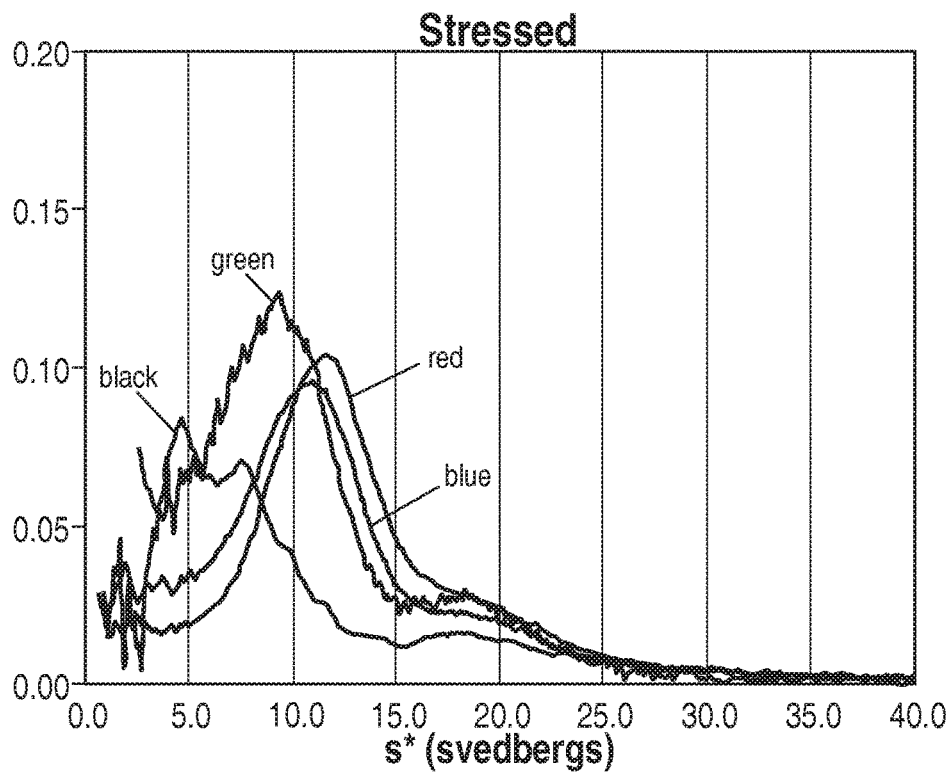
FIG. 12 depicts exemplary results illustrating the stressed reading from a WDA analysis at the highest concentration at pH 6.0, in 5 mM Na phosphate and 150 mM NaCl.
Figure 13:
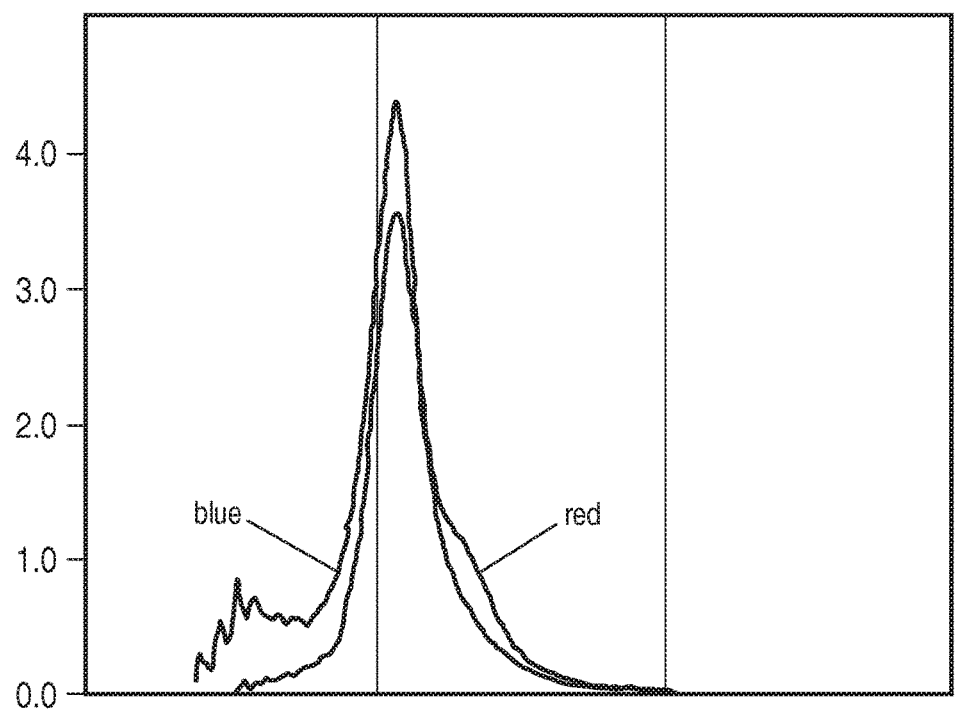
FIG. 13 graphically compares and overlays baseline and stressed GalC samples.

The stressed and baseline samples of GalC in 5 mM Na phosphate, pH 6.0, with 150 mM NaCl were compared in a dilution series experiment (red7blue7green7black). The results for the lowest concentration (black) ~0.03 mg/mL have been smoothed which is why the curve seems to have less noise. In the stressed sample there is an aggregate around ln(s*)=3.0(~20S) that is present in much higher concentration than in the baseline sample. It represents a nearly constant fraction of the sample as evidenced by its persistence upon dilution in the normalized plots (FIG. 11, FIG. 12, FIG. 13). It is therefore an irreversible aggregate with a molar mass of at least 500 kg/mol.

hGalC with Sodium Taurocholate in Solution

Figure 14:
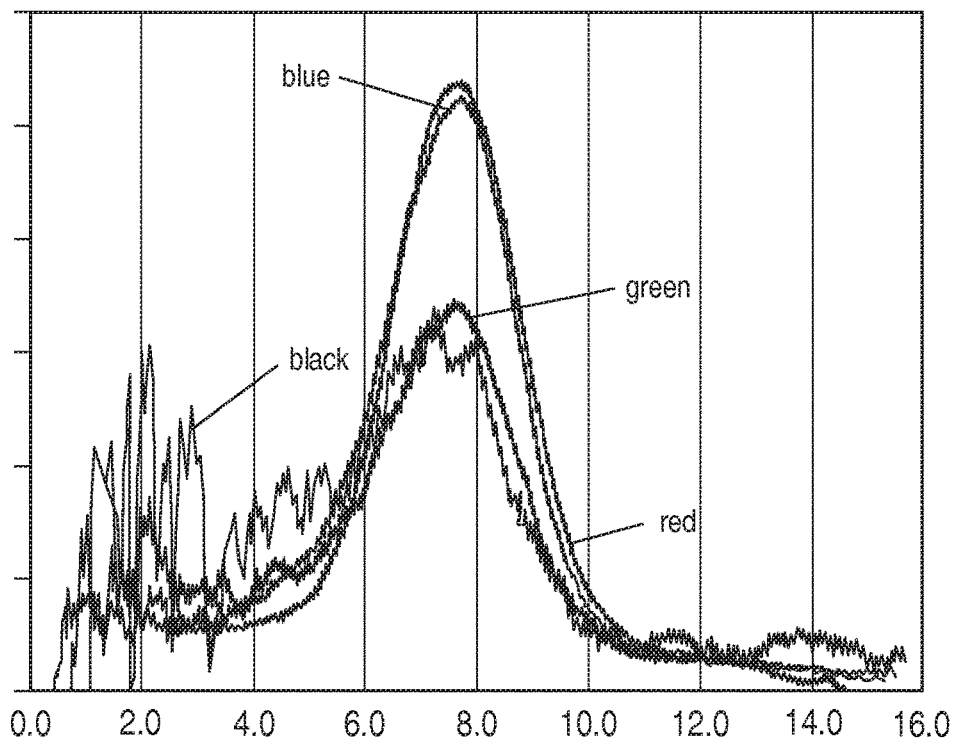
FIG. 14 depicts exemplary results illustrating a dilution series of hGalC in the presence of 1% NaTC.

In sodium taurocholate (NaTC)(1%), the self association is significantly reduced. The main boundary is shifted to lower s values and the higher oligomerization is suppressed (FIG. 14).

hGalC with 5% Dextrose

Figure 15:
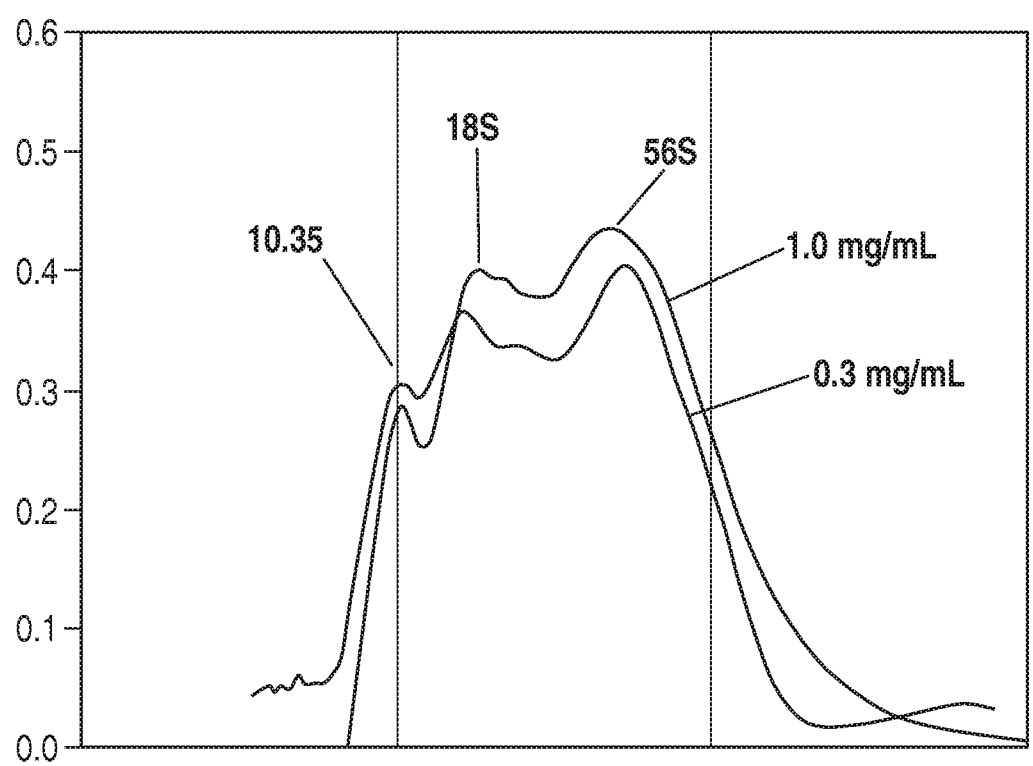
FIG. 15 depicts exemplary results illustrating a dilution series of hGalC in the presence of 1% NaTC (1.0 mg/mL and 0.3 mg/mL).
Figure 16:
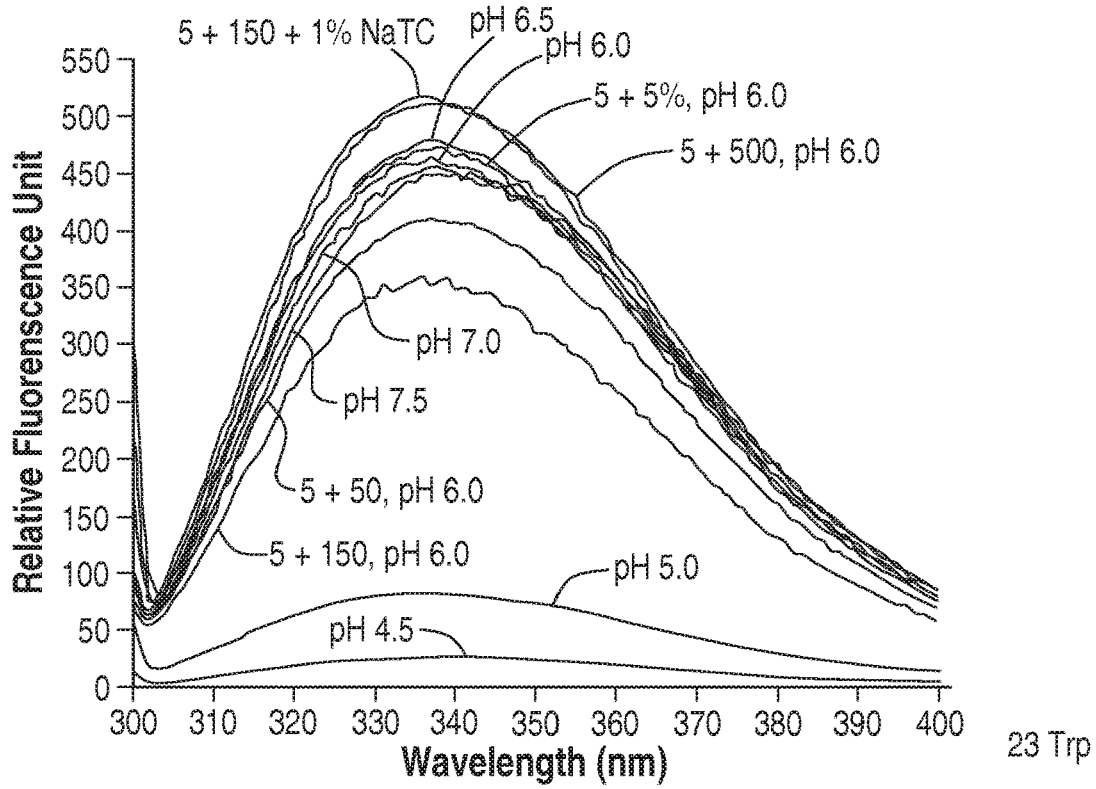
FIG. 16 depicts exemplary results illustrating the intrinsic fluorescence of hGalC (1 mg/mL) in different buffers and pHs.
Figure 17:
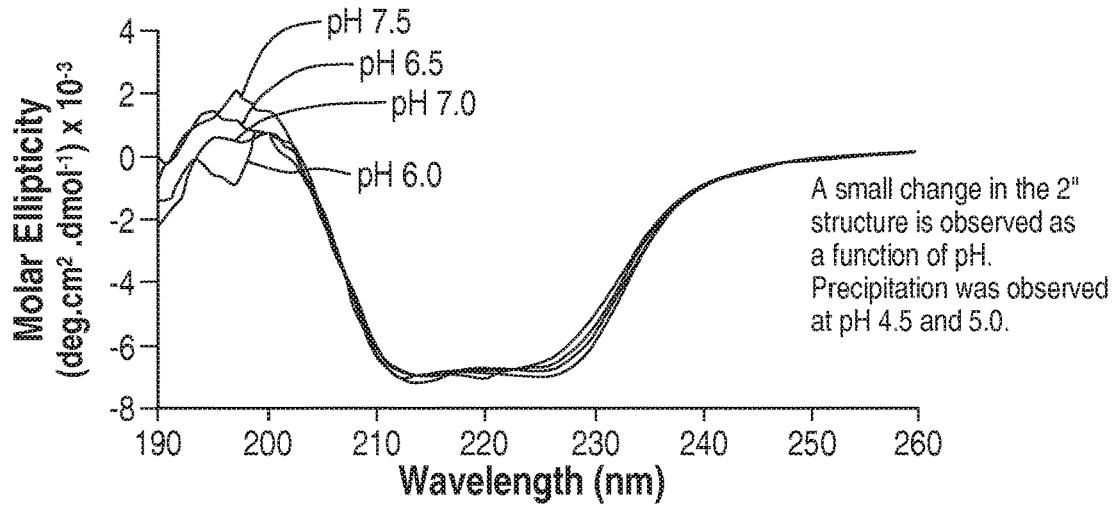
FIG. 17 depicts exemplary results illustrating the circular dichroism of hGalC as a function of pH.
Figure 18:
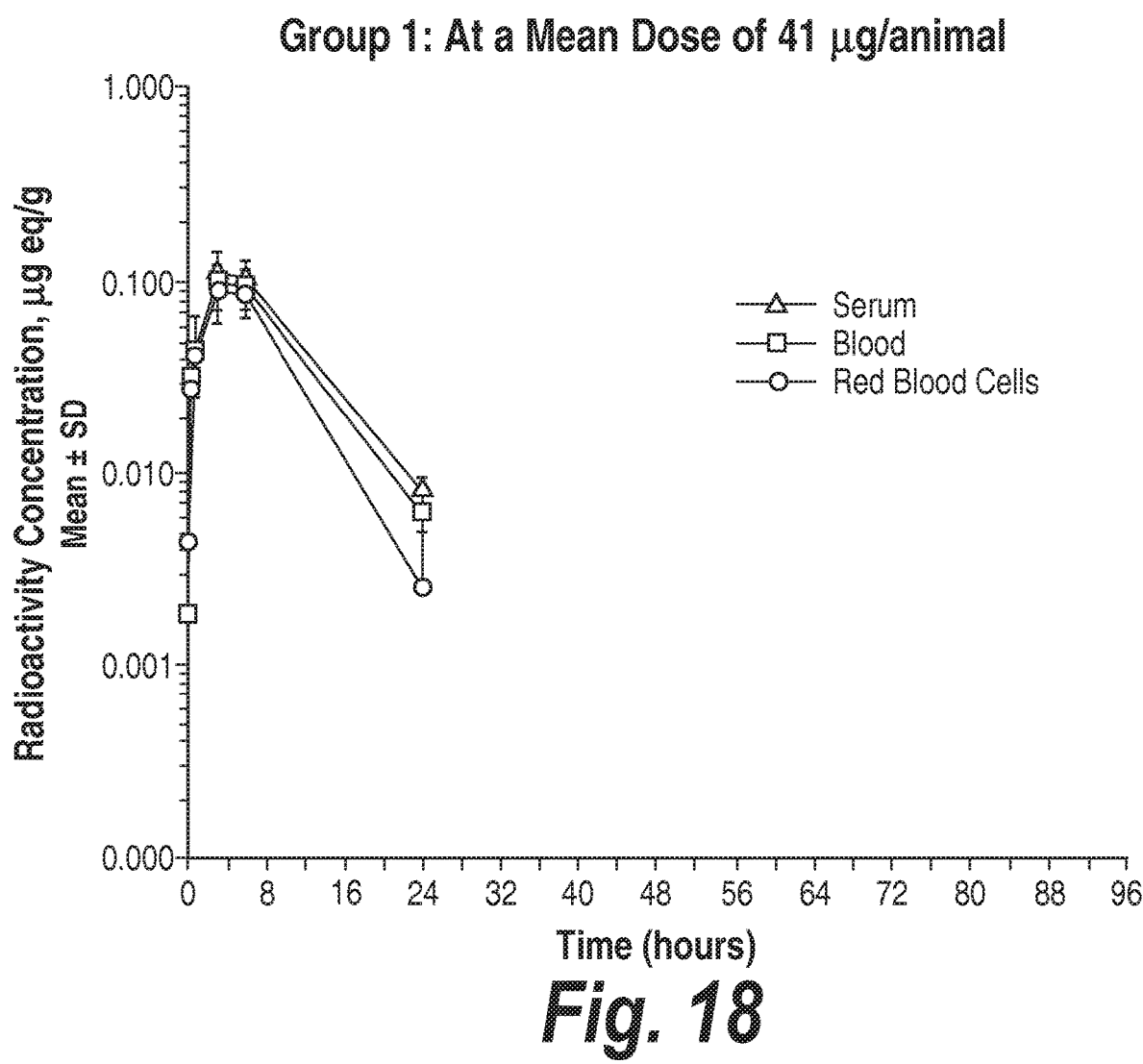
FIG. 18 depicts exemplary results illustrating the group mean concentration of radioactivity in serum, blood and red blood cells of male Sprague-Dawley rats following a single intrathecal dose of $^{125}$I-hGalC.
Figure 19:
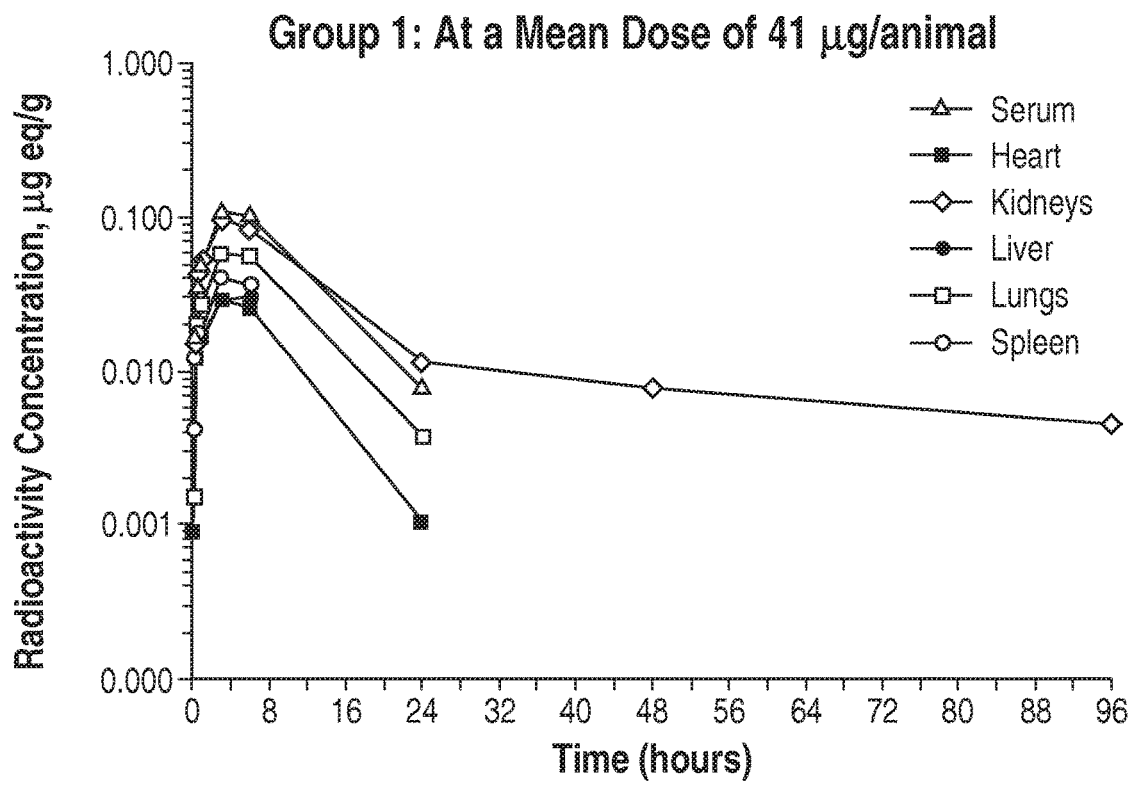
FIG. 19 depicts exemplary results illustrating the group mean concentrations of radioactivity in serum, heart, kidneys, liver, lungs, spleen of male Sprague-Dawley rats following a single intrathecal dose of $^{125}$I-hGalC.
Figure 20:
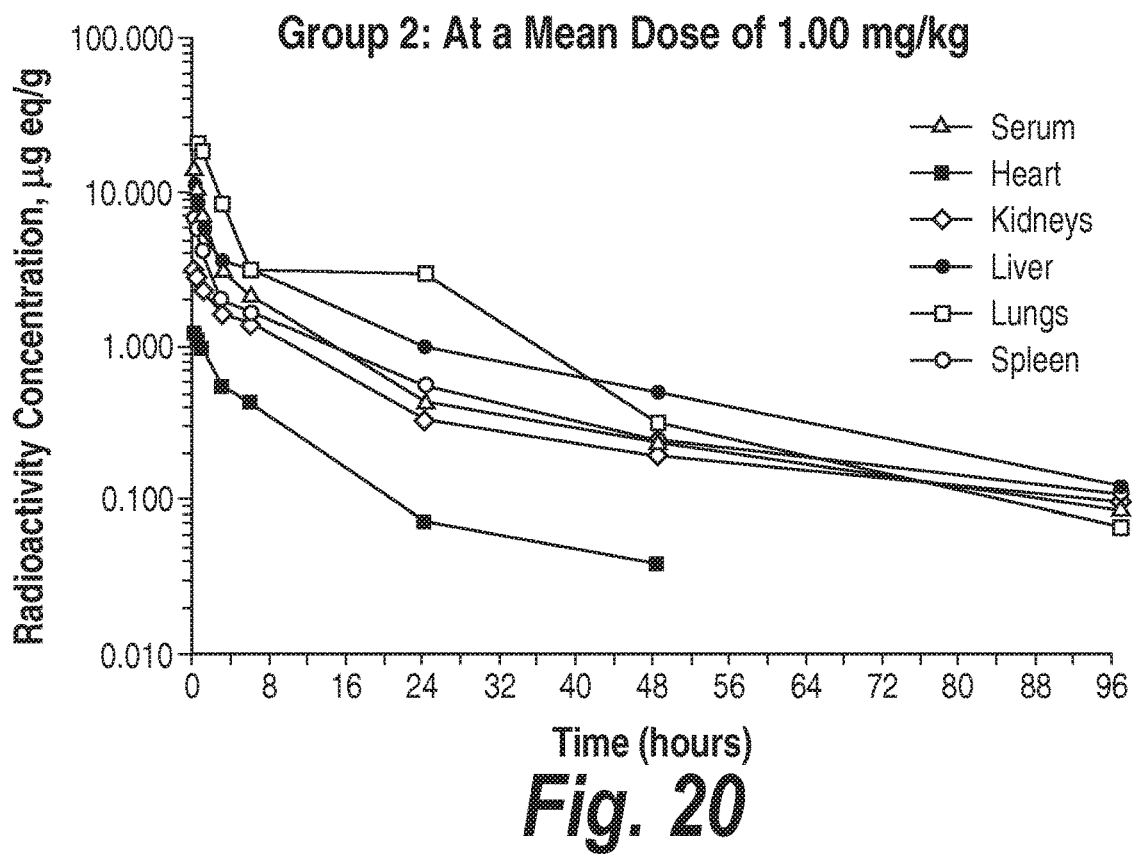
FIG. 20 depicts exemplary results illustrating the group mean concentrations of radioactivity in serum, heart, kidneys, liver, lungs, spleen of male Sprague-Dawley rats following a single intravenous bolus injection of $^{125}$I-hGalC.
Figure 21:
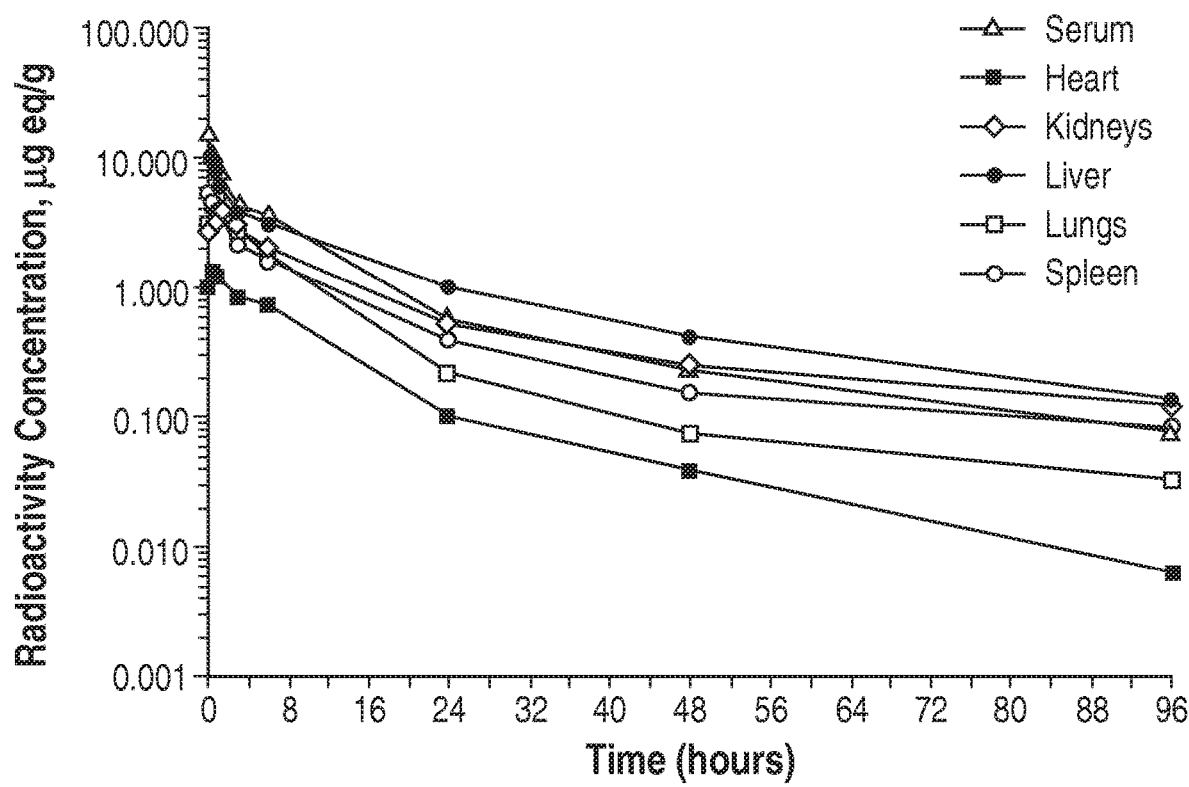
FIG. 21 depicts exemplary results illustrating the group mean concentrations of radioactivity in serum, heart, kidneys, liver, lungs, spleen of male Sprague-Dawley rats following a single intrathecal dose and intravenous bolus injection of $^{125}$I-hGalC.
Figure 22:
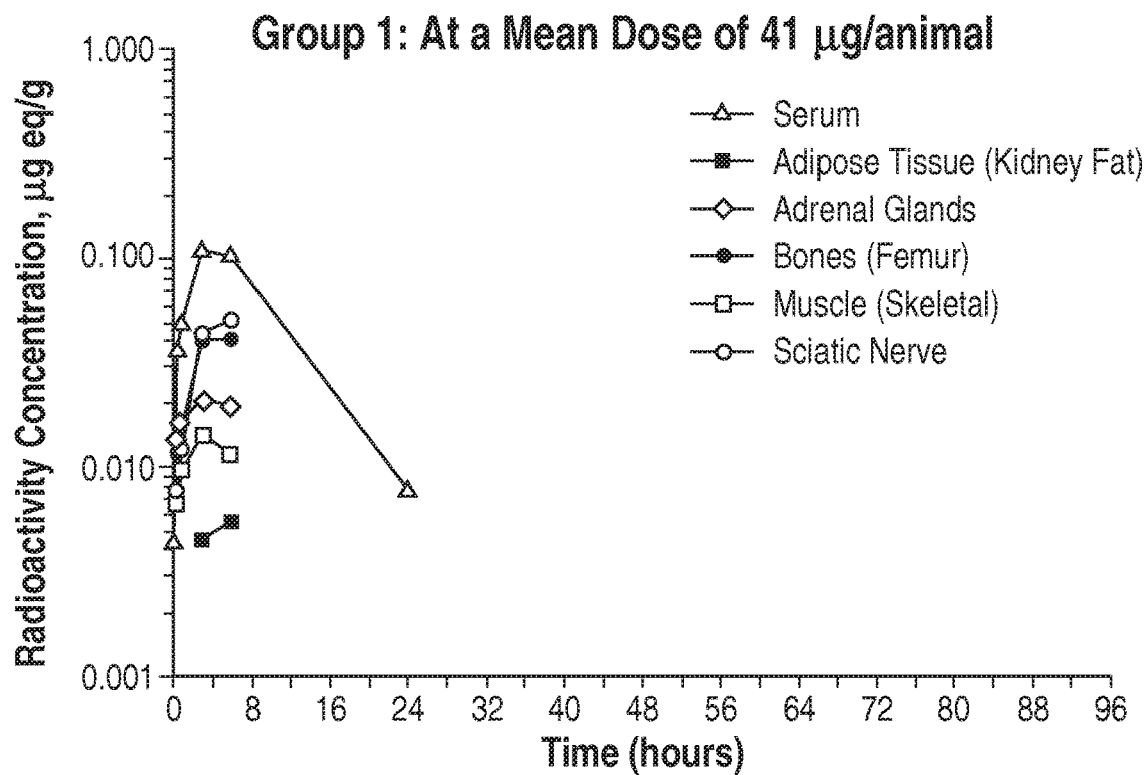
FIG. 22 depicts exemplary results illustrating the mean concentrations of radioactivity in serum and various tissues (adipose tissues (kidney fast), adrenal glands, bone (femur), muscle (skeletal), sciatic nerve)) of male Sprague-Dawley rats following a single intrathecal dose of $^{125}$I-hGalC.
Figure 23:
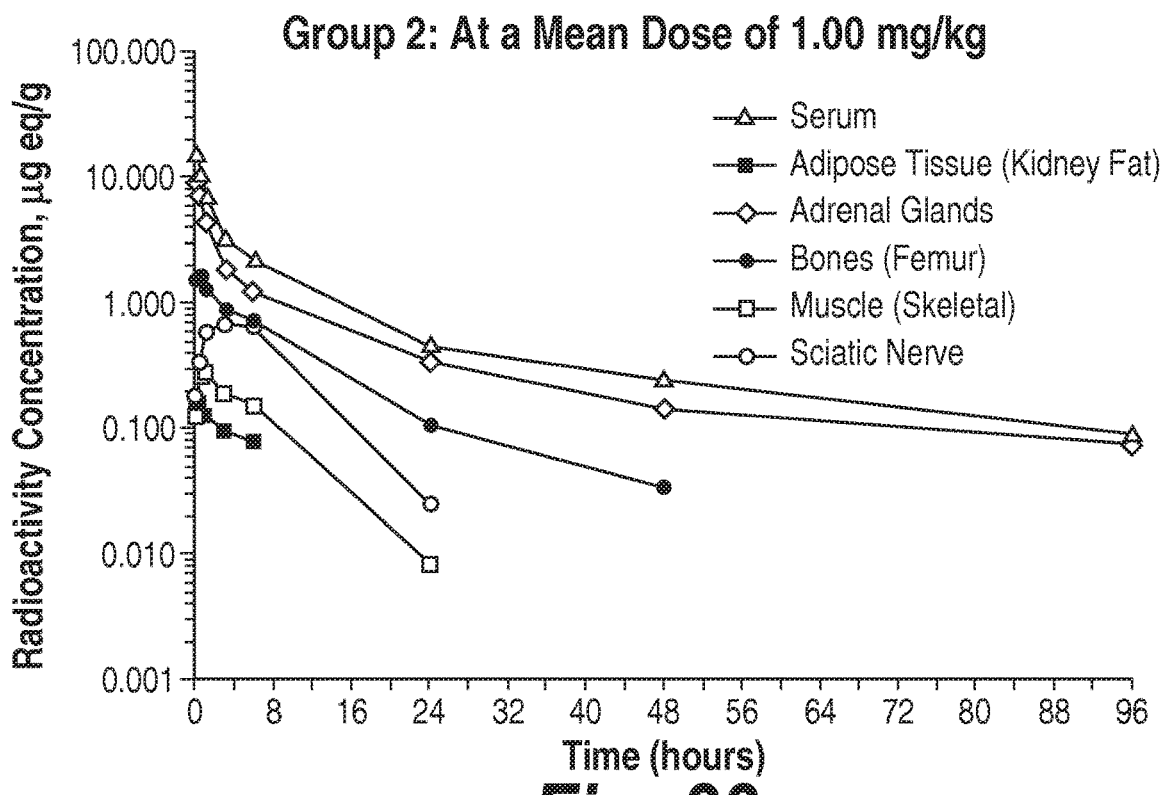
FIG. 23 depicts exemplary results illustrating the mean concentrations of radioactivity in serum and various tissues (adipose tissues (kidney fast), adrenal glands, bone (femur), muscle (skeletal), sciatic nerve)) of male Sprague-Dawley rats following a single intravenous bolus injection of $^{125}$I-hGalC.
Figure 24:
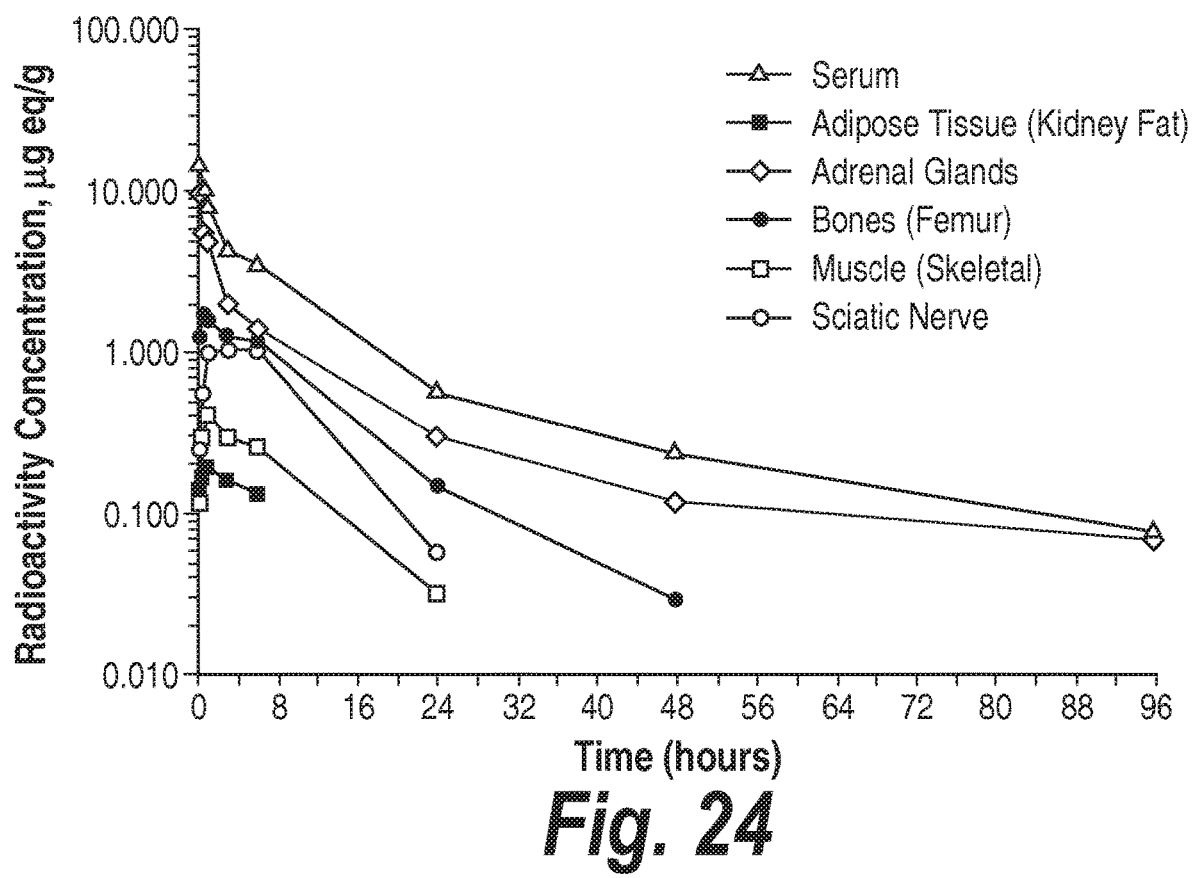
FIG. 24 depicts exemplary results illustrating the mean concentrations of radioactivity in serum and tissues (adipose tissues (kidney fast), adrenal glands, bone (femur), muscle (skeletal), sciatic nerve)) of male Sprague-Dawley rats following a single intrathecal dose and intravenous bolus injection of $^{125}$I-hGalC.
Figure 25:
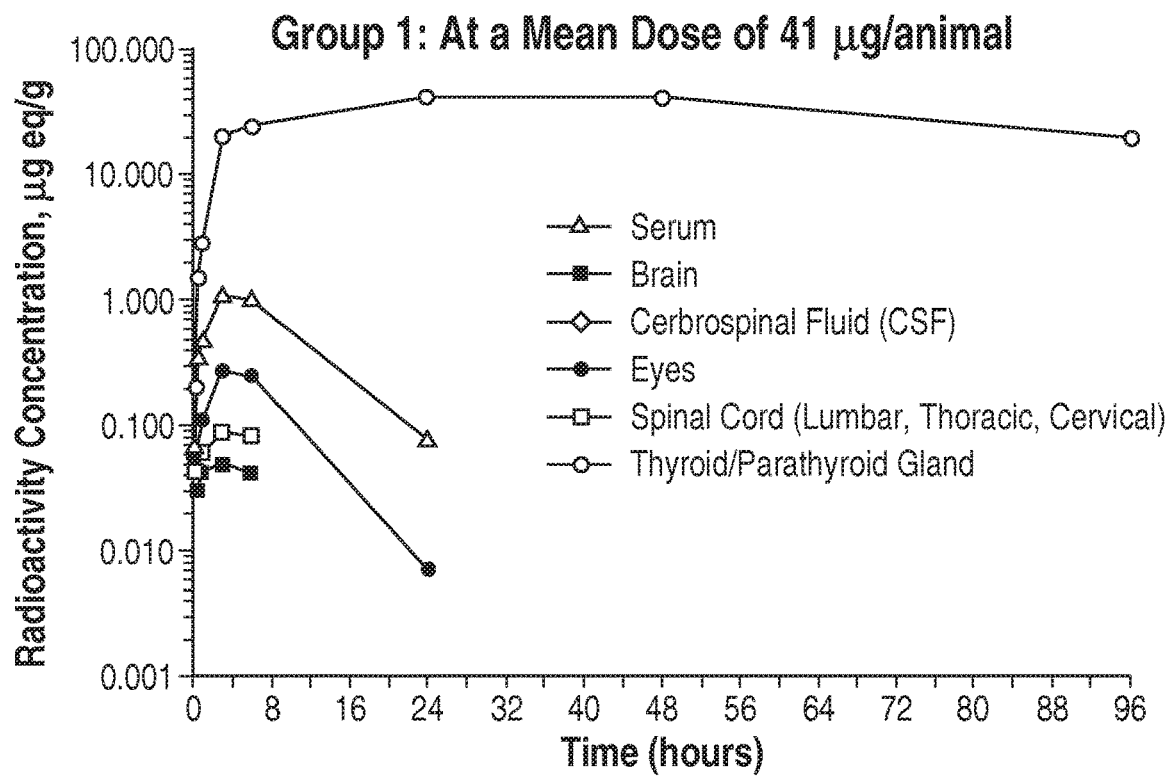
FIG. 25 depicts exemplary results illustrating the mean concentrations of radioactivity in serum, cerebrospinal fluid and various other tissues of male Sprague-Dawley rats following a single intrathecal dose of $^{125}$I-hGalC.
Figure 26:
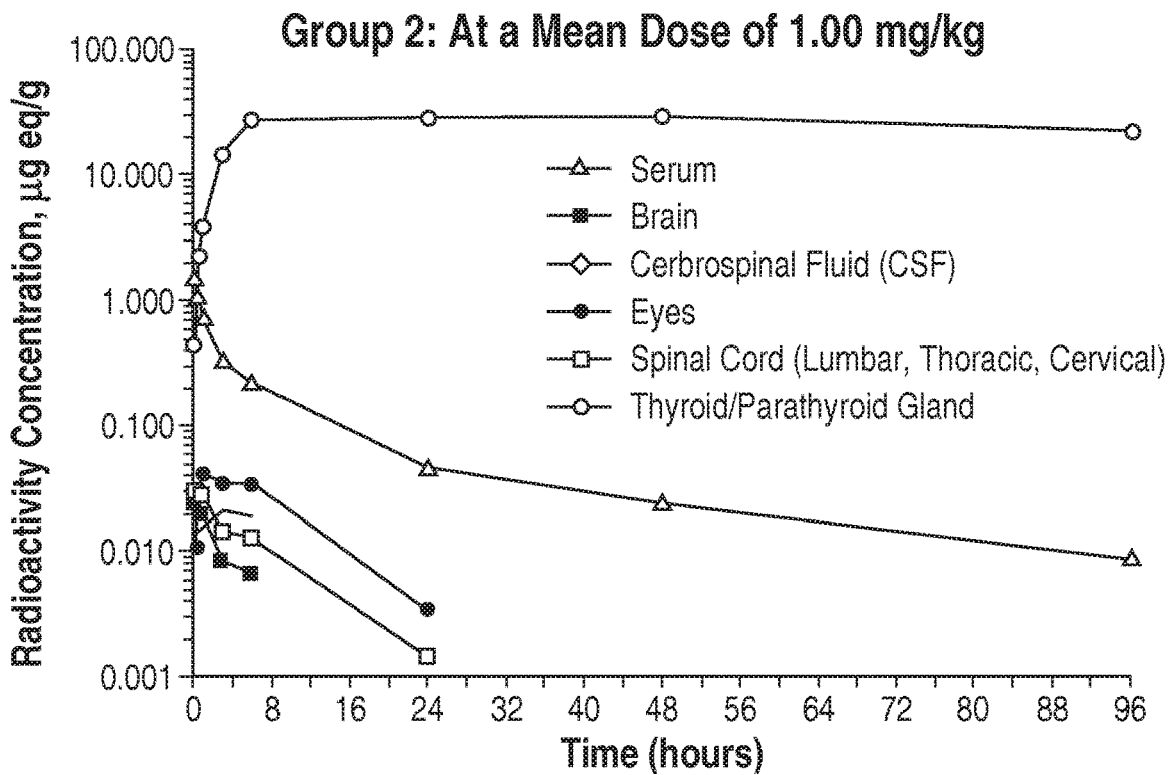
FIG. 26 depicts exemplary results illustrating the mean concentrations of radioactivity in serum, cerebrospinal fluid and various other tissues of male Sprague-Dawley rats following a single intravenous bolus injection of $^{125}$I-hGalC.
Figure 27:
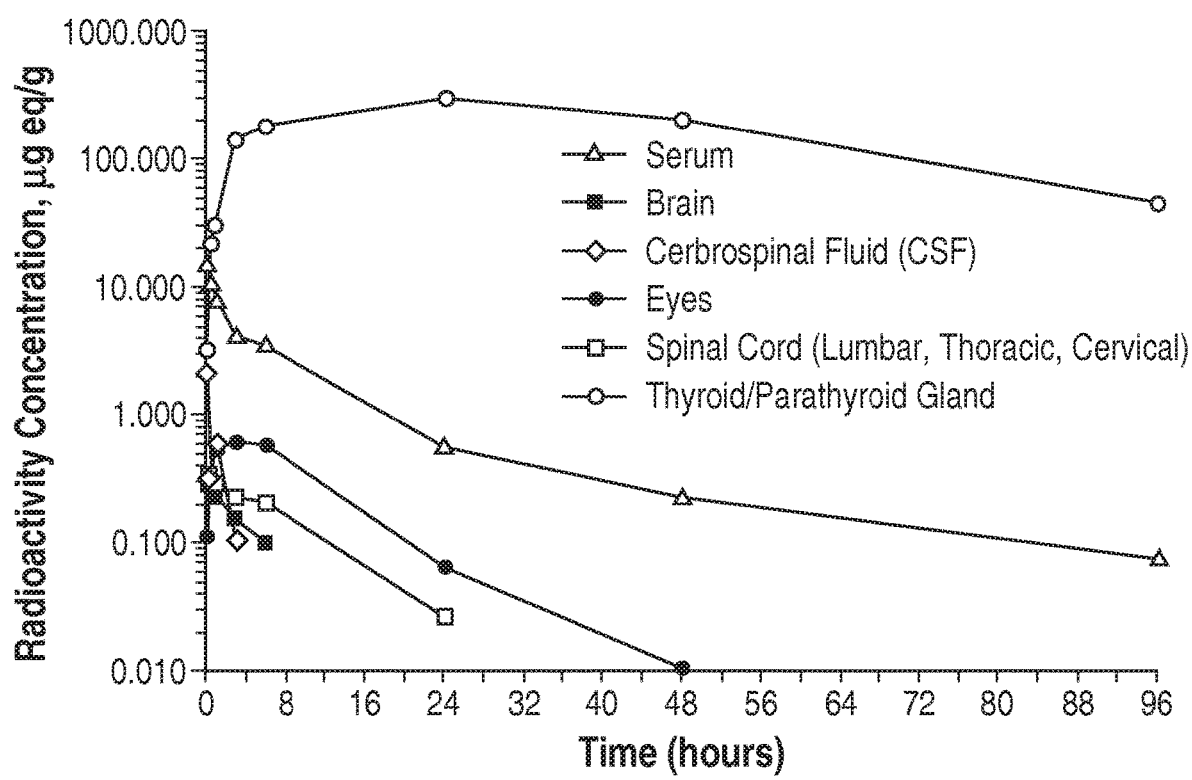
FIG. 27 depicts exemplary results illustrating the mean concentrations of radioactivity in serum, cerebrospinal fluid and tissues of male Sprague-Dawley rats following a single intrathecal dose and intravenous bolus injection of $^{125}$I-hGalC.
Figure 28:
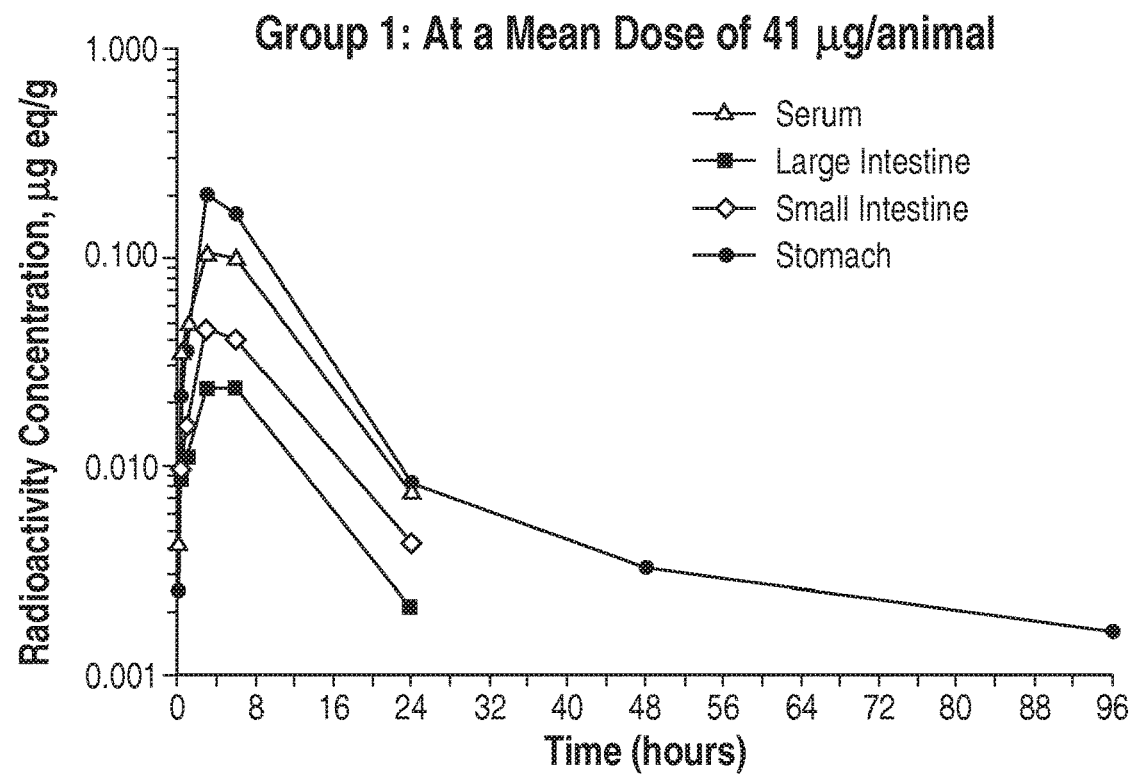
FIG. 28 depicts exemplary results illustrating the mean concentrations of radioactivity in serum and tissues of male Sprague-Dawley rats following a single intrathecal dose of $^{125}$I-hGalC.
Figure 29:
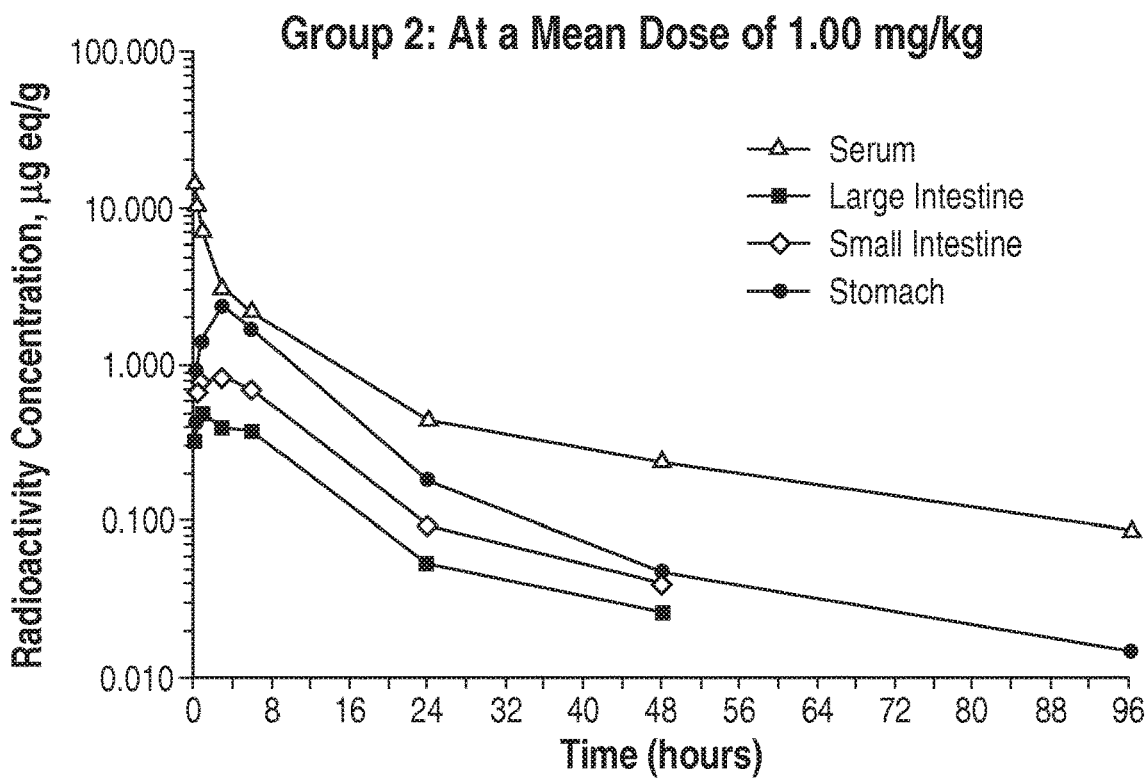
FIG. 29 depicts exemplary results illustrating the mean concentrations of radioactivity in serum and tissues of male Sprague-Dawley rats following a single intravenous bolus injection of $^{125}$I-hGalC.
Figure 30:
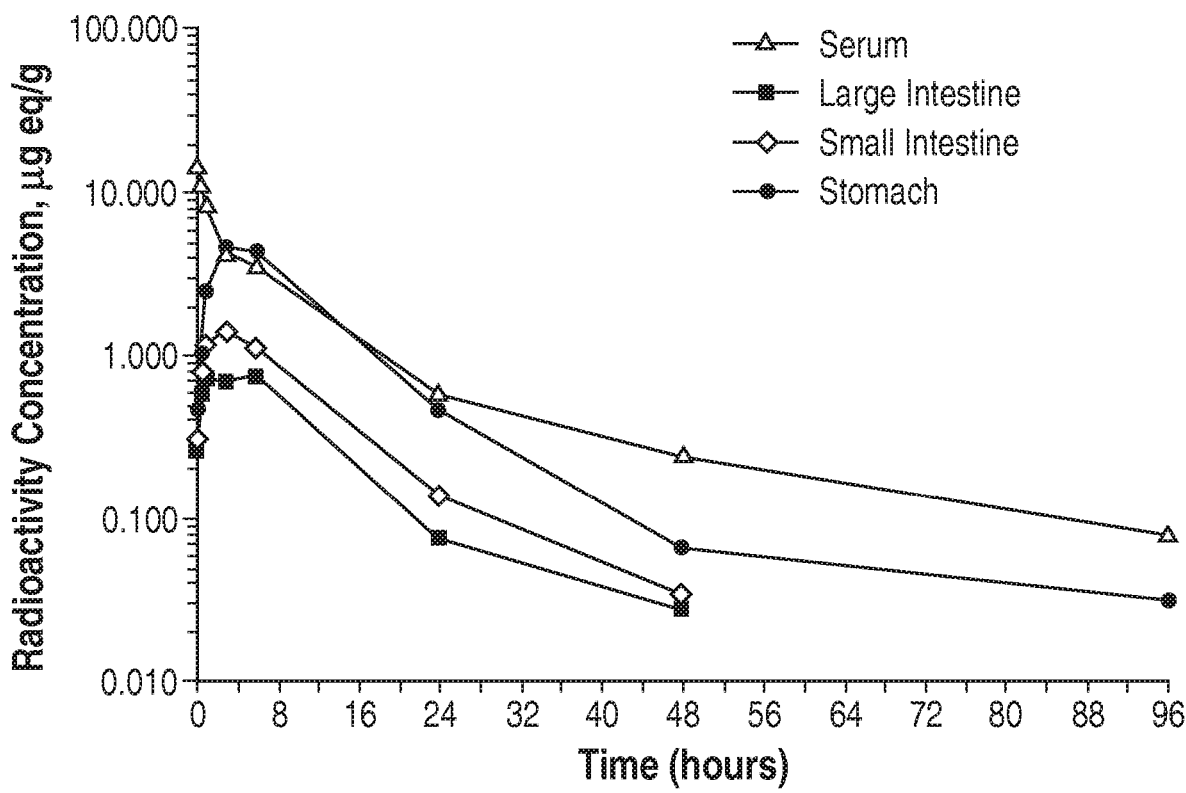
FIG. 30 depicts exemplary results illustrating the mean concentrations of radioactivity in serum and tissues of male Sprague-Dawley rats following a single intrathecal dose and intravenous bolus injection of $^{125}$I-hGalC.

The addition of 5% dextrose to GalC in 5 mM Na phosphate, pH 6.0 resulted in the formation of large aggregates (FIG. 15). The peak at 18S corresponds to a minimum molar mass of about 440 kDa and the peak at 56S corresponds to a minimum molar mass of 2.4 MDa with a tail extending beyond 150S, corresponding to molar masses greater than 10.0 MDa. There is very little change in this pattern upon dilution from 1.0 to 0.3 mg/mL indicating that these oligomers are mostly irreversible on the time scale of the sedimentation experiment, a period of 5-6 hours hGalC Intrinsic Fluorescence Intrinsic fluorescence studies of hGalC (using 23 Trp) were performed to evaluate the role of pH and salt concentration on molecular interactions (FIG. 16 and FIG. 17). Molecular interactions were the least (highest relative fluorescence between 330 nm-350 nm) in either 500 mM NaCl or 1% NaTC (FIG. 16). A small change in the secondary structure was observed as a function of pH. Precipitation was observed at pH 4.5 and 5.0 (FIG. 17).

Summary

To evaluate the relative solubility of hGalC and mGalC, a polyethylene glycol (PEG)-induced solid phase approach was used (Middaugh et al., J. Biol. Chem. 1979, 254, 367-370). This approach allows for the relative solubility of proteins to be measured in a quantifiable manner. Solubility measurements were performed by introducing buffered solutions (5 mM sodium phosphate with 150 mM NaCl, pH 6.0) of each GalC to the different concentrations of PEG (10 kDa). Plots of log protein solubility vs. PEG concentrations produced a linear trend. Extrapolation of the apparent solubility to zero PEG concentration was made to obtain the relative solubility of each protein. Relative solubility of the mGalC vs. hGalC did not show any difference. In solubility experiments of hGalC, no precipitation or loss of activity was observed after 3 weeks at 2-8° C. (in 5 mM sodium phosphate with different salt concentrations, pH 6.0-6.5). Solubility at ~30 mg/mL was achieved with the formulation 5 mM Na phosphate +150 mM NaCl, pH 6.0, and no precipitation was observed after 50 days at 2-8° C.

The AUC data suggest that the "native" state of GalC is a concentration dependent reversible association to higher order oligomers. The biophysical data suggest that there may be a functional and structural importance to the higher order oligomers. At higher pH values, there is less retention of activity, lower Tm values and a more homogenous system as determined by AUC. In 5 mM sodium phosphate with 150 mM NaCl, pH 6.0, there is likely an equilibrium between monomer, tetramer and other higher order species. Furthermore, pH does not dramatically affect the AUC profiles in the pH range of 6.5-7.5. Overall, the GalC system is a rapidly reversible, highly self-associating system in the tested buffers.

Example 2: Pharmacokinetics and Tissue Distribution of Radioactivity in Sprague-Dawley Rats Following a Single Intrathecal Dose or a Single Intravenous Bolus Injection of $^{125}$I-HGALC The present Example depicts an exemplary result illustrating pharmacokinetics and tissue distribution of $^{125}$I-hGALC in male Sprague-Dawley rats following a single intrathecal dose or a single intravenous bolus injection. The concentration and content of radioactivity in whole blood, serum, red blood cells, cerebrospinal fluid (CSF) and tissues were measured and non-compartmental pharmacokinetic analyses were performed on the resulting data. The intrathecal and intravenous routes were selected as they are the intended routes of administration in humans. The dose levels were selected based on potential human exposure, existing toxicity and pharmacokinetic data and any limitations imposed by the test article. The rat was selected for the study because it is an accepted species for use in pharmacokinetic and tissue distribution studies. The number of animals used in this study was the minimum needed to adequately assess the expected variability at each time point and meet the experimental objectives.

Materials and Methods

Test System 82 male Sprague-Dawley rats (*Rattus norvegicus*) were received from Charles River Canada Inc. (St. Constant, Quebec, Canada) on 15 Apr. 2009. At the onset of treatment, the animals were approximately 10-11 weeks old. A further 9 male rats were received from Charles River Canada on 28 Apr. 2009; these animals were approximately 9 weeks old on arrival and were required to ensure that sufficient cannulated animals were available in order to complete dosing of the study.

The body weights of the male rats ranged from 342 to 453 g at the onset of treatment. The body weights of all but one of the male rats on dosing were higher than the range stated in the protocol (250-350 g), however this minor deviation was not considered to have affected the study or the data obtained since the animals were healthy and the actual body weight was used for dose administration.

Animal Management

Following arrival at PCS-MTL, all animals were subjected to a general physical examination by a qualified member of the veterinary staff. No significant abnormalities were detected in the animals received. Animals were housed individually in stainless steel cages with a wire-mesh bottomed floor and an automatic watering valve. The environmental enrichment program was in accordance with the appropriate SOP. Each cage was clearly labelled with a colour-coded cage card indicating study, group, animal numbers and sex. Each animal was uniquely identified using the AIMS® tattoo system. Environmental conditions during the study conduct were controlled at a target temperature and relative humidity of 19 to 25° C. and 30 to 70%, respectively. The photo period was 12 hours light and 12 hours dark except when interrupted due to scheduled activities.

Diet

All animals had free access to a standard certified pelleted commercial laboratory diet (PMI Certified Rodent Diet 5002: PMI Nutrition International Inc.) except during designated procedures. Maximum allowable concentrations of contaminants in the diet (e.g., heavy metals, aflatoxin, organophosphate, chlorinated hydrocarbons, PCBs) are controlled and routinely analyzed by the manufacturers. Municipal tap water, suitable for human consumption (filtered through a 0.5 µm bacteriostatic polycarbonate filter) was available to the animals ad libitum except during designated procedures. It was considered that there were no known contaminants in the dietary materials that could interfere with the objectives of the study.

Acclimation and Randomization

At least 6 days (for animals received on 15 Apr. 2009) or 3 days (for the 9 additional animals received on 28 Apr. 2009) were allowed between the receipt of the animals and surgery to place the intrathecal cannula, to allow the animals to become acclimated to the physical and environmental conditions. During the acclimation period, all animals were weighed and randomized, using a computer-based randomization procedure. Randomization was performed following stratification using body weight as the parameter. Animals at the extremes of the body weight range were not assigned to groups.

The animals were assigned to the study groups as follows:

TABLE 7

| Group Number | Route of Administration and Dose | | Projected Dose Volume | | Animal Numbers |
|---|---|---|---|---|---|
| | Intravenous | Intrathecal | Intravenous (mL/kg) | Intrathecal (mL) | Males |
| 1 | — | 60 µg | — | 0.02 | 1001-1024 |
| 2 | 1 mg/kg | — | 3.33 | — | 2001-2024 |
| 3[a] | 1 mg/kg | 60 µg | 3.33 | 0.02 | 3001-3024 |

[a]The IV dose was administered within 5 minutes after the intrathecal dose.

Each rat in Groups 1 and 2 received a nominal radiochemical dose of approximately 3 µCi/animal. Each rat in Group 3 received a nominal radiochemical dose of approximately 6 µCi/animal.

Intrathecal Dose Formulation

The intrathecal dose formulation was prepared on the day of first administration of the intrathecal dose. Sufficient $^{125}$I-hGALC solution was measured and added to sufficient measured unlabelled hGALC solution. A measured volume of vehicle was added and the whole mixed gently. A solution of concentration 3 mg/mL at a target radioactivity level of approximately 150 µCi/mL was prepared. The resulting formulation was filtered through a low protein binding filter (0.22 µm GV PVDF filter unit) into a sterile vessel and kept refrigerated (2-8° C.), protected from light, pending use for dosing.

Intravenous Dose Formulation

The intravenous dose formulation was prepared on the day of first administration of the intravenous dose. Sufficient $^{125}$I-hGALC solution was measured and added to sufficient measured unlabelled hGALC solution. A measured volume of vehicle was added and the whole mixed gently. A solution of concentration 0.3 mg/mL at a target radioactivity level of approximately 3 µCi/mL was prepared. The resulting formulation was filtered through a low protein binding filter (0.22 µm GV PVDF filter unit) into a sterile vessel and kept refrigerated (2-8° C.), protected from light, pending use for dosing.

Analysis of the Dose Formulations

Each radiolabelled dose formulation was analyzed at PCS-MTL on each day of dosing by liquid scintillation spectroscopy to determine the radioactivity concentration before and after treatment. The radioactivity concentration was determined by preparing appropriate dilutions of the dose formulation in vehicle and duplicate aliquots of each dilution were analyzed. The remaining dose formulations were discarded following completion of analysis (including repeat analysis).

Calculation of Specific Activity of Test Article

The specific activity of the test article in the dose formulations was calculated from the mean (pre and post dose) measured levels of radioactivity and the total mass of test article (based on the concentrations provided) in the dose formulations.

Clinical Observations

All animals were examined twice daily for mortality and signs of ill health and reaction to treatment throughout the acclimation and study periods, except on the days of arrival and termination of the study, on which days the animals were only examined once. A detailed examination was performed weekly.

Body Weight

Individual body weights were measured once during acclimation, before surgery and on the day prior to dose administration. Only the body weights recorded on the day prior to dose administration were reported.

Surgery

A minimum of 6 days (or 3 days for the 9 additional animals) was allowed between the receipt of the animals and the surgery to allow the animals to become accustomed to the laboratory environmental conditions. All animals, including the spares, received a single intramuscular injection of Benzathine Penicillin G +Procaine Penicillin G antibiotic on the day of surgery and again 2 days following surgery. In general, Buprenorphine 0.05 mg/kg was administered subcutaneously prior to surgery and approximately 8 hours post first administration, and as deemed necessary thereafter. For some animals, Buprenorphine was administered approximately 6 hours post first administration instead of 8-12 hours. Considering the half-life of Buprenorphine in rats, this deviation from the protocol did not affect the health of these animals, and thus had not impact on the validity or data obtained in the study.

The animals were prepared for surgery by shaving from the cranium to the dorso-thoracic region of the neck. The animals were anesthetized with isoflurane/oxygen gas prior to surgery and maintained under isoflurane gas anesthesia throughout the surgical procedure. Prior to surgery, and at the end of the surgical procedure, while under anesthesia, a bland lubricating ophthalmic agent was administered to each eye. Prior to the surgery, and on 2 other occasions at approximately 24-hour intervals following the first administration, each animal received an anti-inflammatory (Carprofen at 5 mg/kg) by subcutaneous injection.

The animal was positioned within the stereotaxic table. A skin incision, of approximately 2 cm, was made from the caudal edge of the cranium to the neck. The dorsal neck muscles were separated in order to expose the atlanto-occipital membrane. A retractor was used to facilitate access to the membrane. The atlanto-occipital membrane was incised and the intrathecal catheter was slowly inserted caudally until the catheter was located in the lumbar region. Excess fluid was removed using cotton-tipped swabs and the atlanto-occipital membrane was dried. Immediately thereafter, adhesive was used to anchor the catheter bulb to the membrane. Once the glue had dried and the catheter was solidly anchored, the retractors were removed. A small loop was made with the catheter on the cranium and the bulb was attached using a suture of non-absorbable material. Once the catheter was secured, it was passed to the dorsal thoracic region where an incision was made to place an access port. This was sutured in place using non-absorbable material.

Prior to closing the neck muscles, a 2 mL flush of warm saline (i.e.: approximately 37.5° C.) was made in the wound. The muscles were closed using simple interrupted sutures of absorbable material. The access port site was flushed with 2 mL of warm saline and the skin was closed using a continuous subcuticular suture of absorbable suture material. A topical antibiotic ointment was administered to surgical sites post-surgery and once daily thereafter until considered unnecessary.

The dead volume of the catheter and access port was determined at the time of surgery. A patency check was performed once during the pre-treatment period between the surgery day and the treatment day.

Treatment

A period of at least 7 days was allowed between the surgical implantation of the catheter/access port and treatment initiation to allow for adequate recovery. Prior to intrathecal dosing, the access port area was shaved, if necessary. The puncture site was cleaned using chlorhexidine gluconate and water, and the site wiped with soaked gauze of sterile water followed by 3 passages of povidone iodine 10%. The access port was punctured with a needle connected to the dosing syringe and the test article was administered slowly. After dosing, the site was wiped with iodine in order to limit contamination.

On Day 1 of the study, Group 1 animals were administered the formulated $^{125}$I-hGALC by slow bolus intrathecal injection into the subcutaneous lumbar access port followed by a saline flush of 0.04 mL to deliver a target dose level of 60 μg/animal and a radioactivity dose of approximately 3 μCi/animal.

On Day 2 of the study, Group 3 animals were administered formulated $^{125}$I-hGALC by slow bolus intrathecal injection into the subcutaneous lumbar access port followed by a saline flush of 0.04 mL to deliver a target dose level of 60 μg/animal and a radioactivity dose of approximately 3 μCi/animal. Within 5 minutes of the slow bolus intrathecal injection, Group 3 animals also received an intravenous injection via an intravenous catheter into the tail vein (3.33 mL/kg) followed by a 0.6 mL saline flush to deliver a target dose level of 1 mg/kg, with an approximate radioactivity level of 3 μCi/animal.

On Day 3 of the study, Group 2 animals were administered formulated $^{125}$I-hGALC by intravenous injection via an intravenous catheter into the tail vein (3.33 mL/kg) followed by a 0.6 mL saline flush to deliver a target dose level of 1 mg/kg animal and a radioactivity dose of approximately 3 μCi/animal.

The volume administered was based on the most recent practical body weight of each animal. The weights of the syringes filled with formulated $^{125}$I-hGALC and empty after delivery to the animals were recorded. The dose delivered to each animal was calculated on the basis of the net weight of dosage formulation expelled from the syringe and the measured radioactivity concentration in the formulated dose.

During dosing, gauzes were available to absorb any small amounts of reflux of dose formulation and the test article loss was accounted for by liquid scintillation counting according to a project specific procedure. The syringes and intravenous catheters used for administration of formulated test article were retained. The intravenous catheters and selected intrathecal access port/catheters were analyzed for the level of radioactivity according to a project specific procedure.

Sample Collection
Blood/Serum and Tissues

A terminal blood sample (maximum possible volume) was collected at 10 minutes, 30 minutes and 1, 3, 6, 24, 48 and 96 h post dose from 3 animals/time point for Groups 1 to 3. The intrathecal administration preceded the intravenous administration in Group 3, and the timing for the terminal blood sample was based on the time of the intravenous administration. Terminal blood samples were collected from the abdominal aorta of rats (Groups 1, 2 and 3, and 3 spare animals) euthanized under isoflurane anesthesia by exsanguination from the abdominal aorta. Approximately 3 mL of blood (Groups 1, 2 and 3) was transferred to a suitable tube containing $K_3$-EDTA, to furnish whole blood samples and was kept on wet ice pending processing. For Groups 2 and 3, and the spare animals, an additional 1.5 mL of blood was transferred into tubes containing sodium citrate for analysis of prothrombin time (PTT), activated partial thromboplastin time (APTT) and fibrinogen. Blood samples were stored on wet ice, pending centrifugation at 2700 RPM and 4° C. for 15 minutes. Plasma samples were stored frozen at approximately −80° C., before shipment and analysis at a laboratory designated by the Applicant. Plasma from the spare animals was to serve as blank samples for the analysis of PTT, APTT and fibrinogen. Where insufficient blood volume was obtained to perform all analyses (Groups 1, 2 and 3), then blood for radioactivity analysis had the priority.

The remaining blood (Groups 1, 2 and 3, and 3 spare animals) was transferred into tubes containing clotting activator for serum production and was allowed to clot, at room temperature, over a period of approximately 30 minutes before centrifugation. The samples collected from the spare animals were used to assess the clotting of blood samples from non-treated animals.

Following exsanguination, the following tissues were collected from 3 animals/time point from Groups 1 to 3, as indicated: Adipose tissue (kidney fat), Adrenal glands, Bone (femur), Brain, Eyes, Heart, Kidneys, Large intestine, Large intestine content, Liver, Lungs, Muscle (skeletal), Sciatic nerve, Small intestine, Small intestine content, Spinal cord (lumbar, thoracic, cervical), Spleen, Stomach, Stomach content, Thyroid/parathyroid gland, Urinary bladder content.

Upon collection, tissues were weighed and then processed and analyzed for total radioactivity. All tissues mentioned above, as well as terminal blood and serum, were also collected from a spare animal and were used to determine background levels of radioactivity. The remaining carcasses were kept frozen (−10° C. to −20° C.) in the designated freezer in order to allow for radioactive decay before being disposed as biological waste. The carcass of the first animal at each time point from Groups 1 and 3 were retrieved from the freezer, thawed and the access port and catheter removed, flushed with water and verified for residual radioactivity.

Cerebrospinal Fluid

Cerebrospinal fluid (CSF) samples were collected from all animals at necropsy immediately before euthanasia. Three animals/time-point from Groups 1 to 3 were euthanized at 10 minutes, 30 minutes and 1, 3, 6, 24, 48 and 96 h post dose. A sample (maximum possible volume) of CSF was removed via the cisterna magna, using a stereotaxic table were necessary to hold the head in alignment. CSF was transferred into a plain tube and placed on wet ice. A portion (approximately 20 μL) was processed and analyzed for total radioactivity content. CSF was also collected from a spare animal and was used to determine background levels of radioactivity.

Determination of Background Radioactivity Levels

The blood, serum and tissues collected from the spare animal, were used for the determination of background radioactivity levels for blood, serum and tissues of animals in Groups 1, 2 and 3. The CSF collected from the spare animal, was used for the determination of background radioactivity levels for CSF.

Sample Processing for Radioactivity Measurements

All samples were weighed following collection, except for blood, plasma, serum and CSF. For all groups, duplicate 100 μL weighed aliquots of whole blood collected on $K_3$-EDTA, were taken for analysis of radioactivity. Protein precipitation using trichloroacetic acid (TCA) of whole blood was performed as follows: an equivalent volume of a 15% aqueous solution of TCA was added to duplicate 100 μL weighed aliquots of whole blood. Samples (100 μL whole blood+100 μL TCA) were mixed by vortexing and then centrifuged at 4° C. for approximately 15 minutes at 10000 rpm, and the supernatant decanted into a separate tube. Both the supernatant and the pellet were analyzed for radioactivity content.

The blood for serum collection was kept at room temperature for approximately 30 minutes, to allow for clotting, before being centrifuged at 4° C. at 2700 rpm (1250 rcf) for approximately 10 minutes to separate serum. Serum samples were then kept on wet ice pending aliquotting for radioactivity analysis (2×100 μL weighed aliquots). The packed red blood cells (obtained after serum separation) were kept on wet ice pending processing for radioactivity analysis. Remaining serum was stored frozen (−10° C. to −20° C.). Duplicate 100 μL weighed aliquots of whole blood and red blood cells (obtained after serum separation, mixed with an equal volume of deionized water (w/v) and homogenized with a Polytron emulsifier) were solubilized in Soluene-350, decolorized with hydrogen peroxide (30% w/v), and mixed with liquid scintillation fluid for analysis of radioactivity.

The TCA blood precipitate pellet was solubilized in 35% tetraethylammonium hydroxide (TEAH), decolorized with hydrogen peroxide (30% w/v), and mixed with liquid scintillation fluid for radioactivity measurement. Urinary bladder contents, TCA blood supernatant, duplicate weighed aliquots of dose formulations (diluted) and serum were mixed directly with liquid scintillation fluid for radioactivity measurement. Duplicate weighed aliquots of CSF (approximately 10 μL/aliquot) were solubilized in 35% TEAH prior to mixing with liquid scintillation fluid for radioactivity measurement.

Tissue samples were solubilized in toto in 35% TEAH. Duplicate aliquots were then mixed with liquid scintillation fluid prior to radioactivity measurement. Large intestine contents were homogenized in a known volume of water. Duplicate weighed aliquots of large intestine content (LINC) homogenates, stomach contents (STC) and small intestine contents (SINC) were solubilized in 35% TEAH and mixed with liquid scintillation fluid for radioactivity measurement.

Radioactivity Measurements

Radioactivity measurements were conducted by liquid scintillation spectroscopy according to Standard Operating Procedures (SOP). Each sample was counted for 5 minutes or to a two-sigma error of 0.1%, whichever occurred first. All counts were converted to absolute radioactivity (DPM) by automatic quench correction based on the shift of the spectrum for the external standard. The appropriate background DPM values were subtracted from all sample DPM values. Following background subtraction, samples that exhibited radioactivity less than or equal to the background values were considered as zero for all subsequent manipulations.

Data Analysis

Radioactivity Concentration

All radioactivity measurements were entered into a standard computer database program (Debra Version 5.2) for the calculation of concentrations of radioactivity (dpm/g and mass eq/g) and percentage-administered radioactivity in sample. Blood, serum, tissues and CSF concentrations of radioactivity in dpm/g and mass eq/g were calculated on the basis of the measured specific activity (dpm/mg or appropriate mass unit) of radiolabelled test article in the dose solutions. The radioactivity concentration in blood samples was converted to mass eq/mL on the basis of the density of rat blood. Total tissue content was calculated for the total organ weights.

Pharmacokinetics

The pharmacokinetic (PK) profile of total radioactivity in blood, serum, CSF and tissues was characterized by non-compartmental analysis of the concentration versus time data using validated computer software (WinNonlin, version 3.2, Pharsight Corp., Mountain View, California, USA). Models were selected based on the intravenous and extravascular routes of administration. Concentration values reported as not detectable or quantifiable were not estimated; they were treated as absent samples. Concentration data were obtained from different animals at each time point, and mean values were used to generate a composite pharmacokinetic profile. The 10-minute sampling for Group 1 (Animal Nos. 1001, 1002, 1003) and Group 2 (Animal Nos. 2001, 2002, 2003), and the 48-hour for Group 1 (Animal Nos. 1019, 1020) deviated by more than 10% or 6 minutes of the nominal timepoint. This deviation from the protocol did not affect the validity of the study or the data obtained, since the mean time was calculated and used in the pharmacokinetic analyses.

The area under the radioactivity concentration vs. time curve (AUC) was calculated using the linear trapezoidal method (linear interpolation). When practical, the terminal elimination phase of the PK profile was identified based on the line of best fit ($R^2$) using at least the final three observed concentration values. The slope of the terminal elimination phase was calculated using log-linear regression using the unweighted concentration data. Parameters relying on the determination of kel were not reported if the coefficient of determination ($R^2$) was less than 0.8, or if the extrapolation of the AUC to infinity represented more than 20% of the total area.

Results

Analysis of the Dosing Formulations (Table 8)

On each day of dosing, aliquots of each formulation were analyzed by liquid scintillation spectroscopy prior to and following dose administration to all groups, and the specific activity of the test article calculated from these analyses. The overall mean radioactivity concentration(±S.D.) in the formulation for intrathecal administration was $345.4 \times 10^6 \pm 4.92 \times 10^6$ dpm/g (155.60 μCi/g) for Group 1 and $334.4 \times 10^6 \pm 5.87 \times 10^6$ dpm/g (150.62 μCi/g) for Group 3. The overall mean radioactivity concentration in the formulation for intravenous administration was $4.4 \times 10^6 \pm 4.22 \times 10^5$ dpm/g (1.97 μCi/g) for Group 2 and $4.7 \times 10^6 \pm 2.31 \times 10^5$ dpm/g (2.11 μCi/g) for Group 3. The specific activity of the test article in the intrathecal formulation was calculated as 51.16 μCi/mg for the Group 1 dose and 49.53 μCi/mg for the Group 3 dose. The specific activity of the test article in the intravenous formulation was calculated as 6.53 μCi/mg for the Group 2 dose and 6.99 μCi/mg for the Group 3 dose.

TABLE 8

Summary Results of the Concentration of Radioactivity in the Dosing Formulations by Liquid Scintillation Spectroscopy

| Group No. | Route of Administration | Occasion | Mean Concentration of Radioactivity | | |
|---|---|---|---|---|---|
| | | | (dpm/g) | | (μCi/g) |
| | | | Mean ± SD | CV | Mean |
| 1 | Intrathecal | Pre-dose | 348445137 ± 3391878 | 0.97% | 156.96 |
| | | Post-dose | 342426851 ± 4484476 | 1.31% | 154.25 |
| | | Overall | 345435994 ± 4924300 | 1.43% | 155.60 |
| 2 | Intravenous Bolus Injection | Pre-dose | 4091887 ± 61669 | 1.51% | 1.84 |
| | | Post-dose | 4672629 ± 430335 | 9.21% | 2.10 |
| | | Overall | 4382258 ± 421765 | 9.62% | 1.97 |

TABLE 8-continued

Summary Results of the Concentration of Radioactivity in the Dosing Formulations by Liquid Scintillation Spectroscopy

| Group No. | Route of Administration | Occasion | Mean Concentration of Radioactivity | | |
|---|---|---|---|---|---|
| | | | (dpm/g) | | (µCi/g) |
| | | | Mean ± SD | CV | Mean |
| 3 | Intrathecal | Pre-dose | 332418463 ± 3013337 | 0.91% | 149.74 |
| | | Post-dose | 336332353 ± 7582128 | 2.25% | 151.50 |
| | | Overall | 334375408 ± 5868250 | 1.75% | 150.62 |
| 3 | Intravenous Bolus Injection | Pre-dose | 4827255 ± 92785 | 1.92% | 2.17 |
| | | Post-dose | 4545578 ± 247903 | 5.45% | 2.05 |
| | | Overall | 4686417 ± 231271 | 4.93% | 2.11 |

Animal Body Weights and Doses Administered (Table 9)

The mean body weights of the rats in Groups 1, 2 and 3 on the day prior to dosing were 405 g (range 373 g to 452 g), 410 g (range 367 g to 453 g), and 395 g (range 342 g to 444 g), respectively. The calculated mean dose of $^{125}$I-hGALC administered intrathecally to Group 1 animals was 41±0.014 µg/animal, this was equivalent to a radiochemical dose of 2.12±0.72 µCi/animal. The mean dose of $^{125}$I-hGALC administered by the intravenous route to Group 2 animals was 1.00±0.02 mg/kg (2.69±0.14 µCi/animal). For Group 3, the calculated mean dose of $^{125}$I-hGALC administered intrathecally and intravenously was 1.08±0.04 mg/kg (5.72±0.31 µCi/animal).

The mean chemical dose and the radiochemical dose administered to rats in Group 1 were lower (approximately 32% and 29%, respectively) than the target dose levels and this constituted a deviation from the protocol. However, since the actual doses administered to the animals were used throughout the calculations, these lower values were considered not to affect the validity of the study or the data obtained.

Clinical Observations

No treatment related clinical signs were observed in any of the rats following administration of $^{125}$I-hGALC intrathecally at 60 µg/animal and/or intravenously at 1 mg/kg.

Clotting Assessment

At the earlier time points (10 minutes to 6 hours post dose) it was noted that blood collected from treated animals did not fully clot within the 30 minutes allowed. However the blood collected from 3 untreated spare rats clotted readily, suggesting some interference of the test article with the clotting process. Clotting times of less than or greater than 30 minutes constituted a deviation from the protocol. However, the longer clotting times were required for some samples in order to provide some serum for analysis. A review of the results obtained revealed no correlation between concentration values obtained in serum and the length of time the blood took to clot. Therefore, this extended or shortened clotting time did not affect the validity of the study or the data obtained.

Pharmacokinetics of Total Radioactivity in Blood, Serum, Red Blood Cells, CSF and Tissues Total Radioactivity Concentrations in Blood, Serum and Red Blood Cells (Table 10, Table 11, Table 12, FIGS. 18-21)

Mean concentrations of radiolabelled material in serum of male rats following intrathecal and/or intravenous doses of $^{125}$I-hGALC are given in Table 10. Mean concentrations of radiolabelled material in whole blood and in red blood cells are presented in Table 11. Mean data are presented graphically in FIG. 18. Mean percentage of radioactivity recovered in supernatant and pellet of blood following TCA precipitation are presented in Table 12.

Group 1 (Intrathecal Mean Dose of 41 µg/Animal)

Following intrathecal dosing, the highest mean concentration ($C_{max}$) of radiolabelled material in serum and blood were observed at 3 hours following dosing (0.108±0.026 µg eq/g and 0.093±0.023 µg eq/g respectively). Radioactivity levels in blood remained relatively constant between 3 and 6 hours post dose whereas radioactivity levels in serum declined slightly. Thereafter, radioactivity concentrations in serum and blood declined and were below the limit of quantitation (LOQ) by 48 hours post dose. For red blood cells, $C_{max}$ was observed at 6 hours post dose and was 0.089±0.024 µg eq/g. Thereafter, red blood cells radioactivity concentrations declined and were below LOQ by 48 hour post dose. Mean blood to serum ratios following the intrathecal dose were less than 1 throughout the study period (range from 0.7 to 0.9), indicating that the radiolabelled material was not particularly associated with the blood cells. The values of the red blood cell to serum ratios (ranging from 0.8 to 0.9) also supported that radioactivity was not substantially associated with blood cells. The percentage of the dose found in the blood was estimated, using a standard blood volume/body weight (i.e. 64.0 mL/kg). At $t_{max}$ (the time at which the highest radioactivity concentration occurred), approximately 6% of the administered dose was associated with blood.

Group 2 (Intravenous Mean Dose of 1.00 mg/kg)

Following intravenous administration, the highest mean concentration ($C_{max}$) of radiolabelled material in serum (14.864±0.853 µg eq/g) and blood (10.228±0.447 µg eq/g) were observed at 10 minutes following dosing (i.e. the first time point analyzed). Thereafter, radioactivity concentrations in serum and blood declined slowly but were still detectable at 96 hours post dose (serum: 0.088±0.006 µg eq/g, 0.59% of $C_{max}$; blood: 0.051±0.002 µg eq/g, 0.50% of $C_{max}$), with the estimated percent of dose in blood decreasing from 68.4% to 0.3%. For red blood cells, a $C_{max}$ of

TABLE 9

Group Mean Body Weights and Specifications of $^{125}$I-hGALC Dose Administered to Male Sprague-Dawley Rats

| Group | Body Weight (kg) | Route of Administration | Radioactivity [a] | | | | | µg/animal |
|---|---|---|---|---|---|---|---|---|
| | | | DPM/animal | µCi/animal | µCi/kg | mg/animal | mg/kg | |
| 1 | 0.405 ± 0.022 | IT | 4,715,057 ± 1,600,366 | 2.12 ± 0.72 | 5.26 ± 1.86 | 0.041 ± 0.014 | 0.102 ± 0.037 | 41 |
| 2 | 0.410 ± 0.021 | IV | 5,961,365 ± 306,654 | 2.69 ± 0.14 | 6.55 ± 0.15 | 0.411 ± 0.022 | 1.00 ± 0.023 | — |
| 3[b] | 0.395 ± 0.027 | IT and IV | 12,698,351 ± 686,160 | 5.72 ± 0.31 | 14.5 ± 0.62 | 0.425 ± 0.034 | 1.08 ± 0.042 | — |

5.136±1.529 μg eq/g was observed at 10 minutes post dose. Thereafter, red blood cells radioactivity concentrations declined and were below LOQ by 96 hours post dose. Mean blood to serum ratios following the intravenous dose were less than 1 throughout the study period (range from 0.6 to 0.8), indicating that the radiolabelled material was not particularly associated with the blood cells. The values of the red blood cell to serum ratios (ranging from 0.4 to 0.6) also supported that radioactivity was not substantially associated with blood cells.

Group 3 (Intrathecal Followed by Intravenous Dose: 1.08 mg/kg (Combined Dose))

Following the intrathecal dose (target 60 μg/animal) and the intravenous dose (1 mg/kg), the highest mean concentration ($C_{max}$) of radiolabelled material in serum (14.675±0.810 μg eq/g) and blood (9.974±0.558 μg eq/g) were observed at 10 minutes following dosing (i.e. the first time point analyzed. Thereafter, radioactivity concentrations in serum and blood declined slowly but were still detectable at 96 hours post dose (serum: 0.077±0.010 μg eq/g, 0.52% of $C_{max}$; blood: 0.037±0.033 μg eq/g, 0.37% of $C_{max}$), with the extrapolated percent of dose in blood decreasing from 32.6% to 0.1%. For red blood cells, a $C_{max}$ of 6.113±1.748 μg eq/g was observed at 10 minutes post dose. Thereafter, red blood cells radioactivity concentrations declined and were below the limit of quantification by 96 hours post dose. Radiolabelled material was not particularly associated with the blood cells as shown by the mean blood to serum and red blood cell to serum ratios of less than 1 (ranging from 0.7 to 0.8 and 0.4 to 0.7, respectively).

TABLE 10a

Group Mean Concentration of Radioactivity in Serum of Male Sprague-Dawley Rats following a Single Intrathecal Dose of $^{125}$I-hGALC
Group 1: At a Mean Dose of 41 μg/animal

| Time Point | Radioactivity Concentration | |
|---|---|---|
| | DPM/g | μg eq/g |
| 10 min | 504 ± 462 | 0.004 ± 0.004 |
| 30 min | 4125 ± 2327 | 0 036 ± 0.020 |
| 1 h | 5705 ± 1535 | 0 050 ± 0.014 |
| 3 h | 12311 ± 2960 | 0 108 ± 0.026 |
| 6 h | 11473 ± 2596 | 0.101 ± 0.023 |
| 24 h | 884 ± 122 | 0.008 ± 0.001 |
| 48 h | 0 ± 0 | 0.000 ± 0.000 |
| 96 h | 0 ± 0 | 0.000 ± 0.000 |

TABLE 10b

Group Mean Concentration of Radioactivity in Serum of Male Sprague-Dawley Rats following a Single Intravenous Bolus Injection of $^{125}$I-hGALC
Group 2: At a Mean Dose of 1.00 μg/kg

| Time Point | Radioactivity Concentration[a] | |
|---|---|---|
| | DPM/g | μg eq/g |
| 10 min | 215632 ± 12377 | 14.864 ± 0.853 |
| 30 min | 157259 ± 14339 | 10.840 ± 0988 |
| 1 h | 106804 ± 6790 | 7.362 ± 0.468 |
| 3 h | 47009 ± 3754 | 3.240 ± 0.259 |
| 6 h | 31898 ± 2417 | 2.199 ± 0.167 |
| 24 h | 6584 ± 194 | 0.454 ± 0.013 |
| 48 h | 3523 ± 503 | 0.243 ± 0.035 |
| 96 h | 1278 ± 86 | 0.088 ± 0.006 |

TABLE 10c

Group Mean Concentration of Radioactivity in Serum of Male Sprague-Dawley Rats following a Single Intrathecal and Intravenous Bolus Injection of $^{125}$I-hGALC
Group 3: At a Mean Dose of 1.08 mg/kg

| Time Point | Radioactivity Concentration[a] | |
|---|---|---|
| | DPM/g | μg eq/g |
| 10 min | 227675 ± 12574 | 14.675 ± 0.810 |
| 30 min | 171721 ± 10165 | 11.069 ± 0.655 |
| 1 h | 127621 ± 7765 | 8.226 ± 0.502 |
| 3 h | 66561 ± 1164 | 4.290 ± 0.075 |
| 6 h | 54374 ± 4044 | 3.505 ± 0.261 |
| 24 h | 8894 ± 686 | 0.573 ± 0.044 |
| 48 h | 3622 ± 45S | 0.233 ± 0.030 |
| 96 h | 1199 ± 157 | 0.077 ± 0.010 |

TABLE 11a

Group Mean Concentration and Content of Radioactivity in Blood and Blood to Serum Ratios of Male Sprague-Dawley Rats following a Single Intrathecal Dose of $^{125}$I-hGALC
Group 1: At a Mean Dose of 41 μg/animal

| Time Point | Radioactivity Concentration[a] | | | Blood to Serum Ratio | Percent of Dose |
|---|---|---|---|---|---|
| | DPM/g | μg eq/g | μg eq/mL | | |
| 10 min | 210 ± 364 | 0.002 ± 0.003 | 0.002 ± 0.003 | 0.696[b] | 0.074 ± 0 128 |
| 30 min | 3579 ± 1918 | 0.032 ± 0.017 | 0.033 ± 0.01S | 0.878 ± 0.029 | 1.822 ± 0.351 |
| 1 h | 4933 ± 1446 | 0.043 ± 0.013 | 0.046 ± 0.013 | 0.860 ± 0.027 | 3.890 ± 0.253 |
| 3 h | 10617 ± 2586 | 0.093 ± 0.023 | 0.093 ± 0.024 | 0.862 ± 0.006 | 5 582 ± 0 554 |
| 6 h | 10530 ± 2507 | 0.093 ± 0.022 | 0.097 ± 0.023 | 0.917 ± 0.035 | 4.664 ± 0.576 |
| 24 h | 677 = US | 0.006 ± 0.001 | 0.006 ± 0.001 | 0.764 ± 0.032 | 0.600 ± 0.114 |
| 48 h | 0 = 0 | 0.000 ± 0.000 | 0.000 ± 0.000 | n/a | 0.000 ± 0.000 |
| 96 h | 0 | 0.000 ± 0.000 | 0.000 ± 0.000 | n/a | 0.000 = 0.000 |

TABLE 11b

Group Mean Concentration and Content of Radioactivity in Blood and Blood to Serum Ratios of Male Sprague-Dawley Rats following a Single Intravenous Bolus Injection of $^{125}$I-hGALC Group 2: At a Mean Dose of 1.00 mg/kg

| Time Point | Radioactivity Concentration[a] | | | | |
|---|---|---|---|---|---|
| | DPM/g | μg eq/g | μg eq/mL | Blood to Serum Ratio | Percent of Dose |
| 10 min | 148373 ± 6480 | 10.228 ± 0.447 | 10.739 ± 0.469 | 0.6S8 ± 0.012 | 68.393 ± 3.453 |
| 30 min | 107195 ± 5739 | 7.389 ± 0.396 | 7.759 ± 0.415 | 0.683 ± 0.036 | 49.317 ± 1.788 |
| 1 h | 77163 ± 694 | 5.319 ± 0.048 | 5.585 ± 0.051 | 0.724 ± 0.040 | 36.460 ± 0.174 |
| 3 h | 35469 ± 3124 | 2.445 ± 0.215 | 2.567 ± 0.226 | 0.754 ± 0.007 | 16.355 = 1.166 |
| 6 h | 24364 ± 1639 | 1.679 ± 0.113 | 1.763 ± 0.119 | 0.764 ± 0.007 | 11.184 ± 0.612 |
| 24 h | 4794 ± 160 | 0.330 ± 0.011 | 0.347 ± 0.011 | 0 729 ± 0.030 | 2.218 ± 0 076 |
| 48 h | 2259 ± 233 | 0.156 ± 0.016 | 0.163 ± 0.017 | 0.644 ± 0.028 | 1.042 = 0.141 |
| 96 h | 738 ± 29 | 0.051 ± 0.002 | 0.053 ± 0.003 | 0.579 ± 0.052 | 0.341 ± 0.011 |

TABLE 11c

Group Mean Concentration and Content of Radioactivity in Blood and Blood to Serum Ratios of Male Sprague-Dawley Rats following a Single Intrathecal Dose and Intravenous Bolus Injection of $^{125}$I-hGALC Group 3: At a Mean Dose of 1.08 mg/kg

| Time Point | Radioactivity Concentration[a] | | | | |
|---|---|---|---|---|---|
| | DPM/g | μg eq/g | μg eq/mL | Blood to Serum Ratio | Percent of Dose |
| 10 min | 154742 ± 8651 | 9 974 ± 0.558 | 10.473 ± 0.586 | 0.680 ± 0.009 | 32.599 ± 1.331 |
| 30 min | 117563 ± 4922 | 7.578 ± 0.317 | 7.957 ± 0.333 | 0.6S5 ± 0013 | 24.596 ± 1.523 |
| 1 h | 92086 ± 2812 | 5.936 ± 0.181 | 6.233 ± 0.191 | 0.723 ± 0.022 | 19.132 ± 1.432 |
| 3 h | 52419 ± 244 | 3.379 ± 0.016 | 3.548 ± 0.016 | 0.788 ± 0.017 | 11.283 ± 0.344 |
| 6 h | 43097 ± 4071 | 2.778 ± 0.262 | 2.917 ± 0.276 | 0.792 ± 0.019 | 9.263 ± 0 836 |
| 24 h | 6561 ± 78 | 0.423 ± 0.005 | 0.444 ± 0.006 | 0.740 ± 0.054 | 1.345 ± 0.080 |
| 48 h | 2362 ± 398 | 0.152 ± 0.026 | 0.160 ± 0.027 | 0.650 ± 0.029 | 0.465 ± 0.083 |
| 96 h | 581 ± 513 | 0.037 ± 0.033 | 0.039 ± 0.035 | 0.684 ± c | 0.124 ± 0 109 |

TABLE 11d

Group Mean Concentration and Content of Radioactivity in Red Blood Cells and Red Blood Cells to Serum Ratios of Male Sprague-Dawley Rats following a Single Intrathecal Dose of $^{125}$I-hGALC Group 1: At a Mean Dose of 41 μg/animal

| Time Point | Radioactivity Concentration[a] | | | |
|---|---|---|---|---|
| | DPM/g | μg eq/g | RB Cells to Serum Ratio | Percent of Dose |
| 10 min | 0 ± 0 | 0.000 = 0.000 | n/a | 0.000 ± 0.000 |
| 30 min | 3044 ± 1261 | 0.027 ± 0.011 | 0.793 ± 0.148 | 0.213 ± 0067 |
| 1 h | 4454 ± 1396 | 0.039 = 0.012 | 0.773 ± 0.059 | 0.357 ± 0.336 |
| 3 h | 9763 ± 2664 | 0.086 ± 0.023 | 0.789 ± 0.031 | 0.734 ± 0.300 |
| 6 h | 10038 ± 2682 | 0.089 ± 0.024 | 0.876 ± 0.083 | 0.616 ± 0 200 |
| 24 h | 287 ± 497 | 0.003 ± 0.004 | 0.841[b] | 0.044 ± 0.075 |
| 48 h | 0 ± 0 | 0.000 ± 0.000 | n/a | 0.000 ± 0.000 |
| 96 h | 0 ± 0 | 0.000 ± 0.000 | n/a | 0.000 ± 0.000 |

TABLE 11e

Group Mean Concentration and Content of Radioactivity in Red Blood Cells and Red Blood Cells to Serum Ratios of Male Sprague-Dawley Rats Following a Single Intravenous Bolus Injection of $^{125}$I-hGALC
Group 2: At a Mean Dose of 1.00 mg/kg

| Time Point | Radioactivity Concentration[a] | | | |
|---|---|---|---|---|
| | DPM/g | μg eq/g | RB Cells to Serum Ratio | Percent of Dose |
| 10 min | 74506 ± 22185 | 5.136 ± 1 529 | 0.350 ± 0.119 | 4.110 ± 2.794 |
| 30 min | 59201 ± 14694 | 4.081 ± 1.013 | 0.377 ± 0 086 | 2.600 ± 1 087 |
| 1 h | 52799 ± 23155 | 3.639 ± 1.596 | 0.487 ± 0.196 | 3.229 ± 2.403 |
| 3 h | 28039 ± 3432 | 1.933 ± 0.237 | 0.599 ± 0.083 | 1.709 ± 0.734 |
| 6 h | 19662 ± 2540 | 1.355 ± 0.175 | 0.616 ± 0.057 | 1.143 ± 0315 |
| 24 h | 3714 ± 292 | 0.256 ± 0 020 | 0.564 ± 0.040 | 0.164 ± 0.111 |
| 48 h | 1619 ± 482 | 0.112 ± 0.033 | 0.453 ± 0 082 | 0.076 ± 0.064 |
| 96 h | 0 ± 0 | 0.000 ± 0.000 | n/a | 0.000 ± 0.000 |

TABLE 11f

Group Mean Concentration and Content of Radioactivity in Red Blood Cells and Red Blood Cells to Serum Ratios of Male Sprague-Dawley Rats Following a Single Intrathecal Dose and Intravenous Bolus Injection of $^{125}$I-hGALC
Group 3: At a Mean Dose of 1.08 mg/kg

| Time Point | Radioactivity Concentration[a] | | | |
|---|---|---|---|---|
| | DPM/g | μg eq/g | RB Cells to Serum Ratio | Percent of Dose |
| 10 min | 94843 ± 27122 | 6.113 ± 1.748 | 0.414 = 0.104 | 3.640 ± 1.162 |
| 30 min | 65477 ± 23687 | 4.220 ± 1.527 | 0.378 ± 0.117 | 2.266 ± 1.583 |
| 1 h | 61906 ± 14623 | 3.990 ± 0.943 | 0.489 ± 0.130 | 2.253 ± 1.300 |
| 3 h | 38985 ± 8524 | 2.513 ± 0.549 | 0.586 ± 0.128 | 0.992 ± 0.458 |
| 6 h | 37327 ± 4497 | 2.406 ± 0.290 | 0.685 ± 0.038 | 1.479 ± 0.417 |
| 24 h | 5250 ± 334 | 0.338 ± 0.022 | 0.591 ± 0.032 | 0.139 ± 0 070 |
| 48 h | 2109 ± 319 | 0.136 = 0.021 | 0.581 ± 0.022 | 0.060 ± 0.017 |
| 96 h | 0 ± 0 | 0.000 ± 0.000 | n/a | 0.000 ± 0.000 |

TABLE 12a

Mean Percent Radioactivity Recovered in Supernatant and Pellet of Blood from Male Sprague-Dawley Rats Following a Single Intrathecal Dose of $^{125}$I-hGALC
Group 1: At a Mean Dose of 0.10 mg/kg

| Time Point | Percent Recovery of Radioactivity[a] | |
|---|---|---|
| | Pellet | Supernatant |
| 10 min | 100 ± 0 | 0 ± 0 |
| 30 min | 75.1 ± 10.7 | 24.9 ± 10.7 |
| 1 h | 71.8 ± 11.7 | 28.2 ± 11.7 |
| 3 h | 81.2 ± 2.38 | 18.8 ± 2.38 |
| 6 h | 67.3 ± 13.5 | 32.7 ± 13.5 |
| 24 h | 100 ± 0 | 0 ± 0 |
| 48 h | 100 ± 0 | 0 ± 0 |
| 96 h | 100 ± 0 | 0 ± 0 |

TABLE 12b

Mean Percent Radioactivity Recovered in Supernatant and Pellet of Blood from Male Sprague-Dawley Rats Following a Single Intravenous Bolus Injection of $^{125}$I-hGALC
Group 2: At a Mean Dose of 1.00 mg/kg

| Time Point | Percent Recovery of Radioactivity[a] | |
|---|---|---|
| | Pellet | Supernatant |
| 10 min | 99.2 ± 0.03 | 0.85 = 0.03 |
| 30 mil | 97.5 ± 0.32 | 2.48 ± 0.32 |

TABLE 12b-continued

Mean Percent Radioactivity Recovered in Supernatant and Pellet of Blood from Male Sprague-Dawley Rats Following a Single Intravenous Bolus Injection of $^{125}$I-hGALC
Group 2: At a Mean Dose of 1.00 mg/kg

| Time Point | Percent Recovery of Radioactivity[a] | |
|---|---|---|
| | Pellet | Supernatant |
| 1 h | 95.8 ± 0.56 | 423 ± 0.56 |
| 3 h | 92.5 ± 0.17 | 7.49 ± 0.17 |
| 6 h | 90.7 ± 0.45 | 9.26 ± 0.45 |
| 24 h | 100 ± 0 | 0 ± 0 |
| 48 h | 100 ± 0 | 0 ± 0 |
| 96 h | 100 ± 0 | 0 ± 0 |

TABLE 12c

Mean Percent Radioactivity Recovered in Supernatant and Pellet of Blood from Male Sprague-Dawley Rats Following a Single Intrathecal Dose and Intravenous Bolus Injection of $^{125}$I-hGALC
Group 3: At a Mean Dose of 1.08 mg/kg

| Time Point | Percent Recovery of Radioactivity[a] | |
|---|---|---|
| | Pellet | Supernatant |
| 10 min | 99.0 ± 0.11 | 1.02 ± 0.11 |
| 30 min | 95.9 ± 0.49 | 4.07 ± 0.49 |
| 1 h | 94.5 ± 0.56 | 5.55 ± 0.56 |
| 3 h | 88.1 ± 5.34 | 11.9 ± 5.34 |
| 6 h | 8S.9 ± 1.03 | 11.1 ± 1.03 |
| 24 h | 90.7 ± 3.48 | 9.33 ± 3.48 |
| 48 h | 100 ± 0 | 0 ± 0 |
| 96 h | 100 ± 0 | 0 ± 0 |

$^{125}$I-Precipitable in Whole Blood (Table 12)

The mean values for recovery of radioactivity in pellet and supernatant following precipitation in whole blood by trichloroacetic acid (TCA) for Groups 1, 2 and 3 are summarized in Table 12. When using a 15% aqueous solution of TCA to precipitate the proteins in whole blood, the radioactivity was mainly recovered in the pellet of the blood (ranging from 100% to 67% in Group 1; 100% to 91% in Group 2; 100% to 88% in Group 3) suggesting that the majority of circulating radioactivity was associated with protein and therefore not reflective of free $^{125}$iodine.

Radioactivity Concentration in Tissues and Cerebrospinal Fluid (CSF) (Table 13, Table 14, Table 15, FIGS. 19-30)

Mean concentrations of radioactivity in tissues and CSF of rats following a single intrathecal and/or intravenous dose of $^{125}$I-hGALC are given in Table 13. Mean data are presented graphically in FIGS. 19-30. Mean tissue to serum ratios are presented in Table 14 and the recovery of the administered dose in the tissues, CSF and gastrointestinal and urinary bladder contents are given in Table 15.

TABLE 13a

Group Mean Concentration of Radioactivity in Tissues, Cerebrospinal Fluid of Male Sprague-Dawley Rats Following a Single Intrathecal Dose of $^{125}$I-hGALC
Group 1: At a Mean Dose of 41 μg/animal

| Sample | Concentration of Radioactivity, μg eq/g [a] | | | |
|---|---|---|---|---|
| | 10 min | 30 min | 1 h | 3 h |
| Adipose Tissue (Kidney Fat) | 0.000 ± 0.000 | 0.000 ± 0.000 | 0.000 ± 0.000 | 0.005 ± 0.004 |
| Adrenal Glands | 0.000 ± 0.000 | 0.014 ± 0.006 | 0.017 ± 0.006 | 0.021 ± 0.005 |
| Bone Femur | 0.000 ± 0.000 | 0.011 ± 0.006 | 0.016 ± 0.005 | 0.040 ± 0.012 |
| Brain | 0.000 ± 0.000 | 0.003 ± 0.003 | 0.004 ± 0.004 | 0.005 ± 0.001 |
| Cerebrospinal Fluid (CFS) | 0.000 [b] | 0.000 [b] | 0.000 [b] | 0.000 ± 0.000 |
| Eyes | 0.000 ± 0.000 | 0.006 ± 0.004 | 0.011 ± 0.003 | 0.027 ± 0.006 |
| Heart | 0.001 ± 0.002 | 0.014 ± 0.006 | 0.017 ± 0.005 | 0.028 ± 0.006 |
| Kidneys | 0.004 ± 0.004 | 0.042 ± 0.023 | 0.052 ± 0.014 | 0.096 ± 0.018 |
| Large Intestine | 0.000 ± 0.000 | 0.009 ± 0.004 | 0.011 ± 0.003 | 0.024 ± 0.010 |
| Liver | 0.000 ± 0.000 | 0.012 ± 0.007 | 0.015 ± 0.006 | 0.029 ± 0.008 |
| Lungs | 0.002 ± 0.003 | 0.020 ± 0.010 | 0.027 ± 0.008 | 0.058 ± 0.014 |
| Muscle (Skeletal) | 0.000 ± 0.000 | 0.007 ± 0.003 | 0.010 ± 0.002 | 0.014 ± 0.003 |
| Sciatic Nerve | 0.000 ± 0.000 | 0.008 ± 0.008 | 0.012 ± 0.011 | 0.043 ± 0.017 |
| Small Intestine | 0.000 ± 0.000 | 0.011 ± 0.005 | 0.016 ± 0.005 | 0.046 ± 0.013 |
| Spinal Cord (Lumbar, Thoracic, Cervical) | 0.000 ± 0.000 | 0.004 ± 0.004 | 0.006 ± 0.002 | 0.009 ± 0.001 |
| Spleen | 0.000 ± 0.000 | 0.014 ± 0.008 | 0.019 ± 0.006 | 0.040 ± 0.010 |
| Stomach | 0.003 ± 0.002 | 0.022 ± 0.010 | 0.037 ± 0.017 | 0.203 ± 0.101 |
| Thyroid/Parathyroid Gland | 0.020 ± 0.019 | 0.149 ± 0.083 | 0.278 ± 0.147 | 2.031 ± 1.228 |

| Sample | Concentration of Radioactivity, μg eq/g [a] | | | |
|---|---|---|---|---|
| | 6 h | 24 h | 48 h | 96 h |
| Adipose Tissue (Kidney Fat) | 0.006 ± 0.000 | 0.000 ± 0.000 | 0.000 ± 0.000 | 0.000 ± 0.000 |
| Adrenal Glands | 0.020 ± 0.002 | 0.000 ± 0.000 | 0.000 ± 0.000 | 0.000 ± 0.000 |
| Bone Femur | 0.041 ± 0.007 | 0.000 ± 0.000 | 0.000 ± 0.000 | 0.000 ± 0.000 |
| Brain | 0.004 ± 0.001 | 0.000 ± 0.000 | 0.000 ± 0.000 | 0.000 ± 0.000 |
| Cerebrospinal Fluid (CFS) | 0.000 [b] | 0.000 ± 0.000 | 0.000 ± 0.000 | 0.000 ± 0.000 |
| Eyes | 0.024 ± 0.003 | 0.001 ± 0.001 | 0.000 ± 0.000 | 0.000 ± 0.000 |
| Heart | 0.026 ± 0.004 | 0.001 ± 0.002 | 0.000 ± 0.000 | 0.000 ± 0.000 |
| Kidneys | 0.082 ± 0.012 | 0.012 ± 0.001 | 0.008 ± 0.002 | 0.005 ± 0.001 |
| Large Intestine | 0.024 ± 0.003 | 0.002 ± 0.002 | 0.000 ± 0.000 | 0.000 ± 0.000 |
| Liver | 0.030 ± 0.008 | 0.000 ± 0.000 | 0.000 ± 0.000 | 0.000 ± 0.000 |
| Lungs | 0.055 ± 0.012 | 0.004 ± 0.000 | 0.000 ± 0.000 | 0.000 ± 0.000 |
| Muscle (Skeletal) | 0.012 ± 0.002 | 0.000 ± 0.000 | 0.000 ± 0.000 | 0.000 ± 0.000 |
| Sciatic Nerve | 0.050 ± 0.013 | 0.000 ± 0.000 | 0.000 ± 0.000 | 0.000 ± 0.000 |
| Small Intestine | 0.041 ± 0.015 | 0.004 ± 0.001 | 0.000 ± 0.000 | 0.000 ± 0.000 |
| Spinal Cord (Lumbar, Thoracic, Cervical) | 0.008 ± 0.003 | 0.000 ± 0.000 | 0.000 ± 0.000 | 0.000 ± 0.000 |
| Spleen | 0.036 ± 0.007 | 0.000 ± 0.000 | 0.000 ± 0.000 | 0.000 ± 0.000 |
| Stomach | 0.163 ± 0.060 | 0.008 ± 0.001 | 0.003 ± 0.000 | 0.002 ± 0.001 |
| Thyroid/Parathyroid Gland | 2.453 ± 0.554 | 4.126 ± 1.073 | 4.127 ± 1.635 | 1.927 ± 1.585 |

TABLE 13b

Group Mean Concentration of Radioactivity in Tissues, Cerebrospinal Fluid of Male Sprague-Dawley Rats Following a Single Intravenous Bolus Injection of $^{125}$I-hGALC
Group 2: At a Mean Dose of 1.00 mg/kg

| Sample | Concentration of Radioactivity, μg eq/g [a] | | | |
|---|---|---|---|---|
| | 10 min | 30 min | 1 h | 3 h |
| Adipose Tissue (Kidney Fat) | 0.138 ± 0.054 | 0.158 ± 0.019 | 0.128 ± 0.007 | 0.092 ± 0.008 |
| Adrenal Glands | 8.827 ± 2.435 | 7.090 ± 0.547 | 4.360 ± 0.574 | 1.873 ± 0.070 |
| Bone Femur | 1.568 ± 0.013 | 1.584 ± 0.223 | 1.286 ± 0.166 | 0.887 ± 0.090 |
| Brain | 0.252 ± 0.041 | 0.236 ± 0.017 | 0.195 ± 0.018 | 0.083 ± 0.002 |

TABLE 13b-continued

Group Mean Concentration of Radioactivity in Tissues, Cerebrospinal Fluid of Male Sprague-Dawley Rats Following a Single Intravenous Bolus Injection of $^{125}$I-hGALC
Group 2: At a Mean Dose of 1.00 mg/kg

| Cerebrospinal Fluid (CFS) | 0.137 ± 0.238 | 0.000 ± 0.000 | 0.000[b] | 0.210 ± 0.363 |
|---|---|---|---|---|
| Eyes | 0.110 ± 0.010 | 0.307 ± 0.016 | 0.406 ± 0.027 | 0.344 ± 0.049 |
| Heart | 1.215 ± 0.122 | 1.108 ± 0.039 | 0.999 ± 0.052 | 0.558 ± 0.093 |
| Kidneys | 3.027 ± 0.330 | 2.872 ± 0.139 | 2.288 ± 0.149 | 1.657 ± 0.190 |
| Large Intestine | 0.328 ± 0.072 | 0.467 ± 0.110 | 0.492 ± 0.103 | 0.397 ± 0.031 |
| Liver | 11.335 ± 1.436 | 8.688 ± 0.788 | 5.904 ± 0.367 | 3.590 ± 0.192 |
| Lungs | 11.584 ± 0.906 | 20.629 ± 2.125 | 18.436 ± 3.906 | 8.526 ± 0.815 |
| Muscle (Skeletal) | 0.128 ± 0.011 | 0.261 ± 0.039 | 0.275 ± 0.025 | 0.189 ± 0.007 |
| Sciatic Nerve | 0.173 ± 0.023 | 0.336 ± 0.108 | 0.584 ± 0.059 | 0.689 ± 0.056 |
| Small Intestine | 0.424 ± 0.004 | 0.691 ± 0.031 | 0.786 ± 0.125 | 0.832 ± 0.166 |
| Spinal Cord (Lumbar, Thoracic, Cervical) | 0.293 ± 0.028 | 0.272 ± 0.000 | 0.277 ± 0.008 | 0.142 ± 0.010 |
| Spleen | 6.595 ± 0.625 | 5.952 ± 1.316 | 4.187 ± 0.311 | 2.010 ± 0.333 |
| Stomach | 0.433 ± 0.088 | 0.939 ± 0.204 | 1.430 ± 0.076 | 2.404 ± 0.139 |
| Thyroid/Parathyroid Gland | 4.485 ± 1.194 | 22.335 ± 2.598 | 37.990 ± 11.900 | 147.644 ± 56.596 |

| | Concentration of Radioactivity, µg eq/g [a] | | | |
|---|---|---|---|---|
| Sample | 6 h | 24 h | 48 h | 96 h |
| Adipose Tissue (Kidney Fat) | 0.077 ± 0.007 | 0.000 ± 0.000 | 0.000 ± 0.000 | 0.000 ± 0.000 |
| Adrenal Glands | 1.213 ± 0.031 | 0.339 ± 0.033 | 0.142 ± 0.013 | 0.074 ± 0.010 |
| Bone Femur | 0.726 ± 0.053 | 0.106 ± 0.016 | 0.034 ± 0.030 | 0.000 ± 0.000 |
| Brain | 0.066 ± 0.009 | 0.000 ± 0.000 | 0.000 ± 0.000 | 0.000 ± 0.000 |
| Cerebrospinal Fluid (CFS) | 0.185 ± 0.321 | 0.000 ± 0.000 | 0.000 ± 0.000 | 0.000 ± 0.000 |
| Eyes | 0.336 ± 0.080 | 0.033 ± 0.006 | 0.000 ± 0.000 | 0.000 ± 0.000 |
| Heart | 0.440 ± 0.032 | 0.075 ± 0.011 | 0.040 ± 0.002 | 0.000 ± 0.000 |
| Kidneys | 1.418 ± 0.108 | 0.337 ± 0.021 | 0.199 ± 0.009 | 0.099 ± 0.010 |
| Large Intestine | 0.376 ± 0.077 | 0.054 ± 0.009 | 0.026 ± 0.003 | 0.000 ± 0.000 |
| Liver | 3.179 ± 0.188 | 1.020 ± 0.091 | 0.506 ± 0.046 | 0.126 ± 0.014 |
| Lungs | 3.187 ± 0.079 | 2.958 ± 1.012 | 0.325 ± 0.114 | 0.069 ± 0.003 |
| Muscle (Skeletal) | 0.153 ± 0.018 | 0.008 ± 0.014 | 0.000 ± 0.000 | 0.000 ± 0.000 |
| Sciatic Nerve | 0.643 ± 0.063 | 0.025 ± 0.043 | 0.000 ± 0.000 | 0.000 ± 0.000 |
| Small Intestine | 0.691 ± 0.121 | 0.094 ± 0.025 | 0.041 ± 0.012 | 0.000 ± 0.000 |
| Spinal Cord (Lumbar, Thoracic, Cervical) | 0.128 ± 0.017 | 0.014 ± 0.013 | 0.000 ± 0.000 | 0.000 ± 0.000 |
| Spleen | 1.667 ± 0.091 | 0.565 ± 0.046 | 0.250 ± 0.038 | 0.111 ± 0.009 |
| Stomach | 1.688 ± 0.310 | 0.180 ± 0.057 | 0.047 ± 0.005 | 0.015 ± 0.013 |
| Thyroid/Parathyroid Gland | 267.423 ± 177.568 | 280.829 ± 84.988 | 294.521 ± 52.953 | 218.917 ± 45.098 |

TABLE 13c

Group Mean Concentration of Radioactivity in Tissues, Cerebrospinal Fluid of Male Sprague-Dawley Rats Following a Single Intrathecal Dose and Intravenous Bolus Injection of $^{125}$I-hGALC
Group 3: At a Mean Dose of 1.08 mg/kg

| | Concentration of Radioactivity, µg eq/g [a] | | | |
|---|---|---|---|---|
| Sample | 10 min | 30 min | 1 h | 3 h |
| Adipose Tissue (Kidney Fat) | 0.140 ± 0.029 | 0.176 ± 0.051 | 0.188 ± 0.020 | 0.161 ± 0.008 |
| Adrenal Glands | 9.567 ± 1.678 | 5.487 ± 1.129 | 4.868 ± 0.930 | 2.010 ± 0.331 |
| Bone Femur | 1.227 ± 0.137 | 1.707 ± 0.160 | 1.571 ± 0.071 | 1.261 ± 0.030 |
| Brain | 0.283 ± 0.062 | 0.276 ± 0.010 | 0.230 ± 0.008 | 0.153 ± 0.023 |
| Cerebrospinal Fluid (CFS) | 2.087 ± 2.912 | 0.380 ± 0.371 | 0.598 ± 1.035 | 0.105 ± 0.182 |
| Eyes | 0.110 ± 0.018 | 0.372 ± 0.042 | 0.539 ± 0.019 | 0.611 ± 0.079 |
| Heart | 1.034 ± 0.049 | 1.315 ± 0.156 | 1.188 ± 0.028 | 0.845 ± 0.039 |
| Kidneys | 2.864 ± 0.353 | 3.324 ± 0.265 | 3.390 ± 0.183 | 2.822 ± 0.020 |
| Large Intestine | 0.261 ± 0.026 | 0.567 ± 0.051 | 0.716 ± 0.098 | 0.681 ± 0.102 |
| Liver | 10.181 ± 0.600 | 8.475 ± 0.204 | 6.237 ± 0.341 | 3.740 ± 0.055 |
| Lungs | 3.133 ± 0.350 | 5.162 ± 0.564 | 5.305 ± 0.194 | 2.727 ± 0.198 |
| Muscle (Skeletal) | 0.119 ± 0.006 | 0.297 ± 0.011 | 0.411 ± 0.009 | 0.298 ± 0.015 |
| Sciatic Nerve | 0.244 ± 0.037 | 0.558 ± 0.023 | 0.994 ± 0.096 | 1.043 ± 0.057 |
| Small Intestine | 0.304 ± 0.093 | 0.778 ± 0.037 | 1.149 ± 0.110 | 1.401 ± 0.152 |
| Spinal Cord (Lumbar, Thoracic, Cervical) | 0.327 ± 0.062 | 0.319 ± 0.025 | 0.285 ± 0.044 | 0.227 ± 0.019 |
| Spleen | 5.042 ± 0.902 | 4.721 ± 0.302 | 3.740 ± 0.406 | 2.186 ± 0.218 |
| Stomach | 0.465 ± 0.068 | 1.028 ± 0.175 | 2.450 ± 0.569 | 4.454 ± 1.455 |
| Thyroid/Parathyroid Gland | 3.191 ± 1.542 | 21.727 ± 8.873 | 30.411 ± 18.766 | 139.771 ± 37.999 |

TABLE 13c-continued

Group Mean Concentration of Radioactivity in Tissues, Cerebrospinal Fluid of Male Sprague-Dawley Rats Following a Single Intrathecal Dose and Intravenous Bolus Injection of $^{125}$I-hGALC
Group 3: At a Mean Dose of 1.08 mg/kg

| Sample | Concentration of Radioactivity, μg eq/g [a] | | | |
|---|---|---|---|---|
| | 6 h | 24 h | 48 h | 96 h |
| Adipose Tissue (Kidney Fat) | 0.131 ± 0.005 | 0.000 ± 0.000 | 0.000 ± 0.000 | 0.000 ± 0.000 |
| Adrenal Glands | 1.412 ± 0.137 | 0.301 ± 0.014 | 0.118 ± 0.013 | 0.069 ± 0.016 |
| Bone Femur | 1.165 ± 0.066 | 0.148 ± 0.012 | 0.029 ± 0.026 | 0.000 ± 0.000 |
| Brain | 0.098 ± 0.012 | 0.000 ± 0.000 | 0.000 ± 0.000 | 0.000 ± 0.000 |
| Cerebrospinal Fluid (CFS) | 0.000 [b] | 0.000 [b] | 0.000 [b] | 0.000 ± 0.000 |
| Eyes | 0.574 ± 0.085 | 0.064 ± 0.006 | 0.010 ± 0.009 | 0.000 ± 0.000 |
| Heart | 0.723 ± 0.057 | 0.101 ± 0.008 | 0.038 ± 0.007 | 0.006 ± 0.011 |
| Kidneys | 2.046 ± 0.229 | 0.515 ± 0.019 | 0.249 ± 0.029 | 0.124 ± 0.005 |
| Large Intestine | 0.726 ± 0.173 | 0.074 ± 0.014 | 0.027 ± 0.004 | 0.000 ± 0.000 |
| Liver | 3.156 ± 0.143 | 0.996 ± 0.035 | 0.418 ± 0.036 | 0.137 ± 0.018 |
| Lungs | 1.830 ± 0.133 | 0.223 ± 0.007 | 0.076 ± 0.020 | 0.033 ± 0.008 |
| Muscle (Skeletal) | 0.253 ± 0.029 | 0.032 ± 0.002 | 0.000 ± 0.000 | 0.000 ± 0.000 |
| Sciatic Nerve | 1.039 ± 0.133 | 0.056 ± 0.098 | 0.000 ± 0.000 | 0.000 ± 0.000 |
| Small Intestine | 1.102 ± 0.101 | 0.136 ± 0.027 | 0.033 ± 0.008 | 0.000 ± 0.000 |
| Spinal Cord (Lumbar, Thoracic, Cervical) | 0.202 ± 0.032 | 0.026 ± 0.003 | 0.000 ± 0.000 | 0.000 ± 0.000 |
| Spleen | 1.648 ± 0.109 | 0.395 ± 0.017 | 0.152 ± 0.009 | 0.083 ± 0.009 |
| Stomach | 4.242 ± 1.361 | 0.463 ± 0.357 | 0.064 ± 0.014 | 0.031 ± 0.005 |
| Thyroid/Parathyroid Gland | 182.099 ± 38.422 | 296.957 ± 57.793 | 199.316 ± 26.285 | 43.962 ± 23.164 |

TABLE 14a

Group Mean Tissue, Cerebrospinal Fluid to Serum Radioactivity Ratios of Male Sprague-Dawley Rats Following a Single Intrathecal Dose $^{125}$I-hGALC
Group 1: At a Mean Dose of 41 μg/animal

| Sample | Tissue, CSF to Serum Ratio [a] | | | |
|---|---|---|---|---|
| | 10 min [b] | 30 min | 1 h | 3 h |
| Adipose Tissue (Kidney Fat) | n/a | n/a | n/a | 0.071 [b] |
| Adrenal Glands | n/a | 0.421 ± 0.116 | 0.324 ± 0.033 | 0.196 ± 0.012 |
| Bone Femur | n/a | 0.308 ± 0.010 | 0.319 ± 0.038 | 0.369 ± 0.028 |
| Brain | n/a | 0.097 [b] | 0.110 ± 0.018 | 0.045 ± 0.006 |
| Cerebrospinal Fluid (CFS) | n/a | n/a | n/a | n/a |
| Eyes | n/a | 0.177 ± 0.032 | 0.216 ± 0.020 | 0.253 ± 0.007 |
| Heart | 0.333 | 0.412 ± 0.076 | 0.329 ± 0.008 | 0.265 ± 0.012 |
| Kidneys | 0.976 | 1.157 ± 0.040 | 1.036 ± 0.062 | 0.895 ± 0.058 |
| Large Intestine | n/a | 0.249 ± 0.027 | 0.220 ± 0.023 | 0.220 ± 0.048 |
| Liver | n/a | 0.351 ± 0.028 | 0.302 ± 0.036 | 0.265 ± 0.015 |
| Lungs | 0.576 | 0.565 ± 0.050 | 0.533 ± 0.034 | 0.532 ± 0.003 |
| Muscle (Skeletal) | n/a | 0.197 ± 0.032 | 0.192 ± 0.011 | 0.134 ± 0.021 |
| Sciatic Nerve | n/a | 0.249 [b] | 0.317 [b] | 0.382 ± 0.074 |
| Small Intestine | n/a | 0.318 ± 0.035 | 0.312 ± 0.035 | 0.426 ± 0.018 |
| Spinal Cord (Lumbar, Thoracic, Cervical) | n/a | 0.144 [b] | 0.117 ± 0.017 | 0.082 ± 0.010 |
| Spleen | n/a | 0.395 ± 0.036 | 0.382 ± 0.013 | 0.368 ± 0.007 |
| Stomach | 0.577 | 0.627 ± 0.072 | 0.723 ± 0.252 | 1.801 ± 0.619 |
| Thyroid/Parathyroid Gland | 4.443 | 4.035 ± 0.750 | 5.680 ± 2.612 | 17.423 ± 8.215 |

| Sample | Tissue, CFS to Serum Ratio [a] | | | |
|---|---|---|---|---|
| | 6 h | 24 h | 48 h | 96 h |
| Adipose Tissue (Kidney Fat) | 0.057 ± 0.012 | n/a | n/a | n/a |
| Adrenal Glands | 0.197 ± 0.026 | n/a | n/a | n/a |
| Bone Femur | 0.407 ± 0.022 | n/a | n/a | n/a |
| Brain | 0.040 ± 0.005 | n/a | n/a | n/a |
| Cerebrospinal Fluid (CFS) | n/a | n/a | n/a | n/a |
| Eyes | 0.245 ± 0.023 | 0.284 [b] | n/a | n/a |
| Heart | 0.258 ± 0.022 | 0.343 [b] | n/a | n/a |
| Kidneys | 0.821 ± 0.066 | 1.491 ± 0.128 | n/a | n/a |
| Large Intestine | 0.250 ± 0.074 | 0.395 [b] | n/a | n/a |
| Liver | 0.293 ± 0.029 | n/a | n/a | n/a |
| Lungs | 0.547 ± 0.009 | 0.489 ± 0.105 | n/a | n/a |
| Muscle (Skeletal) | 0.115 ± 0.013 | n/a | n/a | n/a |
| Sciatic Nerve | 0.496 ± 0.030 | n/a | n/a | n/a |

TABLE 14a-continued

Group Mean Tissue, Cerebrospinal Fluid to Serum Radioactivity Ratios of
Male Sprague-Dawley Rats Following a Single Intrathecal Dose $^{125}$I-hGALC
Group 1: At a Mean Dose of 41 µg/animal

| Sample | | | | |
|---|---|---|---|---|
| Small Intestine | 0.400 ± 0.059 | 0.550 ± 0.021 | n/a | n/a |
| Spinal Cord (Lumbar, Thoracic, Cervical) | 0.079 ± 0.009 | n/a | n/a | n/a |
| Spleen | 0.357 ± 0.009 | n/a | n/a | n/a |
| Stomach | 1.604 ± 0.478 | 1.085 ± 0.155 | n/a | n/a |
| Thyroid/Parathyroid Gland | 24.297 ± 0.831 | 527.002 ± 100.186 | n/a | n/a |

TABLE 14b

Group Mean Tissue, Cerebrospinal Fluid to Serum Radioactivity Ratios of
Male Sprague-Dawley Rats Following a Single Intravenous Bolus Injection of $^{125}$I-hGALC
Group 2: At Mean Dose of 1.00 mg/kg

| Sample | Tissue CFS Serum Ratio [a] | | | |
|---|---|---|---|---|
| | 10 min | 30 min | 1 h | 3 h |
| Adipose Tissue (Kidney Fat) | 0.009 ± 0.003 | 0.015 ± 0.003 | 0.017 ± 0.001 | 0.028 ± 0.003 |
| Adrenal Glands | 0.589 ± 0.133 | 0.654 ± 0.010 | 0.594 ± 0.089 | 0.580 ± 0.039 |
| Bone Femur | 0.106 ± 0.006 | 0.146 ± 0.019 | 0.174 ± 0.012 | 0.273 ± 0.008 |
| Brain | 0.017 ± 0.002 | 0.022 ± 0.003 | 0.027 ± 0.002 | 0.026 ± 0.002 |
| Cerebrospinal Fluid (CFS) | 0.028 [b] | n/a | n/a | 0.188 [b] |
| Eyes | 0.007 ± 0.001 | 0.028 ± 0.002 | 0.055 ± 0.008 | 0.106 ± 0.009 |
| Heart | 0.082 ± 0.004 | 0.103 ± 0.006 | 0.136 ± 0.007 | 0.171 ± 0.016 |
| Kidneys | 0.203 ± 0.011 | 0.266 ± 0.019 | 0.311 ± 0.015 | 0.512 ± 0.043 |
| Large Intestine | 0.022 ± 0.004 | 0.043 ± 0.009 | 0.067 ± 0.012 | 0.123 ± 0.019 |
| Liver | 0.766 ± 0.119 | 0.802 ± 0.026 | 0.805 ± 0.085 | 1.110 ± 0.055 |
| Lungs | 0.781 ± 0.070 | 1.903 ± 0.100 | 2.496 ± 0.452 | 2.642 ± 0.316 |
| Muscle (Skeletal) | 0.008 ± 0.001 | 0.024 ± 0.004 | 0.037 ± 0.002 | 0.059 ± 0.004 |
| Sciatic Nerve | 0.012 ± 0.002 | 0.032 ± 0.012 | 0.080 ± 0.009 | 0.213 ± 0.007 |
| Small Intestine | 0.029 ± 0.002 | 0.064 ± 0.007 | 0.107 ± 0.019 | 0.255 ± 0.032 |
| Spinal Cord (Lumbar, Thoracic, Cervical) | 0.019 ± 0.002 | 0.025 ± 0.002 | 0.038 ± 0.001 | 0.044 ± 0.007 |
| Spleen | 0.443 ± 0.016 | 0.547 ± 0.090 | 0.571 ± 0.075 | 0.618 ± 0.065 |
| Stomach | 0.029 ± 0.004 | 0.086 ± 0.013 | 0.194 ± 0.012 | 0.743 ± 0.028 |
| Thyroid/Parathyroid Gland | 0.305 ± 0.092 | 2.074 ± 0.319 | 5.106 ± 1.355 | 46.707 ± 21.839 |

| Sample | Tissue CFS Serum Ratio [a] | | | |
|---|---|---|---|---|
| | 6 h | 24 h | 48 h | 96 h |
| Adipose Tissue (Kidney Fat) | 0.035 ± 0.003 | n/a | n/a | n/a |
| Adrenal Glands | 0.554 ± 0.045 | 0.747 ± 0.061 | 0.593 ± 0.104 | 0.845 ± 0.120 |
| Bone Femur | 0.330 ± 0.004 | 0.234 ± 0.030 | 0.2256 | n/a |
| Brain | 0.030 ± 0.002 | n/a | n/a | n/a |
| Cerebrospinal Fluid (CFS) | 0.232 [b] | n/a | n/a | n/a |
| Eyes | 0.152 ± 0.024 | 0.073 ± 0.012 | n/a | n/a |
| Heart | 0.200 ± 0.010 | 0.165 ± 0.024 | 0.167 ± 0.025 | n/a |
| Kidneys | 0.649 ± 0.086 | 0.741 ± 0.025 | 0.833 ± 0.169 | 1.118 ± 0.086 |
| Large Intestine | 0.171 ± 0.035 | 0.119 ± 0.020 | 0.109 ± 0.008 | n/a |
| Liver | 1.449 ± 0.096 | 2.245 ± 0.142 | 2.109 ± 0.302 | 1.440 ± 0.229 |
| Lungs | 1.453 ± 0.071 | 6.505 ± 2.210 | 1.345 ± 0.431 | 0.780 ± 0.033 |
| Muscle (Skeletal) | 0.069 ± 0.005 | 0.052 [b] | n/a | n/a |
| Sciatic Nerve | 0.292 ± 0.011 | 0.169 [b] | n/a | n/a |
| Small Intestine | 0.316 ± 0.065 | 0.207 ± 0.057 | 0.175 ± 0.070 | n/a |
| Spinal Cord (Lumbar, Thoracic, Cervical) | 0.058 ± 0.003 | 0.047 [b] | n/a | n/a |
| Spleen | 0.762 ± 0.084 | 1.247 ± 0.134 | 1.030 ± 0.098 | 1.263 ± 0.069 |
| Stomach | 0.774 ± 0.176 | 0.397 ± 0.129 | 0.197 ± 0.047 | 0.263 [b] |
| Thyroid/Parathyroid Gland | 124.616 ± 86.507 | 615.613 ± 169.527 | 1231.684 ± 285.895 | 2484.660 ± 471.907 |

TABLE 14c

Group Mean Tissue, Cerebrospinal Fluid to Serum Radioactivity Ratios of
Male Sprague-Dawley Rats Following a Single Intrathecal Dose and Intravenous Bolus
Injection of $^{125}$I-hGALC
Group 3: At Mean Dose pd 1.08 mg/kg

| Sample | Tissue CFS Serum Ratio [a] | | | |
|---|---|---|---|---|
| | 10 min | 30 min | 1 h | 3 h |
| Adipose Tissue (Kidney Fat) | 0.010 ± 0.002 | 0.016 ± 0.005 | 0.023 ± 0.003 | 0.037 ± 0.002 |
| Adrenal Glands | 0.649 ± 0.076 | 0.493 ± 0.072 | 0.589 ± 0.077 | 0.468 ± 0.069 |
| Bone Femur | 0.083 ± 0.006 | 0.155 ± 0.012 | 0.191 ± 0.013 | 0.294 ± 0.005 |
| Brain | 0.019 ± 0.003 | 0.025 ± 0.001 | 0.028 ± 0.003 | 0.035 ± 0.005 |
| Cerebrospinal Fluid (CFS) | 0.204 [b] | 0.053 [b] | 0.221 [b] | 0.072 [b] |
| Eyes | 0.007 ± 0.001 | 0.034 ± 0.005 | 0.066 ± 0.007 | 0.143 ± 0.021 |
| Heart | 0.071 ± 0.001 | 0.119 ± 0.015 | 0.145 ± 0.011 | 0.197 ± 0.012 |
| Kidneys | 0.195 ± 0.013 | 0.302 ± 0.041 | 0.413 ± 0.022 | 0.658 ± 0.016 |
| Large Intestine | 0.018 ± 0.002 | 0.051 ± 0.005 | 0.087 ± 0.011 | 0.159 ± 0.023 |
| Liver | 0.694 ± 0.007 | 0.768 ± 0.061 | 0.759 ± 0.023 | 0.872 ± 0.024 |
| Lungs | 0.214 ± 0.030 | 0.465 ± 0.025 | 0.646 ± 0.045 | 0.635 ± 0.036 |
| Muscle (Skeletal) | 0.008 ± 0.001 | 0.027 ± 0.002 | 0.050 ± 0.003 | 0.070 ± 0.005 |
| Sciatic Nerve | 0.017 ± 0.003 | 0.050 ± 0.004 | 0.122 ± 0.018 | 0.243 ± 0.012 |
| Small Intestine | 0.021 ± 0.007 | 0.071 ± 0.007 | 0.140 ± 0.016 | 0.326 ± 0.029 |
| Spinal Cord (Lumbar, Thoracic, Cervical) | 0.022 ± 0.005 | 0.029 ± 0.001 | 0.035 ± 0.007 | 0.053 ± 0.004 |
| Spleen | 0.342 ± 0.044 | 0.427 ± 0.036 | 0.455 ± 0.044 | 0.510 ± 0.049 |
| Stomach | 0.032 ± 0.005 | 0.094 ± 0.020 | 0.300 ± 0.078 | 1.039 ± 0.348 |
| Thyroid/Parathyroid Gland | 0.217 ± 0.108 | 1.960 ± 0.776 | 3.781 ± 2.521 | 32.561 ± 8.787 |

| Sample | Tissue CFS Serum Ratio [a] | | | |
|---|---|---|---|---|
| | 6 h | 24 h | 48 h | 96 h |
| Adipose Tissue (Kidney Fat) | 0.038 ± 0.003 | n/a | n/a | n/a |
| Adrenal Glands | 0.405 ± 0.059 | 0.527 ± 0.029 | 0.514 ± 0.108 | 0.918 ± 0.317 |
| Bone Femur | 0.333 ± 0.006 | 0.258 ± 0.026 | 0.1836 | n/a |
| Brain | 0.028 ± 0.001 | n/a | n/a | n/a |
| Cerebrospinal Fluid (CFS) | n/a | n/a | n/a | n/a |
| Eyes | 0.163 ± 0.012 | 0.113 ± 0.019 | 0.068b | n/a |
| Heart | 0.206 ± 0.001 | 0.177 ± 0.018 | 0.164 ± 0.008 | 0.246b |
| Kidneys | 0.583 ± 0.022 | 0.900 ± 0.037 | 1.071 ± 0.104 | 1.623 ± 0.270 |
| Large Intestine | 0.207 ± 0.044 | 0.131 ± 0.031 | 0.116 ± 0.018 | n/a |
| Liver | 0.902 ± 0.028 | 1.744 ± 0.121 | 1.815 ± 0.316 | 1.770 ± 0.023 |
| Lungs | 0.522 ± 0.009 | 0.391 ± 0.040 | 0.321 ± 0.044 | 0.428 ± 0.084 |
| Muscle (Skeletal) | 0.072 ± 0.011 | 0.056 ± 0.008 | n/a | n/a |
| Sciatic Nerve | 0.296 ± 0.016 | 0.293[b] | n/a | n/a |
| Small Intestine | 0.314 ± 0.008 | 0.239 ± 0.063 | 0.140 ± 0.019 | n/a |
| Spinal Cord (Lumbar, Thoracic, Cervical) | 0.057 ± 0.007 | 0.046 ± 0.009 | n/a | n/a |
| Spleen | 0.471 ± 0.033 | 0.692 ± 0.067 | 0.661 ± 0.104 | 1.087 ± 0.230 |
| Stomach | 1.206 ± 0.373 | 0.807 ± 0.616 | 0.274 ± 0.032 | 0.405 ± 0.112 |
| Thyroid/Parathyroid Gland | 52.475 ± 13.382 | 525.335 ± 143.883 | 854.144 ± 52.674 | 571.341 ± 305.367 |

TABLE 15a

Group Mean Radioactivity Content in Tissues, Cerebrospinal Fluid,
Gastrointestinal Tract and Urinary Bladder Contents of Male Sprague-Dawley Rats Following
a Single Intrathecal Dose of $^{125}$I-hGALC
Group 1: At a Mean Dose of 41 μg/animal

| Sample | Percent of Dose [a] | | | |
|---|---|---|---|---|
| | 10 min | 30 min | 1 h | 3 h |
| Adrenal Glands | 0.000 ± 0.000 | 0.002 ± 0.000 | 0.004 ± 0.000 | 0.003 ± 0.001 |
| Brain | 0.000 ± 0.000 | 0.010 ± 0.009 | 0.027 ± 0.024 | 0.023 ± 0.003 |
| Cerebrospinal Fluid (CSF) | 0.000 [b] | 0.000 [b] | 0.000 [b] | 0.000 ± 0.000 |
| Eyes | 0.000 ± 0.000 | 0.003 ± 0.001 | 0.011 ± 0.002 | 0.017 ± 0.001 |
| Heart | 0.002 ± 0.003 | 0.037 ± 0.003 | 0.066 ± 0.009 | 0.077 ± 0.004 |
| Kidneys | 0.027 ± 0.025 | 0.252 ± 0.086 | 0.553 ± 0.057 | 0.632 ± 0.104 |
| Liver | 0.000 ± 0.000 | 0.417 ± 0.057 | 0.748 ± 0.108 | 0.907 ± 0.181 |
| Lungs | 0.003 ± 0.005 | 0.055 ± 0.009 | 0.122 ± 0.021 | 0.166 ± 0.013 |
| Sciatic Nerve | 0.000 ± 0.000 | 0.001 ± 0.001 | 0.002 ± 0.002 | 0.003 ± 0.001 |
| Spinal Cord (Lumbar Thoracic, Cervical) | 0.000 ± 0.000 | 0.004 ± 0.004 | 0.013 ± 0.001 | 0.012 ± 0.000 |
| Spleen | 0.000 ± 0.000 | 0.024 ± 0.009 | 0.054 ± 0.010 | 0.066 ± 0.011 |
| Thyroid/Parathyroid Gland | 0.001 ± 0.001 | 0.007 ± 0.002 | 0.024 ± 0.012 | 0.108 ± 0.021 |

TABLE 15a-continued

Group Mean Radioactivity Content in Tissues, Cerebrospinal Fluid, Gastrointestinal Tract and Urinary Bladder Contents of Male Sprague-Dawley Rats Following a Single Intrathecal Dose of $^{125}$I-hGALC
Group 1: At a Mean Dose of 41 μg/animal

| Gastrointestinal Tract: | | | | |
|---|---|---|---|---|
| Small Intestine | 0.000 ± 0.000 | 0.193 ± 0.054 | 0.364 ± 0.069 | 0.763 ± 0.107 |
| Small Intestine Contents | 0.000 ± 0.000 | 0.399 ± 0.062 | 0.778 ± 0.084 | 2.611 ± 0.291 |
| Large Intestine | 0.000 ± 0.000 | 0.090 ± 0.018 | 0.165 ± 0.037 | 0.238 ± 0.070 |
| Large Intestine Contents | 0.000 ± 0.000 | 0.000 ± 0.000 | 0.000 ± 0.000 | 0.598 ± 0.114 |
| Stomach | 0.008 ± 0.007 | 0.086 ± 0.009 | 0.216 ± 0.094 | 0.836 ± 0.336 |
| Stomach Contents | 0.000 ± 0.000 | 0.489 ± 0.052 | 1.774 ± 0.326 | 5.004 ± 0.346 |
| Urinary Bladder Contents | 0.003 ± 0.003 | 0.110 ± 0.030 | 0.156 ± 0.077 | 1.207 ± 1.029 |

| | Percent of Dose [a] | | | |
|---|---|---|---|---|
| Sample | 6 h | 24 h | 48 h | 96 h |
| Adrenal Glands | 0.002 ± 0.000 | 0.000 ± 0.000 | 0.000 ± 0.000 | 0.000 ± 0.000 |
| Brain | 0.015 ± 0.001 | 0.000 ± 0.000 | 0.000 ± 0.000 | 0.000 ± 0.000 |
| Cerebrospinal Fluid (CSF) | 0.000[b] | 0.000 ± 0.000 | 0.000 ± 0.000 | 0.000 ± 0.000 |
| Eyes | 0.013 ± 0.003 | 0.001 ± 0.001 | 0.000 ± 0.000 | 0.000 ± 0.000 |
| Heart | 0.056 ± 0.006 | 0.005 ± 0.008 | 0.000 ± 0.000 | 0.000 ± 0.000 |
| Kidneys | 0.452 ± 0.115 | 0.130 ± 0.034 | 0.059 ± 0.007 | 0.029 ± 0.006 |
| Liver | 0.775 ± 0.078 | 0.000 ± 0.000 | 0.000 ± 0.000 | 0.000 ± 0.000 |
| Lungs | 0.132 ± 0.019 | 0.019 ± 0.005 | 0.000 ± 0.000 | 0.000 ± 0.000 |
| Sciatic Nerve | 0.003 ± 0.001 | 0.000 ± 0.000 | 0.000 ± 0.000 | 0.000 ± 0.000 |
| Spinal Cord (Lumbar Thoracic, Cervical) | 0.009 ± 0.001 | 0.000 ± 0.000 | 0.000 ± 0.000 | 0.000 ± 0.000 |
| Spleen | 0.048 ± 0.007 | 0.000 ± 0.000 | 0.000 ± 0.000 | 0.000 ± 0.000 |
| Thyroid/Parathyroid Gland | 0.125 ± 0.037 | 0.348 ± 0.013 | 0.195 ± 0.075 | 0.086 ± 0.023 |
| Gastrointestinal Tract: | | | | |
| Small Intestine | 0.571 ± 0.165 | 0.117 ± 0.027 | 0.000 ± 0.000 | 0.000 ± 0.000 |
| Small Intestine Contents | 1.740 ± 0.925 | 0.385 ± 0.045 | 0.000 ± 0.000 | 0.000 ± 0.000 |
| Large Intestine | 0.1922 ± 0.022 | 0.029 ± 0.025 | 0.000 ± 0.000 | 0.000 ± 0.000 |
| Large Intestine Contents | 0.864 ± 0.100 | 0.000 ± 0.000 | 0.000 ± 0.000 | 0.000 ± 0.000 |
| Stomach | 0.557 ± 0.117 | 0.059 ± 0.023 | 0.015 ± 0.002 | 0.009 ± 0.007 |
| Stomach Contents | 3.996 ± 1.013 | 0.758 ± 0.167 | 0.122 ± 0.107 | 0.000 ± 0.000 |
| Urinary Bladder Contents | 0.525 ± 0.264 | 0.178 ± 0.130 | 0.014[b] | 0.021 ± 0.028 |

TABLE 15b

Group Mean Radioactivity Content in Tissues, Cerebrospinal Fluid, Gastrointestinal Tract and Urinary Bladder Contents of Male Sprague-Dawley Rats Following a Single Intravenous Bolus Injection of $^{125}$I-hGALC
Group 2: At a Mean Dose of 1.00 mg/kg

| | Percent of Dose [a] | | | |
|---|---|---|---|---|
| Sample | 10 min | 30 min | 1 h | 3 h |
| Adrenal Glands | 0.113 ± 0.023 | 0.117 ± 0.022 | 0.059 ± 0.009 | 0.026 ± 0.002 |
| Brain | 0.129 ± 0.022 | 0.120 ± 0.011 | 0.098 ± 0.005 | 0.044 ± 0.001 |
| Cerebrospinal Fluid (CSF) | 0.001 ± 0.002 | 0.000 ± 0.000 | 0.000 [b] | 0.001 ± 0.001 |
| Eyes | 0.007 ± 0.001 | 0.021 ± 0.001 | 0.028 ± 0.007 | 0.024 ± 0.005 |
| Heart | 0.382 ± 0.055 | 0.319 ± 0.018 | 0.292 ± 0.025 | 0.161 ± 0.024 |
| Kidneys | 2.168 ± 0.172 | 1.966 ± 0.081 | 1.658 ± 0.014 | 1.168 ± 0.068 |
| Liver | 41.711 ± 3.901 | 31.161 ± 1.934 | 20.702 ± 1.140 | 13.029 ± 0.875 |
| Lungs | 4.024 ± 0.305 | 7.047 ± 0.512 | 6.456 ± 1.094 | 2.842 ± 0.248 |
| Sciatic Nerve | 0.001 ± 0.001 | 0.003 ± 0.003 | 0.004 ± 0.001 | 0.006 ± 0.003 |
| Spinal Cord (Lumbal, Thoracic, Cervical) | 0.045 ± 0.005 | 0.042 ± 0.008 | 0.039 ± 0.003 | 0.023 ± 0.002 |
| Spleen | 1.234 ± 0.045 | 1.014 ± 0.093 | 0.784 ± 0.123 | 0.393 ± 0.013 |
| Thyroid/Parathyroid Gland | 0.024 ± 0.001 | 0.100 ± 0.009 | 0.186 ± 0.050 | 0.947 ± 0.340 |
| Gastrointestinal Tract: | | | | |
| Small Intestine | 0.749 ± 0.121 | 1.477 ± 0.237 | 1.548 ± 0.186 | 1.535 ± 0.191 |
| Small Intestine Contents | 0.530 ± 0.056 | 1.921 ± 0.346 | 3.737 ± 1.427 | 5.446 ± 2.102 |
| Large Intestine | 0.327 ± 0.072 | 0.478 ± 0.076 | 0.529 ± 0.065 | 0.412 ± 0.008 |
| Large Intestine Contents | 0.000 ± 0.000 | 0.345 ± 0.029 | 0.517 ± 0.135 | 0.782 ± 0.083 |
| Stomach | 0.176 ± 0.032 | 0.437 ± 0.050 | 0.632 ± 0.047 | 0.992 ± 0.059 |
| Stomach Contents | 0.343 ± 0.127 | 1.537 ± 0.287 | 5.330 ± 0.937 | 10.263 ± 1.971 |
| Urinary Bladder Contents | 0.100 ± 0.041 | 0.409 ± 0.179 | 0.675 ± 0.660 | 0.945 ± 0.571 |

TABLE 15b-continued

Group Mean Radioactivity Content in Tissues, Cerebrospinal Fluid,
Gastrointestinal Tract and Urinary Bladder Contents of Male Sprague-Dawley Rats Following
a Single Intravenous Bolus Injection of $^{125}$I-hGALC
Group 2: At a Mean Dose of 1.00 mg/kg

| Sample | Percent of Dose [a] | | | |
|---|---|---|---|---|
| | 6h | 24 h | 48 h | 96 h |
| Adrenal Glands | 0.019 ± 0.002 | 0.005 ± 0.001 | 0.002 ± 0.000 | 0.001 ± 0.000 |
| Brain | 0.034 ± 0.004 | 0.000 ± 0.000 | 0.000 ± 0.000 | 0.000 ± 0.000 |
| Cerebrospinal Fluid (CSF) | 0.003 ± 0.005 | 0.000 ± 0.000 | 0.000 ± 0.000 | 0.000 ± 0.000 |
| Eyes | 0.023 ± 0.007 | 0.002 ± 0.001 | 0.000 ± 0.000 | 0.000 ± 0.000 |
| Heart | 0.121 ± 0.007 | 0.022 ± 0.003 | 0.012 ± 0.001 | 0.000 ± 0.000 |
| Kidneys | 0.909 ± 0.076 | 0.251 ± 0.006 | 0.140 ± 0.003 | 0.072 ± 0.002 |
| Liver | 10.311 ± 0.361 | 3.891 ± 0.283 | 1.980 ± 0.065 | 0.498 ± 0.016 |
| Lungs | 1.027 ± 0.037 | 0.991 ± 0.289 | 0.112 ± 0.037 | 0.023 ± 0.001 |
| Sciatic Nerve | 0.004 ± 0.000 | 0.000 ± 0.001 | 0.000 ± 0.000 | 0.000 ± 0.000 |
| Spinal Cord (Lumbar, Thoracic. Cervical) | 0.017 ± 0.002 | 0.002 ± 0.002 | 0.000 ± 0.000 | 0.000 ± 0.000 |
| Spleen | 0.362 ± 0.028 | 0.100 ± 0.003 | 0.046 ± 0.010 | 0.022 ± 0.001 |
| Thyroid/Parathyroid Gland | 1.405 ± 0.830 | 1.333 ± 0.115 | 1.440 ± 0.604 | 0.997 ± 0.329 |
| Gastrointestinal Tract: | | | | |
| Small Intestine | 1.537 ± 0.436 | 0.175 ± 0.033 | 0.074 ± 0.031 | 0.000 ± 0.000 |
| Small Intestine Contents | 3.051 ± 0.706 | 0.500 ± 0.184 | 0.254 ± 0.101 | 0.000 ± 0.000 |
| Large Intestine | 0.380 ± 0.063 | 0.054 ± 0.007 | 0.030 ± 0.003 | 0.000 ± 0.000 |
| Large Intestine Contents | 1.055 ± 0.116 | 0.396 ± 0.058 | 0.155 ± 0.134 | 0.000 ± 0.000 |
| Stomach | 0.744 ± 0.196 | 0.078 ± 0.023 | 0.021 ± 0.003 | 0.006 ± 0.005 |
| Stomach Contents | 8.294 ± 0.670 | 1.055 ± 0.057 | 0.296 ± 0.159 | 0.000 ± 0.000 |
| Urinary Bladder Contents | 1.531 ± 1.303 | 0.079 [b] | 0.019 ± 0.021 | 0.007 ± 0.002 |

TABLE 15c

Group Mean Radioactivity Content in Tissues, Cerebrospinal Fluid,
Gastrointestinal Tract and Urinary Bladder Contents of Male Sprague-Dawley Rats
Following a Single Intrathecal Dose and Intravenous Bolus Injection of $^{125}$I-hGALC
Group 3: At a Mean Dose of 1.08 mg/kg

| Sample | Percent of Dose [a] | | | |
|---|---|---|---|---|
| | 10 min | 30 min | 1 h | 3 h |
| Adrenal Glands | 0.066 ± 0.013 | 0.037 ± 0.010 | 0.032 ± 0.009 | 0.015 ± 0.002 |
| Brain | 0.071 ± 0.009 | 0.071 ± 0.007 | 0.058 ± 0.002 | 0.039 ± 0.008 |
| Cerebrospinal Fluid (CSF) | 0.046 ± 0.071 | 0.002 ± 0.002 | 0.010 ± 0.017 | 0.002 ± 0.003 |
| Eyes | 0.004 ± 0.001 | 0.012 ± 0.002 | 0.018 ± 0.001 | 0.021 ± 0.003 |
| Heart | 0.147 ± 0.008 | 0.188 ± 0.020 | 0.165 ± 0.008 | 0.136 ± 0.014 |
| Kidneys | 1.005 ± 0.107 | 1.157 ± 0.073 | 1.179 ± 0.061 | 0.985 ± 0.006 |
| Liver | 18.955 ± 0.723 | 14.647 ± 0.420 | 10.032 ± 1.037 | 6.754 ± 0.213 |
| Lungs | 0.506 ± 0.053 | 0.811 ± 0.104 | 0.871 ± 0.037 | 0.457 ± 0.031 |
| Sciatic Nerve | 0.001 ± 0.000 | 0.002 ± 0.000 | 0.003 ± 0.001 | 0.003 ± 0.002 |
| Spinal Cord (Lumbar, Thoracic, Cervical) | 0.028 ± 0.007 | 0.025 ± 0.005 | 0.023 ± 0.005 | 0.018 ± 0.004 |
| Spleen | 0.468 ± 0.027 | 0.435 ± 0.037 | 0.329 ± 0.032 | 0.217 ± 0.007 |
| Thyroid/Parathyroid Gland | 0.008 ± 0.004 | 0.055 ± 0.019 | 0.073 ± 0.041 | 0.392 ± 0.071 |
| Gastrointestinal Tract: | | | | |
| Small Intestine | 0.286 ± 0.046 | 0.641 ± 0.033 | 1.118 ± 0.264 | 1.176 ± 0.044 |
| Small Intestine Contents | 0.288 ± 0.037 | 1.150 ± 0.013 | 2.414 ± 0.038 | 4.314 ± 1.755 |
| Large Intestine | 0.131 ± 0.013 | 0.272 ± 0.015 | 0.360 ± 0.032 | 0.335 ± 0.051 |
| Large Intestine Contents | 0.000 ± 0.000 | 0.212 ± 0.070 | 0.351 ± 0.089 | 0.696 ± 0.181 |
| Stomach | 0.100 ± 0.017 | 0.206 ± 0.034 | 0.493 ± 0.124 | 0.931 ± 0.293 |
| Stomach Contents | 0.161 ± 0.029 | 0.806 ± 0.191 | 2.870 ± 1.090 | 8.789 ± 1.443 |
| Urinary Bladder Contents | 0.029 ± 0.021 | 0.182 ± 0.251 | 0.834 ± 0.663 | 0.273 ± 0.087 |

| Sample | Percent of Dose [a] | | | |
|---|---|---|---|---|
| | 6 h | 24 h | 48 h | 96 h |
| Adrenal Glands | 0.010 ± 0.002 | 0.002 ± 0.000 | 0.001 ± 0.000 | 0.001 ± 0.000 |
| Brain | 0.024 ± 0.003 | 0.000 ± 0.000 | 0.000 ± 0.000 | 0.000 ± 0.000 |
| Cerebrospinal Fluid (CSF) | 0.000 [b] | 0.000 [b] | 0.000 [b] | 0.000 ± 0.000 |
| Eyes | 0.019 ± 0.004 | 0.002 ± 0.000 | 0.000 ± 0.000 | 0.000 ± 0.000 |
| Heart | 0.106 ± 0.008 | 0.015 ± 0.001 | 0.005 ± 0.001 | 0.001 ± 0.002 |
| Kidneys | 0.689 ± 0.063 | 0.183 ± 0.013 | 0.081 ± 0.007 | 0.048 ± 0.002 |

TABLE 15c-continued

Group Mean Radioactivity Content in Tissues, Cerebrospinal Fluid,
Gastrointestinal Tract and Urinary Bladder Contents of Male Sprague-Dawley Rats
Following a Single Intrathecal Dose and Intravenous Bolus Injection of $^{125}$I-hGALC
Group 3: At a Mean Dose of 1.08 mg/kg

| | | | | |
|---|---|---|---|---|
| Liver | 5.085 ± 0.292 | 1.653 ± 0.097 | 0.757 ± 0.043 | 0.281 ± 0.022 |
| Lungs | 0.297 ± 0.011 | 0.038 ± 0.001 | 0.012 ± 0.003 | 0.006 ± 0.002 |
| Sciatic Nerve | 0.004 ± 0.001 | 0.000 ± 0.000 | 0.000 ± 0.000 | 0.000 ± 0.000 |
| Spinal Cord (Lumbar, Thoracic, Cervical) | 0.016 ± 0.003 | 0.002 ± 0.000 | 0.000 ± 0.000 | 0.000 ± 0.000 |
| Spleen | 0.146 ± 0.020 | 0.039 ± 0.003 | 0.015 ± 0.003 | 0.009 ± 0.000 |
| Thyroid/Parathyroid Gland | 0.496 ± 0.064 | 0.973 ± 0.162 | 0.567 ± 0.088 | 0.124 ± 0.088 |
| Gastrointestinal Tract: | | | | |
| Small Intestine | 0.954 ± 0.153 | 0.125 ± 0.046 | 0.032 ± 0.007 | 0.000 ± 0.000 |
| Small Intestine Contents | 2.054 ± 0.707 | 0.298 ± 0.019 | 0.113 ± 0.039 | 0.000 ± 0.000 |
| Large Intestine | 0.359 ± 0.097 | 0.036 ± 0.009 | 0.013 ± 0.002 | 0.000 ± 0.000 |
| Large Intestine Contents | 0.971 ± 0.095 | 0.290 ± 0.115 | 0.041 ± 0.071 | 0.000 ± 0.000 |
| Stomach | 0.943 ± 0.323 | 0.102 ± 0.084 | 0.014 ± 0.004 | 0.008 ± 0.002 |
| Stomach Contents | 3.501 ± 3.698 | 0.610 ± 0.365 | 0.175 ± 0.053 | 0.000 ± 0.000 |
| Urinary Bladder Contents | 0.114 ± 0.034 | 0.199 ± 0.266 | 0.003 ± 0.002 | 0.005 ± 0.008 |

Group 1 (Intrathecal Mean Dose of 41 µg/animal)

Following the intrathecal dose, there was a general distribution of $^{125}$I-labelled material into all of the tissues examined, however, radioactivity levels in the CSF were below the LOQ. The highest mean concentrations of $^{125}$I-labelled material in tissues of male rats were observed at 48 hours post dose in thyroid/parathyroid gland (4.127±1.635 µg eq/g) and at 3 hours post dose in stomach (0.203±0.101 µg eq/g), kidneys (0.096±0.014 µg eq/g) and lungs (0.058±0.014 µg eq/g). Levels were lower in the other tissues with $t_{max}$ values generally observed between 3 and 6 hours post dose. The lowest $C_{max}$ values were observed in brain (0.005±0.001 µg eq/g) and kidney fat (0.006±0.000 µg eq/g). By 48 and 96 hours post dose the radioactivity levels in the majority of the tissues were below the limit of detection, the exceptions being thyroid/parathyroid gland, kidneys and stomach. At 96 hours post dose, the highest mean concentration was observed in thyroid/parathyroid gland (1.927±1.585 µg eq/g, 46.7% of $C_{max}$) followed by the kidneys (0.005±0.001 µg eq/g, 5.2% of $C_{max}$) and the stomach (0.002±0.001 µg eq/g, 1% of $C_{max}$).

Tissue to serum ratios were generally less than 1 for the tissues up to 24 hours post-intrathecal dose. The exceptions were the thyroid/parathyroid gland, kidneys and stomach. The highest ratios were, by far, observed for the thyroid/parathyroid gland. By 48 and 96 hours post dose, tissue to serum ratios could not be calculated since serum concentrations were below the LOQ.

The levels of radioactivity recovered in all tissues were less than 1% of the administered dose with the highest proportions observed in liver (0.91%) at 3 hours post dose. At 1 hour post dose, proportions greater than 1% of the administered dose were only found in stomach contents (1.8%). By 3 hours post-dosing, proportions of greater than 1% of the administered dose were detected in small intestine contents (2.6%), stomach contents (5.0%) and urinary bladder contents (1.2%). At 6 hours post-dosing, proportions of greater than 1% of the administered dose were found in small intestine contents (1.7%) and stomach contents (4.0%). By 96 hours post dose, small amounts of $^{125}$I-hGALC-derived radioactivity (less than 0.1%) was still recovered in kidneys, thyroid/parathyroid gland, stomach and urinary bladder contents, with the highest recoveries observed in the thyroid/parathyroid gland (0.09%).

Group 2 (Intravenous Mean Dose of 1.00 mg/kg)

Following intravenous administration, the highest mean concentration ($C_{max}$) of radiolabelled material in tissues of Group 2 rats were observed in thyroid/parathyroid glands (294.521±52.953 µg eq/g; at 48 hours post dose), followed by lungs (20.629±2.125 µg eq/g; 30 minutes post dose), liver (11.335±1.436 µg eq/g; 10 minutes post dose), adrenal glands (8.827±2.435 µg eq/g; 10 minutes post dose), spleen (6.595±0.625 µg eq/g; 10 minutes post dose) and kidneys (3.027±0.330 µg eq/g; 10 minutes). The $t_{max}$ values for the tissues occurred between 10 minutes and 3 hours post dose except for the thyroid/parathyroid glands (48 hours post dose). The lowest mean radioactivity $C_{max}$ values were observed in kidney fat (0.158±0.019 µg eq/g), CSF (0.210±0.363 µg eq/g), brain (0.252±0.041 µg eq/g), skeletal muscle (0.275±0.025 µg eq/g) and spinal cord (0.293±0.028 µg eq/g). By 96 hours post-dosing, radioactivity was still detected, in 7 of the 18 tissues analyzed, with the highest mean concentrations being detected in the thyroid/parathyroid glands (218.917±45.098 µg eq/g, 74.3% of $C_{max}$), followed by liver (0.126±0.014 µg eq/g, 1.1% of $C_{max}$), spleen (0.111±0.009 µg eq/g, 1.7% of $C_{max}$) and kidneys (0.099±0.010 µg eq/g, 3.3% of $C_{max}$).

At 10 minutes post dose, mean tissue-to-serum ratios were less than 1 for all tissues analyzed. By 30 minutes and 1 hour post dose, mean tissue-to-serum ratios were greater than 1 for lungs and thyroid/parathyroid gland. At 3 and 6 hours post dose, mean tissue-to-serum ratios were greater than 1 for liver, lungs and thyroid/parathyroid gland. At 24 and 48 hours post dose liver, lungs, spleen and thyroid/parathyroid gland had mean tissue-to-serum ratios above 1. At 96 hours post dose, mean tissue-to-serum ratios were greater than 1 for kidneys, liver, spleen and thyroid/parathyroid gland. The highest tissue-to-serum ratios were observed in thyroid/parathyroid glands (2485 at 96 hours), lungs (6.5 at 24 hours) and liver (2.2 at 24 hours).

In terms of proportion of the radioactivity administered, the highest mean values in tissues were observed in the liver (41.7% at 10 minutes post dose), lungs (7.0% at 30 minutes), kidneys (2.2% at 10 minutes), small intestine (1.5% at 1 hour) and thyroid/parathyroid glands (1.4% at 48 hours). In gastro-intestinal tract contents, the highest mean values were 10.3% of the dose in stomach contents (at 3 hours post dose), 5.4% in small intestine contents (at 3 hours post dose) and 1.1% in large intestine contents (6 hours). By 96 hours post dosing, the highest proportions of the administered dose were detected in thyroid/parathyroid glands (1.0%), liver (0.5%), and kidneys (0.1%). At this time point post dose, less than 0.01% of the administered dose remained in the stomach and urinary bladder contents.

Group 3 (Intrathecal Followed by Intravenous Dose: 1.08 mg/kg (Combined Dose))

Following the intrathecal and the intravenous dose, the highest mean concentration ($C_{max}$) of radiolabelled material in tissues of Group 3 rats were observed in thyroid/parathyroid glands (296.957±57.793 μg eq/g; at 24 hours post dose), followed by liver (10.181±0.600 μg eq/g; 10 minutes post dose), adrenal glands (9.567±1.678 μg eq/g; 10 minutes post dose), lungs (5.305±0.194 μg eq/g; 1 hour post dose), spleen (5.042±0.902 μg eq/g; 10 minutes post dose), stomach (4.454±1.455 μg eq/g; 3 hour, post dose, kidneys (3.390±0.183 μg eq/g; 1 hour) and CSF (2.087±2.912 μg eq/g; 10 minutes). The $t_{max}$ values for the tissues occurred between 10 minutes and 3 hours post dose except for the large intestine (6 hours post dose) and thyroid/parathyroid glands (24 hours post dose). The lowest mean radioactivity $C_{max}$ values were observed in kidney fat (0.188±0.020 μg eq/g), brain (0.283±0.062 μg eq/g, spinal cord (0.327±0.062 μg eq/g) and skeletal muscle (0.411±0.009 μg eq/g). By 96 hours post-dosing, radioactivity was still detected, in 8 of the 18 tissues analyzed, the highest mean concentrations being detected in the thyroid/parathyroid glands (43.962±23.164 μg eq/g, 14.8% of $C_{max}$), followed by liver (0.137±0.018 μg eq/g, 1.3% of $C_{max}$), kidneys (0.124±0.005 μg eq/g, 3.7% of $C_{max}$), spleen (0.083±0.009 μg eq/g, 1.6% of $C_{max}$) and adrenal glands (0.069±0.016 μg eq/g, 0.7% of $C_{max}$).

At 10 minutes post dose, mean tissue-to-serum ratios were less than 1 for all tissues analyzed. By 30 minutes and 1 hour post dose, mean tissue-to-serum ratios were greater than 1 for thyroid/parathyroid gland. At 3 and 6 hours post dose, mean tissue-to-serum ratios were greater than 1 for stomach and thyroid/parathyroid gland. At 24 hours post dose liver and thyroid/parathyroid gland had mean tissue-to-serum ratios above 1. At 48 and 96 hours post dose, mean tissue-to-serum ratios were greater than 1 for kidneys, liver and thyroid/parathyroid gland and for the spleen (96 hours). The highest tissue-to-serum ratios were observed in thyroid/parathyroid glands (854 at 48 hours), liver (1.8 at 48 hours) and kidneys (1.6 at 96 hours).

In terms of proportion of the radioactivity administered, the highest mean values in tissues were observed in the liver (19.0% at 10 minutes post dose), kidneys (1.2% at 1 hour) and small intestine (1.2 at 3 hours). In gastro-intestinal tract contents, the highest mean values were 8.8% of the dose in stomach contents (at 3 hours post dose), 4.3% in small intestine contents (at 3 hours post dose) and 1.0% in large intestine contents (6 hours). By 96 hours post dosing, the highest proportions of the administered dose were detected liver (0.3%), in thyroid/parathyroid glands (0.1%), and kidneys (0.05%). At this time point post dose, less than 0.01% of the administered dose remained in the adrenal glands, heart, lungs, spleen, stomach and urinary bladder contents.

Pharmacokinetics of Radioactivity in Blood, Serum, Red Blood Cells, CSF and Tissues (Table 16 and Table 17)

Mean pharmacokinetic parameters for radioactivity in blood, serum, red blood cells, CSF and tissues of rats following a single intrathecal and/or intravenous dose of $^{125}$I-hGALC are given in Table 16 and Table 17.

TABLE 16

Disposition Kinetics of the Total Radioactivity in Serum, Blood and Red Blood Cells of Male Sprague-Dawley Rats Following a Single Intrathecal Dose of $^{125}$I-hGALC Serum
Group 1: At a Mean Dose of 41 μg/animal

| $t_{max}$ (h) | $C_{max}$ (μg eq/g) | $t_{last}$ (h) | $AUC_{0\text{-}tlast}$ (μg eq · h/g) | k (h$^{-1}$) | R$^2$ | $t_{1/2}$ (h) | $AUC_{0\text{-}inf}$ (μg eq · h/g) | % Extrapolation $AUC_{0\text{-}inf}$ |
|---|---|---|---|---|---|---|---|---|
| 3 | 0.108 | 24 | 1.48 | 0.130 | 0.988 | 5.34 | 1.54 | 4.00 |
| | | | | | Blood | | | |
| 3 | 0.0930 | 24 | 1.33 | 0.138 | 0.983 | 5.02 | 1.37 | 3.16 |
| | | | | | Red Blood Cells | | | |
| 6 | 0.0890 | 24 | 1.24 | 0.170 | 0.980 | 4.08 | 1.25 | 1.41 |

TABLE 16b

Disposition Kinetics of the Total Radioactivity in Serum, Blood and Red Blood Cells of Male Sprague-Dawley Rats Following a Single Intravenous Bolus Injection of $^{125}$I-hGALC
Group 2: At a Mean Dose of 1.00 mg/kg

| $t_{max}$ (h) | $C_{max}$ (μg eq/g) | $t_{last}$ (h) | $AUC_{0\text{-}tlast}$ (μg eq · h/g) | k (h$^{-1}$) | R$^2$ | $t_{1/2}$ (h) | $AUC_{0\text{-}inf}$ (μg eq · h/g) | % Extrapolation $AUC_{0\text{-}inf}$ | $V_Z$ (mL/kg) | CL (mL/h/kg) |
|---|---|---|---|---|---|---|---|---|---|---|
| | | | | | Serum | | | | | |
| 0 | 20.1 | 96 | 71.1 | 0.0226 | 0.997 | 30.7 | 75.0 | 5.21 | 591 | 13.3 |
| | | | | | Blood | | | | | |
| 0 | 14.0 | 96 | 51.2 | 0.0256 | 0.994 | 27.1 | 53.2 | 3.75 | 735 | 18.8 |
| | | | | | Red Blood Cells | | | | | |
| 0 | 6.40 | 48 | 33.9 | 0.0635 | 0.941 | 10.9 | 35.7 | 4.94 | 441 | 28.0 |

TABLE 16c

Disposition Kinetics of the Total Radioactivity in Serum, Blood and Red Blood Cells of Male Sprague-Dawley Rats Following a Single Intrathecal Dose and Intravenous Bolus Injection of $^{125}$I-hGALC
Group 3: At a Mean Dose of 1.08 mg/kg

| $t_{max}$ (h) | $C_{max}$ (µg eq/g) | $t_{last}$ (h) | $AUC_{0\text{-}tlast}$ (µg eq · h/g) | k (h$^{-1}$) | $R^2$ | $t_{1/2}$ (h) | $AUC_{0\text{-}inf}$ (µg eq · h/g) | % Extrapolation $AUC_{0\text{-}inf}$ | $V_Z$ (mL/Kg) | CL (mL/h/kg) |
|---|---|---|---|---|---|---|---|---|---|---|
| Serum ||||||||||||
| 0 | 16.9 | 96 | 89.8 | 0.0272 | 0.983 | 25.5 | 92.6 | 3.06 | 429 | 11.7 |
| Blood ||||||||||||
| 0 | 11.4 | 96 | 66.9 | 0.0332 | 0.990 | 20.9 | 68.0 | 1.64 | 478 | 15.9 |
| Red Blood Cells ||||||||||||
| 0 | 7.36 | 48 | 49.2 | 0.0721 | 0.947 | 9.61 | 51.0 | 3.69 | 293 | 21.2 |

TABLE 17a

Disposition Kinetics of the Total Radioactivity in Tissues and Cerebrospinal Fluid of Male Sprague-Dawley Rats Following a Single Intrathecal Dose of $^{125}$I-hGALC

| Samples | $t_{max}$ (h) | $C_{max}$ (µg eq/g) | $t_{last}$ (h) | $AUC_{0\text{-}tlast}$ (µg eq · h/g) | k (h$^{-1}$) | $R^2$ | $t_{1/2}$ (h) | $AUC_{0\text{-}inf}$ (µg eq · h/g) | % Extrapolation ($AUC_{0\text{-}inf}$) |
|---|---|---|---|---|---|---|---|---|---|
| Adipose Tissue (Kidney Fat) | 6 | 0.0060 | 6 | 0.0215 | a | a | a | a | a |
| Adrenal Glands | 3 | 0.0210 | 6 | 0.109 | a | a | a | a | a |
| Bone (Femur) | 6 | 0.0410 | 6 | 0.186 | a | a | a | a | a |
| Brain | 3 | 0.0050 | 6 | 0.0247 | a | a | a | a | a |
| Cerebrospinal Fluid (CSF) | b | 0.000 | b | 0.000 | b | b | b | b | b |
| Eyes | 3 | 0.0270 | 24 | 0.345 | 0.164 | 0.990 | 4.23 | 0.351 | 1.74 |
| Heart | 3 | 0.0280 | 24 | 0.379 | 0.167 | 0.987 | 4.16 | 0.385 | 1.56 |
| Kidneys | 3 | 0.0960 | 96 | 1.84 | 0.0118 | 0.979 | 58.6 | 2.27 | 18.6 |
| Large Intestine | 3 | 0.0240 | 24 | 0.347 | 0.125 | 0.983 | 5.54 | 0.363 | 4.40 |
| Liver | 6 | 0.0300 | 6 | 0.141 | a | a | a | a | a |
| Lungs | 3 | 0.0580 | 24 | 0.801 | 0.134 | 0.987 | 5.18 | 0.831 | 3.60 |
| Muscle (Skeletal) | 3 | 0.0140 | 6 | 0.0683 | a | a | a | a | a |
| Sciatic Nerve | 6 | 0.0500 | 6 | 0.201 | a | a | a | a | a |
| Small Intestine | 3 | 0.0460 | 24 | 0.606 | 0.121 | 0.992 | 5.74 | 0.639 | 5.18 |
| Spinal Cord (lumbar, thoracic, cervical) | 3 | 0.0090 | 6 | 0.0436 | a | a | a | a | a |
| Spleen | 3 | 0.0400 | 6 | 0.183 | a | a | a | a | a |
| Stomach | 3 | 0.203 | 96 | 2.60 | 0.0177 | 0.831 | 39.1 | 2.71 | 4.16 |
| Thyroid/Parathyroid Gland | 48.1 | 4.13 | 96 | 313 | c | 0.892 | c | c | 35.2 | a No reportable results as the terminal phase could not be identified.
b PK parameters not estimated due to samples being <LLOQ
c Values are not reported because the $AUC_{0\text{-}inf}$ was extrapolated by more than 20% or $R^2$ is <0.8.

TABLE 17b

Disposition Kinetics of the Total Radioactivity in Tissues and Cerebrospinal Fluid of Male Sprague-Dawley Rats Following a Single Intravenous Bolus Injection of $^{125}$I-hGALC
Group 2: At a Mean Dose of 1.00 mg/kg

| Samples | $t_{max}$ (h) | $C_{max}$ (µg eq/g) | $t_{last}$ (h) | $AUC_{0\text{-}tlast}$ (µg eq · h/g) | k (h$^{-1}$) | $R^2$ | $t_{1/2}$ (h) | $AUC_{0\text{-}inf}$ (µg eq · h/g) | % Extrapolation ($AUC_{0\text{-}inf}$) |
|---|---|---|---|---|---|---|---|---|---|
| Adipose Tissue (Kidney Fat) | 0.5 | 0.158 | 6 | 0.617 | a | 0.920 | a | a | 56.0 |
| Adrenal Glands | 0 | 10.9 | 96 | 43.1 | 0.0201 | 0.927 | 34.6 | 46.8 | 7.89 |
| Bone (Femur) | 0.5 | 1.58 | 48 | 15.3 | 0.0777 | 0.965 | 8.92 | 15.7 | 2.79 |

TABLE 17b-continued

Disposition Kinetics of the Total Radioactivity in Tissues and Cerebrospinal Fluid of Male Sprague-Dawley Rats Following a Single Intravenous Bolus Injection of $^{125}$I-hGALC
Group 2: At a Mean Dose of 1.00 mg/kg

| Samples | $t_{max}$ (h) | $c_{max}$ (µg eq/g) | $t_{last}$ (h) | $AUC_{0-tlast}$ (µg eq·h/g) | k ($h^{-1}$) | $R^2$ | $t_{1/2}$ (h) | $AUC_{0-inf.}$ (µg eq·h/g) | % Extrapolation ($AUC_{0-inf.}$) |
|---|---|---|---|---|---|---|---|---|---|
| Brain | 0 | 0.268 | 6 | 0.735 | a | 0.897 | a | a | 26.8 |
| Cerebrospinal Fluid (CSF) | 3 | 0.210 | 6 | 0.854 | b | b | b | b | b |
| Eyes | 1 | 0.406 | 24 | 5.35 | 0.113 | 0.981 | 6.15 | 5.64 | 5.19 |
| Heart | 0 | 1.33 | 48 | 10.2 | 0.0726 | 0.909 | 9.54 | 10.8 | 5.12 |
| Kidneys | 0 | 3.18 | 96 | 40.7 | 0.0167 | 0.988 | 41.6 | 46.7 | 12.7 |
| Large Intestine | 1 | 0.492 | 48 | 7.30 | 0.0658 | 0.938 | 10.5 | 7.70 | 5.14 |
| Liver | 0 | 14.6 | 96 | 100 | 0.0290 | 1.00 | 23.9 | 105 | 4.15 |
| Lungs | 0.5 | 20.6 | 96 | 165 | 0.0497 | 0.939 | 13.9 | 167 | 0.832 |
| Muscle (Skeletal) | 1 | 0.275 | 24 | 2.64 | 0.154 | 0.996 | 4.50 | 2.69 | 1.93 |
| Sciatic Nerve | 3 | 0.689 | 24 | 9.62 | 0.166 | 0.987 | 4.18 | 9.77 | 1.54 |
| Small Intestine | 3 | 0.832 | 48 | 13.2 | 0.0693 | 0.932 | 10.0 | 13.8 | 4.29 |
| Spinal Cord (lumbar, thoracic, cervical) | 0 | 0.315 | 24 | 2.39 | 0.115 | 0.991 | 6.04 | 2.51 | 4.87 |
| Spleen | 0 | 7.27 | 96 | 46.1 | 0.0218 | 0.964 | 31.8 | 61.2 | 8.33 |
| Stomach | 3 | 2.40 | 96 | 31.9 | 0.0330 | 0.945 | 21.0 | 32.3 | 1.41 |
| Thyroid/Parathyroid Gland | 48 | 295 | 96 | 24989 | b | b | b | b | b | a Values are not reported because the $AUC_{0-inf.}$ was extrapolated by more than 20% or $R^2$ is <0.8.
b No reportable results as the terminal phase could not be identified.

TABLE 17c

Disposition Kinetics of the Total Radioactivity in Tissues and Cerebrospinal Fluid of Male Sprague-Dawley Rats Following a Single Intrathecal Dose and Intravenous Bolus Injection of $^{125}$I-hGALC
Group 3: At a Mean Dose of 1.08 mg/kg

| Samples | $t_{max}$ (h) | $c_{max}$ (µg eq/g) | $t_{last}$ (h) | $AUC_{0-tlast}$ (µg eq·h/g) | k ($h^{-1}$) | $R^2$ | $t_{1/2}$ (h) | $AUC_{0-inf.}$ (µg eq·h/g) | % Extrapolation ($AUC_{0-inf.}$) |
|---|---|---|---|---|---|---|---|---|---|
| Adipose Tissue (Kidney Fat) | 1 | 0.188 | 6 | 0.954 | a | 0.999 | a | a | 65.6 |
| Adrenal Glands | 0 | 12.6 | 96 | 43.9 | 0.0354 | 0.835 | 19.6 | 45.8 | 4.25 |
| Bone (Femur) | 0.5 | 1.71 | 48 | 21.9 | 0.0869 | 0.985 | 7.98 | 22.3 | 1.50 |
| Brain | 0 | 0.287 | 6 | 1.03 | a | 0.992 | a | a | 36.1 |
| Cerebrospinal Fluid (CSF) | 0 | 4.89 | 3 | 1.94 | a | 0.775 | a | a | 5.95 |
| Eyes | 3 | 0.611 | 48 | 9.88 | 0.0947 | 0.988 | 7.32 | 9.99 | 1.06 |
| Heart | 0.5 | 1.32 | 96 | 15.7 | 0.0391 | 1.00 | 17.7 | 15.9 | 0.967 |
| Kidneys | 1 | 3.39 | 96 | 57.9 | 0.0190 | 0.960 | 36.4 | 64.4 | 10.1 |
| Large Intestine | 6 | 0.726 | 48 | 12.4 | 0.0764 | 0.911 | 9.07 | 12.8 | 2.77 |
| Liver | 0 | 11.2 | 96 | 96.5 | 0.0269 | 0.986 | 25.7 | 102 | 5.00 |
| Lungs | 1 | 5.31 | 96 | 44.1 | 0.0252 | 0.932 | 27.5 | 45.4 | 2.88 |
| Muscle (Skeletal) | 1 | 0.411 | 24 | 4.37 | 0.110 | 0.997 | 6.31 | 4.66 | 6.25 |
| Sciatic Nerve | 3 | 1.04 | 24 | 15.6 | 0.147 | 0.983 | 4.71 | 16.0 | 2.38 |
| Small Intestine | 3 | 1.40 | 48 | 20.2 | 0.0851 | 0.974 | 8.14 | 20.6 | 1.88 |
| Spinal Cord (lumbar, thoracic, cervical) | 0 | 0.331 | 24 | 3.52 | 0.105 | 0.994 | 6.58 | 3.77 | 6.55 |
| Spleen | 0 | 5.21 | 96 | 46.9 | 0.0347 | 0.860 | 20.0 | 49.3 | 4.85 |
| Stomach | 3 | 4.45 | 96 | 72.1 | 0.0557 | 0.858 | 12.4 | 72.6 | 0.766 |
| Thyroid/Parathyroid Gland | 24 | 297 | 96 | 16776 | 0.0272 | 0.982 | 25.4 | 18390 | 8.78 | a Values are not reported because the $AUC_{0-inf.}$ was extrapolated by more than 20% or $R^2$ is <0.8.

Blood, Serum and Red Blood Cells

Following the intrathecal dose (Group 1: 41 µg/animal), the mean calculated areas under the radioactivity concentration vs. time curves from time zero to the last measurable time point ($AUC_{0-tlast}$) for serum, whole blood and red blood cells were 1.48 µg eq·h/g, 1.33 µg eq·h/g and 1.24 µg eq·h/g, respectively. The apparent terminal $t_{1/2}$ values reported for radioactivity in serum, whole blood and red blood cells were 5.34, 5.02 and 4.08 hours, respectively. The elimination rate constant, k, was calculated as 0.130 $h^{-1}$, 0.138 $h^{-1}$ and 0.170 $h^{-1}$ in serum, whole blood and red blood cells, respectively. $AUC_{0-inf}$ was calculated as 1.54 µg eq·h/g, 1.37 µg eq·h/g and 1.25 µg eq·h/g in serum, whole blood and red blood cells, respectively. The elimination phases for radioactivity from serum, whole blood and red blood cells were well-defined, as evidenced by the very low percentage extrapolation values (4.0, 3.2 and 1.4%, respectively) required for calculation of $AUC_{0\text{-}inf}$.

Following the intravenous dose (Group 2: 1.00 mg/kg), the mean $AUC_{0\text{-}tlast}$ values for serum, whole blood and red blood cells were 71.1 μg eq·h/g, 51.2 μg eq·h/g and 33.9 μg eq·h/g, and the apparent terminal $t_{1/2}$ values were 30.7, 27.1 and 10.9 hours, respectively. The value of k was calculated as 0.0226 $h^{-1}$, 0.0256 $h^{-1}$ and 0.0635 $h^{-1}$ in serum, whole blood and red blood cells, respectively. The elimination phases for radioactivity from serum, whole blood and red blood cells were well-defined and $AUC_{0\text{-}inf}$ was calculated as 75.0 μg eq·h/g (extrapolation 5.21%), 53.2 μg eq·h/g (extrapolation 3.75%) and 35.7 μg eq·h/g (extrapolation 4.94%) in serum, whole blood and red blood cells, respectively. The apparent volume of distribution ($V_z$) was greatest in whole blood (735 mL/kg) followed by serum (591 mL/kg) and red blood cells (441 mL/kg). Clearance of the test article was estimated at 13.3 mL/h/kg from serum and 18.8 mL/h/kg for whole blood.

Following the intrathecal dose and intravenous dose (combined 1.08 mg/kg) to Group 3 animals, the mean $AUC_{0\text{-}tlast}$ values for serum, whole blood and red blood cells were 89.8 μg eq·h/g, 66.9 μg eq·h/g and 49.2 μg eq·h/g, respectively. The apparent terminal $t_{1/2}$ values reported for radioactivity in serum, whole blood and red blood cells were 25.5, 20.9 and 9.61 hours, respectively, with k as 0.0272 $h^{-1}$, 0.0332 $h^{-1}$ and 0.0721 $h^{-1}$. Again, the elimination phases for all three matrices were well-defined, with $AUC_{0\text{-}inf}$ calculated as 92.6 μg eq·h/g, 68.0 μg eq·h/g and 51.0 μg eq·h/g (extrapolation of 3.06%, 1.64% and 3.69%) in serum, whole blood and red blood cells, respectively. The $V_z$ was greater in whole blood (478 mL/kg) followed by serum (429 mL/kg) and red blood cells (293 mL/kg). Clearance values were 15.9 mL/h/kg for whole blood and 11.7 mL/h/kg for serum.

Tissues

The highest $AUC_{0\text{-}tlast}$ value in tissues from rats, following an intrathecal dose of $^{125}$I-hGALC (Group 1: 41 μg/animal), was observed in thyroid/parathyroid gland (313 μg eq·h/g), followed by stomach (2.60 μg eq·h/g) and kidneys (1.84 μg eq·h/g). For several tissues, it was not possible to estimate k or any parameters derived from k (i.e. $t_{1/2}$ and $AUC_{0\text{-}inf}$) since the % extrapolation of the AUC to infinity was greater than 20% or due to lack of data in the terminal phase. For those tissues where it could be estimated (eyes, heart, kidneys, large intestine, lungs, small intestine and stomach), k ranged from 0.01 to 0.17 $h^{-1}$ and the $t_{1/2}$ generally ranged from 4 to 6 h, the exceptions being 58.6 h for kidneys and 39.1 h for stomach.

Following the intravenous dose (Group 2; 1.00 mg/kg), the highest values for $AUC_{0\text{-}tlast}$ were observed in thyroid/parathyroid gland (24989 μg eq·h/g), followed by lungs (165 μg eq·h/g), liver (100 μg eq·h/g), spleen (56.1 μg eq·h/g), adrenal glands (43.1 μg eq·h/g) and kidneys (40.7 μg eq·h/g). The lowest $AUC_{0\text{-}tlast}$ values were observed for kidney fat (0.617 μg eq·h/g) and brain (0.735 μg eq·h/g). Parameters derived from k were not reported for tissues where the elimination phase was poorly defined (thyroid/parathyroid gland and CSF), or where the extrapolation to $AUC_{0\text{-}inf}$ was greater than 20% (kidney fat and brain). Only the $AUC_{0\text{-}inf}$ values for liver and lungs were greater than that of serum (75 μg eq·h/g). The highest reported $AUC_{0\text{-}inf}$ value was for lungs (167 μg eq·h/g; extrapolation 0.832%), followed by liver (105 μg eq·h/g; extrapolation 4.15%), spleen (61.2 μg eq·h/g; extrapolation 8.33%), adrenal glands (46.8 μg eq·h/g; extrapolation 7.89%) and kidneys (46.7 μg eq·h/g; extrapolation 12.7%).

The lowest reported value for $AUC_{0\text{-}inf}$ value was calculated for spinal cord (2.51 μg eq·h/g; extrapolation 4.87%) followed by muscle (2.69 μg eq·h/g; extrapolation 1.93%) and eyes (5.64 μg eq·h/g; extrapolation 5.19%). The longest calculable $t_{1/2}$ in tissues was 41.6 hours for kidneys, followed by 34.6 hours for the adrenal glands and 31.8 hours for the spleen. The shortest reported t½ was 4.18 hours for sciatic nerve.

For Group 3, after an intrathecal and an intravenous dose (1.08 mg/kg, combined dose), the highest values for $AUC_{0\text{-}tlast}$ was observed in thyroid/parathyroid gland (16776 μg eq·h/g) followed by liver (96.5 μg eq·h/g), stomach (72.1 μgeq·h/g), kidneys (57.9 μg eq·h/g), spleen (46.9 μg eq·h/g), lungs (44.1 μg eq·h/g) and adrenal glands (43.9 μg eq·h/g). The lowest $AUC_{0\text{-}tlast}$ values were observed for kidney fat (0.954 μg eq·h/g) and brain (1.03 μg eq·h/g). Parameters derived from k were not reported for tissues where the extrapolation to $AUC_{0\text{-}inf}$ was greater than 20% (kidney fat and brain) or $R^2$ lower than 0.8 (CSF). Only the $AUC_{0\text{-}inf}$ values for thyroid/parathyroid gland and liver were greater than that of serum (92.6 μg eq·h/g). The highest reported $AUC_{0\text{-}inf}$ value was for thyroid/parathyroid gland (18390 μg eq·h/g; extrapolation 8.78%), followed by liver (102 μg eq·h/g; extrapolation 5.0%), stomach (72.6 μg eq·h/g; extrapolation 0.766%), kidneys (64.4 μg eq·h/g; extrapolation 10.1%), spleen (49.3 μg eq·h/g; extrapolation 4.85%), adrenal glands (45.8 μg eq·h/g; extrapolation 4.25%) and lungs (45.4 μg eq·h/g; extrapolation 2.88%). The lowest reported value for $AUC_{0\text{-}inf}$ value was calculated for spinal cord (3.77 μg eq·h/g; extrapolation 6.55%) followed by muscle (4.66 μg eq·h/g; extrapolation 6.25%). The longest calculable $t_{1/2}$ in tissues was 36.4 hours for kidneys, followed by 27.5 hours for lungs, 25.7 hours for liver and 25.4 hours thyroid/parathyroid gland. The shortest reported $t_{1/2}$ was 4.71 hours for sciatic nerve.

Discussion

Following intrathecal administration, the highest mean concentrations of radioactivity in serum and whole blood were observed at 3 hours post dose suggesting relatively rapid distribution of dose-related material to the systemic circulation. Following intravenous administration, the highest mean concentrations of radioactivity in serum and whole blood were observed at the first time point measured. Concentrations in serum were always higher than those in whole blood, as reflected by blood-to-serum ratios of less than 1. This indicated that dose-related material was not particularly associated with the blood cells of any groups at any time post dose. Following TCA precipitate of blood proteins, the radioactivity was mainly recovered in the pellet suggesting that the majority of circulating radioactivity was protein associated, indicating that radioactivity distribution observed was not largely reflective of the disposition of free $^{125}$iodine.

When comparing Group 2 (intravenous dose 1.00 mg/kg) to Group 3 (intrathecal and intravenous combined dose 1.08 mg/kg), concentrations in Group 3 serum and whole blood appeared to be generally similar to those of Group 2. The decline of radioactivity in both matrices for both groups was also very similar, as assessed by blood-to-serum ratios. Comparing $AUC_{0\text{-}tlast}$ and $AUC_{0\text{-}inf}$ for Group 2 and Group 3 serum and blood, indicated that exposure to dose-related material was slightly higher for Group 3 animals.

In Group 1, levels of radioactivity in CSF were very low, a finding which does not appear to be in accordance with the administration of the test article directly to the intrathecal space, although very low levels were observed in brain. However, radioactivity was observed in the systemic circulation, and in systemic tissues, shortly following dosing, suggesting that dose-related material was fairly rapidly distributed from the intrathecal space following administration. Higher levels in the stomach and intestinal contents suggested that dose-related material was excreted via feces, although direct measurement in the excreta was not performed in this study. In addition, high levels in the urinary bladder contents also suggest excretion via urine. Other than high levels in the thyroid/parathyroid glands, considered to reflect loss of the iodine label and persistence of the label in this tissue rather than distribution/persistence of the test article itself, high levels of radioactivity were observed in liver, lungs, adrenal glands spleen and kidneys; tissues which were likely to be involved in the metabolism and/or excretion of the test article.

Distribution of radioactivity was general and widespread by the first time point post dose in Groups 2 and 3. The highest concentrations were generally associated with the liver, lungs, kidneys, spleen, adrenal gland, and in particular, the thyroid/parathyroid glands. Thus the pattern of distribution of radioactivity in tissues of all three groups was largely similar. Again, high levels of radioactivity observed in the thyroid/parathyroid glands of all animals, particularly considering the marked concentration increase with increasing time post dose, probably indicated loss of the iodine label and persistence of the label in this tissue rather than distribution/persistence of the test article itself. CSF levels were higher in these groups, as compared to Group 1, at early timepoints post dose, suggesting that radiolabelled material was able to cross the blood-brain barrier. Slighty higher levels were observed in this matrix in Group 3, as compared to Group 2, again at early timepoints post dose, suggesting that this concentration was accounted for by test article-related material distributing from the intravenous dose and material directly injected into the intrathecal space. The below LOQ values observed for Group 1 may therefore be a consequence of very low concentrations in very small sample volumes, being below the quantitation possible by this analytical method.

Tissue-to-serum ratios were generally less than 1 in the majority of tissues of all groups by 96 hours post dose, indicating that dose-related material was distributed into the tissues and was generally cleared more readily from the tissues than from the serum. For all groups, exposure of the majority of the tissues to dose-related material (as assessed by $AUC_{0\text{-}tlast}$) was less than that of serum.

Conclusion

Following administration of a single intrathecal (nominal 60 ug/animal) and/or intravenous bolus dose of $^{125}$I-hGALC to male rats (nominal concentrations of 1 mg/kg), concentrations of radioactivity in blood, serum, red blood cells, CSF and tissues were determined.

The highest observed concentrations of radioactivity in both serum and whole blood occurred at 3 hours post dose following intrathecal administration, indication relatively rapid distribution to the systemic circulation, or at the first time point post dose (10 minutes) following intravenous dosing. Concentrations in serum were higher than in blood, indicating that test article-related material was not particularly associated with the blood cells. Distribution of radioactivity into tissues was general and widespread by early time points post dose and, in general, the pattern of distribution to tissues was similar between all three groups. For all groups, exposure of the majority of the tissues to dose-related material (as assessed by $AUC_{0\text{-}tlast}$) was less than that of serum. High concentrations in thyroid/parathyroid glands for all three groups were considered to indicate loss of the iodine label rather than distribution and persistence of dose-related material in this tissue. By 96 hours post intravenous dose, radioactivity was still detected in a few of the tissues examined.

Example 3: Pre-Clinical Study Of ICV and ICV/IP rmGALC Injection and Extended Survival in Twitcher Mice The present Example demonstrates one embodiment of a preclinical study illustrating extended survival in twitcher mice provided with weekly IP injections of rmGALC. In the present embodiment, improved myelination was observed in the sciatic nerve, along with reduced psychosine levels and gross motor function (i.e., gait) improvement. In some embodiments, twitcher mice treated with a single ICV or ICV/IP rmGALC injection exhibited increased survival and up to a 63% reduction in the levels of brain psychosine. The positive results in important endpoints (i.e., survival, brain psychosine levels) following a single ICV administration of rmGALC along with the very minimal improvement in these endpoints following the addition of systemic administration (ICV/IP) suggest that a CNS only regimen is a viable clinical option for the treatment of GLD.

Introduction

Globoid Cell Leukodystrophy (GLD) is an autosomal recessive lysosomal storage disorder that occurs at an incidence of approximately 1:100,000 births (1.9:100,000 births in Scandinavian countries). A progressive peripheral (PNS) and central (CNS) nervous system disorder, GLD is the result of genetic mutations causing a deficiency in the enzyme activity of galactocerebrosidase (GALC) to degrade substrate lipids [i.e., galactosylceramide to galactose and ceramide; galactosylsphingosine (psychosine) to galactose and sphingosine]. This disorder is characterized by a complete loss of oligodendrocytes and myelin as well as the presence of galactosylceramide-engorged macrophages ("globoid" cells).

The clinical features of this disease present in two forms: infantile and late-onset. The infantile form of GLD (also known as Krabbe disease) occurs in 90% of all patients diagnosed with GALC deficiency, and symptoms are usually observed within 3-6 months after birth; there are reports of symptoms manifesting as early as 2-3 weeks of age (Wenger, D. A. et al., 2001, *Galactosylceramide Lipidosis: Globoid Cell Leukodystrophy (Krabbe Disease)*, in *The Metabolic and Molecular Bases of Inherited Disease*, C. R. Scriver, Beaudet, A. L., Sly, W. S., and Valle, D, Editor. 2001, McGraw-Hill. p. 3669-3687; incorporated herein as reference). The late-onset variant of this disease usually presents clinically by 10 years of age, however, patients diagnosed at 40 years of age have been reported (Wenger, D. A. et al., 2001, *Galactosylceramide Lipidosis: Globoid Cell Leukodystrophy (Krabbe Disease)*, in *The Metabolic and Molecular Bases of Inherited Disease*, C. R. Scriver, Beaudet, A. L., Sly, W. S., and Valle, D, Editor. 2001, McGraw-Hill. p. 3669-3687; incorporated herein as reference). The decline of function in late-onset patients proceeds gradually over a period of several years.

Systemic enzyme replacement therapy (ERT) has provided benefit for patients suffering from lysosomal storage disorders (LSDs) such as Gaucher disease, Fabry disease, and Hunter syndrome (Wenger, D. A. et al., 2001, *Galactosylceramide Lipidosis: Globoid Cell Leukodystrophy* (*Krabbe Disease*), in *The Metabolic and Molecular Bases of Inherited Disease*, C. R. Scriver, Beaudet, A. L., Sly, W. S., and Valle, D, Editor. 2001, McGraw-Hill. p. 3669-3687; Neufeld, E. F., 2004, *Enzyme Replacement therapy*. Lysosomal disorders of the Brain, ed. f.m.a. W. Platt, S. V. 2004: Oxford University Press. 327-338; Desnick, R. J., 2004. *J. Inherit. Metab. Dis.*, 27(3): p. 385-410; all of which are incorporated herein as reference). ERT for GLD has not been pursued with rigor, perhaps because the disease affects both the PNS and CNS. Current treatments for patients with GLD include hematopoietic cell transplant (HCT), however this procedure has its limitations due to significant adverse events (i.e., 30% treatment-related mortality, lifelong immunosuppressive therapy) and efficacy only in presymptomatic patients.

The twitcher mouse is the most common experimental animal model used to study GLD, and constitutes the bulk of experimental work on this disease (Wenger, D. A., 2000, *Mol. Med. Today,* 6(11): p. 449-451; incorporated herein as reference), but other naturally occurring animal models of GLD exist with variable degrees of characterization. Spontaneous mutation exists in West Highland White/Cairn Terriers (Kobayashi T., et al., 1980, *Brain Res.,* 202:479-83; incorporated herein as reference), polled Dorset Sheep (Pritchard D., et al., 1980, *Vet.Pathol.,* 17:399-405), the domestic cat (Johnson K., 1970, *J. Am. Vet. Med. Assoc.,* 157:2057-64; incorporated herein as reference) and non-human primate Rhesus macaque (Baskin G., et al., 1998, *Lab Anim. Sci.,* 48:476-82; incorporated herein as reference).

The initial nerve allograft studies demonstrated that the ability to improve peripheral nerve function of twitcher mouse Schwann cells was mediated by enzyme replacement into allograft twitcher cells in situ and that long term recovery of injured twitcher peripheral myelinating cells was possible. This technology, however, could not be generalized as an overall therapy of the twitcher mouse (Baskin G., et al., 1998, *Lab Anim. Sci.,* 48:476-82; incorporated herein as reference). In affected mice, HCT demonstrated significant improvement in the life span and weight gain of affected animals, however variable efficacy is observed with viability documented between 44 days to more than 100 days (in mice receiving myeloreductive conditioning) (Lin, D., et al., 2007, *Mol. Ther.,* 15(1): p. 44-52; Hoogerbrugge, P. M., et al., 1998, *J. Clin. Invest.,* 81(6): p. 1790-4; both of which are herein incorporated as reference). The typical life span of untreated mice in these investigations was approximately 40 days.

In these and other studies, neither the rate of remyelination nor existing brain pathology was improved in treated mice versus untreated controls (Yeager A., et al., 1984, *Science*, 225:1052-4; Toyoshima, E., et al., 1986, *J. Neurol. Sci.,* 74(2-3), p. 307-18; both of which are herein incorporated as reference). Substrate inhibition targeting sphingosine synthesis using L-cycloserine, either alone or in combination with HCT, increases twitcher mouse life span (LeVine S., et al., 2000, *J. Neurosci. Res.,* 60:231-6; Biswas S., et al., 2003, *Neurosci. Lett., p*347:33-6; both of which are herein incorporated as reference). L-cycloserine is too toxic for human use, unlike its enantiomer D-cycloserine, which is indicated for treatment of anxiety. Gene therapy experiments have shown the ability to generate enzyme in transfected cells and to improve lifespan in twitcher mice, either in monotherapy or combination with HCT (Lin, D., et al., 2007, *Mol. Ther.,* 15(1): p. 44-52; incorporated herein as reference). Substrate reduction, HCT, and gene therapy all provide the most significant efficacy when used in presymptomatic animals, with either no or limited impact on disease in symptomatic animals. Therefore, ERT may provide a viable option in the treatment of GLD, especially when given to pre-symptomatic patients.

Results

Figure 31:
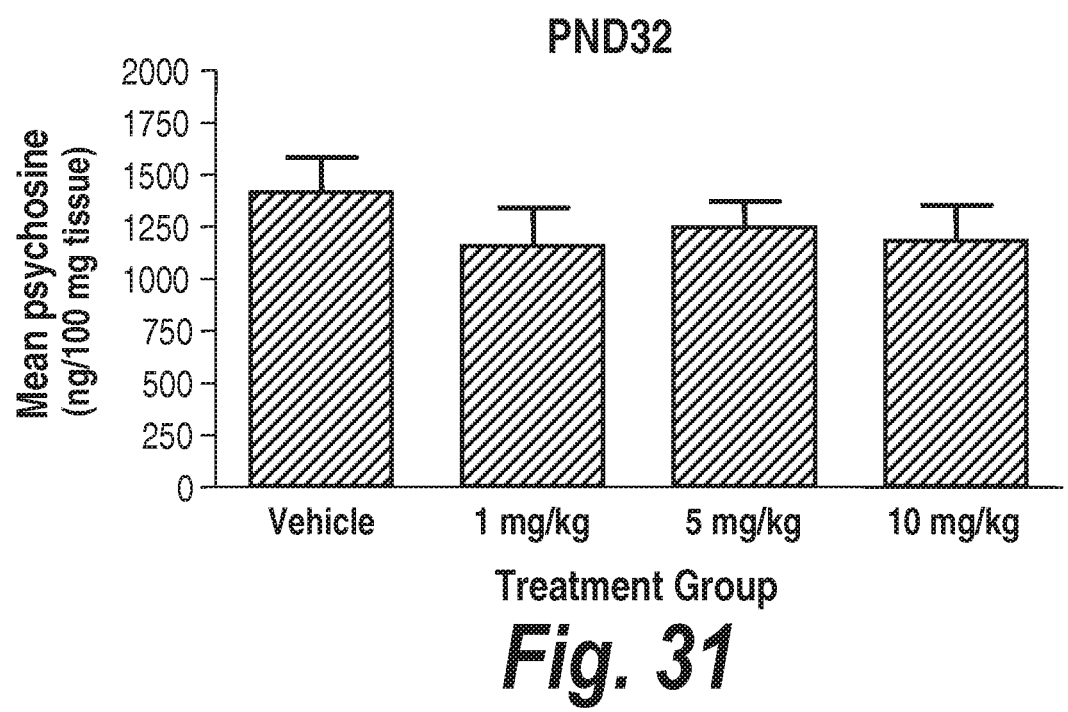
FIG. 31 depicts exemplary results illustrating that IP administration of rmGalC reduces brain psychosine levels in twitcher mice. Data represents mean±SEM for n=4 mice per treatment group.

Systemically administered enzyme replacement therapy using a HEK 293 derived murine GALC (rmGALC; 5 mg/kg), given peripherally as multiple intraperitoneal (IP) injections, improved the life span of twitcher mice and decreased psychosine accumulation by 15% when compared against vehicle-treated animals (Table 18, FIG. 31).

TABLE 18

IP administration of rmGALC improves survival in twitcher mice

| Dose Group | Survival (days) | | | Mann-Whitney Analysis (vs. vehicle) |
|---|---|---|---|---|
| | Mean | Min | Max | |
| | | Range | | |
| Untreated | 42.6 | 39 | 45 | 0.49 |
| Vehicle | 43.2 | 37 | 48 | n/a |
| 1 mg/kg | 43.0 | 40 | 46 | 0.61 |
| 5 mg/kg | 48.9 | 46 | 54 | 0.0003 |
| 10 mg/kg | 49.2 | 47 | 54 | 0.0003 |

Mice treated IP with rmGALC performed better in gait testing, and sciatic nerve histopathology was improved compared to untreated or vehicle-treated animals. Peripherally (IP) administered rmGALC was minimally delivered to the brain resulting in a slight decrease in brain psychosine. However, there did not appear to be any change in brain histopathology. Therefore, the results observed in twitcher mice treated with repeated weekly systemic administration (IP) of rmGALC (5 mg/kg) resulted in a survival benefit, a slight decrease in brain psychosine levels, and an improvement in gross motor function.

Single ICV and Combined ICV/IP rmGALC in Twitcher Mice

Figure 32:
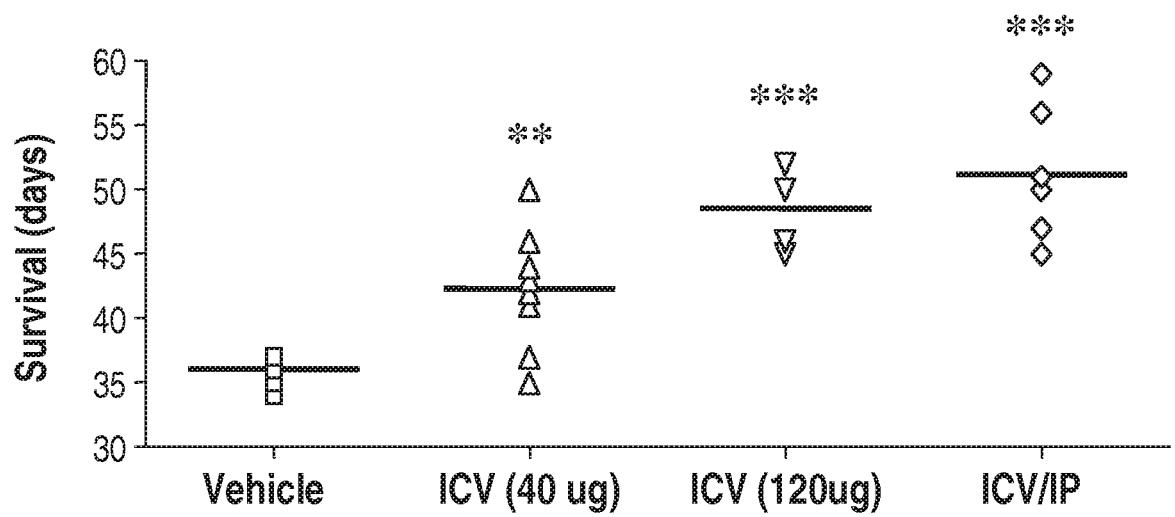
FIG. 32 depicts exemplary results illustrating increased survival with ICV only and ICV/IP rmGalC therapy.
Figure 33:
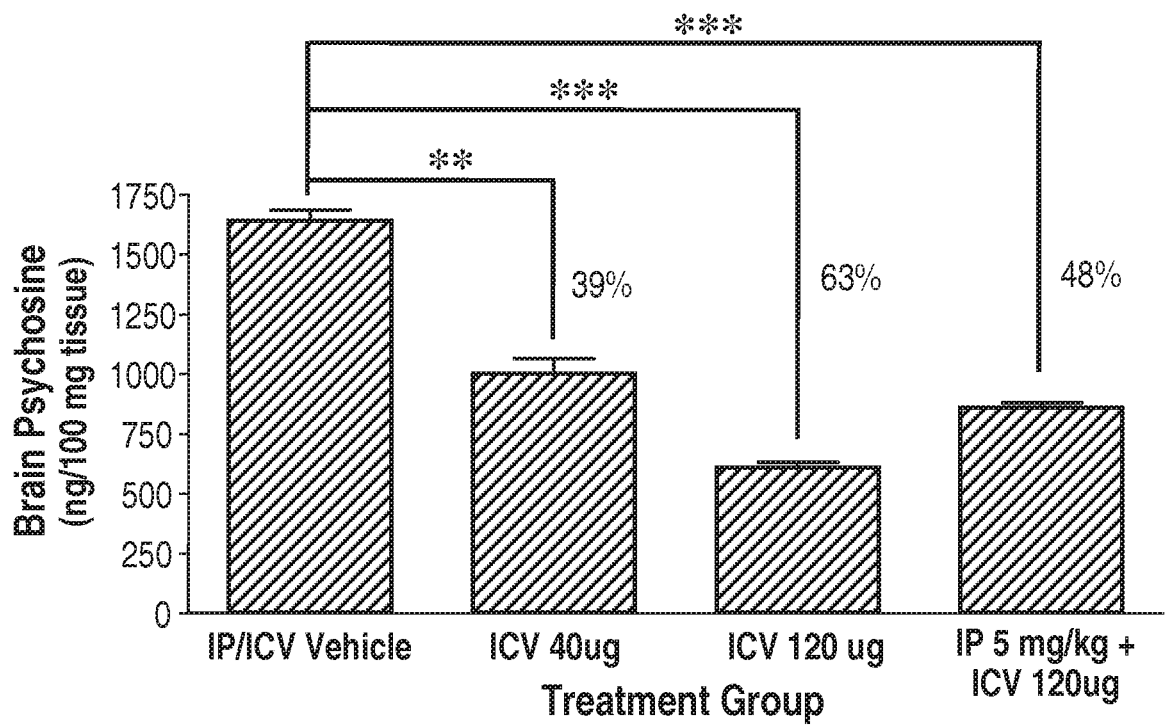
FIG. 33 depicts exemplary results illustrating that brain psychosine is significantly reduced after ICV and ICV/IP injections of rmGalC in twitcher mice.
Figure 34:
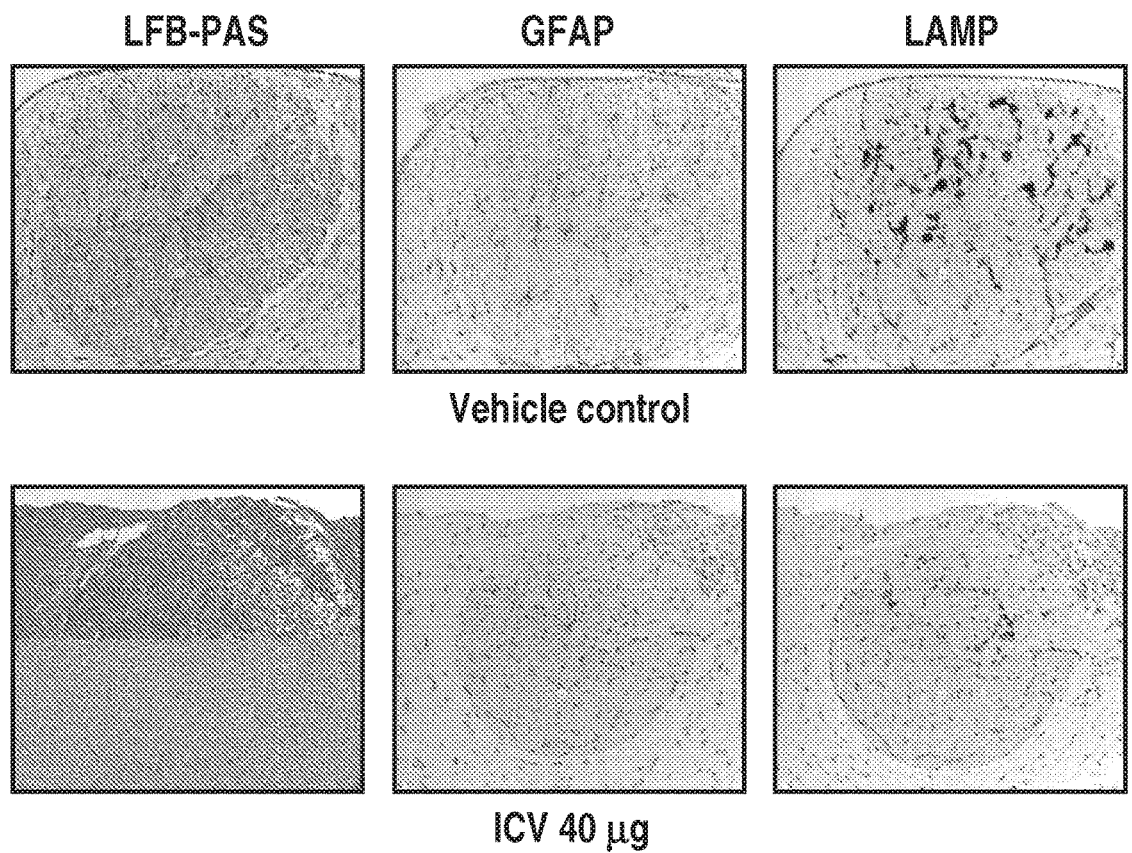
FIG. 34 depicts exemplary results illustrating improvement in histological markers observed in twitcher mice treated with 40 ug of rmGalC. Glial fibrillary acidic protein (GFAP) was used as an astrocytes marker. Iba 1 was used as a microglia/macrophage marker. Lysosomal associated membrane protein-1 (LAMP-1) was used as a lysosomal marker.

Results indicate that the high dose ICV/IP treatment group survived on average 50 days (120 µg/5 mpk) with the vehicle treated animals surviving only 36 days (FIG. 32). Mice treated with ICV rmGALC only showed a dose-responsive mean survival time of 42 days (40 µg) and 48 days (120 µg). A single 120 µg is ICV injection reduced the brain level of psychosine (63%) whereas a single ICV injection of 40 µg rmGALC resulted in a 39% decrease in psychosine (FIG. 33). Although ICV/IP administration did not provide any additional benefit in psychosine reduction compared to ICV alone, the 48% observed reduction in psychosine levels observed with the combined regimen was significantly lower than that observed with weekly IP treatments alone (15%). In addition, an improvement in brain histology at sites distal to the injection site was observed with ICV treatments at the 40 level (FIG. 34). These results confirmed the activity and biodistribution in the brain of rmGALC following direct ICV injection. However, mice treated with ICV rmGALC only failed to demonstrate restoration of sciatic nerve fiber morphology or myelination and only slight improvements in gross motor function (e.g., gait analysis). The significant improvement in key endpoints (i.e., survival, brain psychosine levels) following a single ICV administration of rmGALC suggests a lack of sufficient enzyme concentration in the systemic circulation.

Clinical Dosing Parameters: Psychosine Reaccumulation Rate in Twitcher Mice

The following studies were performed in the twitcher mouse model in an effort to define an appropriate clinical dose range:

Brain psychosine re-accumulation rate in twitcher mice following a single ICV injection at PND19.

Dose finding studies using rmGALC combined intraperitoneal (IP)+intracerebroventricular (ICV) injections in twitcher mice In order to assess the rate of psychosine reaccumulation in the central nervous system, twitcher mice were treated with a single ICV injection of 12 µg or 40 µg of rmGALC at PND19. Groups of mice (n=3) were sacrificed 24 hr after the injection (PND20) and then every three days subsequently. Brain tissue was removed and submitted for psychosine analysis, histopathology, and enzyme activity analysis. A subset of animals was monitored for survival (n=8), and motor function (gait analysis) was analyzed at PND 40.

Figure 35:
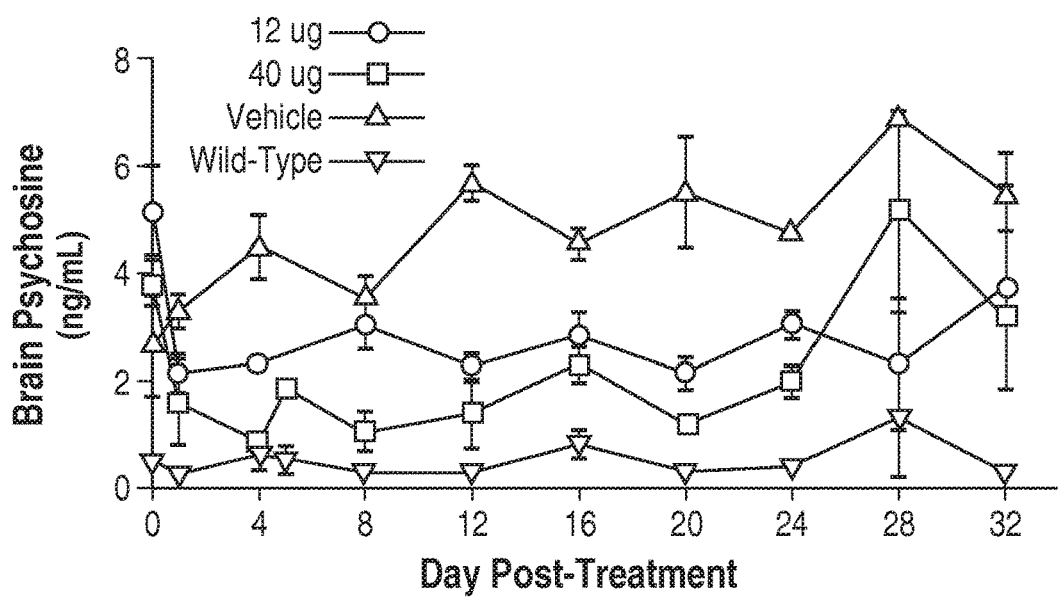
FIG. 35 depicts exemplary results illustrating psychosine re-accumulation following a single ICV injection of rmGalC or vehicle.

Psychosine levels in brain homogenate following a single ICV injection was analyzed via mass spectrometry (LCMS Ltd., North Carolina), and suggests a rapid decrease in psychosine within 24 hr of rmGALC administration (FIG. 35). The trend of psychosine reduction was maintained for 24 day period post enzyme administration. In addition, the decrease in psychosine concentration appeared dose dependent over this period as compared with vehicle-treated animals: Vehicle treated (average: 4.5 ng/ml psychosine) vs. 12 µg rmGALC (average: 2.5 mg/ml psychosine) vs. 40 µg/ml rmGALC (average: 1.6 ng/ml psychosine). Of interest, the increasing psychosine levels observed in both dose groups at the end of the study (days 28-32 post-treatment) suggests that ERT may not be successful if administered on a monthly basis. A more frequent dosing schedule may be required. Due to the small number of animals at each sampling time point, variability in the results was evident. However, based on these results, it is evident that psychosine reaccumulation occurs approximately on a 4 week (28 day) schedule.

Figure 36:
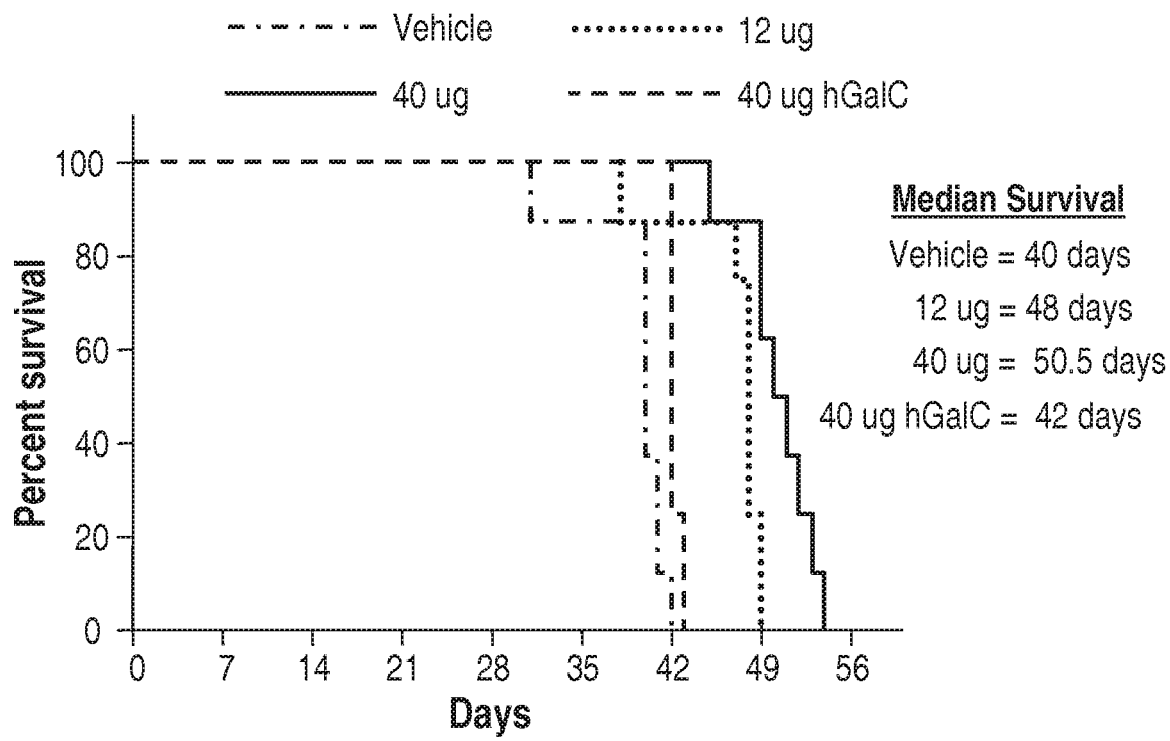
FIG. 36 depicts exemplary results illustrating percent survival in twitcher mice treated with a single ICV injection of rmGalC at PND19/20. Data represents n=8 per group.

When the survival time was analyzed, the results indicated that both the 12 µg/mL and 40 µg/mL rmGALC treatment groups had a median survival of 48 days (12 µg/mL) and 50.5 days (40 µg/mL) with the vehicle treated animals surviving 40 days (FIG. 36). Unexpectedly, mice treated with 40 µg human GALC (rhGALC) showed a survival benefit only to 42 days as compared with the vehicle treated animals surviving 40 days. The reason(s) for this reduced efficacy with rhGALC is not known, but will be discussed in a later section. However, from the results of this study, it is apparent that even at lower doses of rmGALC are effective at showing a survival benefit in the twitcher mouse model.

Clinical Dosing Parameters: rmGALC and rhGALC Dose Ranging Study in Twitcher Mice Previous results indicated that twitcher mice treated with ICV/IP rmGALC (120 µg and 5 mpk) lived 14 days longer than vehicle-treated animals. However, twitcher mice treated only with direct CNS injections showed a dose-responsive improvement in mean survival of 12 days (120 µg ICV) and 6 days (40 µg ICV). A dose of 120 µg in the murine brain translates to a dose of 300 mg/kg brain in patients; it was therefore important to investigate the efficacy of lower doses of rmGALC. In addition, an early lot of rhGALC was examined for efficacy in the twitcher mouse.

Groups of mice were treated with weekly IP injections (5 mg/kg) of rmGALC starting at PND 10 plus a single ICV injection of either 12 µg (30 mg/kg brain weight) or 26 µg (60 mg/kg brain weight) of rmGALC or rhGALC at PND19. At PND39, a subset of mice (n=3/group) were sacrificed for tissue harvest (brain, sciatic nerve, liver, sera). Brain tissue was submitted for psychosine analysis, histopathology, and enzyme activity quantification. The remaining animals survival (n=8) were monitored for survival and gait analysis.

Discussion

Figure 37:
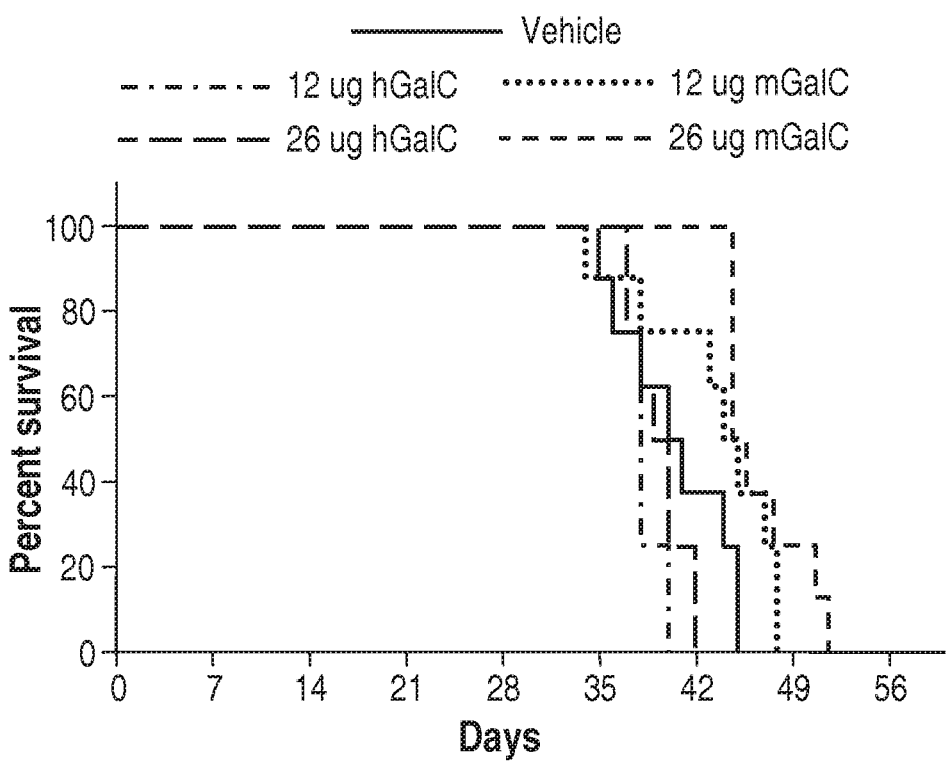
FIG. 37 depicts exemplary results illustrating percent survival in mice treated ICV/IP with rmGalC and rhGalC.
Figure 38:
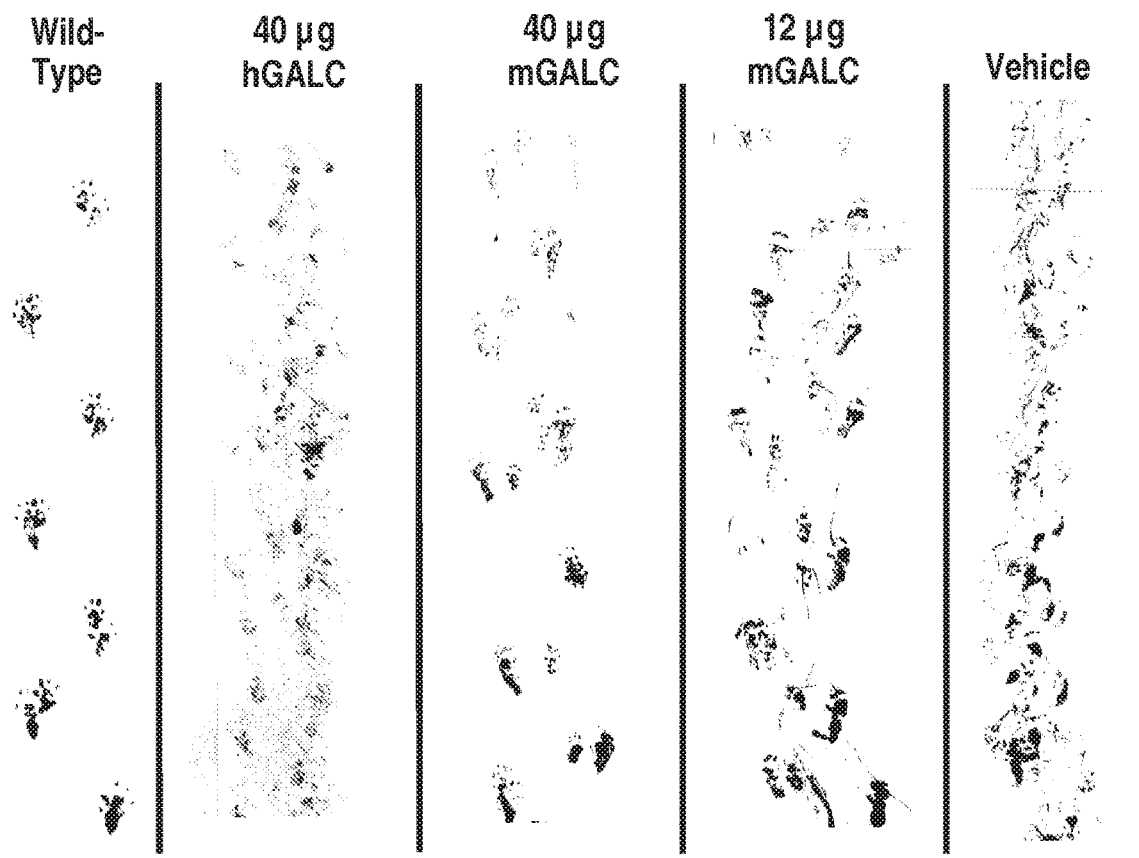
FIG. 38 depicts exemplary results illustrating gait analysis of mice treated with a single ICV injection of rmGalC and rhGalC.

The results of this dose finding study show a survival benefit for rmGALC administration with a trend towards dose dependence (FIG. 37). The 12 µg/5 mpk and 26 µg/5 mpk combination doses of rmGALC extended the mean life span of the twitcher mouse to 44.5 and 45.5 days respectively as compared with 40.5 days for vehicle-treated animals. There was no survival benefit for the 12 µg/5 mpk (38 days) and 26 µg/5 mpk (39.5 days) doses of rhGALC. The 26 µg/5 mpk rhGALC dose extended the lifespan of the affected twitcher mice by days, however neither dose of rhGALC reached the days of survival for the vehicle-treated animals (FIG. 37). As observed previously with animals systemically-treated (IP) with rmGALC, an improvement in gait analysis was observed for all animals receiving the combined ICV/IP administration of rmGALC, while animals treated with a single ICV injection showed less benefit in motor function (FIG. 38). As observed for the benefit in lifespan, no benefit in gait analysis was observed in mice treated with rhGALC. However, the specific activity of rhGALC was found to be approximately 33% of the rmGALC in vitro activity (Table 19). Therefore, these current results suggest that even at lower doses of rmGALC, there is a benefit in both survival and motor function and reinforces the opportunity for ERT for the treatment of GLD. It is evident that psychosine reaccumulation occurs approximately on a 4 week (28 day) schedule.

TABLE 19 rmGALC and rhGALC activity

| Lot | Mean Activity (µmol/hr/mg) | % rmGALC |
|---|---|---|
| rmGALC R5 (3.44 mg/mL) | 154.48 ± 87.5 | n/a |
| rhGALC Lot 73 (8.74 mg/mL) | 51.35 ± 16.2 | 33 |

Figure 39:
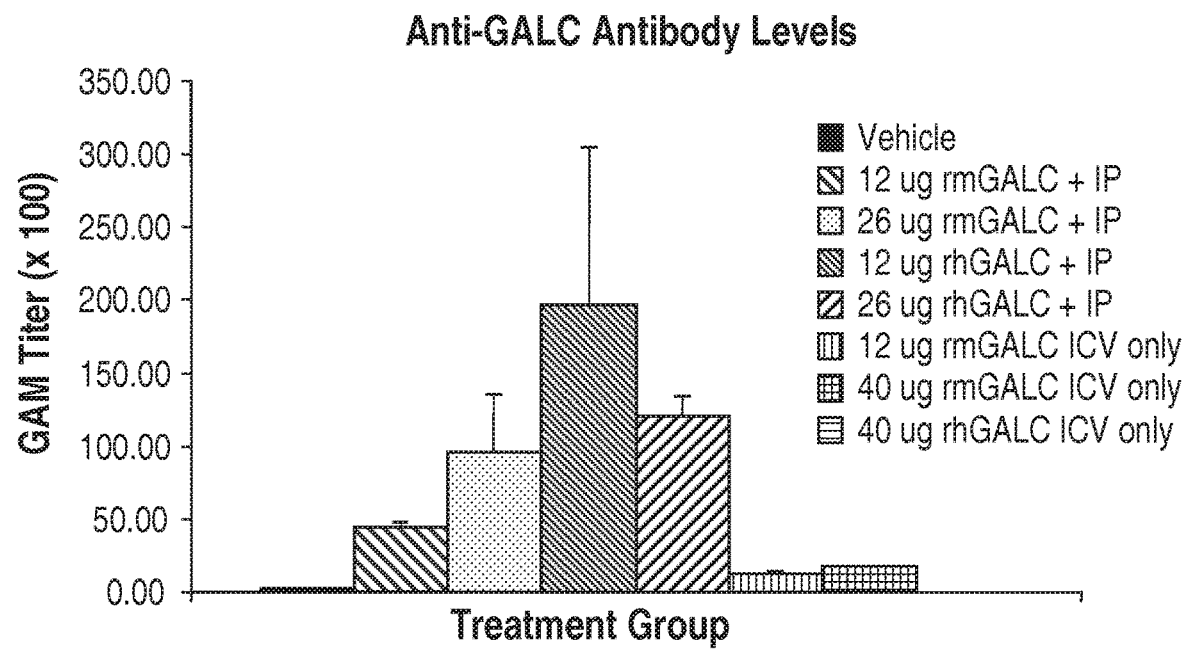
FIG. 39 depicts exemplary results illustrating an antigentic response to rmGalC or rhGalC in twitcher mice.

The antigenicity of rmGALC and rhGALC is to be expected as the twitcher mouse is a null model [i.e., they are cross-reacting immunologic material (CRIM)-negative]. Overall, the maximum serum antibody titer in rhGALC-treated mice (ICV/IP regimen) was significantly higher than mice treated with a comparable ICV/IP rmGALC regimen (FIG. 39). Although antibodies were also present in mice treated with direct CNS injections, the maximum titer was several fold lower than animals receiving ICV/IP treatment. The possibility exists that neutralizing antibodies may have been generated.

Figure 40:
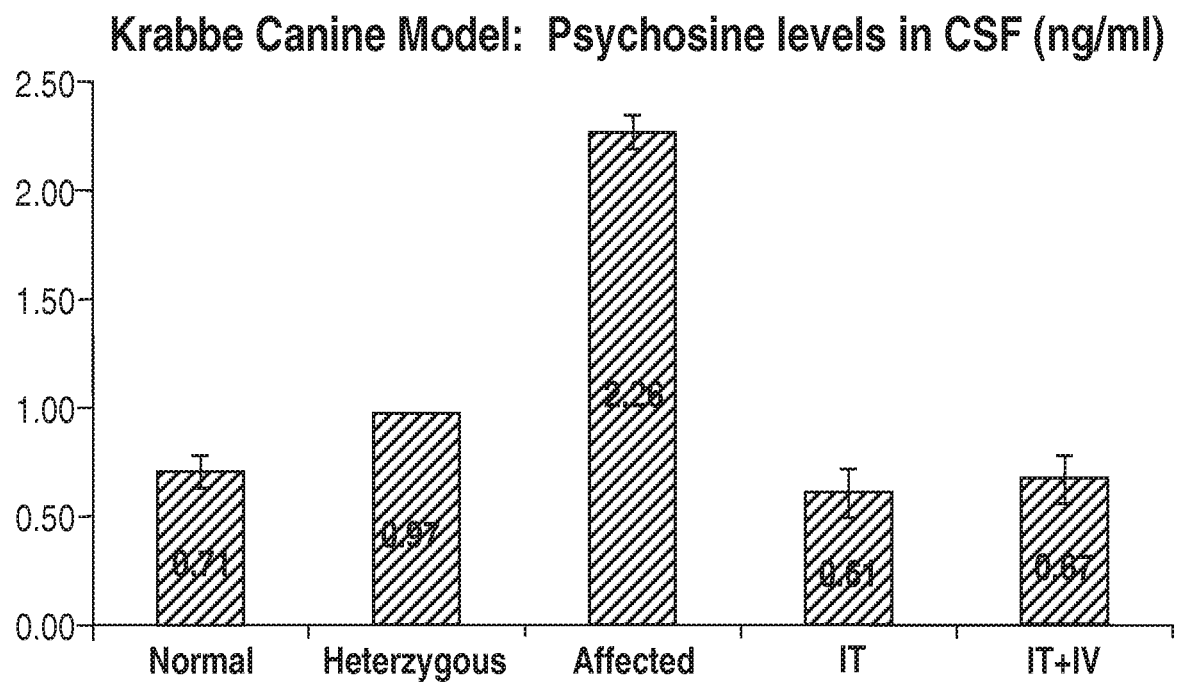
FIG. 40 depicts exemplary results illustrating psychosine levels in the CSF of naïve and rhGalC-treated GLD dogs.

A study with GALC-deficient canines was initiated to characterize the antigenicity of rhGALC. In this study, affected animals (6 weeks after birth) were treated with 2 mg/kg weekly IV and/or 2.25 mg (30 mg/kg brain weight) IT administration of Human GALC or vehicle alone. Additional treatments were administered at 8 weeks and monthly for the remainder of the study (until ~16 weeks after birth). CSF was removed prior to euthanasia and analyzed for antibody formation and psychosine levels (FIG. 40).

Previous studies with recombinant human heparin N-sulfatase in the Huntaway dog model of MPSIIIA demonstrated a marked antibody response to the exogenous enzyme, resulting in the need for tolerization of the animals in the study. However, preliminary results examining CSF from naïve and rhGALC-treated dogs showed an apparent reduction in psychosine levels as compared with untreated controls (FIG. 40).

Example 4: Brain and Liver Histology/Labeling of IT-Injected GALC in Mice

The present Example describes one embodiment of IT-injected hGalC and mGalC in mice and the corresponding detection and localization of GalC antibody in various tissues.

Experimental Design

Experimental Design

| Group | N | Treatment | Dose (µg) | Injection volume (µL) | Route | Frequency | Sacrifice |
|---|---|---|---|---|---|---|---|
| A | 6 | Vehicle control | 0 | 10 µl | IT | Three weekly injections | 24 hr post final injection |
| B | 6 | hGalC (Research) | 100 | | | | |
| C | 6 | hGalC (PD) | | | | | |
| D | 6 | mGalC | | | | | |

Tissue Collection and Histology Staining

There were only three animals available for histological analysis from Group B and C, respectively. Samples from the brains and livers were fixed in 10% neutral buffered formalin for subsequent paraffin embedding. Five p.m paraffin sections were prepared for immunohistochemistry (IHC) of I2S to detect injected proteins. Three anti-GalC antibodies were used for IHC staining of GalCA.
 1. Mouse monoclonal antibody (generated by Dr. Eckman's lab)
 2. Rabbit polyclonal antibody (generated by Group 1)
 3. Rabbit polyclonal antibody (generated by Group 2)
A highly sensitive ABC+Tyramide fluorescence amplification method was used to label the targeted protein. The staining results showed GalC positive cells as green, with nuclei as DAPI blue counterstain, and background areas as black.

Results

Figure 41:
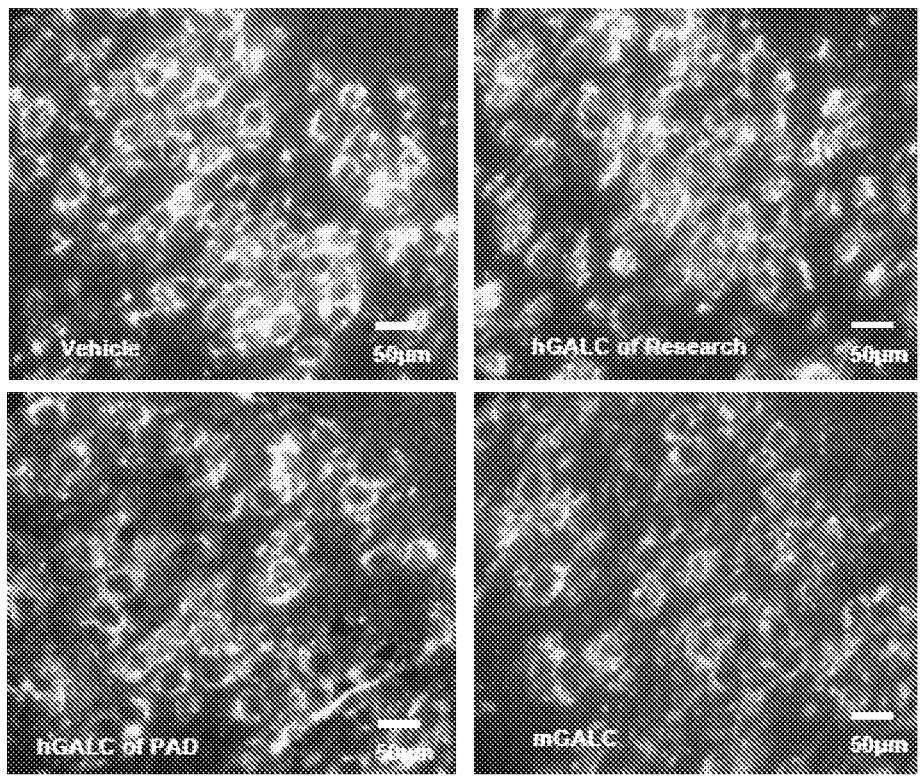
FIG. 41 depicts exemplary results illustrating IHC staining of IT injected GalC in the cerebrum with Group 1 polyclonal antibody.
Figure 42:
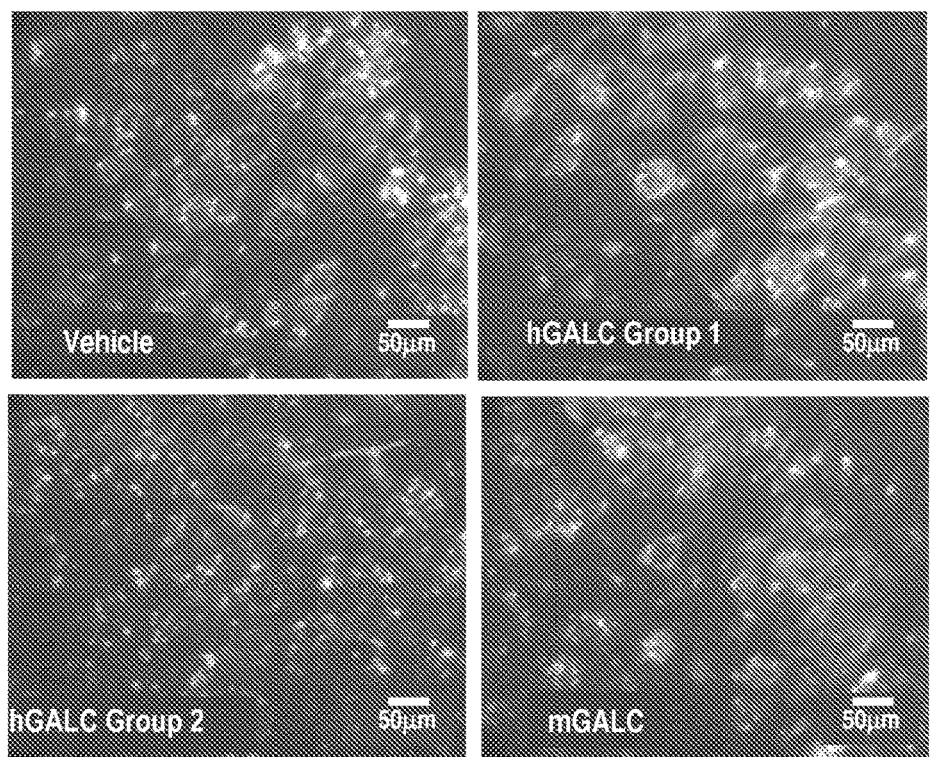
FIG. 42 depicts exemplary results illustrating IHC staining of IT injected GalC in the cerebrum with Group 2 antibody.
Figure 43:
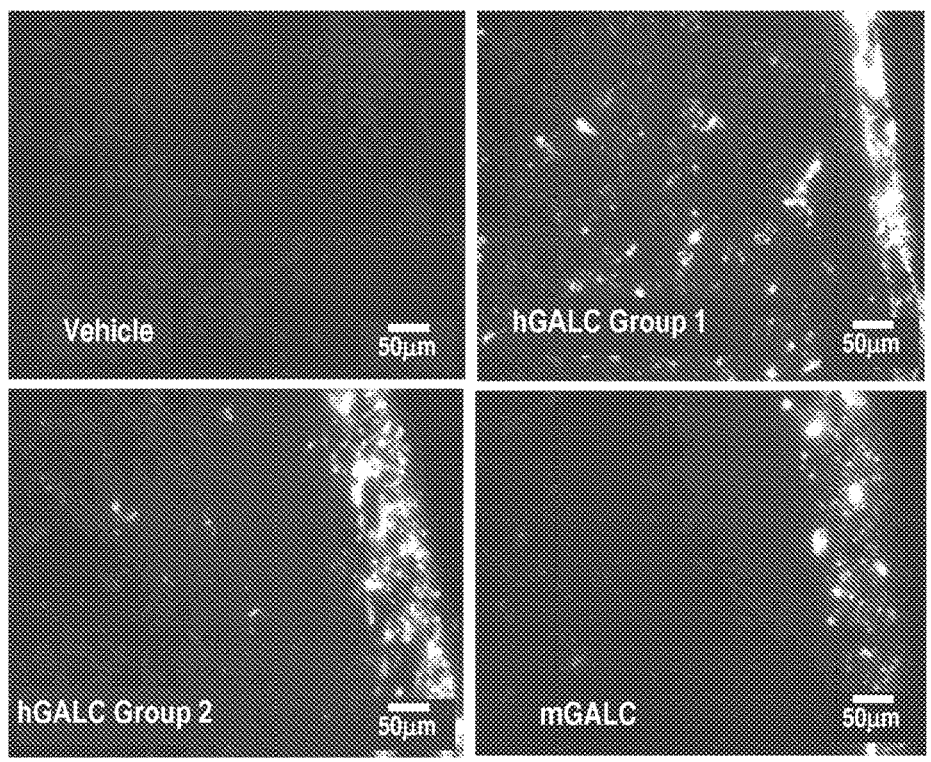
FIG. 43 depicts exemplary results illustrating IHC staining of IT injected GalC in the cerebrum with Mouse monoclonal antibody.
Figure 44:
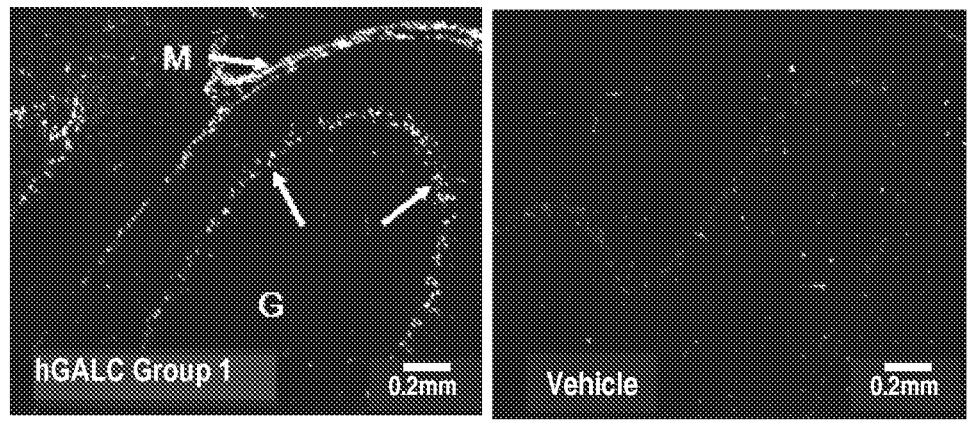
FIG. 44 depicts exemplary results illustrating IHC staining of IT injected GalC in the cerebrum with Mouse monoclonal antibody.
Figure 45:
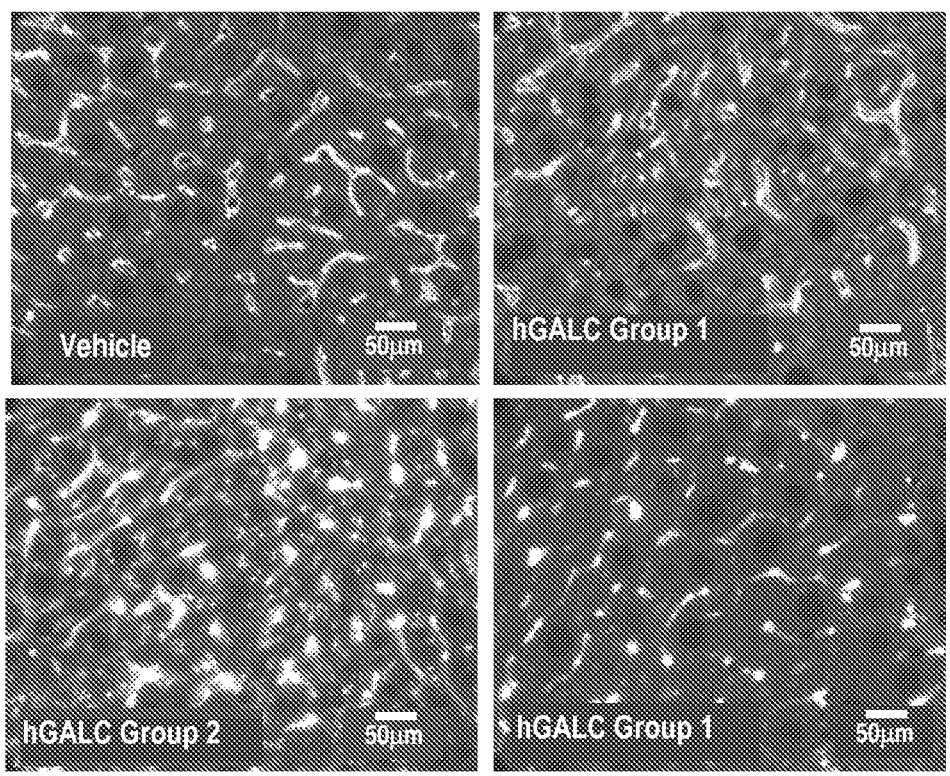
FIG. 45 depicts exemplary results illustrating IHC staining of IT injected GalC in the liver with Mouse monoclonal antibody.
Figure 46:
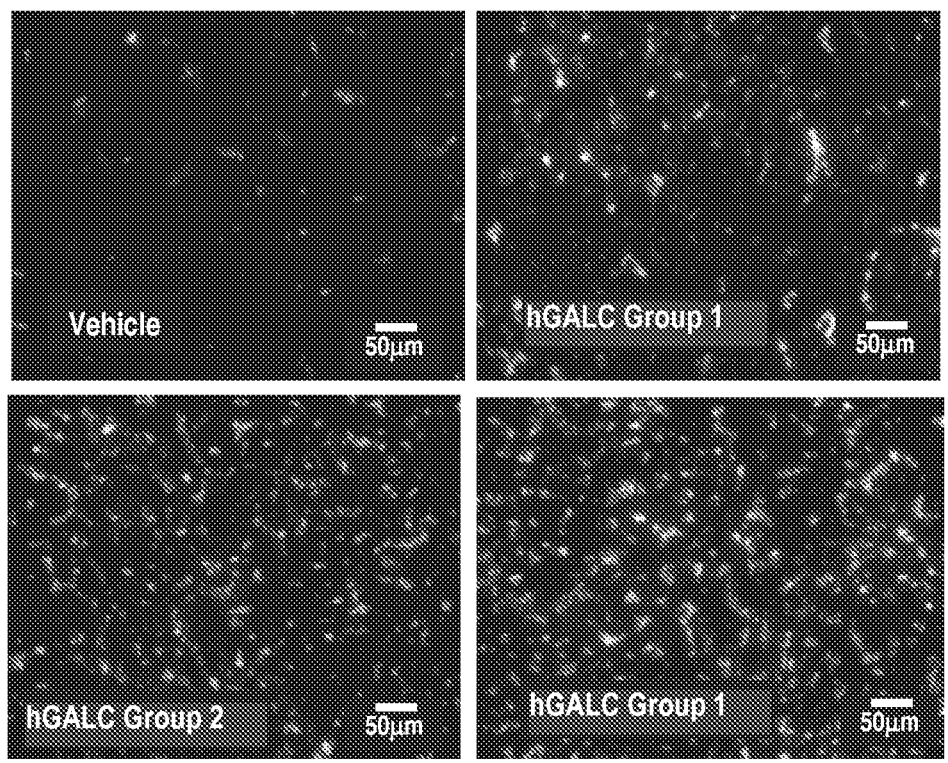
FIG. 46 depicts exemplary results illustrating IHC staining of IT injected GalC in the liver with Group 2 polyclonal antibody.
Figure 47:
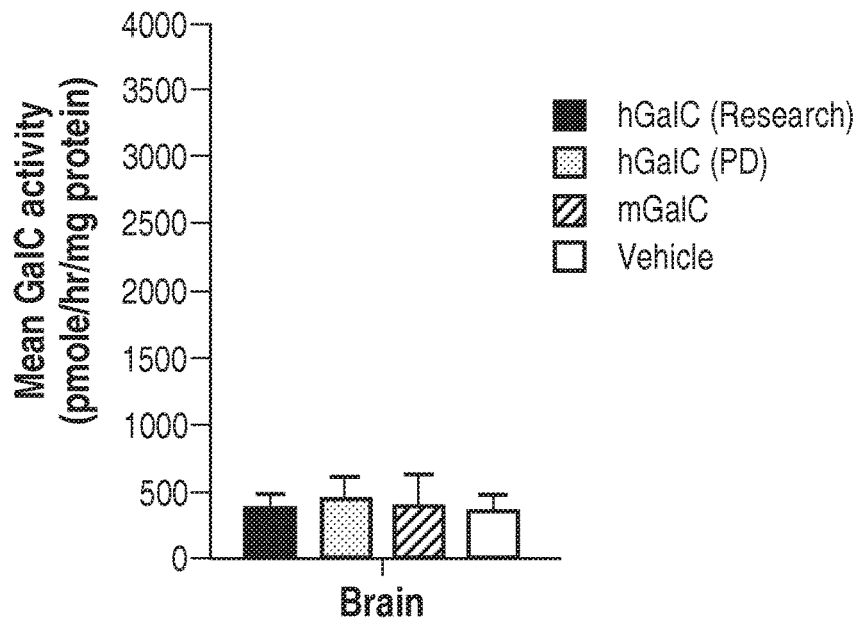
FIG. 47 depicts exemplary results illustrating mean GalC activity in the brain.
Figure 48:
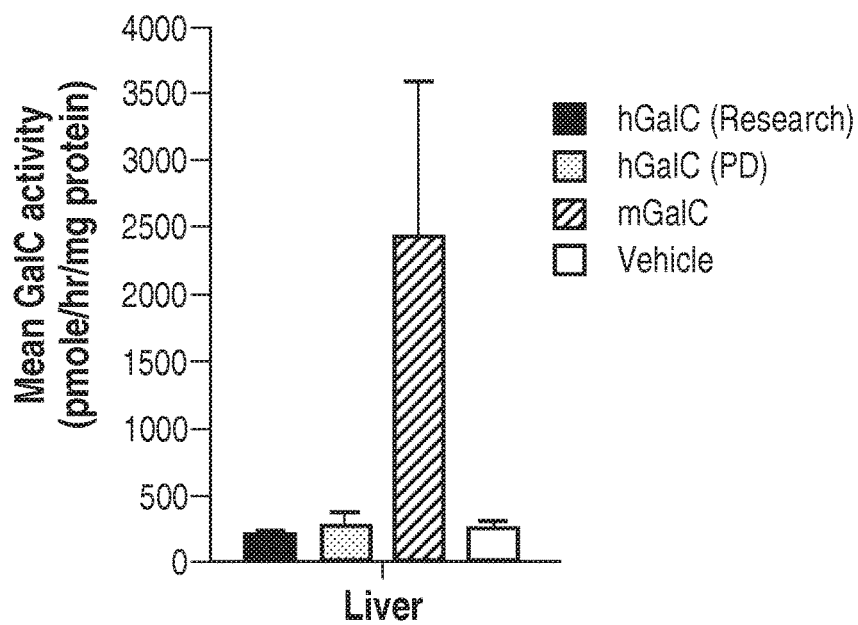
FIG. 48 depicts exemplary results illustrating mean GalC activity in the liver.

Group 1 polyclonal antibody had a strong cross-reaction with endogenous proteins in mouse brains. Even in vehicle control brains, all CNS cells were stained strongly positive. The injected proteins were not identified with such strong background (FIG. 41). Group 2 polyclonal antibody had weaker cross-reaction with endogenous proteins in mouse brains, but CNS cells in vehicle control brains were still positive. The injected proteins were not detected above the background (FIG. 42). Mouse monoclonal antibody had acceptable specificity, with much lower signals in vehicle control brains (data not shown). After IT injection, all proteins were detected in the meninges on the surface of the brain. Both hGalC of Group 1 and Group 2 were detected in the CNS cells (neurons and glial cells) in the regions below the meninges, with relatively stronger signals in hGalC of Group 1 treated animals. No positive neurons and glial cells were detected in mGalC treated brains (FIG. 43). In the cerebellum, hGalC produced staining in the meninges and on the surface of the granular zone, whereas mGalC did not (FIG. 44). Mouse monoclonal antibody worked in the mouse brain but showed strong cross-reactivity with sinusoidal cells in the liver and could not be used to assess cellular uptake of IT injected proteins in the liver (FIG. 45). Group 2 polyclonal antibody showed specificity in liver tissues with much lower signals in vehicle control brains. All IT injected proteins were detected in both sinusoidal cells and hepatocytes in the livers after treatment, with fewer positive cells and weaker signals in the hGalC of Group 1 treated animals (FIG. 46). Although no higher GalC activity was found in any treated groups, positive staining was found in the meninges and the CNS cells in surrounding regions, indicating IHC is sensitive in detecting injected protein which has been taken up at the cellular level (FIG. 47). In the liver, mGalC showed higher activity however IHC via Group 2 Ab detected very little difference between mGalC and hGalC (FIG. 48). Low detectable activity with Group 1 Ab in hGalC was consistent with the low observed IHC levels.

Summary

After IT injection, all injected proteins were detected in the meninges of the cerebrum via IHC. Cellular update of injected hGalC of both Group 1 and Group 2 was detected in CNS cells (neurons and glial cells), with relatively stronger signals in hGalC of Group 1 treated brains. No positive neurons and glial cells were detected in mGalC treated brains. In the cerebellum, in addition to positive signal in the meninges, injected hGalC of both Group 1 and Group 2 were found in a layer of cells on the surface of the granular zone. In the livers of all treated groups, injected proteins were detected in the sinusoidal cells and hepatocytes suggesting eventual uptake of intrathecal I2S into the circulatory system. mGalC and hGalC of Group 2 had similar strong staining signals versus hGalC of Group 1.

Example 5: Brain Histology/Labeling of IT-Injected GALC in Dogs

Figure 49:
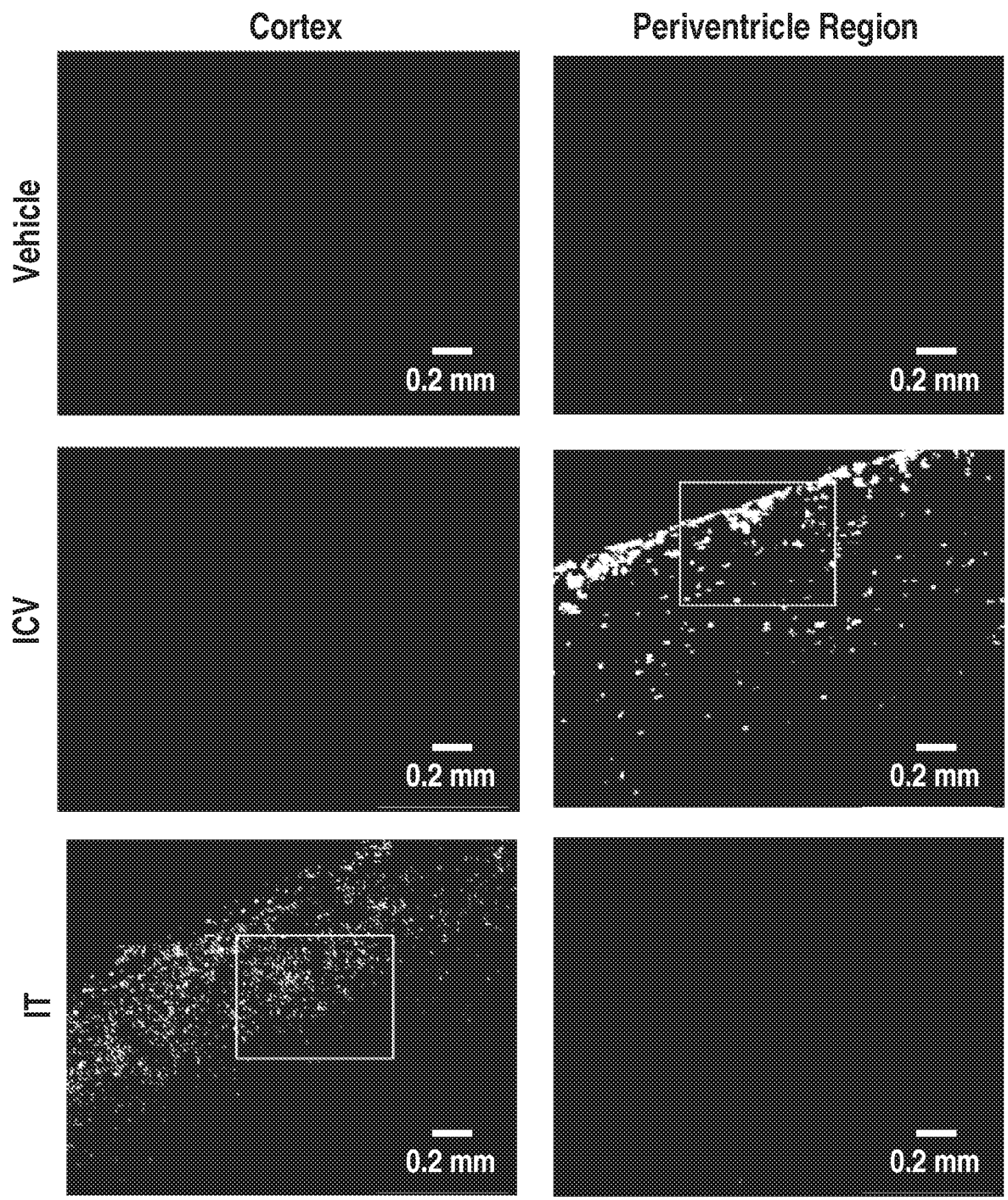
FIG. 49 depicts exemplary results illustrating GalC immunostaining in the brain at 10×.
Figure 50:
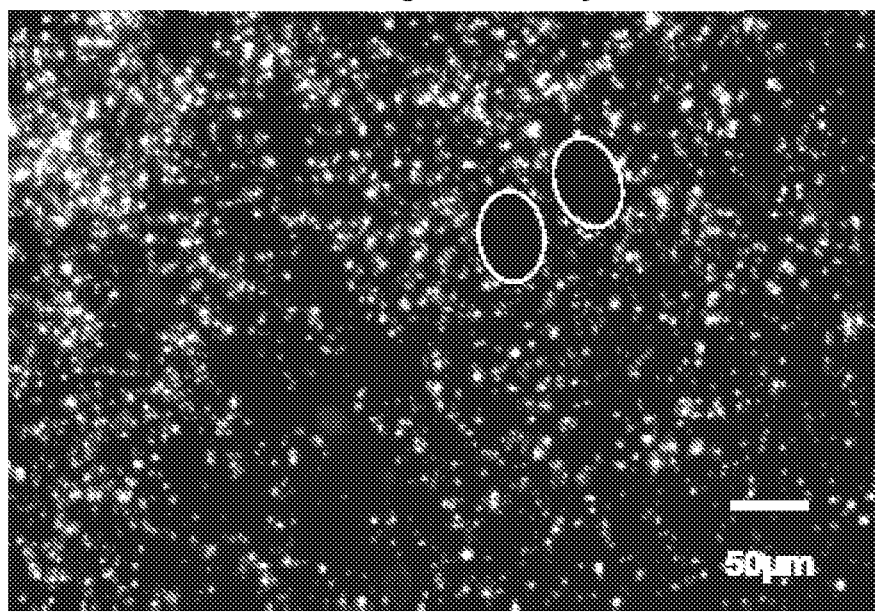
FIG. 50 depicts exemplary results illustrating GalC immunostaining in the brain at 40×.
Figure 50:
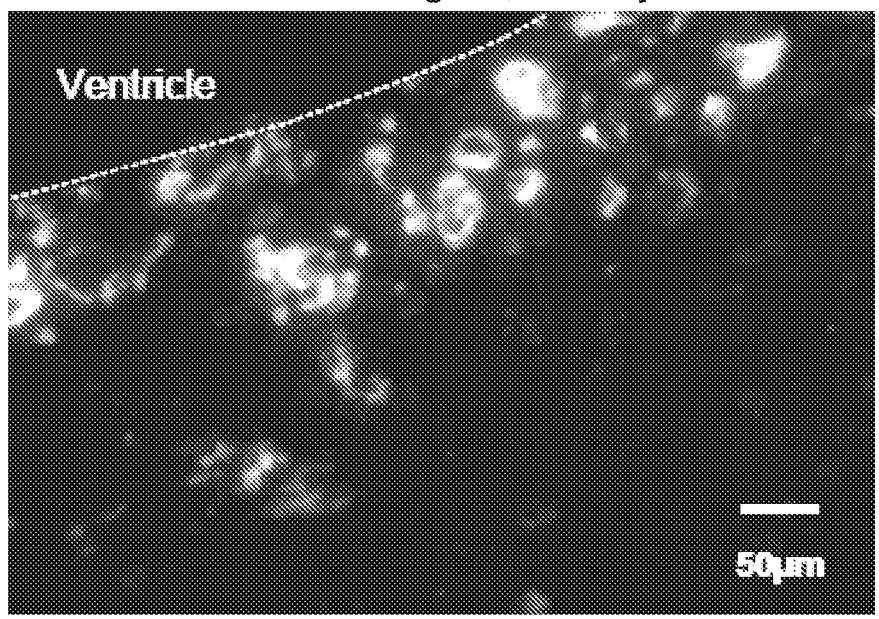
Figure 51:
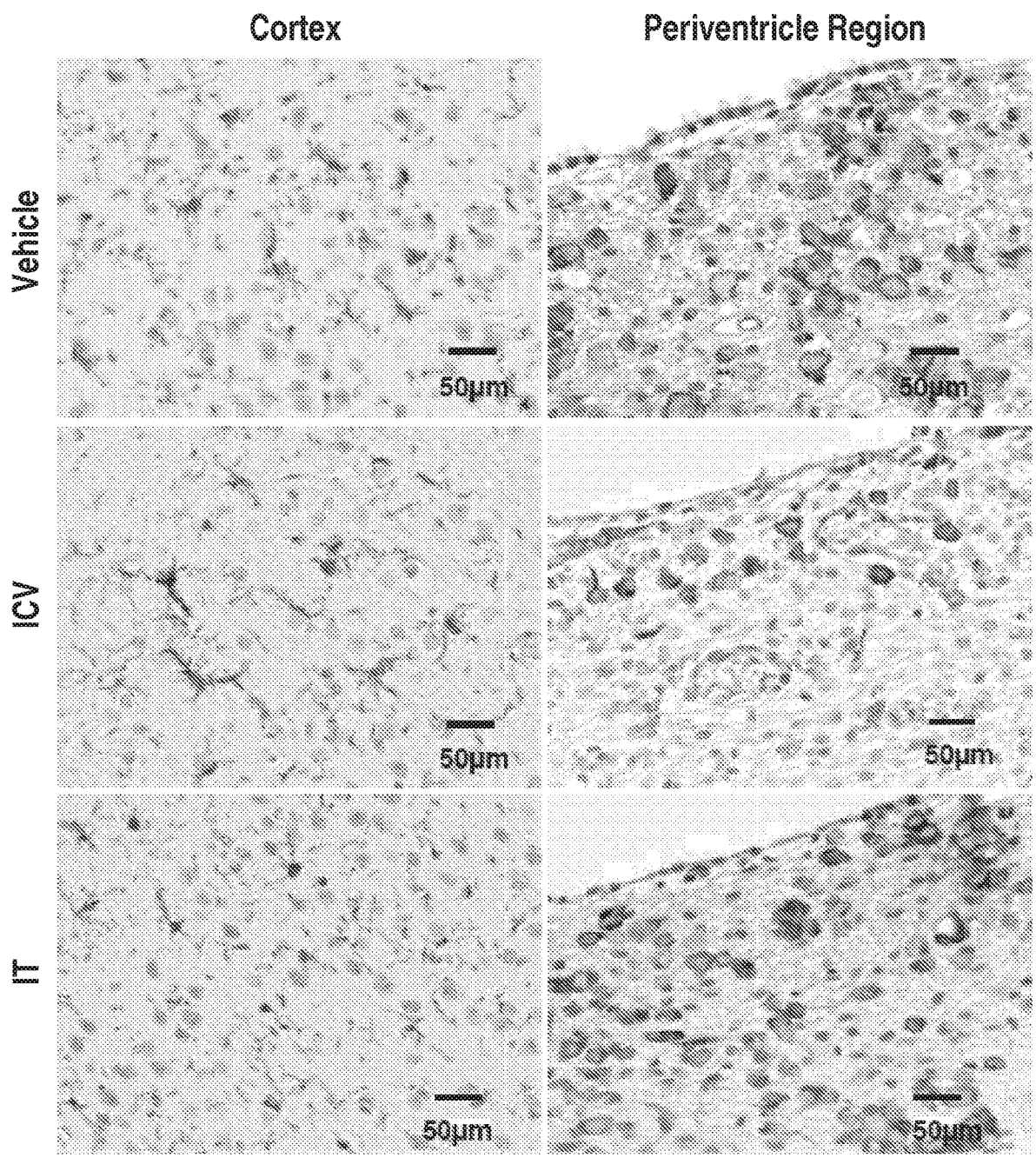
FIG. 51 depicts exemplary results illustrating Iba staining of activated microglia at 40×.
Figure 52:
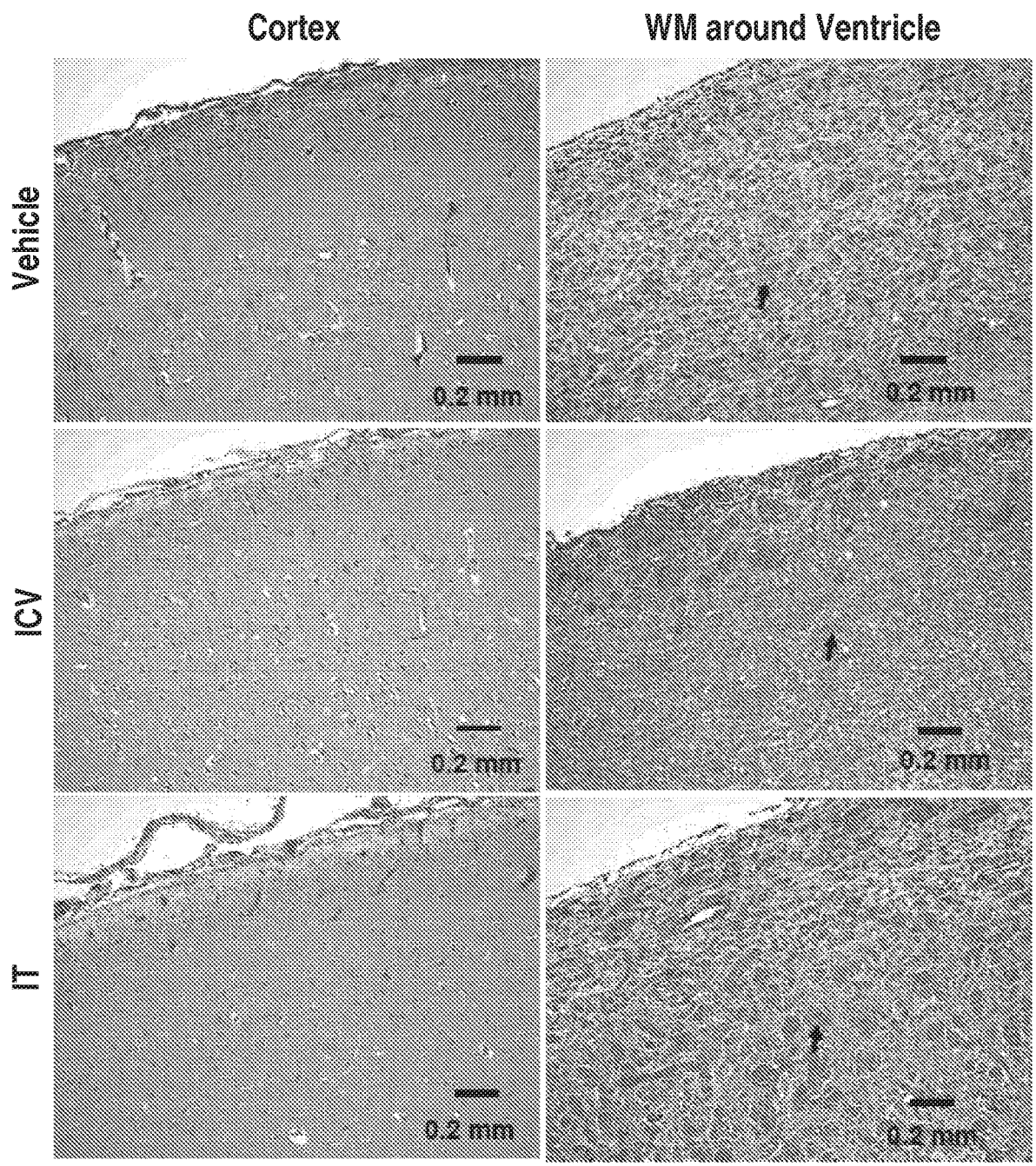
FIG. 52 depicts exemplary results illustrating LFB/PAS staining in the brain at 10×.

The present Example describes one embodiment of IT-injected GalC in dogs and the corresponding detection and localization of GalC antibody in the brain. In this embodiment, IT injected protein was detected in the meninges and in the regions of surface cortex below the meninges. ICV injected protein was found in periventricle regions (FIG. 49). GalC IHC showed diffused extracellular staining pattern in the cortex after IT injection, with negative signal in neurons (circled) (FIG. 50). A limited decrease of activated microglial cells with positive Iba staining was observed in ICV injected periventricle regions and IT injected cortex (FIG. 51). No morphological change (Globoid cells) was found in the cortex with LFB/PAS in vehicle group and no difference was observed across the groups. Globoid cells (arrow) marked by Iba staining were decreased after ICV treatment in 4 limited areas of periventricle regions (FIG. 52).

Examples of IT Delivery of I2S Protein

Example 6: Biodistribution of IT Delivered I2S

The major objective of this study was to determine whether recombinant human I2S could be delivered to the brain of adult MPS II mice by the intrathecal-lumbar route

TABLE 20

SIX GROUPS OF 8-12 WEEK OLD MALE MICE WERE TREATED AS FOLLOWS:

| Group | N | Strain | Treatment | Volume | Dose | Dose/Brain weight | Route |
|---|---|---|---|---|---|---|---|
| A | 3 | IKO | I2S | 10 μL | 260 μg | 520 mg/kg | IT-lumbar |
| B | 3 | IKO | I2S | 10 μL | 260 μg | 520 mg/kg | IT-lumbar |
| C | 3 | IKO | Untreated | N/A | N/A | N/A | N/A |
| D | 1 | IKO | I2S | 10 μL | 260 μg | 520 mg/kg | IT-lumbar |
| E | 3 | IKO | Untreated | N/A | N/A | N/A | N/A |
| F | 3 | C57B1/6 | Untreated | N/A | N/A | N/A | N/A |

Injection schedule: Animals received up to 3 injections of idursulfase (10 μL) via the intrathecal-lumbar route:
  Groups A & D: Administered 3 doses of I2S on days 1, 8, and 15
  Group B: Administered 2 doses of I2S on days 1 and 8
  Groups C & E: Untreated control (IKO) mice
  Group F: Untreated wild-type control mice Materials and Methods Animals:
Mice were housed in groups of up to 4 per cage in a colony room under a 12-hour light-dark cycle. Rodent diet (LabDiet-5001, St Louis, MO) and water (Lexington, MA municipal water purified by reverse osmosis) was available ad libitum for the duration of the experiment. Care of animals was conducted in accordance with the guidelines described in the Guide for the Care and Use of Laboratory Animals (National Academy Press, Washington D.C., 1996). The current IKO breeding colony was established from four carrier female mice heterozygous for the IKO mutation that were obtained from Dr. Joseph Muenzer (University of North Carolina). Carrier females were bred with male mice of the C57BL/6 background strain (C57BL/6NTac, Taconic, Hudson, NY), producing heterozygous females and hemizygous male knockout mice, as well as wild-type male and female littermates. All offspring were genotypes by PCR analysis of tissue DNA. All mice used in this experiment were males identified as either hemizygous IKO (−/0) or wild-type (WT) littermate (+/0) mice between 8 and 12 weeks of age.

Idursulfase:
Twenty-two mL I2S [Recombinant human idursulfase] was dialyzed against four changes of 2 L phosphate buffered saline (PBS). The I2S was then concentrated by Vivaspin column and resuspended in a final volume of 1 mL PBS, followed by filter sterilization using a μm filter. The final concentration was 51 mg/mL.

Intrathecal-Lumbar Injections:
Adult mice were anesthetized using 1.25% 2,2,2 tribromoethanol (Avertin) at 200-300 μL/10 grams body weight (250-350 mg/kg) by intraperitoneal injection. Dorsal hair was removed between the base of the tail and the shoulder blades and the shaved area was swabbed with povidine/betadine scrub followed by isopropyl alcohol. A small midline skin incision (1-2 cm) was made over the lumbosacral spine and the intersection of the dorsal midline and the cranial aspect of the wings of the ilea (singular ileum) identified. The muscle in the iliac fossa (gluteus medius) is a heart shaped muscle and the two sides of the top of the "heart" approximate the location of the wings of the ilea. A 32 gauge needle attached to a gas tight 10-20 μL glass Hamilton syringe was inserted until resistance was felt from the underlying bone. Injection of 10 μL of test article at an approximate rate of 2 μL/20 seconds (10 μL/2 minutes) was performed. The skin incision was closed using wound clips as appropriate and the animal was allowed to recover in a recovery chamber before being returned to the appropriate cage.

Histology Procedures:
Animals were sacrificed at one hour after the final injection.
Brain and liver tissues were collected and fixed in 10% neutral buffered formalin, then processed and embedded in paraffin. Five μm sections were prepared for hematoxylin/eosin (H&E) and immunohistochemistry (IHC) staining.

Hematoxylin and Eosin Staining:
Brain and liver sections were stained with H&E. The staining results showed nuclei as purple and cytoplasm as pink to red. H&E stained slides were used for histopathological morphology evaluation.

Immunohistochemistry:
For I2S biodistribution evaluation, deparaffinized and rehydrated brain and liver sections were incubated overnight with mouse monoclonal antibody 2C4-2B2 (Maine Biotechnology Services, Portland, ME) against recombinant human I2S to detect injected I2S (or an irrelevant mouse IgG as a negative control antibody; Vector Laboratories, Burlingame, CA). Following an overnight incubation at 2-8° C., a secondary goat anti-mouse IgG conjugated with horseradish peroxidase was added. After additional 30 minutes of incubation at 37° C., Tyramide-Alexa Fluor 488 labeling solution (Invitrogen Corp., Carlsbad, CA) was added for an additional 10 minutes. Sections were coverslipped using an antifading mounting medium (VectaShield; Vector Laboratories) containing 1.5 μg/ml 4'-6-diamidino-2-phenylindole (DAPI) as a nuclear counterstain and observed with a multiple channel Nikon fluorescent microscope. The staining results showed I2S positive cells as green, with nuclei as blue, and background areas as black.

For efficacy analysis, brain and liver sections were stained with a rat anti-LAMP-1 (lysosomal associated membrane protein as a lysosomal marker) IgG (Santa Cruz Biotechnology, Santa Cruz, California) as the primary antibody. A rat IgG as an irrelevant antibody was used as negative control. The ABC (avidin biotin complex kits from Vector Labs, Burlingame, California) method was used to amplify the targeted marker.

Briefly, deparaffinized sections were rehydrated and incubated with the primary antibody. Following overnight incubation at 2-8° C., a secondary biotinylated rabbit anti-rat IgG (Vector Labs, Burlingame, California) was added and incubated 30 minutes at 37° C., then samples were washed and treated with avidin-biotin-peroxidase complex (Vector Laboratories) for 30 minutes. For color development, 3,3'-diaminobenzidine tetrahydrochloride (DAB) was used as the chromagen. Sections were then counterstained with hematoxylin and coverslipped. The staining results showed LAMP-1 positive cells as brown and nuclei as blue.

The representative photos were taken and the area of LAMP-1 positive cells was analyzed with Image-Pro Plus software (Media Cybernetics, Inc., Bethesda, MD) and comparative statistics were performed using student's t-test.

Electron Microscope Method:

Brain tissues from 3 doses of I2S treated animals were fixed in 2.5% PFA/2.5% glutaraldehyde in 0.1M sodium cacodylate buffer pH 7.4 at 4 degrees for over night. Then the samples were washed in cacodylate buffer (0.1M, pH7.4) and post-fixed in osmium tetroxide, dehydrated in alcohols and propylene oxide and embedded in Epon resin. Ultrathin sections were cut at 100 nm, stained with lead citrate and examined in a Tecnai™ $G^2$ Spirit BioTWIN transmission electron microscope.

Results

Figure 53:
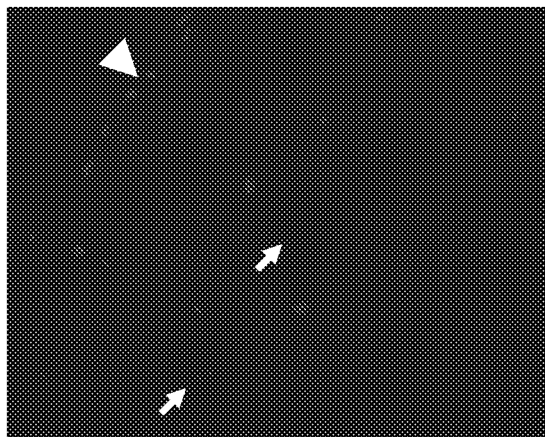
FIG. 53 illustrates exemplary I2S IHC demonstrated I2S detected in the neurons (arrows) in the cerebral and cerebellar cortex including a layer of meningeal cells covering the surface of the brain (arrow heads) following intrathecal injections of 3 doses of I2S. Staining of I2S IHC in 2 dose injected brains was weaker (photo not shown). There was no observed positive I2S staining for any type of cells in the brain of vehicle control animals. 40×.
Figure 53:
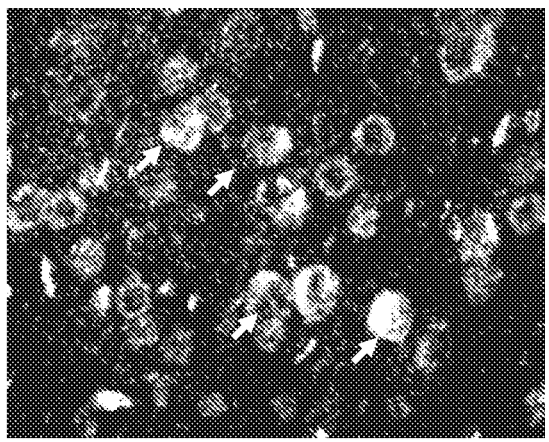
Figure 53:
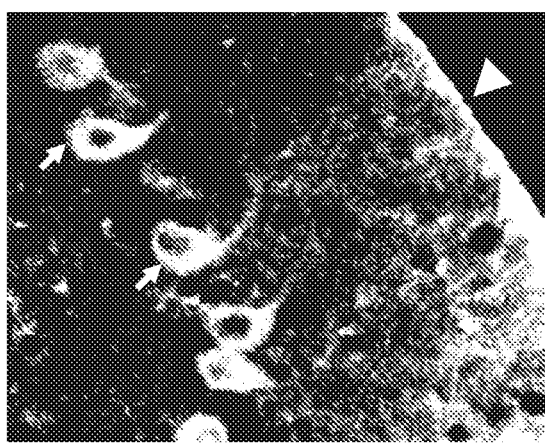

In the brain as determined by immunohistochemistry (IHC), no I2S was found in vehicle control animals. In contrast, meningeal cells, neurons of the cerebrum and cerebellum were positively stained for I2S in I2S injected animals. The staining signal was stronger in animals administered 3 doses (FIG. 53).

Figure 54:
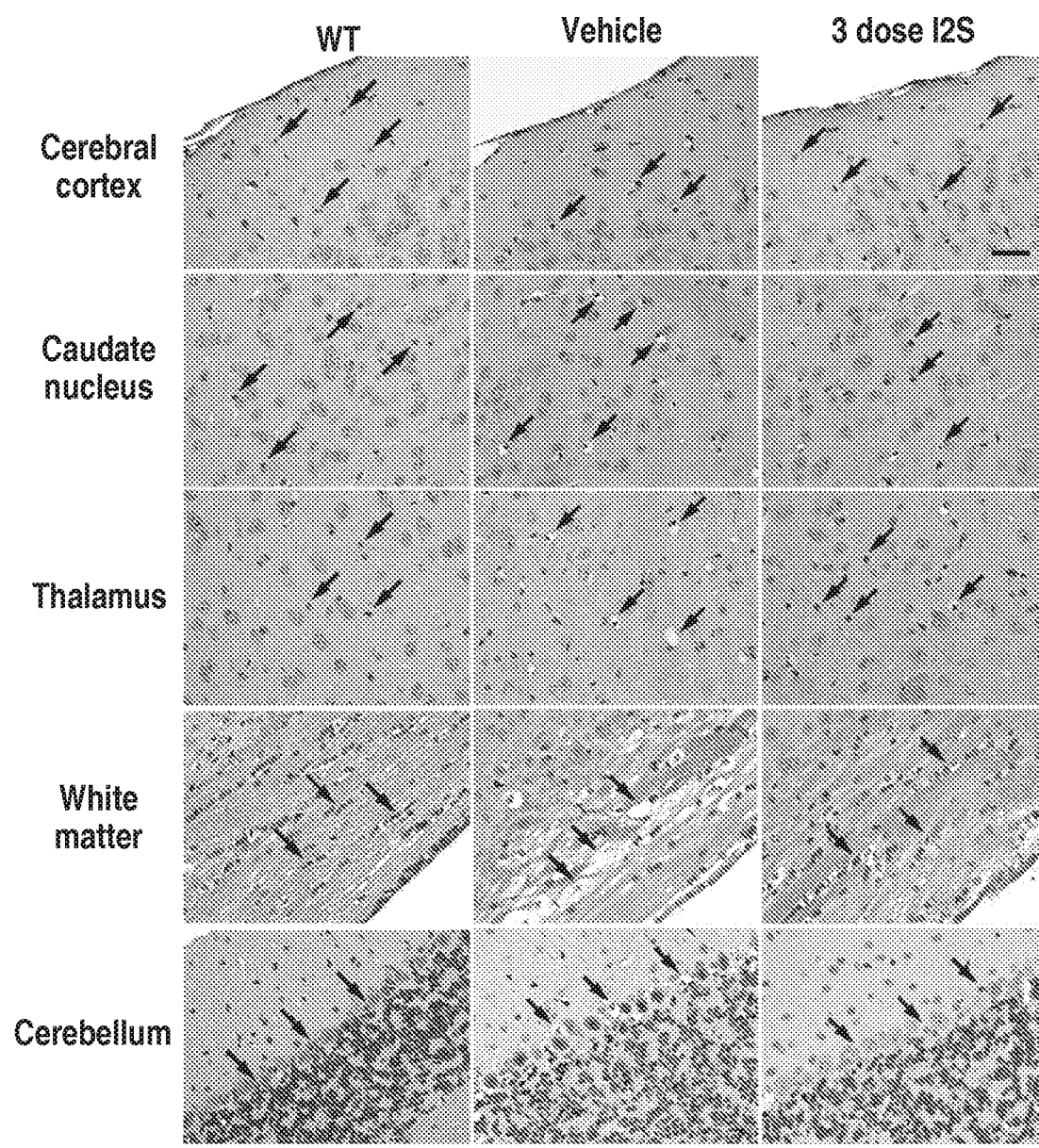
FIG. 54 depicts exemplary reversal of pathology in the brain of IKO mice after intrathecal-lumbar I2S injection. H&E stained brain tissues showed numerous cellular storage vacuoles (arrows) in the vehicle control animals. Cellular vacuolation was reduced throughout the brain in both 2 dose (photo not shown) and 3 dose injected mice. Marked reduction was found in the 3 dose injected ones. 40×.
Figure 55:
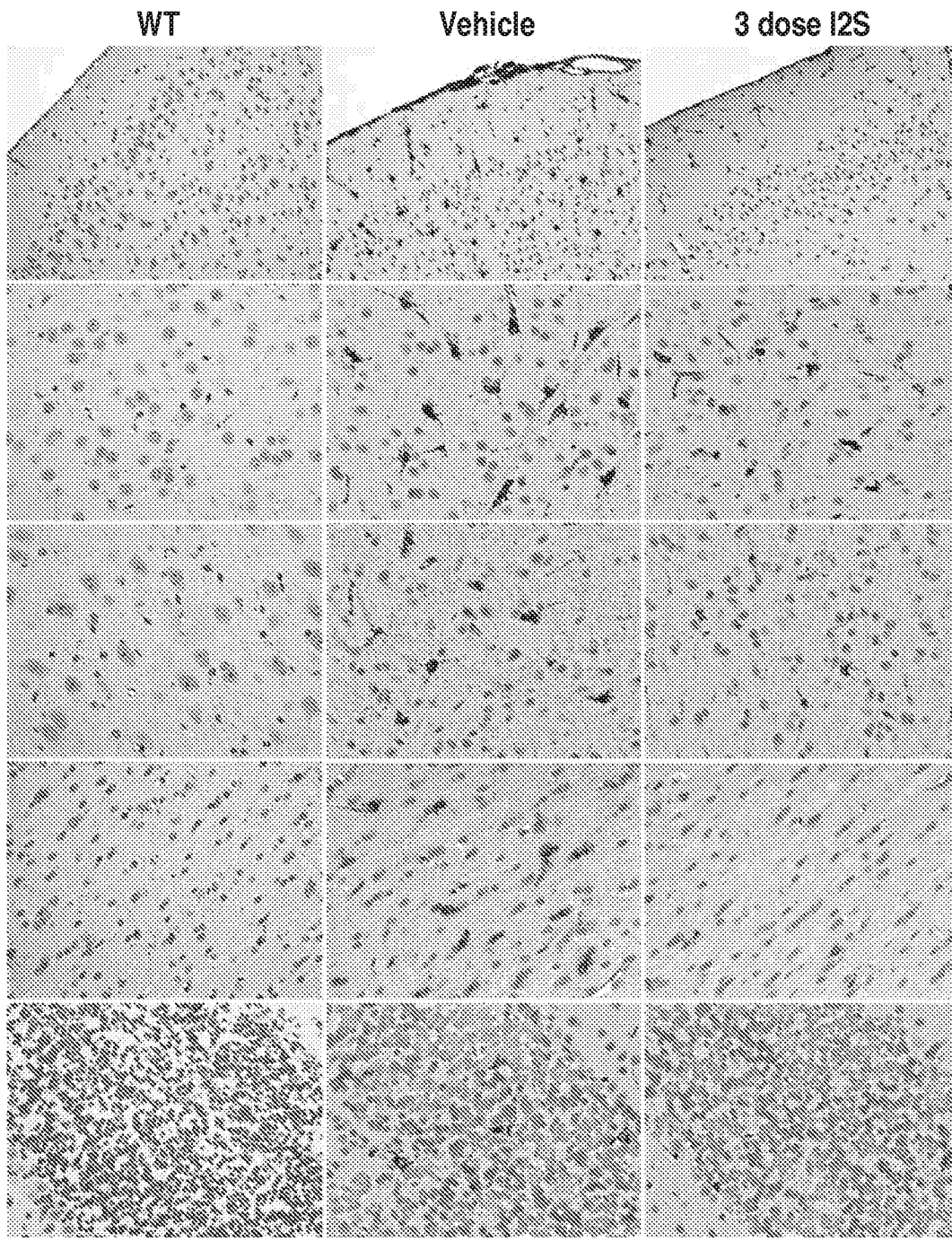
FIG. 55 depicts exemplary immunohistochemical staining of LAMP-1, there was a marked reduction of lysosomal activity in the brains after 2 doses (photo not shown) and3 doses of I2S treatment compared with vehicle controlled mice. The reduction was characterized by the decrease in the number of LAMP-1 positive cells and lighter staining intensity in the regions throughout the brain. 40×.
Figure 56:
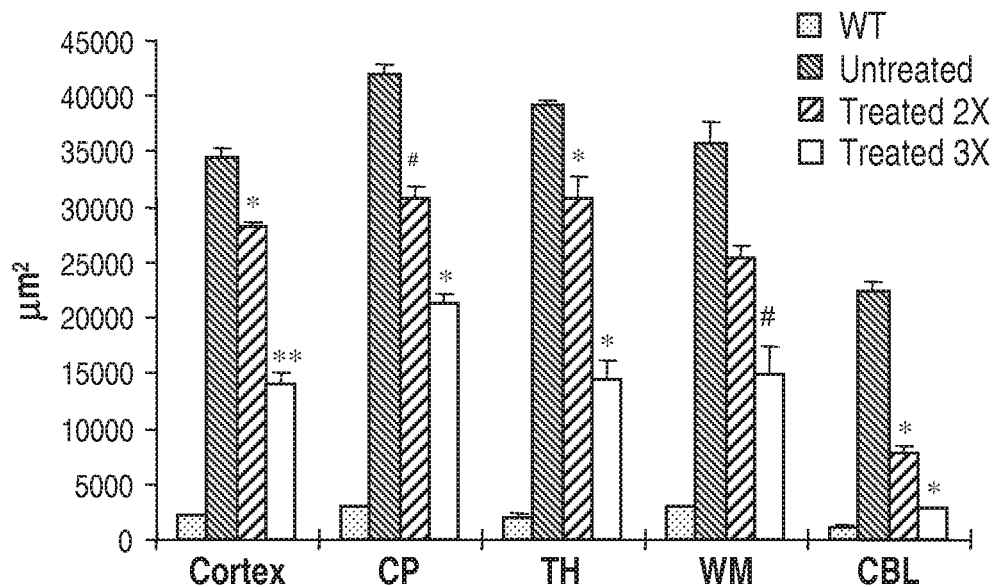
FIG. 56 illustrates exemplary morphometry results from a comparison of the mean LAMP-1 positive area among wild-type (WT), vehicle untreated and I2S (2 and 3 doses) mice in the cerebral cortex (Cortex), caudate nucleus (CP), thalamus (TH), white matter (WM) and cerebellum (CBL) confirmed that there were significant reductions in the LAMP-1 positive staining in all areas of the brain evaluated. Data are represented as the mean±s.d. #=P<0.05; *=P<0.01; **=P<0.001.

In brain tissues of vehicle-treated IKO mice, cellular vacuolation, a histopathological hallmark of lysosomal storage diseases, was found throughout brains compared to wild type animals. In I2S treated IKO mice, there was widespread reduction of cellular vacuolation from the surface cerebral cortex, caudate nucleus, thalamus, cerebellum, to the white matter compared to untreated ones (FIG. 54). Abnormally high lysosomal activity was found by lysosomal-associated membrane protein-1 (LAMP-1) staining, an indicator of lysosomal activity and disease state, in microglial, meningeal and perivascular cells of vehicle-treated IKO mice when compared to wild type animals (FIG. 55). The I2S intralthecal-treated mice had marked reductions in LAMP-1 immunostaining. This reduction was characterized by the decrease in the number of LAMP-1 positive cells and lighter staining. The reduction was found throughout whole brain from the surface cerebral cortex, caudate nucleus, thalamus, cerebellum to white matter (FIG. 56) in both 2 and 3 dose of I2S treated animals. Morphometrical analysis of LAMP-1 immunostaining of various brain regions confirmed that there were significant reductions in the LAMP-1 positive staining in all areas of the brain evaluated (FIG. 56).

Figure 57:
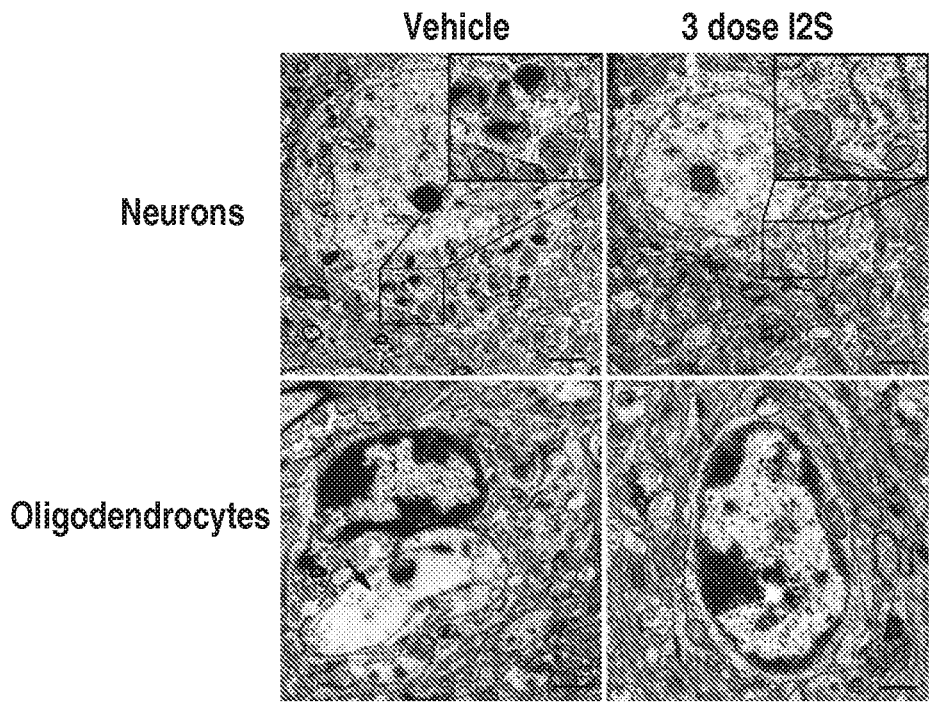
FIG. 57 depicts exemplary electron micrographs of brain cells showed pathological improvements at the ultrastructural level. Neurons of vehicle treated mice had lamellated inclusions, zebra body-like structures, and vacuoles containing granular storage material (insert), which was reduced in I2S injected mice. Oligodendrocytes of vehicle treated mice showed large electron-lucent storage vacuoles (arrow) while oligodendrocytes of I2S-injected mice had minimal vacuolation. Scale bar: in neurons, 2 μm; in oligodendrocytes, 500 nm.

Electron microscopy examination of brain cells in vehicle-treated IKO mice revealed the enlarged vacuoles containing amorphous granular storage material and inclusions with lamellated and zebra body-like structures. These typical pathological features of lysosomal storage at the ultrastructural level were reduced in I2S intrathecal-lumbar injected mice (FIG. 57).

Figure 58:
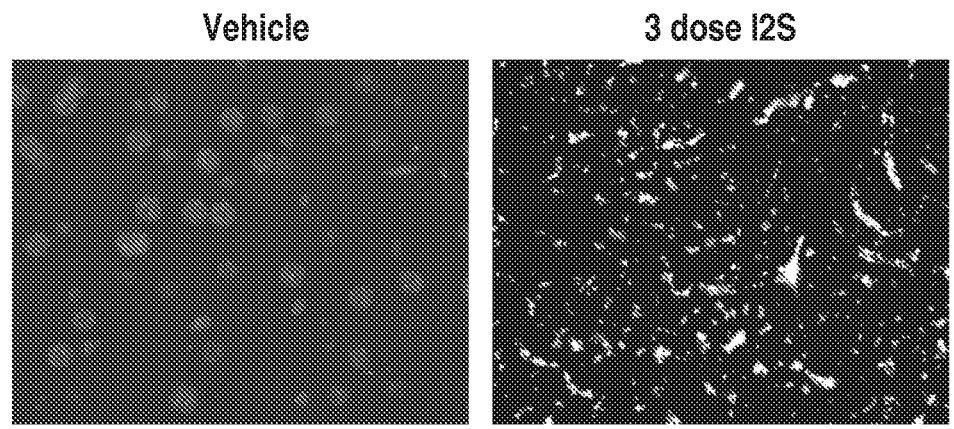
FIG. 58 depicts exemplary immunohistochemistry results demonstrating I2S detected in sinusoidal cells of the liver following intrathecal injections of 3 doses of I2S. 2S IHC staining in 2 dose injected livers was weaker (photo not shown). There was no observed positive I2S staining in the liver of vehicle controlled animals. 40×.

In the liver, there was no positive staining of I2S in the vehicle treated animals. In the I2S intrathecal injected mice, a large amount of injected I2S was clearly found in sinusoidal cells (FIG. 58), which indicated the injected I2S within the intrathecal space circulated with CSF and was then absorbed through the arachnoid granulations into the circulatory system.

Figure 59:
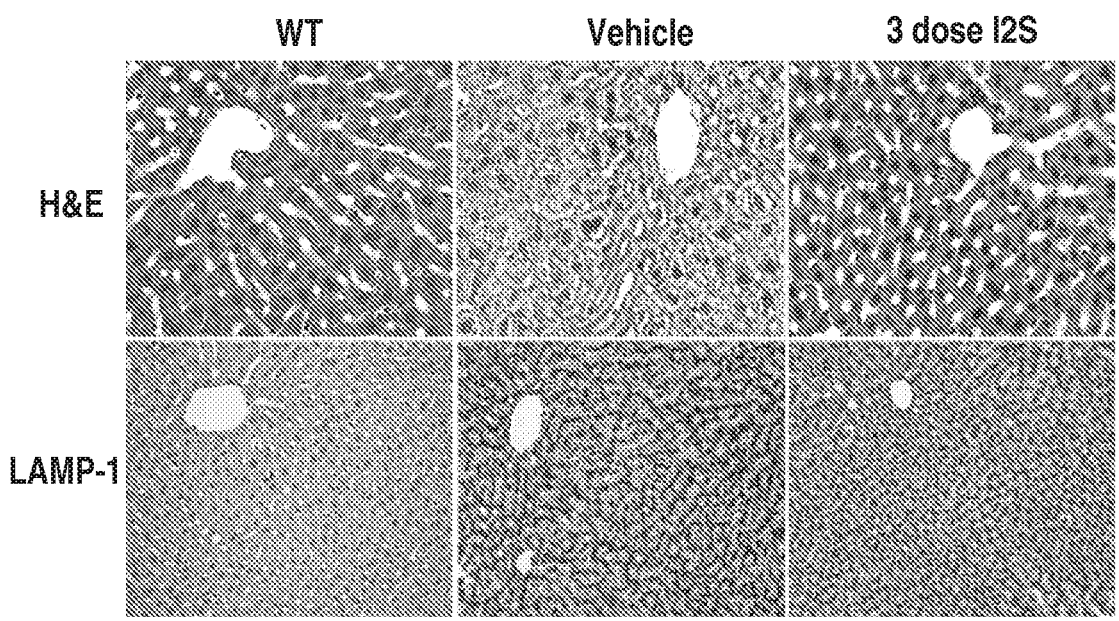
FIG. 59 depicts exemplary tissue from the liver. Severe cellular vacuolation and abnormally high lysosomal activity is revealed by H&E staining and strong LAMP-1 immunostaining were found in vehicle controlled animals compared to WT ones. Marked reduction of cellular vacuolation and LAMP-1 immunostaining was found after interthecal treatment with 3 and 2 (photo not shown) doses of I2S treatment. H&E staining revealed intracytoplasmic vacuolization was almost completely disappear with a nearly normal liver cell structure. H&E, 40x; LAMP-1, 20x.
Figure 60:
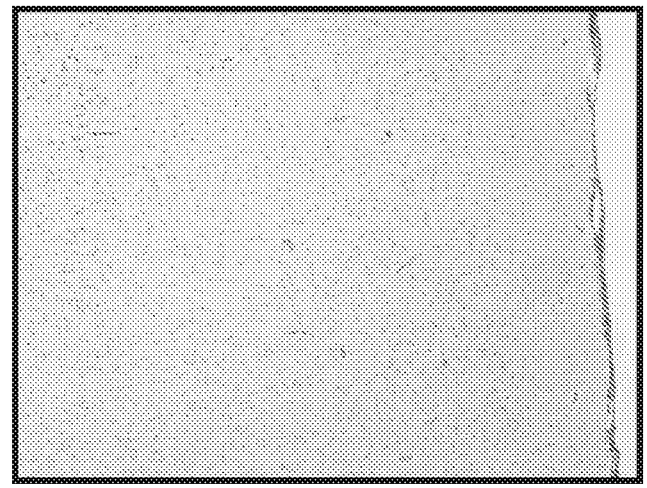
FIG. 60 depicts exemplary tissues showing cerebrum of a 3 mg treatment group animal. Positive I2S staining was observed in meningeal cells. 4x.
Figure 61:
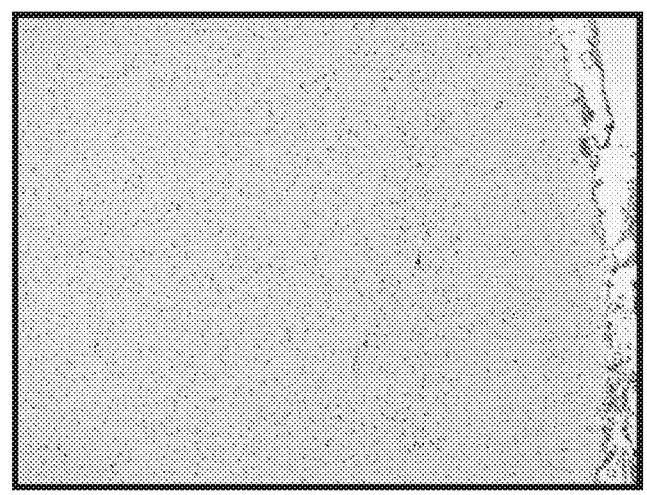
FIG. 61 depicts exemplary tissues showing cerebrum of a 30 mg treatment group animal. Positive I2S staining was observed in neurons and meningeal cells. 4x.
Figure 62:
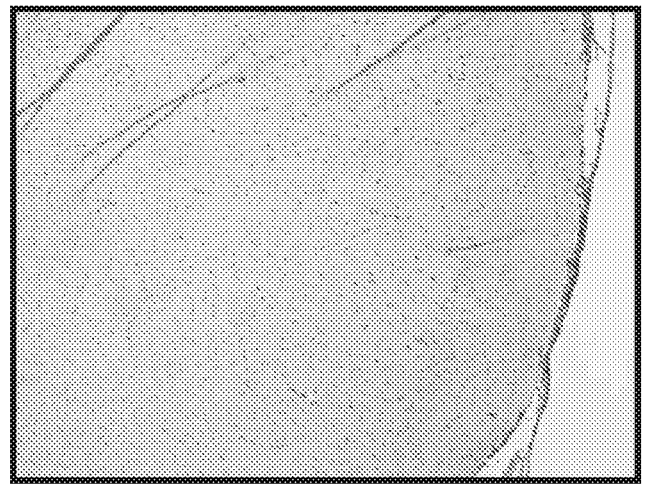
FIG. 62 depicts exemplary tissues showing cerebrum of 100 mg treatment group animal. Positive I2S staining in neurons and meningeal cells was stronger than in 3 and 30 mg treated animals. 4x.
Figure 63:
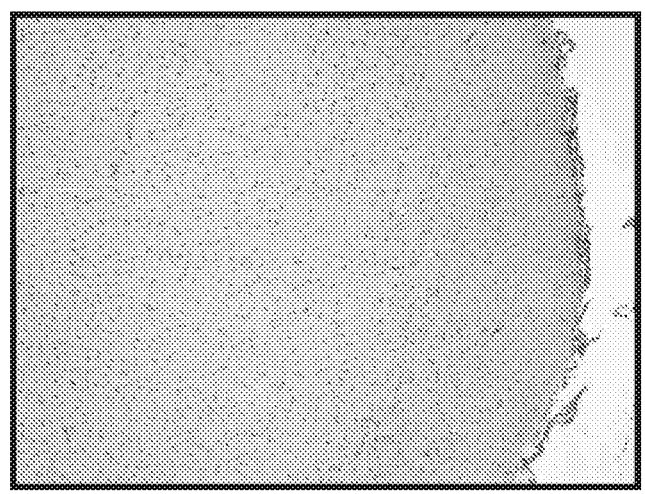
FIG. 63 depicts exemplary tissues showing cerebrum of a 150 mg treatment group animal. A large population of neurons was observed as being I2S positive along with strongly positive meningeal cells.

In liver tissues of vehicle-treated IKO mice, severe cellular vacuolation and abnormally high lysosomal activity demonstrated by H&E staining and strong LAMP-1 immunostaining were found compared to WT mice. Marked reduction of cellular vacuolation and LAMP-1 immunostaining in livers was found after intrathecal treatment with I2S. H&E staining revealed intracytoplasmic vacuolization that almost completely disappeared with a nearly normal liver cell structure (FIG. 59).

In IKO mice, recombinant human I2S was delivered to the brain by the intrathecal-lumbar route and injected I2S cause widespread histopathological improvement in a variety of regions in the brain.

Injected I2S was detected in meningeal cells and neurons in the brain.

Reduced cellular vacuolation throughout the brain at both light and electron microscopy levels.

Reduced LAMP-1 lysosomal marker throughout the brain.

Intrathecal injected I2S entered the peripheral circulation and improved liver morphology and histological marker.

Example 7: Toxicology of IT Delivery of I2S

This example illustrates the clinical signs associated with idursulfase via monthly bolus intrathecal lumbar doses in cynomolgus monkeys. To achieve this, 14 male, cynomolgus monkeys were randomly assigned to five treatment groups as shown in the following Table 21.

TABLE 21

Experimental Design

| Group | Number of Animals | Nominal Dose (mg) | Dose Volume (ml) |
|---|---|---|---|
| 1 | 3 | 0 | 1 |
| 2 | 3 | 3 | 1 |
| 3 | 3 | 30 | 1 |
| 4 | 3 | 150 | 1 |
| 5 | 2 | 100 | 1 |

Animals in all groups were dosed three times at monthly intervals IT at the level of the lumbar spine. The 1 ml dose volume was flushed from the catheter system with 0.3 ml of PBS. One to two days prior to each dosing, approximately 2 ml of CSF was collected from an IT spinal tap at the level of the cisterna magna. Blood samples (2 ml) were also collected at this time. Blood (2 ml) and CSF (0.1 ml) were collected from Group 5 animals predose, 0.5, 1, 2, 4, 8, 24, and 48 hours post dose after the first dose. Clinical signs were recorded at least twice daily. A necropsy was performed approximately 24 hours after the third dose and selected tissues were harvested and saved.

On Day 1, all three Group 4 (150 mg) animals exhibited minimal tending to hind quarters within 3-12 minutes post dose, lasting 5-15 minutes; this sign was deemed related to the test article. There were no changes in body weight, food consumption and neurological/physical examination parameters that were considered related to the test article.

The analysis of the serum and CSF samples and the dosing solution analyses are presented. Variations in endogenous idursulfase activity were observed in different tissues from the cynomolgus monkey; brain and spinal cord had greater endogenous activity than other peripheral organs examined, including liver, heart, and kidney. Idursulfase administration was associated with dose-dependent increases in idursulfase activity in various brain regions, as well as in the brainstem and spinal cord. IT delivery did not result in an observable difference in distribution between the right and left cerebral hemispheres. There was a clear dose-dependent increase in idursulfase activity in the following organs: brain, liver, heart, and kidney. Immunostaining for idursulfase in the brain demonstrated a dose-dependent increase in stainingintensity. In the 3 mg group, meningial cell and limited glial cell staining beneath the meninges was observed; neuronal staining was not evident in animals from the 3 mg treatment group. Idursulfase staining was positive and dose dependent in the spinal cord, with the highest staining intensity in the lumbar region, where IT administration of idursulfase occurred. Idursulfase staining intensity in liver, kidney, and heart was dose-dependent and consistent with increased idursulfase activity in these organs.

In conclusion, IT administration of idursulfase at doses up to 150 mg delivered at monthly intervals had no adverse effects. Thus, the no observed adverse effect level (NOAEL) was interpreted to be 150 mg, the highest dose tested in this study. Idursulfase administration was associated with dose-dependent increases in idursulfase activity in the CNS and resulted in systemic levels in the liver, kidney, and heart.

The test article, idursulfase, was supplied as dosing solutions in 154 mM NaCl, 0.005% Polysorbate 20, pH 5.3-6.1. The nominal concentrations of the supplied dosing solutions were 0, 3, 30 or 150 mg/ml. The test article was stored in a freezer at −82° to −79° C. Phosphate buffered saline (PBS), pH 7.2, was used as a flushing agent after the doses were administered and after serial CSF collections. The PBS was obtained from Gibco, Invitrogen Corporation.

Test Article Dosing Preparation

On the first day of dosing for each time interval, one vial of each concentration was removed from the −80° C. chest freezer and allowed to thaw on the countertop to room temperature. Once thawed, the vials for Groups 1, 2, and 3 were labeled, weighed and 1 ml was withdrawn through a 0.22 µm filter for each animal scheduled for dosing. After all of the doses were administered, the vials were reweighed and placed in the refrigerator.

The following day (day of dosing for Animal 003, Group 4, and Group 5) dosing solutions for Groups 1 and 4 were removed from the refrigerator and placed on the countertop to reach room temperature. Once room temperature was obtained, the vials for Groups 1 and 4 were weighed, Group 4 vial was labeled, and 1 ml was withdrawn through the filter for each animal scheduled for dosing in Groups 1 and 4. The dosing solution for Group 5 was then prepared by injecting the appropriate amount of Group 4 dosing solution and Group 1 (vehicle) into a sterile polypropylene vial. The amount added from Groups 1 and 4 were recorded. The solution was mixed by gently inverting the vial and 2-1 ml doses were withdrawn through the filter for the animals in Group 5. The vials for Groups 1 and 4 were reweighed upon completion of dosing and all the vials (Groups 1-5) were placed in a freezer.

Fourteen animals were randomly assigned to treatment groups as described in Table 21.

The IT route of administration was selected because this is an intended route for human administration. he doses of idursulfase that were selected for this study (3, 30, 100, and 150 mg/ml) were chosen to assess the biodistribution of varying doses levels of enzyme within the non-human primate central nervous system (CNS) after three consecutive monthly bolus IT lumbar injections.

Clinical Observations

The overall incidence of clinical signs was minimal. None of the animals in Group 1(control), Group 2 (3 mg), Group 3 (30 mg), or Group 5 (100 mg) had clinical signs that were considered related to the test article at any time during the study.

On Day 1, all three Group 4 (150 mg) animals (012-014) exhibited minimal tending to hind quarters within 3-12 minutes post dose, lasting 5-15 minutes. This sign was considered related to the test article and was not observed in any of the lower dose groups. There were no other clinical signs immediately after the first dose or on the days immediately following test article administration. The only other sign observed for the Group 4 animals was a single episode of emesis for Animal 013 on Day 35.

Administration of the test article as a single, monthly intrathecal bolus was not associated with any adverse gross or microscopic change when taking into consideration the changes inherent with an implanted drug delivery device. All groups, including the control group, had microscopic changes in the meninges indicating inflammatory reactions to the drug delivery system. In the animals that received doses of the test article of 30 mg and greater, there was a tendency for the inflammatory reaction in the meninges to have a more pronounced eosinophilic component but this difference was not considered to be biologically significant.

Because the differences between the control and test article treated animals were so slight, the no observed adverse effect level (NOAEL) was interpreted to be 150 mg, the highest dose tested in this study.

The overall inflammatory reaction in the meninges in all groups (including controls) was slightly more pronounced than generally encountered in an intrathecal study of this duration in monkeys. However, this was considered to possibly be related to some characteristic of the vehicle or to the act of dosing 24 hours prior to necropsy.

Figure 64:
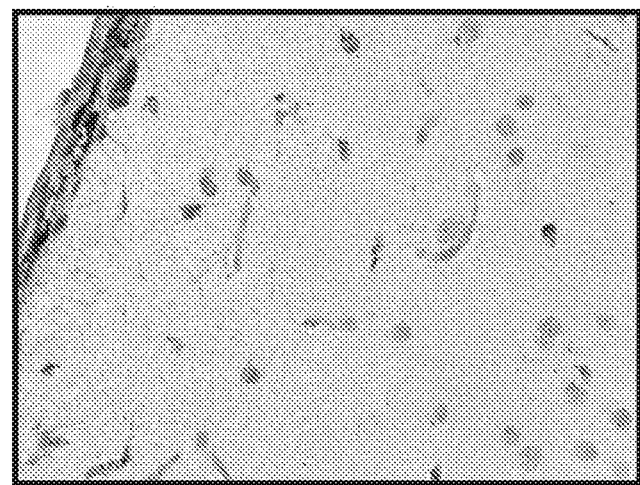
FIG. 64 depicts exemplary tissues showing I2S positive neurons and glial cells, along with meningeal cells, within layer I of the cerebrum in a 30 mg treatment group animal. 40x.
Figure 65:
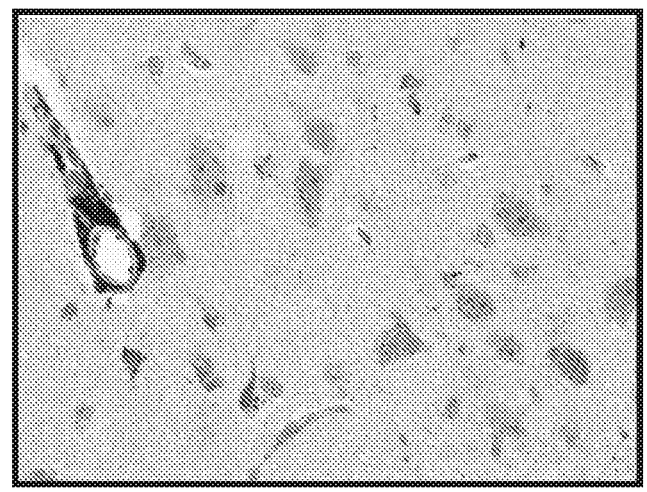
FIG. 65 depicts exemplary tissues showing I2S positive neurons, glial cells, along with perivascular cells, within layer III of the cerebrum in a 30 mg treatment group animal. 40x.
Figure 66:
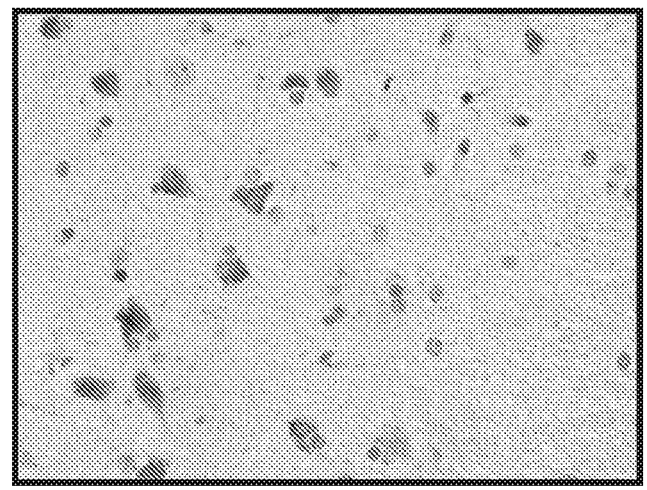
FIG. 66 depicts exemplary tissues showing I2S positive neurons and glial cells within the layer VI of cerebrum adjacent to the white matter in a 30 mg treatment group animal. 40x.
Figure 67:
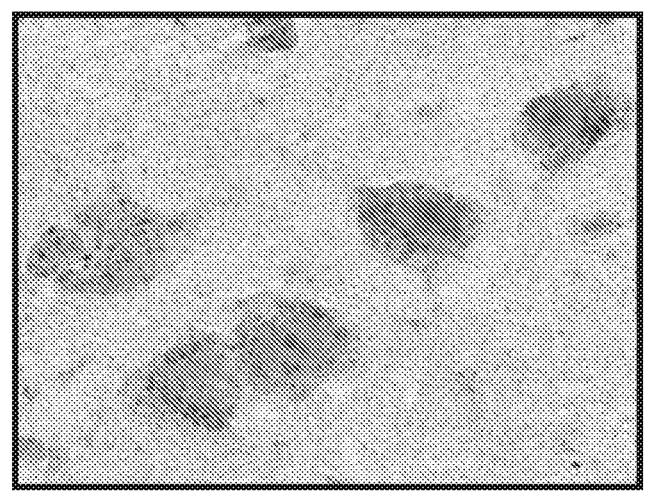
FIG. 67 depicts exemplary tissues showing strongly positive I2S staining in the neurons (cerebrum) of a 150 mg treatment group animal. 100x.

Brain idursulfase staining was positive in all treated animals except one animal in the 3 mg group, with the highest staining intensity found in the 150 mg group (FIGS. 60, 61, 62 and 63). In the 3 mg group, only meningial cells and a few glial cells beneath the meninges were positive; no injected idursulfase was detected in neurons. In the higher dose groups (30, 100 and 150 mg), large populations of cerebral neurons were strongly positive for idursulfase staining, along with meningial cells, glial cells and perivascular cells. Idursulfase immunostaining revealed a wide distribution of injected idursulfase in cerebral neurons from the neurons within layer I at the surface near the meninges, to the ones within the deeper layer VI adjacent to the white matter (FIGS. 64, 65 and 66). Marked staining of neurons was also observed for the 150 mg dose group (FIG. 67). In all animals (dose group from 30-150 mg), no marked difference in the neuronal idursulfase staining was found between frontal, middle, and rear sections of the brain.

Figure 68:
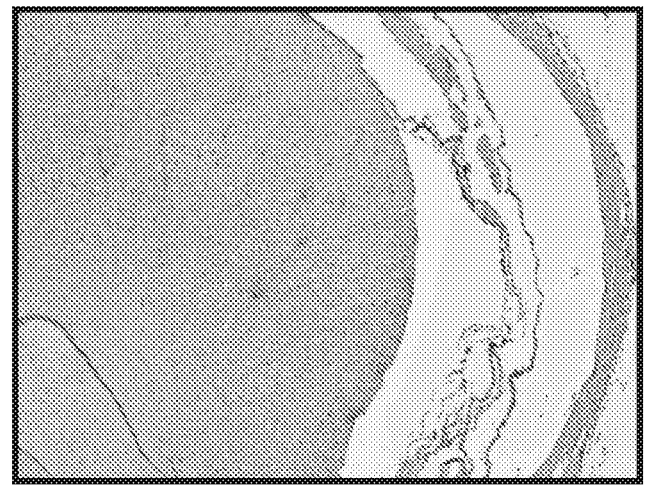
FIG. 68 depicts exemplary tissue showing I2S immunostaining of the cervical spinal cord in a 150 mg treatment group. 4x.
Figure 69:
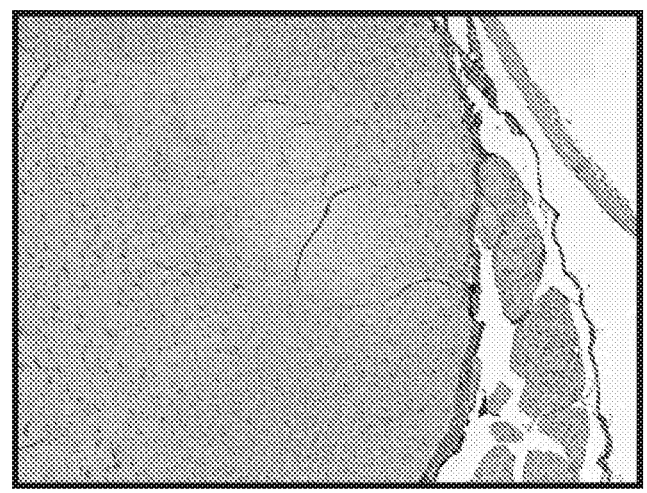
FIG. 69 depicts exemplary tissue showing strong I2S immunostaining in the lumbar spinal cord of a 150 mg treatment group animal. 4x.
Figure 70:
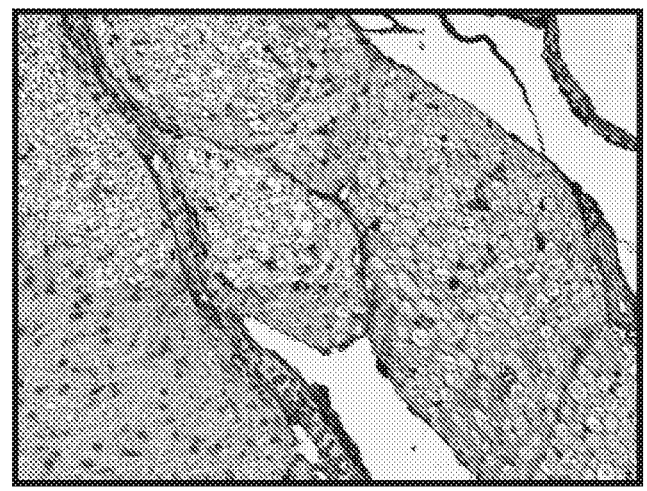
FIG. 70 depicts exemplary tissue showing strongly positive I2S immunostaining of meningial cells, glial cells, and epi/peri/endoneurium (connective cells) in the lumbar section of a 150 mg treatment group animal. 40x.
Figure 71:
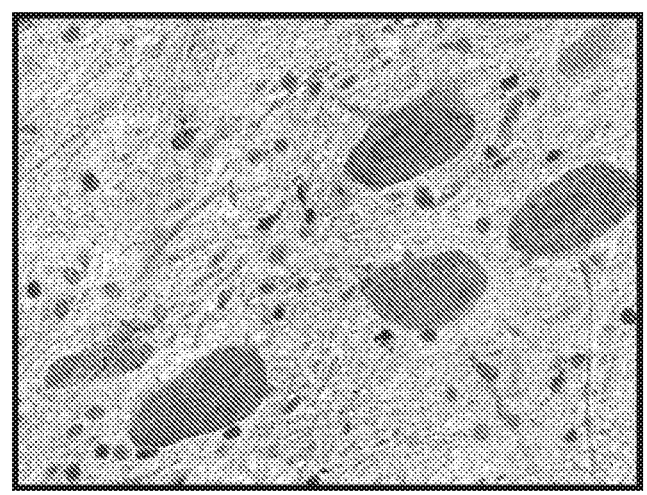
FIG. 71 depicts an image showing that neurons in the lumbar spinal cord of a 150 mg treatment group animal were strongly I2S positive. 40x.

Idursulfase staining was positive in the spinal cords of all animals, with the highest staining intensity in the lumbar region (FIGS. 68 and 69). Idursulfase immunostaining was also dose dependent. Neurons, meningial cells, glial cells, perivascular cells and epi/peri/endoneurium (connective cells) surrounding nerve fibers were strongly positive for idursulfase staining in the 150 mg group (FIGS. 70 and 71).

Figure 72:
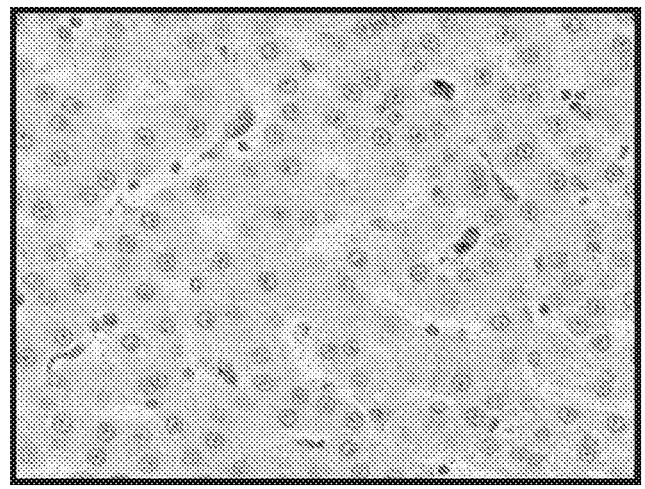
FIG. 72 depicts exemplary results from a liver from a 3 mg treatment group animal. Only sinusoidal cells were I2S positive. 40x.
Figure 73:
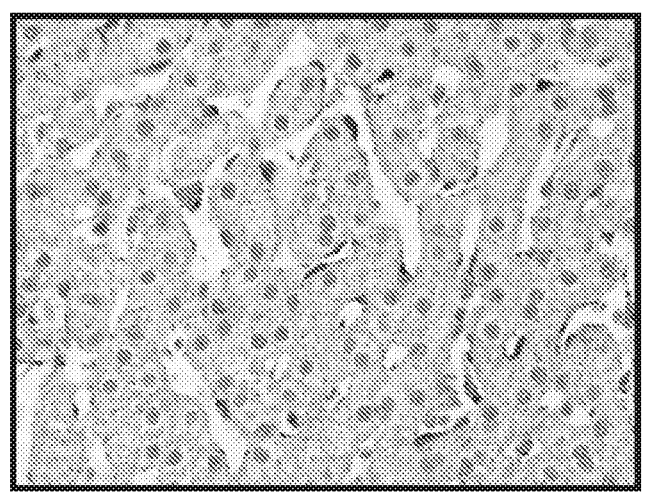
FIG. 73 depicts exemplary results from a liver from a 30 mg treatment group animal. Sinusoidal cells and hepatocytes were I2S positive. 40x.
Figure 74:
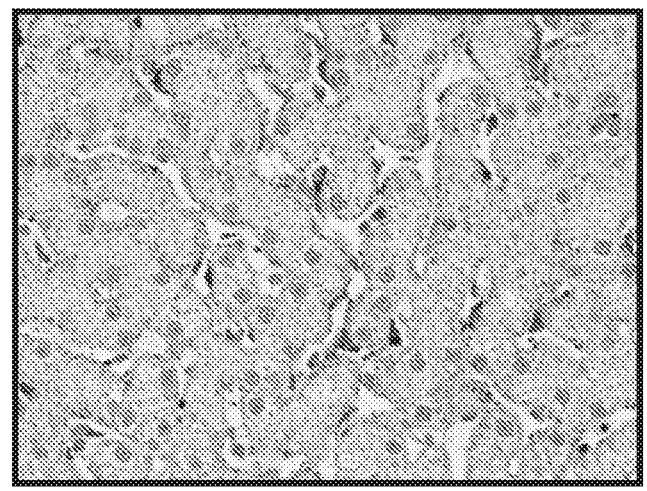
FIG. 74 depicts exemplary results from a liver from a 100 mg treatment group animal. I2S immunostaining was strong in the sinusoidal cells and the hepatocytes. 40x.
Figure 75:
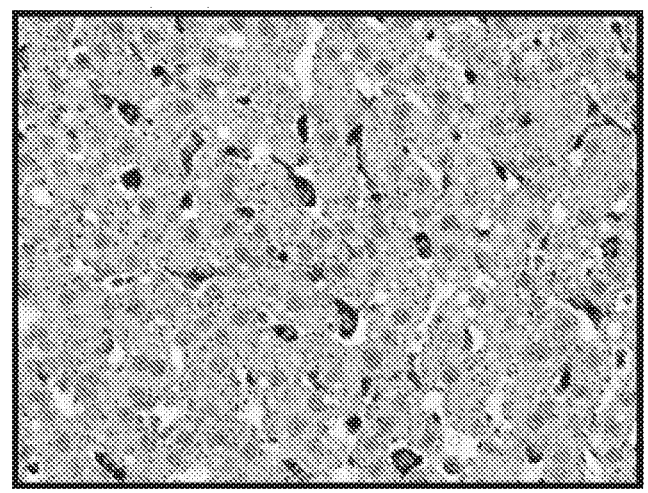
FIG. 75 depicts exemplary results from a liver from a 150 mg treatment group animal. Strongly positive I2S staining was identified in sinusoidal cells and hepatocytes. 40x.

In the liver, positive staining for idursulfase was found in sinusoidal cells (Kupffer cells and endothelial cells) of all animals. Idursulfase, however, was not detected in hepatocytes for the 3 mg treatment group (FIG. 72), while positive idursulfase staining in the hepatocytes was found in the higher dose groups, with the greatest staining intensity in the 150 mg treatment group (FIGS. 73, 74 and 75).

Figure 76:
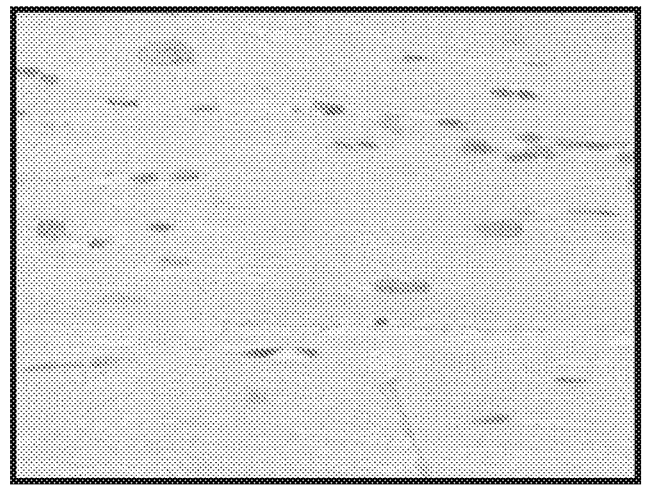
FIG. 76 depicts exemplary results from a heart from a 3 mg treatment group animal. I2S immunostaining was negative. 40x.
Figure 77:
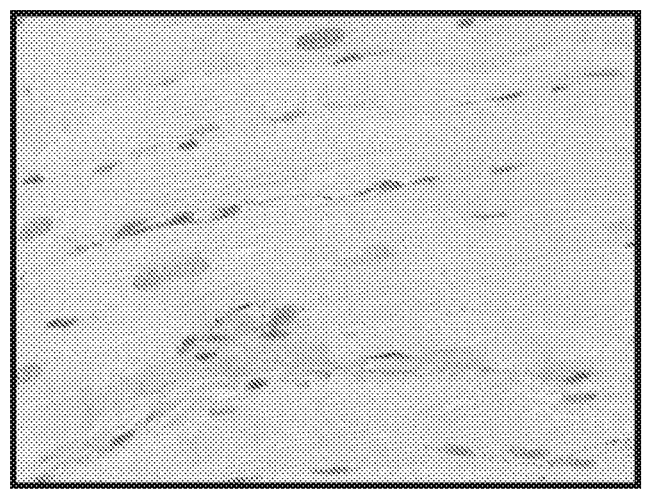
FIG. 77 depicts exemplary results from a heart from a 30 mg treatment group animal. Interstitial cells were I2S positive. 40x.
Figure 78:
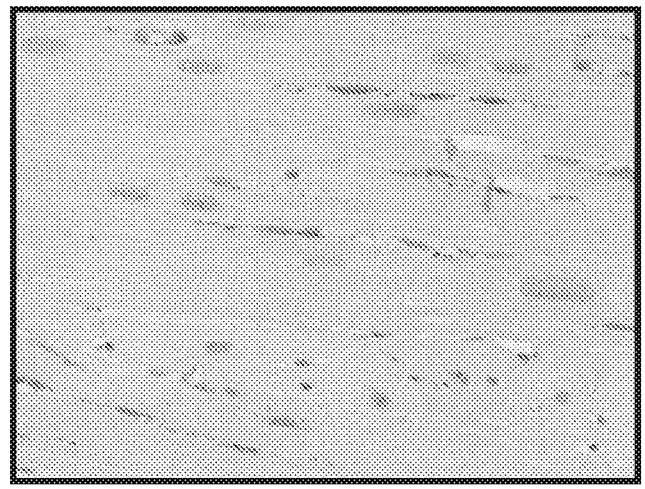
FIG. 78 depicts exemplary results from a heart from a 100 mg treatment group animal. Positive interstitial cell staining for I2S was observed. 40x.
Figure 79:
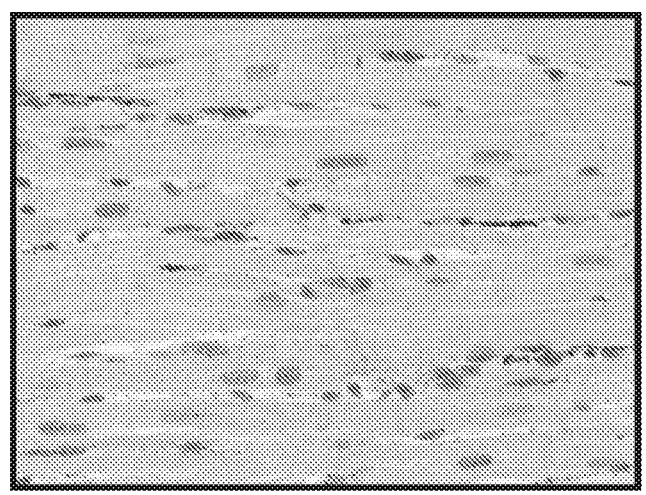
FIG. 79 depicts exemplary results from a heart from a 150 mg treatment group animal. Strongly positive interstitial cell staining for I2S was observed. 40x.

There was no positive staining for idursulfase in animals from the 3 mg treatment group (FIG. 76). In contrast, interstitial cells were positively stained for idursulfase in the 30, 100 and 150 mg groups, with marked staining being observed in the 150 mg group—in terms of positive cell number and staining intensity (FIGS. 77, 78 and 79).

Kidney

Figure 80:
FIG. 80 depicts exemplary results from a kidney from a 3 mg treatment group animal. I2S immunostaining was negative. 40x.
Figure 81:
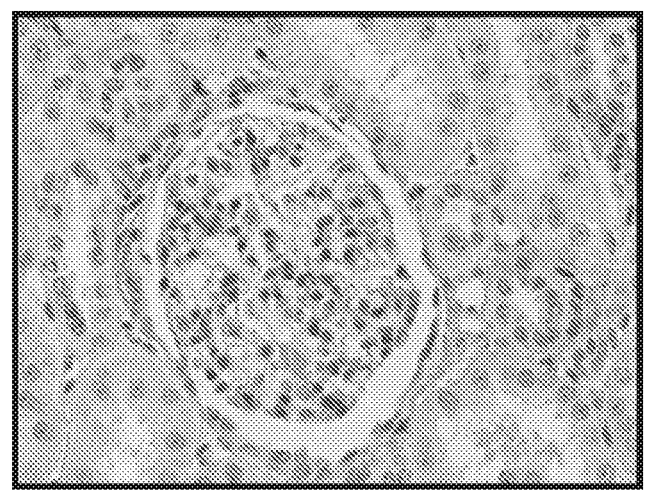
FIG. 81 depicts exemplary results from a kidney from a 30 mg treatment group animal. Glomerular and interstitial cells were I2S positive.
Figure 82:
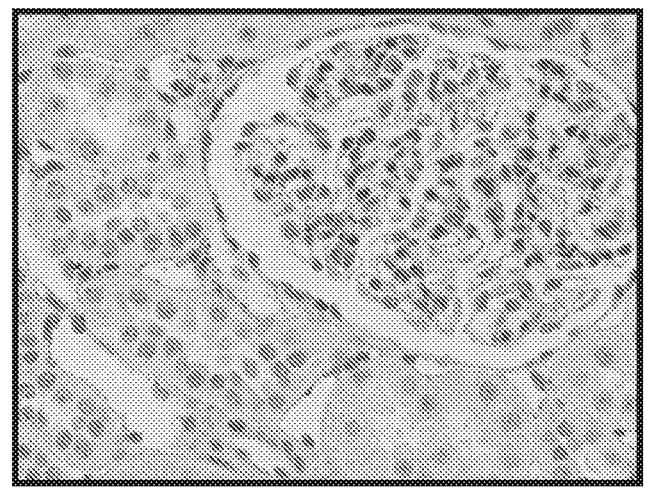
FIG. 82 depicts exemplary results from a kidney from a 100 mg treatment group animal. Increased glomerular and interstitial cell staining for I2S was observed. 40x.
Figure 83:
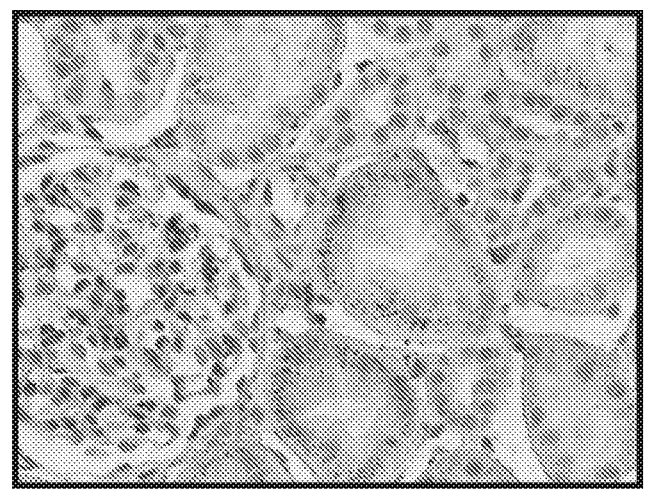
FIG. 83 depicts exemplary results from a kidney from a 150 mg treatment group animal. Positive I2S staining of proximal tubular, glomerular and interstitial cells was observed. 40x.

Little or no injected idursulfase was detected in animals from the 3 mg dose group (FIG. 80). Positive idursulfase staining, however, was found in the glomerular cells and interstitial cells in the 30 and 100 mg groups (FIGS. 81 and 82). In the 150 mg group, idursulfase immunostaining additionally revealed idursulfase staining of proximal tubular cells, along with marked staining of glomerular and interstitial cells (FIG. 83).

Discussion

There were no test article-related clinical signs or effects on body weight, food consumption, physical examination findings and neurological examination findings. On Day 1, the Group 4 (150 mg) animals exhibited minimal tending to hind quarters within 3-12 minutes post dosing, lasting 5 to 15 minutes; this sign was judged to be related to the test article.

Idursulfase administration was associated with dose-dependent increases in idursulfase activity in various brain regions, as well as the brain stem and spinal cord. The highest level of staining intensity in the spinal cord was in the lumbar region, where IT administration of idursulfase occurred. IT administration of idursulfase also resulted in systemic exposure with dose-dependent staining intensity in the liver, kidney, and heart. Animals that received doses of the test article at 30 mg and greater had a tendency for the inflammatory reaction in the meninges to have a more pronounced eosinophilic component IT administration of idursulfase at doses up to 150 mg delivered at monthly intervals had no adverse effects. Thus, the no observed adverse effect level (NOAEL) was interpreted to be 150 mg, the highest dose tested in this Example. Idursulfase administration was associated with dose-dependent increases in idursulfase activity in the CNS and resulted in systemic levels in the liver, kidney, and heart.

Example 8: PK (Serum and CSF) of IT Delivered I2S

This example provides serum and cerebrospinal fluid (CSF) analysis associated with a 6-Month Toxicity Study of ldursulfase Administered Via Monthly Bolus lntrathecal Lumbar injections and Weekly Bolus Intravenous Injections in Cynomolgus Monkeys for test article (TA) concentration.

Experimental Design

The objective oft was to evaluate repeat dose intrathecal (IT) administration of idursulfase (12s) from a toxicology and safety pharmacology perspective over a six month period. The study design is shown in Table 22.

TABLE 22

| Study Design | | | | | |
|---|---|---|---|---|---|
| Group No. | Number of Animals | IV Dose (mg/kg) | No. of IV Doses | IT Dose (mg) | No. of IT Doses |
| 1 | 6 | DC (saline) | 23 | DC (PBS) | 6 |
| 2 | 12 | 0 (IV vehicle) | 23 | 0 (IT vehicle) | 6 |
| 3 | 12 | 0.5 | 23 | 3 | 6 |
| 4 | 6 | 0.5 | 23 | 30 | 6 |
| 5 | 12 | 0.5 | 23 | 100 | 6 |

Test Article
   Identification: ldursulfase IV Dosing—Lot No. FDC06-001 (2.0 mglmL) IT Dosing—idursulfase (0 mglmL)
   idursulfase (3 mglmL)
   idursulfase (30 mg/ml)
   idursulfase (100 mg/ml)

Assay Methods:

Analyses were conducted using an EL1SA (Enzyme Linked lmmunosorbent Assay) for determining idursulfase concentration. The limit of detection (LOD)=1.25 ng/mL prior to multiplying by dilution factor. Samples were screened at a 1:50 dilution, therefore the assay sensitivity is 62.5 ng/mL. Samples falling beyond the high end of the calibration curve were further diluted and retested at an appropriate dilution that resulted in a value within the range of the curve. Selected samples were additionally analyzed using an enzyme activity assay. The LOD for this assay is 0.18 mU/mL at a minimal sample dilution of 1:150.

Animals in groups 1 and 2 that were dosed with saline or vehicle, respectively, all had serum idursulfase levels ranging between 138 ng/mL and <62.5 ng/mL (or <LOD) throughout the period of IV and IT dosing. Of 200 CSF samples tested from group 1 and 2 animals, 62 demonstrated levels of I2S above the assay LOD. Of these, 7 values were high (>1,000 ng/mL). One other CSF sample collected pre IT dose 3 tested above 1,000 ng/mL of I2S. The samples were then tested for idursulfase activity. In each case the activity results indicated the presence of I2S and when the approximate concentration of I2S was calculated based on the activity levels, the results were within 20% of those obtained by the antigen ELISA. (See Table 23) Additional randomly chosen CSF samples with antigen ELISA results <LOD were also tested using the enzyme activity assay to rule out any non-specific activity.

TABLE 23

| Investigation Results from CSF samples | | | | | | | | | |
|---|---|---|---|---|---|---|---|---|---|
| Animal Number | Group | Dose | Dose Number | Dose Mode | Time Point | ELISA Result (mg/mL) | Activity Result (mU/mL) | Calculated ng/mL Based on Activity | Calculated as % of Measured |
| 003 | 1 | Saline | 5 | IT | Predose | 1392 | 4.7 | 1173 | 119% |
| 003 | 1 | Saline | 6 | IT | Predose | 7322 | 29.9 | 7469 | 96% |
| 004 | 1 | Saline | 2 | IT | 2 hr post | 17045 | 62.1 | 15527 | 110% |
| 006 | 1 | Saline | 6 | IT | 4 hr post | 16435 | 70.7 | 17682 | 93% |
| 006 | 1 | Saline | 1 | IT | Predose | 1320 | 5.3 | 1319 | 100% |
| 0016 | 2 | Vehicle | 1 | IT | 2 hr post | 3070 | 11 | 2743 | 112% |

TABLE 23-continued

Investigation Results from CSF samples

| Animal Number | Group | Dose | Dose Number | Dose Mode | Time Point | ELISA Result (mg/mL) | Activity Result (mU/mL) | Calculated ng/mL Based on Activity | Calculated as % of Measured |
|---|---|---|---|---|---|---|---|---|---|
| 017A | 2 | Vehicle | mo. 3 | IV | 4 hr post | 2236 | 8.8 | 2194 | 102% |
| 046 | 5 | 100 mg/kg | 3 | IT | Predose | 2086 | 7 | 1750 | 119% |

In this study, serum and CSF samples were analyzed for idursulfase concentration. Serum samples were collected according to the following schedule:

IV Doses: predose and 2 hours post doses 1 through 10, predose and 4 hours post doses 11 through 23, and at necropsy.

IT Doses: predose and 2 hours post doses 1 and 2, predose and 4 hours post doses 3 through 6, and at necropsy.

CSF samples were collected according to the following schedule:

IV Doses: predose and 2 hours post dose 1, and 4 hours post doses 3 and 6.

IT Doses: predose and 2 hours post doses 1 and 2, predose and 4 hours post doses 3 through 6, and at necropsy.

Generally, serum idursulfase seemed to clear faster than CSF idursulfase. Serum idursulfase levels in groups 1 and 2 animals that were dosed with saline or vehicle, respectively, were less than or equal to 138 ng/mL at all time points tested. Some animals had levels below the assay limit of detection (LOD).

Fewer CSF samples from groups 1 and 2 were above the assay LOD, with 7 notable exceptions that resulted in high (>1,000 ng/mL) levels. One CSF sample collected from an animal pre IT dose 3, also tested above 1,000 ng/mL idursulfase.

The samples giving these out-of-trend results were retested and confirmed. In addition, these samples were tested for idursulfase enzyme activity. These activity results also confirmed high idursulfase levels within 20% of those obtained by the idursulfase mass assay (Table 23).

The specificity of the activity assay was validated within this sample cohort by randomly testing CSF samples with idursulfase mass units below LOD and confirmed that idursulfase levels in these samples were indeed LOD (data not shown).

Example 9. Biodistribution of IT Delivered I2S

Having successfully demonstrated that intrathecal administration is an efficacious way of delivering I2S to the tissues of the CNS, additional studies were conducted to determine whether IT-administered I2S is capable of distributing into the deep tissues of the brain and whether there is cellular localization of IT-administered I2S. A recombinant human iduronate-2-sulfatase (I2S) formulation was prepared and formulated in a vehicle of 154 mM NaCl, 0.005% polysorbate 20 at a pH of 6.0.

Non-human primates were administered either 3 mg, 30 mg, or 100 mg of I2S on a monthly basis by way of an implanted intrathecal port for six consecutive months. The design of the study is summarized in Table 24 below.

TABLE 24

| Group | n | IV Dose (mg/kg)[a] | IT Dose (mg)[a] | Last Day on Study (number of animals) | |
|---|---|---|---|---|---|
| | | | | 6 Months | Recovery |
| 1 | 6 | DC (NS) | DC (PBS) | 6 | — |
| 2 | 12 | 0 (vehicle) | 0 (IT vehicle) | 6 | 6 |
| 3 | 12 | 0.5 | 3 | 6 | 6 |
| 4 | 6 | 0.5 | 30 | 6 | — |
| 5 | 12 | 0.5 | 100 | 6 | 6 |

[a]Idursulfase unless otherwise specified.
DC (device control);
IT (intrathecal);
IV (intravenous);
NS (normal saline);
PBS (phosphate-buffered saline, pH 7.2).

Repeat monthly administration of I2S to the non-human primates for six months was well tolerated at the highest dose tested and not associated with any significant adverse toxicologic events. Twenty-four hours following the administration of the sixth and final dose of I2S, the subject non-human primates were sacrificed and CNS tissues of such non-human primates were examined.

Figure 84A:
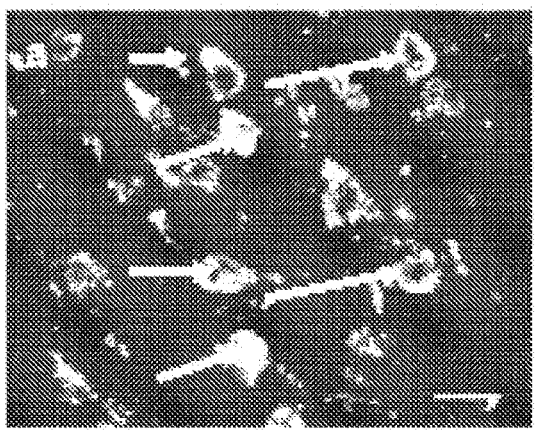
FIG. 84A-F illustrates results of immunohistochemistry (IHC) studies evaluating the CNS tissues of cynomolgus monkeys administered weekly doses of iduronate-2-sulfatase (I2S). As determined by (IHC), there was cellular deposition of I2S throughout the CNS. In the gray matter I2S was detected in the neurons of the cerebrum, cerebellum, brain stem, and spinal cord of all groups in a dose-dependent manner. In the surface gray matter of the higher dose groups, large numbers of cerebral neurons were positive for I2S staining in the surface cortex (FIG. 84A). I2S was also detected in neurons in the thalamus (FIG. 84B), hippocampus (FIG. 84C), caudate nucleus (FIG. 84D) and spinal cord (FIG. 84E). Meningial and perivascular cells were also I2S staining positive (FIG. 84F). The identified scale bars correspond to 25 um.
Figure 84B:
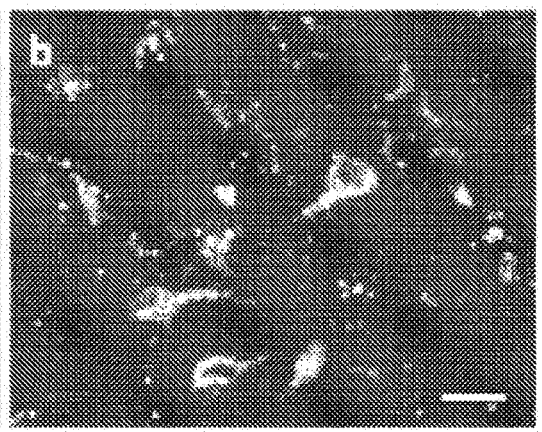
Figure 84C:
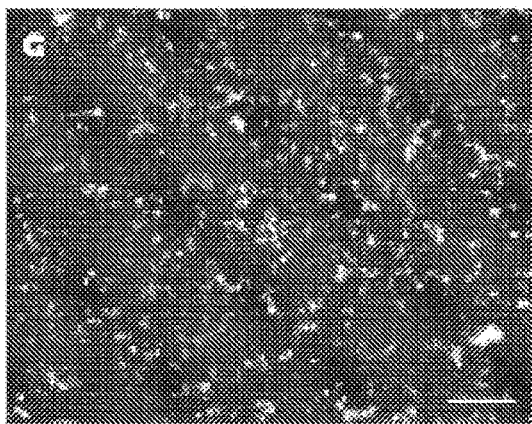
Figure 84D:
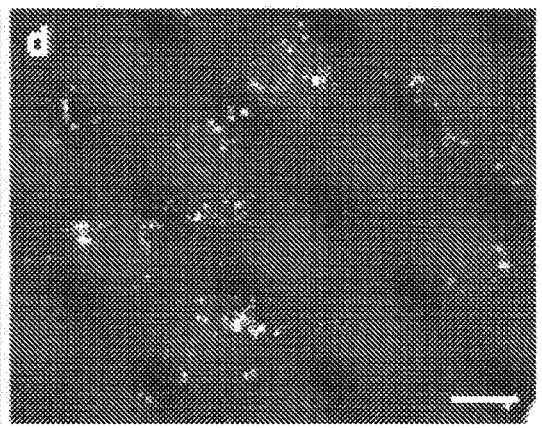
Figure 84E:
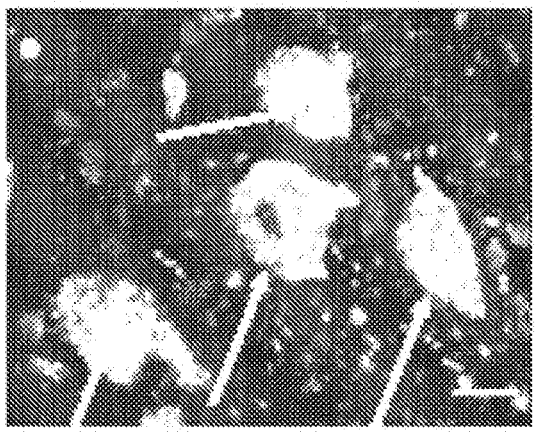
Figure 84F:
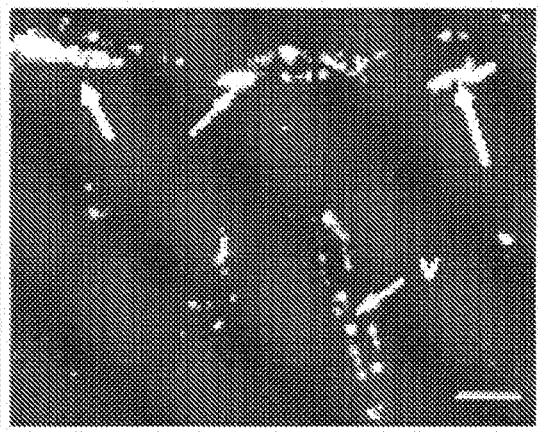

As determined by immunohistochemistry (IHC), there was widespread cellular deposition of I2S throughout the cells and tissues of the CNS. I2S protein was detected in all tissues of the brain by IHC, with a deposition gradient from the cerebral cortex to the ventricular white matter. In the gray matter I2S was detected in the neurons of the cerebrum, cerebellum, brain stem, and spinal cord of all groups in a dose-dependent manner. In the surface gray matter of the higher dose groups, large numbers of cerebral neurons were positive for I2S staining in the surface cortex (FIG. 84A). I2S was also detected in neurons in the thalamus (FIG. 84B), hippocampus (FIG. 84C), caudate nucleus FIG. 84D) and spinal cord (FIG. 84E). Meningial and perivascular cells were also positive for I2S staining (FIG. 84F).

Figure 85:
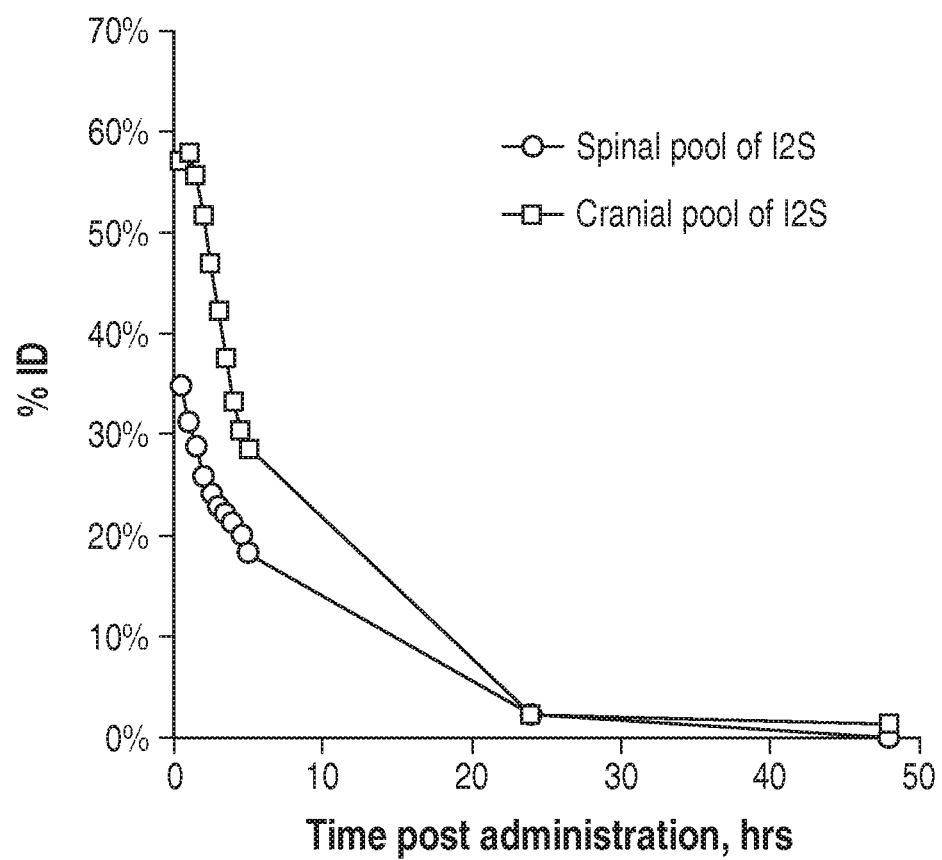
FIG. 85 graphically compares the clearance of iduronate-2-sulfatase (I2S) in the cranial and spinal pools by plotting the amount of I2S in such pools relative to the time following administration.
Figure 86:
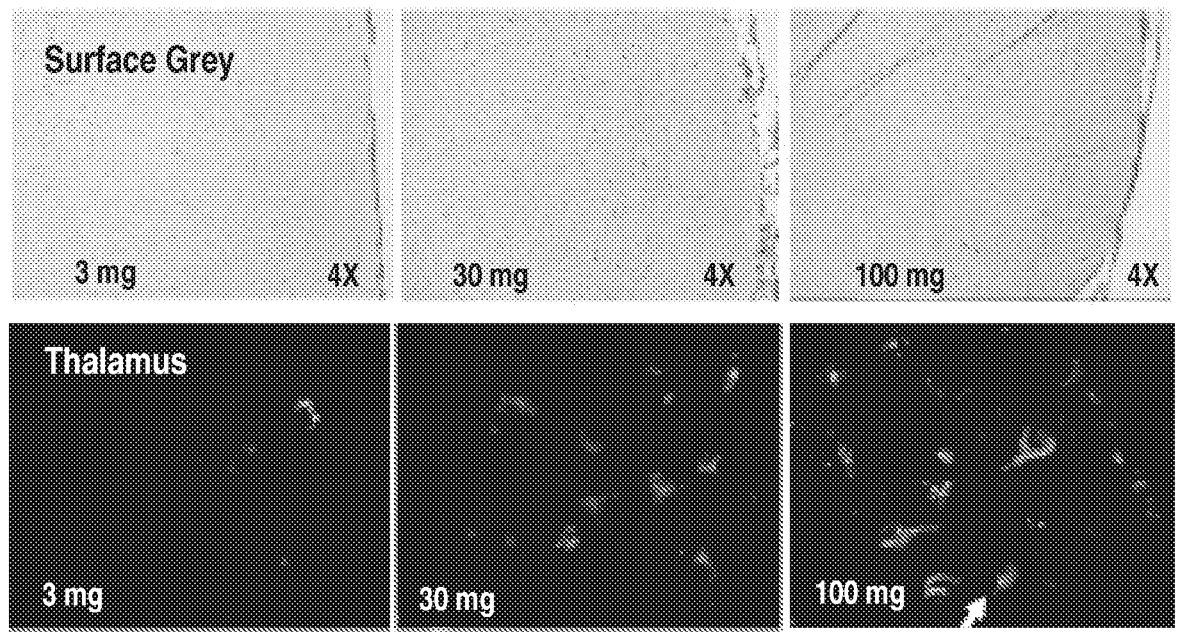
FIG. 86 illustrates the dose dependant gray matter deposition of intrathecally-administered iduronate-2-sulfatase (I2S) to non-human primates over six months. The illustrated staining intensity corresponds with accumulation of iduronate-2-sulfatase in the thalamus. In the present FIG. 86, the nuclei are counterstained by DAPI and appear as blue and protein (I2S) appears as green.
Figure 87:
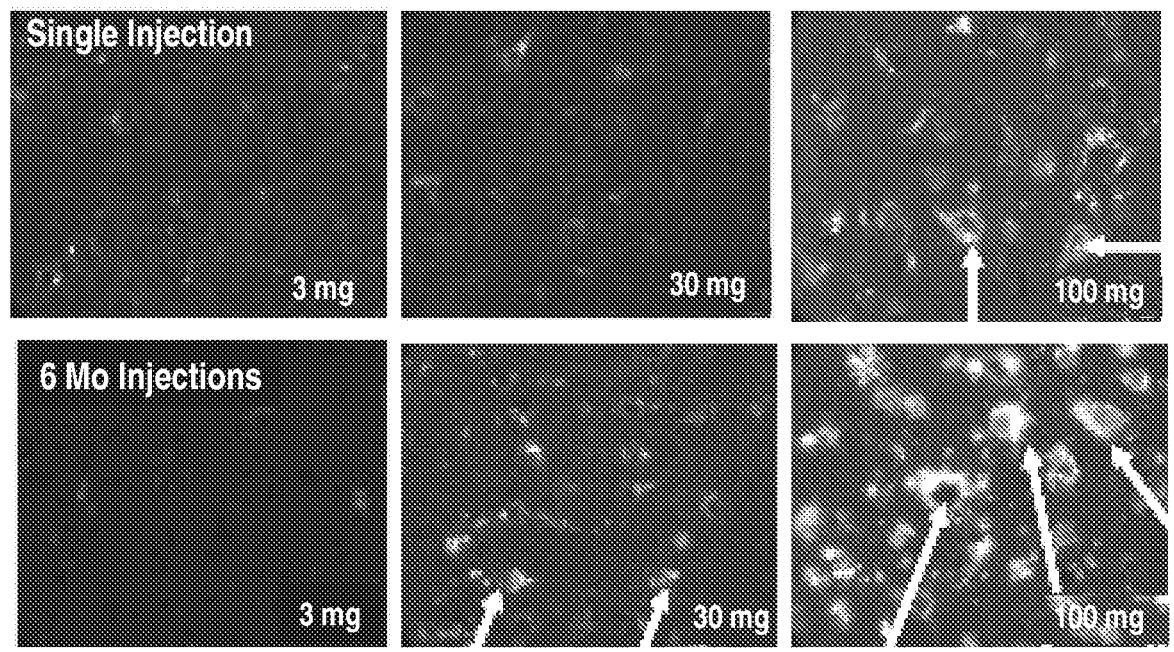
FIG. 87 illustrates the dose dependant accumulation of intrathecally-administered iduronate-2-sulfatase (I2S) to non-human primates following a single injection and following multiple injections over a six month period. The illustrated staining intensity corresponds with accumulation of I2S protein in the cerebral cortex.
Figure 88A:
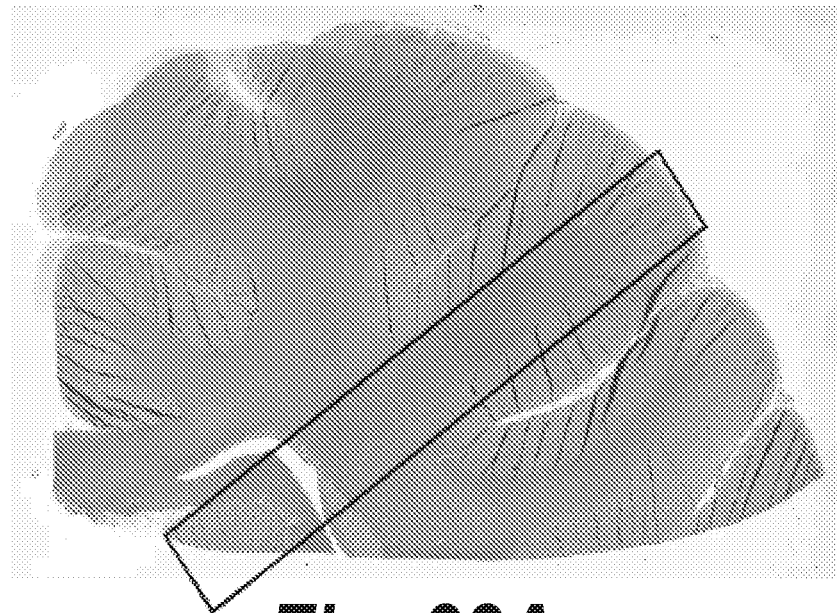
FIG. 88A and FIG. 88B demonstrates the cellular localization of iduronate-2-sulfatase (I2S) throughout the cerebrum of a primate.
Figure 88B:
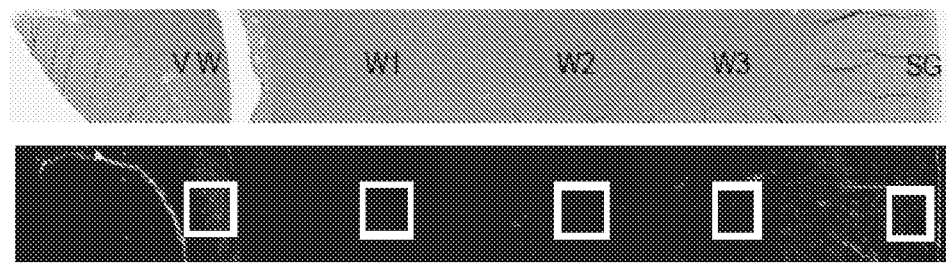
Figure 89A:
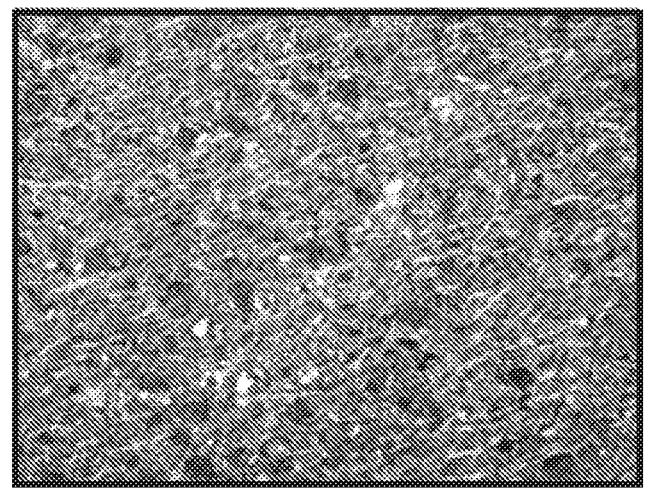
FIG. 89A-D illustrate neuronal and oligodendrocyte uptake and axonal association of intrathecally-administered iduronate-2-sulfatase (I2S) to primates following monthly injections over a six month period. In particular.
Figure 89B:
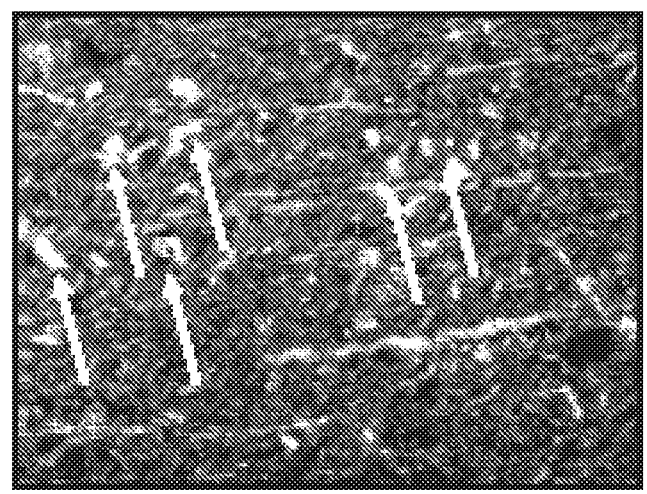
Figure 89C:
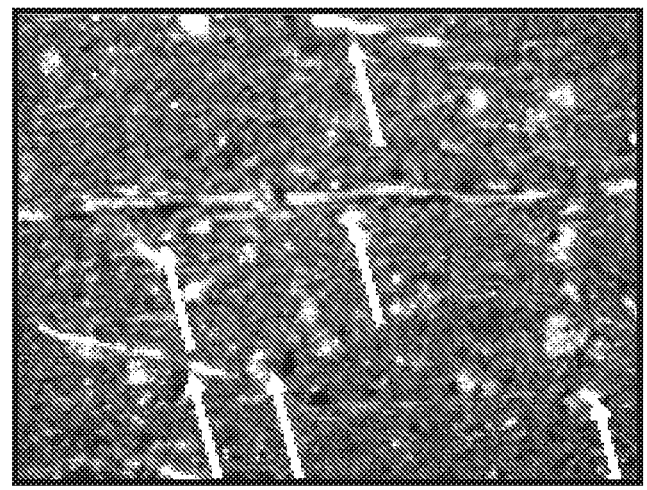
Figure 89D:
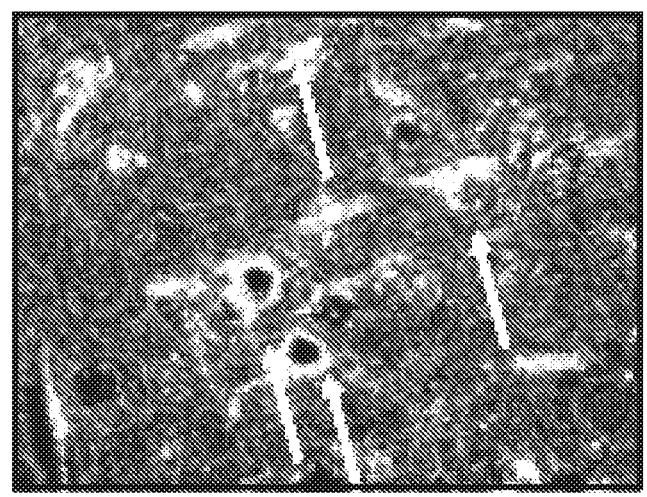

As depicted in FIG. 85 and FIG. 86, distribution of IT-administered I2S into the tissues of the CNS and in particular deposition in the gray matter, thalamus and cerebral cortex of the subject non-human primates is evident. Furthermore, FIG. 86 and FIG. 87 illustrate that the IT-administered I2S accumulates in the depicted CNS tissues of the subject non-human primates in a dose dependant manner. Co-localization staining also revealed that IT administration of I2S associates with both neurons and oligodendrocytes. The IT-administered I2S also distributes and localizes throughout the cerebrum of the subject non-human primates as evidenced by FIG. 88A and FIG. 88B. In particular, FIGS. 89A-D illustrate neuronal uptake and axonal association of the I2S following IT-administration to the non-human primates, as demonstrated by filament staining. Also of particular interest, the present studies illustrate that I2S is selective for neuronal cells and such neuronal cells facilitate the distribution of intrathecally-administered I2S into the deep tissues of the brain and appears to be associated with axonal structures, indicating an anterograde axonal transport of I2S.

Table 25 below present the pharmacokinetic data of various administration routes and doses for a separate animal study.

TABLE 25

| Dose unit | AUClast hr*ng/mL | Body-weight kg | Brain weight kg | Dose mg/kg BW | mg/kg Br wt |
|---|---|---|---|---|---|
| 0.5 mg/kg | 8331 | 2.7 | 0.1 | 0.5 | 5 |
| 1 mg, IT | 1933 | 3.1 | 0.1 | 0.32 | 10 |
| 10 mg, IT | 31316 | 2.7 | 0.1 | 3.66 | 100 |
| 30 mg, IT | 140345 | 2.9 | 0.1 | 10.34 | 300 |

Figure 106:
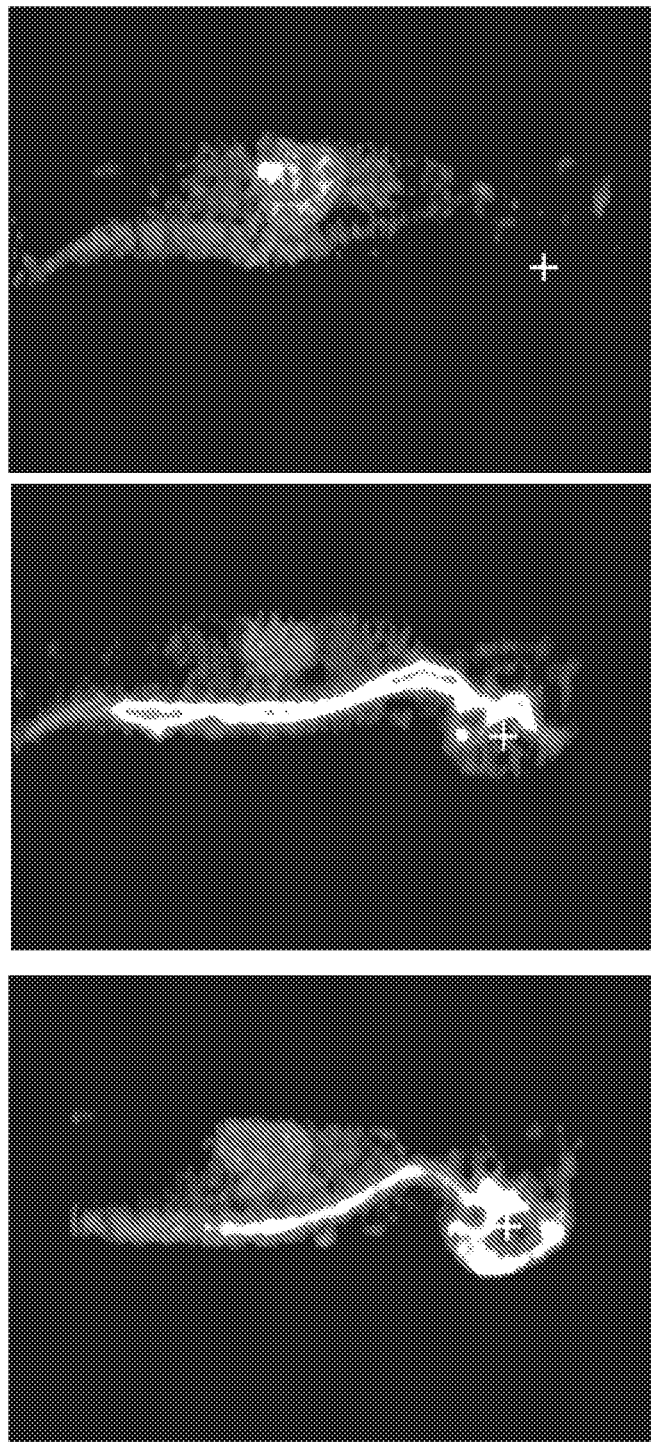
FIG. 106 depicts PET Imaging of $^{124}$I-labeled Idursulfase-IT in Cynomolgus Monkeys at t=5 hours Following IV, IT-L, or ICV dosing.
Figure 107:
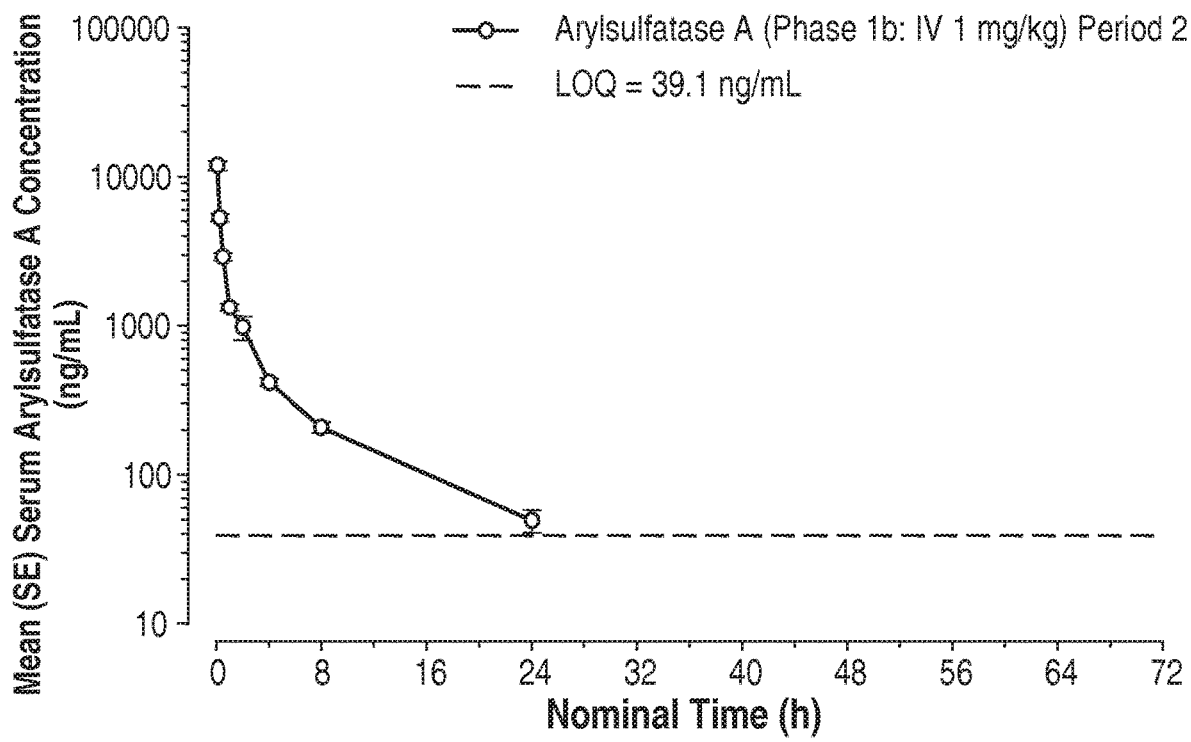
FIG. 107 is an exemplary illustration showing ASA concentration data in serum after intravenous administration.
Figure 108:
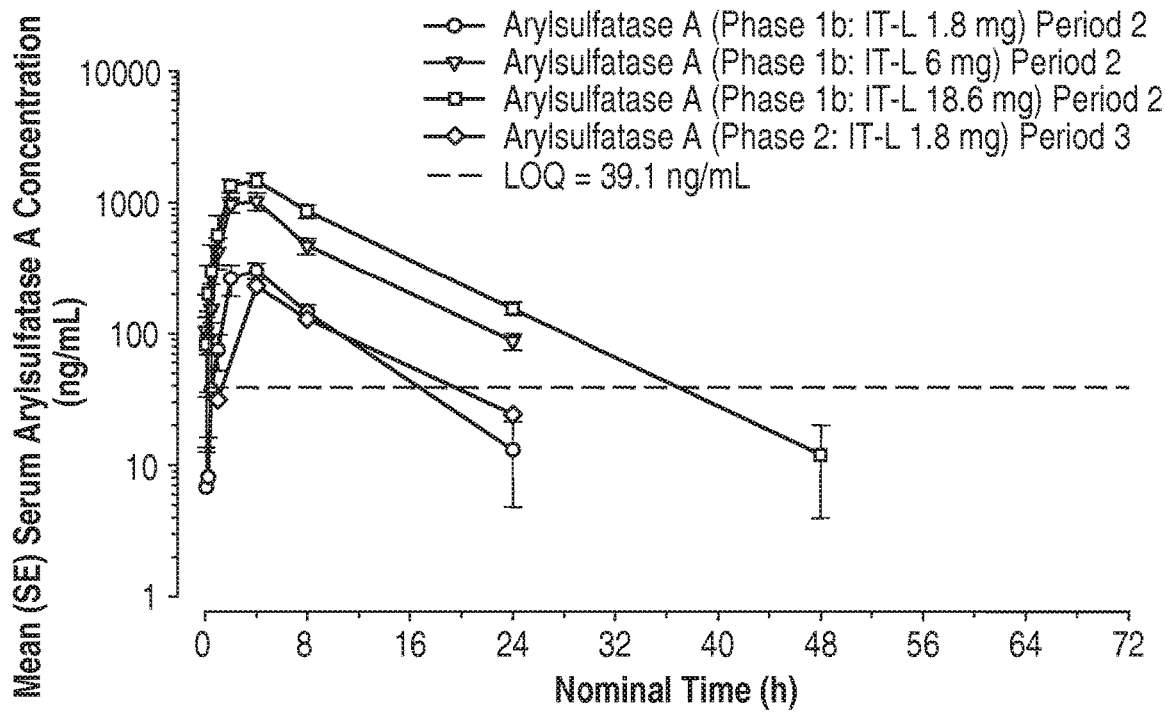
FIG. 108 is an exemplary illustration showing ASA concentration data in serum after IT-lumbar administration.
Figure 109:
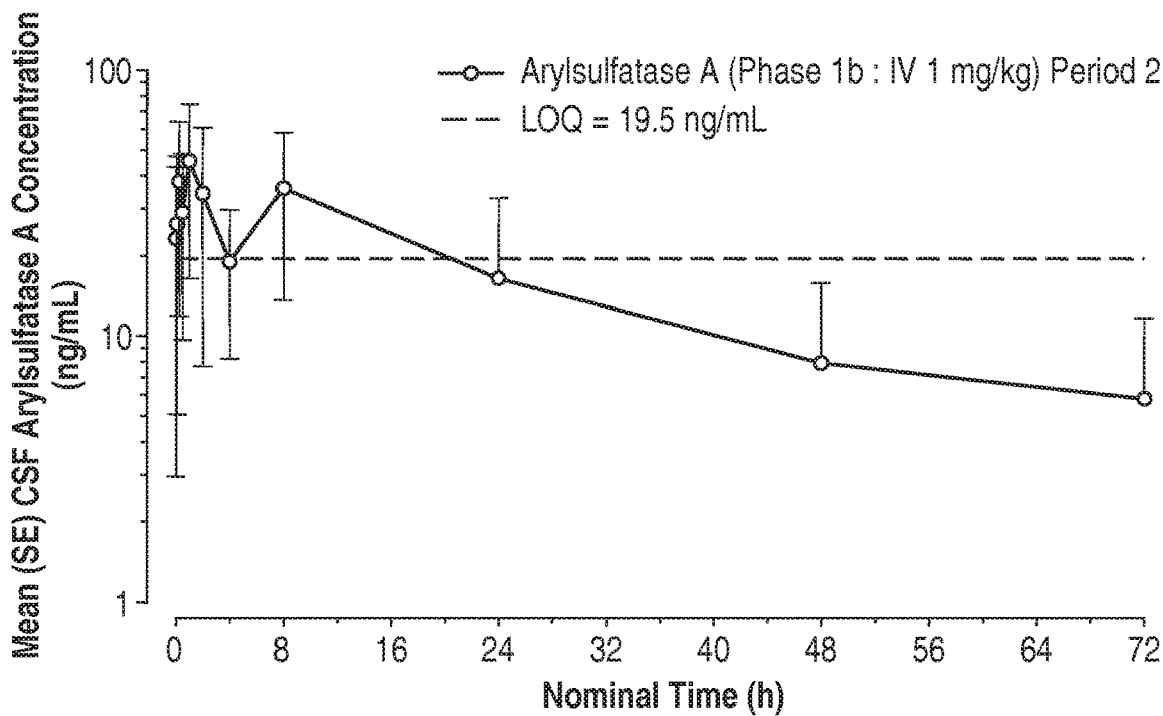
FIG. 109 is an exemplary illustration showing ASA concentration in CSF after IV administration.
Figure 110:
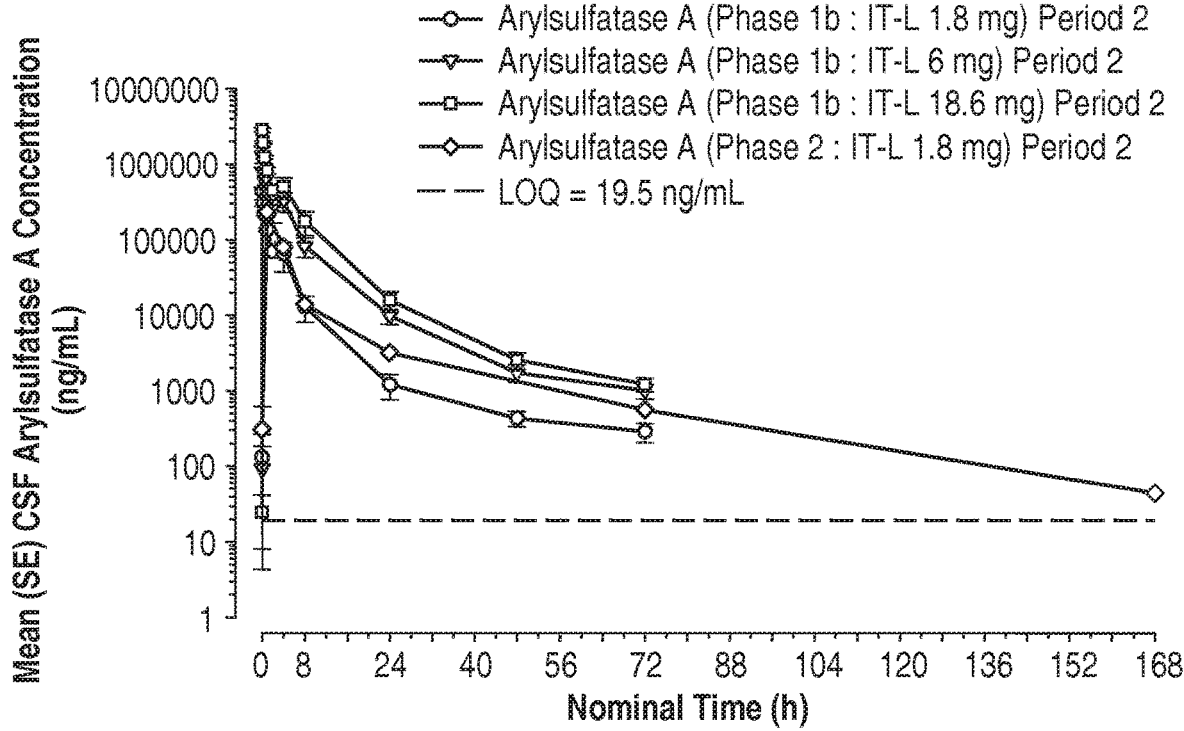
FIG. 110 is an exemplary illustration showing the ASA concentration in CSF after IT-lumbar administration.

$^{124}$I-labeled I2S was administered to test animals as shown in Table 26 below and PET scan results are shown in FIG. 106

TABLE 26

| Group | Animals/Group | Route | Test Article | Dose |
|---|---|---|---|---|
| 1 | 1 | ICV | [124I]-idursulfase | 3 mg |
| 2 | 4 | IT-L | [124I]-idursulfase | 3 mg |
| 3 | 4 | IV | [124I]-idursulfase | 0.1 mg/kg |
| 4 | 4 | IV | [124I]-idursulfase | 1 mg/kg |

Figure 90:
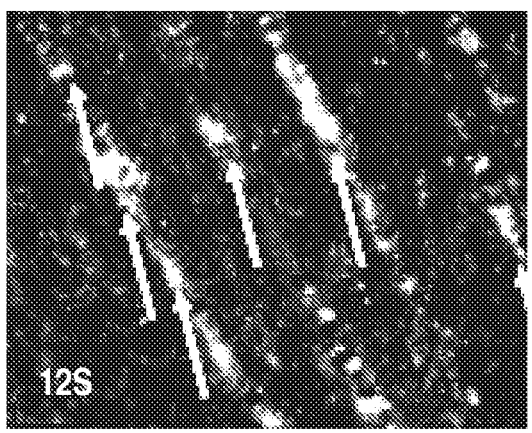
FIG. 90 illustrates the cellular identification of iduronate-2-sulfatase in the white matter near the ventricle (VW) of a non-human primate (arrows in top left). As depicted in the superimposed image (arrows in bottom right), the iduronate-2-sulfatase is not associated with myelin (top right). In the present FIG. 90, the nuclei are counterstained by DAPI (bottom left) Protein (I2S) appears in the top left box.
Figure 90:
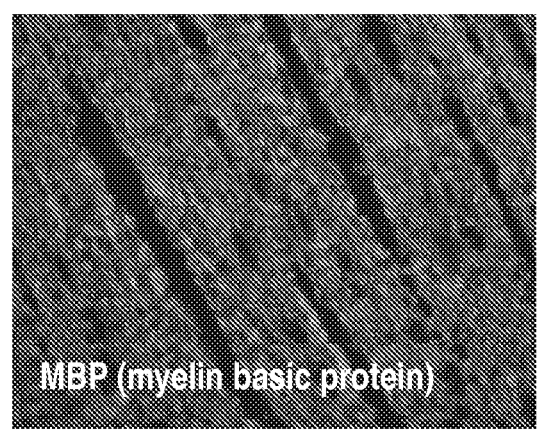
Figure 90:
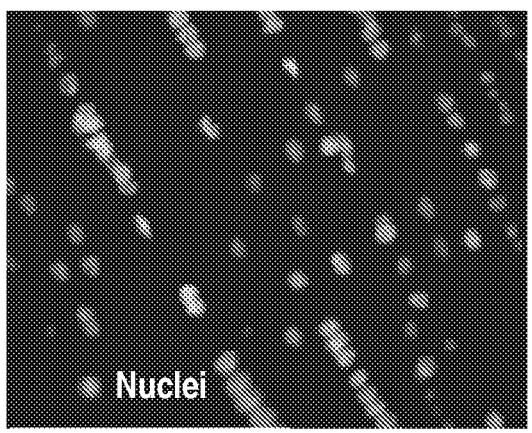
Figure 90:
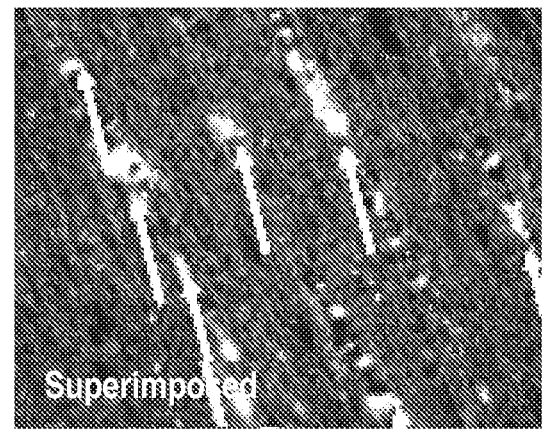

The present studies also demonstrated the cellular identification of IT-administered I2S in white matter brain tissue near the ventricles of the subject non-human primates following IT-administration. While the I2S staining density in the white matter was generally lower than the gray matter, I2S was detected within oligodendrocytes (FIG. 90). In particular, FIG. 90 illustrates the cellular identification of I2S in white matter brain tissues and further demonstrates that I2S does not appear to associate with myelin.

In addition to demonstrating the distribution of IT-administered I2S deep into the tissues of the brain, the present studies also confirmed localization of I2S into the target organelles, and importantly localization of I2S into the lysosomes which are affected organelles in the lysosomal storage disorders, such as Hunter's syndrome. In particular, I2S was located within the lysosomes and also detected within axons. FIG. 90 illustrates the localization of IT-administered I2S within the lysosomes of oligodendrocytes of the subject non-human primate, thereby confirming that IT-administered I2S is capable of distributing into the deep tissues of the brain and is capable of cellular localization.

Figure 104:
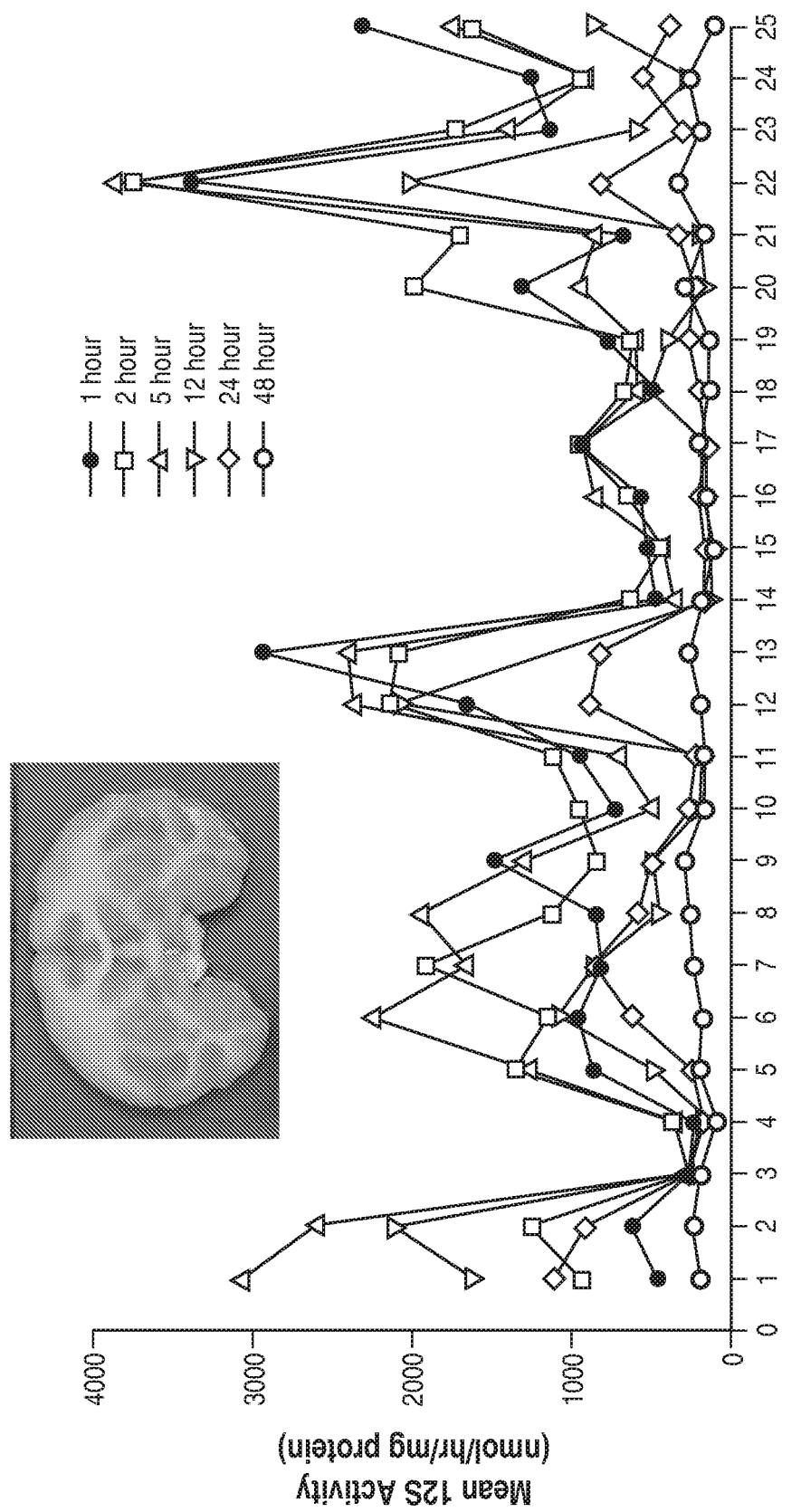
FIG. 104 is an exemplary illustration showing the measurements of I2S concentrations in various sections of brain tissue after 30 mg dose. Different plots correspond to different times of measurement.
Figure 105:
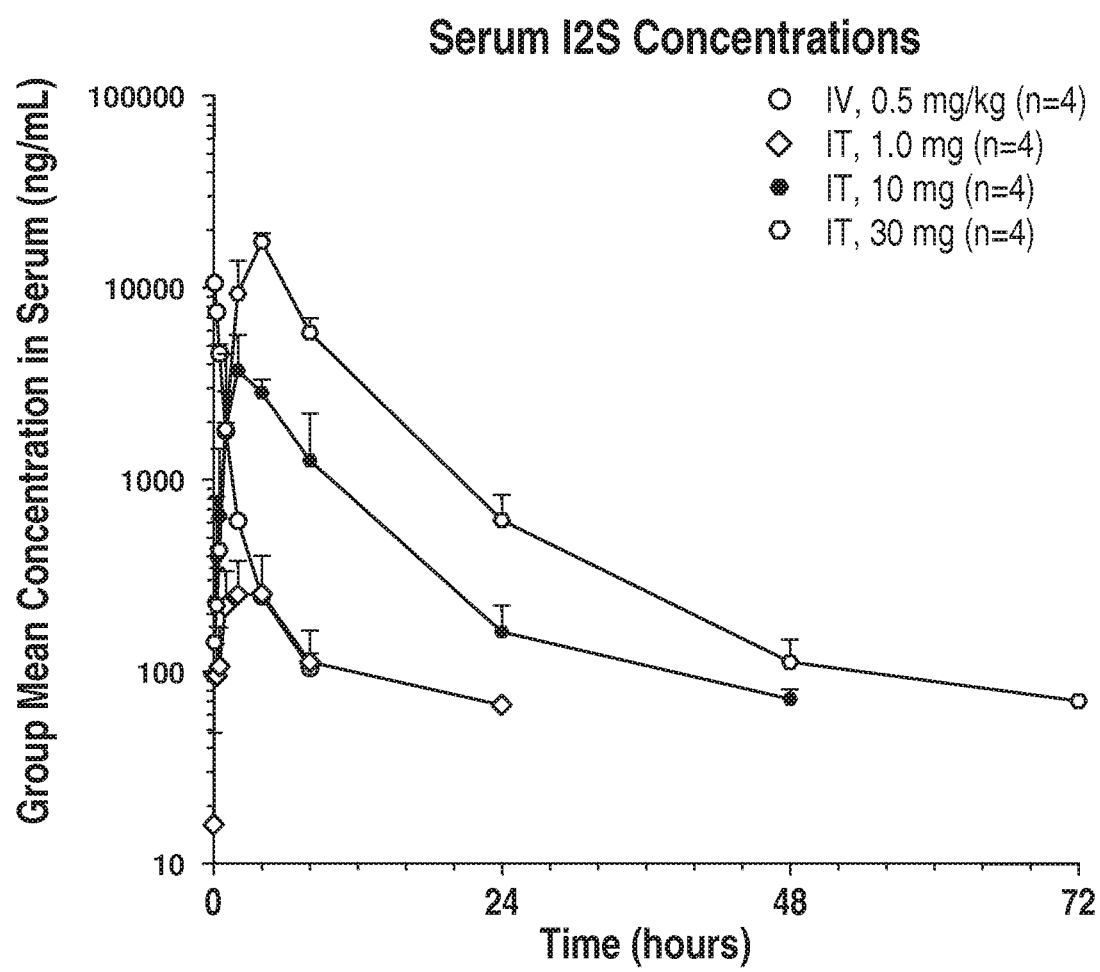
FIG. 105 is an exemplary illustration showing the measurements of I2S concentration after administration over time via various routes of administration for various product concentrations.

In order to discern whether the delivered I2S retained biological activity, levels of I2S in the brain were measured utilizing a specific activity assay. The activity in the brain of the 3 mg IT group 24 hours after the last dose was not apparently different from the basal levels in the device control and vehicle control animals. Enzyme activity in the brain of 30 mg and 100 mg IT dosed animals was above baseline at necropsy (24 hours post-dose). Further animal tests to discern the location of I2S delivery to the brain is shown in FIG. 104 and in Table 27 below.

TABLE 27

| | Location of samples | |
|---|---|---|
| Sample Number | Structure | Slice Number |
| 1 | Cerebral cortex-superficial (L) | 4 |
| 2 | Cerebral cortex-superficial (R) | 4 |
| 3 | Caudate nucleus (R) | 6 |
| 4 | Caudate nucleus (L) | 6 |
| 5 | Corpus callosum | 6 |
| 6 | Cerebral cortex(frontal)-superficial (L) | 8 |
| 7 | Cerebral cortex(frontal)-superficial (R) | 8 |
| 8 | White matter-superficial (L) | 8 |
| 9 | White matter-superficial (R) | 8 |
| 10 | White matter-deep (L) | 8 |
| 11 | White matter-deep (R) | 8 |
| 12 | Cerebal cortex (temporal)-superficial (L) | 8 |
| 13 | Cerebal cortex (temporal)-superficial (R) | 8 |
| 14 | Thalamus (L) | 8 |
| 15 | Thalamus (R) | 8 |
| 16 | Hypothalamus (L) | 8 |
| 17 | Hypothalamus (R) | 8 |
| 18 | Hippocampus (L) | 8 |
| 19 | Hippocampus (R) | 8 |
| 20 | White matter-deep (L) | 10 |
| 21 | White matter- superficial (R) | 10 |
| 22 | Corpus callosum | 10 |
| 23 | White matter-deep (L) | 12 |
| 24 | White matter-deep (R) | 12 |
| 25 | Cerebellum (R) | 14 |

Example 10. Biodistribution of It Delivery in Beagle Dogs

The I2S distribution patterns observed in the foregoing example was also recapitulated in healthy Beagle dogs given a single IT or ICV dose. Male Beagle dogs were randomized using computer-generated numbers into two groups (Group 1 (ICV), N=3; Group 2 (IT); N=4). All had catheters implanted in the subarachnoid space at the lumbar spine or in the left lateral cerebral ventricle (for dosing) and in the cisterna magna (for sampling). All catheters terminated in a subcutaneous titanium access port. An additional dog was used as an un-dosed surgical control.

A single bolus 1 ml injection of I2S (30 mg/ml in 20 mM sodium phosphate, pH 6.0; 137 mM sodium chloride; 0.02% polysorbate-20), was administered IT or ICV, followed by a 0.3 ml flush with phosphate buffered saline (PBS; pH 7.2). Clinical signs were monitored and sacrifice occurred 24 hours following the dose. Brain and spinal cord tissue samples were collected for quantitative I2S analyses as determined by ELISA, I2S enzyme activity and IHC, and compared between the study groups.

Figure 91:
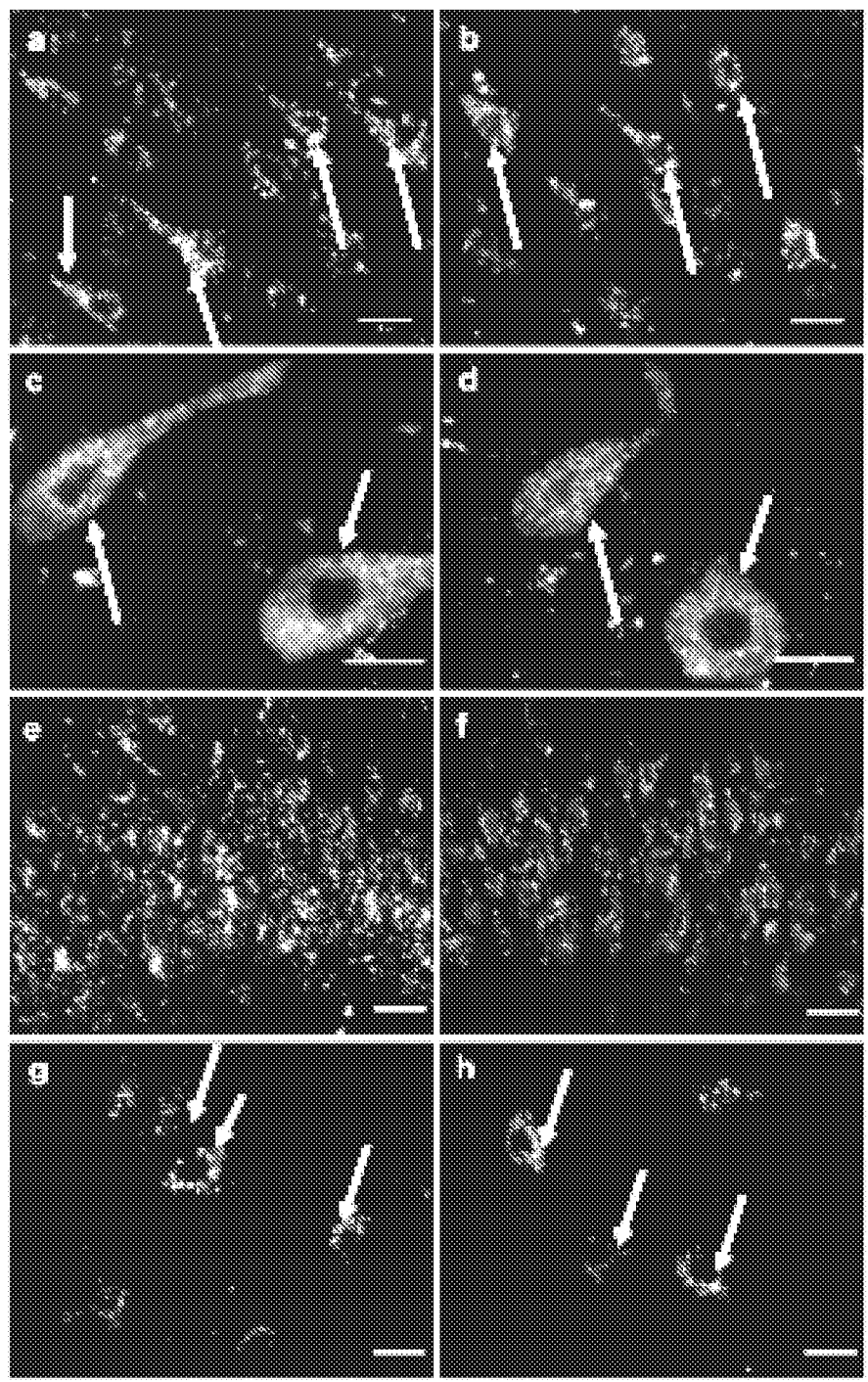
FIG. 91 illustrates staining in the tissues of healthy Beagle dogs that were intracerebroventricularly (ICV) or intrathecally (IT) administered a single injection of iduronate-2-sulfatase (I2S). As depicted in images a-h, I2S was widely distributed throughout the gray matter of both the IT and ICV groups as determined by immunohistochemistry (IHC). Images a and b illustrate that in the cerebral cortex, neurons were positive for I2S in all six neuronal layers, from the surface molecular layer to the deep internal layer in both IT and ICV groups. Images c and d illustrate that in the cerebellar cortex of the IT and ICV groups I2S was detected in neurons, including Purkinje cells. Similarly, images e and f illustrate that in both IT and ICV groups a large population of neurons in the hippocampus were positive for I2S. Finally, images g and h demonstrate that I2S-positive neurons were also found in the thalamus and caudate nucleus in the both the IT and ICV groups. In the present FIG. 91, I2S staining is indicated with arrows.

I2S was widely distributed throughout the gray matter of both IT and ICV groups as determined by IHC. In the cerebral cortex, neurons were positive for I2S in all six neuronal layers, from the surface molecular layer to the deep internal layer in both IT and ICV groups, as illustrated by FIG. 91 (images a and c). In the cerebellar cortex of the IT and ICV groups, I2S was detected in neurons, including Purkinje cells, as illustrated by FIG. 91 (images c and d). In both IT and ICV groups a large population of neurons in the hippocampus were positive for I2S, as demonstrated by FIG. 91 (images e and f). I2S positive neurons were also found in the thalamus and caudate nucleus in both of the groups, as illustrated in FIG. 91 (images g and h).

The present studies therefore confirm the ability of IT-administered enzymes to distribute into the deep cells and tissues of the brain and support the utility of IT-administered enzymes such as I2S for the treatment of the CNS manifestations associated with lysosomal storage diseases, such as Hunter's syndrome.

Example 11. In Vivo Efficacy of IT Delivered I2S

Iduronate-2-sulfatase Deficient Mouse Model

Having demonstrated that IT-administered I2S is capable of distributing into the deep tissues of the brain and cellular localization of I2S, further studies were conducted to determine the therapeutic efficacy of IT-administered I2S. A genetically-engineered iduronate-2-sulfatase knock-out (IKO) mouse model of Hunter syndrome was developed to study the ability of the IT-administered I2S to alter disease progression. The I2S knock-out mouse model was developed using a targeted disruption of the I2S locus which results in an accumulation of glycosaminoglycans (GAG) in tissues and organs. The IKO mouse model exhibits many of the physical characteristics of Hunter syndrome seen in humans, including the characteristic coarse features and skeletal defects. In addition, the IKO mouse model demonstrates elevated glycosaminoglycan (GAG) levels in urine and in tissues throughout the body, as well as widespread cellular vacuolization which was observed histopathologically.

In the present study, commercially-available I2S (Elaprase®) was concentrated and re-suspended in phosphate buffered saline (PBS). Six groups of male IKO mice, 8-12 weeks old, were treated with I2S (10 µl; 26 mg/ml). Groups A and B (N=3) were intrathecally administered three 260 µg doses (at days 1, 8, and 15) and two 260 µg doses (at days 1 and 8) of I2S, respectively. Group D was also treated with three intrathecally administered 260 µg doses at days 1, 8, and 15. Group C and E (N=3) were untreated control groups and group F (N=3) was an untreated wild-type control. Control mice were administered a vehicle without I2S. Mice were sacrificed after 1 hour following the last injection, followed by tissue preparation for immunohistochemistry (IHC) and histopathological analysis.

Following the third injection, there was widespread reduction of cellular vacuolation in the surface cerebral cortex, caudate nucleus, thalamus and the cerebellum in I2S-treated mice compared to vehicle-treated mice. Reductions in cellular vacuolation were also found in the white matter after IT treatment. Distribution of I2S to the brain tissues of the IKO mouse was evident following IT-administration.

Figure 92:
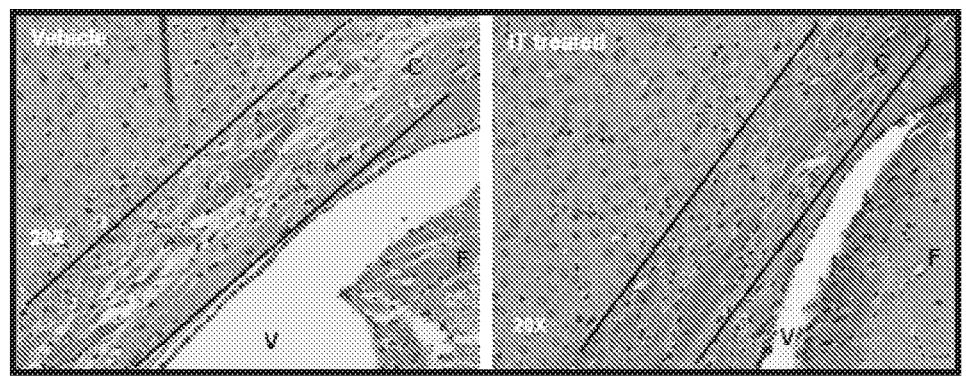
FIG. 92 comparatively illustrates corpus callosum tissues of iduronate sulfatase knock-out (IKO) mice that were either untreated or were administered I2S intrathecally. As depicted, the treated IKO mice exhibited a reduction of cellular vacuolation characteristic of certain lysosomal storage disorders in the corpus callosum and fornix tissues of the I2S-treated IKO mouse.

Three weekly IT administrations of I2S in the IKO mice also demonstrated a marked reduction in CNS cellular vacuolization at both light and electronic microscopic levels. Following IT administration of I2S, a reduction of cellular vacuolation was evident relative to untreated IKO mice, suggesting that IT-administered I2S is capable of altering disease progression. As illustrated in FIG. 92, a reduction of cellular vacuolation was evident in the corpus callosum and fornix of the IKO mice following IT-administration of I2S.

Additionally, electron microscopy demonstrated a reduction in the presence of storage inclusions in neurons in the gray matter and vacuolation in oligodendrocytes in the white matter. In particular, the IKO mice IT-administered I2S also demonstrated a reduction in palisaded lamellar bodies ("zebra bodies") which are characteristic of certain lysosomal storage diseases. In particular, FIG. 57 represents an electron microscope scan illustrating a reduction of the characteristic zebra bodies in the neurons of the IKO mouse that was administered I2S, relative to the untreated IKO mouse. Similarly, FIG. 57 illustrates an electron microscope scan of oligodendrocytes in the corpus callosum.

Figure 93A:
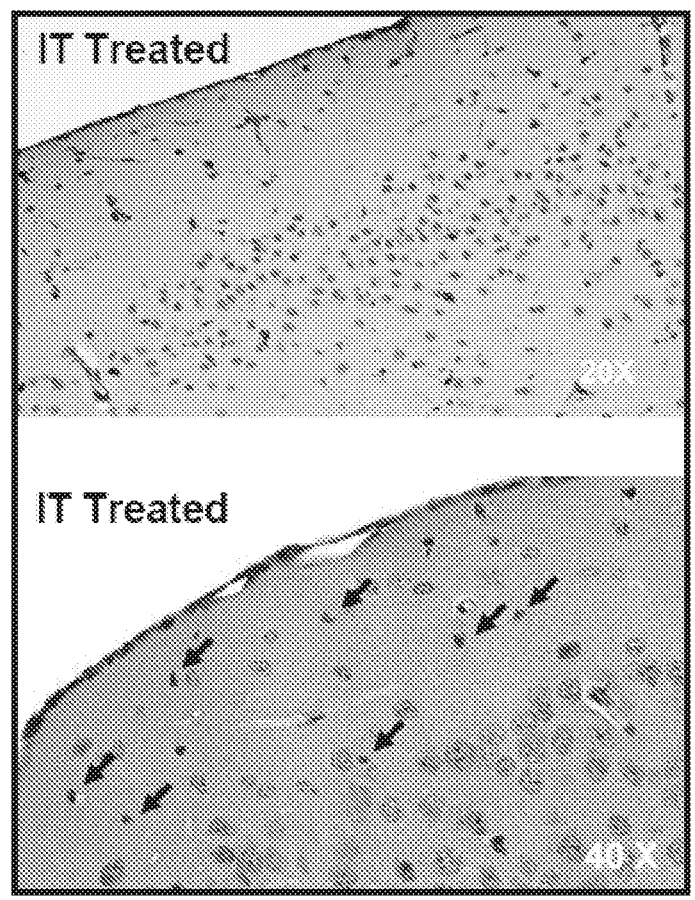
FIG. 93A illustrates a marked reduction in the presence of lysosomal associated membrane protein 1 (LAMP1), a lysosomal disease pathological biomarker, in the surface cerebral cortex tissues of the treated IKO mouse (FIG. 93A) relative to the untreated IKO control mouse (FIG. 93B) under both 20× and 40× magnification.
Figure 93B:
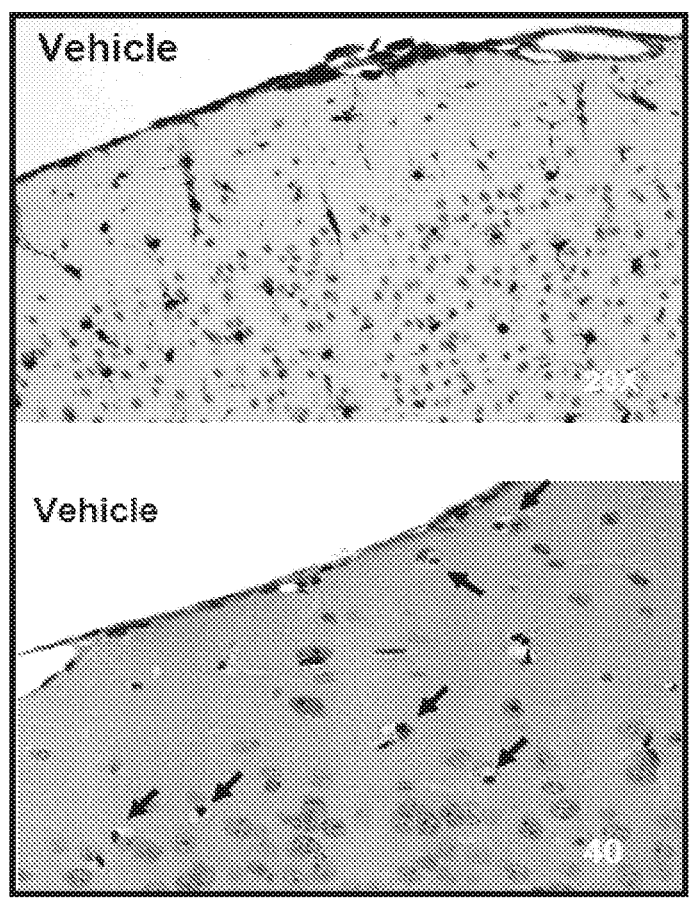
Figure 94:
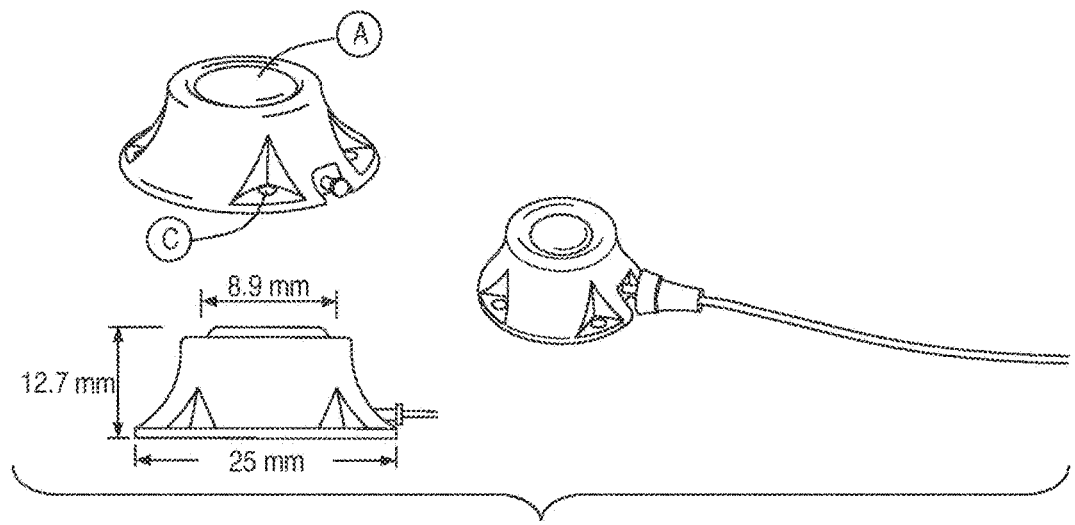
FIG. 94 depicts an exemplary intrathecal drug delivery device (IDDD).
Figure 95:
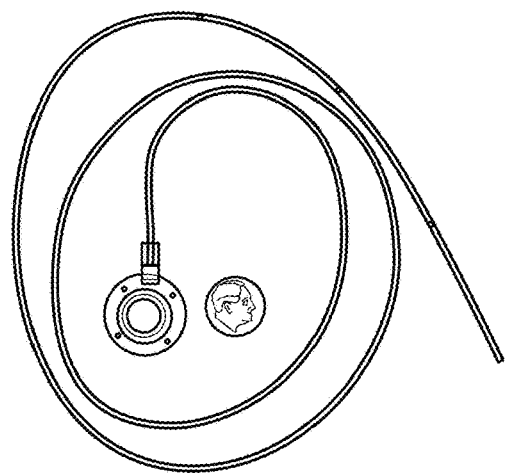
FIG. 95 depicts an exemplary PORT-A-CATH® low profile intrathecal implantable access system.
Figure 96:
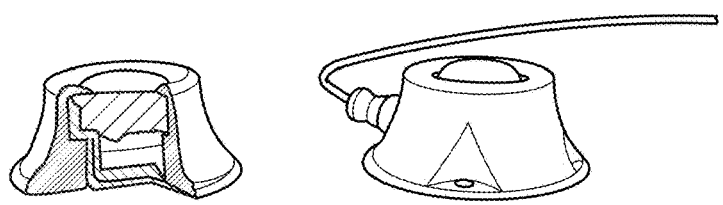
FIG. 96 depicts an exemplary intrathecal drug delivery device (IDDD).
Figure 97:
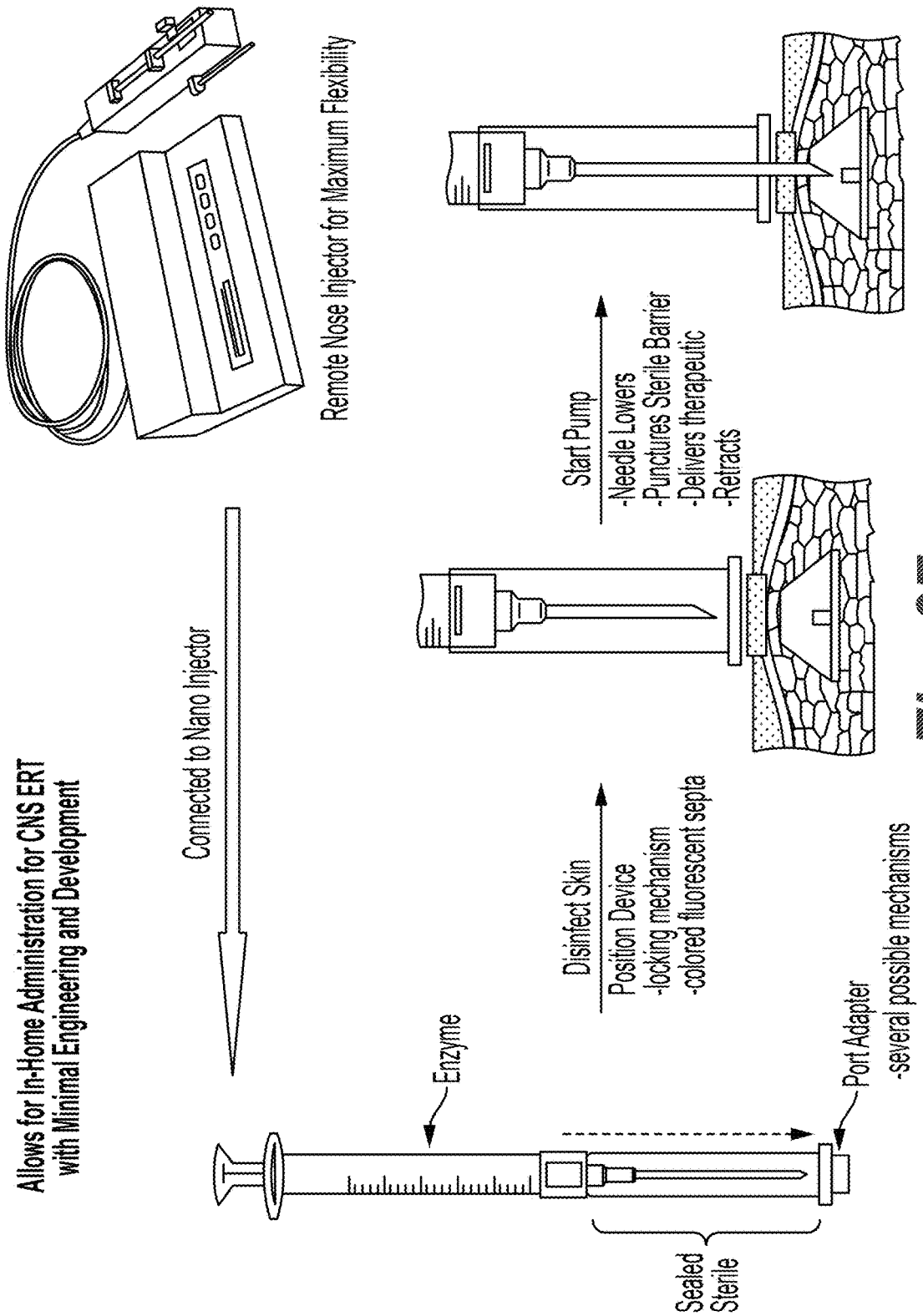
FIG. 97 depicts an exemplary intrathecal drug delivery device (IDDD), which allows for in-home administration for CNS enzyme replacement therapy (ERT).
Figure 98:
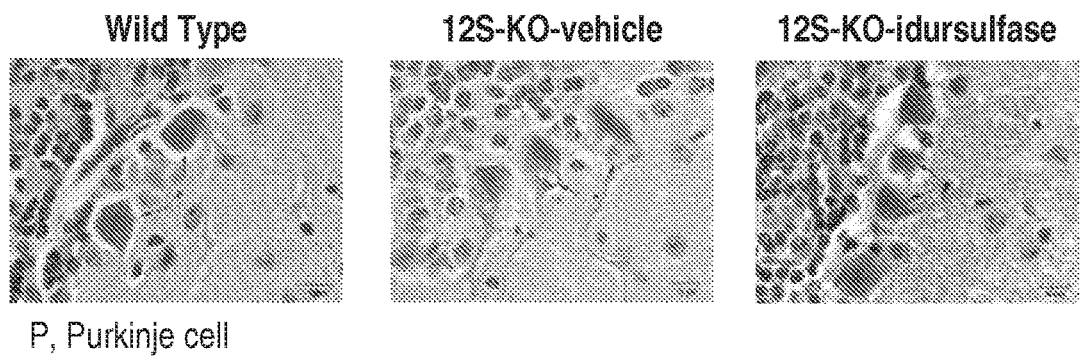
FIG. 98 is an exemplary illustration showing the effect of vacuolization after a single intra-cerebral injection of idursulfase in neurons (Purkinje cells).
Figure 99:
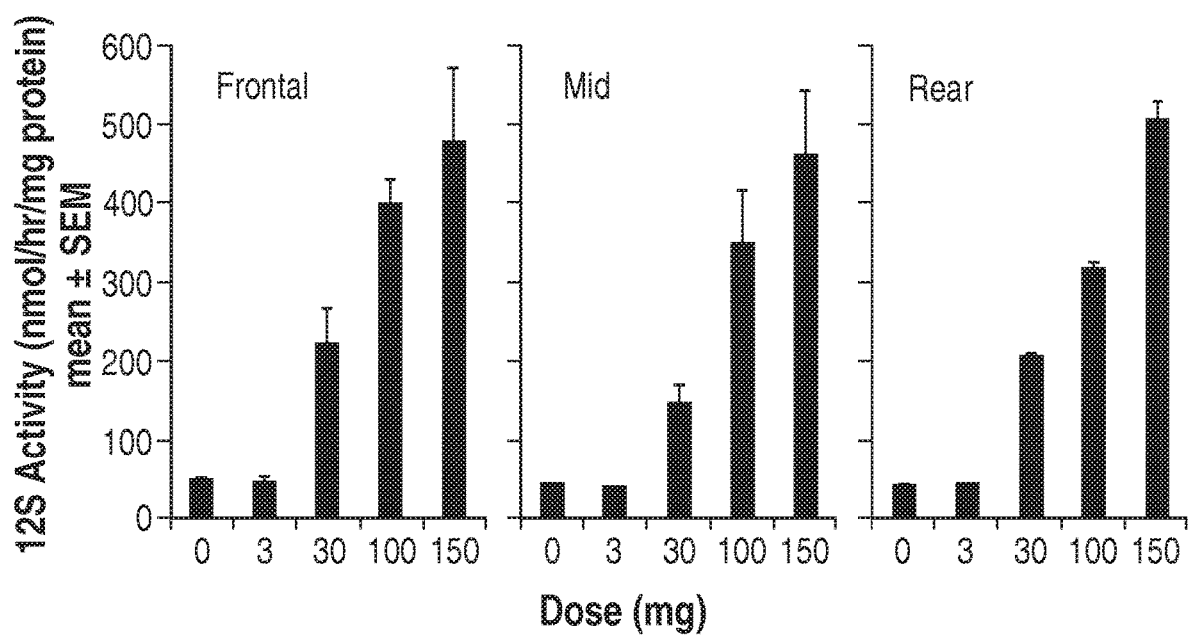
FIG. 99 is an exemplary illustration showing I2S activity in the brain by dose and region.
Figure 100:
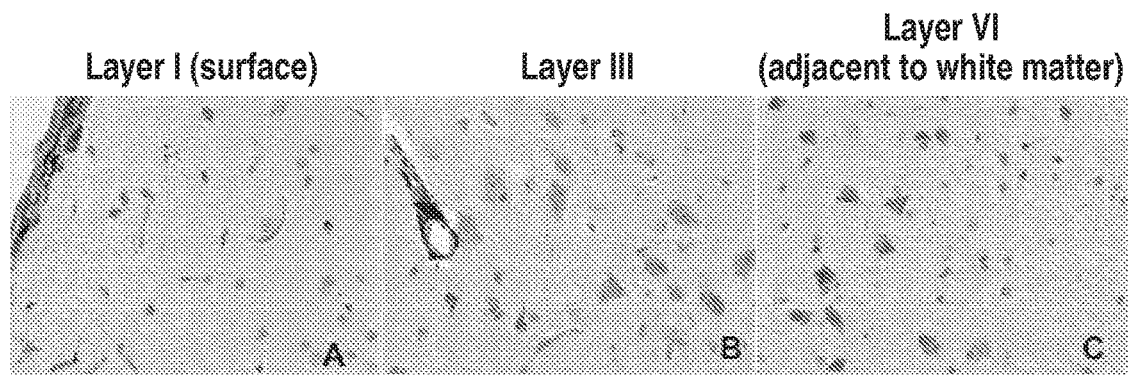
FIG. 100 is an exemplary illustration showing data of immunohistolochemical localization of Idursulfase at different depths of the cerebral cortex.
Figure 101:
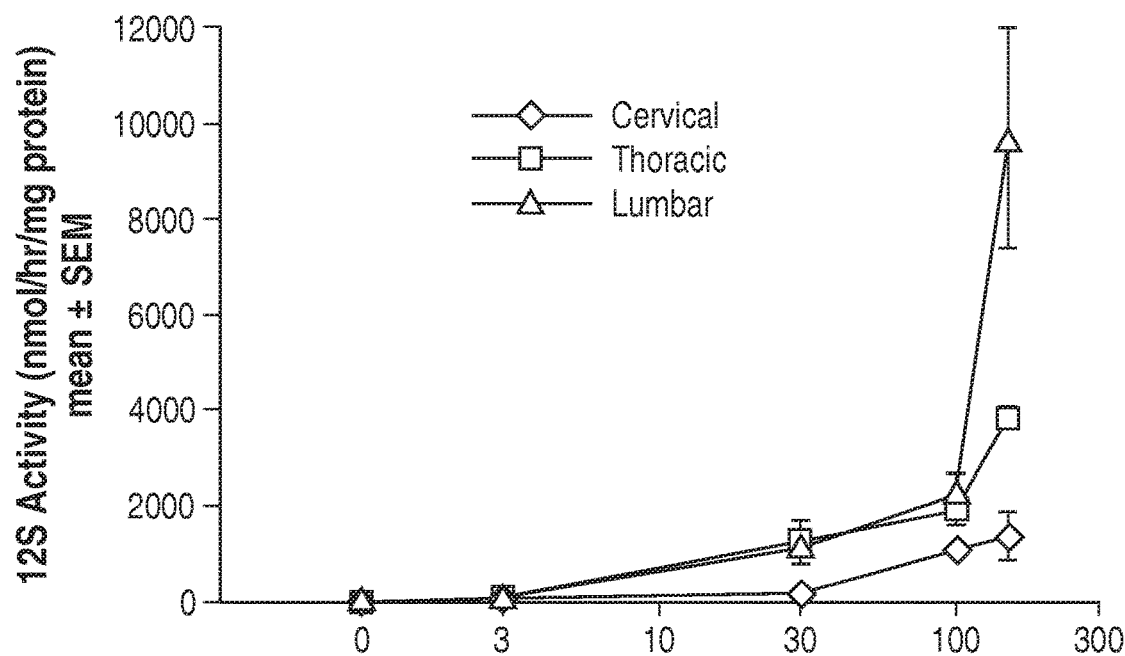
FIG. 101 is an exemplary illustration showing I2S activity in the spinal cord of monkey following intrathecal dosing with idursulfase.
Figure 102:
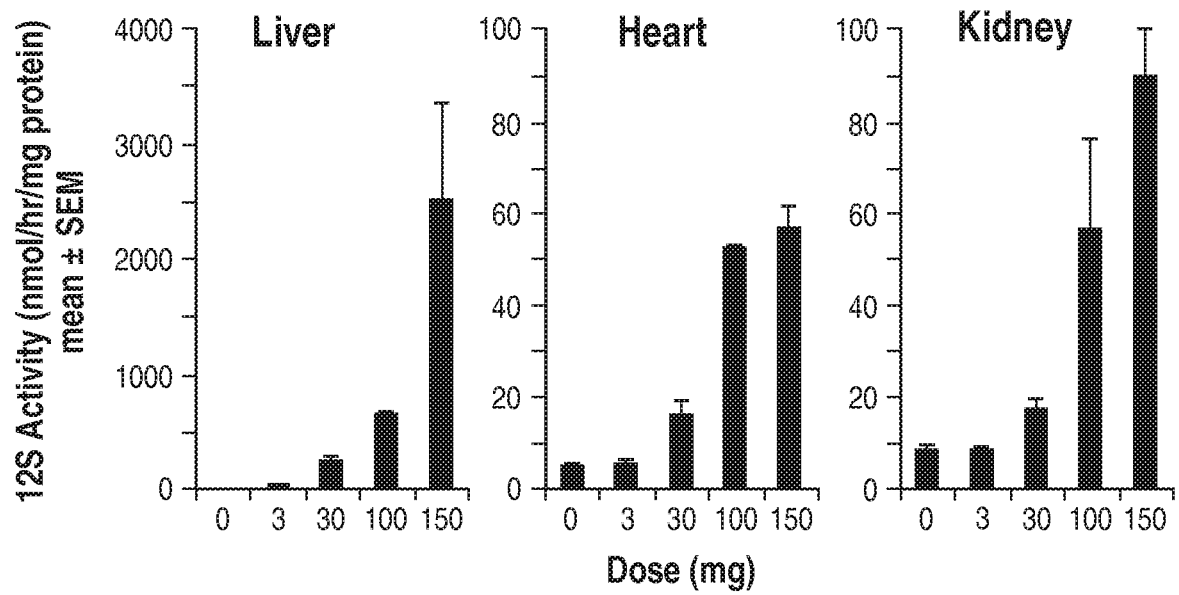
FIG. 102 is an exemplary illustration showing I2S activity in monkey liver, heart and kidney after intrathecal dosing with Idursulfase.
Figure 103:
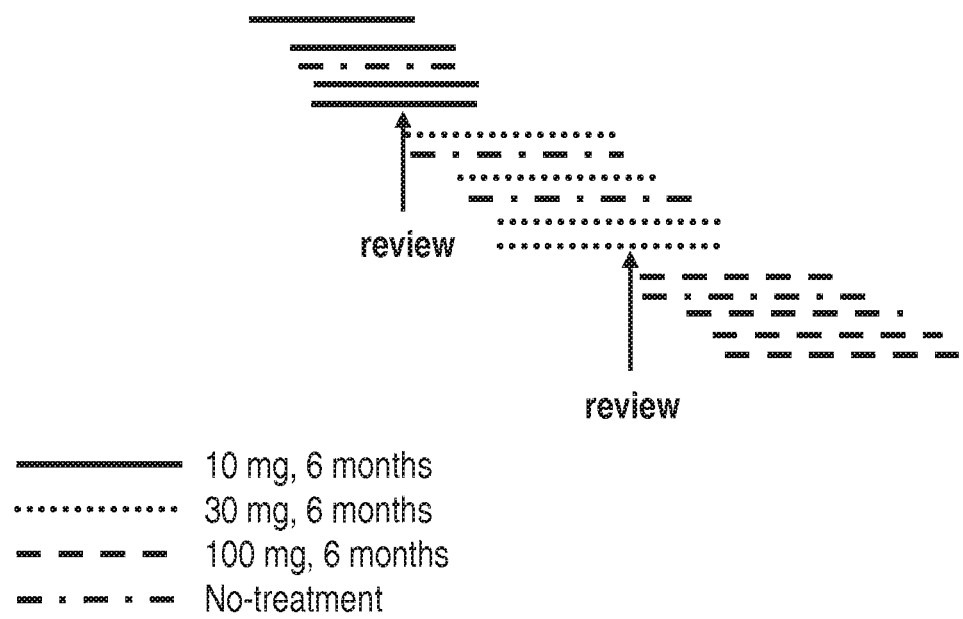
FIG. 103 depicts an exemplary schematic for an escalation Hunter-IT trial program.

In addition, the IT administrations of I2S to the IKO mice also demonstrated a marked reduction in the lysosomal disease pathological biomarker lysosomal associated membrane protein 1 (LAMP1) immunostaining, an indicator of lysosomal activity and disease state, in the surface cerebral cortex, caudate nucleus, thalamus, cerebellum and white matter. As illustrated in FIG. 93A, a marked reduction in LAMP1 immunostaining is evident in the treated IKO mouse surface cerebral cortex tissue relative to the untreated IKO control mouse surface cerebral cortex tissue illustrated in FIG. 93B, reflecting an improvement in disease pathology.

FIG. 56 quantitatively illustrates and compares the concentration of LAMP1 measured in $\mu m^2$ areas of brain tissue. Morphometrical analysis of LAMP-1 immunostaining of various brain regions confirmed that there were significant reductions in the LAMP-1 positive staining in all areas of the brain evaluated. As shown in FIG. 56, in each area of brain tissue evaluated (the cortex, caudate nucleus and putamen (CP), thalamus (TH), cerebellum (CBL) and white matter (WM)) the LAMP-positive area was reduced in the treated IKO mice relative to the untreated IKO control mice, and approached the LAMP-positive area of the wild-type mice. Particularly notable is that the LAMP-positive areas in each area of brain tissue analyzed were further reduced with continued treatment duration.

Reduction of abnormally high lysosomal activity correlated with dramatic morphological improvements in all areas of the brain. These results confirm that IT-administered I2S is capable of altering progression of lysosomal storage diseases, in a genetically-engineered IKO mouse model, further confirming the ability of IT-administered enzymes such as I2S to treat the CNS manifestations associated with lysosomal storage diseases, such as Hunter's syndrome.

Example 12—Treatment of Hunter'S Disease Patients

Direct CNS administration through, e.g., IT delivery can be used to effectively treat Hunter's Disease patients. This example illustrates a multicenter dose escalation study designed to evaluate the safety of up to 3 dose levels every other week (EOW) for a total of 40 weeks of I2S administered via an intrathecal drug delivery device (IDDD) to patients with late infantile Hunter's Disease. Various exemplary intrathecal drug delivery devices suitable for human treatment are depicted in FIG. 89-FIG. 92.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria: (1) appearance of first symptoms prior to 30 months of age; (2) ambulatory at the time of screening (defined as the ability to stand up alone and walk forward 10 steps with one hand held); (3) presence of neurological signs at time of screening. Typically, patients history of hematopoietic stem cell transplantation are excluded.

Safety of ascending doses of I2S administered by IT injection for 40 weeks in children with late infantile Hunter's Disease is determined. In addition, the clinical activity of I2S on gross motor function, and single and repeated-dose pharmacokinetics in serum and concentrations in cerebrospinal fluid (CSF) are assessed.

IT Delivery of rhASA Protein

Example 13: Toxicology Study of IT-delivered Recombinant ASA

To assess the ability of other intrathecally-administered recombinant enzymes to distribute into the cells and tissues of the CNS, GLP study was conducted to evaluate repeat dose intrathecal (IT) administration of recombinantly-prepared human arylsulfatase A (rhASA) from a toxicology and safety pharmacology perspective over a one-month period in juvenile (less than 12 months of age) cynomolgus monkeys. The formulation of rhASA was prepared and formulated in a vehicle of 154 mM NaCl, 0.005% polysorbate 20 at a pH of 6.0.

To achieve this, nine male and nine female juvenile cynomolgus monkeys were randomly assigned by body weight to one of three treatment groups as shown in the following Table 28. The animals (with the exception of 1 male animal for Dose 1) received 0.6 mL short-term IT infusion of 0, 3 or 31 mg/mL of rhASA (total dose of 0, 1.8 or 18.6 mg) every other week for a total of three doses per animal. Body weights, clinical observations, neurological and physical examinations, clinical pathology, ophthalmologic examinations, and toxicokinetic sampling were monitored. All of the animals were necropsied on Day 29, 30 or 31 (~24 hours after the last IT dose). Selected tissues were harvested, saved and examined microscopically.

TABLE 28

| Group | Number of Animals | Nominal Concentration Dose (mg/ml) | Volume Dose (mL) | Dose Administered (mg) |
| --- | --- | --- | --- | --- |
| 1 | 3M, 3F | 0 | 0.6 | 0 |
| 2 | 3M, 3F | 3 | 0.6 | 1.8 |
| 3 | 3M, 3F | 31 | 0.6 | 18.6 |

The concentrations of rhASA detected in the CNS tissues of the cynomolgus monkeys were analyzed by ELISA and compared to a therapeutic target of 10% of normal human rhASA concentrations, corresponding to approximately 2.5 ng/mg of tissue. Tissue samples or punches were extracted from different areas of the brains of the cynomolgus monkeys and further analyzed for the presence of rhASA. FIG. 133-FIG. 138 illustrates the tissues from which the punches were extracted. The punched tissue samples reflected an increase in the concentrations of rhASA, as reflected in FIG. 139A-G, with a deposition gradient from the cerebral cortex to the deep white matter and deep gray matter.

Concentrations of rhASA detected using the same punch from both the IT and ICV routes of administration for six monkeys administered the 18.6 mg dose of rhASA, are illustrated in FIG. 140A-B. The concentrations of rhASA detected in the deep white matter (FIG. 140A) and in the deep grey matter (FIG. 140B) brain tissues of adult and juvenile cynomolgus monkeys intrathecally—(IT) or intracerebroventricularly—(ICV) administered rhASA were comparable.

The punched tissue samples extracted from the brains of adult and juvenile cynomolgus monkeys were then analyzed to determine the concentrations of rhASA deposited in the extracted tissue sample, and to compare such concentrations to the therapeutic target concentration of 2.5 ng rhASA per mg protein (corresponding to 10% of the normal concentration of rhASA in a healthy subject). As illustrated in FIG. 141A, in each tissue sample punch analyzed the 18.6 mg dose of IT-administered rhASA resulted in an rhASA concentration which exceeded the target therapeutic concentration of 2.5 ng/mg of protein. Similarly, when a 1.8 mg dose of rhASA was IT-administered to juvenile cynomolgus monkeys, each tissue sample punch analyzed demonstrated a concentration of rhASA either within or exceeding the therapeutic concentration of 2.5 ng/mg of protein and the median rhASA concentrations were above the therapeutic target for all tissue punches tested (FIG. 141B).

To determine whether IT-administered rhASA was distributing to the relevant cells, tissue was analyzed from the deep white matter of a cynomolgus monkey IT-administered 1.8 mg of rhASA, from the area illustrated in FIG. 142A. Immunostaining of the deep white matter tissue revealed distribution of rhASA in the cynomolgus monkey in oligodendrocyte cells, as illustrated by FIG. 142B. Similarly, FIG. 142C illustrates that the IT-administered rhASA demonstrated co-localization in the deep white matter tissues of the cynomolgus monkey. In particular, under staining co-localization in target organelles, such as the lysosome, is evident (FIG. 142C), supporting the conclusion that IT-administered rhASA is capable of distributing to the relevant cells, tissues and organelles of the CNS, including the lysosomes of oligodendrocytes.

Example 14. ICV-vs. IT-Administration rhASA labeled with the positron emitter $^{124}$I was prepared and formulated in a vehicle of 154 mM NaCl, 0.005% polysorbate 20 at a pH of 6.0. A volume of the formulation equivalent to 3 mg of rhASA (corresponding to approximately 38 mg/kg of brain) was administered to adult cynomolgus monkeys via intracerebroventricular (ICV) and intrathecal (IT) routes of administration. The cynomolgus monkeys were subject to high-resolution PET scan imaging studies (microPET P4) to determine distribution of the administered $^{124}$I-labeled rhASA.

PET imaging data (FIG. 143) illustrates that both the ICV- and IT-administered $^{124}$I-labeled rhASA effectively distributed to the tissues of the CNS, and in particular the $^{124}$I-labeled rhASA administered through the IT-lumbar catheter immediately and uniformly spread in the cerebrospinal fluid (CSF) over the length of the spine. In particular, as depicted in FIG. 143, following ICV- and IT-administration, therapeutic concentrations of $^{124}$I-labeled rhASA were detected in the CNS tissues of the subject cynomolgus monkey, including the brain, spinal cord and CSF. The concentrations of rhASA detected in such CNS tissues, and in particular in the tissues of the brain, exceeded the therapeutic target concentration of 2.5 ng/mg of protein.

While the distribution of rhASA protein was comparable for both IT and ICV routes of administration, ICV resulted in notably less deposition within the spinal column, as evidence by FIG. 143.

Twenty four hours following administration of the formulation, both the ICV- and IT-administered $^{124}$I-labeled rhASA effectively distributed to the tissues of the CNS. In particular, twenty four hours following IT-administration 12.4% of the administered dose was in the cranial region, compared to 16.7% of the ICV-administered dose. Accordingly, the concentrations of rhASA detected in such CNS tissues, and in particular in the tissues of the brain, when rhASA was administered IT approached those concentrations detected following ICV-administration of the same dose.

ICV injection of the $^{124}$I-labeled rhASA results ICV injection results in the immediate transfer of the injected volume to the cisterna magna, cisterna pontis, cisterna interpeduncularis and proximal spine, as illustrated in FIG. 144. As also illustrated in FIG. 144, within 2-5 hr IT administration delivered the $^{124}$I-labeled rhASA to the same initial compartments (cisternae and proximal spine) as shown for the ICV administration. Twenty four hours following both ICV- and IT-administration distribution of the $^{124}$I-labeled rhASA was comparable in the cisternal and proximal spine area, as illustrated in FIG. 145.

These results confirm that rhASA can be delivered to a subject using the less invasive IT route of administration and thereby achieve therapeutic concentrations in target cells and tissues.

The lysosomal storage diseases represent a family of genetic disorders caused by missing or defective enzymes which result in abnormal substrate accumulation. While the peripheral symptoms associated with several of these diseases can be effectively mitigated by intravenous administration of recombinant enzymes, intravenous administration of such recombinant enzymes are not expected to significantly impact the CNS manifestations associated with a majority of the lysosomal storage disease. For example, recombinant human iduronate-2-sulfatase (Idursulfase, Elaprase®; Shire Human Genetic Therapies, Inc. Lexington, MA) is approved for treatment of the somatic symptoms of Hunter syndrome but there is no pharmacologic therapy for the treatment of the neurologic manifestations of Hunter Syndrone, which can include delayed development and progressive mental impairment. This is in part due to the nature of I2S, which is a large, highly-glycosylated enzyme with a molecular weight of approximately 76 kD and that does not traverse the blood brain barrier following intravenous administration.

The present inventors have therefore undertaken a program to investigate the intrathecal (IT) delivery of intrathecal formulations of recombinant human enzymes, such as, for example, iduronate-2-sulfatase (I2S), arylsulfatase A (rhASA) and alpha-N-acetylglucosaminidase (Naglu). The results presented herein represent the first to demonstrate that IT-lumbar administration of a recombinant lysosomal proteins result in the delivery of a significant fraction of the administered protein to the brain and in particular result in the widespread deposition of such proteins in neurons of the brain and spinal cord in both cynomolgus monkeys and dogs. Immunohistochemical analyses of the CNS tissues demonstrated that the protein is targeted to the lysosome, the site of pathologic glycosaminoglycan accumulation in the lysosomal storage disorders. Furthermore, the morphologic improvements demonstrated in the IKO mouse model of Hunter syndrome, the Naglu-deficient mouse model of Sanfilippo syndrome type B, and the ASA knockout mouse model of metachromatic leukodystrohpy (MLD) reinforces the observation that IT-administered enzyme is distributed to the appropriate tissues and transported to the appropriate cellular compartments and organelles.

The similarities observed in brain distribution patterns detected after IT-lumbar and ICV administration of I2S is suggestive of bulk flow and active remixing of the CSF. Thus in a clinical setting, both the IT and the ICV administration routes are potentially feasible, however, the observed deposition of I2S in the spinal cord following IT administration provides a clear advantage in addressing spinal sequelae and components of lysosomal storage diseases such as Hunter syndrome. Moreover, spinal injection ports are less invasive and expected to be more suitable for chronic use, especially in pediatric subjects.

Evidence from perivascular cell staining and protein translocation dynamics observed by the foregoing PET imaging studies indicate that enzyme moves within the perivascular space, presumably by pulsation-assisted convective mechanisms. An additional mechanism of transport is suggested by the observed association of I2S with neurofilaments, indicative of active axonal transport. The latter presumably begins with protein interaction with neuronal mannose-6-phosphate (M6P) receptors, which are widely expressed on cells of the spinal cord and brain and which upon direct administration to the brain parenchyma may cause I2S enzyme to be readily absorbed by target cells. (Begley, et al., Curr Pharm Des (2008) 14: 1566-1580).

While axonal transport of lysosomal enzymes have previously been implied by indirect methods in vivo and by imaging in vitro, the current studies provide the first direct evidence of axonal transport of non-virally or expressed enzymes delivered via the CSF. Thus, protein delivery from the CSF to the brain surface and deeper into the brain tissues seems to depend on active transfer processes, none of which have been previously described or elucidate for protein or enzyme delivery to the cells, tissues and organelles of the brain.

Contrary to the prevailing viewpoint that the flow dynamics of the parenchyma interstitium and CSF would prevent the distribution of IT-lumbar administered proteins to the white matter of the brain, the instant studies clearly demonstrate that IT delivery of a lysosomal enzyme results in protein distribution and accumulation in all brain tissues and deposition in the lysosomal compartment of target cells which are the site of pathologic glycosaminoglycan accumulation. (See, e.g., Fenstermacher et al., Ann NY Acad Sci (1988) 531:29-39 and DiChiro et al., Neurology (1976) 26:1-8.) Together with the less invasive nature of IT-lumbar delivery, this route offers a clinically relevant means of delivering biologic therapeutics to the brain, particularly in children.

Example 15—Toxicology

This example illustrate repeat dose intrathecal (IT) administration of rhASA from a toxicology and safety pharmacology perspective over a six-month period. The IT test article for this study was rhASA. Thirty-six male and 36 female cynomolgus monkeys were randomly assigned to five treatment groups. The animals in Group 1 were untreated implant device control (port & catheter) and were not dosed with the vehicle or test article; however, these animals were dosed with 0.6 mL of PBS on a schedule matching the test article dosing schedule. The animals in Groups 2-5 received 0.6 mL IT infusion of 0, 3, 10 or 31 mg/mL of rhASA (total dose of 0, 1.8, 6.0, or 18.6 mg) every other week (i.e. a total of 12 doses). Animals were necropsied at 6 months (24 hours post last IT dose), and the remaining 4 animals/sex/group were necropsied at the end of a 4-week recovery period. Selected tissues were harvested, saved and examined microscopically.

In general, the test article related changes could be categorized into two major types and were present at all dose levels (1.8, 6.0 and 18.6 mg/dose). Increase of infiltrates (of white blood cells, usually with a prominent eosinophilic component) in the meninges, the brain parenchyma, the spinal cord parenchyma, trigeminal ganglion, and occasionally the spinal nerve roots/ganglia (or the epineurium surrounding those structures). This increase was interpreted to be due to the presence of the test article (a protein) in the intrathecal space and in the nervous system tissues. Slight, focal increase of microglial cells in the spinal cord and brain in occasional animals (microgliosis was not observed in any high dose animals). Both categories of morphologic changes were interpreted to be a response to the presence of the test article. There was no evidence of neuronal necrosis in any animal. None of the test article related changes were related to any biologically adverse reactions in the brain, spinal cord, spinal nerve roots or ganglia. Specifically, there was no evidence of neuronal necrosis or a biologically important glial response. There were no test article related lesions in the non-nervous system tissues.

Following a one-month recovery period (a dosing free period), the test article related changes had either entirely resolved or were limited to remnants of the prior increase in the inflammatory response associated with the presence of the test article. There were no adverse morphologic effects in the recovery animals. As based on a blinded microscopic examination assigning a semi-quantitative staining score, immunohistochemical staining for Arylsulfatase A (rhASA; the test article) was increased in the brain and spinal cord in various cell types, except neurons, for all test article treated groups at the terminal sacrifice. This increase was also apparent in the Kupffer cells of the liver. Following the 1-month recovery period, rhASA staining in the test article treated animals (all dose groups) had returned to control (device and/or vehicle control) levels. In one low dose recovery male, there were multiple foci of astrocytosis and neuronal loss, indicating multiple areas of prior ischemia, in the cerebral cortex. Although the exact pathogenesis of these lesions in this animal was not apparent, the lack of similar lesions in any other test article treated animals, including the high dose animals that received 10× the dose, indicated these lesions were not related to the test article.

The IT test article for this study was rhASA. Thirty-six male and 36 female cynomolgus monkeys were randomly assigned to five treatment groups. The animals in Group 1 were untreated implant device control (port & catheter) and were not dosed with the vehicle or test article; however, these animals were dosed with 0.6 mL of PBS on a schedule matching the test article dosing schedule. The animals in Groups 2-5 received 0.6 mL IT infusion of 0, 3, 10 or 31 mg/mL of rhASA (total dose of 0, 1.8, 6.0, or 18.6 mg) every other week (i.e. a total of 12 doses). Animals were necropsied at 6 months (24 hours post last IT dose), and the remaining 4 animals/sex/group were necropsied at the end of a 4-week recovery period. Selected tissues were harvested, saved and examined microscopically. The table below reflects the study design as it pertained to the pathology aspect of this study.

At the time of sacrifice, the brain was cut in a brain matrix at approximately 3 mm coronal slice thickness. The first slice and every second slice thereafter were fixed in formalin for histopathological evaluation and immunohistochemical analysis. The brain was processed as full coronal sections. These sections included at a minimum the following brain regions.

Neocortex (including frontal, parietal, temporal and occipital cortex): brain sections 1 to 8 (and slice 9 when present)

Paleocortex (olfactory bulbs and/or piriform lobe): brain sections 1 to 3

Basal ganglia (including caudate and putamen): brain sections 3 and 4

Limbic system (including hippocampus and cingulate gyri): brain sections 4 and 5

Thalamus/hypothalamus and midbrain regions including substantia nigra: brain section 4 and 5

Cerebellum, pons and medulla oblongata: brain sections 6 to 8 (and slice 9 when present).

The brain sections are listed in the data tables as sections 1 to 8/9 (a section 9 was provided by the testing facility for some animals). Sectioning varied slightly between animals. The brain sections (1 through 8/9) provided above were the approximate location of the various anatomic areas. The brain sections are listed in the data tables as individual sections, with diagnoses pertinent to that section, to facilitate potential, future additional slide review (if any). During data interpretation, individual brain anatomic sites (as listed above) were compared in order to identify any unique test article effects (i.e. unique to a particular brain region). At TPS, all brain sections from all animals were embedded in paraffin, sectioned at 5 microns, stained with hematoxylin and eosin (H&E) and examined microscopically. In addition, brains from the control and high dose animals were stained with Fluoro-Jade B (a stain increasing the sensitivity of evaluating the brain for neuronal degeneration) and a Bielschowsky's silver stain (a procedure that allows for direct visualization of axons, dendrites and neuronal filaments) and examined.

The spinal cord (cervical, thoracic and lumber) was cut into one centimeter sections. The first slice and every other slice thereafter were fixed in formalin for histopathological evaluation and immunohistochemical analysis. The spinal cord sections (cervical, thoracic (including the catheter tip) and lumbar) from all animals were sectioned at approximately 5 microns, stained with H&E and examined with transverse and oblique sections taken at each level. Serial spinal cord sections from the control and high dose groups were additionally stained with Bielschowsky's silver stain and anti-GFAP (an immunohistochemical stain that allows for the direct visualization of astrocytes and their processes).

Dorsal spinal nerve roots and ganglion (taken at mid-cervical, mid-thoracic, and mid-lumbar) were embedded in paraffin, with serial sections stained with H&E. In addition, serial sections from the control and high dose groups were stained with Bielschowsky's silver stain.

For the sciatic, tibial and sural nerve sections from all animals: A longitudinal section of each nerve was embedded in paraffin, sectioned at approximately 5 microns and stained with H&E. A cross section of each nerve was post-fixed in osmium, embedded in Spurr's resin, sectioned at approximately 1 to 2 microns and stained with toluidine blue. Osmium post-fixation and resin embedding provides for superior preservation of the myelin in peripheral nerves and thus a more detailed examination of the nerve.

All tissues collected and gross lesions harvested at necropsy from all animals were also embedded in paraffin, stained with H&E, and examined microscopically. Histopathological processing and evaluations and immunohistochemical analyses were performed by TPS.

Methods: Arylsulfatase A (rhASA) Staining

Positive control slides were supplied by the study sponsor. The slides were liver sections from mice injected with rhASA. The positive control slides all showed ample evidence of rhASA in Kupffer cells (sinusoidal macrophages) in the liver. The positive control slides are stored with the other slides from this study. All evaluations of the rhASA stained sections were initially conducted blinded to the treatment group of the animal. This was accomplished by having the pathologist initially read the rhASA stained slides with the animal number on the label obscured (by an assistant with knowledge of the actual animal being evaluated), dictating the score (severity grade) during evaluation, and having the same assistant immediately record the staining score (severity grade) into the data tables. The animal ID was then verified by both the study neuropathologist and the assistant to guarantee accurate data entry. This procedure was conducted so as to not introduce any bias into the judging of the overall intensity of staining with the immunohistochemical stain for the detection of intracellular rhASA. The relative degree of staining of neurons, meningeal macrophages, perivascular macrophages and glial cells (astrocytes and microglial cells but likely predominantly microglial cells) was graded in all the brain and spinal cord sections. The average severity scores at each brain and spinal cord level for each group was totaled (by group) and recorded as a total under the tissue heading brain, general, rhASA staining and spinal cord, general, rhASA staining.

In general, rhASA staining in neurons of the brain was a measure of the neurons in the cerebral cortex and other nuclear areas in the brain. rhASA staining in meningeal macrophages was evidence of uptake of the test article by meningeal macrophages and/or endogenous rhASA in meningeal macrophages. rhASA staining of perivascular macrophages was a measure of uptake of rhASA by macrophages in the brain/spinal cord (or endogenous rhASA), although it should be noted that the perivascular space in the brain and spinal cord (the Virchow-Robins space) is continuous with the meninges. In general, the grading of rhASA staining in the glial cells was predominantly a measure of uptake of the test article/penetration of the test article into the gray and/or white matter, especially of the cerebral cortex (the corona radiata is the white matter beneath the cerebral cortex). The rhASA staining in the white matter appeared to be in astrocytes and microglial cells.

The following grading scheme was used to score the degree of rhASA staining the various cell types (neurons, glial cells, macrophages).

Grade Explanation (% of the Possible Cells Stained)
1 Less than 10%
2 Greater than 10 to 25%
3 Greater than 25 to 50%
4 Greater than 50 to 75%
5 Greater than 75%

Note this scheme is not strictly quantitative. It was used as an efficient, semi-quantitative method to assess the brain and spinal cord for the degree of staining with rhASA. It was noted by the Study Neuropathologist that not all neuronal areas had equal rhASA staining. It was also noted that there was endogenous neuronal staining in some control animals and that cells of the choroid plexus and neurons of the dorsal root ganglia tended to stain strongly for rhASA even in control animals. Staining of the choroid plexus and dorsal root ganglia was not graded but was noted by the study neuropathologist to be prominent, even in control animals.

Note: All dose groups: Low Dose=1.8 mg/dose; Mid dose=6.0 mg/dose; High dose=18.6 mg/dose. There were no test article related lesions in the non-nervous system tissues except for increased rhASA staining in the liver of all dose groups (male and female; see below).

Terminal Sacrifice Animals (6 Months of Every Other Week Dosing): rhASA Stained Sections There was an increase of rhASA staining in the following tissues/cell types. When considering a test article effect on the degree of rhASA staining in a particular cell type in a particular dose group, the staining levels in the concurrent vehicle control and the device control (sacrificed with the recovery sacrifice animals) were considered for comparison.

Brain, Meninges, Macrophages (all dose groups, males and females)
Brain, Perivascular, Macrophages (all dose groups, males and females)
Brain, Glial Cells (all dose groups, males and females)
Spinal Cord, Meninges, Macrophages (all dose groups, males and females)
Spinal Cord, Perivascular, Macrophages (all dose groups, males and females)
Spinal Cord, Glial Cells (mid and high dose males and females)
Liver, Kupffer Cells (all dose groups, males and females)

Because of endogenous staining, ARSA staining levels in the neurons of the brain and spinal cord were the most difficult to specifically define. The rhASA staining demonstrated consistently increased levels of rhASA in the meningeal and brain/spinal cord perivascular macrophages and also within glial cells. There were no detectable differences of rhASA staining in neurons between the control and test article treated animals.

Recovery Sacrifice Animals (6 Months of Every Other Week Dosing Followed by a One-Month Period without Dosing)

In general, test article related changes were either totally resolved or were notably diminished in those animals allowed a one-month period without dosing prior to necropsy. The following microscopic changes were present at an incidence and/or severity that indicated a possible relationship to the test article.

Test Article Related Microscopic Changes (Recovery Animals)

Figure 111:
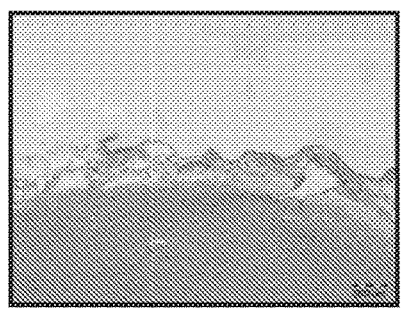
FIG. 111 depicts exemplary photo-micrographs of brain tissue, meninges, infiltrates (mid and high dose groups, both sexes) after treatment.
Figure 112:
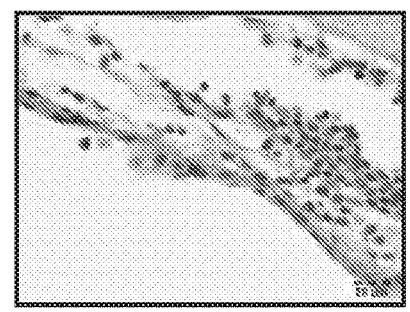
FIG. 112 depicts another exemplary photo-micrographs of brain tissue, meninges, infiltrates (mid and high dose groups, both sexes) after treatment.
Figure 113:
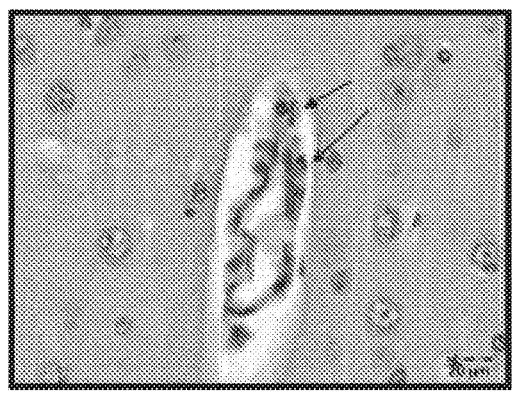
FIG. 113 depicts exemplary photo-micrographs of brain tissue, perivascular, infiltrates (mid dose males; high dose females) after treatment.

Brain, Meninges, Infiltrates (mid and high dose groups, both sexes) (FIG. 111 and FIG. 112)
Brain, Meninges, Infiltrates, % Eosinophils (mid dose males; high dose females)
Brain, Perivascular, Infiltrates (mid dose males; high dose females) (FIG. 113)
Brain, Perivascular, Infiltrates, % Eosinophils (mid dose males; high dose females)
Brain, Gray Matter, Infiltrates (all dose groups, both sexes)
Brain, Gray Matter Infiltrates, % Eosinophils (low dose males)
Brain, Gray Matter, Eosinophils, Necrosis (low dose males)
Spinal Cord, Meninges, Infiltrates (mid and high dose males; low and high dose females)
Spinal Cord, Meninges, Infiltrates, % Eosinophils (mid dose males; low dose females)
Spinal Cord, Gray Matter, Infiltrates (low dose females)
Spinal Cord, Gray Matter, Infiltrates, % Eosinophils (low dose females)
Dorsal Root Ganglion and Roots, Epineurium, Infiltrates (mid dose females)
Spinal Nerve Roots and Ganglia, Infiltrates, Eosinophils (mid and high dose males; all doses, females)
Trigeminal Ganglion, Infiltrates, Eosinophils (mid dose males and females)

All these changes were interpreted to represent remnants of the increased inflammatory changes noted in the terminal sacrifice animals. As in the terminal sacrifice animals, there was no evidence the increase of inflammatory cell infiltrates still present in some recovery animals represented morphologic changes that were causing any adverse effects. There were no test article related lesions in the non-nervous system tissues.

Recovery Sacrifice Animals (6 Months of Every Other Week Dosing Followed by a One-Month Period without Dosing): ARSA Staining There was no indication of increased rhASA staining in the recovery males or females as compared to the device and/or vehicle controls. In the brain of the low, mid and high dose recovery males, there was actually an indication of decreased rhASA staining in some cell types (this varied among the treatment groups) as compared to the device and/or vehicle controls. The reason for this, including whether or not this was an actual effect, was not apparent. One possible explanation would be that administration of exogenous rhASA may cause some decrease in endogenous rhASA production. A similar finding was not present in the spinal cord of the males. In the recovery males and females, staining in the liver was similar to that noted in controls.

In general, the test article related changes could be categorized into two major types and were present at all dose levels (1.8, 6.0 and 18.6 mg/dose).

Increase of infiltrates (of white blood cells, usually with a prominent eosinophilic component) in the meninges, the brain parenchyma, the spinal cord parenchyma, trigeminal ganglion, and occasionally the spinal nerve roots/ganglia (or the epineurium surrounding those structures). This increase was interpreted to be due to the presence of the test article (a protein) in the intrathecal space and in the nervous system tissues.

Slight, focal increase of microglial cells in the spinal cord and brain in occasional animals (microgliosis was not observed in any high dose animals). Both categories of morphologic changes were interpreted to be a response to the presence of the test article. There was no evidence of neuronal necrosis in any animal. Evaluation of the rhASA stained sections is pending as of the writing of this interim report. None of the test article related changes were related to any biologically adverse reactions in the brain, spinal cord, spinal nerve roots or ganglia. Specifically, there was no evidence of neuronal necrosis or a biologically important glial response. There were no test article related lesions in the non-nervous system tissues. Following a one-month recovery period (a dosing free period), the test article related changes had either entirely resolved or were limited to remnants of the prior increase in the inflammatory response associated with the presence of the test article. There were no adverse morphologic effects in the recovery animals.

As based on a blinded microscopic examination assigning a semi-quantitative staining score, immunohistochemical staining for Arylsulfatase A (rhASA; the test article) was increased in the brain and spinal cord in various cell types, except neurons, for all test article treated groups. This increase was also apparent in the Kupffer cells of the liver. Following the 1-month recovery period, rhASA staining in the test article treated animals (all dose groups)had returned to control (device and/or vehicle control) levels. In one low dose recovery male, there were multiple foci of astrocytosis and neuronal loss, indicating multiple areas of prior ischemia, in the cerebral cortex. Although the exact pathogenesis of these lesions in this animal was not apparent, the lack of similar lesions in any other test article treated animals, including the high dose animals that received 10× the dose, indicated these lesions were not related to the test article. At the time of the issuance of this preliminary report, and based strictly on the gross and microscopic findings (on the paraffin embedded, hematoxylin and eosin stained sections) in this study, the no observed adverse effect level (NOAEL) was 18.6 mg.

Example 16—Pharmakinetic Data

6 Month Animal Data

This example provides interpretive analysis for serum and CSF concentrations of rhASA and anti-rhASA serum antibodies from Northern Biomedical Research, Inc.

The objective of the example was to evaluate repeat dose intrathecal (IT) administration of rhASA from a toxicology and safety pharmacology perspective in juvenile (<12 months of age) cynomolgus monkeys. A total of 12 doses were given in a six month period. Animals were necropsied 24 hours or one-month after the last dose. The study design is shown in Table 29.

| | | Study Design | | | |
|---|---|---|---|---|---|
| Group | No. of Animals | Nominal Dose Concentration (mg/mL) | Administered Dose (mg) | No. of Animals, 6 Month Sacrifice | No. of Animals, 1 Month Recovery Sacrifice |
| 1 | 4 M, 4 F | DC | 0 | — | 4 M, 4 F |
| 2 | 8 M, 8 F | 0 | 0 | 4 M, 3 F[a] | 4 M, 4 F |
| 3 | 8 M, 8 F | 3 | 1.8 | 4 M, 4 F | 4 M, 4 F |
| 4 | 8 M, 8 F | 10 | 6.0 | 4 M, 4 F | 4 M, 4 F |
| 5 | 8 M, 8 F | 31 | 18.6 | 4 M, 4 F | 4 M, 4 F |

Assay Methods—Antibody Analysis

Quantitation of anti-rhASA antibodies in the serum and CSF from cynomolgus monkeys was conducted using a validated method. Briefly, the assay begins by blocking a MSD streptavidin coated plate, followed by incubation with biotin-labeled rhASA. After a washing step, diluted samples, calibrators, and QCs are added to the plate and incubated. After an additional wash step, SULFO TAG-labelled drug is added and incubated. A final wash step is performed and MSD read buffer is added. Plates are read immediately. The signal data in relative luminescence units (RLU) are analyzed using SOFTMax Pro templates.

Serum and CSF Concentration

Quantitation of rhASA in the serum and CSF from cynomolgus monkeys was conducted using a validated method. The method is based on Enzyme-Linked Immunosorbent Assay (ELISA) technology. Briefly, a microtiter plate is coated with a rabbit polyclonal antibody (SH040) raised against recombinant human Arylsulfatase A (rhASA). After incubation with rhASA reference standards and test samples, bound rhASA protein is detected by horseradish peroxidase (HRP)-conjugated anti-ASA monoclonal antibody (clone 19-16-3). The plate is then incubated with a substrate for HRP, TMB peroxidase. This enzyme-substrate reaction is stopped by the addition of 2N sulfuric acid ($H_2SO4$) and the absorbance of each well is measured at the absorbance wavelength 450 nm with a reference wavelength 655 nm. The concentrations of rhASA in samples are calculated using the rhASA calibration curve in the same plate.

The summary of serum concentrations of rhASA are presented in Table 30.

The summary CSF concentrations of rhASA are presented in Table 31.

The summary anti-rhASA serum antibody concentrations are presented in Table 32.

The summary anti-rhASA CSF antibody concentrations are presented in Table 33.

Incidence of antibodies by group and sex is presented in Table 36.

TABLE 1

Summary of Serum Concentration of rhASA in Cynomolgus Monkeys

| Time point | Male Mean ng/mL | SD ng/mL | n | Female Mean ng/mL | SD ng/mL | n |
|---|---|---|---|---|---|---|
| Group 1: Vehicle control | | | | | | |
| Prior to Dose 2 | 0 | 0 | 4 | 0 | 0 | 4 |
| Post Dose 2 | 0 | 0 | 4 | 0 | 0 | 4 |
| Prior to Dose 4 | 0 | 0 | 4 | 0 | 0 | 4 |
| Post Dose 4 | 0 | 0 | 4 | 0 | 0 | 4 |
| Prior to Dose 6 | 0 | 0 | 4 | 0 | 0 | 4 |
| Post Dose 6 | 0 | 0 | 4 | 0 | 0 | 4 |
| Prior to Dose 8 | 0 | 0 | 4 | 0 | 0 | 4 |
| Post Dose 8 | 0 | 0 | 4 | 0 | 0 | 4 |
| Prior to Dose 10 | 0 | 0 | 4 | 0 | 0 | 4 |
| Post Dose 10 | 0 | 0 | 4 | 0 | 0 | 4 |
| Prior to Dose 12 | 0 | 0 | 4 | 0 | 0 | 4 |
| Post Dose 12 | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 2: 0 mg | | | | | | |
| Prior to Dose 2 | 0 | 0 | 8 | 0 | 0 | 7 |
| Post Dose 2 | 0 | 0 | 8 | 0 | 0 | 7 |
| Prior to Dose 4 | 0 | 0 | 8 | 0 | 0 | 7 |
| Post Dose 4 | 0 | 0 | 8 | 0 | 0 | 7 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 7 |
| Post Dose 10 | 0 | 0 | 8 | 0 | 0 | 7 |
| Prior to Dose 12 | 0 | 0 | 8 | 0 | 0 | 7 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 3: 1.8 mg | | | | | | |
| Prior to Dose 2 | 0 | 0 | 8 | 0 | 0 | 8 |
| Post Dose 2 | 49.2 | 46.8 | 8 | 40.3 | 27.3 | 8 |
| Prior to Dose 4 | 0 | 0 | 8 | 0 | 0 | 8 |
| Post Dose 4 | 0 | 0 | 8 | 0 | 0 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 4: 6.0 mg | | | | | | |
| Prior to Dose 2 | 0 | 0 | 8 | 0 | 0 | 8 |
| Post Dose 2 | 173.6 | 69.5 | 8 | 143.2 | 89.0 | 8 |
| Prior to Dose 4 | 0 | 0 | 8 | 0 | 0 | 8 |
| Post Dose 4 | 17 | 49 | 8 | 63.8 | 119.9 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 5: 18.6 mg | | | | | | |
| Prior to Dose 2 | 0 | 0 | 8 | 0 | 0 | 8 |
| Post Dose 2 | 348.0 | 272.9 | 8 | 562.3 | 204.3 | 8 |
| Prior to Dose 4 | 0 | 0 | 8 | 0 | 0 | 8 |
| Post Dose 4 | 105.7 | 274.6 | 8 | 172.0 | 141.3 | 8 |
| Prior to Dose 6 | 0 | 0 | 8 | 0 | 0 | 8 |
| Post Dose 6 | 20.4 | 38.4 | 8 | 88.6 | 121.4 | 8 |
| Prior to Dose 8 | 0 | 0 | 8 | 0 | 0 | 8 |
| Post Dose 8 | 0 | 0 | 8 | 54.0 | 89.4 | 8 |
| Prior to Dose 10 | 0 | 0 | 8 | 0 | 0 | 8 |
| Post Dose 10 | 0 | 0 | 8 | 6 | 18 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |

TABLE 2

Summary of CSF Concentrations in Cynomolgus Monkeys

| Time point | Male Mean ng/mL | SD ng/mL | n | Female Mean ng/mL | SD ng/mL | n |
|---|---|---|---|---|---|---|
| Group 1: Vehicle Control | | | | | | |
| Prior to Dose 2 | 0 | 0 | 4 | 0 | 0 | 4 |
| Post Dose 2 | 0 | 0 | 4 | 0 | 0 | 4 |
| Prior to Dose 4 | 0 | 0 | 4 | 0 | 0 | 4 |
| Post Dose 4 | 0 | 0 | 4 | 0 | 0 | 4 |
| Prior to Dose 6 | 0 | 0 | 4 | 0 | 0 | 4 |
| Post Dose 6 | 0 | 0 | 4 | 0 | 0 | 4 |
| Prior to Dose 8 | 0 | 0 | 4 | 0 | 0 | 4 |
| Post Dose 8 | 0 | 0 | 4 | 0 | 0 | 4 |
| Prior to Dose 10 | 0 | 0 | 4 | 0 | 0 | 4 |
| Post Dose 10 | 0 | 0 | 3 | 0 | 0 | 4 |
| Prior to Dose 12 | 0 | 0 | 3 | 0 | 0 | 4 |
| Post Dose 12 | 0 | 0 | 3 | 0 | 0 | 4 |
| Mid Recovery | 0 | 0 | 3 | 0 | 0 | 4 |
| Recovery Necropsy | 0 | 0 | 4 | 0 | 0 | 4 |
| Group 2: 0 mg | | | | | | |
| Prior to Dose 2 | 0 | 0 | 6 | 0 | 0 | 7 |
| Post Dose 2 | 0 | 0 | 5 | 0 | 0 | 7 |
| Prior to Dose 4 | 0 | 0 | 5 | 0 | 0 | 6 |
| Post Dose 4 | 0 | 0 | 5 | 0 | 0 | 5 |
| Prior to Dose 6 | 0 | 0 | 5 | 0 | 0 | 5 |
| Post Dose 6 | 0 | 0 | 5 | 0 | 0 | 5 |
| Prior to Dose 8 | 0 | 0 | 5 | 0 | 0 | 5 |
| Post Dose 8 | 0 | 0 | 5 | 0 | 0 | 5 |
| Prior to Dose 10 | 0 | 0 | 4 | 0 | 0 | 5 |
| Post Dose 10 | 0 | 0 | 4 | 0 | 0 | 5 |
| Prior to Dose 12 | 0 | 0 | 4 | 0 | 0 | 5 |
| Post Dose 12 (Prior to 6-month Necropsy) | 0 | 0 | 5 | 0 | 0 | 5 |
| Mid Recovery | 0 | 0 | 2 | 0 | 0 | 3 |
| Recovery Necropsy | 0 | 0 | 4 | 0 | 0 | 4 |
| Group 3: 1.8 mg | | | | | | |
| Prior to Dose 2 | 42491 | 59255 | 7 | 42217 | 47300 | 6 |
| Post Dose 2 | 95886 | 22626 | 7 | 125717 | 61723 | 6 |
| Prior to Dose 4 | 17664 | 24372 | 6 | 50829 | 41891 | 6 |
| Post Dose 4 | 106783 | 42823 | 6 | 138400 | 49908 | 6 |
| Prior to Dose 6 | 39400 | 50105 | 4 | 45817 | 38404 | 6 |

TABLE 2-continued

Summary of CSF Concentrations in Cynomolgus Monkeys

| | Male | | | Female | | |
|---|---|---|---|---|---|---|
| Time point | Mean ng/mL | SD ng/mL | n | Mean ng/mL | SD ng/mL | n |
| Post Dose 6 | 95275 | 12836 | 4 | 104080 | 37423 | 5 |
| Prior to Dose 8 | 25799 | 31589 | 4 | 58086 | 43821 | 5 |
| Post Dose 8 | 148750 | 34664 | 4 | 119200 | 66556 | 5 |
| Prior to Dose 10 | 25927 | 31380 | 4 | 30380 | 30328 | 5 |
| Post Dose 10 | 89975 | 29494 | 4 | 105200 | 44603 | 5 |
| Prior to Dose 12 | 29746 | 34267 | 4 | 82780 | 65906 | 5 |
| Post Dose 12 (Prior to 6-month Necropsy) | 32030 | 39155 | 7 | 47331 | 49015 | 6 |
| Mid Recovery | 0 | 0 | 3 | 0 | 0 | 2 |
| Recovery Necropsy | 0 | 0 | 4 | 0 | 0 | 4 |
| Group 4: 6.0 mg | | | | | | |
| Prior to Dose 2 | 75203 | 67002 | 8 | 146979 | 233673 | 6 |
| Post Dose 2 | 360000 | 179276 | 8 | 267667 | 103369 | 6 |
| Prior to Dose 4 | 58064 | 77210 | 8 | 53285 | 73340 | 5 |
| Post Dose 4 | 369250 | 241251 | 8 | 305517 | 152232 | 6 |
| Prior to Dose 6 | 77253 | 91407 | 8 | 97987 | 146762 | 6 |
| Post Dose 6 | 418600 | 200098 | 5 | 369000 | 232238 | 5 |
| Prior to Dose 8 | 66342 | 80374 | 5 | 11592 | 23072 | 4 |
| Post Dose 8 | 329400 | 209841 | 5 | 340500 | 135128 | 4 |
| Prior to Dose 10 | 119420 | 148408 | 5 | 74031 | 104609 | 2 |
| Post Dose 10 | 412000 | 149278 | 5 | 245500 | 161927 | 2 |
| Prior to Dose 12 | 68651 | 92902 | 5 | 74577 | 105251 | 2 |
| Post Dose 12 (Prior to 6-month Necropsy) | 141833 | 173933 | 7 | 58986 | 99016 | 4 |
| Mid Recovery | 0 | 0 | 3 | 0 | NA | 1 |
| Recovery Necropsy | 0 | 0 | 4 | 0 | 0 | 4 |
| Group 5: 18.6 mg | | | | | | |
| Prior to Dose 2 | 289917 | 291188 | 7 | 201339 | 250774 | 8 |
| Post Dose 2 | 734429 | 298352 | 7 | 920143 | 448409 | 7 |
| Prior to Dose 4 | 150238 | 210302 | 7 | 169895 | 185675 | 6 |
| Post Dose 4 | 984857 | 570039 | 7 | 965167 | 425924 | 6 |
| Prior to Dose 6 | 265479 | 252067 | 7 | 288879 | 226889 | 6 |
| Post Dose 6 | 758143 | 102009 | 7 | 1270000 | 558533 | 6 |
| Prior to Dose 8 | 190529 | 240081 | 7 | 196021 | 199396 | 6 |
| Post Dose 8 | 1003429 | 538271 | 7 | 989800 | 585072 | 5 |
| Prior to Dose 10 | 176297 | 272500 | 7 | 168864 | 191087 | 6 |
| Post Dose 10 | 1013000 | 390673 | 7 | 773400 | 103717 | 5 |
| Prior to Dose 12 | 142334 | 196793 | 5 | 430542 | 436534 | 6 |
| Post Dose 12 (Prior to 6-month Necropsy) | 291525 | 350251 | 7 | 252142 | 381200 | 6 |
| Mid Recovery | 0 | 0 | 3 | 0 | 0 | 2 |
| Recovery Necropsy | 0 | 0 | 4 | 0 | 0 | 4 |

TABLE 3

Summary of Anti-rhASA Antibody Concentration in Serum

| | Male | | | Female | | |
|---|---|---|---|---|---|---|
| Time Point | Mean ng/mL | SD ng/Ml | n | Mean ng/mL | SD ng/mL | n |
| Group 1: Vehicle control | | | | | | |
| Predose 2 | 0 | 0 | 4 | 0 | 0 | 4 |
| Predose 4 | 0 | 0 | 4 | 0 | 0 | 4 |
| Predose 6 | 0 | 0 | 4 | 0 | 0 | 4 |
| Predose 8 | 0 | 0 | 4 | 0 | 0 | 4 |
| Predose 10 | 0 | 0 | 4 | 0 | 0 | 4 |
| Predose 12 | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 2: 0 mg | | | | | | |
| Predose 2 | 0 | 0 | 8 | 0 | 0 | 8 |
| Predose 4 | 0 | 0 | 8 | 0 | 0 | 8 |
| Predose 6 | 0 | 0 | 8 | 0 | 0 | 7 |
| Predose 8 | 0 | 0 | 8 | 0 | 0 | 7 |
| Predose 10 | 0 | 0 | 8 | 0 | 0 | 7 |
| Predose 12 | 0 | 0 | 8 | 0 | 0 | 7 |
| Necropsy (24 hr after last dose) | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 3: 1.8 mg | | | | | | |
| Predose 2 | 0 | 0 | 8 | 0 | 0 | 8 |
| Predose 4 | 18409 | 21371 | 8 | 27648 | 37504 | 8 |
| Predose 6 | 75913 | 64863 | 8 | 85625 | 79871 | 8 |
| Predose 8 | 132163 | 95576 | 8 | 151900 | 97818 | 8 |
| Predose 10 | 392338 | 606626 | 8 | 290675 | 186213 | 8 |
| Predose 12 | 499438 | 735028 | 8 | 524438 | 569523 | 8 |
| Necropsy (24 hr after last dose) | 261625 | 157865 | 4 | 733550 | 928411 | 4 |
| Mid Recovery | 339250 | 265888 | 4 | 377175 | 218955 | 4 |
| Recovery Necropsy | 712500 | 1107129 | 4 | 295525 | 174718 | 4 |
| Group 4: 6.0 mg | | | | | | |
| Predose 2 | 0 | 0 | 8 | 0 | 0 | 8 |
| Predose 4 | 30419 | 30561 | 8 | 64000 | 89510 | 8 |
| Predose 6 | 143693 | 128094 | 8 | 191750 | 150511 | 8 |
| Predose 8 | 325750 | 190651 | 8 | 305850 | 224707 | 8 |
| Predose 10 | 669125 | 515458 | 8 | 832188 | 846241 | 8 |
| Predose 12 | 946125 | 651530 | 8 | 1060775 | 1088889 | 8 |
| Necropsy (24 hr after last dose) | 713500 | 598812 | 4 | 1047568 | 1132048 | 4 |
| Mid Recovery | 1566000 | 708132 | 4 | 975500 | 1149734 | 4 |
| Recovery Necropsy | 1113250 | 554510 | 4 | 793000 | 991450 | 4 |
| Group 5: 18.6 mg | | | | | | |
| Predose 2 | 0 | 0 | 8 | 0 | 0 | 8 |
| Predose 4 | 56873 | 39107 | 8 | 39994 | 53411 | 8 |
| Predose 6 | 311638 | 237796 | 8 | 193263 | 208952 | 8 |
| Predose 8 | 482875 | 270130 | 8 | 399363 | 360425 | 8 |
| Predose 10 | 1006750 | 857916 | 8 | 866875 | 894776 | 8 |
| Predose 12 | 1419000 | 1382276 | 8 | 1341500 | 1373771 | 8 |
| Necropsy (24 hr after last dose) | 165000 | 147463 | 4 | 407300 | 268570 | 4 |
| Mid Recovery | 2884250 | 1363128 | 4 | 2101500 | 2090420 | 4 |
| Recovery Necropsy | 2504250 | 1118042 | 4 | 1506000 | 1524682 | 4 |

TABLE 4

Summary of Anti-rhASA Antibody Concentration in CSF

| | Male | | | Female | | |
|---|---|---|---|---|---|---|
| Time point | Mean ng/mL | SD ng/mL | n | Mean ng/mL | SD ng/mL | n |
| Group 1: Vehicle control | | | | | | |
| Surgery | 0 | 0 | 4 | 0 | 0 | 4 |
| Predose 2 | 0 | 0 | 4 | 0 | 0 | 4 |
| Predose 4 | 0 | 0 | 4 | 0 | 0 | 4 |
| Predose 6 | 0 | 0 | 4 | 0 | 0 | 4 |
| Predose 8 | 0 | 0 | 4 | 0 | 0 | 4 |
| Predose 10 | 0 | 0 | 4 | 0 | 0 | 4 |
| Predose 12 | 0 | 0 | 3 | 0 | 0 | 4 |
| Mid Recovery | 0 | 0 | 3 | 0 | 0 | 4 |
| Recovery Necropsy | 0 | 0 | 4 | 0 | 0 | 4 |
| Group 2: 0 mg | | | | | | |
| Surgery | 0 | 0 | 7 | 0 | 0 | 6 |
| Predose 2 | 0 | 0 | 6 | 0 | 0 | 7 |
| Predose 4 | 0 | 0 | 5 | 0 | 0 | 6 |
| Predose 6 | 0 | 0 | 5 | 0 | 0 | 5 |
| Predose 8 | 0 | 0 | 5 | 0 | 0 | 5 |
| Predose 10 | 0 | 0 | 4 | 0 | 0 | 5 |
| Predose 12 | 0 | 0 | 4 | 0 | 0 | 5 |
| Necropsy (24 hr after last dose) | 0 | 0 | 3 | 0 | 0 | 2 |
| Mid Recovery | 0 | NA | 1 | 0 | 0 | 3 |
| Recovery Necropsy | 0 | 0 | 4 | 0 | 0 | 4 |
| Group 3: 1.8 mg | | | | | | |
| Surgery | 0 | 0 | 7 | 0 | 0 | 8 |
| Predose 2 | 0 | 0 | 7 | 0 | 0 | 6 |
| Predose 4 | 0 | 0 | 6 | 41 | 101 | 6 |
| Predose 6 | 685 | 1317 | 4 | 632 | 1413 | 5 |
| Predose 8 | 2238 | 2596 | 4 | 2180 | 4875 | 5 |
| Predose 10 | 3393 | 5038 | 4 | 5560 | 12433 | 5 |
| Predose 12 | 6436 | 8266 | 4 | 12700 | 28398 | 5 |
| Necropsy (24 hr after last dose) | 14848 | 12401 | 4 | 21442 | 32382 | 4 |
| Mid Recovery | 29307 | 40617 | 3 | 18700 | 283 | 2 |
| Recovery Necropsy | 21060 | 30010 | 3 | 13078 | 7181 | 4 |
| Group 4: 6.0 mg | | | | | | |
| Surgery | 0 | 0 | 7 | 0 | 0 | 8 |
| Predose 2 | 0 | 0 | 7 | 0 | 0 | 6 |
| Predose 4 | 99 | 172 | 7 | 84 | 187 | 5 |
| Predose 6 | 1117 | 1862 | 8 | 1473 | 2775 | 6 |
| Predose 8 | 3987 | 5580 | 5 | 20824 | 27320 | 4 |
| Predose 10 | 6600 | 9679 | 5 | 2715 | 1237 | 2 |
| Predose 12 | 5285 | 7279 | 5 | 955 | 1237 | 2 |
| Necropsy (24 hr after last dose) | 16870 | 16350 | 4 | 63000 | 63000 | 3 |
| Mid Recovery | 66233 | 42238 | 3 | 16800 | NA | 1 |
| Recovery Necropsy | 53600 | 14388 | 3 | 28880 | 29890 | 4 |
| Group 5: 18.6 mg | | | | | | |
| Surgery | 0 | 0 | 7 | 0 | 0 | 6 |
| Predose 2 | 0 | 0 | 7 | 0 | 0 | 8 |
| Predose 4 | 102 | 192 | 7 | 0 | 0 | 6 |
| Predose 6 | 233 | 351 | 7 | 1506 | 3234 | 6 |
| Predose 8 | 3378 | 5931 | 7 | 6367 | 9865 | 6 |
| Predose 10 | 16327 | 24035 | 7 | 19567 | 27542 | 6 |
| Predose 12 | 11596 | 16406 | 5 | 15143 | 24351 | 6 |
| Necropsy (24 hr after last dose) | 5168 | 7427 | 4 | 12135 | 10341 | 4 |
| Mid Recovery | 54700 | 26439 | 3 | 46315 | 62770 | 2 |
| Recovery Necropsy | 50725 | 29217 | 4 | 37790 | 35967 | 4 |

TABLE 5

Serum and CSF Concentrations of rhASA, Male and Female Combined (ng/mL)

| | Serum rhASA (ng/mL) Group in total | | | CSF rhASA (ng/mL) Group in total | | |
|---|---|---|---|---|---|---|
| Time point | Mean ng/mL | SD ng/mL | n | Mean ng/mL | SD ng/mL | n |
| Group 1: Vehicle control | | | | | | |
| Prior to Dose 2 | 0 | 0 | 8 | 0 | 0 | 8 |
| Post Dose 2 | 0 | 0 | 8 | 0 | 0 | 8 |
| Prior to Dose 4 | 0 | 0 | 8 | 0 | 0 | 8 |
| Post Dose 4 | 0 | 0 | 8 | 0 | 0 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 7 |
| Prior to Dose 12 | 0 | 0 | 8 | 0 | 0 | 7 |
| Post Dose 12 | 0 | 0 | 8 | 0 | 0 | 7 |
| Mid Recovery | 0 | 0 | 8 | 0 | 0 | 7 |
| Recovery Necropsy | 0 | 0 | 8 | 0 | 0 | 8 |
| Group 2: 0 mg | | | | | | |
| Prior to Dose 2 | 0 | 0 | 16 | 0 | 0 | 13 |
| Post Dose 2 | 0 | 0 | 16 | 0 | 0 | 12 |
| Prior to Dose 4 | 0 | 0 | 16 | 0 | 0 | 11 |
| Post Dose 4 | 0 | 0 | 16 | 0 | 0 | 10 |
| Prior to Dose 6 | 0 | 0 | 15 | 0 | 0 | 10 |
| Post Dose 6 | 0 | 0 | 15 | 0 | 0 | 10 |
| Prior to Dose 8 | 0 | 0 | 15 | 0 | 0 | 10 |
| Post Dose 8 | 0 | 0 | 15 | 0 | 0 | 10 |
| Prior to Dose 10 | 0 | 0 | 15 | 0 | 0 | 9 |
| Post Dose 10 | 0 | 0 | 15 | 0 | 0 | 9 |
| Prior to Dose 12 | 0 | 0 | 15 | 0 | 0 | 9 |
| Post Dose 12 (Prior to 6-month Necropsy) | 0 | 0 | 15 | 0 | 0 | 10 |
| Mid Recovery | 0 | 0 | 8 | 0 | 0 | 5 |
| Recovery Necropsy | 0 | 0 | 8 | 0 | 0 | 8 |
| Group 3: 1.8 mg | | | | | | |
| Prior to Dose 2 | 0 | 0 | 16 | 42365 | 51844 | 13 |
| Post Dose 2 | 44.7 | 37.3 | 16 | 109654 | 45639 | 13 |
| Prior to Dose 4 | 0 | 0 | 16 | 34247 | 36982 | 12 |
| Post Dose 4 | 0 | 0 | 16 | 122592 | 47311 | 12 |
| Prior to Dose 6 | 0 | 0 | 16 | 43250 | 40831 | 10 |
| Post Dose 6 | 0 | 0 | 16 | 100167 | 27992 | 9 |
| Prior to Dose 8 | 0 | 0 | 16 | 43736 | 40298 | 9 |
| Post Dose 8 | 0 | 0 | 16 | 132333 | 53926 | 9 |
| Prior to Dose 10 | 0 | 0 | 16 | 28401 | 28890 | 9 |
| Post Dose 10 | 0 | 0 | 16 | 98433 | 37220 | 9 |
| Prior to Dose 12 | 0 | 0 | 16 | 59209 | 58253 | 9 |
| Post Dose 12 (Prior to 6-month Necropsy) | 0 | 0 | 16 | 39092 | 42786 | 13 |
| Mid Recovery | 0 | 0 | 8 | 0 | 0 | 5 |
| Recovery Necropsy | 0 | 0 | 8 | 0 | 0 | 8 |
| Group 4: 6.0 mg | | | | | | |
| Prior to Dose 2 | 0 | 0 | 16 | 105964 | 157408 | 14 |
| Post Dose 2 | 158.4 | 78.7 | 16 | 320429 | 153832 | 14 |
| Prior to Dose 4 | 0 | 0 | 16 | 56226 | 72638 | 13 |
| Post Dose 4 | 40.6 | 91.7 | 16 | 341936 | 203284 | 14 |
| Prior to Dose 6 | 0 | 0 | 16 | 86139 | 113563 | 14 |
| Post Dose 6 | 0 | 0 | 16 | 393800 | 206033 | 10 |
| Prior to Dose 8 | 0 | 0 | 16 | 42009 | 65286 | 9 |
| Post Dose 8 | 0 | 0 | 16 | 334333 | 169995 | 9 |
| Prior to Dose 10 | 0 | 0 | 16 | 106452 | 130375 | 7 |
| Post Dose 10 | 0 | 0 | 16 | 364429 | 160707 | 7 |
| Prior to Dose 12 | 0 | 0 | 16 | 70344 | 87227 | 7 |
| Post Dose 12 (Prior to 6-month Necropsy) | 0 | 0 | 16 | 111707 | 151129 | 11 |

TABLE 5-continued

Serum and CSF Concentrations of rhASA, Male and Female Combined (ng/mL)

| | Serum rhASA (ng/mL) Group in total | | | CSF rhASA (ng/mL) Group in total | | |
|---|---|---|---|---|---|---|
| Time point | Mean ng/mL | SD ng/mL | n | Mean ng/mL | SD ng/mL | n |
| Mid Recovery | 0 | 0 | 8 | 0 | 0 | 4 |
| Recovery Necropsy | 0 | 0 | 8 | 0 | 0 | 8 |
| Group 5: 18.6 mg | | | | | | |
| Prior to Dose 2 | 0 | 0 | 16 | 242676 | 264338 | 15 |
| Post Dose 2 | 455.1 | 257.8 | 16 | 827286 | 378379 | 14 |
| Prior to Dose 4 | 0 | 0 | 16 | 159311 | 191264 | 13 |
| Post Dose 4 | 138.8 | 213.7 | 16 | 975769 | 488021 | 13 |
| Prior to Dose 6 | 0 | 0 | 16 | 276279 | 231010 | 13 |
| Post Dose 6 | 54.5 | 93.8 | 16 | 994385 | 453568 | 13 |
| Prior to Dose 8 | 0 | 0 | 16 | 193064 | 213058 | 13 |
| Post Dose 8 | 27.0 | 67.1 | 16 | 997750 | 531567 | 12 |
| Prior to Dose 10 | 0 | 0 | 16 | 172866 | 228817 | 13 |
| Post Dose 10 | 3.2 | 13 | 16 | 913167 | 319975 | 12 |
| Prior to Dose 12 | 0 | 0 | 16 | 299538 | 365275 | 11 |
| Post Dose 12 (Prior to 6-month Necropsy) | 0 | 0 | 16 | 273348 | 349718 | 13 |
| Mid Recovery | 0 | 0 | 8 | 0 | 0 | 5 |
| Recovery Necropsy | 0 | 0 | 8 | 0 | 0 | 8 |

TABLE 6

Serum and CSF Anti-rhASA Antibody, Male and Female Combined (ng/mL)

| | Serum Anti-rhASA Antibody (ng/mL) Group in total | | | CSF Anti-rhASA Antibody (ng/mL) Group in total | | |
|---|---|---|---|---|---|---|
| Time Point | Mean ng/mL | SD ng/mL | n | Mean ng/mL | SD ng/mL | n |
| Group 1: Vehicle control | | | | | | |
| Surgery | | | | 0 | 0 | 8 |
| Predose 2 | 0 | 0 | 8 | 0 | 0 | 8 |
| Predose 4 | 0 | 0 | 8 | 0 | 0 | 8 |
| Predose 6 | 0 | 0 | 8 | 0 | 0 | 8 |
| Predose 8 | 0 | 0 | 8 | 0 | 0 | 8 |
| Predose 10 | 0 | 0 | 8 | 0 | 0 | 8 |
| Predose 12 | 0 | 0 | 8 | 0 | 0 | 7 |
| Mid Recovery | 0 | 0 | 8 | 0 | 0 | 7 |
| Recovery Necropsy | 0 | 0 | 8 | 0 | 0 | 8 |
| Group 2: 0 mg | | | | | | |
| Surgery | | | | 0 | 0 | 13 |
| Predose 2 | 0 | 0 | 16 | 0 | 0 | 13 |
| Predose 4 | 0 | 0 | 16 | 0 | 0 | 11 |
| Predose 6 | 0 | 0 | 15 | 0 | 0 | 10 |
| Predose 8 | 0 | 0 | 15 | 0 | 0 | 10 |
| Predose 10 | 0 | 0 | 15 | 0 | 0 | 9 |
| Predose 12 | 0 | 0 | 15 | 0 | 0 | 9 |
| Necropsy (24 hr after last dose) | 0 | 0 | 8 | 0 | 0 | 5 |
| Mid Recovery | 0 | 0 | 8 | 0 | 0 | 4 |
| Recovery Necropsy | 0 | 0 | 8 | 0 | 0 | 8 |
| Group 3: 1.8 mg | | | | | | |
| Surgery | | | | 0 | 0 | 15 |
| Predose 2 | 0 | 0 | 16 | 0 | 0 | 13 |
| Predose 4 | 23028 | 29871 | 16 | 21 | 72 | 12 |
| Predose 6 | 80769 | 70467 | 16 | 656 | 1284 | 9 |
| Predose 8 | 142031 | 93979 | 16 | 2206 | 3796 | 9 |
| Predose 10 | 341506 | 436656 | 16 | 4597 | 9386 | 9 |
| Predose 12 | 511938 | 635340 | 16 | 9916 | 20970 | 9 |
| Necropsy (24 hr after last dose) | 497588 | 666122 | 8 | 18145 | 22972 | 8 |
| Mid Recovery | 358213 | 226397 | 8 | 25064 | 29302 | 5 |
| Recovery Necropsy | 504013 | 766860 | 8 | 16499 | 18552 | 7 |
| Group 4: 6.0 mg | | | | | | |
| Surgery | | | | 0 | 0 | 15 |
| Predose 2 | 0 | 0 | 16 | 0 | 0 | 13 |
| Predose 4 | 47209 | 66899 | 16 | 93 | 170 | 12 |
| Predose 6 | 167721 | 137276 | 16 | 1269 | 2205 | 14 |
| Predose 8 | 315800 | 201572 | 16 | 11470 | 19344 | 9 |
| Predose 10 | 750656 | 682210 | 16 | 5490 | 8143 | 7 |
| Predose 12 | 1003450 | 868860 | 16 | 4048 | 6328 | 7 |
| Necropsy (24 hr after last dose) | 880534 | 857199 | 8 | 36640 | 45439 | 7 |
| Mid Recovery | 1270750 | 938646 | 8 | 53875 | 42430 | 4 |
| Recovery Necropsy | 953125 | 763122 | 8 | 39474 | 26274 | 7 |
| Group 5: 18.6 mg | | | | | | |
| Surgery | | | | 0 | 0 | 13 |
| Predose 2 | 0 | 0 | 16 | 0 | 0 | 15 |
| Predose 4 | 48433 | 46054 | 16 | 55 | 146 | 13 |
| Predose 6 | 252450 | 224723 | 16 | 821 | 2204 | 13 |
| Predose 8 | 441119 | 310702 | 16 | 4757 | 7781 | 13 |
| Predose 10 | 936813 | 849893 | 16 | 17822 | 24652 | 13 |
| Predose 12 | 1380250 | 1331905 | 16 | 13531 | 20189 | 11 |
| Necropsy (24 hr after last dose) | 286150 | 238760 | 8 | 8652 | 9129 | 8 |
| Mid Recovery | 2492875 | 1686472 | 8 | 51346 | 36819 | 5 |
| Recovery Necropsy | 2005125 | 1347857 | 8 | 44258 | 31114 | 8 |

TABLE 7

Incidence of Anti-rhASA Antibodies at Necropsy

| | Serum Antibody-Positive Animals (positive/total tested) | | | | CSF Antibody-Positive Animals (positive/total tested) | | | |
|---|---|---|---|---|---|---|---|---|
| | M | | F | | M | | F | |
| Group | 6-month Necropsy | Recovery Necropsy | 6-month Necropsy | Recovery Necropsy | 6-month Necropsy | Recovery Necropsy | 6-month Necropsy | Recovery Necropsy |
| 1 (DC) | NA | 0/4 | NA | 0/4 | NA | 0/4 | NA | 0/4 |
| 2 (vehicle) | 0/4 | 0/4 | 0/4 | 0/4 | 0/3 | 0/4 | 0/2 | 0/4 |

TABLE 7-continued

Incidence of Anti-rhASA Antibodies at Necropsy

| | Serum Antibody-Positive Animals (positive/total tested) | | | | CSF Antibody-Positive Animals (positive/total tested) | | | |
|---|---|---|---|---|---|---|---|---|
| | M | | F | | M | | F | |
| Group | 6-month Necropsy | Recovery Necropsy | 6-month Necropsy | Recovery Necropsy | 6-month Necropsy | Recovery Necropsy | 6-month Necropsy | Recovery Necropsy |
| 3 (1.8 mg IT) | 4/4 | 4/4 | 4/4 | 4/4 | 4/4 | 3/3 | 3/4 | 4/4 |
| 4 (6.0 mg IT) | 4/4 | 4/4 | 4/4 | 4/4 | 4/4 | 3/3 | 2/3 | 4/4 |
| 5 (18.6 mg IT) | 4/4 | 4/4 | 4/4 | 4/4 | 3/4 | 4/4 | 4/4 | 4/4 |

The quantitation limit for rhASA in cynomolgus monkey serum is 39.1 ng/mL, and all serum samples from Groups 1 and 2 were below quantitation limit (BQL), see Table 30. Serum levels of rhASA were tested prior to and at 24 hours after Doses 2, 4, 6, 8, 10, and 12 (6-month necropsy), midway through the recovery period, and prior to the recovery necropsy. rhASA levels were undetectable in Group 3 (1.8 mg/dose), Group 4 (6.0 mg/dose), and Group 5 (18.6 mg/dose) prior to Doses 2, 4, 6, 8, 10, and 12. After Dose 12, midway through the recovery period, and prior to the recovery necropsy. After Dose 2, the levels of rhASA in serum were dose-related. After Dose 4 (Group 3), Dose 6 (Groups 3 and 4), and Doses 8 and 10 (Groups 3 and 4 and Group 5 males), rhASA levels were undetectable. Serum levels of rhASA declined in Group 4 (6.0 mg/dose) after Dose 4 and in Group 5 (18.6 mg/dose) after Doses 4 and 6 for males and Doses 4, 6, 8, and 10 for females. This apparent decline in serum rhASA levels may be related to the increasing concentration of anti-rhASA antibodies. There were no apparent sex differences in serum levels of rhASA, given the sample variability and small group numbers in this study.

The quantitation limit for rhASA in cynomolgus monkey CSF is 19.5 ng/mL, and all CSF samples from Groups 1 and 2 were BQL, see Table 31. rhASA was detectable in CSF prior to and after Doses 2, 4, 6, 8, 10, and 12 (6-month necropsy) in all dosed groups. The levels were higher postdose (approximately 24 hours postdose) and were dose related. The levels in CSF were much greater than those in serum. There were no apparent sex differences in CSF levels of rhASA, given the sample variability and small group numbers in this study. rhASA was not detectable midway through the recovery period and prior to the recovery necropsy in all dosed groups. CSF levels at the Dose 12 (necropsy) collections for rhASA treated groups were lower than levels postdose 8 and 11. Potential reasons for lower rhASA levels at necropsy include the larger volume taken (~2.25 mL total for cell counts, chemistry, rhASA and anti-RHASA antibody) at necropsy vs. those taken at in-life dosing interval (up to 0.5 mL pre- or postdose for rhASA concentration). Additionally, some animals did not have patent catheters at necropsy, and samples were taken via a CM tap rather than via the catheter. This route consistently yielded lower rhASA concentrations as compared with sampling via the catheter. This is likely due to the limited rostrocaudal direction of CSF bulk flow that is acknowledged to occur in vertically-oriented animals like monkeys and man (e.g., it is well known that constituents of CSF exhibit marked rostrocaudal gradients throughout an individuals lifetime).

Anti-rhASA antibodies in serum were detected in every animal treated with RHASA at some time point, see Table 32. Animals are defined as positive for anti-rhASA antibodies if the level of anti-rhASA antibody was above the quantitation limit (78.1 ng/mL). Animals remained positive for anti-rhASA antibodies once they seroconverted. No animals were positive for anti-rhASA antibodies at the predose 2 timepoint. All rhASA animals except Male No. 026 (Group 4; 6.0 mg/dose) were positive for serum anti-rhASA antibodies at the predose 4 timepoint. Male No. 026 was positive for serum antiboday at the predose 6 timepoint. In Group 5 (18.6 mg/kg), the necropsy antibody samples had lower antibody levels. This apparent decrease may be due to the presence of rhASA interfering with the assay. The titer was generally higher in the mid- and high-dose groups (6.0 and 18.6 mg/dose) than the low dose animals (1.8 mg/dose). The presence of anti-rhASA antibodies is an expected result from treating cynomolgus monkeys with a recombinant human protein[i]. Given the variability in the results, there was no apparent sex differences.

All animals with detectable anti-rhASA antibodies in CSF had detectable rhASA antibodies in serum as well, with the exception of Female Nos. 049 (Group 3; 1.8 mg/dose) and 057 (Group 4; 6.0 mg/dose). The variability in the antibody concentration and incidence precludes determination of a dose response. Animals are defined as positive for anti-RHASA antibodies if the level of anti-rhASA antibody was above the quantitation limit (78.1 ng/mL)

Combined values for males and females for serum and CSF RHASA levels and for anti-RHASA antibodies are shown in Table 34 and Table 35. Combined male and female results are similar to the individual sexes, discussed above.

Example 17—Efficacy

In this example, 11 Wild-type control (mASA+/+ hASA−/−) mice were assigned to Group A and received no treatment. thirty-four (34) hASAC69S/ASA−/− mice were assigned to each of 5 dose groups and received vehicle (Group B) or rhASA at doses of 20 mg/kg (intravenous [IV]; Group C) or 0.04, 0.12, and 0.21 mg (Groups D, E, and F, respectively) on Days 1, 9, 15/16, and 22. All IV doses were administered via a tail vein. All intrathecal (IT) doses were administered as an infusion in a volume of 12 μL at an approximate range of 2 μL/20 seconds (Table 37).

TABLE 37

Study Design

| Group | No. of Animals | Animal Type | Treatment | Dose | Route | Total No. of Injections | Sacrifice | Dose in mg/kg brain weight[a] |
|---|---|---|---|---|---|---|---|---|
| A | 11 | Wild-type control (mASA +/+ hASA −/−) | None | NA | NA | NA | NA | NA |
| B | 9 | hASAC69S/ ASA −/− | Vehicle Control | Vehicle | IT lumbar | 4 (Days 1, 9, 15/16[b], and 22) dose | 24 hours after the fourth | 0 |
| C | 5 | | rhASA | 20 mg/kg | IV (tail vein) | | | NA |
| D | 5 | | rhASA | 0.04 mg | IT lumbar | | | 100 |
| E | 5 | | rhASA | 0.12 mg | IT lumbar | | | 300 |
| F | 10 | | rhASA | 0.21 mg | IT lumbar | | | 520 |

NA = not applicable;
IT = intrathecal;
IV = intravenous.
[a]Brain weight for mice is approximately 0.0004 kg.
[b]Groups C, D, and E were dosed on Day 15; Groups B and E were dosed on Day 16.

The ASA knockout mouse hASAC69S/ASA(−/−) is an accepted model of MLD, and has been used to test potential treatments for this disease. The intrathecal route is the intended route of administration in humans. The intravenous route of administration has been tested for this compound and a similar compound in MLD mice. An intravenous control group has been added as a positive control for histological changes expected in peripheral organs. Animals received 100, 300, or 520 mg/kg of brain weight (0.04, 0.12, 0.21 mg, respectively) of rhASA. The dose levels normalized to brain weight selected for this study correspond to doses that are planned for use in humans or have been used in toxicology studies or in previous efficacy models of lysosomal storage diseases. These doses were not expected to have any toxicity.

Receipt
Species Mice (*Mus musculus*)
Strain hASAC69S/ASA(−/−) mice and wild type controls
Age Approximately 14-17 months at arrival
No. of Groups 6
No. of Animals 34 ASA knockout mice+11 wild type controls Following arrival, each animal was examined to assess health status.

Housing

Animals were group housed in high-temp polycarbonate filter-top cages, with CareFresh paper bedding and water bottles. Each cage was clearly labeled with a cage card indicating project, group and animal numbers, and sex. Each animal was uniquely identified using an ear punch system.

The targeted conditions for animal room environment and photoperiod were as follows:

Temperature 22° C.±3° C.
Humidity 50%±20%
Light cycle 12 hours light and 12 hours dark All available wild type animals (11) were assigned to Group A and were numbered 35 through 45. ASA (−/−) hASA (+/−) animals were assigned consecutive numbers (1 through 34) as they were removed from their cages, weighed, and ear punched during acclimation. Animals were then assigned to the treatment groups using Research Randomizer (randomizer.org) on Jan. 3, 2011. the first 9 numbers were assigned to Group B, the next 5 to Group C, the next 5 to Group D, the next 5 to Group E, and the final 10 to Group F. Animals were assigned as follows:

TABLE 38

Animal Assignment

| Group | N | Animal Numbers |
|---|---|---|
| A | 11 | 35, 36, 37, 38, 39, 40, 41, 42, 43, 44, 45 |
| B | 9 | 7, 13, 17, 22, 23, 24, 28, 29, 30 |
| C | 5 | 6, 16, 19[a], 21, 32 |
| D | 5 | 5, 9, 14, 18, 27 |
| E | 5 | 1, 2, 4, 8, 11 |
| F | 10 | 3[b], 10, 12, 15, 20, 25, 26, 31, 33, 34 |

[a]Animal No. 19 could not be located at the time of dosing.
[b]Animal No. 3 died before dosing began.

Test Article and Vehicle

| | Test Article |
|---|---|
| Identity | rhASA |
| Description | human recombinant Arylsulfatase A (ARSA) |
| Storage Conditions | Approximately 4° C. |
| Vehicle Identity | rhASA Vehicle (154 mM NaCl, 0.005% polysorbate 20, pH~6.0) |
| Storage Condition | Approximately 4° C. |

Preparation of Vehicle

The vehicle was used as provided. The vehicle was warmed on the bench top (ambient). Once the vehicle was warmed, the material was mixed by gently swirling and inverting. The bottles were not vortexed or shaken. The bottle was dried before accessing the material. Any remaining vehicle was returned to the refrigerator (1° C.-8° C.).

Dose Formulation Preparation rhASA was diluted with vehicle to achieve the necessary concentrations. The test article was warmed on the bench top (ambient). Once the test article was warmed, the material was mixed by gently swirling and inverting. The bottles were not vortexed or shaken.

Dyes to Track Injections:

An infrared dye (such as IRDye®, LI-COR Biosciences, Lincoln, NE) was utilized for tracking the injections. Dyes such as this have been used in intrathecal injections as a survival procedure after intrathecal administration. The dye was mixed with the test article before administration; 1 nmole of dye in 1 µL was added to the test article. In addition to the infrared dye, 1 µL of FD&C blue #1 (0.25%) was used for tracking injections. This blue dye is a common food additive and is generally considered safe and non-toxic.

Lumbosacral IT Injection of rhASA or Vehicle

Animals in Groups B, D, E, and F received intrathecal injections on Days 1, 9, 15 or 16, and 22.

Adult mice were anesthetized using 1.25% 2,2,2 tribromoethanol (Avertin) at 200-300 µL/10 grams body weight (250-350 mg/kg) by intraperitoneal injection. Dorsal hair was removed between the base of the tail and the shoulder blades using a clippers. The shaved area was cleaned with povidine/betadine scrub followed by isopropyl alcohol. A small midline skin incision (1-2 cm) was made over the lumbosacral spine, and the intersection of the dorsal midline and the cranial aspect of the wings of the ilea (singular ileum) was identified. The muscle in the iliac fossa (gluteus medius) is a heart shaped muscle. The two sides of the top of the "heart" approximate the location of the wings of the ilea. A 32-gauge needle attached to a gas tight 10-20 µL glass Hamilton syringe was inserted until resistance was felt from the underlying bone. Injection of 10 µL of test article, 1 µL of infrared dye, and 1 µL of FD&C blue #1 (total injection volume of 12 µL) was performed at an approximate rate of 2 µL/20 seconds (12 µL/2 minutes). The skin incision was closed using wound clips. The success of the injection was judged by imaging to determine if the infrared dye had distributed throughout the CNS, as well as the visible blue dye. After imaging, the animal was allowed to recover in a recovery chamber.

Intravenous Injection of rhASA

Animals in Group C received intravenous injections on Days 1, 9, 15, and 22.

For IV injections, animals were anesthetized using isoflurane, if required, and were placed in a restrainer. The tail vein was dilated by warming by flicking the tail gently with the finger. The injection site was then wiped with 70% ethanol. Alternatively, the animal was placed in a warm chamber (40° C.) for 1-1.5 minutes. A 28- to 30-gauge needle was used to inject test material. The volume of injection was 5-10 mL/kg.

Approximately 24 hours after the fourth dose, animals in Groups B-F were euthanized. Animals were subjected to different tissue collection procedures, as detailed below. Animals in Group A were not treated; however, they were euthanized on Jan. 27 or 28, 2011 and subjected to tissue collection procedures, as detailed below.

Serum (All Animals)

A terminal blood sample (approximately 0.5 mL) was collected from all animals (Groups A-F) via retroorbital puncture under isoflurane anesthesia. A glass tube was placed in the orbit, gently penetrating the area behind the eye and thus disrupting the venous drainage located behind the eye. Blood was collected by capillary action and/or gravity flow. Following blood collection, pressure was applied to the orbit to stop the bleeding.

The whole blood samples were processed to serum and frozen at <−80° C. The serum was stored at −80° C. and analyzed for antibodies.

Tissues for Light Microscopy Investigations (Groups A-F; 5 Mice Per Group)

After blood collection, animals were euthanized via $CO_2$ asphyxiation. A tail snip was collected prior to perfusion and frozen for possible genotyping. The pericardial cavity was exposed. Three (3) mice per group were transcardially perfused with heparinized saline solution (1 U/mL sodium heparin in 0.9% NaCl, sterile-filtered) chilled ice-cold and then with 4% paraformaldehyde at approximately 4° C. The brain was removed, and the abdomen was cut to expose the internal organs further. The brain and carcass were placed in paraformaldehyde, except for the tail snip which was frozen.

Tissues for Lipid Analysis (Groups A, B, and F; 6, 4, and 5 Animals, Respectively)

After blood collection, animals were euthanized via $CO_2$ asphyxiation. A tail snip was collected prior to perfusion and frozen for possible genotyping. The pericardial cavity was exposed. For lipid analyses, 4-6 mice per group were transcardially perfused with heparinized saline solution (1 U/mL sodium heparin in 0.9% NaCl, sterile-filtered) chilled ice-cold.

TABLE 39

Tissues Collected for Lipid Analysis
Tissues Collected for Lipid Analysis

| | |
|---|---|
| Brain (separated into left and right hemispheres and weighed) | Kidney (2) |
| Spinal cord (removed from spinal column) | |
| Sciatic nerve (2) (dissected free from muscle) | Tail snip (prior to perfusion) |

Upon collection, tissues were weighed and then frozen, either on dry ice or by placing in a −80° C. freezer. The brain was separated into left and right hemispheres. The right will be utilized for lipid analysis by MS. The left will be analyzed for possible N-acetyl-L-aspartate (NAA) analysis. Tissues were stored at −80° C. until analysis.

TABLE 40

Sample Storage Conditions

Figure 114:
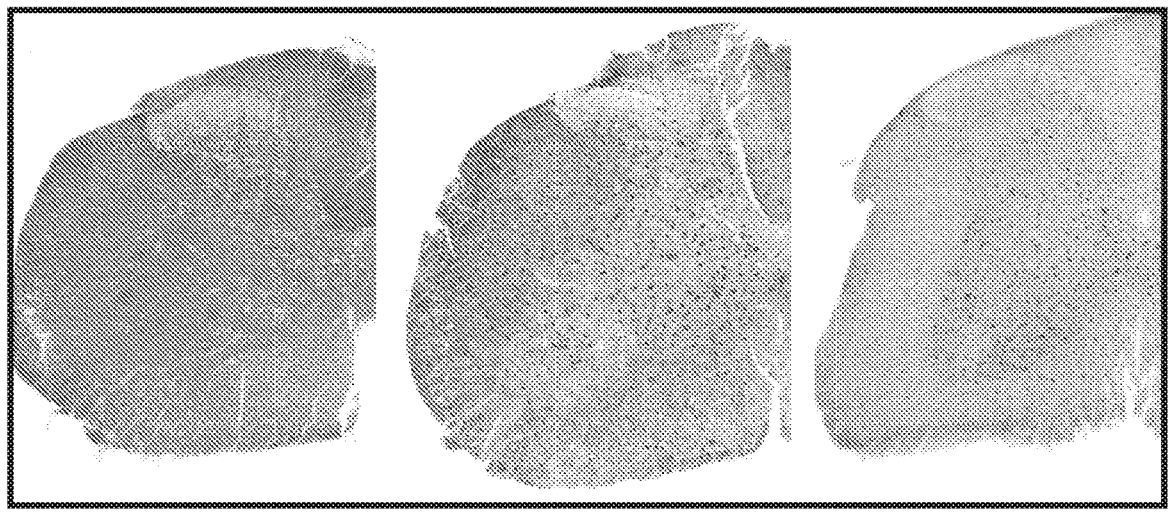
FIG. 114 depicts exemplary Alcian blue staining of spinal cord of immunotolerant MLD Mice treated with rhASA1 and results illustrating sulfatide reduction as determined by Alcian blue staining of the cervical spinal cord in animals that received intrathecal injections of rhASA at days 1, 8, 15 and 22 at doses of 520 mg/kg brain weight or vehicle control. As demonstrated, treatment with intrathecally injected rhASA resulted in reduction of sulfatide accumulation in the spinal cord, including in the cervical region of the spinal cord.
Figure 115:
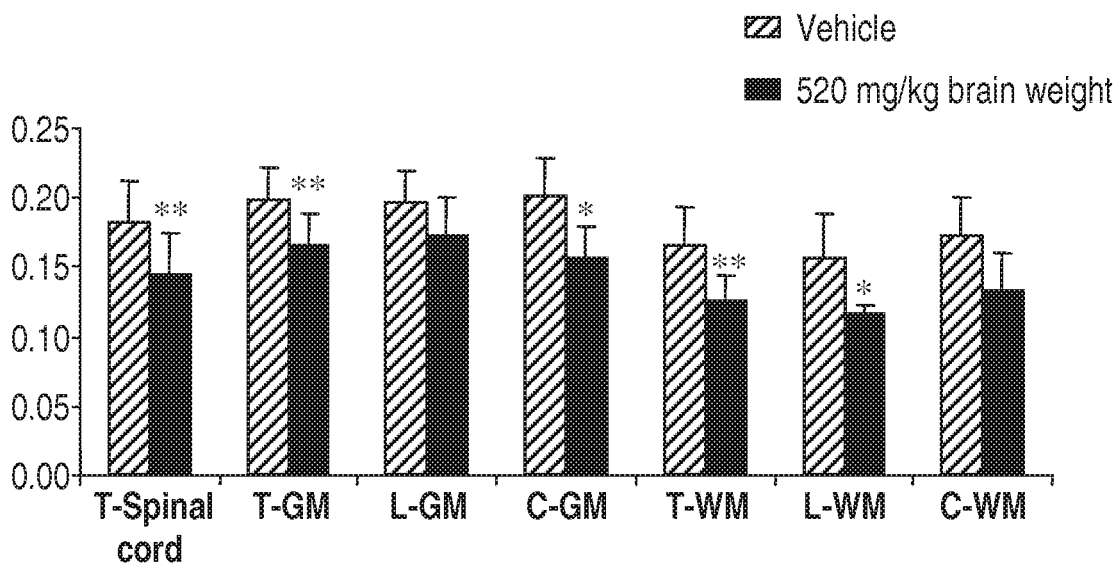
FIG. 115 illustrates exemplary morphometry analysis of Alcian blue stained spinal cord sections from immunotolerant MLD Mice treated with rhASA1 and results illustrating optical density of Alcian blue in total spinal cord (T-Spinal Cord), total gray matter (T-GM), lumbar gray matter (L-GM), cervical gray matter (C-GM), total white matter (T-WM), lumbar white matter (L-WM), and cervical white matter (C-WM) as determined by morphometry analysis. As demonstrated, a statistically significant reduction in Alcian blue staining was observed in animals treated with rhASA as compared to a vehicle control.
Figure 116:
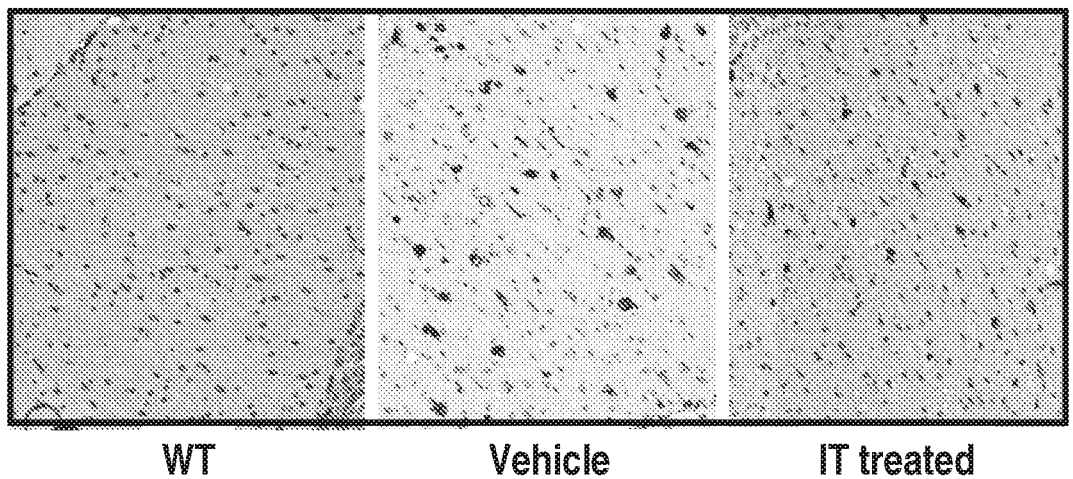
FIG. 116 depicts exemplary reduction of LAMP staining in white matter (Fimbria) of immunotolerant MLD mice treated with rhASA1 depicts exemplary results illustrating LAMP-1 levels in fimbria as determined by immunohistochemistry. Magnification=20×. As demonstrated, treatment with intrathecally injected rhASA resulted in reduction of LAMP-1 in the cerebral white matter.
Figure 117:
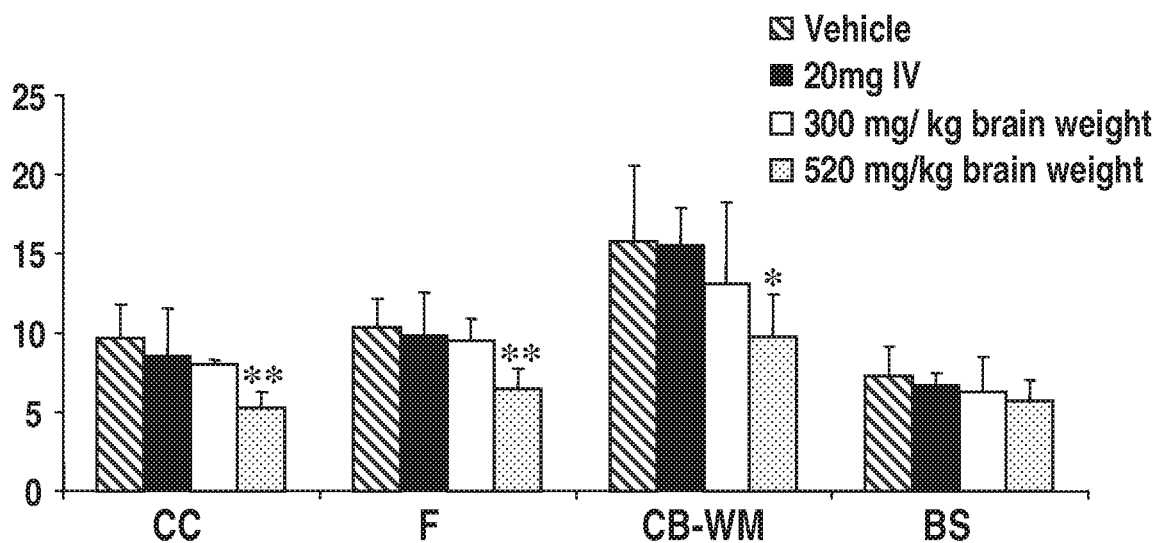
FIG. 117 illustrates exemplary morphometry analysis of LAMP staining of brain from immunotolerant MLD mice treated with rhASA1 and results illustrating LAMP-1 staining intensity in corpus collosum (CC), fimbria (F), cerebellar white matter (CB-WM) and brain stem (BS) of animals treated with 20 mg/kg intravenous rhASA, 300 mg/kg brain weight intrathecal rhASA, 520 mg/kg brain weight intravenous rhASA, or vehicle control.
Figure 118:
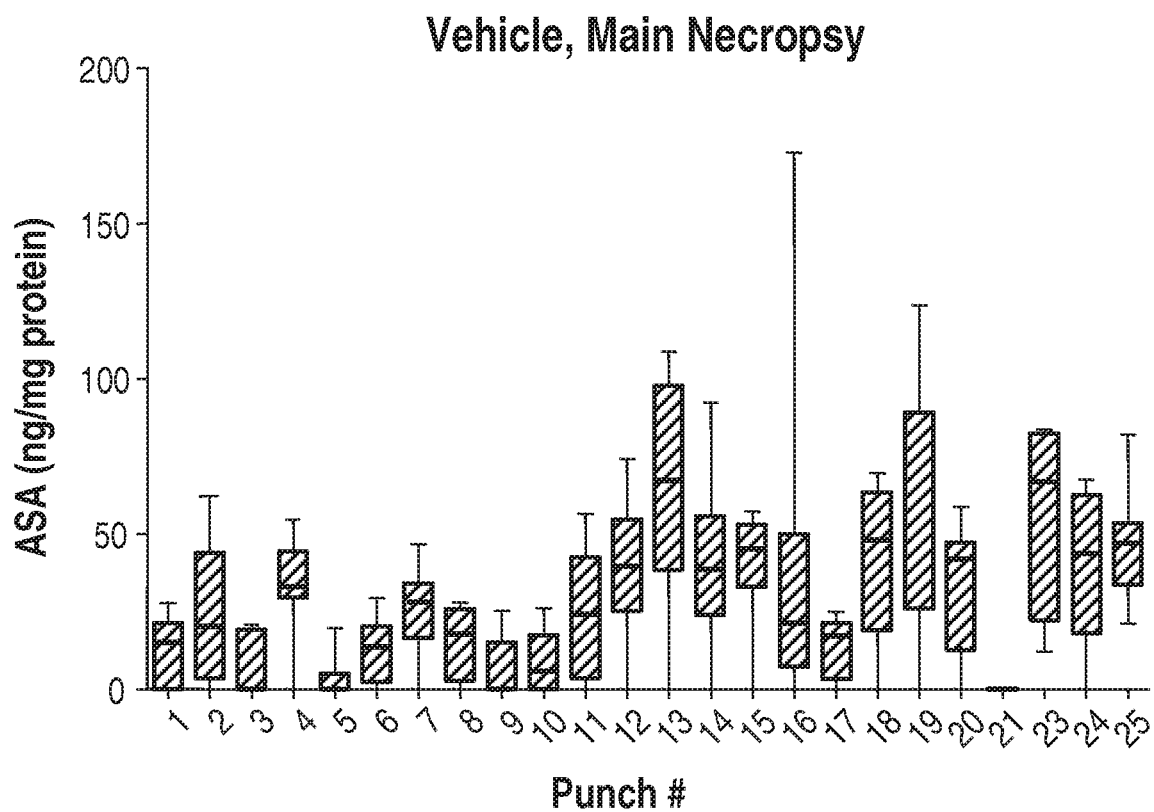
FIG. 118 is an exemplary illustration showing the concentration of ASA in brain punches of vehicle-dosed juvenile Cynomolgus monkeys following every-other-week (EOW) IT dosing for 6-months (main necropsy).
Figure 119:
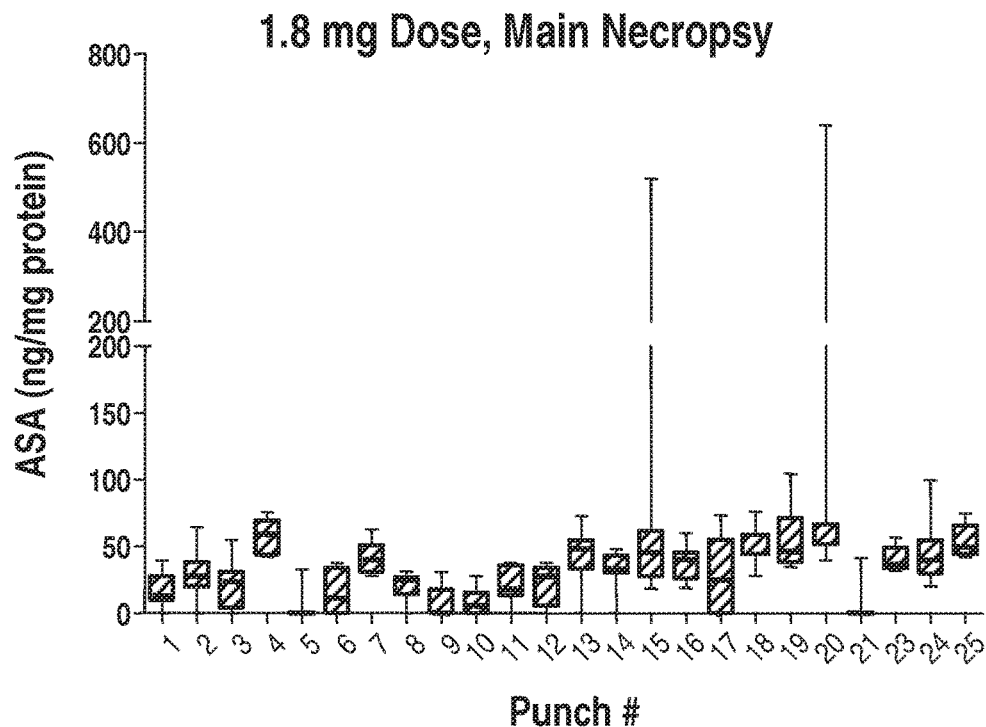
Figure 120:
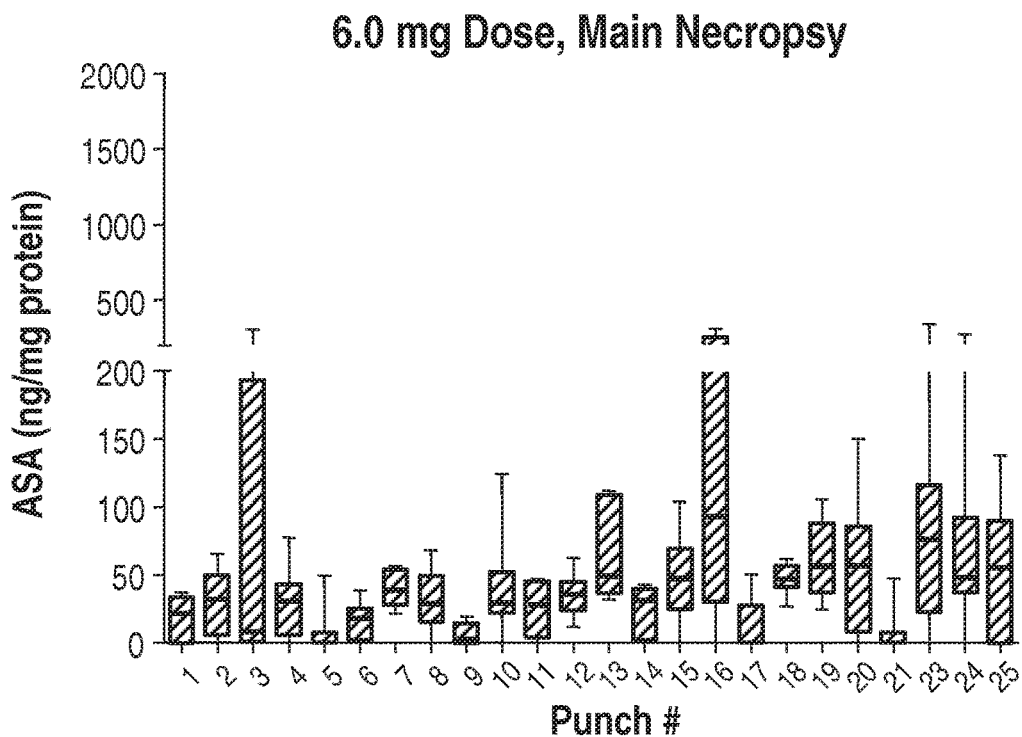
Figure 121:
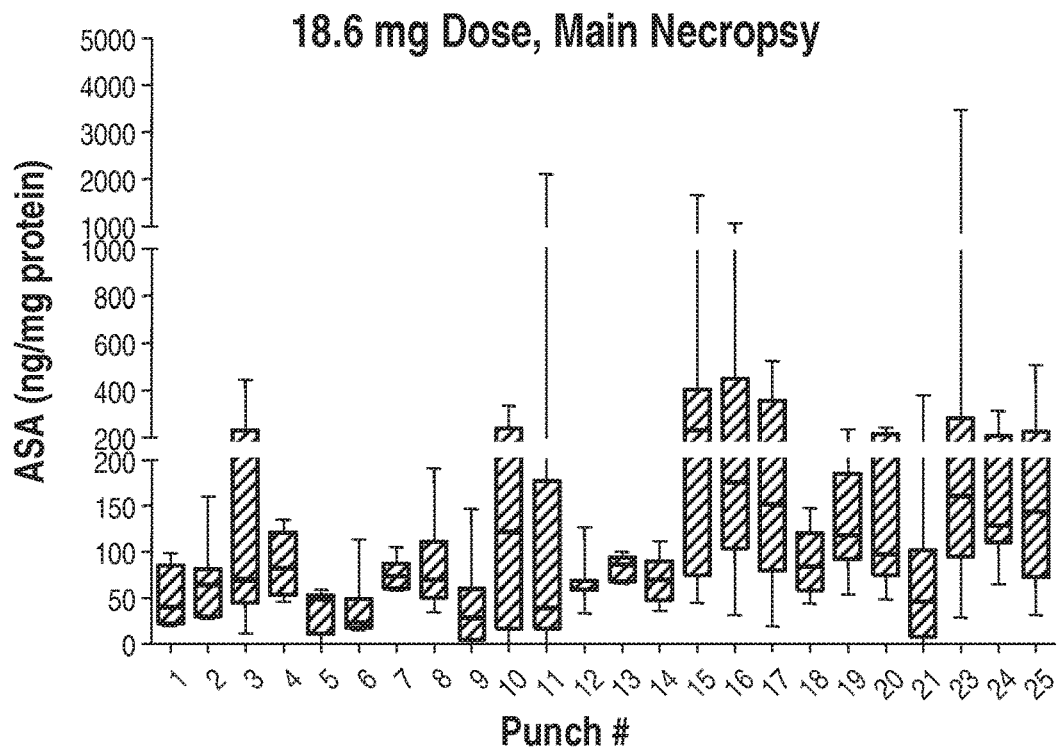
Figure 122:
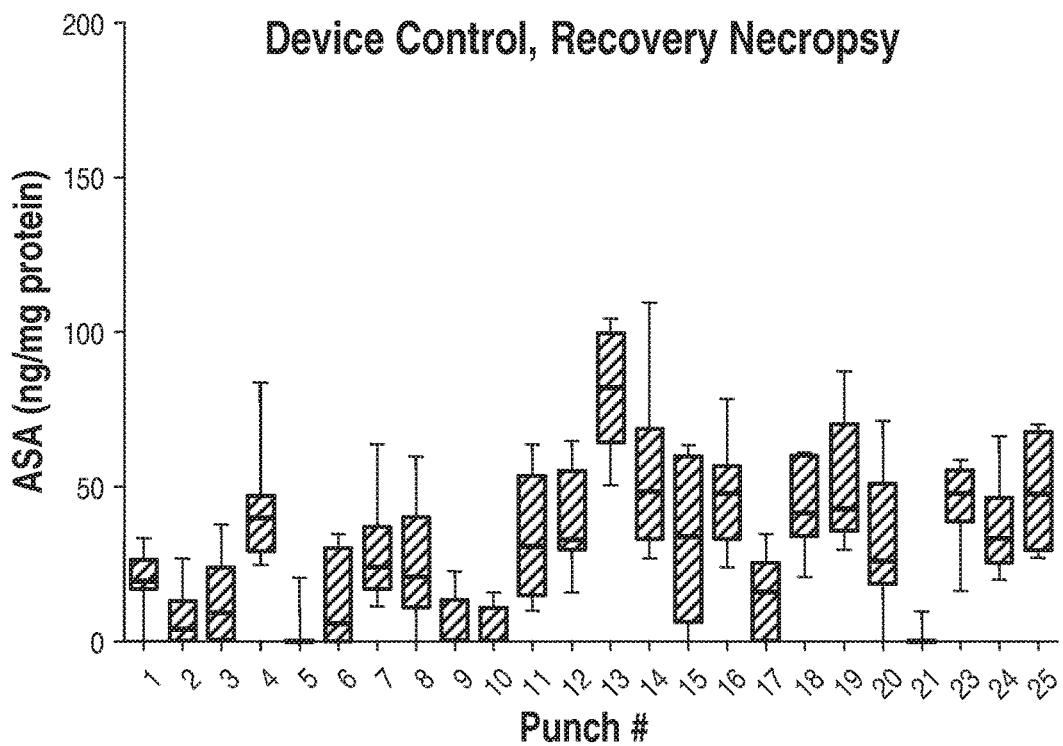
Figure 123:
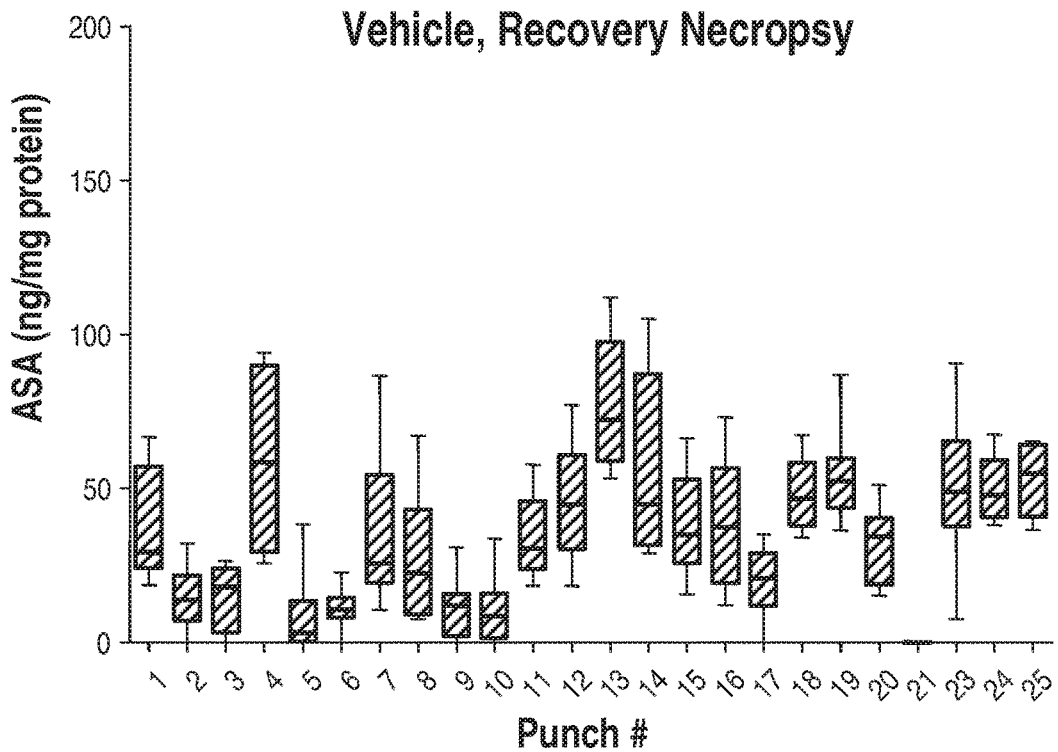
Figure 124:
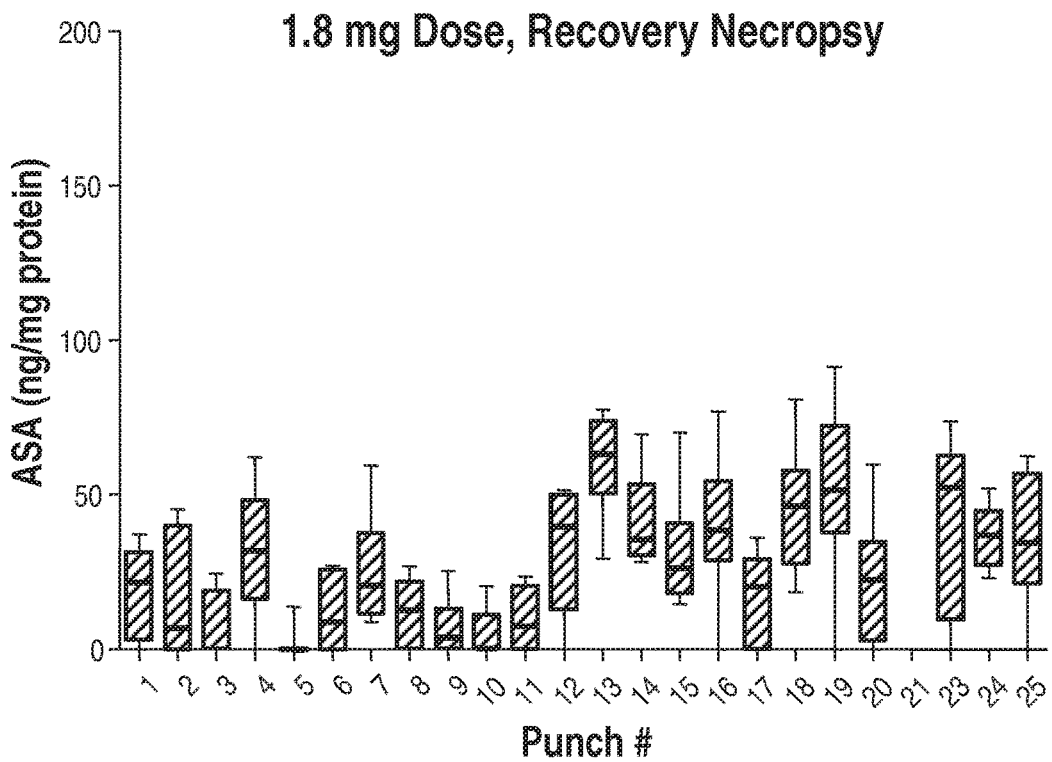
Figure 125:
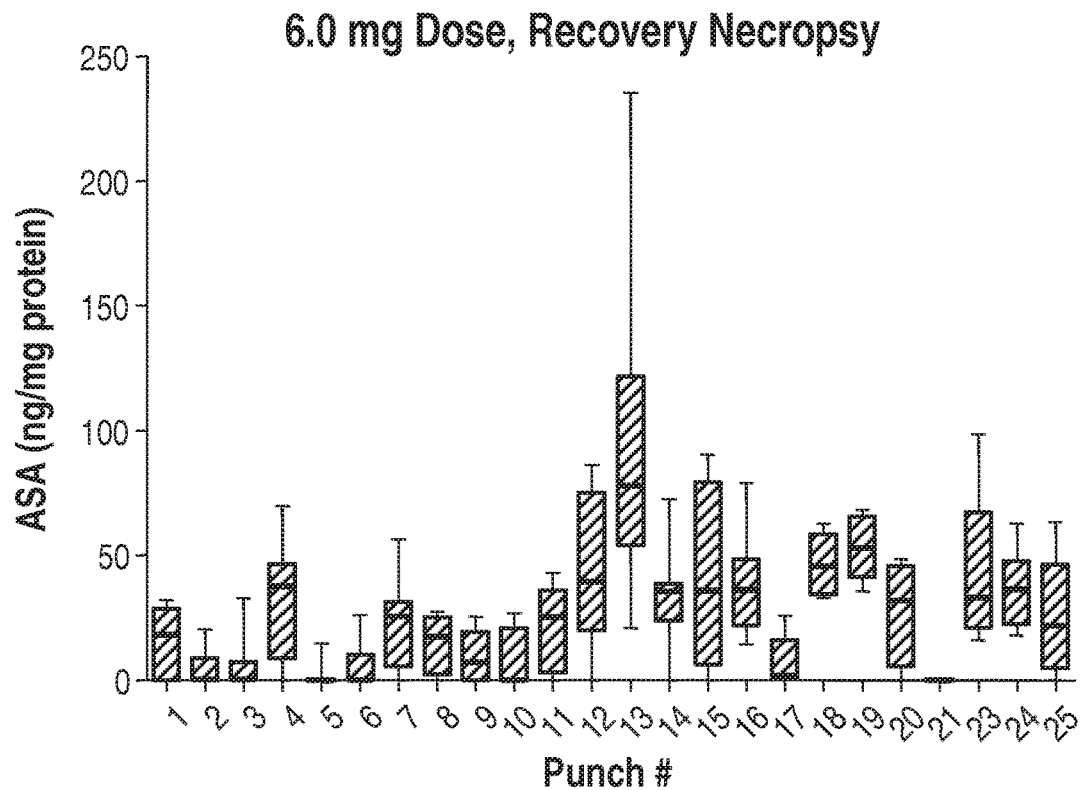
Figure 126:
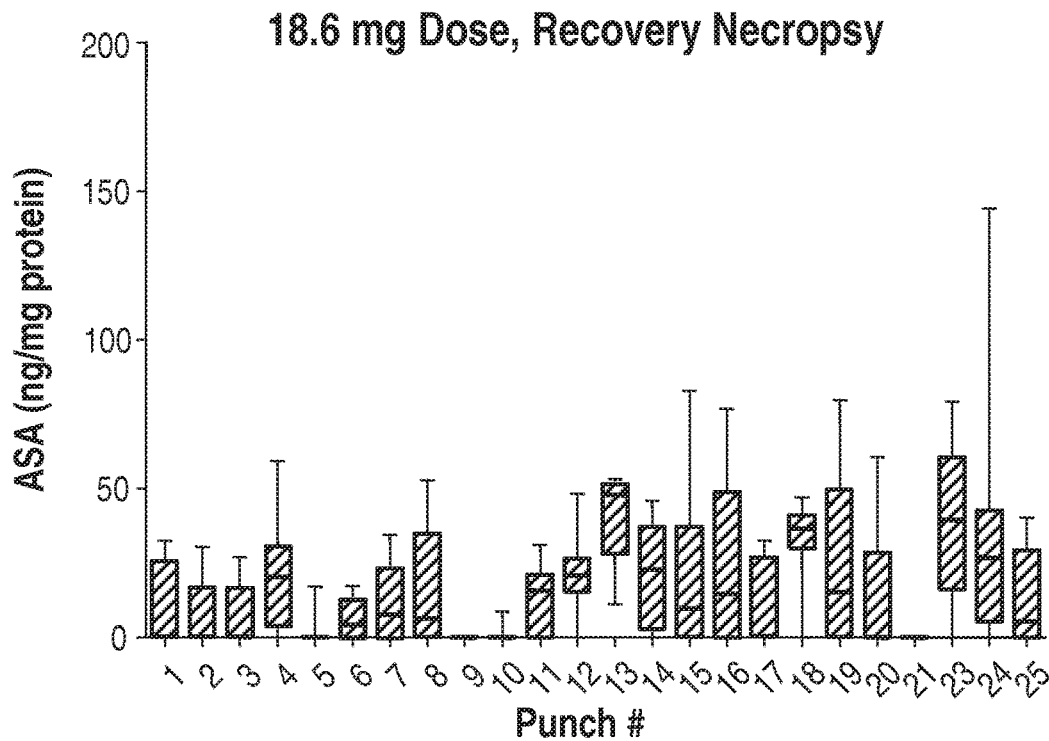

| Type of Sample | Storage Temperature |
|---|---|
| Serum | frozen at circa −80° C. |
| tissues for lipid analysis | frozen at circa −80° C. |
| Tail snips | frozen at circa −80° C. |
| Tissues for light microscopy | Approximately 4° C. | rhASA reduced sulfatide storage in the spinal cord of MLD mice, particularly in the white matter, FIG. 114. Morphometry analysis of the spinal cord demonstrated that the optical density of alcian blue staining was statistically significantly reduced after rhASA dosing, FIG. 115. rhASA treated MLD mice also exhibited reduced lysosomal activity in the brain, FIG. 116. This reduction was statistically significant in the high-dose group (0.21 mg-520 mg/kg brain weight) compared with vehicle treated animals, FIG. 117.

Immunotolerant MLD mice (hASAC69S/ASA(−/−)) over 1 year in age received intrathecal-lumbar administration of rhASA one time each week for 4 weeks (a total of 4 doses). Doses were vehicle (154 mM NaCl, 0.005% polysorbate 20, pH ~6.0), 0.04, 0.12, 0.21 mg/dose (normalized doses were 100, 300 and 520 mg/kg of brain weight, respectively). At terminal timepoints efficacy was evaluated by immunohistochemistry assessment of sulfatide clearance and lysosome activity within the brain and spinal cord. Spinal cord and brain sections were stained using alcian blue stain targeting sulftatides in tissues. Brain sections were also stained for the presence of lysosomal-associated membrane protein (LAMP), an indicator of lysosomal processes. Additionally, morphometry analysis was performed on alcian blue and LAMP stained sections of the spinal cord (cervical, thoracic and lumbar) and brain.

These preliminary results demonstrate efficacy of intrathecal lumbar administration of rhASA. Compared to vehicle control mice, rhASA treated MLD mice exhibit evidence of improvement within the histological markers of disease, such as reduced sulfatide storage (noted by alcian blue staining) and lysosomal activity in the brain. These histopathological changes were observed near the site of administration (lumbar region of the spinal cord), in the distal spinal cord, as well as in the distal portions of the brain.

Example 18—Biodistribution 2

Overview

In this study, 36 male and 36 female juvenile cynomolgus monkeys (<12 months at initiation) were assigned to each of 5 dose groups and received rhASA at doses of 0 (device control; animals were dosed with 0.6 mL of PBS), 0 (vehicle control), 1.8, 6.0, or 18.6 mg (Groups 1, 2, 3, 4, and 5, respectively) every other week for 6 months for a total of 12 doses. All doses were administered as an infusion in a volume of 0.6 mL, followed by a flush of 0.5 mL PBS given over approximately 10 minutes (Table 41).

TABLE 41

Study Design

| Group | No. of Animals | Nominal Dose Concentration (mg/mL) | Administered Dose (mg) | No. of Animals, 6 Month Sacrifice | No. of Animals, 1 Month Recovery Sacrifice |
|---|---|---|---|---|---|
| 1 | 4 M, 4 F | DC | 0 | — | 4 M, 4 F |
| 2 | 8 M, 8 F | 0 | 0 | 4 M, 3 F[a] | 4 M, 4 F |
| 3 | 8 M, 8 F | 3 | 1.8 | 4 M, 4 F | 4 M, 4 F |
| 4 | 8 M, 8 F | 10 | 6.0 | 4 M, 4 F | 4 M, 4 F |
| 5 | 8 M, 8 F | 31 | 18.6 | 4 M, 4 F | 4 M, 4 F |

DC = Device Control; Animals in Group 1 were not dosed with vehicle or test article.
[a]Vehicle Control Animal No. 044 was sacrificed early on Day 50 due to a leaking catheter Material And Methods Tissue Collection The brains were cut in a brain matrix at 3 mm thick coronal slice thickness. Each brain was sectioned into full coronal slices including: neocortex (including frontal, parietal, temporal, and occipital cortex), paleocortex (olfactory bulbs and/or piriform lobe), basal ganglia (including caudate and putamen), limbic system (including hippocampus and cingulate gyri), thalamus/hypothalamus, midbrain regions (including substantia nigra), cerebellum, pons, and medulla oblongata. The locations from which individual tissue samples were obtained (via 4-mm biopsy punch) are shown in FIGS. 133-138. The images in FIGS. 133-138 are from the University of Wisconsin and Michigan State Comparative Mammalian Brain Collections, (also the National Museum of Health and Medicine). Punch number 22 was not collected, as this structure was not present during necropsy. All brain samples were frozen and stored at −60° C. or below prior to analysis for rhASA using an enzyme-linked immunosorbent assay.

The first brain slice and every second slice thereafter were fixed in formalin for histopathological evaluation and immunohistochemical. The second brain slice and every second slice thereafter were frozen for test article concentration analysis. Prior to freezing, samples of brain were taken from the right portion of the even-numbered, test article analysis brain slices for biodistribution analysis. The location of the brain samples were photographed at necropsy and the brain slice number was recorded. The samples were obtained using either a 4-mm circular punch or cut with a scalpel to optimize the amount of white matter collected. All punches were frozen and stored at −60° C. or below for test article analysis. The remainder of the brain slice was frozen and stored at −60° C. or below for possible test article analysis.

The spinal cord (cervical, thoracic and lumbar) was cut into one-centimeter sections. The first slice and every second slice thereafter was fixed in formalin for histopathological and immunohistochemical analysis. The second slice of spinal cord and every second slice thereafter was frozen and stored at −60° C. or lower for test article analysis. The distribution of slices was adjusted so that the slice with the tip of the intrathecal catheter (Slice 0) was fixed in formalin and analyzed for histopathology.

Preparation of Brain, Liver, and Spinal Extracts and Determination of rhASA Concentration Brain punches, spinal cord, and liver samples were analyzed using a validated method in compliance with the United States Food and Drug Administration (FDA) Good Laboratory Practice (GLP) regulations 21 CFR, Part 58 and with applicable Midwest BioResearch standard operating procedures. Tissue samples were homogenized in lysis buffer, centrifuged to remove any tissue debris, and stored at −80° C. until assayed. rhASA concentration in the soluble fractions of the homogenates was determined by an ELISA using polyclonal rabbit antibody SH040 as the capture antibody and HRP (horseradish peroxidase)-conjugated anti-ASA monoclonal antibody 19-16-3 as the detection antibody. After a wash step to remove unbound materials, tetramethylbenzidine (TMB) substrate solution reacted with the peroxide in the presence of HRP-conjugated antibody to produce a colorimetric signal that was proportional to the amount of rhASA bound by the anti ASA antibody in the initial step. The resulting amount of rhASA in each tissue homogenate was interpolated from a standard curve.

Samples were also analyzed by a bicinchoninic acid (BCA) protein determination assay to obtain the concentration of protein in the sample. The protein concentration for each sample was determined by interpolation of an albumin standard curve. rhASA concentration results were then normalized to total protein in tissue extracts, as determined by bicinchoninic acid assay.

The rhASA levels of all punches for the vehicle, 1.8 mg/dose, 6.0 mg/dose, and 18.6 mg/dose groups are shown in FIG. 118, FIG. 119, FIG. 120, and FIG. 121, respectively. The rhASA levels of all punches for the recovery animals for the device control, vehicle, 1.8 mg/dose, 6.0 mg/dose, and 18.6 mg/dose groups are shown in FIG. 122, FIG. 123, FIG. 124, FIG. 125, and FIG. 126, respectively.

The rhASA levels for selected punches that were taken near the surface (meninges) of the brain are shown in FIG.

Figure 128:
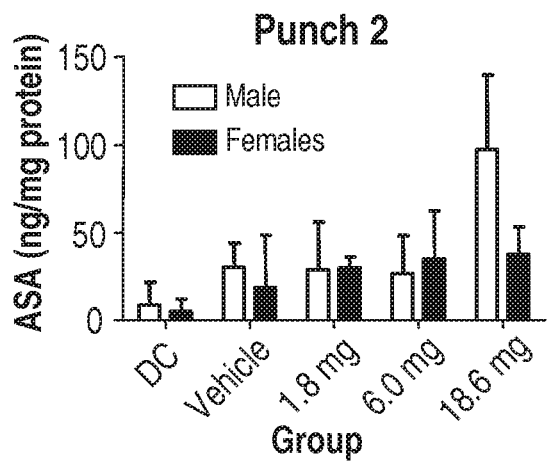
Figure 128:
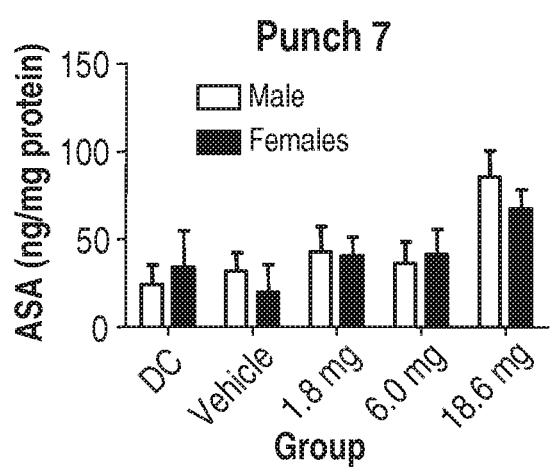
Figure 128:
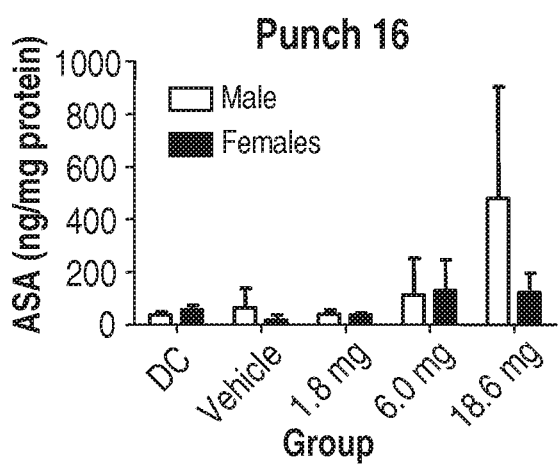
Figure 128:
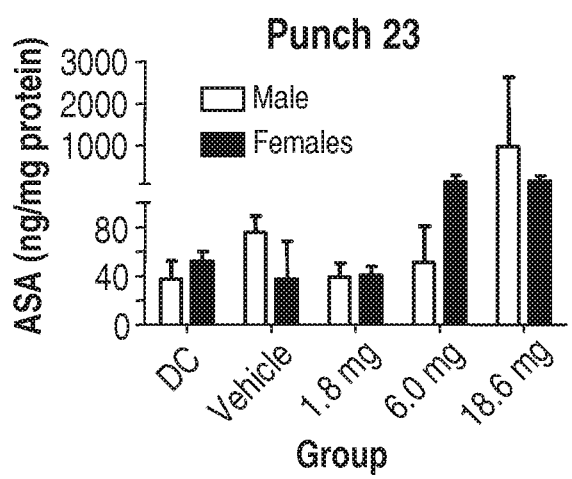
Figure 128:
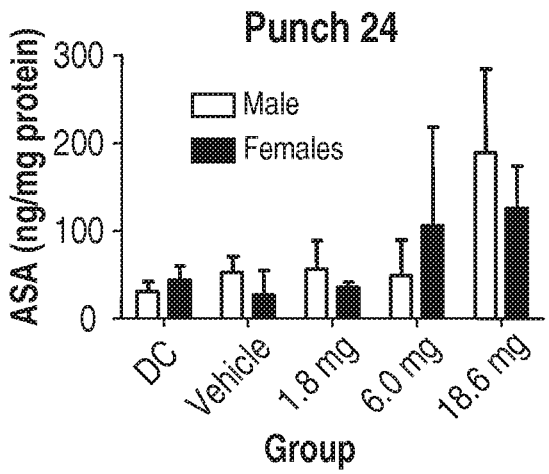
Figure 129:
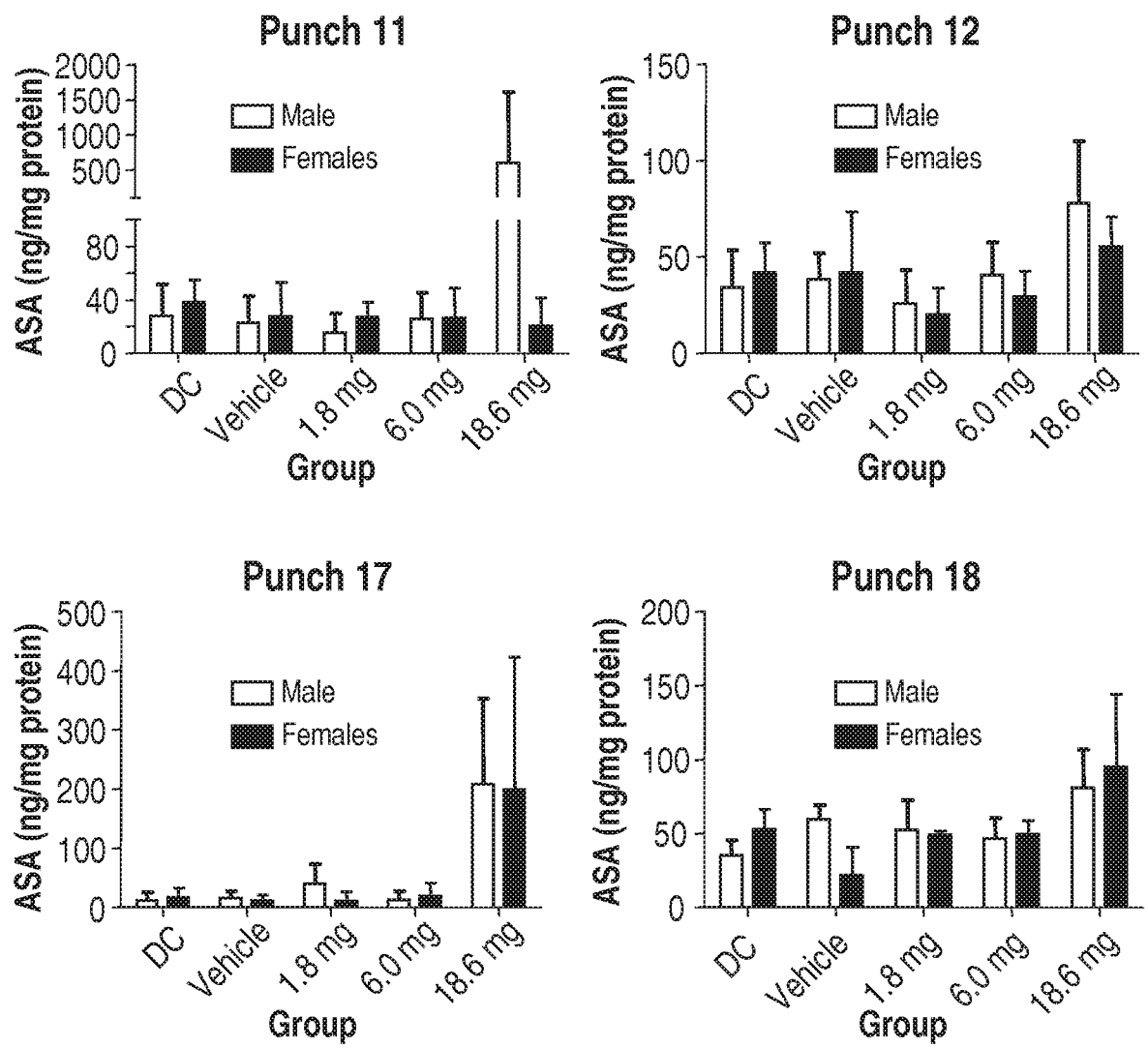
Figure 130:
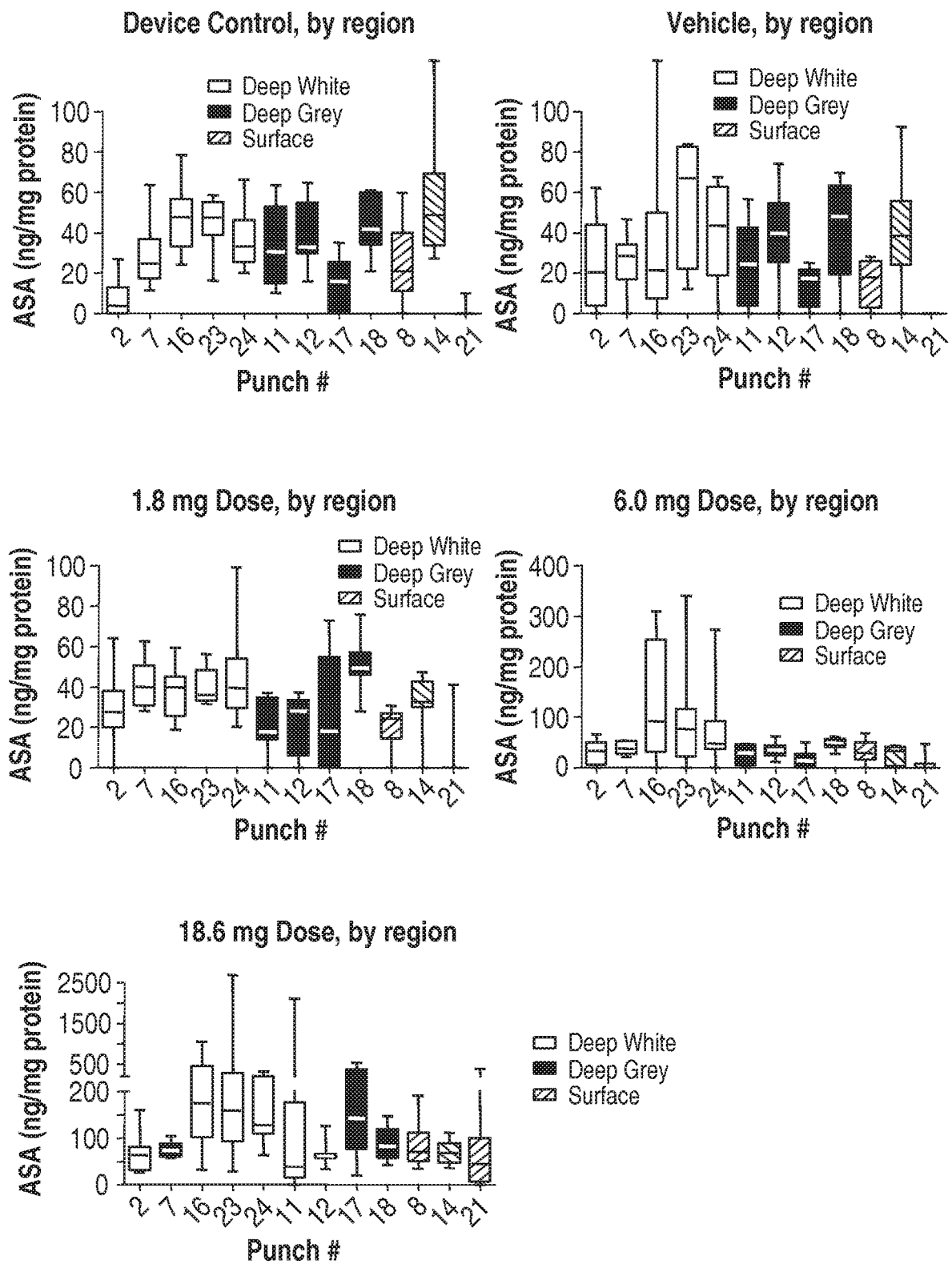

127. rhASA levels for selected punches that are considered to contain mostly deep white brain matter are shown in FIG. 128. White matter is composed of bundles of myelinated nerve cell processes (or axons). Selected punches which contain mostly material from the deep grey brain matter are shown in FIG. 129. Grey matter contains neural cell bodies, in contrast to white matter. The values of rhASA in selected punches from the surface, deep white and deep grey are shown for each dose group in FIG. 130.

Spinal cord concentration data is shown in FIG. 131.

Liver concentration data is shown in FIG. 132.

rhASA concentration levels in the liver, spinal cord, and brain of the device and vehicle-dosed control groups were in some cases measurable. The levels in liver and spinal cord were lower than any of the rhASA-treated groups. The level of rhASA measured in the device control and vehicle-dosed animals represents a cross-reactivity between the anti-rhASA antibody used in the ELISA with the native cynomolgus monkey protein. The reported values in the device control and vehicle tissues do not represent quantitative values for cynomolgus monkey rhASA in the tissues, because the degree of cross-reactivity between the antibody and cynomolgus ASA is not known, and the fact that the assay standards use rhASA. However, the variation in the levels of rhASA detected between device control and vehicle-dosed tissues is may be interpreted as demonstrated variability in the relative amounts of cynomolgus rhASA in different tissues and anatomical regions.

Figure 127:
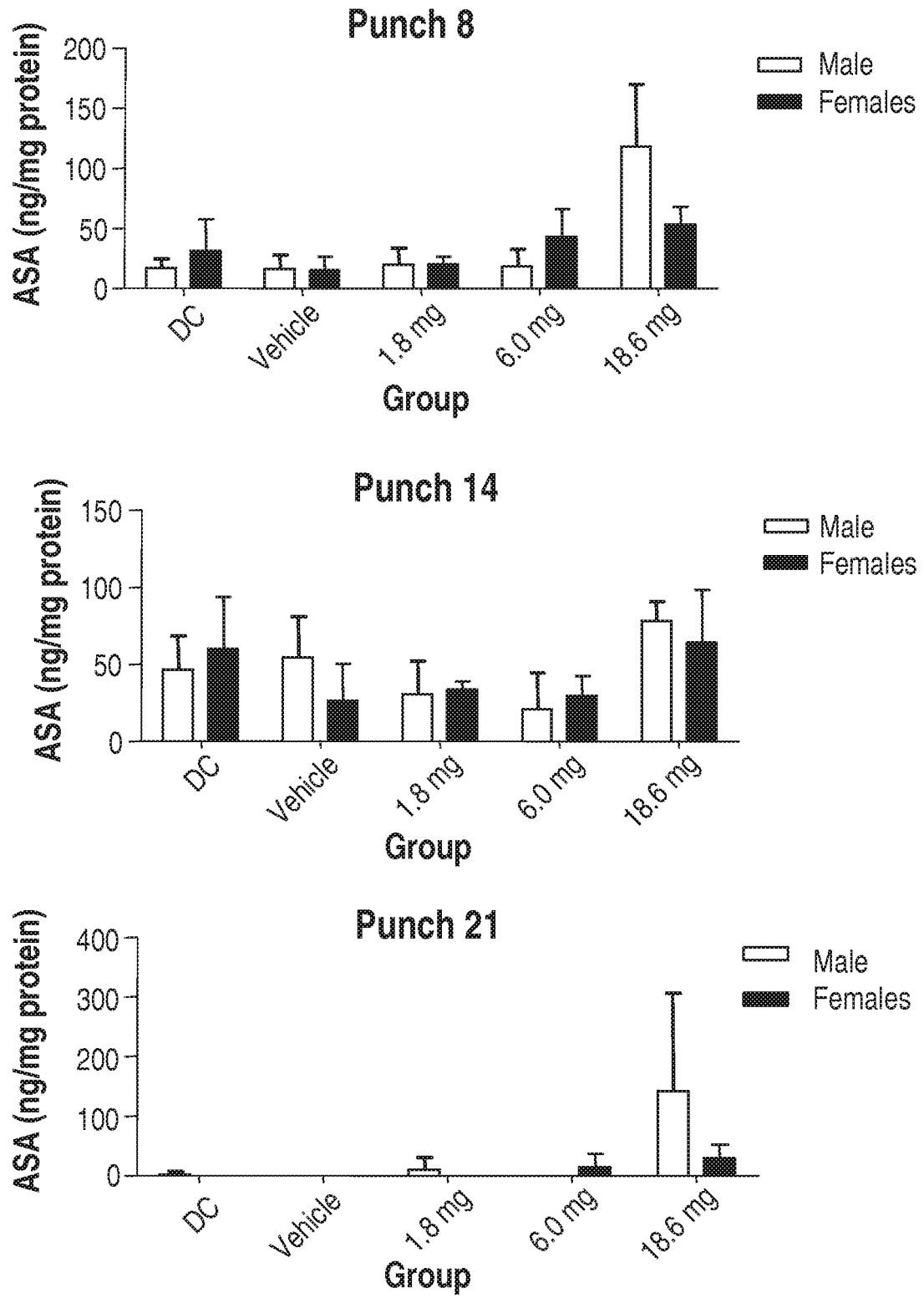

The rhASA levels in spinal cord slices ranged from 160-2352, 1081-6607, and 1893-9252 ng/mg protein in males and 0-3151, 669-6637, and 1404-16424 ng/mg protein in females for the 1.8, 6.0, and 18.6 mg/dose groups, respectively (FIG. 127). Levels of rhASA were higher in the lumbar region of the spine than in the cervical region. Levels of rhASA protein detected in the liver were dose responsive in the rhASA treated groups and were very low in the vehicle group. Mean rhASA levels were 88, 674, and 2424 in males and 140, 462, and 1996 ng/mg protein in females for the 1.8, 6.0, and 18.6 mg/dose groups, respectively (FIG. 128).

Overall, the level of rhASA appeared to be dose-related in samples prepared from the spinal cord slices and liver of the rhASA-dosed groups. Many of the brain regions tested demonstrated a clear dose relationship between rhASA levels and rhASA administration, while others were more equivocal. In general, rhASA levels in the brain increased with rhASA dose.

Example 19: Pharmacokinetic (PK) and Biodistribution of IT vs. IV Administered rhASA The objective this study is to evaluate the pharmacokinetic (PK) and biodistribution of various therapeutic replacement enzymes after intrathecal (IT) and intravenous (IV) administration to cynomolgus monkeys.

In this study, a total of twelve male and twelve female cynomolgus monkeys with intrathecal-lumbar (IT-L) catheters were randomly assigned by body weight into four treatment groups for Phase 1a (I2S administration) and Phase 1b (rhASA administration).

Blood and CSF (from IT-CM catheter) were collected at specified intervals post dosing for both phases. After the last samples were collected from Phase 1a, the animals were allowed a 7-day washout period before initiation of Phase 1b.

After the last samples were collected from Phase 1b, the animals will be allowed a 7-day washout period between initiation of Phase 2. A total of 12 male and female cynomolgus monkeys from Phase 1b were randomly assigned by body weight into 12 treatment groups of I2S (Groups 1a-6a) and rhASA (Groups 1b-6b).

The absolute bioavailability of rhASA in serum following IT-L administration is ~30 to 40%. In contrast, only 0.5% of the IV dose is bioavailable in CSF.

Exposure to rhASA in serum increases in a more than proportional manner following IT-L administration.

Following IT-L administration, exposure to rhASA in CSF increases in a less than proportional manner as dose increases.

TABLE 42

Summary PK Parameters of rhASA in Serum of Cynomolgus Monkeys

| Mean (CV %) | Serum Arylsulfatase A | | | |
|---|---|---|---|---|
| | Arylsulfatase A (Phase 1b: IV 1 mg/kg) | Arylsulfatase A (Phase 1b: IT-L 1.8 mg) | Arylsulfatase A (Phase 1b: IT-L 6 mg) | Arylsulfatase A (Phase 1b: IT-L 18.6 mg) |
| N | 8 | 6 | 8 | 8 |
| AUC0-t (ng · h/mL) | 10505 (16.9) | 2219 (41.9) | 10352 (31.9) | 17583 (28.2) |
| AUC0-∞ (ng · h/mL) | 11069 (17.2) | NC (NC)b | 9634 (28.9)c | 20789 (27.8)d |
| Cmax (ng/mL) | 11911 (20.0) | 363 (40.4) | 1160 (29.9) | 1621 (25.1) |
| Tmaxa (h) | 0.08 (0.08, 0.08) | 4.00 (2.00, 4.00) | 4.00 (1.00, 4.00) | 3.00 (1.00, 4.00) |
| t½ (h) | 6.55 (31.8) | NC (NC)b | 6.77 (21.4)c | 7.40 (32.8)d |
| CL or CL/F (mL/h) | 261 (17.0) | NC (NC)b | 654 (25.0)c | 944 (25.4)d |
| Vz or Vz/F (mL) | 2418 (32.4) | NC (NC)b | 6523 (41.3)c | 9686 (25.8)d |

TABLE 43

Summary PK Parameters of rhASA in CSF of Cynomolgus Monkeys

| Mean (CV %) | Arylsulfatase A (Phase 1b: IV 1 mg/kg) | Arylsulfatase A (Phase 1b: IT-L 1.8 mg) | Arylsulfatase A (Phase 1b: IT-L 6 mg) | Arylsulfatase A (Phase 1b: IT-L 18.6 mg) |
|---|---|---|---|---|
| N | 4 | 6 | 8 | 8 |
| AUC0-t (ng · h/mL) | 1629 (179.8) | 1267266 (86.6) | 5334329 (68.8) | 8028775 (71.2) |
| AUC0-∞ (ng · h/mL) | 8221 (NC)b | 1595942 (79.1)c | 4291829 (84.2)d | 9406664 (64.5)e |
| Cmax (ng/mL) | 69.3 (94.2) | 345167 (48.7) | 1039079 (73.6) | 1841125 (62.8) |
| Tmaxa (h) | 6.00 (1.00, 8.00) | 0.08 (0.08, 4.00) | 0.29 (0.08, 4.00) | 2.04 (0.08, 4.00) |
| t½ (h) | 37.6 (NC)b | 23.6 (68.3)c | 17.1 (31.3)d | 13.4 (29.3)e |
| CL or CL/F (mL/h) | 392 (NC)b | 1.95 (74.1)c | 38.1 (214.8)d * | 3.04 (66.1)e |
| Vz or Vz/F (mL) | 21237 (Nc)b | 80.6 (110.4)c | 11090 (215.1)d | 67.6 (81.2)e |

TABLE 44

Bioavailability of rhASA in Serum and CSF

Absolute Bioavailability Comparison

| | Arylsulfatase A (Phase 1b: IT-L 1.8 mg) | Arylsulfatase A (Phase 1b: IT-L 6 mg) | Arylsulfatase A (Phase 1b: IT-L 18.6 mg) |
|---|---|---|---|
| Fabs (%) | NC | 39.9 | 27.3 |

The bioavailability of rhASA in serum following IT-L administration is ~30-40%. In contrast, only 0.5% of the dose administered by IV route is bioavailable in CSF.

TABLE 45

CSF: Serum Partition
CSF: Plasma Partition

| Arylsulfatase A (Phase 1b: IV 1 mg/kg) | Arylsulfatase A (Phase 1b:IT-L 1.8 mg) | Arylsulfatase A (Phase 1b: IT-L 6 mg) | Arylsulfatase A (Phase 1b:IT-L 18.6 mg) |
|---|---|---|---|
| 0.74 | NC | 445 | 452 |

Example 20—Treatment of MLD Patients

Direct CNS administration through, e.g., IT delivery can be used to effectively treat MLD patients. This example illustrates a multicenter dose escalation study designed to evaluate the safety of up to 3 dose levels every other week (EOW) for a total of 40 weeks of rhASA administered via an intrathecal drug delivery device (IDDD) to patients with late infantile MLD. Various exemplary intrathecal drug delivery devices suitable for human treatment are depicted in FIG. 94, FIG. 95, FIG. 96 and FIG. 97.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria: (1) appearance of first symptoms prior to 30 months of age; (2) ambulatory at the time of screening (defined as the ability to stand up alone and walk forward 10 steps with one hand held); (3) presence of neurological signs at time of screening. Typically, patients history of hematopoietic stem cell transplantation are excluded.

Safety of ascending doses of rhASA administered by IT injection for 40 weeks in children with late infantile MLD is determined. In addition, the clinical activity of rhASA on gross motor function, and single and repeated-dose pharmacokinetics in serum and concentrations in cerebrospinal fluid (CSF) are assessed.

Examples of IT Delivery of HNS

Example 21: Chronic Intrathecal Administration of Heparann-Sulfatase

This example demonstrates that intrathecal administration can be used to effectively deliver a lysosomal enzyme, such as recombinant human heparan N-sulfatase (rhHNS), into brain tissues for the treatment of the neurologic symptoms of mucopolysaccharidosis IIIA (MPS IIIA; Sanfilippo syndrome type A), the defining clinical feature of this disorder. Experiments described in this example demonstrate that chronic IT administration of rhHNS was well tolerated with dose-related enzyme activity detected in the brain, spinal cord and liver.

In summary, an intrathecal (IT) formulation of recombinant human heparan N-sulfatase (HNS) has been developed for the treatment of the neurologic symptoms of mucopolysaccharidosis IIIA (MPS IIIA; Sanfilippo syndrome type A), the defining clinical feature of this disorder. Since the average age of MPS IIIA patients is 4.5 years, the pivotal toxicology studies for HNS were conducted in juvenile cynomolgus monkeys to evaluate the effects on the developing brain. Monkeys were implanted with an intrathecal (IT)-lumbar drug delivery device and dosed every other week by short-term infusion (1.5, 4.5, or 8.3 mg/dose HNS for 6 months; 12 doses), with device and vehicle controls receiving phosphate-buffered saline or vehicle, respectively. Eight animals per group (4/sex) were necropsied at 3 and 6 months (device-control group necropsied at 3 months), and 8 animals from the vehicle group and the 3 HNS dose groups were necropsied 1 month after the final IT dose. No FINS-related clinical signs or gross central nervous system lesions were observed. Compared to controls, there were cellular infiltrates of slight-to-minimal mean severity in the meninges/perineurium surrounding the brain/spinal cord correlating with transient increases in cerebrospinal fluid (CSF) leukocytes, predominantly eosinophils, which largely resolved 1-month post-final dose. These changes were not associated with any adverse morphologic changes in the brain or spinal cord. There appeared to be a dose related trend toward higher mean CSF HNS levels and in tissue HNS activity levels in the brain, spinal cord, and liver. The no-observed-adverse-effect-level was 8.3 mg/dose given every other week, the highest dose administered, indicating that HNS may be safely administered intrathecally at various concentration including concentrations higher than 8.3 mg/dose.

Sanfilippo Syndrome Type A

Mucopolysaccharidosis type IIIA (MPS IIIA; Sanfilippo Syndrome type A), a rare lysosomal storage disorder affecting approximately 1 in 100,000 people worldwide, results from the absence or defective function of heparan N-sulfatase (HNS) (Neufeld E F, et al. The Metabolic and Molecular Bases of Inherited Disease (2001) pp. 3421-3452), an exosulfatase involved in the lysosomal catabolism of glycosaminoglycan (GAG) heparan sulfate. In the absence of this enzyme, GAG heparan sulfate accumulates in lysosomes of neurons and glial cells, with lesser accumulation outside the brain. The defining clinical feature of this disorder is central nervous system (CNS) degeneration, which results in loss of, or failure to attain, major developmental milestones. The progressive cognitive decline culminates in dementia and premature mortality.

IT Delivery of rhHNS

Since the average age of MPS IIIA patients is 4.5 years, the pivotal toxicology studies for HNS were conducted in juvenile cynomolgus monkeys (species selection based upon genetic and anatomic similarity to humans) to evaluate the effects on the developing brain. The age equivalence of monkeys to humans as cited in the literature ranges from 7.6 months to 12.1 months for children 30 to 40 months old (Hood R D, Developmental and Reproductive Toxicology: A practical approach (2006) p. 276). As part of this effort, a 6-month toxicology study was conducted in juvenile cynomolgus monkeys to evaluate IT lumbar administration of HNS. The data obtained from a prior 1-month juvenile cynomolgus monkey toxicity study guided the dose level selection and design of the 6-month repeated-dose juvenile monkey study. To our knowledge, this is the first study involving the chronic IT administration of ERT in juvenile nonhuman primates.

Fifty-six male and 56 female juvenile cynomolgus monkeys (*Macaca fascicularis*) approximately 6 to 9 months old and weighing 0.82 to 1.81 kg were used in this study. Monkeys were fed 15 biscuits of PMI-Certified Primate Diet 5048 (Richmond, Inf.) daily. Water was provided ad libitum via a filtered automatic water system and was withheld during urine collection periods. Monkeys were group-housed (two per cage) for 2 to 4 weeks in stainless steel cages upon arrival with the exception of the 3-month monkeys; these were individually housed in stainless steel cages. For the duration of the study, all monkeys were housed in individual stainless steel cages in rooms with controlled temperature and humidity with a cycle of 12 hours of light and 12 hours of darkness.

Prior to study initiation, all monkeys were implanted surgically with SC ports and IT catheters. Prednisolone sodium succinate (IV, 30 mg/kg) and flunixin meglumine (intramuscular [IM], 2 mg/kg) were administered prior to surgery. The monkeys were pretreated with SC atropine sulfate (0.04 mg/kg), sedated with IM ketamine HCl; 8 mg/kg), intubated, and maintained on approximately 1 L/min of oxygen and 2.0% isoflurane. An incision was made over the dorsal processes of the lumbar spine (L4, L5, or L6), and a hemilaminectomy was made for the insertion of a tapered polyurethane catheter (25 cm in length, 0.9 mm outer diameter×0.5 mm inner diameter, with six side holes of 0.33 mm diameter) at L3, L4, or L5. The catheter was inserted through a small dural incision and was advanced approximately 10 cm anterograde to the area of the thoracolumbar junction. A titanium SC port was attached to the IT catheter and implanted in the SC tissue. Proper catheter placement was confirmed by myelogram using Isovue-300 (0.8 ml; Bracco Diagnostics, Inc., Princeton, NJ). After recovering from surgery, monkeys received butorphanol tartrate (IM, 0.05 mg/kg) and ceftiofur sodium (IM, 5.0 mg/kg twice daily for 2 days).

In this example, HNS was provided in an IT formulation vehicle including 5 mM sodium phosphate, 145 mM sodium chloride, and 0.005% polysorbate 20 (pH 7.0). EOW doses of HNS were administered as a short-term infusion over approximately eleven minutes: 0.6 mL (4 minutes) followed with a flush of 0.5 mL phosphate-buffered saline (PBS) (7 minutes). Monkeys in the vehicle-control group received the IT formulation alone; DC monkeys received PBS (pH 7.2) IT.

Morbidity and Mortality

There were no HNS-related deaths or early sacrifices. There were no HNS-related clinical signs noted at dosing or during the daily observations. Misplacement, pruritis, tremors, and ataxia observed during and after dosing resolved within a few minutes to approximately 4 hours of administration, and were considered a volume-related response rather than a reaction to HNS or the vehicle. Clinical signs observed during and immediately after dosing were seen at a comparable incidence in control groups (DC and/or vehicle-dosed group); there was no evidence of a dose response. In general, the incidence of clinical signs at dosing decreased with each subsequent dose. There were no HNS-related changes in body weight, food consumption, and physical and neurologic findings, or alterations in ECG or ophthalmology examinations.

Clinical Pathology

There were no changes considered related to HNS in hematology, serum chemistry, coagulation, or urinalysis parameters at any interval.

CSF Cell Counts and Chemistry

There were dose-related increases in mean CSF leukocyte counts for all groups, including DC and 0 mg/dose groups, 24 hours postdose. There was a general increase in leukocyte counts with each dose administered. Collection of CSF from approximately one half of the monkeys prior to dosing showed that these effects had abated in the 2 weeks since the previous dose. After dose 5, in addition to an increase in leukocytes, higher group mean CSF total protein and albumin were observed for the HNS-dosed males in the 4.5 and 8.3 mg/dose groups (up to 4- to 5-fold) compared with the predose mean (P<0.05 versus the DC and the 0 mg/dose group); less of a trend was evident in the female HNS-dosed groups.

HNS Concentrations and Antibody Analysis

Typically, the mean HNS levels in serum were <limit of detection (LOD) for all test groups for all time points. The HNS concentration in CSF from monkeys in the DC- and vehicle-dosed control group was generally below the limit of quantification (LOQ). Although no statistical analyses were performed, there appeared to be a dose-related trend towards higher mean HNS levels in CSF in the 1.5, 4.5, and 8.3 mg/dose groups. The predose CSF mean HNS levels were significantly lower than the postdose CSF levels. The mean HNS concentrations for the 6-month cohort (both sexes) at study termination (main and recovery necropsy) are sumarized in Table 46. At a given dose level, mean concentrations of HNS in the CSF appeared to be maintained in the same range (FIG. 146A) despite the anti-HNS antibody levels in the serum and CSF, which continued to rise throughout the study.

TABLE 46

CSF HNS concentrations at study termination (main and recovery necropsies).

| Group | Main Necropsy | | Recovery Necropsy | |
| --- | --- | --- | --- | --- |
| | n | Mean ± SD$^a$ (ng/mL) | n | Mean ± SD (ng/mL) |
| Vehicle | 8 | — | 8 | NA |
| 1.5 mg IT | 8 | 516,366 ± 1,024,084 | 8 | NA |
| 4.5 mg IT | 7 | 377,460 ± 304,996 | 7 | NA |
| 8.3 mg IT | 8 | 419,492 ± 345,975 | 8 | NA |

CSF, cerebrospinal fluid; HNS, human heparan N-sulfatase; n = number of samples above the LOQ; IT, intrathecal; SD, standard deviation.
$^a$samples collected approx. 24 hours postdose.
NA = no samples available for analysis or samples below the LOQ.

In the 6-month/recovery cohort, none of the monkeys in the device control group (PBS only) or those dosed with vehicle developed anti-FINS antibodies in serum or CSF at any time point tested. All monkeys in the 1.5, 4.5, and 8.3 mg/dose groups tested negative (<LOD) for anti-FINS antibodies in serum and CSF samples collected prestudy (for CSF) and at predose 2. By the end of the study, all monkeys tested positive for anti-HNS antibodies in serum.

All monkeys in the 1.5 mg/dose and 8.3 mg/dose groups and six of eight monkeys in the 4.5 mg/dose group tested positive for anti-FINS antibodies in the CSF at one or more time points. Since two monkeys in the 4.5 mg group had no sample collected at any time point including necropsy, these results would appear to indicate that all monkeys dosed with HNS produced an antibody response.

At all three dose levels, anti-FINS antibody concentrations in serum were detected after dose 2, and levels increased markedly after dose 4. Although no statistical analyses were performed, there appeared to be a dose-related trend towards higher serum antibody concentration; by the end of the study, levels were comparable across the 3 HNS dose groups (FIG. 146B). Anti-HNS antibody levels in the serum were always higher than in the CSF over the time course of this study (from 9 to 236-fold serum/CSF antibody concentrations); the highest ratios of serum to CSF concentrations (98 and 236-fold) were seen at 8.3 mg dose level in the earlier course of dosing (6 and 10 weeks).

Anti-HNS antibody concentrations in the serum increased 9-, 16-, and 16-fold at 1.5 mg, 4.5 mg, and 8.3 mg/dose levels, respectively, in the early time of dosing (from week 6 to week 14). During the same time period, CSF antibody concentrations increased 30-, 41-, and 52-fold at 1.5 mg, 4.5 mg, and 8.3 mg/dose levels, respectively (FIG. 146B); substantial levels remained after the 1-month dose-free recovery phase (Table 47).

TABLE 47

CSF anti-HNS antibody concentrations at study termination (main and recovery necropsies).

| Group | Main Necropsy$^a$ | | Recovery Necropsy | |
| --- | --- | --- | --- | --- |
| | n | Mean ± SD (ng/mL) | n | Mean ± SD (ng/mL) |
| Vehicle | 8 | — | 8 | — |
| 1.5 mg IT | 8 | 351,456 ± 244,171 | 8 | 299,512 ± 226,654 |
| 4.5 mg IT | 7 | 147,187 ± 213,095 | 7 | 193,045 ± 157,896 |
| 8.3 mg IT | 8 | 185,227 ± 315,858 | 8 | 238,727 ± 185,785 |

CSF, cerebrospinal fluid; HNS, human heparan N-sulfatase; IT, intrathecal; n, number of sample above the limit of quantification; SD, standard deviation.
$^a$Samples collected approximately 1 week prior to dosing.

Anti-HNS antibodies appeared later in the CSF than in serum (FIG. 146C). No apparent dose-related differences of antibody concentrations in the serum or CSF were observed (statistical analysis was not done due to small sample sizes); there was no observable difference between males and females in antibody responses.

In the presence of anti-HNS antibody in the CSF, the mean concentrations of HNS in the CSF appeared to be maintained, suggesting that the presence of anti-HNS antibodies in the serum and CSF did not alter the concentration level of the IT-dosed HNS. The 6-month/recovery cohort analyses of the 6-month repeat-dose administration of HNS indicated that the anti-HNS antibody concentrations for the 3-month interim and 6-month cohort sacrifice monkeys were comparable (FIG. 146C).

Gross and Histopathologic Findings

At all dose levels (although not at all sacrifice intervals, gender-specific, nor in a dose-related manner), eosinophilic infiltrates (FIG. 147A) were present in the parenchyma of the brain (predominantly gray matter), spinal cord (gray and white matter), dorsal spinal nerve roots/ganglia and the trigeminal ganglia (mid-dose males only) (FIG. 147B-D). The infiltrates were interpreted to be secondary to the meningeal/perineurium infiltrates and/or to the presence of (penetration by) HNS within the parenchyma of the tissue. Although there were numerous inflammatory type changes, the monkeys appeared to tolerate administration of HNS and none of the infiltrates were considered related to or causing adverse morphologic changes in the nervous system parenchyma. Specifically, there was no evidence of neuronal necrosis/degeneration and no glial response related to HNS administration.

Microgliosis in the gray matter of the brain and spinal cord, in association with cellular infiltrates, predominantly eosinophilic, was relatively common in a previously performed 1-month juvenile monkey toxicity study; these changes were relatively uncommon by the 3-month interim sacrifice in the 6-month study, but residual evidence of such a response could still seen in the 6-month cohort (FIG. 147F). Microglial reactions tend to be a relatively early event in the reaction to some (typically protein-based) centrally administered (or centrally-reactive) test articles. The eosinophilic infiltrates did correlate with increased number of eosinophils in the CSF of HNS-dosed monkeys, although the cells were not present in sufficient numbers to elicit an adverse reaction.

At all dose levels, eosinophilic infiltrates were observed in the dorsal spinal nerve roots/ganglia for most HNS-dosed groups, regardless of gender. The infiltrates in the various nervous system tissues were interpreted to be secondary to the meningeal/perineurium infiltrates and/or to the presence of (penetration by) HNS within the parenchyma of the tissue. In the recovery sacrifice monkeys, HNS-related effects were generally either absent or reduced to control levels. Some changes, such as microgliosis in the spinal cord, were completely resolved after the recovery period. None of the HNS-related changes appeared to be associated with any adverse structural microscopic changes in the brain or spinal cord. There was no neuronal necrosis noted in the brain, spinal cord, or ganglia.

HNS Enzyme Activity

In the 6-month/recovery cohorts, HNS enzyme activity in the spinal cord and brain of the vehicle-dosed group (0.0-0.154 nmol/hr/mg protein) were similar to levels shown in tissues from the 3-month interim cohort (0.0-0.0.154 nmol/hr/mg protein). Enzyme activity levels in the spine were higher (approximately an order of magnitude higher in the lumbar spine) than levels measured in brain or liver, the 4.5 mg and 8.3 mg/dose groups having similar levels. The HNS enzyme activity in spinal cord slices ranged from 3.9-18.6, 13.1-67.1, and 3.6-69.2 nmol/hr/mg protein in males (FIG. 148A) and 1.8-16.2, 4.5-61.2, and 21.1-66.0 nmol/hr/mg protein in females (FIG. 148B) for the 1.5, 4.5, and 8.3 mg/dose groups, respectively. In spinal tissue after a 1-month recovery period, enzyme activity levels returned to levels consistent with vehicle control values.

The HNS enzyme activity in brain slices ranged from 0.03-16.0, 0.30-55.7, and 0.15-21.2 nmol/hr/mg protein in males (FIG. 148C), and 0.04-5.1, 0.0-14.4 and 0.9-33.2 nmol/hr/mg protein in females (FIG. 148D) for the 1.5, 4.5, and 8.3 mg/dose groups, respectively. In brain tissue after recovery, enzyme activity levels returned to levels consistent with control values.

The fold-change in activity for different areas of the brain compared with endogenous levels (DC group) is shown in FIG. 149A. Although a trend toward increased distribution was noted in surface samples, lumbar-IT administered HNS could be shown to penetrate to periventricular areas of the brain.

In the 6-month cohort/recovery cohorts, mean activity levels in liver were 0.50, 2.41, and 6.65 nmol/hr/mg protein in males and 1.04, 4.15, and 7.62 nmol/hr/mg protein in females for the 1.5, 4.5, and 8.3 mg/dose groups, respectively (FIG. 149B). Levels in vehicle control monkeys were 0.089 nmol/hr/mg protein for males and 0.083 nmol/hr/mg protein for females. Following the recovery period, HNS activity levels in liver were comparable to baseline control levels for all dose groups.

Immunohistochemistry

FINS delivery to the CNS via bolus IT injection in the 3-month interim and 6-month/recovery cohorts resulted in delivery of immunoreactive test article to the pia-arachnoid tissues of the spinal cord and brain. In the monkeys that received IT HNS, the immunoreactive material was consistently present in meningeal and perivascular macrophages (brain/spinal cord) and variably present in the adjacent glial and neuronal cell populations. The lack of staining in vehicle-dosed control monkeys (FIG. 150A) demonstrated the specificity of the antibody to human HNS. Generally, the immunoreactivity was dose related (i.e., using a semi-quantitative grading scale, increased immunohistochemical staining was noted in a generally dose-dependent manner). HNS delivery to the CNS via bolus IT resulted in positive immunostaining in the cerebral cortex and cerebellum (FIG. 150B-D); however, immunoreactivity was not consistently evident in the caudate/putamen region, midbrain, or deeper regions of the pons or medulla. Immunoreactivity was evident in the livers (in sinusoidal lining cells including Kupffer cells, but not in hepatocytes) of all monkeys administered HNS. Immunoreactivity was not evident in the one female sacrificed early (4.5 mg/dose group) because of a leaking catheter that could not be repaired.

In the 1.5 mg/dose group, essentially full recovery was evident with the exception of liver and the meninges of the brain and spinal cord where some residual immunoreactivity was evident. At higher doses (4.5 and 8.3 mg/dose), the intensity and incidences of immunoreactivity were lower than at the end of dosing. At all dose levels, the levels of HNS in spinal cord, brain, and liver approximated those seen in vehicle-dosed controls after the 1-month recovery period.

In this study, EOW delivery of HNS administered IT for 6 months was generally well tolerated. No remarkable changes were observed in body weight, clinical status, ophthalmologic/neurologic/physical examinations, ECGs, organ weights, or gross organ appearance. Findings were limited to transient changes in CSF clinical pathology accompanied by slight to mild meningeal infiltrates and epidural inflammation, with nearly complete reversal in all but the highest dose group following the recovery period. Widespread distribution of HNS throughout the brain and spinal cord was observed.

IT administration of HNS EOW elicited an inflammatory response characterized by residual leukocyte infiltration and effusion of albumin noted at 24 hours postdose and at necropsy. Without wishing to be bound by any particular theory, this presumably reflects a transient, localized, and incomplete opening of the BBB related to changes in the tight junctions near the catheter tip, resulting in entry of leukocytes and plasma proteins into the CSF (Simard J M, et al. Lancet Neurol. (2007) 6, 258-268; Stamatovic S M, et al. Curr. Neuropharmacol. (2008) 6, 179-192). This may be the result of two components: one related to the dose administration procedures or volume and another related to IT administration of a protein.

The transient changes in BBB permeability (no significant differences between dose groups and controls 24 hours postdose at the main necropsy), were not accompanied by any clinical signs.

There appeared to be a dose-related trend for higher mean CSF HNS levels; at a given dose level, mean concentrations of HNS in the CSF appeared to be maintained in the same range despite the increasing anti-HNS antibody levels in the serum and CSF.

Meningeal cellular infiltration of slight-to-minimal mean severity was observed in the brains and spinal cords of HNS-dosed juvenile monkeys. This microscopic change was also noted in vehicle-dosed controls, indicating some of the response was related to IT catheter placement, as well as a nonspecific inflammatory response to foreign protein. The introduction of a biologic/protein into the IT space, especially one that penetrates the CNS, nearly always elicits some degree of an inflammatory response (Hovland D N, et al. Toxicol. Pathol. (2007) 35, 1013-1029; Butt MT, Toxicol. Pathol. (2011) 39, 213-219), which, if present in numbers that damage adjacent tissue, would represent an adverse effect. In the current study, however, these cells (predominantly eosinoophils) appeared to represent a marker of tissue reaction/penetration and were not found in sufficient quantities to qualify as an adverse effect. None of the HNS-related changes appeared to be associated with any adverse structural microscopic changes in the brain or spinal cord. There was no neuronal necrosis noted in the brain, spinal cord, or ganglia.

Evaluation of anti-test article antibodies is an important aspect of the toxicity studies because of the potential impact of neutralizing or binding antibodies on the clearance or biodistribution of test article (Ponce R P, et al. Regul. Toxicol. Pharmacol. (2009) 54, 164-182). In this study, since dose-related and quantitatively similar levels of HNS enzyme activity were noted in the brain and spinal cord of the 3-month interim and 6-month cohorts, and mean concentrations of HNS in the CSF appeared to be maintained in the same range despite the increasing anti-HNS antibody levels in the serum and CSF, suggesting no neutralizing activity.

There appeared to be a dose-related trend toward higher levels of HNS enzyme activity in spinal cord, brain, and liver, that was highest near the injection site in the lumbar region of the spinal cord and uniform in the brain, with no significant differences rostral to caudal and between right and left hemispheres. No evidence for HNS accumulation was noted in the brain and spinal cord tissue of the 6-month cohort as compared with the 3-month interim cohort. Although a trend toward increased distribution was noted in surface samples, lumbar-IT administered HNS penetrated to deep, periventricular areas of the brain. The FINS enzyme activity in the liver suggested the FINS redistributed systemically after IT delivery; no HNS-related adverse effects were observed in the liver after evaluation of clinical and anatomic pathology parameters in the pivotal toxicity studies.

In general, the immunohistochemistry results corroborated the tissue enzyme activity in that dose-related immunoreactivity was observed in the spinal cord and brain pia-arachnoid meninges and in the nervous tissues (neurons, glial cells) in the immediate proximity of the meninges. There was good gray matter penetration of the cerebrum and cerebellum after bolus IT injection or short-term IT infusion. Although immunoreactivity was not evident in deeper structures such as the basal ganglia or the central regions of the thalamus/hypothalamus, midbrain or the pons/medulla, enzyme activity results indicate that lumbar-IT administered HNS penetrated to deep, periventricular areas of the brain. Thus, immunohistochemistry may be less sensitive technique for detecting biodistribution of a test article. Immunoreactivity was evident in Kupffer cells and the endothelial cells (cells capable of phagocytosis) of the liver, but not parenchymal cells (hepatocytes).

The 6-month/recovery cohort analyses of the 6-month repeated-dose IT toxicity study in juvenile monkeys indicated that HNS-related changes in the 3-month interim and 6-month sacrifice monkeys were comparable, including in-life parameters, clinical and anatomic pathology, concentrations of HNS and anti-HNS antibodies in CSF and serum, and distribution/subcellular location of HNS in spinal cord, brain, and liver. In the recovery sacrifice monkeys, HNS effects were either absent or significantly reduced. Thus, the no-observed-adverse-effect-level for the 6-month juvenile monkey study was 8.3 mg/dose, the highest dose administered.

Monitoring changes in CSF cellularity and protein concentrations appears to be a reliable correlate of the morphological changes noted on histopathologic evaluation and may be useful in patients treated IT with FINS; these changes were considered to be an expected reaction to an IT-administered protein and were largely resolved after the recovery period. These data from animal models provide confidence for pursuing IT therapy as a treatment strategy for the neurological manifestations of lysosomal storage diseases. This juvenile nonhuman primate toxicology study demonstrates the feasibility and tolerability of administering HNS via an IT lumbar drug delivery device to pediatric patients. The nonadverse CNS pathology and lack of adverse clinical signs have supported the recent investigational medical product dossier approval and indicated that IT-administered FINS can safely and effectively treat CNS symptoms of Sanfillippo A syndrome.

Materials and Methods

Exemplary materials and methods used in various experiments described in this examples are provided below.
Study Design and HNS Dosing The monkeys were randomized into five treatment groups; group 1 was untreated (implant device control [DC], port and catheter) and was not dosed with the vehicle or test article. Groups 2 through 5 received 0.6 mL of 0, 2.5, 7.5 or 13.8 mg/mL HNS IT, (i.e., a total dose of 0, 1.5, 4.5, or 8.3 mg) EOW. Four monkeys/sex/group were necropsied at 3 months (interim necropsy; 24 hours after the $6^{th}$ dose), four monkeys/sex/group (except the DC group, which were necropsied at 3 months) were necropsied at 6 months of dosing (main necropsy; 24 hours after the $12^{th}$ dose), and the remaining four monkeys/sex/group were necropsied at the end of a 1-month recovery period. At necropsy, selected tissues were harvested, processed, and examined microscopically.

HNS was provided in an IT formulation vehicle consisting of 5 mM sodium phosphate, 145 mM sodium chloride, and 0.005% polysorbate 20 (pH 7.0). Every other week doses of HNS were administered as a short-term infusion over approximately eleven minutes: 0.6 mL (4 minutes) followed with a flush of 0.5 mL phosphate-buffered saline (PBS) (7 minutes). Monkeys in the vehicle-control group received the IT formulation alone; DC monkeys received PBS (pH 7.2) IT.
Clinical Evaluation Clinical signs and morbidity and mortality observations were recorded at least twice daily starting at the first dose. Body weights were measured prior to surgery, on the day of surgery, weekly during the study, and at necropsy. Food consumption was monitored daily starting before surgery. Physical (heart rate, respiration, body temperature, auscultation, gait, disposition, abdominal palpation, lymph nodes, and general appearance) and neurologic (level of consciousness, tracking) examinations were performed before the study was initiated, each month during the study, and before necropsy. Motor functions, cerebral reflexes (pupillary, blink, and corneal reflex), and spinal reflexes (sensory foot, knee jerk, cutaneous, proprioceptive, and tail reflex) were also assessed. Electrocardiographic (ECG; leads I, II, and III) and ophthalmologic examinations were completed prior to the first dose of HNS and in the week before the interim (3-month) or the main (6-month) necropsy. Ophthalmic examinations were performed by indirect ophthalmoscope, the monkeys were sedated with ketamine HCl (IM, 8 mg/kg), and eyes were dilated with 1% tropicamide.
Clinical Pathology Blood samples were collected from fasted monkeys for hematology and serum chemistry prior to the study start, after IT doses 1, 3, 5, 7, 9 and 11, mid-recovery, and at necropsy. Urine samples were collected via pan catch predose, once monthly during the dosing and recovery period, and prior to necropsy. CSF samples were collected via the lumbar catheter for total cell count and chemistry analysis at the time of surgery, and 24 hours following IT doses 1, 3, 5, 7, 9, 11, mid-recovery, and at necropsy; on occasion, samples were not collected due to partial catheter obstruction. Because higher than expected CSF leukocyte counts were noted, the 3-month dose 5 CSF samples were collected from half the monkeys in each group before dosing and from the remaining monkeys 24 hours after dosing. The predose sample collection occurred at least 1 day prior to dosing so as not to significantly alter the CSF volume just prior to dosing. For the 6-month and recovery monkeys, CSF for total cell count and chemistry was collected from half the monkeys in each group before dosing and from the remaining monkeys 24 hours after dosing. If a monkey had a nonsampling catheter due to an obstruction, a spinal tap (cisterna magna) was performed at the necropsy.

HNS Analysis

Blood samples for HNS analysis were collected from a peripheral vein prior to and 24 hours post IT doses 2, 4, 6, 8, 10, 12; mid-recovery, and at necropsy. CSF samples were collected via the lumbar catheter prior to and 24 hours post IT doses 2, 4, 6, 8, 10, 12, mid-recovery, and at necropsy. HNS concentrations were determined by enzyme-linked immunosorbent assay. The capture antibody was a polyclonal rabbit anti-HNS IgG and the detection antibody was a horseradish peroxidase-conjugate of the same rabbit anti-HNS IgG. The LOD was 0.22 ng/mL; thus, the LOQ was calculated to be 0.66 ng/mL. Serum and CSF samples were screened in duplicate at 1:100 and 1:5 dilutions; samples exceeding the high end of the calibration curve were further diluted and retested.

Anti-HNS Antibody Analysis

Blood for antibody analysis was collected from a peripheral vein approximately 1 week prior to IT doses 2, 4, 6, 8, 10, 12; mid-recovery, and at necropsy. CSF samples for antibody analysis were collected at surgery, and via the lumbar catheter approximately 1 week prior to IT doses 2, 4, 6, 8, 10, 12; mid-recovery; and at necropsy. A Meso Scale Discovery (MSD®) technology electrochemiluminescent bridge test was used for detection of anti-HNS antibodies. The assay is a general, but sensitive, screening method for anti-FINS antibodies from any species and all immunoglobulin isotypes. The LOD was 5 ng/mL, and the samples were screened in duplicate at a 1:20 dilution, resulting in an effective assay sensitivity of 100 ng/mL. Samples exceeding the high end of the calibration curve were further diluted and retested.

Necropsy and Preparation of Tissues

Monkeys underwent a full necropsy either 24 hours after the final IT dose (main necropsy) or at the end of the 1-month recovery period (recovery necropsy). All monkeys were sedated with ketamine HCl (IM, 8 mg/kg), were maintained on an isoflurane/oxygen mixture, and received an IV bolus of heparin sodium (200 IU/kg). Monkeys were perfused via the left cardiac ventricle with room temperature 0.001% sodium nitrite in saline at a rate of 200 ml/min for 12 min (~2400 ml). After collection, tissue samples were then fixed in 10% neutral buffered formalin for histopathologic examination/immunohistochemical analysis or were frozen on dry ice and stored at −60° C. or lower for analysis of HNS activity.

The brain was cut in a brain matrix (MBM-2000C, ASI Instruments, Inc., Warren, MI) at 3-mm coronal slice thickness. The slices were numbered, with the most rostral slice designated as slice 1. Slices 1, 4, 7, 10, 13, and 16 were processed for histopathology and slices 2, 5, 8, 11, 14, and 17 (if available) were processed for immunohistochemistry. Slices 3, 6, 9, 12, and 15 were frozen for analysis of HNS activity. The spinal cords (cervical, thoracic, and lumbar portions) were cut into 1-cm sections. The first slice and every third slice thereafter were processed for histopathologic evaluation and the second slice and every third slice thereafter were processed for immunohistochemical analysis. The third slice and every third slice thereafter were frozen for FINS analysis. The distribution of slices was adjusted so that the slice containing the tip of the intrathecal catheter (slice 0) was fixed in formalin and analyzed for histopathology. Duplicate samples of ~5 g of the liver were taken from two separate lobes and frozen for HNS analysis and an additional sample of ~5 g was fixed for immunohistochemical analysis.

Histopathology

The brains, spinal cords, dorsal spinal nerve roots/ganglion, sciatic, tibial and sural nerves, a complete tissue list (typical for preclinical drug safety studies of this duration in this species), and any gross lesions were harvested at necropsy from all monkeys. Tissue sections were embedded in paraffin and stained with hematoxylin and eosin (in addition to any special staining/embedding procedures noted below) for comprehensive microscopic evaluation.

Brain sections from the prepared paraffin blocks from the device and vehicle-control groups, and the high-dose monkeys were stained with Fluoro-Jade B (a stain increasing the sensitivity of evaluating neuronal degeneration) and Bielschowsky's silver (a procedure that allows direct visualization of axons, dendrites, and neuronal filaments). The Fluoro-Jade B stained slides were examined under fluorescent lighting using a fluorescein isothiocyanate filter cube.

Spinal cords were sectioned serially, with a transverse and oblique sections taken at the cervical, thoracic, and lumbar regions (one slice examined at each level) including sections at the catheter tip; an additional transverse section was taken from the cauda equina region. Dorsal spinal roots and ganglia (midcervical, midthoracic, and midlumbar) were processed and examined. Peripheral nerves (sciatic, tibial, and sural) were sectioned longitudinally, embedded in paraffin and stained with hematoxylin and eosin (H&E). Cross sections were postfixed in osmium, embedded in Spurr's resin, sectioned (2 μm) and stained with toluidine blue. Serial spinal cord sections, as well as dorsal spinal nerve roots and ganglia, from the device and vehicle control groups and the high-dose group were stained with Bielschowsky's silver. Spinal cord sections from these groups also were stained with anti-glial fibrillary acidic protein, an immunohistochemical stain that allows for direct visualization of astrocytes and their processes.

Preparation of Tissue Extracts for Quantitative Analysis

Frozen brain slices 3, 6, 9, 12, and 15 were dissected by separating the left and right hemispheres. Surface tissue was taken by measuring 4 mm from the surface, and the remaining tissue in each hemisphere was considered deep tissue. If present (e.g., slices 6 and 9), an additional periventricular sample was cut from the coronal slices. Since only one-half of the brain (the right side) was processed (the left side was retained frozen), the sectioning resulted in two to three samples per slice: right surface, right deep, and, if present, right periventricular (i.e., Ventricle deep; Vdeep). Cerebellar and brain stem tissues, when present, were isolated prior to separating the hemispheres and were processed independently. Spinal cord sections were prepared similarly, weighed, and homogenized.

Tissue samples were homogenized in lysis buffer (1 ml/0.25 g tissue) formulated with 10 mM Tris, 5 mM ethylenediaminetetracetic acid, 0.1% Igepal supplemented with Alpha Complete protease inhibitor minitablets (Roche Diagnostics, Indianapolis, IN) using TeenA Lysing Matrix A tubes or conical polypropylene tubes. Samples were processed for 40 seconds in the Fastprep-24 automated homogenizer (MP Biomedicals, Solon, OH) or PowerGen Model 125 powered homogenizer (Omni International, Kennesaw, GA). Once homogenized, samples were subjected to five freeze-thaw cycles using an ethanol/dry ice bath and a 37°C. water bath and then centrifuged at 4°C. to pellet tissue debris; supernatants were stored at −80°C. until assayed. FINS activity was determined using a specific substrate (4-methylumbelliferyl-□-D-N-sulphoglucosaminide) with a 2-step fluorometric assay.

Tissue Processing and Staining for Immunohistochemistry

Six formalin-fixed coronal brain slices (slice numbers 2, 5, 8, 11, 14, and 17) of 3-mm thickness from each monkey were numbered 1 to 6 rostral to caudal. Generally, slices 1 to 4 contained basal nuclei/thalamus/midbrain and cerebrum, and the caudal two slices contained cerebellum and brain stem (medulla oblongata) tissue. Brain, spinal cord and liver sections (from the same paraffin blocks as those used for H&E and the various special stains) were immunohistochemically stained for HNS. A specific mouse monoclonal antibody (clone 2C7; Maine Biotech, Portland, ME) was used to detect intracellular uptake of IT-administered HNS; this reagent demonstrated no cross-reactivity with endogenous cynomolgus monkey HNS. Negative controls were performed using an irrelevant mouse IgG. Deparaffinized slides were incubated with primary mouse anti-HNS antibody overnight at 2 to 8° C. A secondary goat anti-mouse biotinylated immunoglobulin G was added and incubated for 30 minutes at 37° C. Avidin/biotinylated horseradish peroxidase complex was added and incubated for 30 minutes. Slides were incubated in peroxidase substrate diaminobenzidine solution until the desired stain intensity developed. Nuclei were counterstained with hematoxylin.

Statistical Analyses

Body weights, body weight changes, food consumption, respiratory rate, body temperature, heart rate, CSF cell count, CSF chemistry, clinical pathology data, urine data, and absolute and relative organ weights were analyzed by a one-way analysis of variance and a comparison of the device and vehicle control groups to each HNS-dosed group by Dunnett's test. In addition, the statistical analysis compared the two control groups to each other. Analysis was two-tailed for significance levels of 5% and 1%. All data are presented as mean±standard deviation.

Example 22: Heparan N-sulfatase Biodistribution and Pharmacokinetic Studies

The experiments in this example were designed to determine tissue distribution of HNS in rats after a single intravenous or intrathecal dose (1 or 10 mg/kg) of HNS. For example, among other things, the purpose of these experiments were to characterize the biodistribution (BD) properties of HNS in rats using positron emission tomography (PET); to compare distribution patterns of HNS when given in different routes (IV or IT) and at different doses (1 or 10 mg/kg); and to determine pharmacokinetic properties of HNS in each of the interest organs in these dosing regimens.

Pharmacokinetic (PK) and biodistribution (BD) profiles of $^{124}$I-sulfamidase (HNS) were studied by tissue PET imaging in rats after single intravenous (IV) or intrathecal (IT) administration of 1 or 10 mg/kg of $^{124}$I-HNS. Radioactivity-time data in the region of interest were obtained from dynamic images in the first 20 min and from static images at 0.05 (only for IT administration), 1, 2, 4, 8, 24, 48, 96 and 192 hours post IV or IT dosing.

Four rats in each of four groups (1 mg/kg IV, 1 mg/kg IT, 10 mg/kg IV and 10 mg/kg IT) were used in this study. Radioactivity-time data were measured in the head, brain (including cerebrospinal fluid, CSF), spine and liver regions after IT administration; and in the blood, brain (including CSF), liver, kidney, heart (including lungs) and skin after IV administration. The data were corrected by the decay half-life of 124-iodine (100.2 hours), expressed as percentage of injected dose (% ID) of a region of interest or % ID per gram (% ID/g) of the imaged tissues, and then normalized for the body weight of 200 grams. The total amounts (ug) or concentrations (ug/g) of the dosed protein in the region of interest were calculated from the corresponding % ID or % ID/g data.

In the first 20 min after IT dosing, total amount of HNS in the head region was reduced at a constant rate of 0.002/min-0.011/min ($\lambda z$) at 1 and 10 mg/kg. Clearance rates and distribution volumes were not used for pharmacokinetic comparisons between the two doses and the two administration routes in this report (see Results section for more information). The constant rates of elimination from the brain were essentially the same at two test doses ($\lambda z$: 0.016/hr versus 0.014/hr for 1 and 10 mg/kg, respectively) with a similar half-life of about two days as determined by static imaging up to 192 hours after IT dosing. The values of Cmax and AUC (0-last or 0-infinite) were proportional to the administered doses. A linear PK behavior was indicated in the dose range of 1 to 10 mg/kg given in these IT single-dosing regimens. Concentration gradients were observed from the proximal to distal sections of the spine at both dose levels.

After IT dosing, HNS protein was measurable in the liver up to 96 hours at 1 mg/kg and up to 192 hours at 10 mg/kg of HNS. The concentrations in the liver reached the peak 2 hours at 1 mg/kg, and 7 hours at 10 mg/kg. The elimination was 0.030±0.011/hr (mean $\lambda z$) at 1 mg/kg, which was not significantly different from that at 10 mg/kg ($\lambda z$ 0.017±0/hr) (p=0.10), with a corresponding t½ (28 versus 42 hours at the doses of 1 and 10 mg/kg, respectively).

After IV dosing, the elimination half-lives in the liver, kidney, heart and skin were 47±10 and 38±13 hours for the liver, 54±25 and 29±16 hours for the kidney, 36±15 and 42±19 hours for the heart, and 40±21 and 31±13 hours for the skin at 1 and 10 mg/kg, respectively; while the half-lives in the brain were 71±23 and 60±53 hours. The mean values of Cmax for the liver, skin, kidney, heart and brain were 9.6, 0.30, 0.25, 0.22, and 0.08 ug/g at 1 mg/kg and 132, 7.9, 3.9, 3.7 and 1.8 ug/g at 10 mg/kg. After the Cmax values from individual animal were normalized for dose, the Cmax/dose values at 10 mg/kg were significantly higher than that at 1 mg/kg in all these organs (mostp values <0.05, p=0.06 for the liver). The values of AUClast for the liver, skin, kidney, heart and brain were 525, 16, 14, 9 and 7 hr·ug/g at 1 mg/kg; and 6747, 276, 183, 201 and 86 hr·ug/g at 10 mg/kg. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

When the same dose of HNS was injected, intrathecal administration resulted in a three-log greater brain exposure than that with intravenous administration. The elimination half-life in the brain was 2 days by IT and 3 days by IV administration. However, hepatic exposures after IT dosing were similar to that after IV dosing at the same dose of HNS. The exposure (Cmax and AUClast) for the liver by IT/IV at 1 mg/kg and 10 mg/kg were in a range of 0.4-1.2.

Experimental Design

The central nervous system (CNS) is vulnerable in most lysosome storage diseases and is seriously damaged in some types of these diseases, such as Sanfilippo syndrome type A or B (mucopolysaccharidosis III), Metachromatic Leukodystrophy (MLD) and Hunter Syndrome. As described herein, it is contemplated that, due to poor penetration through blood-brain barrier when administered peripherally, direct administration of enzymatic proteins into the CNS may increase their concentrations in the central nervous tissues and further enhance their therapeutic effects. Intrathecal (IT, or cisterna magna) administration was investigated and compared with IV administration at different dose levels in this study.

PET is a non-invasive, repeatable and quantitative technology to provide dynamic change of drug concentration over time in the organ of interest. The dynamic concentration-time data from target organs (active sites, rather than in blood circulation) are valuable, and are directly related to the biological activity of the dosed drug. Furthermore, the information on tissue exposures from PET study in animals can be used to guide the selection of the first-dose in human.

Materials and Methods

Test Articles

Heparin N-Sulfatase (HNS) was formulated at a concentration of 20 mg/mL of HNS in 5 mM sodium phosphates buffer with 145 mM sodium chloride at pH 7.0. The material was purified by RP-HPLC and contained 98.7% of Heparin N-Sulfatase with 99.9% of dimer. HNS was labeled with $^{124}$iodine.

Sample Source

Radioactivity images were from rats after IV and IT dosing $^{124}$I—H—N-sulfatase at 1 and 10 mg/kg.

Animals

Sixteen male Sprague-Dawley rats were purchased from Charles River Laboratories (190±60 g, n=16), and were separated into four groups (n=4). Single IV or IT injection at two different doses (1 mg/kg and 10 mg/kg) was given to each group of these rats (total 4 groups). The dose and injected volume were individualized based on the body weight of each animal. In two IV-treated groups, sedation was induced by IV injection of sodium pentobarbital at a dose of 35 mg/kg. Intravenous doses were injected in a bolus through a tail vein. In two IT-treated groups, animals were anesthetized by intra-peritoneal administration of sodium pentobarbital at a dose of 50 mg/kg. Intrathecal doses were administered over 1 min at cisterna magna level through the atlanto-occipital membrane. The actual administered radioactivity was measured by PET, and served as the injected dose.

Experimental and/or Assay Method(s)

Dynamic images (every 2 min) were obtained in the first 20 minutes in the regions of the heart (including the lungs), liver and kidneys post IV injection; and in the head region post IT administration of both doses. Static imaging was acquired in the regions including the brain (including cerebrospinal fluid, CSF), liver, kidney, heart (including lungs), muscle, skin and bone in IV-treated group; and in the region of head, brain (including CSF) and liver of IT-treated animals at 0.05 (only available for IT groups), 1, 2, 4, 8, 24, 48, 96 and 192 hours post-dosing. The images were reconstructed and the three body sections were fused into one image.

Data Analyses

PET data were expressed in nanocurie (nCi) per mL (for fluid) or per gram (for tissue). Relative activity was obtained for the brain, liver, kidneys, skeletal muscle, stomach, heart (with lungs) and skin regions in static images. Absolute activity in the whole head or brain regions was obtained for the animals that received IT injections. Radioactivity per millimeter of spinal column was determined in the IT injected animals at three selected sections: the proximal (neck), mid (against upper edge of the liver), and distal (1 cm from the distal end of the protein containing compartment) spine.

All data were corrected by the decay half-life of $^{124}$I (100.2 hours) and normalized for registration efficacy based on calibration with a $^{124}$I source with externally measured activity. The data were then expressed as percentage of injected dose (% ID) of a whole region (the head and brain) or % ID per gram (% ID/g) of a tissue, and then normalized for a body weight of 200 grams [data normalization: (% ID or % ID/g)/body weight of the animal×200]. The normalization was adopted to reduce the variability of the data, as only four animals were used in each group.

In this example, HNS protein concentrations or amount were calculated using the injected protein dose to each animal: protein concentration (ug/g)=(% ID/g)×(mg/kg of injected dose×1000×0.2); total amount of the dosed protein (ug) in a region of interest=% ID×(mg/kg of injected dose× 1000×0.2), here the injected dose was 1 mg/kg or 10 mg/kg and 0.2 is the normalizing factor for body weight. Group mean and standard deviation of each PK parameter were calculated based on the individual non-compartmental data in each of the four groups. A Student t-test was performed to compare the values of λz, t½, Cmax and AUC between the two test doses and the two administration routes. Statistical significance was defined as ap-values less that 0.05 (p<0.05).

Results

The amounts (ug) or concentrations (ug/g) of HNS in the following tables, figures and PK analyses were calculated by multiplying the injected protein dose (1 mg/kg or 10 mg/kg) with the corresponding values of % ID or % ID/g.

Intrathecal Treatment with 124I-HNS at Doses of 1 and 10 mg/kg

The amount of the dosed protein (ug) in the head region from dynamic images was plotted as a function of time in FIG. 151. The concentration (ug/g) in the brain regions from static images was plotted as a function of time in FIG. 152. The total amount of injected protein (ug) in the brain and head regions from static images were plotted with time in FIG. 153 and FIG. 154, respectively. Concentration-time curves (ug/mm) at the proximal, mid and distal spine are shown in FIG. 155 to FIG. 157. FIG. 158 shows the changes of HNS concentration (ug/g) in the liver with time after IT administration of $^{124}$I-HNS at 1 and 10 mg/kg.

The total amount-time (ug) or concentration-time (ug/g) data were analyzed by non-compartmental models (Win-Nonlin 5.2, Pharsight, Mountain View, CA). The PK parameters, such as the constant rate of elimination (λz), peak concentration ($C_{max}$), terminal half-life (t½), area under curve (AUClast and AUC0-inf) and others were estimated from the data of each individual animal.

Clearance rates and distribution volumes were estimated however, they were not used for PK comparisons between the two doses and the two administration routes in this report for two reasons (1) this study focused on biodistribution of HNS in solid tissues, rather than on blood PK; and (2) the radioactivity in the brain region was the sum of those from the brain tissue (solid) and CSF (liquid), which could not be separated from each other in the study. The $\lambda z$ was evaluated, and used for comparison, because it indicated a percentage of the injected dose eliminated per unit of time.

The group means and standard deviations (SD) were calculated and compared between two test doses. These PK parameters are tabulated in Table 48 below

TABLE 8

| | \multicolumn{8}{c}{1 mg/kg IV} |
| --- | --- | --- | --- | --- | --- | --- | --- | --- |
| | Brain (ug/g)* | | Liver | | Brain (ug)# | | Head (ug)# | |
| Parameter | Mean | SD | Mean | SD | Mean | SD | Mean | SD |
| \multicolumn{9}{c}{1 mg/kg IT} |
| $\lambda Z$ | 0.016 | 0.003 | 0.030 | 0.011 | 0.017 | 0.002 | 0.016 | 0.002 |
| $t_{1/2}$ | 45 | 7 | 28 | 16 | 42 | 5 | 45 | 7 |
| $T_{max}$ | 0.1 | 0.0 | 2.3 | 1.3 | 2.0 | 4.0 | 0.1 | 0.0 |
| $C_{max}$ | 257.0 | 89.9 | 4.9 | 1.3 | 68.6 | 8.0 | 200.1 | 0.0 |
| $AUC_{last}$ | 8393 | 2457 | 204 | 50 | 3809 | 622 | 8216 | 782 |
| $AUC_{inf}$ | 8942 | 2416 | 216 | 57 | 4030 | 643 | 8904 | 1069 |
| $MRT_{last}$ | 46 | 6 | 32 | 13 | 44 | 5 | 46 | 5 |
| \multicolumn{9}{c}{10 mg/kg IT} |
| $\lambda Z$ | 0.014 | 0.001 | 0.017 | 0.000 | 0.014 | 0.001 | 0.010 | 0.001 |
| $t_{1/2}$ | 49 | 4 | 42 | 1 | 51 | 5 | 70 | 9 |
| $T_{max}$ | 0.1 | 0.0 | 7.0 | 2.0 | 0.1 | 0.0 | 0.1 | 0.0 |
| $C_{max}$ | 2628 | 265 | 105 | 41 | 836 | 117 | 1844 | 314 |
| $AUC_{last}$ | 83962 | 10083 | 7987 | 3276 | 59115 | 8624 | 128751 | 15723 |
| $AUC_{inf}$ | 89460 | 12098 | 8345 | 3424 | 63836 | 9466 | 151405 | 15123 |
| $MRT_{last}$ | 56 | 1 | 51 | 1 | 58 | 2 | 65 | 3 |

| | Proximal | | Mid | | Distal | |
| --- | --- | --- | --- | --- | --- | --- |
| Parameter | Mean | SD | Mean | SD | Mean | SD |
| \multicolumn{7}{c}{1 mg/kg IT} |
| $\lambda Z$ | 0.025 | 0.012 | 0.020 | 0.008 | 0.028 | 0.016 |
| $t_{1/2}$ | 32 | 13 | 39 | 16 | 30 | 12 |
| $T_{max}$ | 0.3 | 0.5 | 1.8 | 1.5 | 1.0 | 0.0 |
| $C_{max}$ | 0.5 | 0.1 | 0.2 | 0.0 | 0.1 | 0.0 |
| $AUC_{last}$ | 9 | 3 | 7 | 3 | 2 | 1 |
| $AUC_{inf}$ | 11 | 3 | 8 | 3 | 3 | 2 |
| $MRT_{last}$ | 31 | 17 | 34 | 20 | 16 | 5 |
| \multicolumn{7}{c}{10 mg/kg IT} |
| $\lambda Z$ | 0.018 | 0.008 | 0.014 | — | 0.006 | — |
| $t_{1/2}$ | 45 | 18 | 50 | — | 123 | — |
| $T_{max}$ | 0.3 | 0.5 | 8.7 | 13.3 | 8.0 | — |
| $C_{max}$ | 6 | 4 | 1 | 0 | 1 | — |
| $AUC_{last}$ | 83 | 67 | 35 | 20 | 38 | — |
| $AUC_{inf}$ | 98 | 66 | 60 | — | 73 | — |
| $MRT_{last}$ | 31 | 2 | 32 | 7 | 61 | — |

| | Brain (ug/g)* | | Liver | | Kidney | | Heart | | Skin | |
| --- | --- | --- | --- | --- | --- | --- | --- | --- | --- | --- |
| \multicolumn{11}{c}{1 mg/kg IV} |
| $\lambda Z$ | 0.011 | 0.005 | 0.015 | 0.003 | 0.016 | 0.009 | 0.021 | 0.006 | 0.021 | 0.010 |
| $t_{1/2}$ | 71 | 23 | 47 | 10 | 54 | 25 | 36 | 15 | 40 | 21 |
| $T_{max}$ | 7 | 12 | 5 | 4 | 10 | 12 | 2 | 1 | 5 | 4 |
| $C_{max}$ | 0.1 | 0.0 | 9.6 | 1.5 | 0.2 | 0.1 | 0.2 | 0.0 | 0.3 | 0.1 |
| $AUC_{last}$ | 7 | 2 | 525 | 104 | 14 | 5 | 9 | 3 | 16 | 4 |
| $AUC_{inf}$ | 9 | 3 | 576 | 138 | 16 | 6 | 10 | 3 | 18 | 5 |
| $MRT_{last}$ | 61 | 16 | 47 | 5 | 47 | 18 | 36 | 13 | 41 | 16 |
| \multicolumn{11}{c}{10 mg/kg IV} |
| $\lambda Z$ | 0.102 | 0.180 | 0.021 | 0.012 | 0.035 | 0.024 | 0.020 | 0.010 | 0.026 | 0.012 |
| $t_{1/2}$ | 60.5 | 53.1 | 37.8 | 13.4 | 28.4 | 16.4 | 41.6 | 18.6 | 31.0 | 12.7 |
| $T_{max}$ | 13 | 12 | 2 | 1 | 12 | 11 | 16 | 9 | 3 | 1 |
| $C_{max}$ | 1.8 | 0.2 | 131.6 | 26.8 | 3.9 | 0.7 | 3.7 | 0.7 | 7.9 | 2.3 |
| $AUC_{last}$ | 86 | 66 | 6747 | 2837 | 183 | 123 | 201 | 89 | 276 | 40 |
| $AUC_{inf}$ | 118 | 98 | 7171 | 3029 | 198 | 131 | 230 | 110 | 292 | 43 |
| $MRT_{last}$ | 43 | 32 | 40 | 14 | 33 | 21 | 41 | 18 | 33 | 13 |

In the first 20 min after dosing, total amount (ug) of HNS in the head region was reduced at a constant rate of 0.002-0.011 per min (λz, 0.005±0.004/min) at 1 mg/kg and 0.003-0.010 per min (0.007±0.003/min) at 10 mg/kg. These constant rates of elimination were not significantly different at these two dose levels (p=0.57, FIG. 151).

The concentration-time curve (ug/g from 0.05 to 192 hours) for the brain indicated a bi-phasic profile (FIG. 152). The early phase lasts for about two hours. The terminal phase follows first-order kinetics. The constant rates of elimination from the brain were very similar at two tested doses (0.0016±0.003 and 0.014±0.001 per hour) with a similar half-life of about two days (45±7 and 49±4 hours at 1 and 10 mg/kg, respectively). The values of peak concentrations (257±90 and 2628±265 ug/g) and AUClast (8393±2457 and 83962±10083 hr·ug/g at 1 and 10 mg/kg, respectively) increase approximately ten-fold when the dose was increased from 1 to 10 mg/kg. These observations indicated a linear PK behavior in the dose range of 1 to 10 mg/kg given in these IT single dosing regimens. The peak concentration appeared in the brain 3 min (Tmax) after IT dosing.

The total amount-time curve (ug from 0.05 to 192 hours) in the brain and head regions followed the same bi-phasic pattern as seen with concentration-time curves (ug/g) in the brain (FIG. 153 and FIG. 154). The values of Cmax in the brain region were significantly lower than that in the head region (69±8 versus 200±0 at 1 mg/kg, p<0.01; and 836±117 versus 1844±314 ug, p<0.01 at 10 mg/kg, respectively). The constant rates of elimination were 0.017±0.002/hr and 0.014±0.001/hr for the brain, and 0.016±0.002 and 0.010±0.001/hr for the head region at 1 and 10 mg/kg, respectively. The values of mean residual time were 42±5 versus 51±5 hours for the brain (p=0.048), and 45±7 versus 70±9 hours for the head (p<0.01) at 1 and 10 mg/kg, respectively. These observations suggested that the dosed protein was eliminated from both regions more rapidly at lower dose than at higher doses. The mean half-lives were in a range of 42 to 70 hours in these regions after IT dosing 1 mg/kg and 10 mg/kg of HNS.

A concentration gradient was observed from the proximal, to the mid and to the distal sections of the spine at both dose levels (data not shown). After IT dosing, the peak concentration (ug/mm of spine column) was seen around 30 min (0 to 1 hour) at the proximal, 1 to 4 hours at the mid (except of one rat being 24 hours) and 1 to 8 hours at the distal section. The half-lives in these sections were variable (mean t½: 32±13 and 45±18 hours for the proximal, 39±16 and about 50 hours for the mid, and 30±12 and about 123 hours for the distal sections of spine at 1 mg/kg and 10 mg/kg, respectively). The mean values of peak concentrations were roughly proportional to the doses at each of these three sections at 1 and 10 mg/kg of $^{124}$I-HNS (0.5 versus 6.0, 0.2 versus 0.9 and 0.1 versus 0.5 ug/mm at the proximal, mid and distal sections of the spine, respectively). The mean values of AUClast followed the same proportional pattern as seen in the peak concentration (9.5 versus 83, 6.8 versus 35, and 2 versus 38 hr·ug/mm at the proximal, mid and distal sections, respectively).

Even though HNS was not detectable in most peripheral organs, it was measurable in the liver from as early as 1 hour (the first imaging time point after dosing) to 96 hours (three of four animals) at 1 mg/kg and to 192 hours (all four rats) at 10 mg/kg after IT dosing (FIG. 158). The concentrations in the liver reached the peak 2 hours after IT dosing of 1 mg/kg, and 7 hours after IT dosing of 10 mg/kg, which was followed by an elimination phase with first-order kinetics.

The constant rate of elimination was faster at 1 mg/kg (λz 0.030±0.011/hr) than that at 10 mg/kg (λz 0.017±0/hr) (p=0.10), with a corresponding shorter t½ (28±16 versus 42±1 hours at the doses of 1 and 10 mg/kg, respectively, p=0.76). The value of AUClast at 1 mg/kg reduced about 40-fold in comparison with that at 10 mg/kg (204±50 versus 7987±3276 ug/g, respectively).

Intravenous Treatment with $^{124}$I-HNS at Doses of 1 and 10 mg/kg

The concentration in the brain, liver, kidney, heart (including lung tissue) and skin were plotted as a function of time after IV dosing 1 and 10 mg/kg of HNS as shown in FIG. 159 through FIG. 163, respectively. Since the first static imaging time point for these organs was one hour after dosing, the initial phase of these concentration-time curves cannot be observed in this study. The concentration-time curves for the liver, kidney, heart and skin showed a flat phase from 1 to 8 hours after IV dosing. This flat phase lasted for 24 hours in the brain post-dosing, suggesting that the brain took up the IV dosed protein slower than that by the peripheral organs. The remaining data indicated a terminal elimination phase with approximately first-order kinetics.

The elimination half-lives in the liver, kidney, heart and skin 47±10 and 38±13 hours for the liver, 54±25 and 29±16 hours for the kidney, 36±15 and 42±19 hours for the heart and 40±21 and 31±13 hours for the skin at 1 and 10 mg/kg, respectively; while the half-lives in the brain were 71±23 and 60±53 hours (Rat 3 in 10 mg/kg group was excluded for insufficient data to determine t½) at 1 and 10 mg/kg, respectively. No statistical differences were seen between the half-lives at 1 and 10 mg/kg in these organs, with an exception of p value <0.03 for kidney.

The mean values of Cmax for the liver, skin, kidney, heart and brain were 9.6, 0.3, 0.25, 0.22, and 0.08 ug/g at 1 mg/kg and 132, 7.9, 3.9, 3.7 and 1.8 ug/g at 10 mg/kg. The ratios of Cmax at 10 mg/kg to the corresponding values at 1 mg/kg were 14, 26, 16, 17 and 23 for these organs. After the Cmax values from individual animal were normalized for dose, the Cmax/dose values at 10 mg/kg were significantly higher than that at 1 mg/kg in all these organs (mostp values <0.05, p=0.06 for the liver). The values of AUClast for the liver, skin, kidney, heart and brain were 525, 16, 14, 9.3 and 7 hr·ug/g at 1 mg/kg; and 6747, 276, 183, 201 and 86 hr·ug/g at 10 mg/kg. The ratios of AUClast at 10 mg/kg to the corresponding values of AUClast at 1 mg/kg were 13, 17, 13, 22 and 12 for these organs, respectively. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

These observations suggested (1) the half-lives in most organs were about 2 days, with the exception of the brain (about 3 days); (2) the exposure per gram in the liver was larger than that of the skin, heart and kidney, which are larger than that of the brain; (3) with a ten-fold increase in dose (10/1 mg/kg), the values of Cmax at 10 mg/kg from all tested organs increased more than 10 times than that at 1 mg/kg.

The peak concentration in the brain was reached 1-24 hours (Tmax) after IV dosing.

Comparison of IV Versus IT Treatments

The concentration-time curves in the brain and liver after IV and IT administration at 1 and 10 mg/kg are compared in FIG. 164 and FIG. 165, respectively. The ratios of Cmax in the brain by IT/IV at 1 and 10 mg/kg were 3212 and 1501, respectively. These ratios of AUC0-192 hr were 1136 and 978. These observations indicated that, when the same dose of HNS was injected, intrathecal administration resulted in an approximately three-log greater exposure of the brain than that with intravenous administration. The elimination half-life in the brain was 2 days (45 and 49 hours at 1 and 10 mg/kg) by IT and 3 days (71 and 60 hours at 1 and 10 mg/kg) by IV administration at both dose levels. However, hepatic exposures after IT dosing were similar to that after IV dosing at the same dose of HNS. The ratios of Cmax in the liver by IT/IV at 1 mg/kg and 10 mg/kg were 0.5 and 0.8, and the ratios of AUClast were 0.4 and 1.2, respectively.

Conclusions

Pharmacokinetic and biodistribution profiles of 124I-sulfamidase (HNS) were studied by tissue PET images in rats after single intravenous or intrathecal administration of 1 or 10 mg/kg of $^{124}$I-sulfamidase. Concentration-time data were obtained both dynamically (the first 20 min) and statically in the regions of interest at 0.05, 1, 2, 4, 8, 24, 48, 96 and 192 hours post dosing. By dynamic imaging after IT dosing, total amount of HNS in the head region was reduced at a similar constant rate of 0.005/min-0.007/min (mean λz) in the first 20 min. By static imaging, the rates of elimination from the brain were essentially the same at two tested doses (λz: 0.016/hr versus 0.014/hr for 1 and 10 mg/kg, respectively) with a similar half-life about two days.

The values of Cmax and AUClast were proportional to the administered doses, and a linear PK behavior was indicated in the dose range of 1 to 10 mg/kg given in these IT single dosing regimens.

Concentration gradients were observed from the proximal to distal spine at both dose levels.

After IT dosing, the peak concentration was seen around 20 min at the proximal, 1 to 4 hours at the mid and 1 to 8 hours at the distal sections. Linear PK behavior was also indicated in the different sections of the spine.

After IT dosing, HNS protein was measurable in the liver from very early time up to 96 hours at 1 mg/kg and 192 hours at 10 mg/kg. The rate of elimination was faster at 1 mg/kg (λz 0.030/hr) than that at 10 mg/kg (λz 0.017/hr), with a corresponding shorter t½ at the lower dose (28±16 versus 42±1 hours at the doses of 1 and 10 mg/kg, respectively).

After IV dosing, the elimination half-lives in the liver, kidney, heart and skin 47±10 and 38±13 hours for the liver, 54±25 and 29±16 hours for the kidney, 36±15 and 42±19 hours for the heart and 40±21 and 31±13 hours for the skin at 1 and 10 mg/kg, respectively; while the half lives in the brain were 71±23 and 60±53 hours. The mean values of Cmax for the liver, skin, kidney, heart and brain were 9.6, 0.30, 0.25, 0.22, and 0.08 ug/g at 1 mg/kg and 132, 7.9, 3.9, 3.7 and 1.8 ug/g at 10 mg/kg. After the Cmax values from individual animal were normalized for dose, the Cmax/dose values at 10 mg/kg were significantly higher than that at 1 mg/kg in all these organs (mostp values <0.05, p=0.06 for the liver). The values of AUClast for the liver, skin, kidney, heart and brain were 525, 16, 14, 9.3 and 7 hr·ug/g at 1 mg/kg; and 6747, 276, 183, 201 and 86 hr·ug/g at 10 mg/kg. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

Example 23: Treatment of Sanfilippo Syndrome Type A (Sanfilippo A) Patients with HNS Direct CNS administration through, e.g., IT delivery can be used to effectively treat Sanfilippo A patients. This example illustrates a multicenter dose escalation study designed to evaluate the safety of up to 3 dose levels every other week (EOW) for a total of 40 weeks of rhHNS administered via an intrathecal drug delivery device (IDDD) to patients with Sanfilippo A. Various exemplary intrathecal drug delivery devices suitable for human treatment are depicted in FIGS. 94-97.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria:

Safety of ascending doses of HNS administered by IT injection for 40 weeks in patients with Sanfilippo A is determined. In addition, the clinical activity of HNS on cognitive function, and single and repeated-dose pharmacokinetics in serum and concentrations in cerebrospinal fluid (CSF) are assessed.

Examples of IT Delivery of Naglu-IGFII

Example 24: In Vitro Study of rhNaglu and Naglu-IGFII

The mechanism of cellular uptake by each of the Naglu variants was studied using two strains of Sanfilippo B patient fibroblast cells, GM02391 (P359L) and GM 01426 (E153K), and a normal human fibroblast cell line. Attributed to M6P receptor expression on the cell line, fibroblast cells are traditionally used by researchers for the study of lysosomal enzymes cellular uptake.

Cellular uptake studies were done by incubation of fibroblast cells with rhNaglu or Naglu-IGFII for four hours at 37° C. Cells were washed and lysed after incubation, and Naglu enzymatic activity in cell lysates was measured. Incubation of rhNaglu with fibroblast cells resulted in barely detectable amount of enzyme intracellularly. In contrast, incubation of Naglu-IGFII with fibroblast cells resulted in pronounced level of enzyme intracellularly (FIG. 166). The amount of internalized Naglu-IGFII reached saturation as the amount of enzyme used for incubation increased. The dose dependant saturating uptake is a typical finding for receptor mediated cellular uptake. Furthermore, the internalization of Naglu-IGFII was not inhibited by exogenous M6P, but was inhibited by exogenous IGFII completely (FIG. 166). This result indicated that Naglu-IGFII internalization into fibroblast cells is dependant on M6P/IGFII receptor in a glycosylation independent manner.

An experiment was also conducted to study the trafficking of rhNaglu and Naglu-IGFII to lysosomes. Sanfilippo B patient fibroblast cells (GM01426) were used for this study. Detection of rhNaglu and Naglu-IGFII was examined by staining the cells with anti-human Naglu polyclonal antibody after initial incubation of the proteins with the cells. Immunofluorescent staining of LAMP-1 (lysosomal associated membrane protein 1) was used for the detection of lysosomes. Co-localization of rhNaglu and Naglu-IGFII with lysosomes was visualized by confocal microscopy (FIG. 167).

Extensive internalization of Naglu-IGFII was observed after 4 hours of incubation of the protein with the cells, co-localization of Naglu-IGFII with lysosomes was demonstrated. Contrarily, rhNaglu failed to show internalization in the same time frame, and no co-localization with the lysosomes was observed. This result further provided the evidence that Naglu-IGFII was internalized into cells and transported to the correct cellular compartment, the lysosomes. The half life of internalized Naglu-IGFII in Sanfilippo B patient fibroblast cells was determined to be 1.5 days (data not shown).

Example 25: In Vivo Studies in Mouse Models

Wild Type (wt) Cannulated Rat

In addition to the Sanfilippo B mouse model, the wt cannulated rat, a non-deficient animal model, was also used for molecule screening in vivo. The wt cannulated rats had surgically implanted cannula at the upper lumber and lower thoracic region of the spinal cord, and a single injection of 35 ul to the CSF was done through the cannula. The criteria assessed for molecule screening using this animal model were Naglu activity assay and immunohistochemistry of the brain and spinal cord.

Sanfilippo Syndrome Type B Mouse Model

The mouse model of Sanfilippo syndrome type B (Naglu−/− mouse, Sanfilippo B mouse) was generated by E. Neufeld and colleague (Li HH, et al., PNAS 96(25):14505-14510; 1999). The exon 6 of the mouse's Naglu gene is disrupted by insertion of a selection marker, neomycin resistant gene. The resulting homozygote Naglu−/− mouse are completely Naglu deficient (FIG. 168), and have total GAG accumulation in liver and kidney. Despite the total deficiency of Naglu, these mice are generally healthy and have life span of 8-12 month. Changes of other lysosomal enzymes' expression happen at age around 5 months, these changes include compensatory increase of β-galactosidase, α-glucosidase, β-glucuronidase and β-hexosaminidase in liver and brain, elevation of α-L-iduronidase in liver but not in brain, and the reduction of neuraminidase in liver and brain. Death usually occurs as a result of urinary retention and urinary infection. The Sanfilippo B mouse model has been studied extensively in the literature to depict Sanfilippo B pathological changes. The phenotype related to CNS pathology of Naglu−/− mouse is reported to be hypo-activity at the age 4.5 month, but hyperactivity at other ages has also been observed.

The neuro-pathological changes in Naglu−/− mouse are described as vacuoles and inclusion bodies in neurons, macrophages and epithelial cells as observed by EM (electron-microscopy). These pathological changes typically start at 33 days of age, and progressively worsen as animals get older. Activated astrocyte and microglial cells are also demonstrated by histo-pathological analysis. Biochemical analysis of two gangoliosides, GM2 and GM3, showed 5 fold and 9 fold increase the brain. (Since GM2 and GM3 are not direct substrates of Naglu, and it could be challenging to demonstrate significant reduction after ERT for short period of time, they were not used as end biomarkers for POC).

Biochemical analysis was done by measurement of Naglu enzyme activities and GAG levels, histological analysis was done by anti-human Naglu antibody, anti-LAMP-1 antibody, anti-Iba-1 antibody and anti-GFAP antibody immunohistochemistry. The anti-human Naglu antibody used for this study was a mouse monoclonal antibody that doesn't bind endogenous murine Naglu in wt mouse or the mutated Naglu in Sanfilippo B mouse. LAMP-1 immunostaining used an antibody binds to lysosomal membrane protein, lysosomal associated membrane protein-1. Iba-1 staining used an antibody binds to ionized calcium-binding adaptor protein that is specific for microglial and macrophage cells. GFAP staining used an antibody that binds to glial fibrillary acidic protein which is specific for astrocytes.

In Vivo Biological Activity Screening by Intracranial (IC) Injection into Sanfilippo B Mouse The objective of this study was to evaluate the biological activity of Naglu enzymes in vivo. In this study, proteins were administered through IC injection into the brain of the Sanfilippo B mouse. The age of Sanfilippo B mice for the study was closely matched to be at 8 weeks of age. The IC injection route offered the best case scenario to evaluate the efficacy of the molecules. Naglu proteins were assessed by the ability to be taken up into neuronal cells and to reduce lysosomal storage. Immunohistochemistry was used to assess biodistribution. And lysosomal storage was characterized by the number and the size of positive staining using LAMP-1 immunostaining.

IC injection was done by direct injection through the skull of the Sanfilippo B mouse into the right cerebrum cortex. Two microliters, or 35 µg of Naglu protein was injected into each animal. Sacrifices of the animals took place 7-days after injection. The time of sacrifice was pre-determined in a pilot study where sacrifices of the animal took place 3, 7, and 14 day after injection. From the pilot study, it was determined that 7 days post injection is the optimum time for immunohistochemical study. Brain sections were cut transversally (FIG. 169), and Naglu and Lamp-1 immunostaining were performed. Cellular uptake into both the neurons and the glial cells in rhNaglu and Naglu-IGFII treated Sanfilippo B mouse was demonstrated by immunohistochemistry using an anti-human Naglu antibody (FIG. 170 and FIG. 171). There was no significant difference between rhNaglu and Naglu-IGFII treated Sanfilippo B mouse in regards to the cellular uptake was observed. Additionally, LAMP-1 immunostaining of the brain tissue of both the rhNaglu and the Naglu-IGFII treated mouse indicates significant level of reduction of lysosomal storage. The level of lysosomal storage reduction in both rhNaglu and Naglu-IGFII treated groups was almost at the same level of normal wt mouse.

Reduction of lysosomal storage was also observed in Naglu-TAT, Naglu-Kif and PerT-Naglu tested Sanfilippo B mice after IC injection (data not shown). This study demonstrated the in vivo biological activity of all of the variants of Naglu.

In a separate study, Naglu-deficient mice were IT-administered a vehicle or alternatively one, two or three weekly doses of a recombinant Naglu-IgF-II fusion protein construct (Naglu) in PBS. An untreated wild-type group of mice served as an untreated wild-type control and were administered a vehicle without Naglu. Mice were sacrificed after 24 hours following the final injection, followed by tissue preparation for immunohistochemistry (IHC) and histopathological analysis.

Distribution of Naglu to the brain tissues of the Naglu-deficient mice was evident following IT-administration of the recombinant Naglu. As illustrated in FIG. 172A, IT-administration of the recombinant Naglu to the Naglu-deficient mice resulted in the widespread reduction of cellular vacuolation in the white matter tissues compared to Naglu-deficient mice which were IT-administered the vehicle. Similarly, and as illustrated in FIG. 172B, morphometrical analysis revealed a marked reduction in LAMP1 immunostaining in the white matter tissues of the treated mice relative to the untreated Naglu-deficient mice, thereby reflecting an improvement in disease pathology.

As shown in FIGS. 173A-B, in each area of brain tissue evaluated (the cortex, caudate nucleus and putamen (CP), thalamus (TH), cerebellum (CBL) and white matter (WM)) the LAMP-positive area was reduced in the Naglu-treated mice relative to the untreated Naglu-deficient control mice, and approached the LAMP-positive area of the wild-type mice. Particularly notable is that the LAMP-positive areas in each area of brain tissue analyzed were further reduced following the IT-administration of two or three doses (FIG. 173B) relative to a single dose (FIG. 173A) of Naglu.

These results confirm that IT-administered Naglu is capable of altering progression of lysosomal storage diseases such as Sanfilippo syndrome type B in the Naglu-deficient mouse model, further confirming the ability of IT-administered enzymes such as Naglu to treat the CNS manifestations associated with lysosomal storage diseases, such as Sanfilippo syndrome type B.

Molecule Screening by Intrathecal (IT) Injection into wt Cannulated Rat

This study directly mimics a port-mediated approach for drug administration. Naglu protein was administered via IT injections into wt cannulated rats to determine biodistribution into the parenchyma of the brain.

The cannula in these animals was placed in the upper lumbar and lower thoracic portion of the spinal cord (FIG. 174). Animals were injected with 35 µl, or 385 µg of rhNaglu, Naglu-TAT, Naglu-IGFII and PerT-Naglu, through the cannula (due to the solubility limitation, Naglu Kif was injected with only 38.5 ug, which is 10 fold less than the rest of the Naglu). Sacrifices happened 4 hr and 24 hr after injections.

Brain and spinal cord tissues were collected and measured by the Naglu activity assay. In the brain of treated animals, Naglu-TAT and Naglu-IGFII treated animals exhibited higher activity than the rhNaglu and all other Naglu variants treated animals (FIG. 175). As a general trend, the Naglu activity was significantly higher in the spinal cord than in the brain for all treated animals (data not shown). This phenomenon may indicate that proteins were taken up more at the site closer to the IT injection.

Immunohistochemistry analysis indicated that the biodistribution of the Naglu-IGFII treated group was more extensive in the brain than all other Naglu variants treated group 24 hr after IT injections (FIG. 176 and FIG. 177). In the rhNaglu treated animals the protein was observed in the meninges of the brain only. In the spinal cord section, IHC indicated some cellular uptake of rhNaglu in the neurons of the grey matter, but to a much lesser extent than Naglu-IGFII uptake in the neurons of spinal cord (data not shown).

In Naglu-TAT IT injected group, even though highest Naglu activity was observed in brain tissue by biochemical analysis, but IHC failed to indicate any Naglu-TAT penetration into the parenchyma of the brain, other than remaining on the meninges. Besides from Naglu-IGFII, all of the other Naglu variants failed to show biodistribution beyond the meninges, a strong testimony of the dependency on M6P/IGFII receptors for the cellular uptake of Naglu in the brain after IT injection. This study pointed to Naglu-IGFII as the lead molecule for drug development for Sanfilippo B.

Example 26: Proof of Concept Study Using Naglu-IGFII

Experimental Design

The proof of concept study was designed to show both biodistribution and the reversal of lysosomal storage after IT injection of Naglu-IGFII in Sanfilippo B mouse. For this study, three groups of Sanfilippo B mice at 8 weeks of age were treated with an IT injection of Naglu-IGFII. Each IT injection constituted a 10 ul volume or 260 ug of Naglu-IGFII. There were three treated groups, 1× injection, 2× injection and 3× injections group. For the 1× injection group, a single dose of protein was administrated at day 0. Animals were sacrificed 24 hr after injection. For the 2× injection group, two IT injections were administrated at day 0 and day 7, and animals were sacrificed 24 hr after the last injection. For the 3× injection group, IT injections were administrated at day 0, day 7 and day 14, and animals were sacrificed 24 hr after the last injection. Three groups of vehicle treated mouse were also included. For the vehicle control groups, Sanfilippo B mice were injected with vehicle at the same time interval as the treated groups and sacrificed the same way as the treated groups.

Both biochemical and histological analyses were applied to evaluate the outcome of the study. The biochemical analyses include a Naglu activity assay to measure the amount of enzymes in the tissue and a total GAG assay to evaluate the reduction of lysosomal storage. Liver and brain were the two subjected tissue for biochemical analyses (FIG. 178 and FIG. 179). The histological analyses include H&E staining of the tissues for morphological evaluation (data not shown), and immunohistochemical staining with anti-human Naglu antibody, LAMP, Iba and GFAP (data for Iba and GFAP staining not shown).

The anti-human Naglu antibody used for this study was a mouse monoclonal antibody that doesn't bind endogenous murine Naglu in wt mouse or the mutated Naglu in Sanfilippo B mouse. LAMP-1 immunostaining used an antibody binds to lysosomal associated membrane protein. Iba-1 staining used an antibody binds to ionized calcium-binding adaptor protein that is specific for microglial and macrophage cells. GFAP staining used an antibody that binds to glial fibrillary acidic protein which is specific for astrocytes.

Representative microscopic pictures of Naglu immunofluorescence are shown in FIG. 180. FIG. 181 shows a representative section schematic of the brain. Even though Naglu-IGFII was detected into the cerebral cortex which is closer to the meninges, it was not found in the subcortical region such as the caudate nucleus, the thalamus and the white matter (data not shown). Since the immunostaining of LAMP-1, Iba-1 and GFAP of the same subcortical areas did demonstrate reversal of lysosomal storage, it was believed that the negative immunostaining of Naglu in the deep brain areas was probably due to the sensitivity of the Naglu immunofluorescence.

Representative microscopic pictures of Lamp-1 immunostaining are shown in FIG. 182 through FIG. 186. To demonstrate the extent of protein distribution and efficacy, cerebral cortex and subcortical regions, such as caudate nucleus, thalamus and white matter, and cerebellar cortex were selected for immunohistological analysis. The result from Iba-1 and GFAP immunostaining (data not shown) indicated that what was seen in the LAMP-1 immunostaining was the combined effect of the changes of microglial cells and astrocytes, the two cell types that were reported to be affected in Sanfilippo B mouse model (Li 2002, Ohmi 2002) in addition to neurons. Due to technical limitations, LAMP-1 immunostaining was not able to reveal lysosomal storage in neurons. To best observe the lysosomal accumulation in neurons, such vacuoles and inclusions, electron microscopy is usually utilized (EM was not included in current study).

It will be appreciated that the identification of cell types was limited to neurons and glial cells. The neurons were typically identified by the relatively large and pale nucleus that contains one or more densely stained nucleoli, and the frequently detectable cytoplasm. The glial cells were generally identified by the small dense nucleus and the inconspicuous cytoplasm. The distinction between the different types of glial cells, such as astrocytes, microglial cells, ependymal cells and oligodendrocytes, is typically best done by staining with cell type specific markers.

In addition to the reduction of lysosomal storage exhibited by the LAMP-1 immunostaining, the Iba-1 immunostaining indicated the reduction of cell size and number of processes in microgial cells, and GFAP immunostaining indicated the reduction of cell size and length/number of processes in astrocytes, in the cerebral cortex, caudate nucleate, thalamus, white matter and cerebellum after IT injections of Naglu-IGFII (data not shown). Furthermore, histopathological analysis by H&E staining (hematoxylin and eosin) of the brain tissues from the same areas as examined for immunohistochemistry, demonstrated the reduction of vacuoles in glial cell after 3× IT injection of Naglu-IGFII. All of the result mentioned above also suggested the dose-related effect of Naglu-IGFII IT injections.

The biochemical analyses of Sanfilippo B mice after IT injection of Naglu-IGFII detected Naglu activity in the brain and liver. Efficacy of the Naglu-IGFII was demonstrated by total GAG reduction in the brain and liver. Immunohistochemistry demonstrated the biodistribution of Naglu-IGFII in the parenchyma of the brain. Immunostaining of LAMP-1, Iba-1, GFAP and histopathological analysis by H&E staining exhibited reduction of lysosomal storage, the reduction of size and process by microglial and astrocytes in not only the cerebral cortical area of the brain, but also in the subcortical areas, white matter and cerebellar cortex of the brain.

Conclusions

Among other things, it has been demonstrated that the fusion protein, Naglu-IGFII, exhibited enzymatic activity in vitro toward a substrate that has similar structure to the native substrate of Naglu. In vitro cellular uptake study demonstrated that the molecule was taken up to cells by the M6P/IGFII receptor in a manner that was independent of M6P glycosylation. Internalized Naglu-IGFII was shown to co-localize with lysosomes. Naglu-IGFII was shown to reduce lysosomal storage in vivo after IC injection into the Sanfilippo B mouse. In comparison to rhNaglu and other Naglu fusions and modifications, Naglu-IGFII surpassed them all in penetrating into the parenchyma of the brain of wt cannulated rat after IT injection. Finally, IT injection of Naglu-IGFII into Sanfilippo B mice demonstrated extensive distribution well beyond the meninges, and observed reversal of lysosomal storage in the cerebral cortex as well as in the subcortical regions. Taken together, these data indicate that Naglu-IGFII is a candidate drug for treatment of Sanfilippo B disease.

Example 27: Toxicity, Pharmacokinetics (PK) and Tissue Biodistribution Studies of IT Delivered Naglu-IGFII Proof of Concept Studies in Mouse Three groups (n=3) of Naglu(−/−) mice were injected with 10 uL containing 260 ug of Naglu-IGFII given as a single bolus IT lumbar injection. The 260 ug dose translates into a 520 mg/kg brain weight dose (mouse brain=0.0005 kg). One group was injected at Day 0 and sacrificed 24 hr post injection. A second group was injected on Days 0 and 7, and sacrificed 24 hr after the last injection. The third group was injected on Days 0, 7, and 14, and sacrificed 24 hr after the last injection. Each Naglu-IGFII-dosed group was paired with a vehicle control group in order to control for age/disease severity.

Naglu enzyme activity in the brain and the liver was similar for the three Naglu-IGFII-dosed groups. Comparing rhNaglu enzyme activity in the liver to brain, more than 10-fold rhNaglu enzyme activity was found in the liver. It was contemplated that since levels of rhHNS enzyme activity were comparable in the brain and liver after 1-, 3-, and 6-months of dosing in the pivotal toxicity studies in rats and juvenile monkeys, some portion of rhNaglu dose given to the Naglu(−/−) mice may not have been delivered IT, but rather systemically. Nevertheless, the total GAG level in the brain showed a statistically-significant reduction (p <0.05) after 3 IT injections. A dose-related trend for total GAG level reduction was seen in the livers, which was statistically-significant (p <0.05) in the groups receiving 2 or 3 doses.

The biodistribution of Naglu-IGFII after IT injection was observed well beyond meninges into the parenchyma of the brain, but deep subcortical regions were negative for anti-Naglu antibody immunostaining. A reduction of lysosomal activity by lysosomal-associated membrane protein (LAMP) immunostaining was observed in the groups given 2 or 3 doses only. Areas of lysosomal activity reduction included cerebral cortex and deep subcortical regions of caudate nucleus, thalamus, and white matter. Thus, the reduction of various immunostaining parameters in Naglu-IGFII-dosed animals suggested that therapeutic levels of NAGLU might be present despite the absence of anti-NAGLU immunostaining. An attenuated inflammatory response was evidenced by reduction of glial fibrillary acidic protein (GFAP) immunostaining of astrocytes and reduction of ionized calcium-binding adaptor molecule (Iba) staining of microglia/macrophages in groups given 2 or 3 doses only. Areas of analysis included cerebral cortex and deep subcortical regions of caudate nucleus, thalamus, and white matter.

Studies in Rat

The S-D rat was selected as the rodent species for toxicological evaluation of IT-administered Naglu-IGFII. As a result, sixteen rats (eight per sex) are dosed with recombinant Naglu-IGFII at the maximal feasible dose (MFD), and at approximately ¼ and ½ the MFD (low- and mid-dose levels, respectively) every 4 days for a total of 8 doses.

Single-dose PK/biodistribution study in S-D rats is performed to determine CSF and serum concentration, or tissue distribution, respectively, following IT-L administration to male and female animals.

Toxicology studies are designed to evaluate IT-L administration of Naglu-IGFII from a toxicology and safety pharmacology (neurologic, respiratory, and cardiovascular safety) perspective in both male and female animals. Toxicological evaluation in these studies includes clinical observations, body weights, food consumption, clinical pathology, appropriate safety pharmacology assessments (by physical examination or electrocardiography), gross tissue and microscopic evaluation. A limited number of CSF and serum samples are collected and analyzed for Naglu-IGFII, and for antibodies to the test article. Naglu-IGFII tissue distribution and subcellular localization are quantified by enzyme activity assay and immunohistochemistry, respectively. Additionally, selected studies include a recovery period to assess the reversibility, or potential delayed appearance, of any noted significant toxicological findings.

Studies in Monkeys

The cynomolgus monkey was been selected as the non-rodent species for toxicological evaluations of IT-administered Naglu-IGFII due to their genetic and anatomical similarity to humans and hence is thought to be the more relevant species. Given that the planned patient population for the Sanfilippo syndrome type B clinical trials is pediatric, a chronic 6-month toxicology study in juvenile cynomolgus monkeys featuring intrathecal drug deliver device (IDDD) administration of Naglu-IGFII is performed. Juvenile cynomolgus monkeys are generally less than 1 year of age at initiation of study (approximately 7-9 months of age) and weigh between 900 g to 1,500 g at study initiation. The data obtained from a 1-month repeated-dose juvenile cynomolgus monkey toxicity study guide the dose level selection and design of the 6-month juvenile monkey study. The repeated-dose toxicology studies are designed to mimic the expected clinical route (IT-L bolus) and frequency of administration (every other week; EOW) over a period of 1 through 6 months.

As described above, toxicology studies are designed to evaluate IT-L administration of Naglu-IGFII from a toxicology and safety pharmacology (neurologic, respiratory, and cardiovascular safety) perspective in both male and female animals. Toxicological evaluation in these studies includes clinical observations, body weights, food consumption, clinical pathology, appropriate safety pharmacology assessments (by physical examination or electrocardiography), gross tissue and microscopic evaluation. A limited number of CSF and serum samples are collected and analyzed for Naglu-IGFII, and for antibodies to the test article. Naglu-IGFII tissue distribution and subcellular localization are quantified by enzyme activity assay and immunohistochemistry, respectively. Additionally, selected studies include a recovery period to assess the reversibility, or potential delayed appearance, of any noted significant toxicological findings.

Example 28: EOW Intrathecal Administration of Naglu-IGFII

This example was designed to determine the feasibility of IT-lumbar dosing EOW for 6 injections (3 month study) in the Naglu−/− mouse model. This dosing regimen may be more clinically relevant as compared to weekly dosing.

Eight week old Naglu −/− male and female mice were studied according to the following experimental design:

Physiological studies, including Naglu activity assay on liver, brain and serum, anti-Naglu antibody assay on serum, and BCA assay on liver and brain, were performed. Histological studies, including Naglu IHC on brain, spinal cord and liver, and Lamp staining on brain and spinal cord, were performed.

Brain, spinal cord and liver were collected and fixed in 10% NBF. Five μm paraffin sections were prepared for histological staining. Immunohistochemical (IHC) staining of Naglu was used to detect cellular uptake of the injected protein. H&E staining was used to observe morphological changes. LAMP, an indicator of lysosomal activity and disease state, GFAP and Iba-1, two CNS pathological markers for activated astrocytes and microglial cells, were used for histopathological improvement evaluation.

Naglu immunostaining of brain, spinal cord and liver of vehicle and Naglu-IGFII treated mice demonstrated that, in the brain and spinal cord, injected Naglu was detected in meninges (M) only by IHC and no Naglu positive staining was detected in any other regions (FIG. 187). In the liver, sinunoidal cells (S) were Naglu positive and no Naglu uptake was found in hepatocytes (H).

LAMP immunostaining and H & E staining of the liver and spinal cord of vehicle and Naglu-IGFII treated mice demonstrated that, compared with the vehicle animals, LAMP staining was decreased throughout in both livers and spinal cords treated with Naglu. H&E staining showed cellular vacuolation in hepatocytes was evidently reduced in the treated group compared with vehicle treated animals (FIG. 188 and FIG. 189).

H & E staining of the brain of vehicle and Naglu-IGFII treated mice demonstrated a morphology improvement in the brain after 6 every other week IT injection of Naglu-IGFII for 3 months. In the treated brain, the cellular vacuolation (arrows) in all examined regions decreased compared with the vehicle group (FIG. 190)

LAMP IHC in various brain regions after 6 IT Naglu injections for 3 months demonstrated that, compared with the vehicle treated group, Naglu IT administration to SFB mice resulted in a reduction of lysosomal activity in all examined regions revealed by LAMP immunostaining (FIG. 190). This reduction was characterized by the decrease in the number of LAMP positive cells, smaller cell size and lighter staining. A marked reduction was found in the cerebellum and brainstem, which are located in the caudate part of the brain close to the spinal cord, compared with other brain regions. A clear reduction was also found in the deep brain regions, including the white matter, hippocampus and thalamus.

Iba IHC in various brain regions after 6 IT Naglu injections for 3 months revealed activation of microglial cells (FIG. 191). Compared with vehicle treated group, no decease in the number of positive cells and staining intensity

TABLE 49

Experimental Design for EOW IT Delivery of Naglu-IGFII

| Group | N | Treatment | Dose | Frequency | Sacrifice |
|---|---|---|---|---|---|
| A | 3 | Vehicle | N/A | IT injection EOW for 3 months (total of 6 injections) | 24 h after last injection |
| B | 6 | Naglu-IGFII | 60 mg/kg brain weight (30 ug) | IT injection EOW for 3 months (total of 6 injections) | 24 h after last injection | was observed in Naglu treated group. However, the cellular morphology of positive microglial cells changed with reduced cell size in all examined brain regions compared to large and vacuolated one in the vehicle group (inserts).

GFAP IHC in various brain regions after 6 IT Naglu injections for 3 months revealed astrocytic activation (FIG. 192). Compared with the vehicle treated group, GFAP positive staining was decreased in the cerebellum and brainstem, and slightly decreased in other examined regions.

With respect to cellular uptake, these data demonstrate that in the brain and spinal cord, Naglu was detected in meningial cells only after 6 time every other week Naglu IGFII IT injection for 3 month. Naglu was undetectable by IHC in any other regions of the brain and spinal cord. In the liver, Naglu positive staining was found in sinusoidal cells.

In the brain and spinal cord, after 6 every other week IT injection of Naglu-IGFII for 3 months, histopathological improvement was seen throughout the brain and spinal cord even though injected Naglu was undetectable by IHC. H&E staining demonstrated cellular vacuolation reduction in all examined brain regions. LAMP staining decreased throughout treated spinal cords and in all evaluated brain regions including the white matter, hippocampus and thalamus which are deep brain areas, with marked decrease in the cerebellum and brainstem in the Naglu-IGFII treated group. The decreased staining pattern of GFAP staining for astrocytes was consistent with LAMP staining while not dramatically decreased as LAMP. Iba-1 staining showed reduction of the cell size of microglial cells in all examines brain regions. In the liver, H&E staining demonstrated cellular vacuolation reduction with marked reduction in LAMP staining in the Naglu treated group.

Example 29: Treatment of Sanfilippo B Patients

Direct CNS administration through, e.g., IT delivery can be used to effectively treat Sanfilippo syndrome type B (Sanfilippo B) patients. This example illustrates a multi-center dose escalation study designed to evaluate the safety of up to 3 dose levels every other week (EOW) for a total of 40 weeks of Naglu-IGFII and/or rhNaglu administered via an intrathecal drug delivery device (IDDD) to patients with Sanfilippo B Syndrome. Various exemplary intrathecal drug delivery devices suitable for human treatment are depicted in FIGS. 94-97.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria:

Safety of ascending doses of Naglu-IGFII administered by IT injection for 40 weeks in patients with Sanfilippo B is determined. In addition, the clinical activity of Naglu-IGFII and/or rhNaglu on cognitive function and single and repeated-dose pharmacokinetics in serum and concentrations in cerebrospinal fluid (CSF) are assessed.

Typically, a therapeutically effective amount of Naglu-IGFII and/or rhNaglu is administered intrathecally at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, Naglu-IGFII and/or rhNaglu is administered intrathecally bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress, if anti-Naglu antibodies become present or increase, or if disease symptoms worsen, the interval between doses can be decreased.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A formulation comprising a lysosomal enzyme at a concentration of at least 5 mg/ml and a surfactant, wherein the formulation comprises no greater than 5 mM phosphate and has a pH of 5.5-7.0, wherein the surfactant is polysorbate 20 or polysorbate 80, and wherein the formulation is suitable for CNS delivery.

2. The formulation of claim 1, wherein the lysosomal enzyme is present at a concentration ranging from 10-20 mg/ml.

3. The formulation of claim 1, wherein the lysosomal enzyme is present at a concentration of 10 mg/ml.

4. The formulation of claim 1, further comprising sodium chloride present at a concentration up to 175 mM.

5. The formulation of claim 1, wherein the formulation is a liquid formulation.

\* \* \* \* \*